US010472648B2

(12) United States Patent
Brown et al.

(10) Patent No.: US 10,472,648 B2
(45) Date of Patent: Nov. 12, 2019

(54) METHOD OF MAKING ADENOVIRUS AND CORRESPONDING PLASMIDS

(71) Applicant: PSIOXUS THERAPEUTICS LIMITED, Oxfordshire (GB)

(72) Inventors: Alice Claire Noel Brown, Oxfordshire (GB); Tamara Nicolson, London (GB)

(73) Assignee: Psioxus Therapeutics Limited, Abingdon, Oxfordshire (GB)

( * ) Notice: Subject to any disclaimer, the term of this patent is extended or adjusted under 35 U.S.C. 154(b) by 0 days.

(21) Appl. No.: 15/107,451

(22) PCT Filed: Dec. 23, 2014

(86) PCT No.: PCT/EP2014/079162

§ 371 (c)(1),
(2) Date: Jun. 22, 2016

(87) PCT Pub. No.: WO2015/097220

PCT Pub. Date: Jul. 2, 2015

(65) Prior Publication Data

US 2016/0319304 A1 Nov. 3, 2016

(30) Foreign Application Priority Data

Dec. 23, 2013 (GB) .................................. 1322851.5
Oct. 24, 2014 (WO) ................. PCT/EP2014/072919

(51) Int. Cl.

*C12N 15/86* (2006.01)
*C12N 15/87* (2006.01)
*C12N 7/00* (2006.01)
*A01K 67/00* (2006.01)
*A61K 48/00* (2006.01)

(52) U.S. Cl.

CPC ............... *C12N 15/86* (2013.01); *C12N 7/00* (2013.01); *A61K 48/00* (2013.01); *C12N 2710/10321* (2013.01); *C12N 2710/10332* (2013.01); *C12N 2710/10341* (2013.01); *C12N 2710/10343* (2013.01); *C12N 2710/10351* (2013.01); *C12N 2800/30* (2013.01); *C12N 2820/55* (2013.01)

(58) Field of Classification Search

CPC .......... C12N 15/86; C12N 2710/10332; C12N 2710/10341; C12N 2710/10351; C12N 2710/10321; C12N 2710/10343

See application file for complete search history.

(56) References Cited

U.S. PATENT DOCUMENTS

| | | | |
|---|---|---|---|
| 7,510,868 B2 | | 3/2009 | Harden et al. |
| 8,052,965 B2 | | 11/2011 | Van Beusechem et al. |
| 2004/0213764 | A1 | 10/2004 | Wold et al. |
| 2006/0292682 | A1 | 12/2006 | Hawkins et al. |
| 2013/0243731 | A1 | 9/2013 | Dias et al. |

FOREIGN PATENT DOCUMENTS

| | | | |
|---|---|---|---|
| CN | 102 586 327 | A | 7/2012 |
| CN | 102586327 | A | 7/2012 |
| JP | 2009505680 | A | 2/2009 |
| JP | 2010514418 | A | 5/2010 |
| WO | 0015823 | A1 | 3/2000 |
| WO | 2005086922 | A2 | 9/2005 |
| WO | 2005107474 | A2 | 11/2005 |
| WO | 2005118825 | A2 | 12/2005 |
| WO | WO 2006/060314 | A2 | 6/2006 |
| WO | 2007027860 | A2 | 3/2007 |
| WO | 2008080003 | A2 | 7/2008 |
| WO | WO 2012/024351 | A2 | 2/2012 |
| WO | 2014138314 | A1 | 9/2014 |
| WO | 2015077624 | A1 | 5/2015 |
| WO | 2016174200 | A1 | 11/2016 |

OTHER PUBLICATIONS

Marino et al. Development of a versatile oncolytic virus platform for local intra-tumoural expression of therapeutic transgenes. PLoS ONE 12(5):e0177810. https://doi.org/10.1371/journal.pone.0177810, 2017, pp. 1-23.*

Janssen, Josephine M. et al., "Development of an AdEasy-based system to produce first- and second-generation adenoviral vectors with tropism for CAR- or CD46-positive cells", *J. of Med.*, 15(1), Jan. 1, 2013, pp. 1-11.

Hoffmann, Dennis et al., "Efficient generation of double heterologous promoter controlled oncolytic adenovirus vectors by a single homologous recombination step in *Escherichia coli", BMC Biotechnology*, 6(36), Aug. 3, 2006, pp. 1-12.

(Continued)

*Primary Examiner* — Quang Nguyen

(74) *Attorney, Agent, or Firm* — Saul Ewing Arnstein & Lehr LLP; Debora Plehn-Dujowich

(57) ABSTRACT

The present disclosure relates to a method of making an adenovirus plasmid comprising a part or all of an adenovirus genome and one or more original restriction sites allowing rapid and flexible manipulation of the adenovirus genome, and methods of preparing adenovirus constructs, for example comprising a transgene. The disclosure also extends to novel intermediates employed in and generated by the method, to plasmids and shuttle vectors of the method and to adenoviruses or adenoviral vectors obtainable from the plasmid and/or method. The disclosure further relates to use of the viruses or vectors, for example obtained from a method disclosed herein, in therapy, such as use in the treatment of cancer.

18 Claims, 27 Drawing Sheets

Specification includes a Sequence Listing.

(56) References Cited

OTHER PUBLICATIONS

Li et al., “A one-step ligation system for rapid generation of armed, conditionally-replicating adenoviruses.”, *Biotechnology Letters*, 35, Aug. 2013, pp. 1215-1221.
McVey, D. et al., “Rapid Construction of Adenoviral Vectors by Lambda Phage Genetics”, *J. of Virology*, 76(8), 2002-04-15, pp. 3670-3677.
Choi, et al., “Concurrent delivery of GM-CSF and B7-1 using an oncolytic adenovirus elicits potent antitumor effect”, Gene Ther. 13(13), 2006, 1010-1020.
Jin, et al., “Identification of novel insertion sites in the Ad5 genome that utilize the Ad splicing machinery for therapeutic gene expression”, Mol Ther. 12(6), 2005, 1052-1063.
Lee, et al., “Enhanced antitumor effect of oncolytic adenovirus expressing interleukin-12 and B7-1 in an immunocompetent murine model”, Clin Cancer Res. 12(19), 2006, 5859-5868.
Paul et al., “The combination of a chemokine, cytokine and TCR-based T cell stimulus for effective gene therapy of cancer”, Cancer Immunol Immunother. Dec. 2002;51(11-12):645-54. Epub Oct. 9, 2002.
Champion, et al., “Arming” the chimeric oncolytic adenovirus enadenotucirev to deliver checkpoint inhibitors and other therapeutics directly to tumours, Journal for ImmunoTherapy of Cancer 2(Suppl. 3) ,2014 ,46.
Dias, et al., Targeted cancer immunotherapy with oncolytic adenovirus coding for a fully human monoclonal antibody specific for CTLA-4, Gene Ther. 19(10) ,2012 ,988-998.
Forrester, et al., Serotype-Specific Inactivation of the Cellular DNA Damage Response during Adenovirus Infection, Journal of Virology 85(5) ,2011 ,2201-2211.
Frentzen, et al., Anti-VEGF single-chain antibody GLAF-1 encoded by oncolytic vaccinia virus significantly enhances antitumor therapy, Proc Natl Acad Sci U S A. 106(31) ,2009 ,12915-12920.
Hermiston, et al., Gene delivery from replication-selective viruses: arming guided missiles in the war against cancer, J Clin Invest. 105(9) ,2000 ,1169-1172.
Ibrahimi, et al., Highly efficient multicistronic lentiviral vectors with peptide 2A sequences, Hum Gene Ther. 20(8) ,2009 ,845-860.
Jiang, et al., The Controlled Transgene Expression in Oncolytic Adenoviral Vectors with Major Late Promoter for Therapy of Cancer, Molecular Therapy 13(Supplement 1) ,2006 ,S251.
Kangasniemi, et al., Improving oncolytic adenoviral therapies for gastrointestinal cancers and tumor initiating cells, Academic Dissertation Molecular Cancer Biology Program & Transplantation Laboratory & HUSLAB & Haartman Institute & Finnish Institute for Molecular Medicine, University of Helsinki and Helsinki University Central Hospital ,2010 ,1-70.
Kuhn, et al., Directed evolution generates a novel oncolytic virus for the treatment of colon cancer, PLoS One. 3(6) ,2008 ,e2409.
Liao, et al., Stable expression of chimeric anti-CD3 receptors on mammalian cells for stimulation of antitumor immunity, CancerGene Therapy 10 ,2003 ,779-790.
Paul, et al., Tumor gene therapy by MVA-mediated expression of T-cell—stimulating antibodies, Cancer Gene Therapy 9 ,2002 ,470-477.
Raum, et al., Abstract 2434: Novel primate-crossreactive BiTE antibodies that eliminate cancer cells expressing cMet, IGFR-1, FAP-alpha, PSCA, Endosialin, CAIX or Her2/neu, AACR 101st Annual Meeting 2010—Apr. 17-21, 2010; Washington, DC , 2010 ,Abstract Only.
Yang, et al., Anti-CD3 scFv-B7.1 fusion protein expressed on the surface of HeLa cells provokes potent T-lymphocyte activation and cytotoxicity, Biochem Cell Biol. 85(2) ,2007 ,196-202.
Holterman, et al., Novel replication-incompetent vector derived from adenovirus type 11 (Ad11) for vaccination and gene therapy: low seroprevalence and non-cross-reactivity with Ad5, J Virol. 78(23) ,2004 ,13207-13215.
Stone, et al., The complete nucleotide sequence, genome organization, and origin of human adenovirus type 11, Virology. 309(1) ,2003 ,152-165.
Hoffmann, et al., Efficient generation of double heterologous promoter controlled oncolytic adenovirus vectors by a single homologous recombination step in *Escherichia coli*, BMC Biotechnol. 6 ,Aug. 2006 ,36.
Janssen, et al., Development of an AdEasy-based system to produce first- and second-generation adenoviral vectors with tropism for CAR- or CD46-positive cells, J Gene Med. 15(1) ,Jan. 2013 ,1-11.

* cited by examiner

METHOD OF MAKING ADENOVIRUS AND CORRESPONDING PLASMIDS

CROSS REFERENCE TO RELATED APPLICATIONS

The present invention is filed under 35 U.S.C. § 371 as the U.S. national phase of International Application No. PCT/EP2014/079162, filed Dec. 23, 2014, which designated the U.S. and claims the benefit of priority to United Kingdom Patent Application No. GB 1322851.5 filed Dec. 23, 2013, and to PCT Application No. PCT/EP2014/072919 filed Oct. 24, 2014, each of which is hereby incorporated by reference in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on May 4, 2018, is named 370908-3012US1 (00044)_SequenceListing.txt and is 469 kilobytes in size.

The present disclosure relates to a method of making an adenovirus plasmid comprising a part or all of an adenovirus genome and one or more original restriction sites allowing rapid and flexible manipulation of the adenovirus genome, and methods of preparing adenovirus constructs, for example comprising a transgene. The disclosure also extends to novel intermediates employed in and generated by the method, to plasmids and shuttle vectors of the method and to adenoviruses or adenoviral vectors obtainable from the plasmid and/or method. The disclosure further relates to use of the viruses or vectors, for example obtained from a method disclosed herein, in therapy, such as use in the treatment of cancer.

BACKGROUND

It is desirable to insert transgenes into adenoviruses for many reasons, for example, to arm therapeutic viruses to increase therapeutic impact or to deliver genes to target cells using a replication competent virus or a replication deficient viral vector.

Typically, to insert a transgene into a virus genome, a plasmid is generated comprising the adenoviral genome, the transgene is then inserted into the plasmid, for example employing homologous recombination and then the viral genome is excised from the plasmid. However, for reasons described herein, flexible plasmids that can be used for both replication competent viruses and replication deficient viral vectors and, for example which can accept large transgenes in a known and predictable location are not always readily available, especially if the transgene is to be inserted in an unusual location, such as outside the E1 or E3 region.

The problems associated with inserting transgenes into adenoviruses for therapeutic and diagnostic purposes fall into 3 main categories. Firstly, not all adenoviruses are ideal candidates for therapeutic and diagnostic applications, for example, Ad5 (a subgroup C adenovirus) immunity is prevalent in the human population and consequently the virus is rapidly cleared by the immune system after it is administered. To overcome this problem, adenoviruses to which there is less prevalent immunity have been utilised. However, much of the genomic work to date has been on Ad5. Therefore, the materials and resources for alternative adenoviruses are often not available.

Secondly, not all adenoviruses can accept large transgenes and maintain their stability as a viable viruses. Furthermore, the adenovirus genome is large and there is little room to insert additional genetic material without affecting a function of the virus, for example the function of packaging the virus into the viral capsid may be adversely affected, which in turn is likely to impact the infectivity of the virus.

To overcome this problem deletions have been made to the genome. This strategy is particularly suitable for replication deficient viral vectors because one or more genes are removed which are essential to replication. This both limits the vector's ability to replicate in vivo and creates space in the genome thereby allowing insertion of large transgenes. These transgenes can be expressed in vivo, regardless of the viral vector's inability to replicate. Most frequently the E1 gene has been deleted. Prior art systems, such as the ADEASY system (Agilent Technologies), allow insertion of transgenes to the E1 region. In some instances part, or all, of the E3 region is deleted, see for example WO2011/0123564 and the gene may be inserted in the region deleted.

Thus typically the transgene is inserted in the same position that the deletion occurred. Thus, the site of transgene insertion has largely been limited to the location of early genes which can be problematic because it is more likely to affect virus gene expression, virus life-cycle and/or speed of replication. In particular, deleting the E1 region is not appropriate for the replication competent adenoviruses and as discussed it may be useful to insert a transgene such that it is not in a location of an early gene to ensure that the impact on the virus life-cycle is minimised.

Thirdly, the adenovirus genome is not easy to manipulate because the genome is densely packed and has very little intergenic material where a transgene might be safely inserted without affecting the virus life-cycle and/or a function, such as transcription. Furthermore, there are few, if any, restriction sites in the intergenic regions and even fewer that only occur once in the genome. The latter is relevant because when a restriction site occurs more than once in the virus genome then the ability to selectively insert a transgene in one location employing that restriction site is severely impeded.

Therefore it is desirable to provide a plasmid that can be used to manipulate a replication competent virus and wherein transgenes may be inserted in a location removed from the early genes.

One strategy that can be utilised with replication competent viruses is to employ a non-biasedly inserting transposon to insert the transgene into the genome (as described in Jin et al 2004). The transposon may be inserted in the late genes and thus this technology does not suffer from the disadvantages of the systems described above. Jin et al hypothesised that the site of location of insertion of the gene is influenced by the type the gene being inserted and, whilst it was possible to replace some of the genes after insertion, in some instances this was difficult to replace the inserted gene or the replacement gene was inserted in a different orientation. The random nature of transposon insertion provides many possible insertion sites. Therefore, predictability and reproducibility of insertion may be compromised as a result. Furthermore the transposon inserts itself into the genome along with the transgene and in theory could "move" the location of the gene in the virus genome at a later date. However, whilst the randomly inserting transposon is a wonderful tool for investigating the virus genome the biggest disadvantage of this approach is that it does not allow rational design of the virus construct.

Therefore, it is desirable to provide a plasmid that can be used to manipulate a replication competent virus and in which transgenes can reproducibly be inserted in a location removed from the early genes. The present inventors set out to overcome one or more of the problems described above by generating a plasmid with a combination of restriction sites that can be used to selectively insert a transgene specifically into a location that this not the site of an early gene.

The present inventors have developed adenovirus plasmids comprising original restriction sites in the vicinity of the L5 gene. The plasmids of the present disclosure allow generation of viruses with restriction sites/transgenes in locations other than the early gene sites, for example for replication competent adenoviruses with the E1 region intact or replication deficient adenoviruses, such as with E1 and/or E3 deleted or interrupted.

SUMMARY OF INVENTION

In one aspect there is provided a method of preparing a shuttle vector comprising a selection marker gene and a low copy bacterial replication of origin, said adenovirus genome comprising a 5' ITR, a 3' ITR, an L5 gene said method comprising the steps:

a) preparing an adenovirus shuttle vector comprising ligating equal proportions the following three fragments:
   i) a vector fragment comprising a selection marker gene and a low copy bacterial replication of origin, wherein the 5' end of the vector fragment starts with a first restriction enzyme site and terminates at the 3' end of the vector fragment in a second restriction enzyme site,
   ii) a 5'-arm comprising the 5' end of the adenovirus genome including the 5' ITR, wherein the 5' end of the 5' arm starts with a second restriction enzyme site and terminates at the 3' end of the 5' arm with a third restriction enzyme site,
   iii) a 3'-arm comprising the 3' end of the adenovirus genome including the 3' ITR and the L5 gene, wherein the 5' end of the 3' arm starts with a third restriction enzyme site and terminates at the 3' end of the 3' arm with a first restriction enzyme site, and performing a one-step three-way ligation to join:

the 3' end of the 3' arm (fragment iii) to the 5' end of the vector fragment (fragment i) at the first restriction enzyme site, the 3' end of the vector fragment (fragment i) to the 5' end of the 5' arm (fragment ii) at the second restriction enzyme site, and the 3' end of the 5' arm (fragment ii) to the 5' end of the 3' arm (fragment iii) at the third restriction enzyme site at least the L5 gene, to form a circularised shuttle vector arranged as a first restriction enzyme site followed by a vector fragment followed by a second restriction enzyme site followed by a 5' arm, followed by a third restriction enzyme site followed by a 3' arm, b) introducing at least one original restriction site and/or transgene into the shuttle vector in a location between the L5 gene and a site selected from the group comprising (or consisting of) an E3 site, an E4 site or both said sites.

In one embodiment the method comprises a further step c):

c) performing homologous recombination between the shuttle vector of step a) or step b) and the adenovirus genome to form a plasmid.

In one aspect there is provided a method of preparing an adenovirus plasmid comprising an adenovirus genome, a selection marker gene and a low copy bacterial replication of origin, said adenovirus genome comprising a 5' ITR, a 3' ITR, an L5 gene, an E3 site and an E4 site, said method comprising the steps:

a) preparing an adenovirus shuttle vector comprising ligating equal proportions the following three fragments:
   i) a vector fragment comprising a selection marker gene and a low copy bacterial replication of origin, wherein the 5' end of the vector fragment starts with a first restriction enzyme site and terminates at the 3' end of the vector fragment in a second restriction enzyme site,
   ii) a 5'-arm comprising the 5' end of the adenovirus genome including the 5' ITR, wherein the 5' end of the 5' arm starts with a second restriction enzyme site and terminates at the 3' end of the 5' arm with a third restriction enzyme site,
   iii) a 3'-arm comprising the 3' end of the adenovirus genome including the 3' ITR and the L5 gene, wherein the 5' end of the 3' arm starts with a third restriction enzyme site and terminates at the 3' end of the 3' arm with a first restriction enzyme site, and performing a one-step three-way ligation to join:

the 3' end of the 3' arm (fragment iii) to the 5' end of the vector fragment (fragment i) at the first restriction enzyme site, the 3' end of the vector fragment (fragment i) to the 5' end of the 5' arm (fragment ii) at the second restriction enzyme site, and the 3' end of the 5' arm (fragment ii) to the 5' end of the 3' arm (fragment iii) at the third restriction enzyme site to form a circularised shuttle vector arranged as a first restriction enzyme site followed by a vector fragment followed by a second restriction enzyme site followed by a 5' arm, followed by a third restriction enzyme site followed by a 3' arm, b) introducing at least one original restriction site into the shuttle vector in a location between the L5 gene and a site selected from the group comprising (consisting of) the E3 site, the E4 site and both said sites, and c) performing homologous recombination between the shuttle vector of step a) or step b) and the adenovirus genome to form a plasmid.

In one embodiment step b) is preformed prior to step a).

In one embodiment step b) is performed after step a).

In one embodiment the 5' arm comprises about 2.4 to 4.7 kb of the 5' end of an adenovirus genome.

In one embodiment the 3' arm comprises about 3.3 to 4.8 kb of the 3' end of an adenovirus genome.

In one embodiment the period over which the one-step three-way ligation performed is at least 50 minutes, for example 1 hour or more, such as 2, 3, 4, 5, 6, 7, 8, 9, 10, 11, 12, 13, 14, 15, 16, 17, 18, 19, 20, 21, 22, 23 or 24 hours.

In one embodiment the one-step three-way ligation is performed in a temperature range of about 10 to 40° C., for example 20 to 25° C., such as at approximately room/ambient temperature.

In one embodiment the adenovirus is a human adenovirus, for example a type B subgroup, such as a virus selected from EnAd, OvAd1, OvAd2, Ad3, Ad5 (which is a group C virus)

and Ad11. In one embodiment the adenovirus is not Ad5. In one embodiment the adenovirus is not a group A virus. In one embodiment the adenovirus is not a group C virus.

In one embodiment the adenovirus is replication capable or competent, such as replication competent.

In one embodiment the adenovirus is not a conditionally replicating virus. In one embodiment the adenovirus is replication deficient.

In one embodiment an original restriction site is independently selected from FseI, NotI, SbfI and SgfI, such as NotI or SbfI and SgfI or FseI and NotI and SbfI and SgfI.

In one embodiment the first restriction site in the vector fragment and the first restriction site in the 3'-arm are the same. In one embodiment the second restriction site in the vector fragment and the second restriction site in the 5'-arm are the same. In one embodiment the third restriction site in the 5'-arm and the third restriction site in the 3'-arm are the same.

In one embodiment the first and second restriction sites are the same.

In one embodiment the vector fragment is dephosphorylated prior to ligation.

In one embodiment the origin of replication is p15A.

In one embodiment the selection marker gene is KanR or AmpR, such as KanR.

In one embodiment step c) is performed at a ratio of 3.5 parts:1.5 parts, shuttle vector of step a) or b) to adenovirus genome respectively, for example in electrocompetent BJ5183 cells.

In one embodiment the method comprises the further step of inserting at least one transgene, for example in a location other than the location of an early gene, such as associated with the fibre L5. In one embodiment the transgene is in the form of cassette, for example that comprises a splice acceptor sequence.

In one embodiment the transgene is under the control of an endogenous adenovirus promoter, for example the major late promoter. In one embodiment a gene or genes placed after L5 are under the control of the major late promoter or under the E4 promoter. In one embodiment a gene or genes placed before L5 are under the control of the major late promoter or the E3 promoter. Genes placed directly before L5 start codon can be under the control of the major late promoter and will generally need to contain a regulatory element that allows the expression of L5.

In one embodiment a gene or genes placed after L5 are under the control of an exogenous promoter.

In one embodiment the method further comprises the step of excising the adenovirus genome from the plasmid and forming a virus or viral vector.

Thus the method of the present disclosure provides plasmids of the present disclosure and intermediates such as the shuttle vector.

In embodiment the method comprises a further step of preparing a pharmaceutical formulation of the virus or viral vector.

In one embodiment the method comprises a further step of administering a virus or viral vector or a pharmaceutical composition according to the present disclosure to a patient in need thereof.

In one embodiment there is provided an adenovirus plasmid comprising:

a) an adenovirus genome comprising an L5 gene, an E3 site and an E4 site,
b) at least one original restriction site in a location between the L5 gene and a site selected from the group consisting of the E3 site, the E4 site and each of the E3 and E4 sites,
c) a low copy bacterial origin of replication, and
d) a selection marker gene.

In one embodiment the plasmid further comprises a transgene, for example in the form of a transgene cassette.

In one embodiment the transgene is selected from the group comprising a therapeutic gene of interest which encodes a therapeutic protein, peptide or RNA such as an antibody or antibody domain, pro-drug converting enzyme, immunomodulator, enzyme, siRNA, transcription factor, intracellular signalling or surface membrane protein, antigen; and a reporter gene or imaging agent, such as luciferase or eGFP.

Advantageously the method provides a flexible means of generating novel adenovirus plasmids and the intermediate shuttle vectors wherein the introduction of original restriction sites, for example in step b) permits manipulation of the adenovirus genome outside of the regions regulating early gene expression.

A—The 5' arm PCR amplification product. A ~4.6 kb fragment containing ColoAd1 5' ITR, E1A, E1B and partial E2B genes flanked by 5' AscI and 3' PspOMI restriction sites.

B—The 3' arm PCR amplification product. A ~4.5 kb fragment containing E3, fibre, E4 and 3' ITR of ColoAd1 flanked by 5' PspOMI and 3' AscI restriction sites.

C—The p15A-KanR vector fragment PCR product. A ˜2.9 kb fragment containing 5' and 3' AscI restriction sites.

FIG. 11 shows:

A—PCR products of the 5' arm, 3' arm and p15a KAN vector fragment. Products were 4.6 kb, 4.5 kb and 3 kb respectively B—PCR products of the 5' arm and 3' arm.

Figure 12:
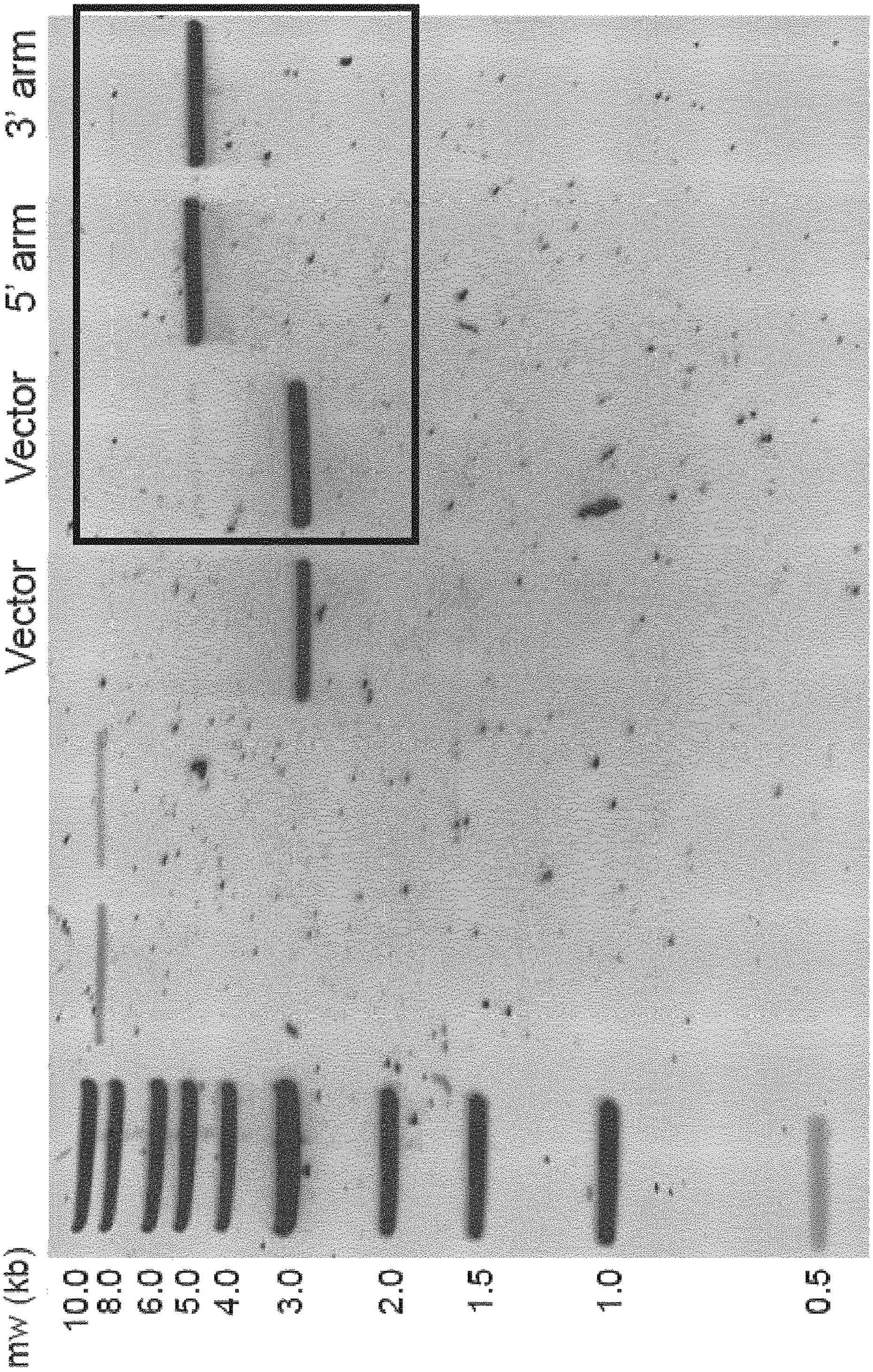

FIG. 12 shows AscI and AscI/PsPOMI digested p15A-Kan vector fragment and 5' and 3' arm. Digest products are highlighted in the black box.

Figure 13:
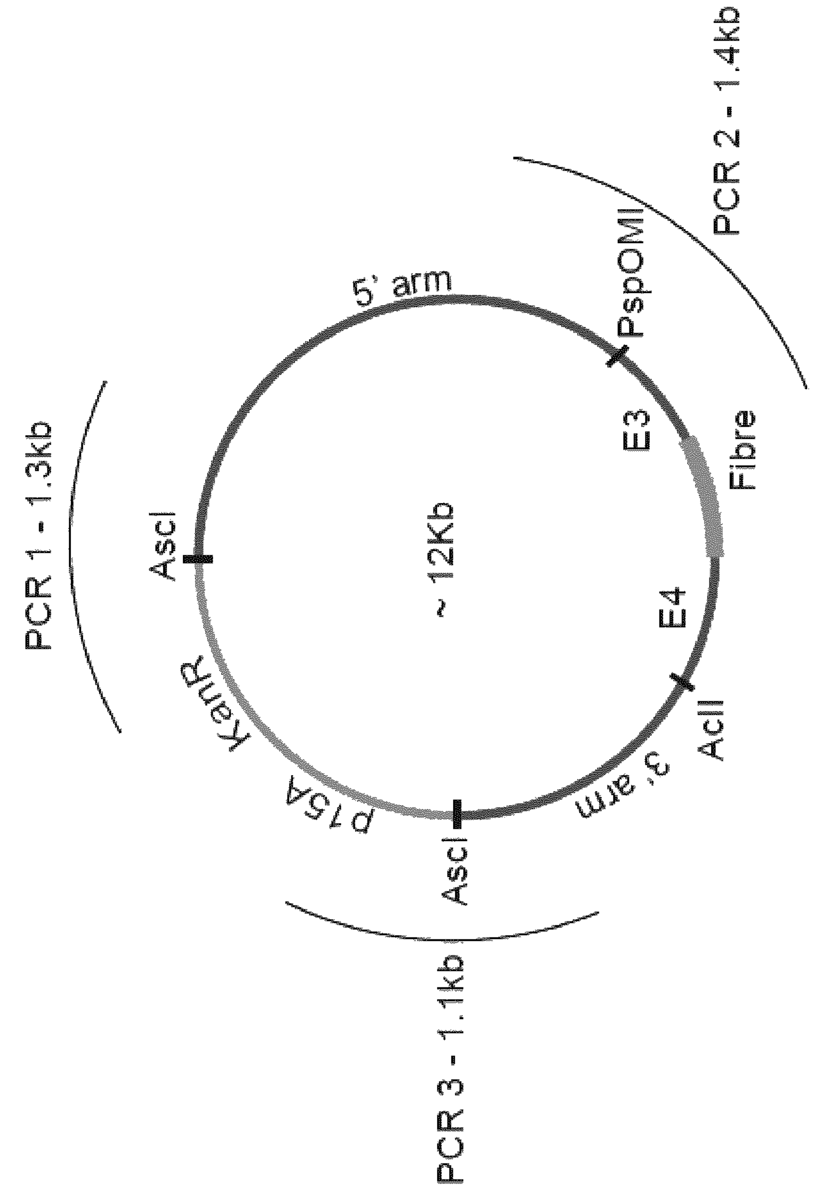

FIG. 13 shows a schematic showing the primer binding regions and products expected for each PCR amplification.

Figure 14:
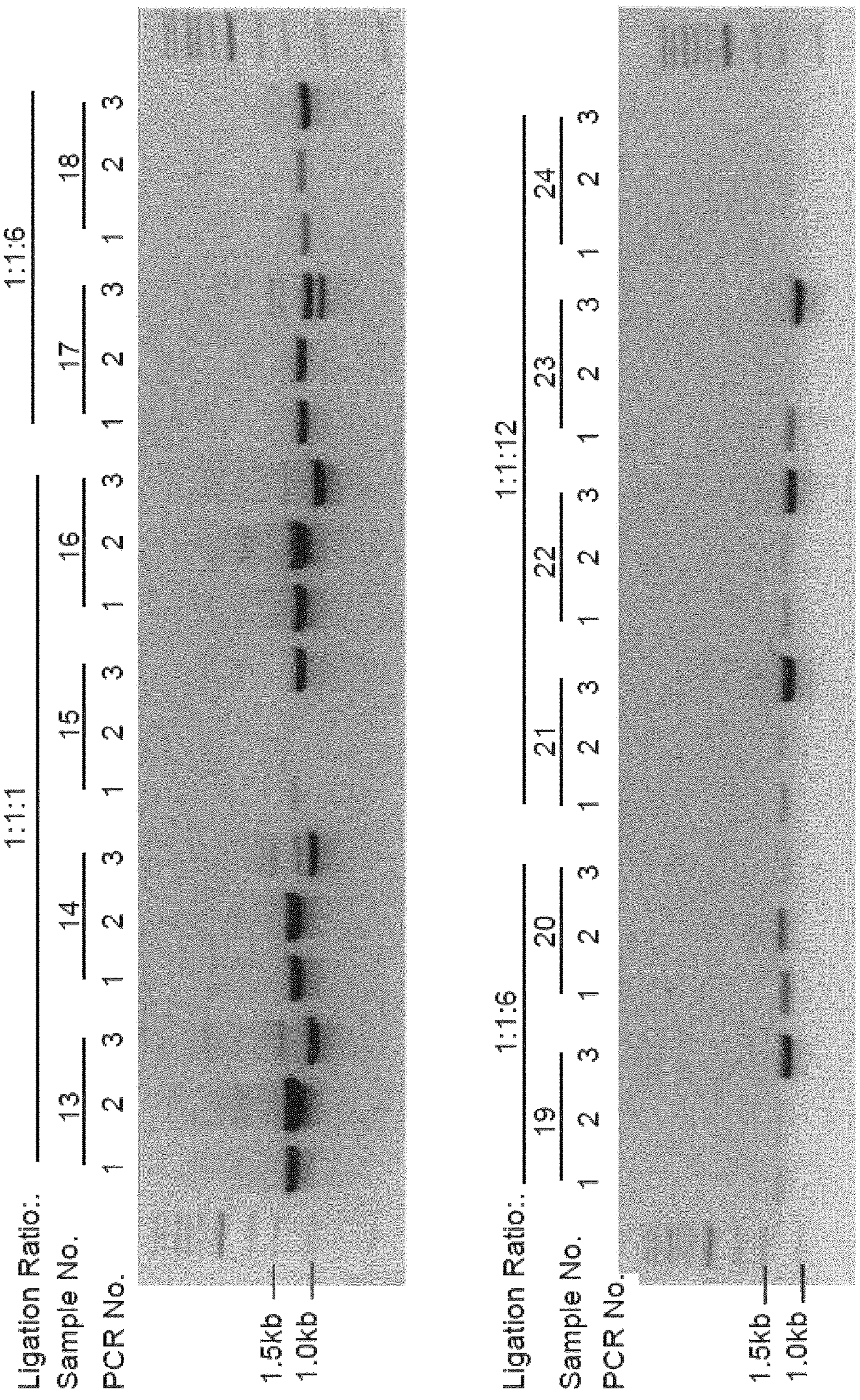

FIG. 14 shows gels showing PCR products from representative screened clones. Constructs 13, 14 and 16 showed correctly sized PCR products. These constructs were produced following three-way ligation reaction at a 1:1:1 (5'arm:3'arm:p15a vector fragment). None of the constructs using the 1:1:6 or 1:1:12 ligation ratios showed the correctly sized PCR products.

Figure 15:
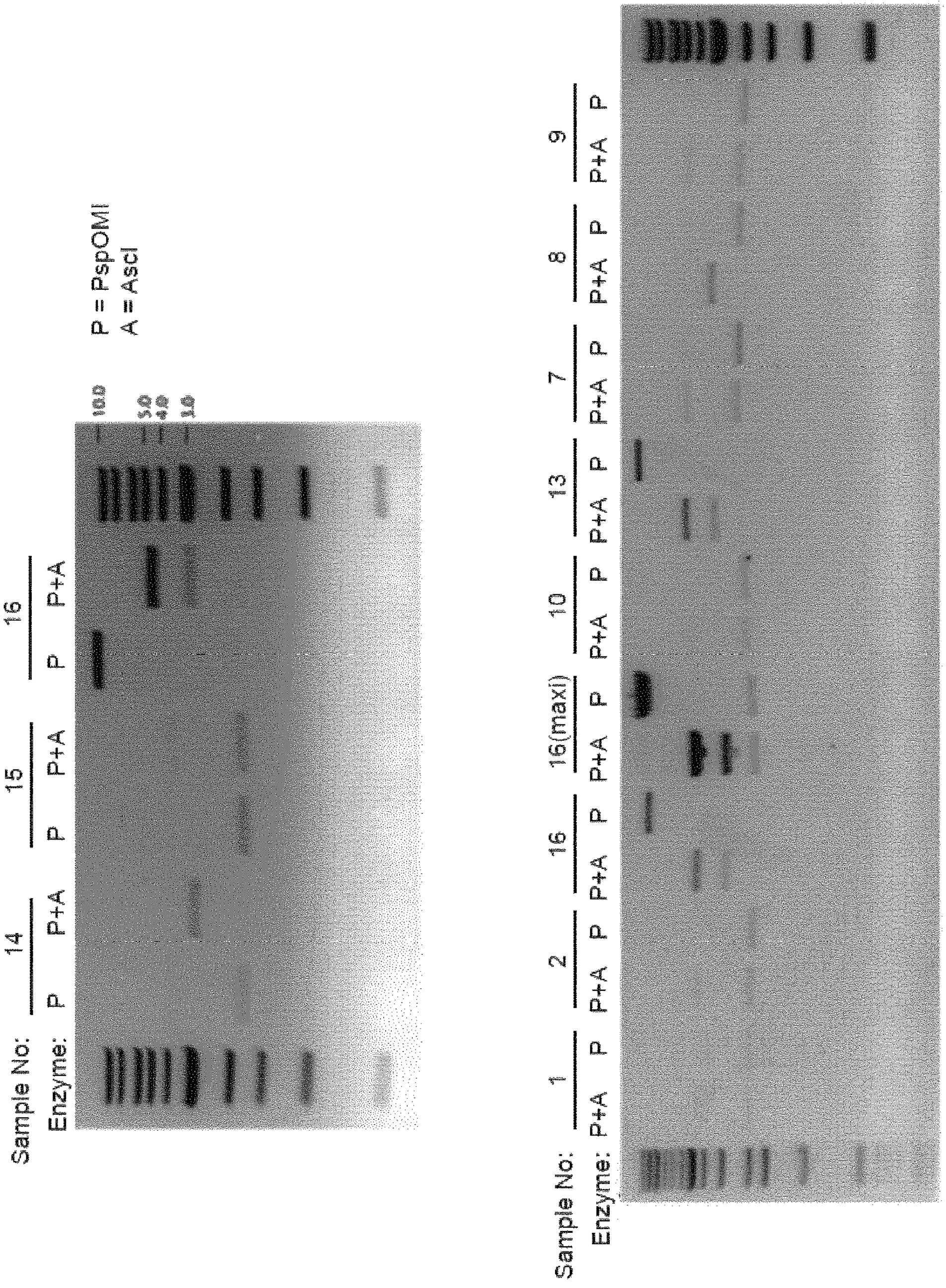

FIG. 15 shows restriction analysis with PspOMI or AscI/PspOMI of selected constructs. Constructs 13 and 16 produced following three-way ligation at a ratio of 1:1:1 showed correctly sized digest products. Sample no. 16 (maxi) corresponds to a digested maxi prep which had been produced from construct 16.

Figure 16:
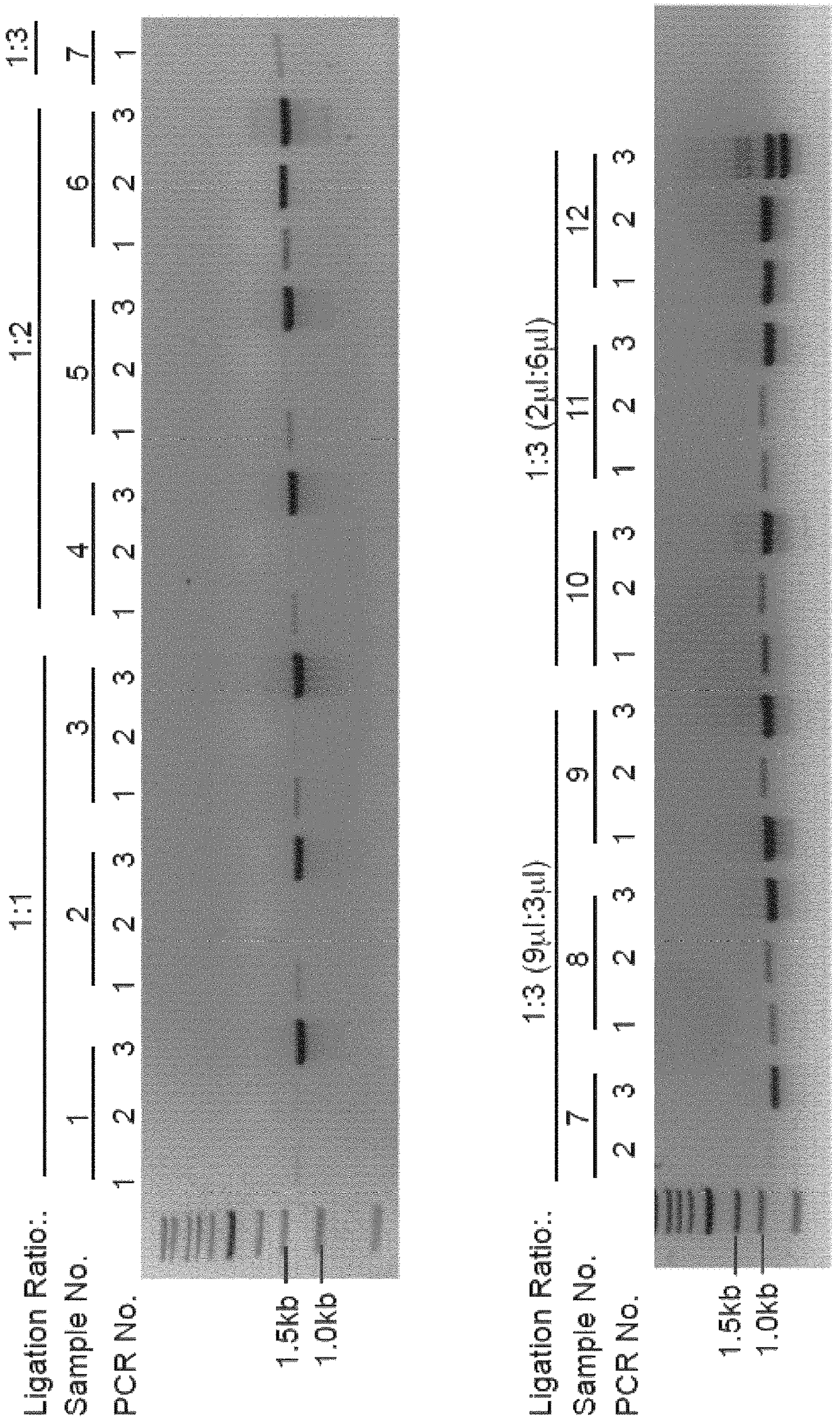

FIG. 16 shows gels showing PCR products from constructs generated using the two-step ligation method to make the ColoAd1 Shuttle vector. None of the constructs screened showed the correct PCR products.

Figure 17:
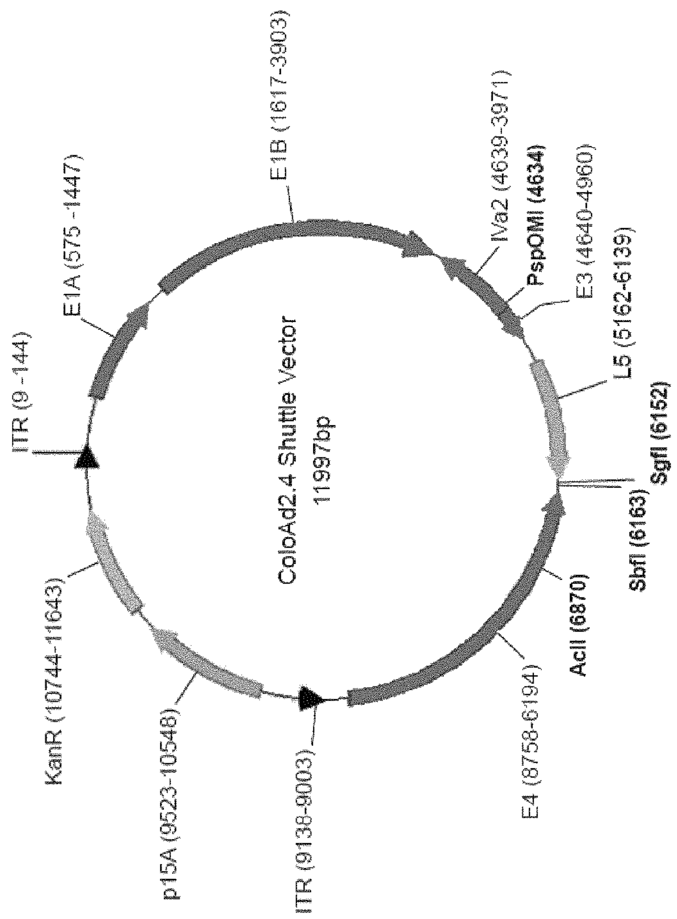

FIG. 17 shows the ColoAd2.4 shuttle vector. The shuttle vector contains SgfI and SbfI original restriction sites downstream of the Fibre gene.

Figure 18:
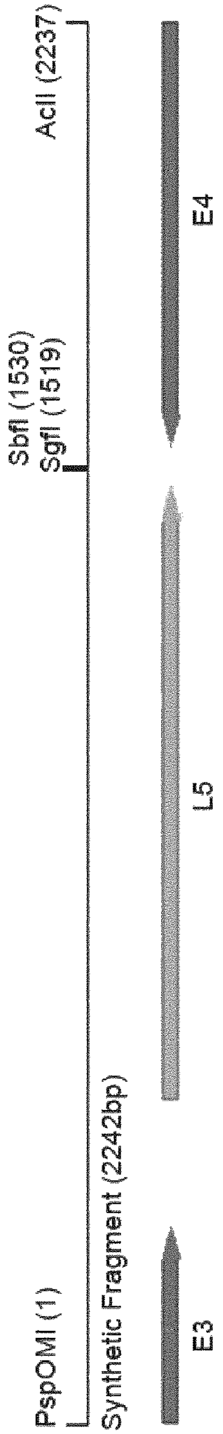

FIG. 18 shows schematic of the ColoAd2.4 synthetic fragment with flanking PsPOMI and AclI restriction sites.

Figure 19:
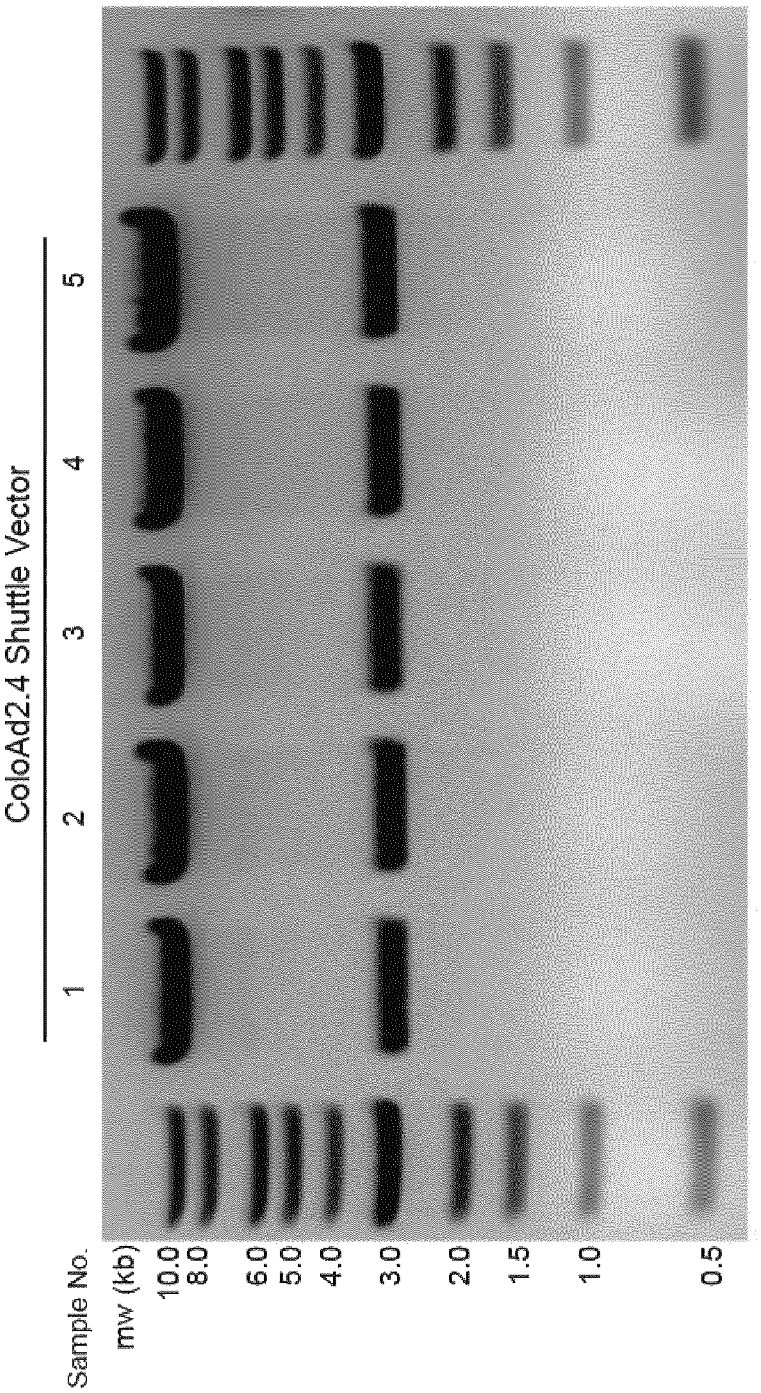
Figure 20:
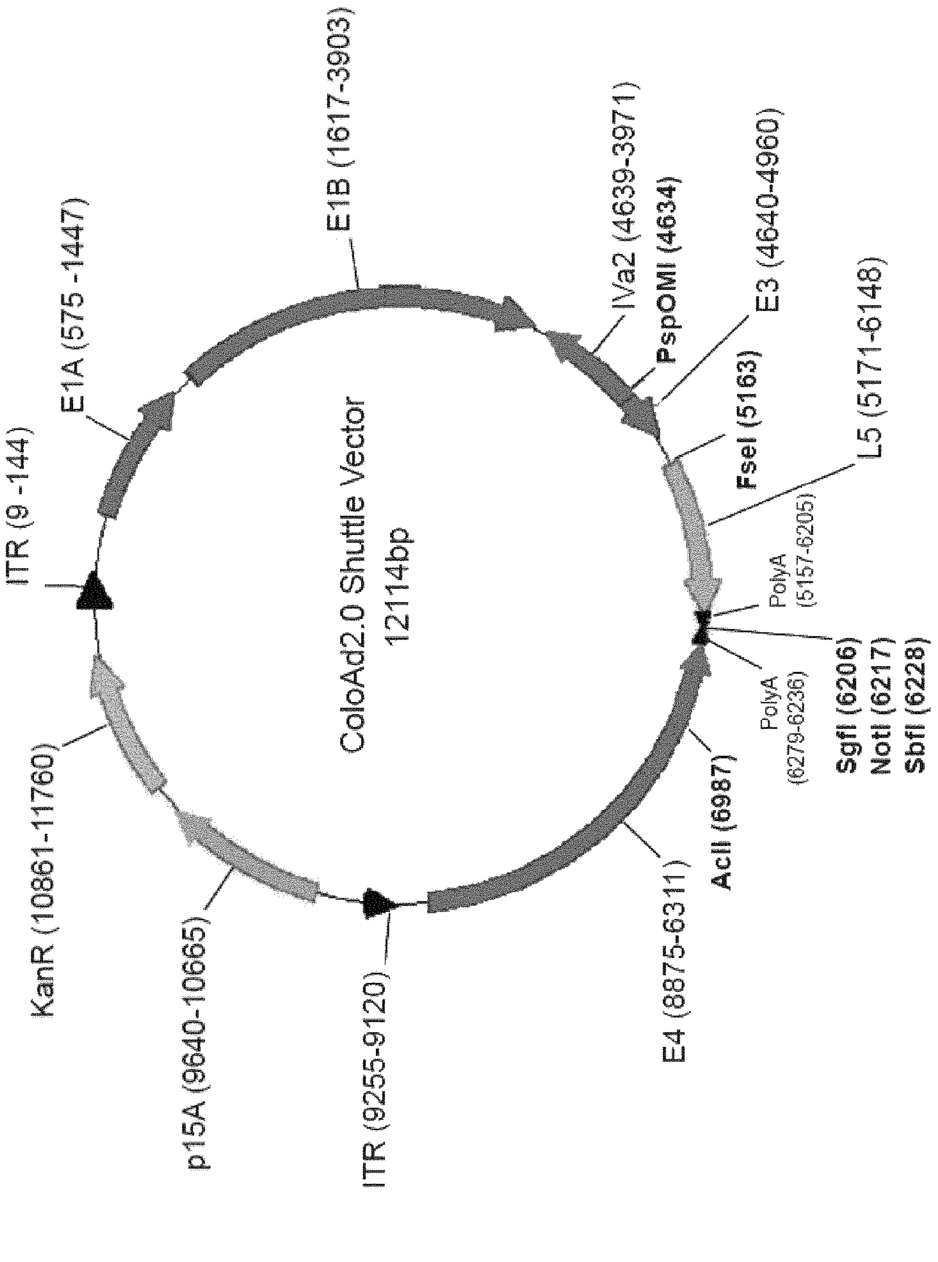

FIG. 19 shows restriction analysis of putative ColoAd2.4 shuttle vector constructs. All 5 constructs showed correctly sized bands corresponding to the ColoAd2.4 shuttle vector; a 3 kb and 9 kb band following EcoRV and SbfI digest FIG. 20 shows the ColoAd2.0 shuttle vector. The shuttle vector contains an original FseI site upstream of the Fibre (L5) gene and 2 polyA sequences and original SgfI, NotI, SbfI sites downstream of the Fibre (L5) gene.

Figure 21:
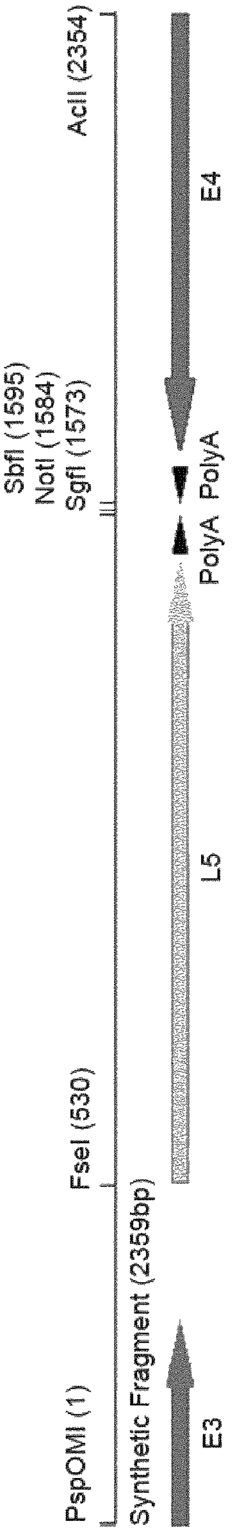
Figure 22:
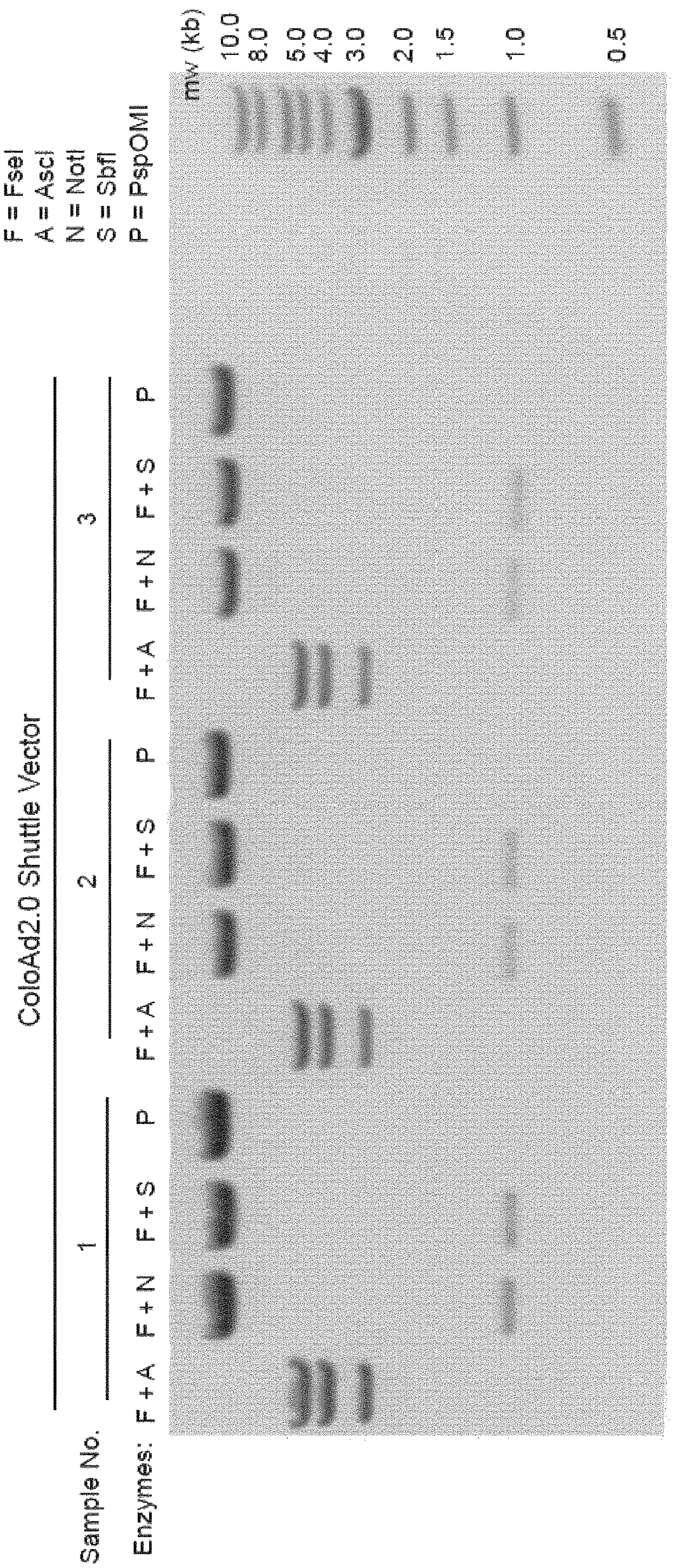
Figure 23:
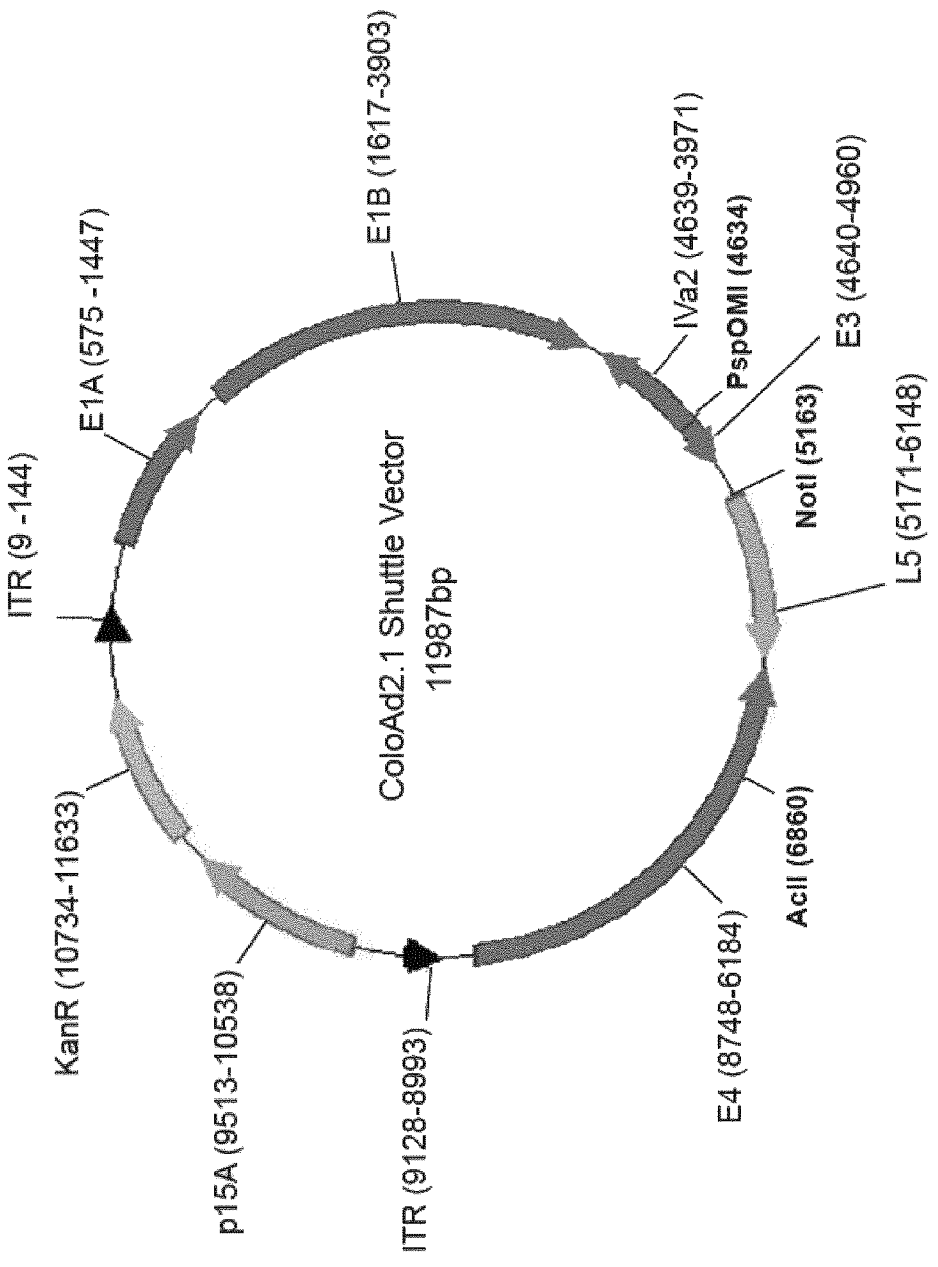

FIG. 21 shows a schematic of the ColoAd2.0 synthetic fragment with flanking PspOMI and AclI restriction sites FIG. 22 shows restriction analysis of putative ColoAd2.0 shuttle vector constructs with the enzymes FseI, AscI, SbfI or PspOMI. All five constructs show the correctly sized bands corresponding to the ColoAd2.0 shuttle vector FIG. 23 shows the ColoAd2.1 shuttle vector. The shuttle vector contains an original NotI site upstream of the Fibre (L5) gene.

Figure 24:
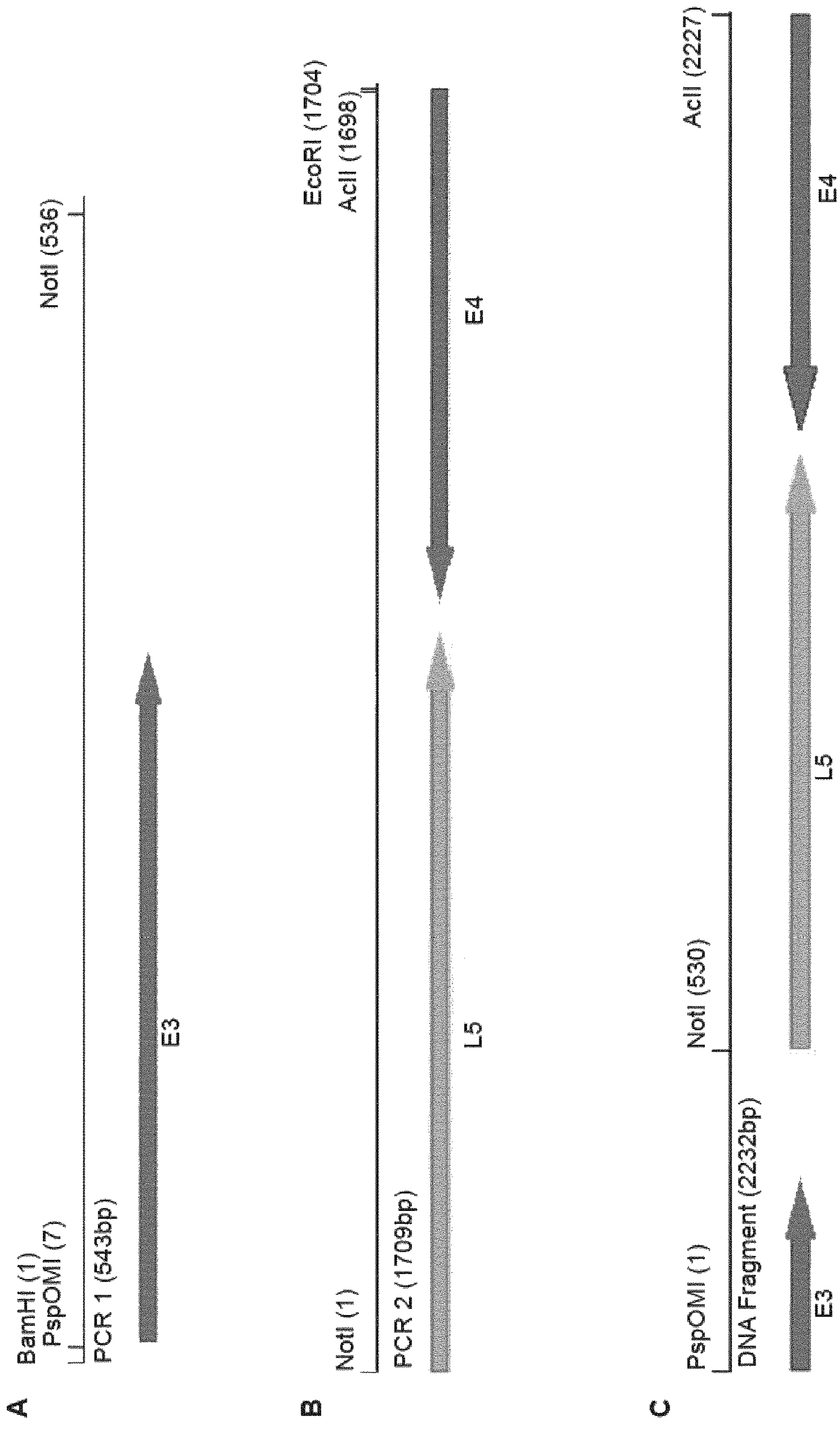
Figure 25:
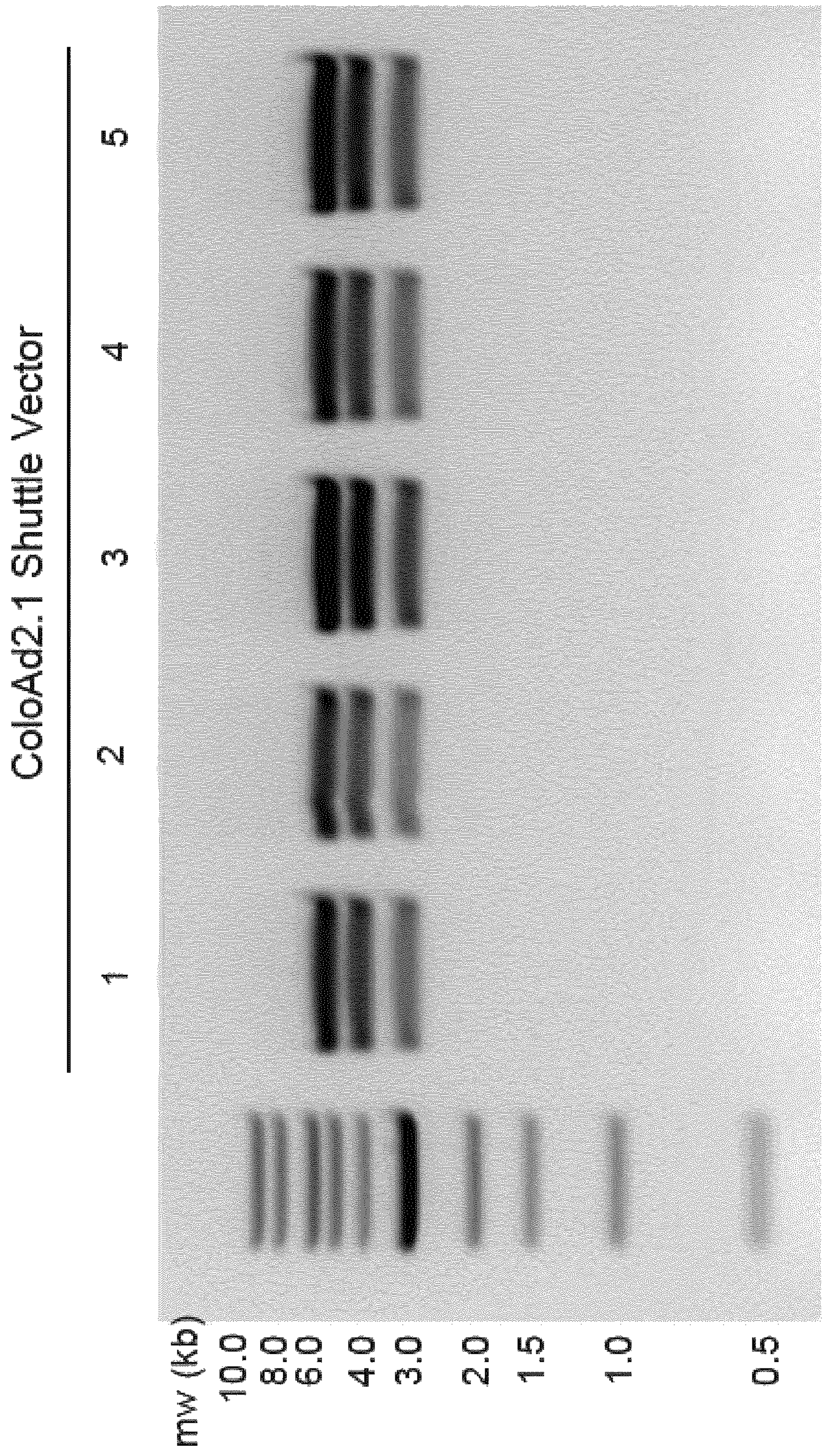

FIG. 24 schematics of the PCR 1 (A) and PCR 2 (B) products used to construct the DNA fragment (C) for insertion into the ColoAd1 shuttle vector to generate the ColoAd2.1 shuttle vector FIG. 25 shows restriction analysis of putative ColoAd2.1 shuttle vector constructs. All 5 constructs showed correctly sized bands corresponding to the ColoAd2.1 shuttle vector; 3 kb, 4 kb and 5 kb bands following AscI and NotI digest.

Figure 26:
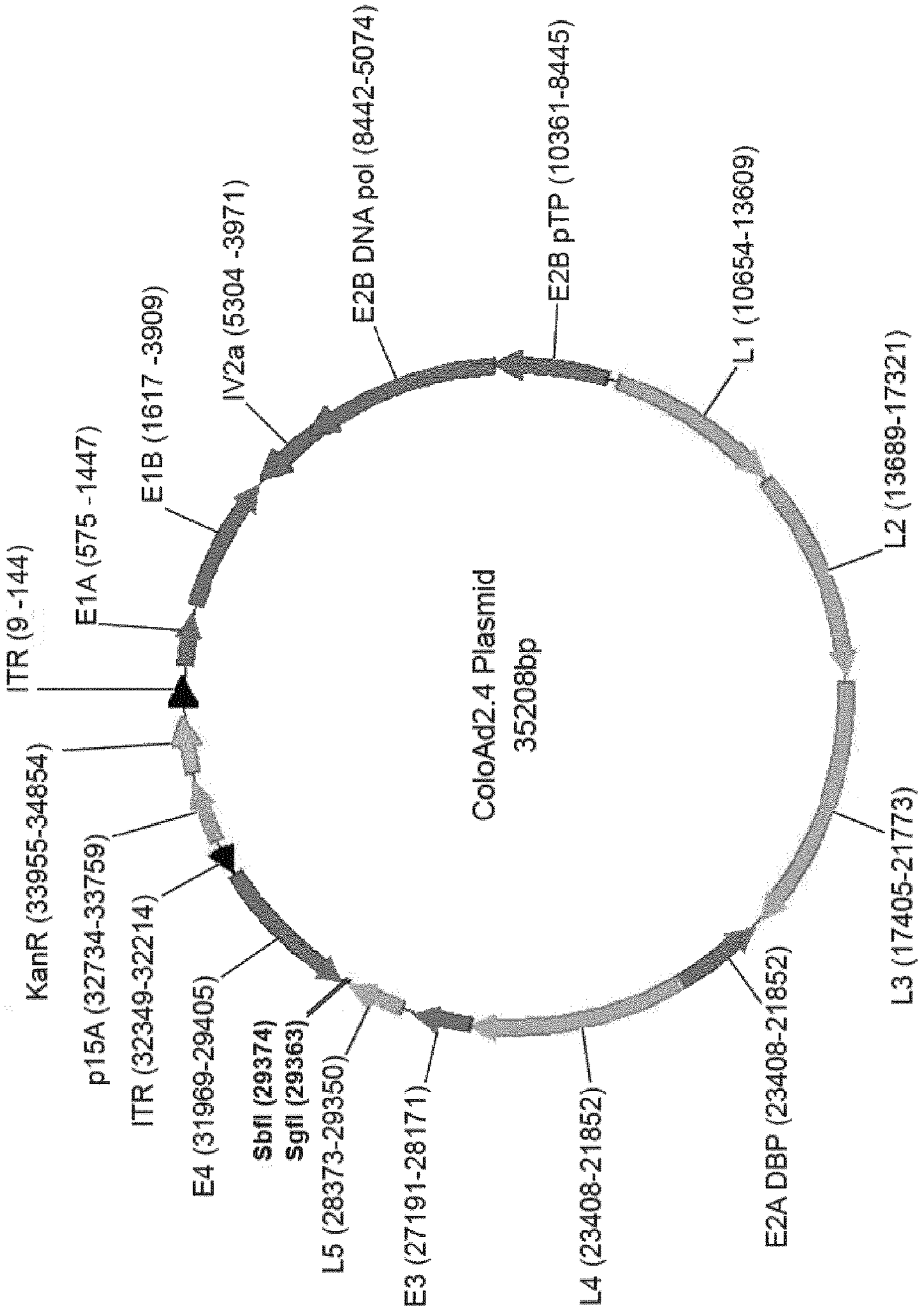

FIG. 26 shows the recombinant ColoAd2.4 plasmid. The recombinant contains a p15A origin of replication, kanamycin resistance and the ColoAd1 genome with original SgfI and SbfI restriction sites downstream of fibre.

FIG. 27 shows:

A—LB+Kanamycin plates spread with electroporated BJ5183 cells. The left plate is the negative control and right plate is the ColoAd1+linearised ColoAd2.4 shuttle vector recombination.

Figure 28:
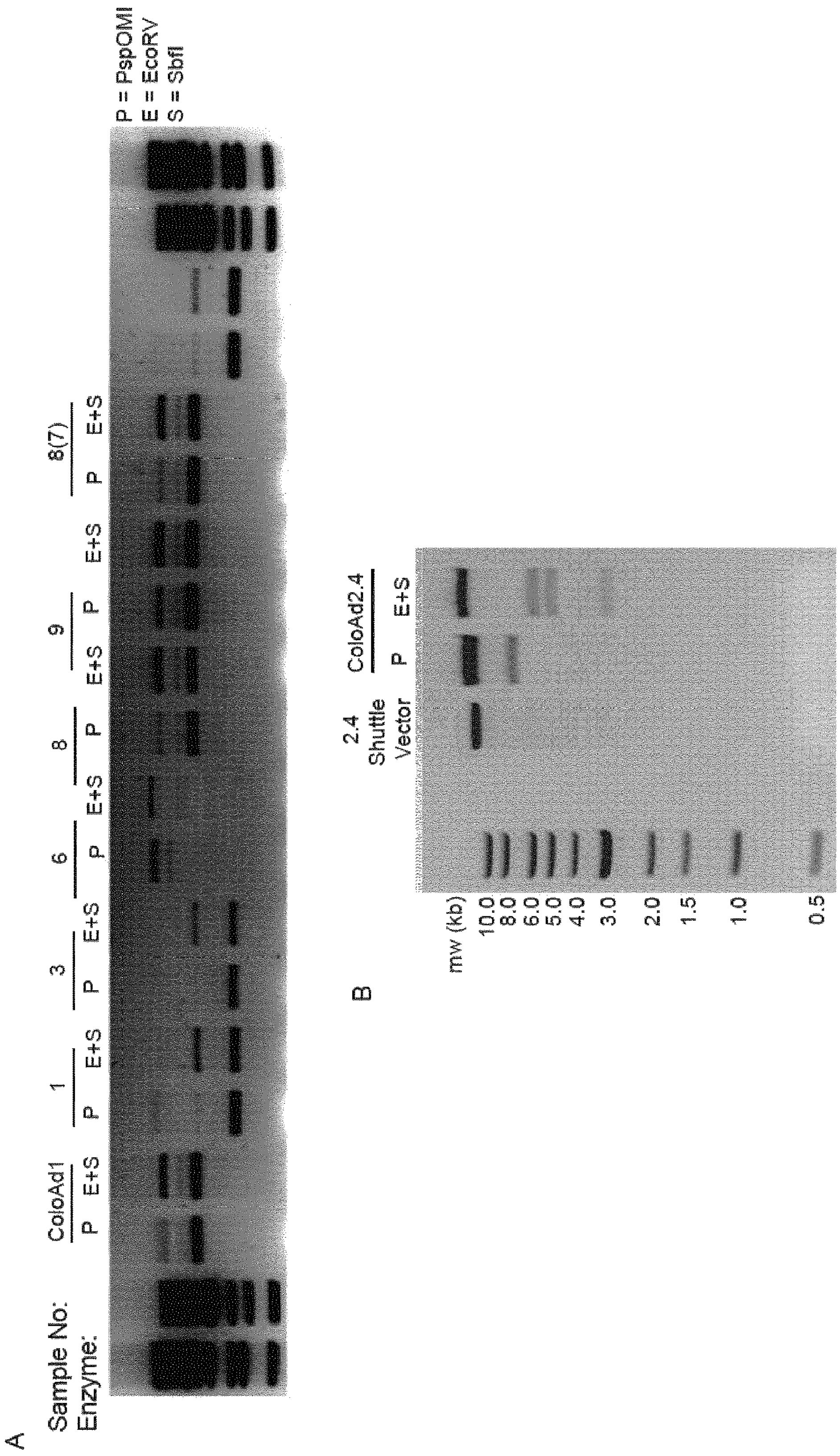

B—Restriction digested ColoAd2.4 recombinants. Candidate recombinants were digested with EcoRV and SbfI (E+S). Recombinants 3, 8 and 10 showed bands of 22 kb, 5.5 kb, 4.7 kb and 2.8 kb indicating a correctly formed recombinant. Recombinants were also digested with PspOMI (P) giving bands of 16 kb, 12 kb and 7 kb FIG. 28 shows restriction Analysis of putative ColoAd2.4 recombinants. Recombinant 4 showed correct sized bands of 16 kb, 12 kb and 7 kb on PspOMI digestion (P) and bands of 22 kb, 4.7 kb, 5.5 kb and 2.8 kb on SbfI and EcoRV digestion (E+S). The digests confirmed the presence of a recombinant ColoAd2.4 in #4 only.

FIG. 29 shows:

A—PCR amplification products following 5'arm-3' arm ligation. PCRs following low volume ligations produced ˜9.1 kb fragments using either 0198 (1) or 0199 (2) primers. PCRs following high volume ligations were not efficient.

B—AscI digested low volume 5' arm-3'arm ligation products (˜9.1 kb, lanes 1 & 2) and AscI digested p15A-Kan vector fragment (˜3 kb, lane 3).

Figure 30:
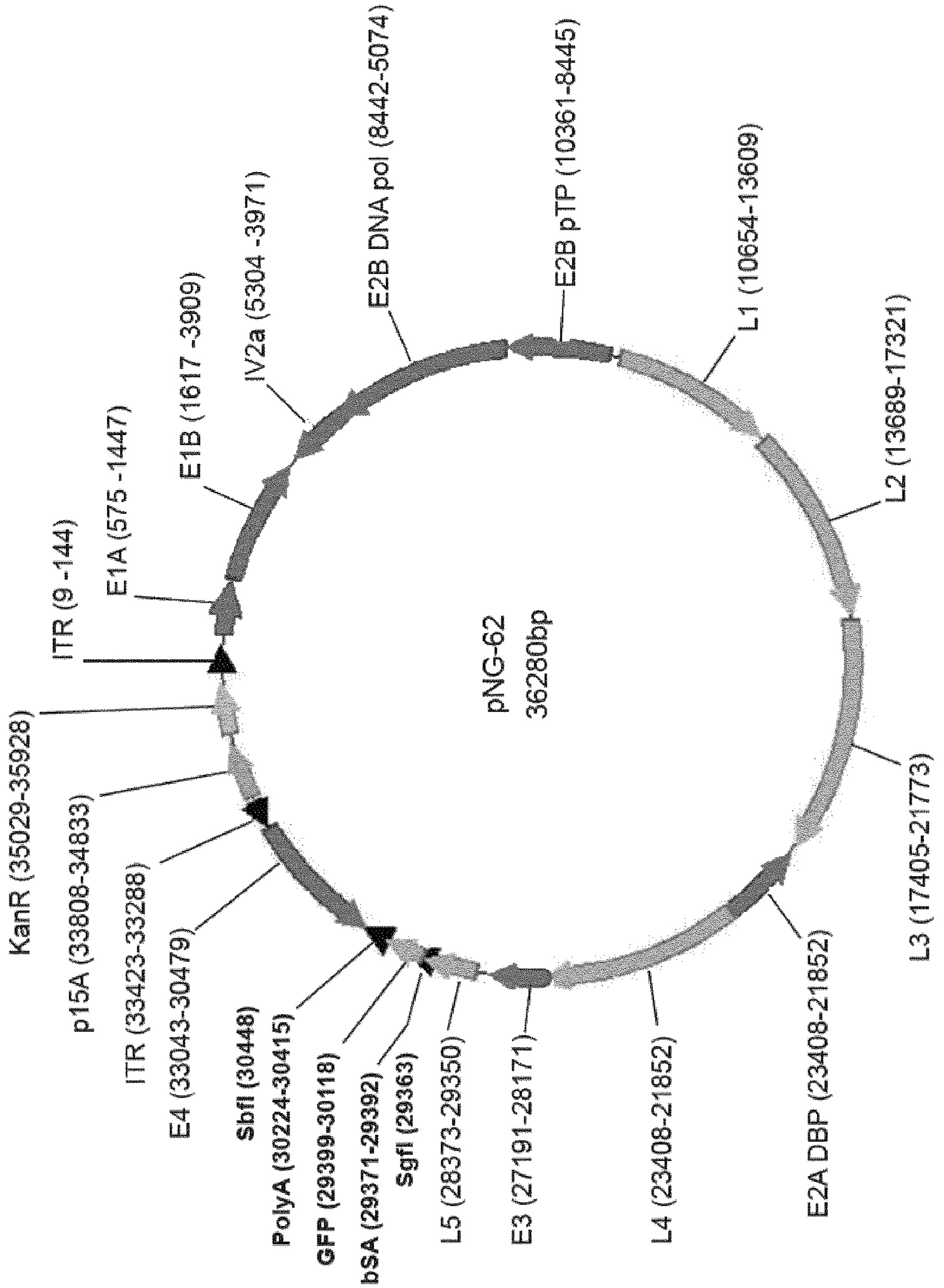
Figure 33:
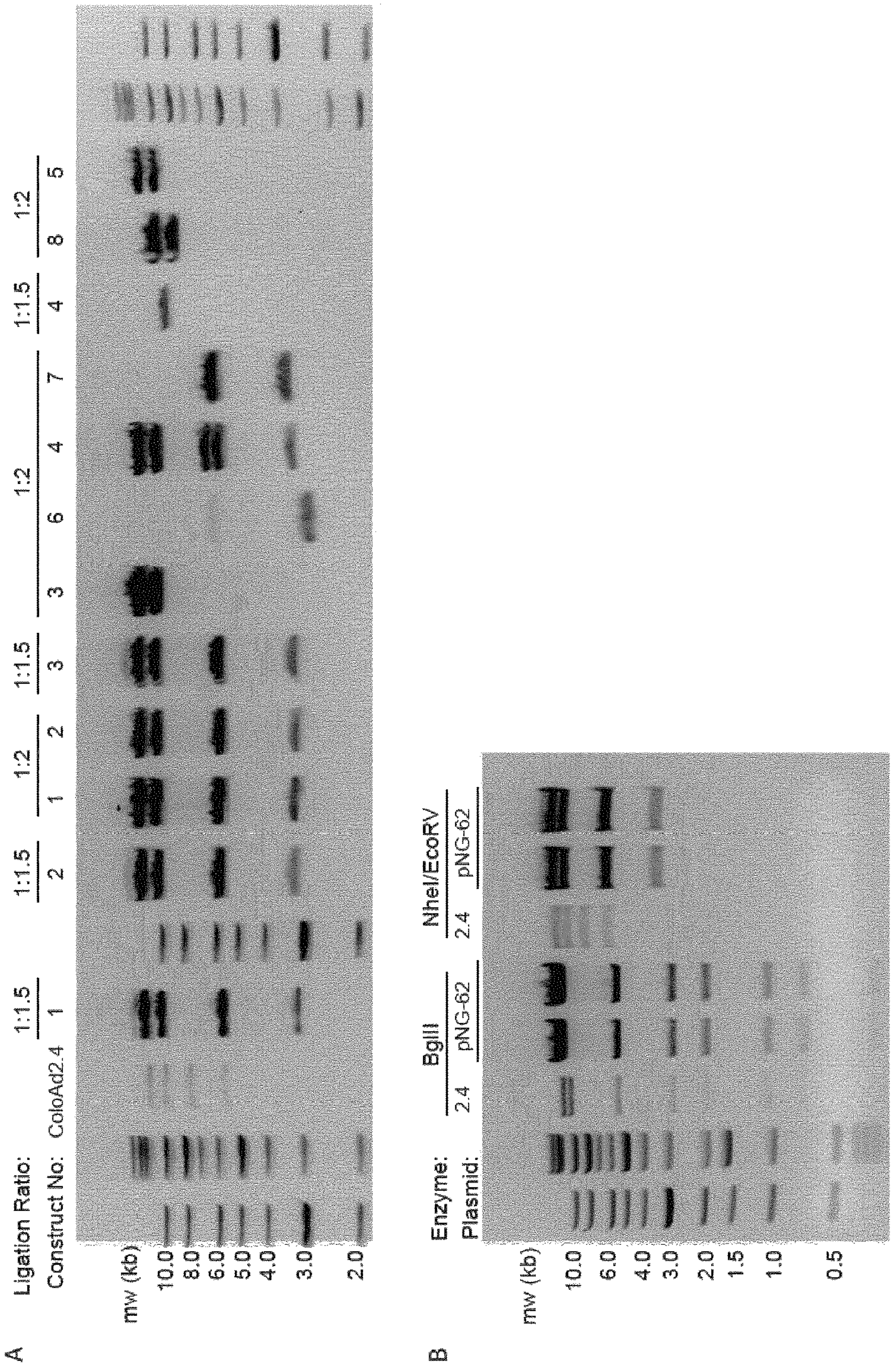
Figure 34:
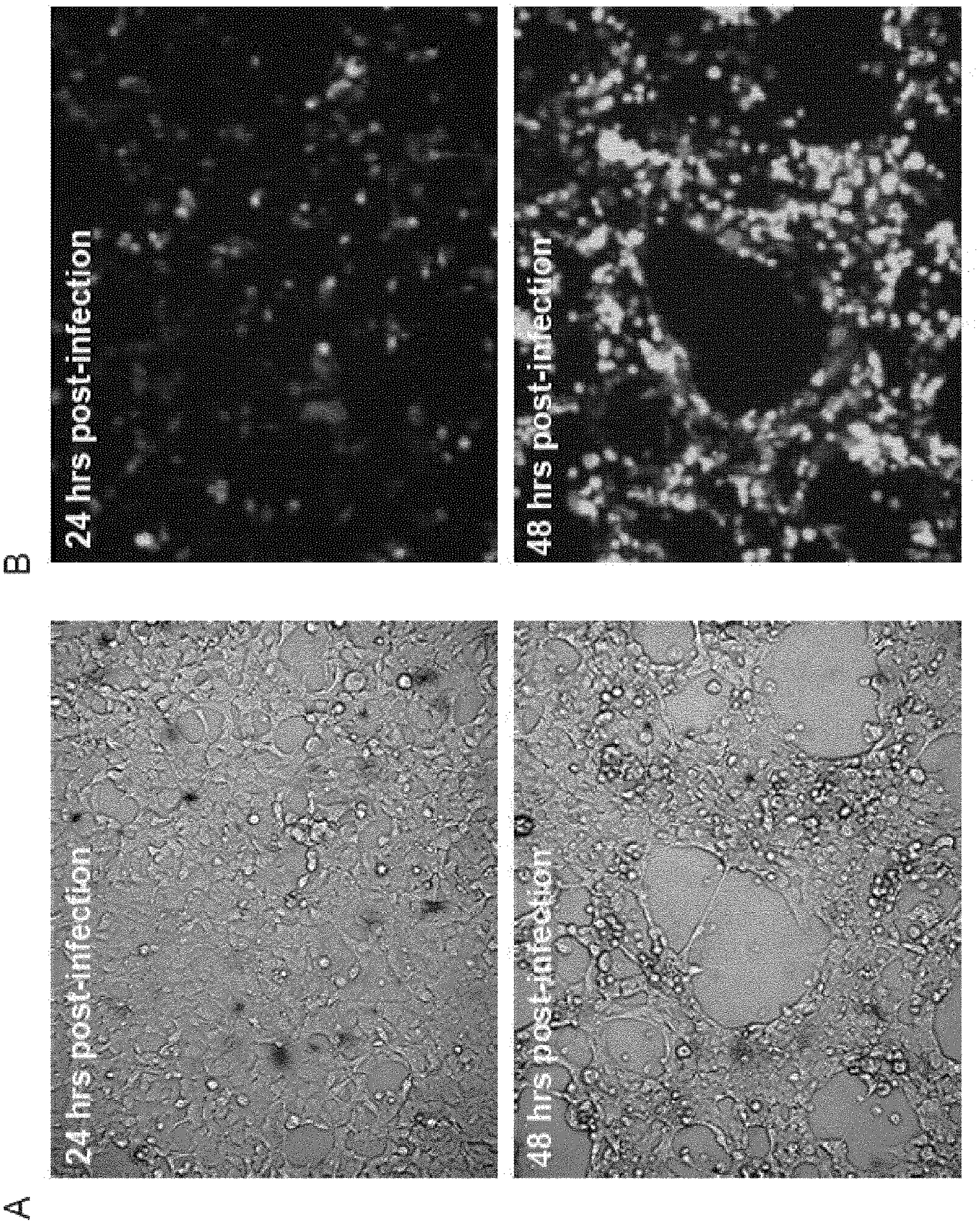

FIG. 30 shows a map of the plasmid pNG-62. The was generated from plasmid ColoAd2.4 and contains a p15A origin of replication, kanamycin resistance cassette and the ColoAd1 genome with a GFP reporter gene transgene cassette inserted between original SgfI and SbfI restrictions sites FIG. 31 schematic of the transgene cassette present in the pNG-62 plasmid. The cassette contains a branched splice acceptor sequence (bSA), KOZAK sequence, green fluorescent protein (GFP) cDNA and a SV40 late polyA sequence. The cassette is flanked by SgfI and SbfI restriction sites for insertion in the ColoAd2.4 vector FIG. 32 restriction digested constructs containing the pNG-62 transgene cassette. All five constructs contain the correctly sized cassette FIG. 33 A—shows preliminary restriction analysis of pNG-62 plasmids digested with the enzymes NheI and EcoRV. Constructs numbered 1, 2 & 3 from a 1.5:1 ligation ratio and 1, 2 & 4 from a 2:1 ligation ratio showed correct banding patterns corresponding to the pNG-62 plasmid B—shows diagnostic restriction digest with the enzyme BglII or enzymes NheI and EcoRV of two pNG-62 constructs and the plasmid from which pNG-62 was constructed, ColoAd2.4. The banding pattern of DNA fragments confirmed construction of the pNG-62 plasmid FIG. 34 A—Brightfield microscopy images of AD293 cells infected for 24 hrs (upper panel) or 48 hrs (lower panel) with NG-62 virus particles harvested from Hek293 cells transfected with NG-62 genomic DNA B—Fluorescent microscopy images corresponding to the brightfield images in A, showing GFP expression in AD293 cells infected for 24 hrs (upper panel) or 48 hrs (lower panel) with NG-62 virus particles

DETAILED DESCRIPTION

Vector as employed herein refers to a DNA molecule used as a vehicle to artificially carry genetic material into another construct or cell, for example where it can be replicated and/or expressed. The method of preparing the shuttle vector and the shuttle vectors themselves have allowed the present inventors to build plasmids that contain all the necessary functionality to allow manipulation of the adenovirus genome.

Shuttle vector as employed herein refers to a vector that, for example can propagate in two types of host cells, typically bacterial and mammalian cells.

Prior art shuttle vectors generally contain only a minimal amount of adenovirus genomic DNA in the 3' arm, such as an inverted terminal repeat (ITR) sequence of about 100 base pairs. This 3' fragment is sufficient to allow recombination, but does not allow any manipulation of the genome at the 3' end, where the E4, E3 and the L5 genes are located. Assembling small shuttle vectors with short 3' arms is usually carried out using PCR methods and a simple ligation of two DNA fragments. However, ligations to generate larger shuttle vectors, in which a number of adenovirus genes can be manipulated, become more difficult and unpredictable because three DNA fragments of significant size are used. Generally the 3'-arm (fragment iii) employed in the methods according to the present disclosure includes a E3 site and/or E4 site, as appropriate. In one embodiment the 3'-arm comprises the 3' ITRs, L5 and an E3 site, for example as a fragment of the virus genome, i.e. wherein the genetic elements have the corresponding positions as found naturally in the virus (and for example the fragment does not comprise an E4 site). In one embodiment the 3'-arm comprises the 3' ITRs, L5 and an E4 site, for example as a fragment of the virus genome, i.e. wherein the genetic elements have the corresponding positions as found naturally in the virus (and for example the fragment does not comprise an E3 site). In one embodiment the 3'-arm comprises the 3' ITRs, L5, an E3 site and an E4 site, for example as a fragment of the virus genome, i.e. wherein the genetic elements have the corresponding positions as found naturally in the virus.

In general in the prior art, when ligating three pieces of DNA to form a shuttle vector, a two-step ligation is employed wherein two pieces are ligated in the first step and then the third piece is ligated in the second step. This is because ligating large pieces of DNA together is an inefficient process. Surprisingly, the usual method did not successfully generate adenoviruses shuttle vectors and plasmids of the required size. Thus the use of PCR methods and ligation of two DNA fragments via a two-step method of ligation, after several months of work in hands of the present inventors, did not generate any adenovirus shuttle vectors.

The inventors overcame the problem by employing the present one step, three way ligation method. Surprisingly a robust and efficient one-step, three-way ligation was eventually identified, after performing several experiments under various conditions. The proportions of DNA components in the three-way ligation appear to be of importance in the successful ligation. The one-step method is a little counter intuitive because in theory it is more difficult to assemble three DNA segments simultaneously than two DNA segments simultaneously. However the presently disclosed methods have been shown by the present inventors to work thereby allowing the preparation of shuttle vector and plasmids of the required size.

Once a shuttle vector comprising the E3 site, L5 gene and E4 site was generated, the inventors were able to introduce original restriction sites into the shuttle vector and then create the plasmid containing the full genome, with novel, original restrictions sites in a location removed from the early genes into which transgenes may be instruced. In this embodiment step b), introduction of the restriction sites, was performed after step a). An alternative approach is to, for example prepare the 3' arm (fragment ii) already containing the restriction sites and or transgenes. One way to achieve this is by synthesising the 3' arm fragment to have all the desired structure and function prior to performing the ligation step. In the latter embodiment step b) is performed prior to step a). If a cloning platform is required that can employed over and over again then the restriction sites are employed. If only one specific virus construct is required then one may simply insert only the transgenes and machinery necessary for the same to function. Thus in one alternative aspect of the disclosure no restriction sites are inserted and rather a transgene or transgenes are inserted directly in the required location.

Clearly the 5' arm fragment may also be prepared, for example synthesised, with the required elements, sequence and/or functionality.

When synthetic adenovirus fragments are employed they may be assembled to provide a fully functioning virus or viral vector.

DNA construct as employed herein refers to a shuttle vector or plasmid.

Virus construct as employed herein refers to replication capable virus or replication deficient virus according to the present disclosure.

Adenoviruses

The present disclosure is broadly applicable to all types of adenoviruses and is particularly suitable for human adenoviruses for example as shown in Table 1, such as subgroup B adenoviruses and specifically to the chimeric adenoviruses EnAd (Enadenotucirev), OvAd1 and OvAd2.

Unless the context indicates otherwise adenovirus as employed herein is a generic term referring and adenovirus or any origin, serotype and including viral vectors. Unless the context indicates otherwise adenovirus genome as employed herein means the entirety of an adenovirus' genetic DNA.

Genomic DNA is part or all of the DNA from an adenovirus genome.

Adenoviruses are non-enveloped icosahedral double-stranded DNA viruses with a linear genome of approximately 34 to 48 kilobase pairs (Kb). Due to the size of the genome, the virus can incorporate about an additional 10% of the genome of foreign DNA without significant impact on its stability or its infectivity. The introduction of longer sequences therefore generally requires the removal of some of the virus' genes.

In one embodiment the adenovirus is a human adenovirus. As employed herein human adenovirus refers to any adenovirus that can be assigned to any of the over 50 currently known adenoviral serotypes, which are classified into subgroups A-F based on various attributes including their haemagglutination properties (see Shenk 2001), and further extends to any, as yet, unidentified or unclassified adenoviral serotypes. See, for example, Strauss, "Adenovirus infections in humans," in The Adenoviruses, Ginsberg, Plenum Press, New York, N.Y., pp. 451-596 (1984) and Shenk, "Adenoviridae: The Viruses and Their Replication," in Fields Virology, Vol. 2, Fourth Edition, Knipe, 35ea., Lippincott Williams & Wilkins, pp. 2265-2267 (2001), as shown in Table 1:

| SubGroup | Adenoviral Serotype |
|---|---|
| A | 12, 18, 31 |
| B | 3, 7, 11, 14, 16, 21, 34, 35, 51 |
| C | 1, 2, 5, 6 |

-continued

| SubGroup | Adenoviral Serotype |
|---|---|
| D | 8-10, 13, 15, 17, 19, 20, 22-30, 32, 33, 36-39, 42-49, 50 |
| E | 4 |
| F | 40, 41 |

All human adenovirus genomes examined to date have the same general organisation i.e., the genes encoding specific functions are located at the same position in the viral genome. Each end of the viral genome has a short sequence known as the inverted terminal repeat (or ITR), which is required for viral replication. The viral genome contains five early transcription units (E1A, E1B, E2, E3, and E4), three delayed early units (IX, IVa2 and E2 late) and one late unit (major late) that is processed to generate five families of late mRNAs (L1-L5). Proteins encoded by the early genes are primarily involved in replication and modulation of the host cell response to infection, whereas the late genes encode viral structural proteins. Early genes are prefixed by the letter E and the late genes are prefixed by the letter L.

A summary of the location of genes in the Ad11 genome is provided in the Examples.

ITRs are common to all known adenoviruses. The Inverted Terminal Repeat (ITR) sequences were so named because of their symmetry, and are the viral chromosome origins of replication. Another property of these sequences is their ability to form a hairpin. The 5' ITR as employed herein refers to the ITR at the 5' end of the genome. The 3' ITR as employed herein refers to the ITR at the 3' end of the genome.

L5 gene as employed herein means the fibre gene. The fibre gene encodes the fibre protein which is a major capsid component of adenoviruses. The fibre functions in receptor recognition and contributes to adenovirus' ability to selectively bind and infect cells. The fibre gene, may for example comprise in region of 986 base pairs. In one embodiment the fibre is defined by positions 30811-31788 of the genome, for example the Ad11 genome, in particular as defined in SEQ ID NO: 1 of U.S. Pat. No. 7,459,153 incorporated herein by reference or by reference to virus deposit Genbank accession: AY598970.

Non-human adenoviruses include ovine, porcine, canine and chimp viruses.

In one embodiment the adenovirus genome is a subgroup B adenovirus genome. Subgroup B as employed herein means a serotype B adenovirus. Subgroup B adenovirus include Ad3, Ad7, Ad11, Ad14, Ad16, Ad21, Ad34, Ad35, Ad51. The most widely studied adenovirus, Ad5, is a subgroup C adenovirus. Ad5 immunity is common in the human population making it a poor candidate for therapy because the virus is likely to be neutralised by a rapid immune response.

In one embodiment the adenovirus is selected from EnAd (Enadenotucirev SEQ ID NO: 1 also known as ColoAd1 a replication competent oncolytic chimeric adenovirus—see WO2005/118825), OvAd1 (see WO2008080003—SEQ ID NO: 1 therein and incorporated herein by reference), OvAd2 (see WO2008080003—SEQ ID NO: 2 therein and incorporated herein by reference), Ad3 (Genbank accession: DQ086466), Ad11 such as Ad11p (Genbank accession: AY598970) and Ad5, for example EnAd (SEQ ID NO.1), OvAd1 or OvAd2, in particular EnAd.

In one embodiment the adenovirus genome employed in the method of the present disclosure has at least 95% sequence identity to EnAd (SEQ ID NO: 1), such as 96, 97, 98, 99 or 100% sequence identity. In one embodiment the adenovirus genome has at least 95% sequence identity to OvAd1 (SEQ ID NO: 1 of WO2008080003), such as 96, 97, 98, 99 or 100% sequence identity. In one embodiment the adenovirus genome has at least 95% sequence identity to OvAd2 (SEQ ID NO.2 of WO2008080003), such as 96, 97, 98, 99 or 100% sequence identity. In one embodiment the adenovirus genome has at least 95% sequence identity to Ad3 (Genbank accession: DQ086466), such as 96, 97, 98, 99 or 100% sequence identity. In one embodiment the adenovirus genome has at least 95% sequence identity to Ad11p (Genbank accession: AY598970), such as 96, 97, 98, 99 or 100% sequence identity. Advantageously, EnAd has a wild type Ad11p capsid, a chimeric E2B region derived from both Ad3 and Ad11 and deletions in the E3 and E4 region (in particular the whole of E3 is deleted and E4orf4 is deleted). These structural changes provide additional 'space' in the ColoAd1 genome for the insertion of transgene cassettes expressing, for example therapeutic or immunomodulatory agents. Furthermore, because it is a subgroup B adenovirus, pre-existing immunity in humans is less common in comparison to Ad5.

The structural changes in EnAd result in a genome that is approximately 3.5 kb smaller than Ad11p thereby providing additional "space" for the insertion of transgene cassettes. EnAd is a suitable vehicle for delivering a wide range of therapeutic proteins, for example that augment or synergise with EnAd's potent anti-cancer activity. OvAd1 and OvAd2 are also chimeric adenoviruses similar to ColoAd1 which also have additional "space" in the genome (see WO2008/080003).

Sequence identity as employed herein refers to two polynucleotide or amino acid sequences being identical (i.e., on a nucleotide-by-nucleotide or residue-by-residue basis) over the comparison window, for example over their full length. The term "percentage of sequence identity" is calculated by comparing two optimally aligned sequences over the window of comparison, determining the number of positions at which the identical nucleic acid base (e.g., A, T, C, G, U, or I) or residue occurs in both sequences to yield the number of matched positions, dividing the number of matched positions by the total number of positions in the comparison window (i.e., the window size), and multiplying the result by 100 to yield the percentage of sequence identity.

The term "substantial identity" as used herein denotes a characteristic of a polynucleotide or amino acid sequence, wherein the polynucleotide or amino acid comprises a sequence that has at least 85 percent sequence identity, for example at least 90 to 95 percent sequence identity, in particular at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

The term "similarity", when used to describe a polypeptide, is determined by comparing the amino acid sequence and the conserved amino acid substitutes of one polypeptide to the sequence of a second polypeptide.

The term "homologous", when used to describe a polynucleotide, indicates that two polynucleotides, or designated sequences thereof, when optimally aligned and compared, are identical, with appropriate nucleotide insertions or deletions, in at least 70% of the nucleotides, usually from about 75% to 99%, and in particular at least about 98 to 99% of the nucleotides. In one embodiment the comparison is performed across the full length of a given sequence.

In one embodiment the adenovirus genome has a chimeric E2B region, for example a recombinant chimeric adenovirus, or a variant or derivative thereof, having a genome comprising an E2B region wherein said E2B region comprises a nucleic acid sequence derived from a first adenoviral serotype and a nucleic acid sequence derived from a second adenoviral serotype; wherein said first and second serotypes are each independently selected from the adenoviral subgroups B, C, D, E, or F and are distinct from each other; and wherein said chimeric adenovirus is oncolytic and demonstrates an enhanced therapeutic index for a tumor cell, in particular as disclosed in WO2005/118825 incorporated herein by reference.

In one embodiment the adenovirus genome has part or all of the E3 region deleted or mutated, for example the E3 region is mutated. In one embodiment the adenovirus genome has part or all of the E4 region deleted or mutated, for example E4orf4 is deleted.

Replication Deficient and Replication Capable

In one embodiment the adenovirus genome employed is from an adenovirus capable of replication, in particular replication competent. In one embodiment a virus or viral construct of the present disclosure is replication capable, in particular replication competent. In one embodiment EnAd is capable of replication.

Capable of replication as employed herein generally refers viruses capable of replicating, for example without the need for a packaging cell line. They are also referred to herein as viruses, replication competent viruses (which is a subgroup of replication capable viruses), and conditionally replicating viruses (also a subgroup of replication capable viruses) or live viruses. Thus replication capable viruses as employed herein refers to conditionally replicating viruses and replication competent viruses. Conditionally replicating viruses as employed herein refers to viruses that can replicate in cells, such as cancers cells, which express or over-express or under-expresses a certain gene, for example cells which under express p53 gene.

Replication competent viruses are viruses that have all the necessary machinery to replicate, for example in vivo and/or ex vivo, without the assistance of a help virus or complementary/packaging cell line.

Unless the context indicates otherwise "virus" (as opposed to adenovirus which is defined above) as employed herein refers to a replication capable, for example a replication competent virus. Thus in one embodiment virus as employed herein generally refers to a replication competent virus, such as a therapeutic virus, such as an oncolytic virus.

In one embodiment the adenovirus genome employed in a method according to the present disclosure is from an adenoviral vector which is not capable of replication. In one embodiment the virus or viral construct of the present disclosure is non-replication (also referred as replication deficient). Non-replicating adenoviruses, for example viral vectors (employed as a vehicle for delivering transgenes, such as vaccine antigens, intracellular delivery of antibodies and the like) generally have one or more genes removed which are essential to replication. Unless indicated otherwise viral vector as employed herein refers to a replication deficient Replication deficient adenoviruses are those which require a helper virus or complementary/packaging cell line to replicate. Generally adenoviruses (for example those comprising a transgene) that require a packaging cell line to replicate are referred to as viral vectors. In one embodiment EnAd is rendered replication deficient, for example by deletion of part or all of the E1 region.

The reasons for the removal of the replication-essential gene or genes are two-fold. Firstly, it is considered that the vectors have a simplified safety profile due to their inability to replicate in vivo. Secondly, the deletion of the genes allows insertion of large transgenes by creating space in the genome. These transgenes can be expressed in vivo, regardless of the viral vector's inability to replicate. In one embodiment the E1 gene is deleted from the virus in the creation of a viral vector and alternatively or in addition in some instances part or all of the E3 region is deleted.

A packaging cell line is a recombinant cell line which has been prepared to supplement the virus in question with the genes in which it is deficient. Packaging cell as employed herein means a cell that is capable of providing an essential element for the replication of a virus where the virus is deficient in that element. Examples of packaging cell lines include the PerC6 cell line. In one embodiment the packaging cell line is a HEK cell.

Virus Genes

E1 plays a role in viral replication. By deleting or mutating the E1 region, viruses are unable to replicate without the aid of a specific "packaging" cell line.

In one embodiment the E1 region in the genome of a viral vector of the present disclosure is wholly or partially deleted. In one embodiment the E1 site is a deletion of the E1 region or a fragment thereof is deleted in the 5' arm.

E1 site as employed herein refers to the location of the E1 region, regardless of whether the whole, part or none of the regions is deleted or replaced. The term "E1 site" includes where E1 is mutated, partially deleted, wholly deleted or wholly intact and non-mutated. The E1 site can be absent when the fragment or sequence starts after or ends before the E1 region, for example including starting after any non-coding region associated with the E1, such as the sequence starting in the E2 region. In one embodiment the E1 site consists of the E1 region or a functional fragment or mutation thereof. In one embodiment E1 is present and complete and/or functional.

The E3 encodes proteins important for modulating the host cell's response to viral infection.

Figure 1:
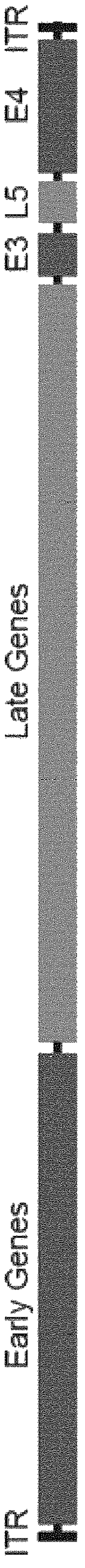
FIG. 1 shows a schematic of the ColoAd1 genome. Early genes (E1, E2, E3 and E4) are represented in dark grey and late genes (L1, L2, L3, L4 and L5) in light grey

E3 site as employed herein refers to the position in the adenovirus genome where the E3 gene or region is found or would be expected to be found. The E3 gene may be wholly present, present as a fragment or wholly absent, partially or fully mutated. Thus the E3 site as employed herein refers to the location of the E3 region, regardless of whether the whole, part or none of the regions is deleted or replaced. Given that the genome architecture of adenoviruses is uniform between all known human adenoviruses (see FIG. 1), the skilled person is able to identify the E3 site whether the gene is present or deleted. The E3 site may in fact be absent when the fragment or sequence concerned starts beyond the E3 region or terminates before the E3 region, for example including any non-coding region associated with the E3, such as the sequence starting in the L5 region.

E4 site as employed herein refers to the position in the adenovirus genome where the E4 gene or region is found or would be expected to be found. The E4 gene may be wholly present, present as a fragment or wholly absent, partially or fully mutated. Thus the E4 site as employed herein refers to the location of the E4 region, regardless of whether the whole, part or none of the regions is deleted or replaced. Given that the genome architecture of adenoviruses is uniform between all known human adenoviruses (see FIG. 1), the skilled person is able to identify the E4 site whether the gene is present or deleted. The E4 site may in fact be absent when the fragment or sequence concerned starts beyond the E4 region or terminates before the E4 region, for example including any non-coding region associated with the E4, such as the sequence starts in the L5 region.

The L5 gene encodes the late expressed capsid protein fibre.

In one embodiment the L5 region is the full length sequence or a function fragment thereof, for example a fragment that retains 50% or more, such as 60, 70, 80, 90 or 100% of the activity of the wild-type gene, in particular in an in vitro assay. In one embodiment the L5 comprises 80% or more of the genomic DNA an L5 gene, for example 85, 90, 91, 92, 93, 94, 95, 96, 97, 98 or 99%.

In one embodiment part or all of the E3, E4 or L5 genes are independently mutated.

Mutated as employed herein refers a modification in the relevant gene, for example a point mutation, a deletion mutation, an addition mutation, a forward mutation, a substitution mutation and/or a frameshift mutation. In one or more embodiments the amount of genetic material that is mutated is 10% or less of the relevant sequence. In essential genes, for example L5 (the fibre gene) the function of the gene is maintained in the mutated gene, such as 50, 60, 70, 80, 90 or 100 of the function is retained, or the function is increased i.e. is greater than 100% of the unmutated gene.

Restriction Sites

Restrict site as employed herein is a short DNA sequence specifically recognised and cut by a restriction enzyme.

Suitable restriction site as employed herein means a site that may be employed (in conjunction with an appropriate restriction enzyme) to specifically cleave the genomic DNA of the virus in a given location, for example in a region of the DNA that is not an early gene. In one embodiment the DNA is cleaved to facilitate the insertion of a transgene. In one embodiment a suitable site typically is present near the 5' end of the genome and/or the 3' end of the virus genome or the corresponding location in the 3' arm fragment and/or the 5' arm fragment, this allows the DNA to be linearised and manipulated, for example as shown in the Figures.

In one embodiment a suitable restriction site is located approximately 4-5 Kb from the ends of the 3' and/or 5' ITRS such that the shuttle vector will have approximately 4-5 Kb 3' and/or 5' arms. Advantageously this permits efficient homologous recombination between the shuttle vector and the adenovirus genome. This design also allows the shuttle vector to contain the E1 gene (for example in the 5' arm) and the Fibre and E4 gene (for example in the 3' arm) so that any regions surrounding these genes may be manipulated for transgene cassette insertion.

In one embodiment the shuttle vector comprises 1, 2, or 3 further suitable/original restriction sites. In one embodiment a suitable restriction site is not inserted at any other location in the shuttle vector. In one embodiment restriction sites are incorporated around at least one early gene or a part thereof, for example independently selected from E1, E2, E3 and E4, to provide further options for the skilled person to manipulate the genome.

A suitable restriction restrictions will general be an original restriction site. Original, novel, unique in the context of restrictions sites are employed interchangeably herein, and is/are intended to refer a restriction site that can be cut specifically. Restriction site or in some instances a pair of restriction sites may be cut specifically, when they only occur in the location that it is desirable to cut. Thus if the restriction site only occurs once or a pair of restrictions sites occur only once in the virus genome or genomic DNA then this restriction site or sites (in the case of a pair) can be cut specifically by an appropriate enzyme. Thus in one embodiment original, novel or unique refers to the introduction of a restriction site or pair of restriction sites that was not previously present anywhere in the virus genome or the relevant genomic DNA. Thus in one embodiment a suitable restriction site is non-natural (exogenous) to the adenovirus genome. In one embodiment the original restriction site or pair of restriction sites occurs only once in the virus genome or genomic DNA. In one embodiment a suitable restriction site will produce sticky ends. In one embodiment a suitable restriction site will be cleaved by an appropriate commercially available restriction enzymes.

Thus a restriction site is a location in a DNA sequence that can be cut by a restriction enzyme, usually an enzyme specific to the sequence. In one embodiment the restriction site comprises 3 to 22 base pairs, for example 4 to 22, such as 5, 6, 7, 8, 9, 10, 11, 12, 13, 14, 15, 16, 17, 18, 19, 20, 21 or 22 base pairs.

Introduced or introducing as employed herein generally refers to inserting a restriction site that is not found in the native, wild-type or starting adenovirus genome.

In one embodiment original restriction site as employed herein means a restriction site that occurs only once in the plasmid or in virus construct. This permits certainty that a given restriction enzyme will cut the plasmid in only one known location. In the context of the present disclosure an original restriction site is typically one which has been introduced into the genome and was not naturally occurring.

In one embodiment original restriction site as employed herein refers to a restriction site introduced into the adenovirus genome by recombinant techniques, in particular where the restriction site introduced in not naturally occurring in the virus and thereby give specificity in the location of the virus is genome is cut when the given restriction enzyme is employed.

Thus in another embodiment original restriction site as employed herein means a restriction site that occurs only once in the plasmid, virus or shuttle vector. This permits certainty that a given restriction enzyme will cut the plasmid in only one known location.

In particular the original restriction sites permit transgene cassettes to be inserted in to the genome at, for example a location removed from the early genes.

The method is broadly applicable to adenoviruses and suitable restriction sites that may provide appropriate 5' and 3' arms from which to build a shuttle vector have been identified in ColoAd1, OvAd1, OvAd2, Ad3, Ad11 and Ad5.

Thus the method of the present disclosure may be used as a starting point to generate therapeutic viruses with enhanced activity conferred by, for example the introduction of transgenes.

In one embodiment the original restriction site is independently selected from FseI, NotI, SbfI and SgfI, for example NotI or SbfI and SgfI or FseI and NotI and SbfI and SgfI. Other restriction enzymes that cut at the same sequence are interchangeable.

FseI as employed herein refers to a restriction site cut by a restriction enzyme at the following sequence -GGCCGG/CC-. Other restriction enzymes that cut at the same sequence are interchangeable.

NotI as employed herein refers to a restriction site cut by a restriction enzyme at the following sequence -GC/GGCCGC-. Other restriction enzymes that cut at the same sequence are interchangeable.

SbfI as employed herein refers to a restriction site cut by a restriction enzyme at the following sequence -CCTGCA/GG-. Other restriction enzymes that cut at the same sequence are interchangeable.

SgfI as employed herein refers to a restriction site cut by a restriction enzyme at the following sequence -GCGAT/CGC-. Other restriction enzymes that cut at the same sequence are interchangeable.

In one embodiment two or more original restriction sites are inserted at a given location in the genome.

In one embodiment the original restriction site is a single original restriction site in a location between the L5 gene and the E3 site. Such as a single original restriction site introduced in a location between the L5 gene and the E3 site, such as NotI. In one embodiment this single original restriction site is the only original restriction site introduced into the plasmid or virus construct.

In one embodiment the original restriction site is one or two (such as two) original restriction sites in a location between the L5 gene and the E4 site, for example two original restriction sites introduced in a location between the L5 gene and the E4 site, such as one SbfI site and one SgfI site. In one embodiment these are the only two original restriction sites introduced into the shuttle vector, plasmid or virus construct.

In one embodiment the original restriction site is a single original restriction site in a location between the L5 gene and the E3 site and three original restriction sites in a location between the L5 gene and the E4 site, for example a single original restriction site introduced in a location between the L5 gene and the E3 site, such as one FseI site, and three original restriction sites introduced in a location between the L5 gene and the E4 site, such as one NotI site, one SlbfI site and one SgfI site. In one embodiment these are the only four original restriction sites introduced into the shuttle vector, plasmid or viral construct.

In one embodiment FseI is an original restriction site suitable for introduction to an adenovirus genome selected from the group ColoAd1, Ad11, Ad3, OvAd1 and OvAd2. RigI is a known restriction enzyme that cuts at the same sequence as FseI, therefore FseI restriction sites are also known as RigI restriction sites.

In one embodiment NotI is an original restriction site suitable for introduction to an adenovirus genome selected from the group ColoAd1 and Ad11. CciNI is a known restriction enzyme that cuts at the same sequence as NotI, therefore NotI restriction sites are also known as CciNI restriction sites.

In one embodiment SbfI is an original restriction site suitable for introduction to an adenovirus genome selected from the group ColoAd1, Ad11, Ad3, OvAd1 and OvAd2. SdaI and Sse83871 are known restriction sites that cut at the same sequence as SbfI, therefore SbfI restriction sites are also known as SdaI restriction sites or Sse83871 restriction sites.

In one embodiment SgfI is an original restriction site suitable for introduction to an adenovirus genome selected from the group ColoAd1, Ad11, Ad3, OvAd1 and OvAd2. AsiSI, RgaI and SfaAI are known restriction sites that cut at the same sequence as SgfI, therefore SgfI restriction sites are also known as AsiSI restriction sites, RgaI restriction sites or SfaAI restriction sites.

In one embodiment ClaI is an original restriction site suitable for introduction to the Ad5 adenovirus genome. ClaI as employed herein means a restriction site cut by a restriction enzyme at the following sequence -AT/CGAT-. BspDI, ZhoI, BspDI, BanIII, Bsa29I, BseCI, BshVI, BsiXI, Bsp106I, BspXI, Bsu15I and BsuTUI are known restriction sites that cut at the same sequence as ClaI, therefore ClaI restriction sites are also known as BspDI restriction sites, ZhoI restriction sites, BspDI restriction sites, BanIII restriction sites, Bsa29I restriction sites, BseCI restriction sites, BshVI restriction sites, BsiXI restriction sites, Bsp106I restriction sites, BspXI restriction sites, Bsu15I restriction sites or BsuTUI restriction sites. In one embodiment PacI is an original restriction site suitable for introduction to the Ad5 adenovirus genome. PacI as employed herein means a restriction site cut by a restriction enzyme at the following sequence -TTAAT/TAA-.

In one embodiment MluI is an original restriction site suitable for introduction to an adenovirus genome selected from the group Ad3 and OvAd2. MluI as employed herein means a restriction site cut by a restriction enzyme at the following sequence -A/CGCGT-.

In one embodiment BstBI is an original restriction site suitable for introduction to the Ad5 adenovirus genome. BstBI as employed herein means a restriction site cut by a restriction enzyme at the following sequence -TT/CGAA-. SfuI, AsuII, Bpu14I, BsiCI, Bsp119I, BspT104I, Csp45I and NspV are known restriction sites that cut at the same sequence as BstBI, therefore BstBI restriction sites are also known as SfuI restriction sites, AsuII restriction sites, Bpu14I restriction sites, BsiCI restriction sites, Bsp119I restriction sites, BspT104I restriction sites, Csp45I restriction sites or NspV restriction sites.

In one embodiment BclI is an original restriction site suitable for introduction to an adenovirus genome selected from the group ColoAd1, Ad11, Ad3, Ad5, OvAd1 and OvAd2. BclI as employed herein means a restriction site cut by a restriction enzyme at the following sequence -T/GATCA-. BsiQI, FbaI and Ksp221 are known restriction sites that cut at the same sequence as MI, therefore MI restriction sites are also known as BsiQI restriction sites, FbaI restriction sites or Ksp221 restriction sites. These restriction sites are generally not preferred.

In one embodiment blunt cutting restriction enzyme sites are employed as original restriction sites, for example PmeI, SrfI and SwaI.

In one embodiment PmeI is an original restriction site suitable for introduction to an adenovirus genome selected from the group ColoAd1, Ad11, OvAd1 and OvAd2. PmeI as employed herein means a restriction site cut by a restriction enzyme at the following sequence -GTTT/AAAC-.

In one embodiment SrfII is an original restriction site suitable for introduction to an adenovirus genome selected from the group ColoAd1, Ad11, Ad3, Ad5, OvAd1 and OvAd2. SrfII as employed herein means a restriction site cut by a restriction enzyme at the following sequence -GCCC/GGGC-.

In one embodiment SwaI is an original restriction site suitable for introduction to an adenovirus genome selected from the group ColoAd1, Ad11, Ad3, Ad5, OvAd1 and OvAd2. SwaI as employed herein means a restriction site cut by a restriction enzyme at the following sequence -ATTT/AAAT-.

In one embodiment the original restriction site other than NotI is in a location between the L5 gene and the E3 site. In one embodiment there are two original restriction sites in a location between the L5 gene and the E4 site, such as one SbfI and one SgfI.

In one embodiment there are 4 original restriction sites wherein one original restriction site is in a location between the L5 gene and the E3 site and wherein three original restriction sites are in a location between the L5 gene and the E4 site. Such as wherein the one original restriction site is FseI and the three original restriction sites are one each of SbfI, SgfI and NotI.

In one embodiment the adenovirus genome comprising one or more original restriction sites has the sequence SEQ ID NO. 32. In one embodiment the adenovirus genome comprising one or more original restriction sites has the sequence SEQ ID NO. 33. In one embodiment the adenovirus genome comprising one or more original restriction sites has the sequence SEQ ID NO. 34.

In one embodiment the adenovirus comprising one or more original restriction sites has at least 95% sequence identity to SEQ ID NO. 32, such as 96, 97, 98, 99 or 100% identity. In one embodiment the adenovirus comprising one or more original restriction sites has at least 95% sequence identity to SEQ ID NO. 33, such as 96, 97, 98, 99 or 100% identity. In one embodiment the adenovirus comprising one or more original restriction sites has at least 95% sequence identity to SEQ ID NO. 34, such as 96, 97, 98, 99 or 100% identity.

The plasmids and shuttle vectors prepared have a novel combination of original restriction sites located around the genome of the adenovirus. These can then be selected and employed to give control over which part the adenovirus genome is to be manipulated.

The original restriction sites are introduced strategically to allow for example a transgene to be inserted at the location of one restriction site or alternatively for sections of genome to be deleted between two chosen restriction sites, as desired.

In one embodiment the plasmid further comprises at least one E1 original restriction site. E1 original restriction site as employed herein refers to a restriction site introduced into the E1 region of the adenovirus genome. In some embodiments the E1 gene is present but interrupted by the introduced E1 original restriction site, in other embodiments the E1 gene is deleted and replaced by the introduced E1 original restriction site, in yet other embodiments the E1 gene is present but its function is not altered by the introduced E1 original restriction site.

In one embodiment the restriction site or sites are independently selected from:

- sequence GCGGCCGC cut by NotI and CciNI leaving 5'-GGCC overhangs,
- sequence GGCCGGCC cut by FseI and RigI leaving 3'-CCGG overhangs,
- sequence GCGATCGC cut by AsiSI, RgaI, SgfI and SfaAI leaving 3'-AT overhangs
- sequence CCTGCAGG cut by SbfI, SdaI and Sse83871 leaving 3'-TGCA overhangs
- sequence TGATCA cut by BclI, FbaI, Ksp221 and BsiQ1 leaving 5'-GATC overhangs
- sequence CAAAACGTCGTGAGACAGTTTG [SEQ ID NO: 41] cut by I-Cre1 leaving 3'-GTGA overhangs
- sequence TAACTATAACGGTCCTAAGGTAGCGAA [SEQ ID NO: 42] cut by I-CeuI leaving 3' CTAA overhangs
- sequence TAGGGATAACAGGGTAAT [SEQ ID NO: 43] cut by I-Sce1 leaving 3' ATAA overhangs
- sequence GCCCGGGC cut by SrfI leaving blunt ends
- sequence GTTTAAAC cut by MssI, PmeI leaving blunt ends
- sequence ATTTAAAT cut by SwaI, SmiI leaving blunt ends
- sequence GGCGCGCC cut by AscI, PalA1 and SgsI leaving 5' CGCG overhangs Other restriction enzymes that cut the same recognition sites may also be suitable.

In one embodiment the first restriction site found in the 3'arm and the vector fragment are the same restriction site (i.e. a site cut by the same restriction enzyme) This facilities joining the 5' end of the vector fragment to the 3' end of the 3' arm.

In one embodiment the second restriction site found in the 5' arm and the vector fragment are the same restriction site (i.e. a site cute by the same restriction enzyme). This facilitates joining the 3' end of the vector fragment to the 5' end of the 5' arm.

In one embodiment the first and second restriction enzyme sites are independently selected from the group FseI, RigI, NotI, CciNI, SbfI, SdaI, Sse83871, SgfI, AsiSI, RgaI, SfaAI, ClaI, BspDI, ZhoI, BspDI, BanIII, Bsa29I, BseCI, BshVI, BsiXI, Bsp106I, BspXI, Bsu15I, BsuTUI, PacI, MluI, BstBI, SfuI, AsuII, Bpu14I, BsiCI, Bsp119I, BspT104I, Csp45I, NspV, BclI, BsiQI, fbaI, Ksp221, PmeI, SrfI and SwaI.

In one embodiment the first restriction sites is AscI. In one embodiment the second restriction enzyme sites is AscI. AscI as employed herein means a restriction site cut by a restriction enzyme at the following sequence -GG/CGCGCC-. Other restriction enzymes that cut at the same sequence are interchangeable. In one embodiment the first and second restriction sites are the same. In one embodiment the first and second restriction enzyme sites are each AscI.

In one embodiment where a restriction enzyme site is used as the first and/or second or third restriction enzyme site the genomic DNA will be cut in more than one location.

In one embodiment a restriction site in an adenovirus genome or genomic DNA (such as the 5' arm), comprises a restriction site PspOMI, for example which is located at positions 4628, 20891 and 27840 of the genome or a position corresponding thereto. In one embodiment the adenovirus is EnAd or genomic DNA is derived therefrom.

Figure 5:
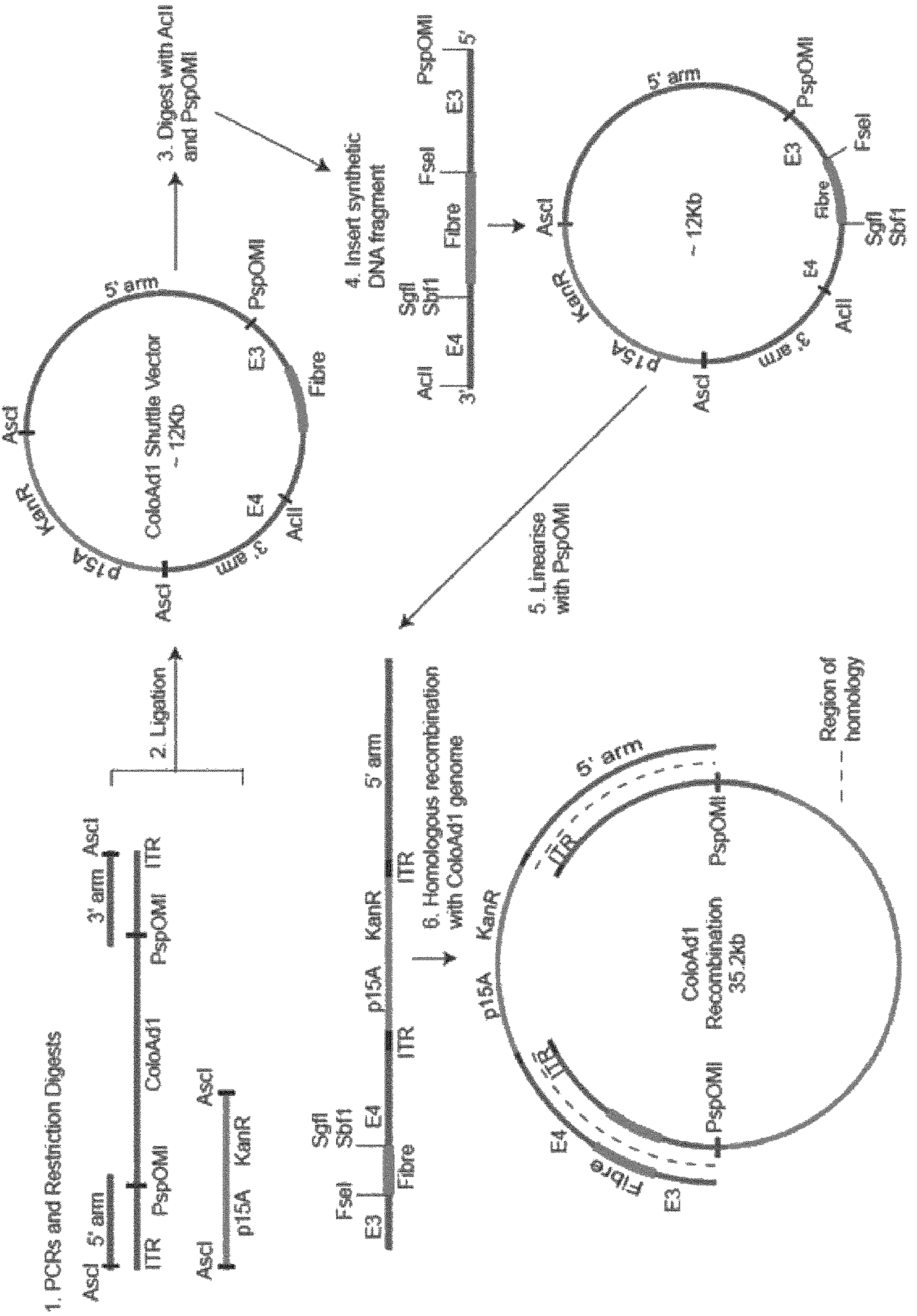
FIG. 5 shows an overview of ColoAd plasmid construction.

In one embodiment the third restriction site refers to one type of restriction site, for example PspOMI. Thus in one embodiment the third restriction site in the 3' arm and the 5' arm are the same. When sequence of the third restriction site in the 3' arm and the 5' arm are the same this facilities the joining the 3' end of the 5' arm to the 5' end of the 3' arm when preparing the shuttle plasmid. Furthermore the shuttle vector can later be cleaved at this site to linearise the sequence and facilitate homologous recombination with the plasmid comprising the adenovirus genome, see for example FIG. 5.

In one embodiment the first and last sites are utilised in generating the shuttle vector, for example as shown in the Figures.

Figure 4:
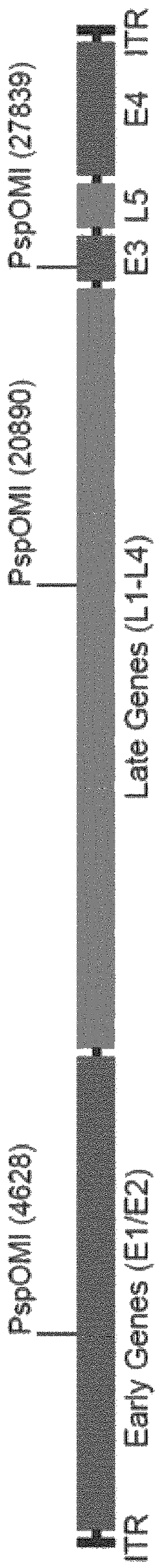
FIG. 4 shows a schematic showing PspOMI restriction site locations in the ColoAd1 genome.

In one embodiment a restriction site is designed to be near the 5' end of the virus genome (for example EnAd genome) and also the 3' end of the virus genome, in particular about 4-5 kb from the ends of the 3' and 5' ITRS such that the shuttle vector had about 4-5 kb 3' and 5' arms, as shown in FIG. 4. Thus in one embodiment PspOMI is the "third restriction site" in the 5' arm and/or the 3' arm. This pair of restrictions site allows the genomic DNA to be linearised and recombined with the virus genome (for example EnAd genome) to form a plasmid, without introducing any undesired alterations to the genome sequence.

This amount of DNA permits efficient homologous recombination between the shuttle vector and the virus genome, for example the EnAd genome. These design criteria also ensured the shuttle vector contains the E1 genes and the Fibre and E4 genes so that these genes and regions surrounding these genes could be manipulated for transgene cassette insertion, as desired.

In one embodiment the first and second restriction sites are the substrate for the same restriction enzyme and third restriction site is the substrate for a different restriction enzyme.

In one embodiment the first restriction site is the substrate for a different restriction enzyme to the second restriction site and the third restriction site is the substrate for a different restriction enzyme to each of the first and second restriction sites.

The present inventors have further identified the following suitable restriction sites in other adenovirus genomes.

In Ad5, the enzyme SphI (-GCATG/C-) may be employed. The restriction sites are located at positions 3661 and 31220 in the Ad5 genome. These sites are at the end of the E1B gene and at the start of fibre gene and produce PCR fragments for shuttle vector construction of 3.6 kb and 4.7 kb. These sites therefore allow construction of a shuttle vector in which transgenes may be inserted into the E1 region or in the vicinity of the fibre gene.

In Ad3, OvAd1 and OvAd2 the site AseI (-AT/TAAT-) may be employed. The restriction sites are located at positions 2469 and 31940 in the Ad3 genome, at positions 2488 and 31724 in the OvAd1 genome and at positions 2483 and 31949 in the OvAd2 genome. For all genomes these sites are located in E1B and inside the fibre gene and produce PCR fragments for shuttle vector construction of 2.5 kb and 3.4 kb. These sites therefore permit construction of a shuttle vector in which transgenes may be inserted into the E1 region or in the vicinity of the fibre gene.

In Ad11 PsiI (-TTA/TAA-) may be employed. Unlike PspOMI, SphI and AseI, this enzyme is a blunt cutter. The PsiI restriction sites are located at positions 2648 and 30890 in the Ad11 genome. These sites are in the E1B gene and at the start of the fibre gene and produce PCR fragments for shuttle vector construction of 2.6 kb and 4 kb. As above, these sites therefore allow construction of a shuttle vector into which original restriction sites may be inserted in the E1 region or in the vicinity of the fibre gene.

In the process of amplifying the 5' and 3' ends of the genome to generate the 3' arm and the 5' arm typically a linking restriction site will be added using suitable primers during PCR. The same linking restriction site is inserted into the vector fragment containing the bacterial replication of origin and the selection marker gene during amplification. This linking restriction site is designed to permit joining of the adenovirus genome to the vector fragment containing the bacterial origin of replication and selection marker gene. The first restriction enzyme site, second restriction enzyme site and third restriction enzyme site are all examples of linking restriction sites.

In one embodiment the third restriction site in the 3' arm and the 5' arm are in corresponding locations in the plasmid containing the adenovirus DNA. In one embodiment the 5' arm has a linking restriction site introduce upstream of the 5' ITR and the 3' arm has a linking restriction site introduced downstream of the 3' ITR. The restriction sites permit excision of the vector fragment comprising bacterial replication of origin and the selection marker gene. These restriction sites, alternatively known as the first and second restriction enzyme sites, permit the excision of the adenovirus genome from the plasmid.

In one embodiment a linking restriction site is AscI. Other restriction enzymes that cut at the same sequence are interchangeable.

Fragments

Vector fragment in the context of the method to make the shuttle vector refers to a fragment of DNA comprising a replication of origin and selection marker. In one embodiment the vector fragment is in the region of 2 to 4 Kb long. The vector fragment starts at the 5' end of the vector fragment with a first restriction enzyme site arranged to permit ligation with the 3' end of the 3' arm. It further comprises a low copy bacterial replication of origin and a selection marker gene and terminates at the 3' end of the vector fragment with a second restriction enzyme site arranged to permit ligation with the 5' end of the 5' arm. In one embodiment the vector fragment is no more than 3 Kb. This is sufficient to include a replication of origin and selection marker gene.

A 5' arm as employed herein refers to a DNA fragment of, for example a few thousand base pair from the 5' end of the adenovirus genome including the 5' ITR (inverted terminal repeat). The precise length of the arm is determined by the location of suitable restriction sites. In one embodiment the 5' arm is in the region of about 2 to 5 Kb in length, such as about 2.1, 2.2, 2.3, 2.4, 2.5 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8 or 4.9 kb long, and contains an E1 site, for example the entire E1 gene or the site from which the E1 gene has been deleted or partially deleted. In one embodiment the 5' arm is 4627 base pair long, for example from the 5' end of the EnAd genome.

The 5' arm starts at the 5' end with a second restriction site (arranged as discussed above to permit ligation with the 3' end of the vector fragment), comprises the 5' ITR and terminates at the 3' end of the 5' arm with a third restriction site (arranged to allow ligation with the 5' end of the 3' arm).

In one embodiment the 5' arm includes a non-mutated E1 region and so can be employed in the preparation of replication competent viruses.

In one embodiment the amount of adenoviral genomic DNA in the 5' arm is minimal, such as ITR. In one embodiment the amount of adenoviral genomic DNA in the 5' arm is in the range of 100 bp to 5 kb.

A 3' arm as employed herein refers to a DNA fragment, for example a few thousand base pairs from the 3' end of the adenovirus genome including the 3' ITR (inverted terminal repeat). The precise length of the arm is determined by the location of suitable restriction site. In one embodiment the 3' arm is in the region of about 3 to 5 kb long such as about 3.1, 3.2, 3.3, 3.4, 3.5, 3.6, 3.7, 3.8, 3.9, 4.0, 4.1, 4.2, 4.3, 4.4, 4.5, 4.6, 4.7, 4.8 or 4.9 kb long, and contains the entire Fibre (L5) gene. In one embodiment in the 3' arm is 4482 base pairs long, for example from the 3' end of the EnAd.

The 3' arm starts at the 5' end of the 3' arm with a third restriction site (for example arranged to permit ligation with the 3' end of the 5' arm) comprises the L5 gene and 3' ITR and terminates at the 3' end with a first restriction enzyme site (for example arranged to permit ligation with the 5' end of the vector fragment).

In one embodiment the 3' arm contains the fibre gene, also known as L5. Advantageously including the fibre gene in the 3' arm allows the manipulation of the late genes and more flexibility in the engineering of the virus.

"In a location between" as employed herein refers to being bordered or sandwiched by the regions specified, for example any location between the last nucleic acid of the one specified region, such as the E3 site and the first nucleic acid of the second specified regions, such as the L5 gene. First nucleic acid in this context includes the first nucleic acid of a fragment of the relevant gene/region (i.e. is not limited the literal first nucleic acid of the full length gene but rather refers to the first occurring nucleic assigned to the gene in a given construct). In one embodiment the location is between the last nucleic acid of the L5 gene and the first nucleic acid of the E4 site when travelling in a 5' to 3' direction.

In the vicinity of the L5 gene as employed herein refers to a location between the E3 site and the L5 gene and/or a location a location between the L5 gene and the E4 site. In one embodiment one or more restriction sites are independently located or inserted in a non-coding region. In one embodiment the genetic material inserted does not change or interrupt the function of the L5 gene.

It is particularly advantageous to insert one or more transgenes into the adenovirus genome in the vicinity of the L5 gene because transgenes in this location are less likely to interfere with viral stability and replication. In one embodiment genes placed after L5 may be under the control of the major late promoter or under the control of the E4 promoter. In one embodiment genes placed after L5 may be under the control of an exogenous promoter. In one embodiment genes placed before L5 may be under the control of the major late promoter or the E3 promoter. In one embodiment genes placed directly before L5 start codon can be under the control of the major late promoter and will generally need to contain a regulatory element that allows the expression of L5.

In some circumstances, inserting the transgene abutted to the fibre gene, for example where the transgene is directly next to or within a few bases of the L5 gene, may be advantageous. In one embodiment is abutted to the L5 gene on the E3 side of the genome and, for example permits a different level of transgene expression compare to the post-fibre site.

In one embodiment locating the transgene gene adjacent to L5 gene also allows regulation of the expression of the fibre protein which in turn allows regulations of virus activity.

Thus in one embodiment the transgene is inserted in a location abutted to the fibre gene, for example on the E3 side of the genome, on the E4 side of the genome or both.

In one embodiment a transgene or transgene are independently inserted in the same direction as the genomic DNA. In one embodiment the transgene or transgenes are independently inserted in a direction opposing the genomic DNA.

In one embodiment the 3' arm comprises in the 5' to 3' direction: a fibre gene; followed by an E4 site, for example an E4 region or a fragment thereof; and followed in turn by the ITR (inverted repeat region).

In one embodiment the 3' arm comprises in the 5' to 3; direction: an E3 site, for example an E3 region. a fragment thereof or an E3 site where the E3 region is deleted; followed by a fibre gene; followed in turn by an E4 region or a fragment thereof also known as the E4 site, in turn followed by the ITR. In one embodiment the 3' arm is in the range of 2 Kb to 5 Kb. In one embodiment adjacent to the fibre gene is a restriction site, for example FseI, in particular on the E3 side of the fibre. In one embodiment adjacent to the fibre gene is a restriction site, for example SgfI and/or Sbf1, for example on the E4 side of the fibre gene. In one embodiment the fibre gene is sandwiched by two restriction site, for example FseI, in particular on the E3 side of the fibre and an SgfI and/or Sbf1 is located, for example on the E4 side of the fibre gene.

In one embodiment the E4 site further comprises an AclI site, for example at a location disclosed in the Figures, examples and/or sequences herein.

In one embodiment the 5' arm and the 3' arm are each of sufficient length to promote efficient homologous recombination, such as approximately 2 Kb to 5 Kb long.

The 5' arm and/or the 3' arm may be synthetic. Advantageously, using synthetic 5' and/or 3' arms permits the introduction of original restrictions sites into the arms prior to ligation to form a shuttle vector.

In one embodiment in a shuttle vector according to the present disclosure (for example an EnAd shuttle vector) PspOMI is the third restriction enzyme site. PspOMI as employed herein refers to a restriction site cut by a restriction enzyme at the following sequence -G/GGCCC-. Other restriction enzymes such as ApaI and Bsp120I, that cut at the same sequence are interchangeable.

In one embodiment there is provided a method of introducing one or more original restriction sites into an adenovirus shuttle vector comprises the steps:

a) identifying two excision restriction sites in the shuttle vector and the DNA sequence between the sites,
b) digesting the shuttle vector at the excision restriction sites identified in step a) to excise a section of DNA,
c) synthesising a DNA fragment wherein the DNA fragment is substantially identical to the excised section of the shuttle vector from step b) further comprising one or more original restriction sites,
d) purifying the digested shuttle vector from step b) and the DNA fragment from step c),
e) ligating the DNA fragment from step d) and the shuttle vector from step d), and
f) identifying a correctly assembled shuttle vectors by transforming cells with the ligated shuttle vector, growing on a selective medium and screening the colonies.

In one embodiment the excision restriction site is AclI. Other restriction enzymes that cut at the same sequence are interchangeable. AclI as employed herein means a restriction site cut by a restriction enzyme at the following sequence -AA/CGTT-.

AclI is used alongside PspOMI to introduce original restriction sites into ColoAd1 shuttle vectors because they flank the fibre gene allowing excision of this region and insertion of a DNA fragment that is substantially identical to the excised region.

Ligation

One-step three-way ligation as employed herein refers to three sequences of DNA being ligated together in a single step to form circular DNA. In one embodiment screening is performed to establish the DNA shuttle vector is made up of all three sequences in an appropriate orientation.

Appropriate orientation as employed herein is intended to refer to an orientation suitable for use in reassembling/constructing an adenovirus according to the present disclosure.

Equal proportions as employed herein refers to ratio of DNA fragments (sequences) employed are approximately the same, even where the overall volume or concentration is varied. In one embodiment equal proportions refers to a 1:1:1 ratio of the vector fragment, 5' arm and the 3' arm. Ligation ratio as employed herein means the ratio or proportion at which the fragments of DNA to be ligated are provided.

In one embodiment, where the first and second restriction enzymes employed in each of the fragments are the same, and the vector fragment is dephosphorylated prior to the one-step, three-way ligation.

Dephosphorylated as employed herein refers to the phosphate ($PO_4^{3-}$) group is removed from the DNA by hydrolysis. Advantageously, dephosphorylation increases the likelihood of the 5' end and the 3' end of a DNA fragment remaining free to ligate with a different DNA fragment (which is typically not dephosphorylated) as opposed to ligating to each other. In one embodiment the dephosphorylation increases the success of a subsequent ligation step.

Ligation or ligating as employed herein refers to the covalent linking of two ends of DNA molecules, for example using a ligase enzyme.

In one embodiment the one-step three-way ligation uses 2 parts DNA ligase, 4 parts ligase buffer and 2 parts of each of the 5' arm, 3' arm and vector fragment.

Part as employed herein refers to a quantity such as a volume, the absolute amount of which can be varied provided the overall proportion in a mixture remains the same, by way of example only where 1 part is 10 mls then 20 mls of DNA ligase, 40 mls of ligase buffer and 20 mls of the 5' arm and 20 mls of the 3' arm will be employed.

In one embodiment about 2 μl of eluted DNA contains about 40 ng of DNA. In one embodiment about 120 ng of DNA are ligated. In one embodiment the 120 ng of DNA ligated consists of about 40 ng each of the 5' arm the 3' arm and the vector fragment.

DNA ligase as employed herein refers to an enzyme that ligates (facilitates the joining) of DNA molecules by catalysing the formation of the phosphodiester bond. In one embodiment the DNA ligase is T4 DNA ligase. T4 DNA ligase is an enzyme derived from bacteriophage T4.

Ligase buffer as employed herein refers to a buffered solution, for example containing magnesium chloride and ATP, such as 50 mM Tris-Hcl, 10 mM $MgCl_2$ and 1 mM ATP.

Circularised or circular as employed herein refers to the ends of a linear piece of DNA being joined to form a circle or loop.

In one embodiment the one-step three-way ligation is performed for at least 30 minutes, for example at least 50 minutes, such as about 1 hour, more specifically 51, 52, 53, 54, 55, 56, 57, 58, 59, 60, 61, 62, 63, 64, 65, 66, 67, 68, 69 or 70 minutes.

In one embodiment the one-step three-way ligation is performed at approximately room temperature, such as about 15 to 25° C., such as 16, 17, 18, 19, 20, 21, 22, 23, or 24° C. Preferably 16 to 24° C.

In one embodiment the method of making an adenovirus shuttle vector comprising the steps:

a) Identifying a suitable restriction sites in the adenovirus genome,
b) creating a 5' PCR arm and a 3' PCR arm, for example by amplifying the 5' end and the 3' end of the genome and inserting a linking restriction site at each terminal end upstream of the ITR therein,
c) selecting and amplifying a vector fragment with a low copy bacterial origin of replication and a selection marker gene and terminal linking restriction sites and terminating in linking restriction sites that permit ligation to the 5' arm and the 3' arm,
d) double digesting the 5' PCR arm and the 3' PCR arm from step b) for about 2 hours at about 37° C., wherein the double digest takes place in buffer, restriction enzymes and nuclease free water followed by heat inactivation at about 65° C. for about 20 minutes to obtain the 5' arm and the 3' arm,
e) single digesting the vector fragment from step b) for about 2 hours at about 37° C., wherein the single digest takes place in buffer, restriction enzyme and nuclease free water followed by treatment with alkaline calf phosphatase at about 37° C. for about 1 hour
f) separating the entire volume of the digest products of steps d) and e) on about 0.8% agarose gel, gel purifying and eluting in elution buffer,
g) ligating the digested 3' arm, 5' arm and vector fragment from step f) in a one-step three-way ligation using DNA ligase and ligase buffer for about 1 hour at room temperature at a 1:1:1 ligation ratio of the 5' arm, 3' arm and vector fragment, and
h) identifying a correctly assembled shuttle vectors by transforming cells with the ligated shuttle vector, growing on a selective medium and screening the colonies.

In one embodiment step a) in the method above is optional and the 3' arm and/5'arm is synthesised with the required restriction site and/or transgene.

In one embodiment the method of making an EnAd shuttle vector comprising the steps:

a) identifying suitable restriction sites in the adenovirus genome,
b) creating a 5' PCR arm and a 3' PCR arm by amplifying the 5' end and the 3' end of the genome and inserting a linking restriction site at each terminal end upstream of the ITR,
c) selecting and amplifying a vector fragment with a low copy bacterial origin of replication and a selection marker gene and terminal linking restriction sites and terminating in linking restriction sites that permit ligation to the 5' arm and the 3' arm,
d) double digesting the 5' PCR arm and the 3' PCR arm for 2 hours at 37° C. at using 20 μl DNA from step b), 4 μl of buffer 4, 2 μl of AscI, 2 μl of PspOMI and 8 μl of nuclease free water or equivalents thereof followed by heat inactivation at 65° C. for 20 minutes to obtain the 5' arm and the 3' arm,
e) single digesting the vector fragment for 2 hours at 37° C. at a concentration of 20 μl DNA from step b), 4 μl of buffer 4, 2 μl of AscI and 8 μl of nuclease free water or equivalents thereof followed by treatment with 1 μl alkaline calf phosphatase at 37° C. for 1 hour,
f) separating the entire volume of the digest products of steps d) and e) on 0.8% agarose gel, gel purifying and eluting in 40 μl of elution buffer or the equivalent thereof,
g) ligating the digested 3' arm, 5' arm and vector fragment from step f) in a one-step three-way ligation using 2 μl T4 DNA ligase and 4 μl ligase buffer for 1 hour at room temperature at a 1:1:1 ligation ratio at 2 μl of each of the 5' arm, 3' arm and vector, and
h) identifying a correctly assembled shuttle vectors by transforming cells with the ligated shuttle vector, growing on a selective medium and screening the colonies.

In one embodiment step a) in the method above is optional and the 3' arm and/5'arm is synthesised with the required restriction site and/or transgene.

The skilled person will appreciate that alternate buffers, ligase and volumes may be used and that the proportions are important rather than absolute volume.

Amplifying as employed herein means the process of increasing a single or a few copies of a piece of DNA, for example across several orders of magnitude, generating thousands to millions of copies of a particular DNA sequence, typically using PCR.

Single digest as employed herein means digesting the DNA with a single restriction enzyme known to target a given site in the DNA sequence.

Double digest as employed herein means digesting the DNA with two different restriction enzymes known to target different sites in the DNA sequence.

Correctly assembled as employed herein means the pieces of DNA have been ligated in the correct orientation and position as intended to provide the shuttle vector desired.

Transforming as employed herein means the genetic alteration of a cell resulting from the direct uptake, incorporation and expression of exogenous genetic material (exogenous DNA) from its surroundings.

Growing as employed herein means culturing as commonly understood by the skilled person.

Screening as employed herein means identifying cells and/or DNA constructs with the desired properties. Typical methods employed include, but are not limited to, PCR using primers that span restriction sites, restriction digests, DNA sequencing.

Upstream as employed herein means before in the direction of reading (i.e. 5' to 3'). Downstream as employed herein means after in the direction of reading (i.e. 5' to 3').

Excision as employed herein means removal of.

In one embodiment the plasmid or shuttle vector further comprises one or more polyadenylation sequences that have been introduced to the DNA construct.

Synthetic as employed herein refers to, for example DNA fragment was made by synthetic chemistry techniques, such as in an automated synthesis.

DNA fragment as employed herein refers to a piece of DNA, in particular a portion of adenovirus genomic DNA or a DNA sequence obtained after manipulation by a method disclosed herein. In one embodiment silent base changes are tolerated.

Silent base changes as employed herein refers to a nucleotide change that does not affect the amino acid sequence encoded due to the redundancy of the genetic code.

Substantially identical as employed herein means the DNA fragment is identical to a piece of shuttle vector save for the addition of one or more novel restriction sites.

Purifying as employed herein refers to decontaminating DNA interest, for example by removing DNA which is not of interest.

In one embodiment the method comprises a further step of propagating a shuttle vector of the present disclosure, for example to obtain greater quantities of it.

In one embodiment ligated DNA is transformed into a bacterial cell or cells, for example about 120 ng of ligated DNA is transformed. In one embodiment the bacterial cells are ultracompetent bacterial cells, such as XL-10 available from Agilent. Alternatively the plasmid prepared by homologous recombination with the shuttle vector may be replicated in, for example *E. coli*, and thus the need to repeat the assembly of the shuttle vector is avoided.

Replacing a DNA Fragment in the Shuttle Vector

In one embodiment the method comprises the step of ligating a DNA fragment into the shuttle vector, for example after excision of a section of the same, in particular to introduce restriction sites and/or transgenes. In one embodiment ration employed is 3:1 DNA fragment to shuttle vector ligation respectively. 3:1 fragment to shuttle vector ligation ratio as employed herein means 3 parts of DNA fragment to 1 part shuttle vector.

In one embodiment the DNA fragment is synthetic or a PCR product. PCR product as employed herein means the DNA fragment was made using PCR.

Further details of modifying the shuttle vector are given in the examples and figures.

Thus the present disclosure provides for the first time an adenovirus shuttle vectors and plasmids that is essentially modular and allows the skilled person to manipulate the adenovirus genome at will.

Preparing the Plasmid

Figure 2:
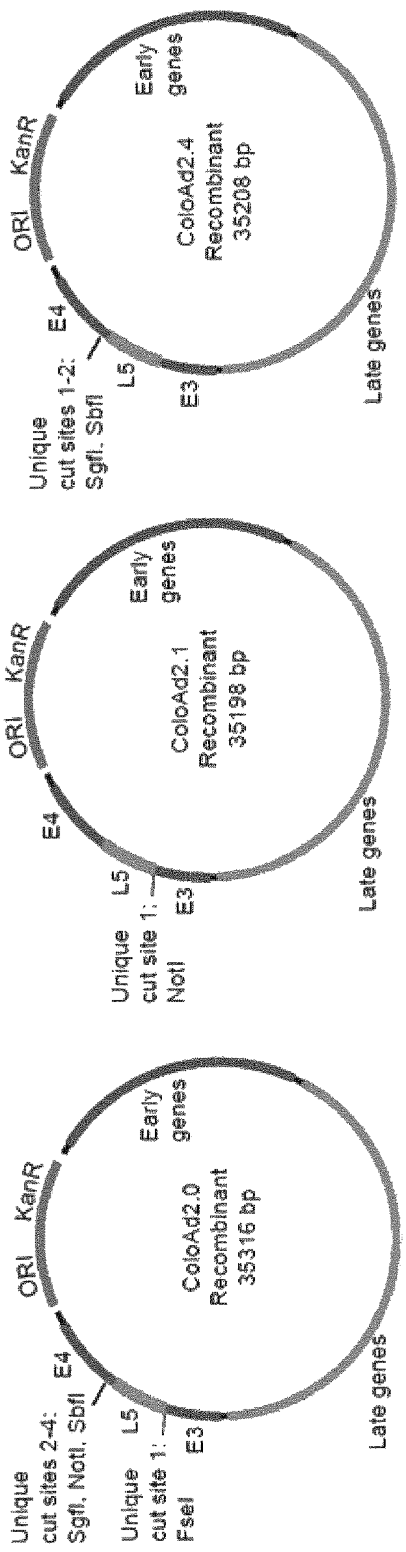
FIG. 2 shows schematics of the ColoAd plasmids—ColoAd2.0, ColoAd2.1 and ColoAd2.4.

Plasmid as employed herein refers to a small DNA molecule that is physically separate from, and can replicate independently of, chromosomal DNA within a cell. For the purpose of the present disclosure a plasmid is a circular DNA vector generally comprising substantially all of the adenovirus genome joined to a vector fragment comprising a bacterial origin of replication and a selection marker gene (see FIG. 2).

Generally the plasmid according to the present disclosure is prepared by homologous recombination of the linearised shuttle vector with an adenovirus genome. Adenovirus genome in this context refers to all or almost all the adenovirus genome. The skilled person will know that this step is part of reassembling the adenovirus and generally is a precursor to realising the adenovirus construct of the present disclosure. Thus the adenovirus genome employed in the recombination step generally comprises all the functional elements, except perhaps a transgene, that will be in the final adenovirus.

In one embodiment the method of performing homologous recombination comprises the steps:

a) linearising the shuttle vector by digesting at the third restriction enzyme site,
b) performing homologous recombination between the linearised shuttle vector and the adenovirus genome in electrocompetent cells,
c) identifying a correctly recombined plasmids by growing the cells on a selective medium and screening the colonies.

Linearising as employed herein refers to the process of making circular DNA into linear DNA, typically by digesting the DNA construct with a single restriction enzyme.

In one embodiment the homologous recombination is performed at a 3.5:1.5 shuttle vector to genome ratio.

Electrocompetent as employed herein means cells that are transformed by means of electroporation. Suitable electrocompetent cells include, but are not limited to, BJ5183 cells.

Correctly recombined as employed herein means the plasmids that have undergone homologous recombination have obtained the desired DNA sequence.

In one embodiment the method comprises the further step of introducing a transgene cassette into the plasmid at a restriction site of interest. Restriction site of interest refers to a site identified as occurring in the genome at a location amenable to the insertion of a transgene cassette. Typically restriction sites of interest are the original restriction sites introduced into the shuttle vector and/or plasmid by the method disclosed herein.

In one embodiment the step of introducing a transgene cassette into a plasmid comprises performing a ligation between linearised plasmid and transgene cassette.

In one embodiment the step of introducing a transgene cassette into the plasmid comprises:

linearising a plasmid and the transgene cassette,
separating the linearised DNA,
purifying the separated linearised DNA,
ligating the plasmid and transgene cassette,
transforming the ligated DNA, for example into *E. coli*, and
selecting correctly transformed colonies.

Figure 7:
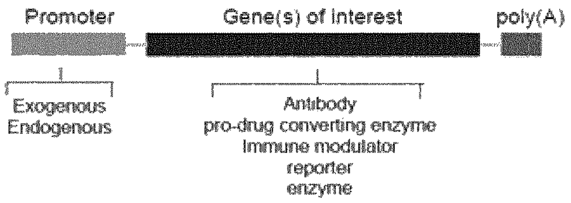
FIG. 7 shows a generic transgene cassette design for insertion into the ColoAd2.4 plasmid or ColoAd2.4 shuttle vector.

Transgene cassette as employed herein refers to, for example a segment of DNA optionally containing a promoter, which is a regulatory sequence that will determine where and when the transgene is active, or a splice site which is a regulatory sequence determining when a mRNA molecule will be cleaved by the splicesome, a protein coding sequence (i.e. the transgene), usually derived from the cDNA for the protein of interest, optionally containing a polyA sequence and a stop sequence. FIG. 7 represents a generic transgene cassette.

In one embodiment the transgene cassette comprises an exogenous promoter, for example a mammalian promoter.

In one embodiment the transgene cassette comprises a regulatory element such as internal ribosome entry sequence.

In one embodiment the transgene cassette comprises a polyA sequence.

In one embodiment, the virus or viral vector can be recovered from the plasmid by cutting the genome with restriction enzymes at the 3' and 5' ends of the sequence to excise the vector fragment DNA comprising the origin of replication and selection marker gene. In one embodiment the same restriction enzyme cuts both sites. The linearised DNA can then be inserted into a suitable host cells, such as a HEK293 cell to generate the final virus or viral vector.

Transgene

In one embodiment one or more transgenes in the transgene cassette are selected from:

a therapeutic gene of interest which encodes a therapeutic protein, peptide or RNA such as an antibody or antibody domain, pro-drug converting enzyme, immunomodulator, enzyme, siRNA, transcription factor, intracellular signalling or surface membrane protein, or antigen.

Antibody as employed herein means a large Y-shaped protein produced by B-cells that is used by the immune system to identify and neutralize foreign pathogens, such as bacteria and viruses. The antibody recognises a unique part of the foreign antigen. A wide range of different forms of antibody may be employed including monoclonal antibodies, polyclonal antibodies, diabodies, chimeric antibodies, humanised antibodies, bi- and tri-specific antibodies, camalid antibodies, Fab fragments, Fc fragments and Fv molecules, including single-chain Fv (ScFv) antibodies.

Pro-drug as employed herein refers to a molecule that is administered as an inactive (or less than fully active) derivative that is subsequently converted to an active pharmacological agent in the body, often through normal metabolic processes or by use of an appropriate enzyme. Thus a pro-drug serves as a type of precursor to the intended drug. A pro-drug converting enzyme serves as the enzyme that converts a pro-drug to its pharmacologically active form. In one embodiment a viral construct according to the present disclosure encode and expresses in vivo a pro-drug and an appropriate converting enzyme.

Immunomodulator as employed herein means a modulator of an immune response. Immunomodulators function in adjusting the quality and quantity of the immune response in a desired direction or to a desired level, as in immunopotentiation, immunosuppression, or induction of immunologic tolerance. In one embodiment the immunomodulator is a immunostimulant, for example an adjuvant, such as a DNA sequence rich in CpG.

Enzyme as employed herein refers to a protein suitable for catalyse a specific chemical reaction, for example regulating the rate at which chemical reactions proceed without itself being altered in the process. In one embodiment the enzyme is capable of catalysing a reaction in a living organisms. Reporter gene as employed herein refers to a gene that produces a product easily detected in eukaryotic cells and may be used as a marker to determine the presence or activity the gene of interest. In one embodiment the reporter gene DNA is closely linked or combined with the DNA sequence of interest. In one embodiment the reporter gene is, for example, luciferase and fluorescent protein such as GFP.

In one embodiment the transgene or genes encode reporter genes for in vitro imaging and localisation such as, but not limited to: Sodium iodide symporter (NIS), intracellular metalloproteins (e.g. ferritin, tyrosinase), herpes simplex virus type 1 thymidine kinase (HSV1-tk), GFP and other fluorophores, luciferase, estrogen receptor and other inducible reporter genes.

In one embodiment the transgene is not a reporter gene or imaging agent, such as luciferase or eGFP. Exogenous mammalian promoter as employed herein refers to a DNA element, usually located upstream of the gene of interest, that regulates the transcription of a gene.

Regulatory element as employed herein refers to a DNA sequence that either permits use of endogenous promoters, such as the major late promoter, or other DNA sequence that regulates expression, for example expression of multiple genes, such as polycystronic sequences.

Internal ribosome entry sequence (IRES) as employed herein refers to a nucleotide sequence that allows for translation initiation in the middle of a messenger RNA (mRNA) sequence.

PolyA sequence as employed herein refers to a DNA sequence, usually containing an AATAAA site, that once transcribed can be recognised by a multiprotein complex that cleaves and polyadenylates the nascent mRNA molecule.

(Therapeutic) gene of interest as employed herein means a gene suitable of for generating a pharmacological effect (generally a beneficial pharmacological effect), for example after expression, in particular the activity may enhance the utility or therapy of the DNA construct or the adenovirus of the present disclosure, such as oncolytic virus activity.

A range of different types of transgene (and combinations thereof) are envisaged that encode molecules that themselves act to modulate tumour or immune responses and act therapeutically, or are agents that directly or indirectly inhibit, activate or enhance the activity of therapeutic molecules. Molecules, which may be encoded include protein ligands or active binding fragments of ligands, antibodies (for example, full length or fragments, such as Fv, ScFv, Fab, F(ab)'2 or smaller specific binding fragments), or other target-specific binding proteins or peptides (e.g. as may be selected by techniques such as phage display etc), natural or synthetic binding receptors, ligands or fragments, specific molecules regulating the transcription or translation of genes encoding the targets, such as siRNA or shRNA molecules, transcription factors and the like. Molecules may be in the form of fusion proteins with other peptide sequences, for example to enhance their activity, stability, specificity etc. In one embodiment, ligands may be fused with immunoglobulin Fc regions to form dimers and enhance stability or provide effector function. In one embodiment the transgene may encode a fusion protein, for example with an entity fused to antibodies or antibody fragments having specificity to antigen presenting cells such as dendritic cells e.g. anti-DEC-205, anti-mannose receptor, anti-dectin.

In one embodiment inserts may also encode reporter genes that can be used, for example to detect cells infected with the adenoviruses or adenoviral vectors according to the invention, imaging of tumours or draining lymphatics and lymph nodes etc.

In one embodiment proteins encoded are human, for example human antibodies or natural ligands to molecules listed below, or siRNA molecules targeting them, or tumour antigens.

In one embodiment the transgene or genes encode T-cell costimulatory receptors or their ligands such as, but not limited to: OX40, OX40 ligand, CD27, CD28, CD30, CD40, CD40 Ligand (CD40L), CD137, GITR, 4-1BB, ICOS, ICOS ligand.

In one embodiment the transgene or genes encode T-cell co-inhibitory molecules or their ligands (checkpoint inhibitory receptors and ligands) such as, but not limited to: Cytotoxic T lymphocyte associated antigen-4 (CTLA-4), programmed cell death-1 (PD-1), PD-Ligand-1 (PD-L1, also known as B7-H1), PD-Ligand-2 (PD-L2, also known as B7-DC), other B7 receptor superfamily members such as B7-H3, B7-H4, herpes virus entry mediator (HVEM), inhibitory receptor Ig-like transcript-3 (ILT-2), ILT-3, ILT-4, T-cell immunoglobulin mucin protein-3 (TIM-3), lymphocyte activation gene-3 (LAG-3), B and T lymphocyte attenuator (BTLA), LIGHT (homologous to lymphotoxin, exhibits inducible expression, and competes with HSV glycoprotein D for herpes virus entry mediator, a receptor expressed by T lymphocytes), CD160.

In one embodiment the transgene or genes encode molecules expressed by regulatory T-cells (natural and induced Tregs, Tr1 etc), Myeloid derived suppressor cells (MDSCs) & other Immunosuppressive Immune cells such as, but not limited to: CD16, CD25, CD33, CD332, CD127, CD31, CD43, CD44, CD162, CD301a, CD301b, and Galectin-3.

In one embodiment the transgene or genes encode dendritic cell (and other antigen-presenting cell) receptors or their ligands such as, but not limited to: Fms-related tyrosine kinase 3 (FLT-3), FLT-3 ligand, Toll-like receptors (TLR) and their ligands (e.g. TLR-9, flagellin as ligand for TLR-5), CCR7 (CD197), CD1a, CD1c (BDCA-1), CD11b, CD11c, CD80 (B7-1), CD83, CD86 (B7-2), CD123 (IL-3Rα), CD172a (SIRPα), CD205 (DEC205), CD207 (Langerin), CD209 (DC-SIGN), CD273 (B7-DC), CD281 (TLR1), CD283 (TLR3), CD286 (TLR6), CD289 (TLR9), CD287 (TLR7), CXCR4 (CD184), GITR Ligand, IFN-α2, IL-12, IL-23, ILT1 (CD85h), ILT2 (CD85j), ILT3 (CD85k), ILT4 (CD85d), 27D6 5148, 42D1 5149, ILT5 (CD85a), ILT7 (CD85g), TSLP Receptor, CD141 (BDCA-3), CD303 (CLEC4c, BDCA-2), CADM1 (NECL2), CLEC9a, XCR1, CD304 (Neuropilin-1, BDCA-4).

In one embodiment the transgene or genes encode antigen processing and presentation mediators such as, but not limited to: MHC Class II transactivator (CTIIA), Gamma-IFN-inducible lysosomal thiol reductase (GILT).

In one embodiment the transgene or genes encode cytokines or their receptors such as, but not limited to: Interleukin-1α (IL-1α), IL-1β, IL-6, IL-9, IL-12, IL-13, IL-17, IL-18, IL-22, IL-23, IL-24, IL-25, IL-26, IL-27, IL-33, IL-35. Interleukin-2 (IL-2), IL-4, IL-5, IL-7, IL-10, IL-15, IL-21, IL-25, IL-1 receptor antagonist (IL-1RA), interferon-α (IFNα), interferon-β (IFNβ), interferon γ (IFNγ), tumour necrosis factor-α (TNFα), transforming growth factor-β (TGFβ-different subtypes), granulocyte macrophage colony stimulating factor (GM-CSF).

In one embodiment the transgene or genes encode chemokines or chemokine receptors such as, but not limited to: Interleukin-8 (IL-8), CCL5 (RANTES), CCL17, CCL22, CCL20, CXCL9, CXCL10, CXCL11, CXCL13, CCR2, CCR4, CCR5, CCR6, CCR7, CCR8, CXCR3, CXCR4, CXCR5, CRTH2.

In one embodiment the transgene or genes encode transcription factors or other regulators of transcription such as, but not limited to: STAT3, STAT1, STAT4, STATE, CTIIA, MyD88, NFκB family members.

In one embodiment the transgene or genes encode pro-drug converting enzymes or other enzymes such as, but not limited to: cytosine deaminase and tyrosine kinases.

In one embodiment the transgene or genes encode intracellular trafficking molecules or regulators of cell function such as, but not limited to: Heat shock protein-70 (HSp70), regulators of cell survival and death (e.g. survivin).

In one embodiment the transgene or genes encode tumour cell or tumour microenvironmental receptors and products such as, but not limited to: EGF Ligands & receptors: amphiregulin, betacelluin (BTC), neuroregulin-1a (NRG1a), NRG1b, NRG3, transforming growth factor-a (TGFa), LRIG1 (leucine-rich repeat and Ig-like domain-containing-1), LRIG3, EGF, EGF-L6, Epigen, HB-EGF, EGFR (ErbB1), Her2 (ErbB2, Her3 (ErbB3), Her4 (ErbB4).

In one embodiment the transgene or genes are ligands & receptors for families of molecules such as, but not limited to: hedgehog, FGF, IGF, Wnt, VEGF, TNF, TGFb, PDGF, Notch.

In one embodiment the transgene or genes encode intracellular tumour cell enzymes such as but not limited to: Indoleamine 2,3 dioxygenase (IDO).

In one embodiment the transgene or genes encode antigens for recognition by immune cells such as but not limited to: Foreign immunogenic proteins from infectious organisms as antigens (e.g. cytomegalovirus antigens, influenza antigens, hepatitis B surface and core antigens, diphtheria toxoid, Crm197, tetanus toxoid), peptides derived from such antigens which are known T-cell or antibody epitopes, or genetically engineered composites or multimers of such antigens.

In one embodiment the transgene or genes encode tumour-derived proteins as antigens, peptides derived from such antigens which are known T-cell or antibody epitopes, or genetically engineered composites or multimers of such antigens. Such antigens could include, for example, WT1, MUC1, LMP2, Idiotype, HPV E6&E7, EGFRvIII, HER-2/neu, MAGE A3, p53 nonmutant, p53 mutant, NY-ESO-1, GD2, PSMA, PCSA, PSA, gp100, CEA, MelanA/MART1, Ras mutant, Proteinase3 (PR1), bcr-abl, Tyrosinase, Survivin, PSA, hTERT, Sarcoma translocation breakpoints, EphA2 PAP ML-IAP AFP EpCAM, ERG (TMPRSS2 ETS fusion gene), NA17, PAX3, ALK, Androgen receptor, Cyclin B1, Polysialic acid, MYCN, RhoC, TRP-2, GD3, Fucosyl GM1, Mesothelin, PSCA, MAGE A1, sLe(a), CYP1B1, PLAC1, GM3, BORIS, Tn, GloboH, ETV6-AML, NY-BR-1, RGS5, SART3, STn, Carbonic anhydrase IX, PAX5, OY-TES1, Sperm protein 17, LCK, HMWMAA, AKAP-4, SSX2, XAGE 1, B7H3, Legumain, Tie 2, Page4, VEGFR2, MAD-CT-1, FAP, PDGFR-β, MAD-CT-2, Fos-related antigen 1 (Cheever et al 2009).

As employed herein pNG-62 means a plasmid comprising ColoAd2.4 genome and a transgene cassette comprising a gene encoding GFP (see SEQ ID NO: 35, FIG. 30).

Preparing Adenoviruses

The present disclosure also provides a method of generating recombinant adenoviruses wherein the early genes, for example those essential for virus replication, particularly E1 and/or E3 can remain intact or an adenoviral vector where genes essential to viral replication are deleted according to the intended purpose. Thus the disclosure facilitates the genetic engineering of live oncolytic viruses, for example the ability to arm them with therapeutic proteins in regions that was not previously possible. The final adenovirus according to the present disclosure may be provided excising the genomic DNA of the from the plasmid with appropriate restriction enzyme, followed by, for example a ligation step to complete, circularise the genome. Thus a virus or viral vector may be recovered from the plasmid by cutting the genome with restriction enzymes at the 3' and 5' ends of the sequence to excise the vector fragment DNA comprising the origin of replication and selection marker gene. In one embodiment the same restriction enzyme cuts both sites. The linearised DNA can then be inserted into a suitable host cells, such as a HEK293 cell to generate the final virus or viral vector.

Shuttle Vectors, Plasmids and Adenoviruses

In one embodiment there is provided an adenovirus shuttle vector, for example obtainable as an intermediate from the method of the disclosure.

Shuttle vectors of the present disclosure comprise 3' arm contain the virus fibre gene. Details of the shuttle vector given above in relation the method are also relevant to the shuttle vector per se embodiments. Shuttle vectors of the present disclosure contain a relatively large amount of adenovirus genomic DNA, for example in range of about 9 Kb to about 11.9 Kb. In one embodiment 50% or more, for example 60, 70, 75 or 80% of the shuttle vector is adenovirus genomic DNA. In one embodiment the shuttle vector in total is about 15 Kb or less, for example 14, 13 or 12 Kb. In contrast, the major part of prior art vectors is the transgene and regulatory elements.

In one aspect there is provided a shuttle vector comprising:

a) a vector fragment comprising an origin of replication, a selection marker, b) a 3'arm comprising at least the fibre gene (L5) and optionally further comprising an E3 site, an E4 or both said sites.

In one embodiment the shuttle vector does not comprise a transgene and/or any regulatory elements associated with a transgene, for example promoters, IRES sequences are similar. This is because the shuttle vector as employed in the present disclosure was developed for introducing mechanisms into the viral genome to facilitate flexible genetic engineering of the virus, as opposed to simply introducing one transgene into the virus.

In one embodiment the shuttle vector is a circular DNA shuttle vector comprising a 5' arm of an adenovirus genome linked directly to a 3' arm of the adenovirus genome via a suitable restriction site, (described above as the third restriction enzyme site) such that the "middle sequence" of the adenovirus genome is absent. The 3' arm and the 5' arm together are referred to herein as the major fragment of the shuttle vector The 3' and 5' ends of the major fragment are turn joined to a vector fragment containing a low copy bacterial origin of replication and a selection marker gene via a linking restriction site (see FIGS. 6 and 8).

Alternatively, as discussed above the shuttle vector may comprise one or more transgenes, for example in the 3' arm of the shuttle vector.

In one embodiment the shuttle vector further comprises a 5' arm. The 5' arm employed in the shuttle vector are the same as the relevant components defined elsewhere, for example described in the context of the method.

In one embodiment the shuttle vector comprises at least one original restriction site, for example that has been introduced to the genome using standard techniques with which the skilled person is familiar. In one embodiment the shuttle vector has the sequence SEQ ID NO: 2. In one embodiment the shuttle vector has the sequence SEQ ID NO: 15. In one embodiment the shuttle vector has the sequence SEQ ID NO: 17. In one embodiment the shuttle vector has the sequence SEQ ID NO: 26.

In one embodiment there is provided an adenovirus plasmid obtainable by the method of the invention.

In a further aspect there is provided a plasmid comprising:

a) an adenovirus genome comprising an L5 gene, an E3 site and an E4 site, b) at least one original restriction site in a location between the L5 gene and a site selected from the group consisting of the E3 site, the E4 site and each of the E3 site and the E4 site, c) a low copy bacterial origin of replication, and d) a selection marker gene.

Advantageously the new plasmids provide novel, original restrictions sites that are in the vicinity of the late-expressed L5 fibre gene. Insertion of transgenes in this location is less likely to interfere with viral stability and replication. In one embodiment the plasmid comprises at least one original restriction site that has been introduced to the genome using standard techniques with which the skilled person is familiar. In one embodiment the plasmid further comprises a transgene cassette. In one embodiment the plasmid has the sequence SEQ ID NO: 28. In one embodiment the plasmid has the sequence SEQ ID NO: 30. In one embodiment the plasmid has the sequence SEQ ID NO: 31.

In a yet further aspect there is provided an adenovirus or adenoviral vector obtainable from the plasmid according to the invention.

In one embodiment adenoviruses or viral vectors contain a small transgenes, for example capable of being inserted without deleting any of the genome. In one embodiment adenoviruses or adenoviral vectors may contain small transgenes capable of being inserted without deleting any of the genome, for example one or more genes which in total are 4.5 kb or less.

In one embodiment the adenovirus or viral vector obtained by the method or from the plasmid according to the present disclosure may contain larger transgenes. In one embodiment a replication competent adenoviruses has additional space (such as EnAd) in the genome, for example because a gene which non-essential to replication is removed, for example part or all of the E3 and/or E4orf4 region is deleted. In one embodiment there is provided a conditionally replicating adenovirus wherein space in the genome has been created by deletion of, for example part or all of the E3 and/or E4orf4 region.

In one embodiment non-replicating adenovirus (i.e. those that need a packaging cell line to replicate) has one or more genes, for example early genes deleted, for example part or all of one or more genes independently selected from E1, E2, E3 and E4 (such as E4 orf4).

In one embodiment the engineered virus is a live replication competent virus.

In one embodiment the engineered virus is replication deficient viral vector. In one embodiment the E1 gene in a viral vector of the present disclosure is deleted. In one embodiment viral vector as employed herein refers to a DNA molecule used as a vehicle to artificially carry genetic material, for example a transgene, into another cell such as a mammalian cell where it can be replicated and/or expressed.

In one embodiment the engineered adenovirus construct of the present disclosure comprises one or more transgenes.

In one embodiment part or all of the E4 gene is deleted in a virus or viral vector according to the present disclosure, such as the E4orf4 section of the gene is deleted.

In one embodiment part or all or the E3 gene is deleted in a virus or viral vector according to the present disclosure.

In one embodiment the E3 gene and part or all of the E4 gene is deleted in a virus or viral vector according to the present disclosure.

In one embodiment part or all of the L5 gene is deleted in a virus or viral vector according to the present disclosure. In a virus of the present disclosure partial deletion of the L5 is allowed provided the L5 function is retained because this function is essential for virus replication.

In one embodiment part or all of the E2 region is deleted in a virus or viral vector according to the present disclosure.

In one embodiment there is provided an adenovirus or adenoviral vector of the present disclosure, for example obtainable from the adenovirus plasmid of the present disclosure.

In one embodiment there is provided use of an adenovirus or adenoviral vector, of the present disclosure, for example obtainable from the plasmid according to the invention in treatment. In another aspect there is provided use of an adenovirus or adenoviral vector obtainable from the plasmid according to the invention in treatment.

The skilled person will appreciate that adenoviruses or adenoviral vectors generated from the plasmid of the invention may be used either as a therapeutic, for example an oncolytic or as a vaccine, or as the gene delivery vector where the virus cannot replicate without the aid of a packaging cell.

In an additional aspect there is provided use of an adenovirus or adenoviral vector, of the present disclosure, for example obtainable from the plasmid according to the invention in treatment of cancer. In another aspect there is provided use of an adenovirus or adenoviral vector of the present disclosure, for example obtainable from the plasmid according to the invention in vaccine therapy.

Obtainable by as employed herein means any plasmid or adenovirus with characteristics of the entity generated utilising a method of the present disclosure. In embodiment obtainable from as employed herein means any adenovirus that can be generated from the adenovirus genome excised from a plasmid of the invention.

In one embodiment adenoviruses or adenoviral vectors of the present disclosure may contain small transgenes capable of being inserted without deleting any of the genome, for example one or more genes which in total are 4.5 kb or less.

In one embodiment there is provided use of an adenovirus or adenoviral vector of the present disclosure, for example obtainable from the plasmid according to the invention in treatment.

Formulations and Methods of Treatment

In a further aspect there is provided a composition comprising an adenovirus or adenoviral vector of the present disclosure, for example obtainable from the plasmid according to the invention and a pharmaceutically acceptable excipient.

The skilled person will appreciate that adenoviruses generated from the plasmid of the invention can be used either as a therapeutic, for example an oncolytic or a vaccine, or as the gene delivery vector where the virus cannot replicate without the aid of a packaging cell, i.e. is a viral vector.

In one embodiment there is provided use of an adenovirus or adenoviral vector obtainable from the plasmid according to the invention in the manufacture of a medicament for the treatment of cancer. Vaccine-based therapy as employed herein means a delivery (e.g. intramuscular, subcutaneous, intradermal, topical, sublingual, intranasal, oral, vaginal or rectal), or a series of such deliveries, of adenoviral vectors of the invention comprising transgenes that encode one or more antigens in order to induce an immune response or quantitatively and/or qualitatively modify an established immune response to the antigens for therapeutic benefit. Whereby each delivery may be formulated with or accompanied by delivery of immunomodulatory agents, for example adjuvants, immunomodulatory peptides, proteins or small molecules as will be understood by the skilled person.

In one embodiment there is provided an effective dose of the adenovirus or adenoviral vector obtainable from the plasmid according to the present disclosure and a pharmaceutically acceptable excipient.

The pharmaceutically acceptable excipient or carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the virus may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the virus, for example if the pH of the formulation is 7 then a pH of from 8-9 or above may be appropriate. Whilst not wishing to be bound by theory it is thought that this may ultimately provide a final formulation with improved stability, for example the virus remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be a virus. As such, it will be susceptible to degradation in the gastrointestinal tract. Thus, if the composition is to be administered by a route using the gastrointestinal tract, the composition will need to contain agents which protect the virus from degradation but which release the virus once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the virus) is of primary importance.

The propellant gases which can be used to prepare the inhalable aerosols are known in the art. Suitable propellant gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellant gases may be used on their own or in mixtures thereof.

Particularly suitable propellant gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellant-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebuliser, for example, a nebuliser connected to a compressor (e.g., the Pari LC-Jet Plus® nebulizer connected to a Pari Master® compressor manufactured by Pari Respiratory Equipment, Inc., Richmond, Va.).

The virus of the invention can be delivered dispersed in a solvent, for example in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension may employ, for example, lyophilised virus diluted on site with a sterile isotonic carrier.

The therapeutic suspensions or solution formulations may also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form.

Sterile manufacturing processes may include production of the virus and sterilisation by filtration of the buffered solvent/solution used for the formulation, aseptic suspension of the virus in the sterile buffered solvent solution, and dispensing of the formulation into sterile receptacles by methods familiar to those of ordinary skill in the art.

Formulations according to the present disclosure, including doses for nebulisation, parenteral, topical, and oral may be provided, for example, as single dose units (such as in the form of sealed plastic containers or vials). In one embodiment each vial contains a unit dose in a volume of solvent/solution buffer, for example in a 2 mL volume.

Solvent, solution, carrier and the like are employed interchangeably herein, unless the context indicates otherwise.

In one embodiment formulations according to the present disclosure, including unit dose formulations are packed in foil envelopes.

In one embodiment the virus constructs, formulations according to the present disclosure for use in treatment are administered paretherally. In one embodiment the virus construct, formulations according to the present disclosure are administered topically, for example intra-nasally, to the colon, to the lung, to the eye or similar. In one embodiment the virus constructs, formulations according to the present disclosure are administered orally.

In one embodiment the viruses disclosed herein may be suitable for delivery via nebulisation.

Thus there is provided use of an adenovirus of the present disclosure or a composition comprising the same for use in treatment, for example cancer, in particular by administering a therapeutically effective amount to a patient in need thereof. Also provided is use of an adenovirus of the present disclosure for the manufacture of a medicament.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Technical references such as patents and applications are incorporated herein by reference.

Any embodiments specifically and explicitly recited herein may form the basis of a disclaimer either alone or in combination with one or more further embodiments.

Aspects of the present disclosure are described in the sequences and the figures, which may form the basis of an amendment. The disclosure of the figures and sequences have general application to the teaching of the present disclosure and not intended to considered as simply very specific combinations of features. The priority filing GB1322851.5 is incorporated herein by reference as is the contents of PCT application PCT/EP2014/072919 including the sequence listing thereof.

EXAMPLES

Ad11 Genome:

| Region | DNA sequence (map units) | No. of nucleotides/ % of total genome | ORF | Position of ORF (nt) |
|---|---|---|---|---|
| ITR | 1-137 (0-0.38) | 137/0.38 | — | |
| E1 A | 480-1504 (1.4-4.3) | 1025/3.0 | 262R | 568-1147, 1232-1440 |
| | | | 231R | 568-1054, 1232-1440 |
| | | | 58R | 568-639, 1232-1336 |
| E1 B | 1556-3930 (4.5-11.3) | 2375/6.8 | 21K | 1610-2152 |
| | | | 55K | 1915-3399 |
| | | | IX | 3483-3902 |
| E2 A | 23402-21803 (67.3-62.7) | 1600/4 · 6 | DNA binding protein (DBP) | 23402-21846 |
| E2 B | 10342-3963 (29.7-11.4) | 6380/18 · 3 | IVa2 | 5588-5576, 5297-3964 |
| | | | Polymerase | 8435-5067 |
| | | | pTP | 10354-8438 |
| E3 | 26867-30625 (77.2-88) | 3759/10.8 | 12.1K | 27185-27502 |
| | | | 16.1K | 27456-27851 |
| | | | 18.5K | 27836-28336 |
| | | | 20.3K | 28356-28901 |
| | | | 20.6K | 28919-29482 |
| | | | 10.3K | 29526-29801 |
| | | | 15.2K | 29806-30210 |
| | | | 15.3K | 30203-30610 |
| E4 | 34493-31808 (99.1-91.4) | 2686/7.7 | 125R | 34413-34036 |
| | | | 130R | 33990-33601 |
| | | | 117R | 33604-33251 |
| | | | 122R | 33242-32874 |
| | | | 299R | 32971-32072 |

-continued

| Region | DNA sequence (map units) | No. of nucleotides/ % of total genome | ORF | Position of ORF (nt) |
|---|---|---|---|---|
| L1 | 10648-13614 (3.6-39.1) | 2967/8.5 | 55K | 10648-11814 |
| | | | pIIIa | 11840-13603 |
| L2 | 13683-17340 (39.3-49.8) | 3658/10.5 | Penton base | 13683-15368 |
| | | | pVIII | 15380-15958 |
| | | | V | 16001-17056 |
| | | | pX | 17085-17315 |
| L3 | 17399-21796 (50-62.6) | 4398/12.6 | pVI | 17399-18139 |
| | | | Hexon | 18255-21101 |
| | | | 23K protease | 21138-21767 |
| L4 | 23433-27496 (67.3-79) | 4064/11.7 | 100K protein | 23433-25871 |
| | | | 33K | 25603-25921, 26090-26452 |
| | | | pVIII | 26502-27185 |
| L5 | 30812-31797 (88.6-91.4) | 986/2.8 | Fibre | 30812-31789 |
| L6 | 33097-33915 (95.1-97.5) | 819/2.4 | 169R agnoprotein | 33097-33606 |
| ITR | 34658-34794 (99.6-100) | 137/0.38 | — | |

Example 1 Construction of the ColoAd1 Shuttle Vector

Figure 6:
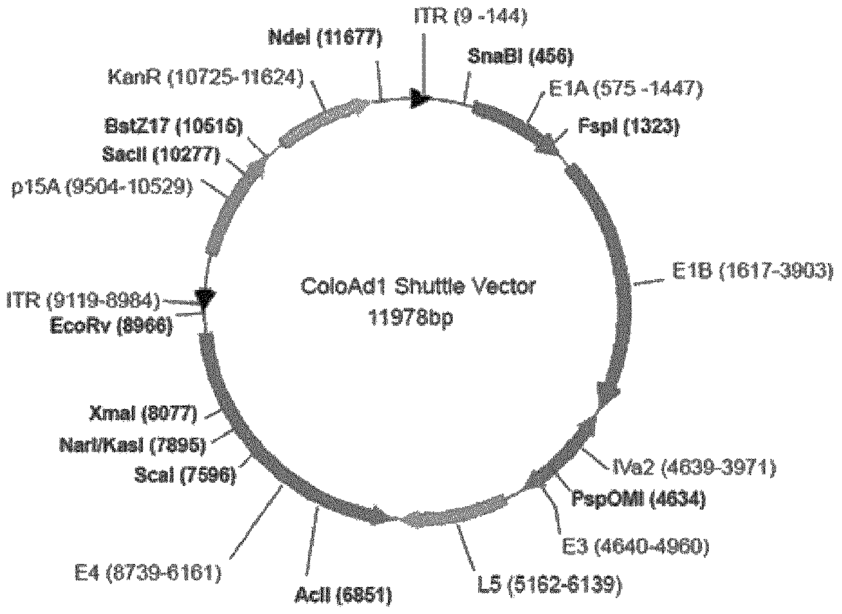
FIG. 6 shows restriction site map of the ColoAd1 shuttle vector

A 11978 bp shuttle vector, referred to as 'ColoAd1 Shuttle Vector', was constructed containing a p15A bacterial origin of replication, a Kanamycin resistance cassette and 5' and 3' arms of ColoAd1 joined by a PspOMI third restriction enzyme site (see FIG. 6).

Three DNA fragments were synthesised by PCR:

1) a "5' arm of ColoAd1" corresponding to the 5' 4627 bp of ColoAd1 with a 5' AscI restriction site and 3' PspOMI restriction site,
2) a "3' arm of ColoAd1" corresponding to the 3' 4482 bp of the ColoAd1 genome with a 5' PspOMI restriction site and 3' AscI restriction site, and
3) a vector fragment containing a low copy p15A origin of replication and a kanamycin resistance cassette flanked by AscI restriction sites PspOMI third restriction site in the 5' arm and the 3' arm was chosen as a suitable restriction site to allow the shuttle vector to be linearised and recombined with the ColoAd1 genome to form a plasmid, without introducing any undesired alterations to the genome sequence.

The restriction site was designed to be near the 5' end of the ColoAd1 genome and also the 3' end of the genome, in particular about 4-5 kb from the ends of the 3' and 5' ITRS such that the shuttle vector had about 4-5 kb 3' and 5' arms, as shown in FIG. 4.

Details of the Fragment Synthesis by PCR

The primers used for the PCR amplifications are listed in Table 1:

| Primer ref number | Primer name | Sequence |
|---|---|---|
| 0196 (SEQ ID NO: 3) | ColoSFVector Asc1 FWD | TTATAGGCGCGCCCTCTCTTAAGGTAGCATCGGG |
| 0197 (SEQ ID NO: 4) | ColoSFVector Asc1 REV | TTATAGGCGCGCCGCTACCTTAAGAGAGAGGTTGA |
| 0198 (SEQ ID NO: 5) | Colo FWD RVS Asc1 | TTGGCGGCGCGCCTATCTATATAATATACC |
| 0199 (SEQ ID NO: 6) | Colo FWD RVS Asc1 Nest | TTGGCGGCGCGCCTATCTA |

-continued

| Primer ref number | Primer name | Sequence |
|---|---|---|
| 0200 (SEQ ID NO: 7) | ColoAd1 5' reverse | AATGCAAATCTGTGAGGGG |
| 0201 (SEQ ID NO: 8) | ColoAd1 3' Forward | CTTAGTGGTGTTGTGGTATTGG |

1) Generation of the 5' arm

Figure 10:
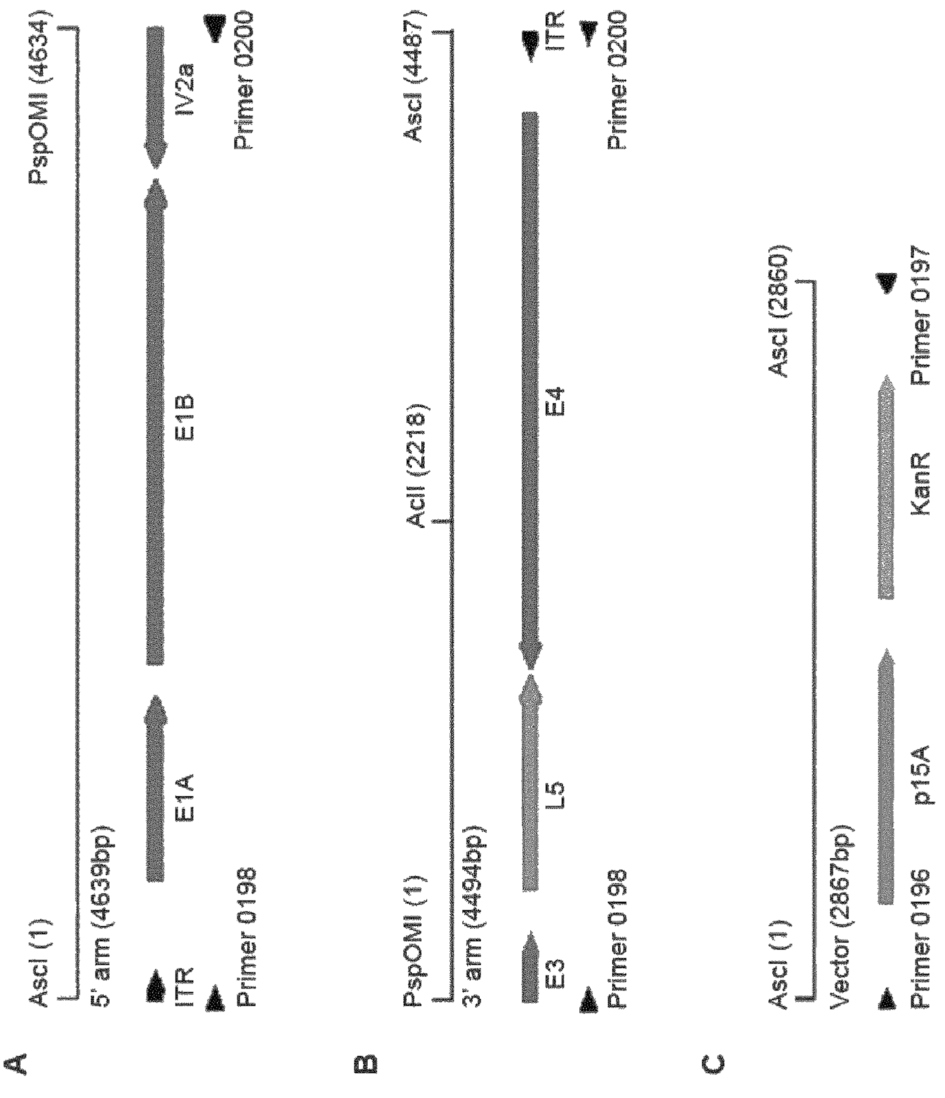
FIG. 10 shows.

To amplify the E1A, E1B and E2B region and the 5' end of ColoAd1 a PCR was performed on native ColoAd1 using primers 0198 (SEQ ID NO.5) and 0200 (SEQ ID NO.7). A 50 μl reaction volume was used for the PCR reaction, according to Table 2 below and a schematic of the PCR product is shown in FIG. 10A.

TABLE 2

| Reagent | Volume (μl) | Supplier |
|---|---|---|
| Phusion PCR Mix | 25 | NEB MO531S |
| Primer 0198 (SEQ ID NO: 5) (10 μM) | 2.5 | Sigma |
| Primer 0200 (SEQ ID NO: 7) (10 μM) | 2.5 | Sigma |
| DNA (ColoAd1) | 1 | Ark Therapeutics |
| Nuclease Free Water | 19 | Fisher Scientific (BPE 2484-100) |

2) Generation of the 3' arm

To amplify the E3, fibre and E4 region and the 3' end of ColoAd1 a PCR was performed on native ColoAd1 using primers 0198 (SEQ ID NO.5) and 0201 (SEQ ID NO.8). A 50 μl reaction volume was used for the PCR reaction as detailed in Table 3 below and a schematic of the PCR product is shown in FIG. 10B.

TABLE 3

| Reagent | Volume (μl) | Supplier |
|---|---|---|
| Phusion PCR Mix | 25 | NEB MO531S |
| Primer 0198 (SEQ ID NO: 5) (10 μM) | 2.5 | Sigma |
| Primer 0201 (SEQ ID NO: 8) (10 μM) | 2.5 | Sigma |
| DNA (ColoAd1) | 1 | Ark Therapeutics |
| Nuclease Free Water | 19 | Fisher Scientific (BPE 2484-100) |

3) Generation of the vector fragment

A third PCR was performed on a vector fragment using primers 0196 (SEQ ID NO.3) and 0197 (SEQ ID NO.4) to produce a ~3 kb fragment containing a p15A origin and a Kanamycin resistance gene with 5' and 3' AscI restriction sites (FIG. 10C). A 50 μl reaction volume was used for the PCR reaction, as detailed in Table 4:

| Reagent | Volume (μl) | Supplier |
|---|---|---|
| Phusion PCR Mix | 25 | NEB MO531S |
| Primer 0197 (SEQ ID NO: 4) (10 μM) | 2.5 | Sigma |
| Primer 0196 (SEQ ID NO: 3) (10 μM) | 2.5 | Sigma |
| DNA (P15A Vector) | 1 | Oxford Genetics |
| Nuclease Free Water | 19 | Fisher Scientific (BPE 2484-100) |

All PCR amplifications employed the following protocol Table 5:

| Step no. | Stage | Temp ( ) | Time (Secs) |
|---|---|---|---|
| Step 1 | Initial Denaturation | 98 | 60 |
| Step 2 | Denaturation | 98 | 8 |
| Step 3 | Annealing | 60 | 20 |
| Step 4 | Extension | 72 | 90 |
| Step 5 | Final Extension | 72 | 300 |
| Step 6 | Hold | 4 | Hold |

30 cycles of amplification were carried out: [Step 1]×1, [Step 2, Step 3, Step 4]×30, [Step 5]×1.

Figure 11:
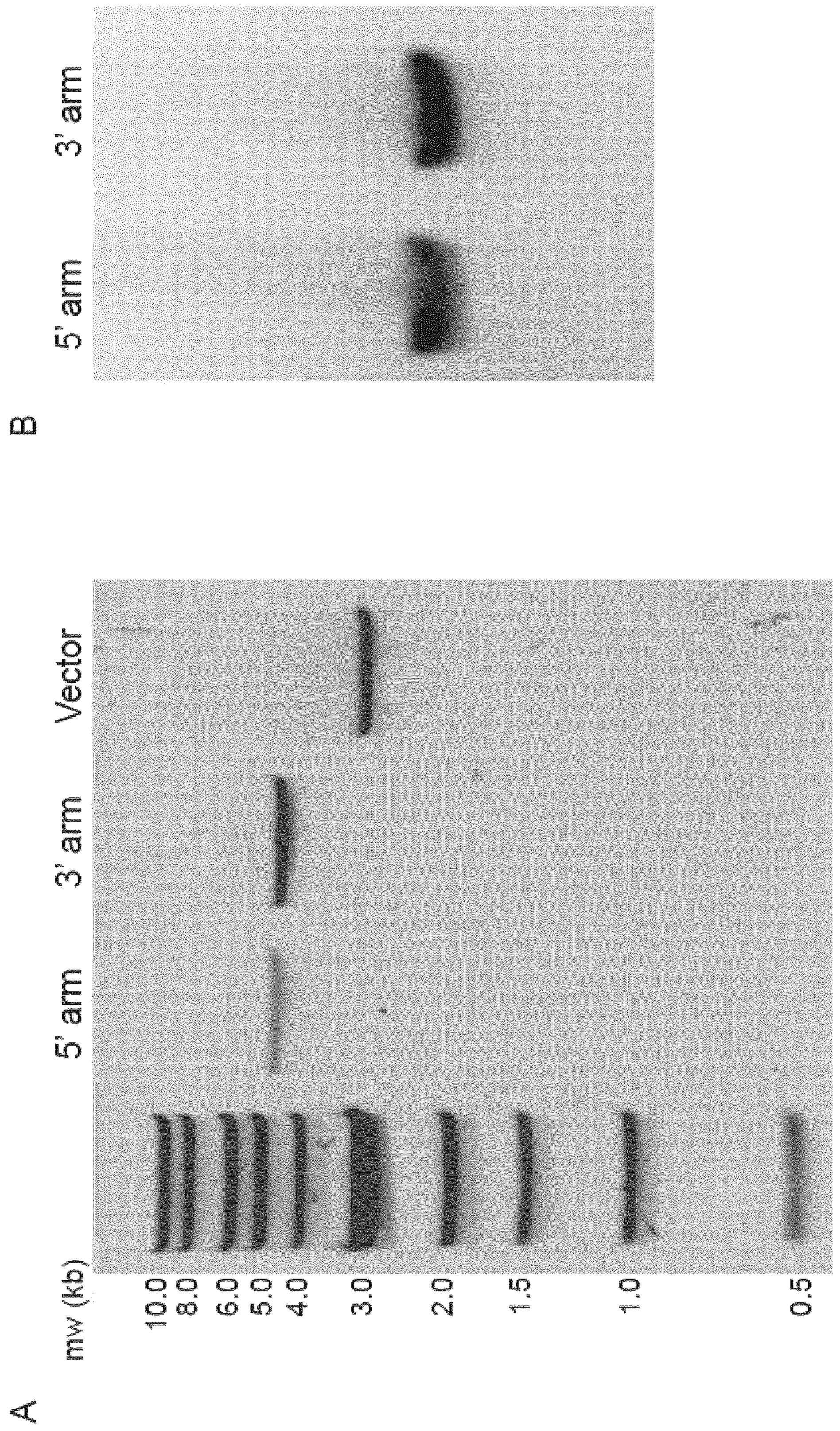

1 μl of each PCR product was then run on a 1% agarose gel at 150V for 1 hr (FIG. 11A). The entire volume of each PCR product was purified by Spin Column Method according to the manufacturer's protocol and eluted into 40 μl of Elution Buffer.

The PCRs for the 5' and 3' arms were repeated in order to obtain higher amplification yields. The same programme and mix was used as detailed previously and 1 μl of the product was run on a 0.8% gel at 150V for 1 hour (FIG. 11B). The entire volume for each PCR product was purified by gel extraction from a 0.8% agarose gel and eluted in 40 μl of elution buffer.

Following PCR amplification numerous methods were attempted to 'stick' the three PCR fragments together to form the ColoAd1 shuttle vector. One method attempted to ligate the PCR products using a two-step reaction. This method, which first ligated the 5' arm to the 3' arm followed by a second ligation reaction to ligate the vector, was unsuccessful (see below for details).

A second method attempted to ligate the three PCR products together in a one-step three-way ligation. To determine the conditions for successful ligation using this method the total amount of DNA, the ratio of the DNA fragments, the time and temperature for ligation and the phosphorylation status of the vector were varied. Several combinations were attempted unsuccessfully until a functioning methodology was achieved.

One-Step Three-Way Ligation to Form the ColoAd1 Shuttle Vector

The PCR products of the 5' arm and 3' arm (~4.6 kb and ~4.5 kb) were double digested using PspOMI & AscI (see Table 6) and the PCR product of the p15a-KAN vector (~3 kb) was digested with AscI only (see Table 7), for 2 hrs at 37° C. according to the tables below:

TABLE 6

| 5' arm or 3' arm | | |
|---|---|---|
| Reagent | Volume (μl) | Supplier |
| DNA (PCR product) | 20 | |
| Buffer 4 | 4 | NEB B7004S |
| PspOM1 | 2 | NEB R0653S |
| AscI | 2 | NEB R0558S |
| Nuclease Free Water | 8 | Fisher Scientific (BPE 2484-100) |

TABLE 7

| p15A-Kan vector | | |
|---|---|---|
| Reagent | Volume (μl) | Supplier |
| DNA (PCR product) | 20 | |
| Buffer 4 | 4 | NEB B7004S |
| Ascl | 2 | NEB R0558S |
| Nuclease Free Water | 8 | Fisher Scientific (BPE 2484-100) |

The 5' and 3' arm digests were heat inactivated at 65° C. for 20 mins. The p15A-Kan vector fragment was treated with 1 μl Alkaline Calf Phosphatase (CIP) for 1 hr at 37° C.

1 μl of all the treated restriction digests were run on a 0.8% agarose gel (FIG. 12). The entire volumes of digest products were separated on a 0.8% agarose gel, gel purified and eluted in 40 μl of elution buffer.

A one-step three way ligation was performed with the purified digest products employing 2 μl T4 DNA ligase and 4 μl ligase buffer for 1 hr at RT: with various ratios of fragments, as per Table 8:

| Ratio of 5' arm:3' arm:vector fragment | Amount of DNA | Formation of Shuttle Vector |
|---|---|---|
| 1:1:6 (2 μl:2 μl:12 μl) | ~20 ng:20 ng:120 ng | No |
| 1:1:3 (2 μl:2 μl:6 μl) | ~20 ng:20 ng:60 ng | No |
| 1:1:1 (2 μl of each) | ~20 ng:20 ng:20 ng | Yes |

The entire ligation mixtures were transformed into bacteria by incubation on ice for 30 minutes with XL-10 Gold Ultracompetent cells followed by 30 second heatshock at 42 degrees. 500 μl of each transformed culture was spread on LB+Kan plates and incubated overnight at 37° C. A control using 6 μl of dephosphorylated p15A-kan vector with 2 μl T4 DNA Ligase was spread on LB+Kan plates. After overnight incubation colonies were present on all plates except the control plate.

Diagnostic PCR Screening and Restriction Digestion of Colonies

4 Colonies were picked from each plate and were cultured overnight in 4 ml LB Broth at 250 rpm, 37° C. DNA was purified by miniprep, which involved harvesting DNA from bacteria by alkaline lysis and purification of DNA on DNA binding columns according to the manufacturer's miniprep protocol The DNA was eluted in 40 μl buffer.

Diagnostic PCRs were performed on the 12 purified DNA samples to determine if a ~12 kb ColoAd1 Shuttle Vector product was present and contained both the 5' and 3' arms in the correct orientation (FIG. 13). Three separate PCRs were employed for each construct using primers across the junctions where ligations should have taken place. The sequences of the primers used in the reactions are shown in Table 9 below.

TABLE 9

| Reference number | Primer name | Sequence |
|---|---|---|
| 0202 (SEQ ID NO: 9) | Kanr 5' arm FWD | ATCGCCTTCTATCGCCTTC |
| 0203 (SEQ ID NO: 10) | Kanr 5' arm REV | AGCAGTGCAAATCACAGTC |
| 0204 (SEQ ID NO: 11) | 5' 3' arms FWD | CAAACTGAGTCTGCTGTCG |
| 0205 (SEQ ID NO: 12) | 5' 3' arms REV | ATAAAGGGGTGTTGGGAGG |
| 0206 (SEQ ID NO: 13) | 3' arm p15A FWD | CCCTCGTAAAACCTGTCATC |
| 0207 (SEQ ID NO: 14) | 3' arm p15A REV | CCCATTCGTCTCTCCATTC |

The PCR reactions were set up according to the mixes detailed in Tables 10-12 below:

TABLE 10

| Mix 1: | |
|---|---|
| Reaction | Volume (μl) |
| Taq PCR mix | 25 |
| Primer 202 (SEQ ID NO: 9) | 1 |
| Primer 203 (SEQ ID NO: 10) | 1 |
| Nuclease free water | 22 |
| DNA | 1 |

TABLE 11

| Mix 2: | |
|---|---|
| Reaction | Volume (μl) |
| Taq PCR mix | 25 |
| Primer 204 (SEQ ID NO: 11) | 1 |
| Primer 205 (SEQ ID NO: 12) | 1 |
| Nuclease free water | 22 |
| DNA | 1 |

TABLE 12

| Mix 3: | |
|---|---|
| Reaction | Volume (μl) |
| Taq PCR mix | 25 |
| Primer 206 (SEQ ID NO: 13) | 1 |
| Primer 207 (SEQ ID NO: 14) | 1 |
| Nuclease free water | 22 |
| DNA | 1 |

The PCR programme was set up according to the manufacturer's instructions for TAO polymerase PCR mix (Qiagen #201443).

1 μl of the PCR products were run on a 1% agarose gel for 1 hr at 150V (FIG. 14)

For correctly sized and orientated constructs 3 PCR products of 1.3 kb, 1.4 kb and 1.1 kb were expected as detailed in the schematic in FIG. 13. Only samples 13, 14 and 16 (FIG. 14) showed correctly sized products. These constructs were all produced using a 1:1:1 ligation ratio. Constructs using the 1:1:6 and 1:1:12 ratios did not produce correctly sized fragments (FIG. 14 #17-24). To confirm the presence of the 12 kb ColoAd1 shuttle vector in the 1:1:1 ligation samples restriction digest with PspOMI or double digest with PspOMI and AscI was carried out on a selection of constructs for 1 hr at 37° C. The digestion reactions used are detailed in Table 13 and Table 14.

TABLE 13

Single digest:

| Reagent | Volume (μl) | Supplier |
|---|---|---|
| DNA (Clones) | 3 | |
| PspOMI | 0.5 | NEB B7004S |
| Buffer 4 | 2 | NEB R0558S |
| Nuclease free water | 14.5 | Fisher Scientific (BPE 2484-100) |

TABLE 14

Double digest:

| Reagent | Volume (μl) | Supplier |
|---|---|---|
| DNA (Clones) | 3 | |
| PspOMI | 0.5 | NEB B7004S |
| AscI | 0.5 | NEB R0653S |
| Buffer 4 | 2 | NEB R0558S |
| Nuclease free water | 14.5 | Fisher Scientific (BPE 2484-100) |

1 μl of each digest was run on a 0.8% gel for 1 hr at 150V (FIG. 15).

Figure 8:
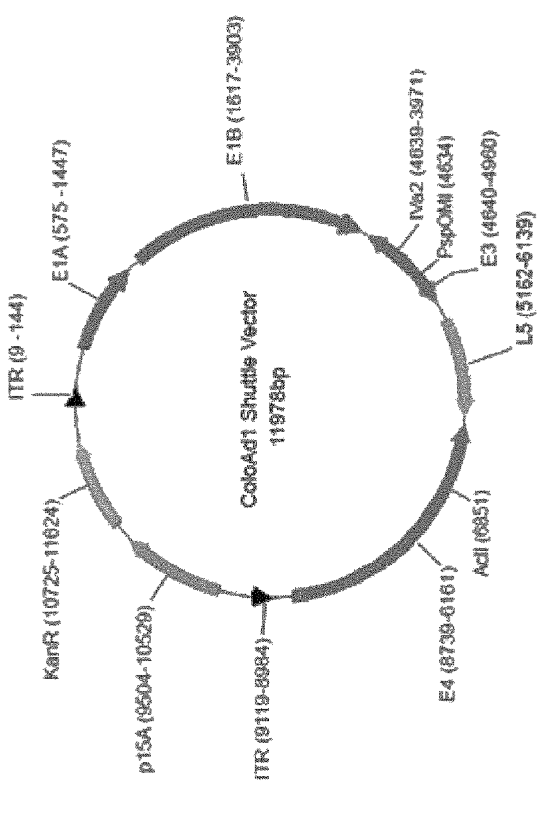
FIG. 8 shows the 12 kb ColoAd1 shuttle vector with a p15A origin of replication, a Kanamycin resistance gene, the ITRs, E1A, E1B genes, partial E2B gene, partial E3 gene, Fibre gene and E4 genes of ColoAd1

For correctly sized and orientated constructs the PspOMI digest would be expected to yield a single ~12 kb band and the PspOMI/AscI digest would be expected to yield a ~3 kb band and ~4.7 kb band. For the double digest the ~4.7 kb band would be expected to have ~twice the intensity of the ~3 kb band due to the presence of both the 5' and 3' arms at this size. Constructs 13 and 16 showed the correct digest banding patterns corresponding to the ColoAd1 Shuttle vector (FIG. 8).

The construct number 16 was then sequenced which confirmed successful construction of a ColoAd1 shuttle vector SEQ ID NO: 2.

Example 2 Construction of the ColoAd2.4 Shuttle Vector

The ColoAd1 shuttle vector generated in Example 1 contained 11 unique (native) restriction sites that occur only once in the genome allowing modification of any region of the ColoAd1 genome present in the shuttle vector (for example, modification of the E1 region). A restriction map showing the location of the sites and the ColoAd1 genes present in the shuttle vector is provided in FIG. 6.

Figure 9:
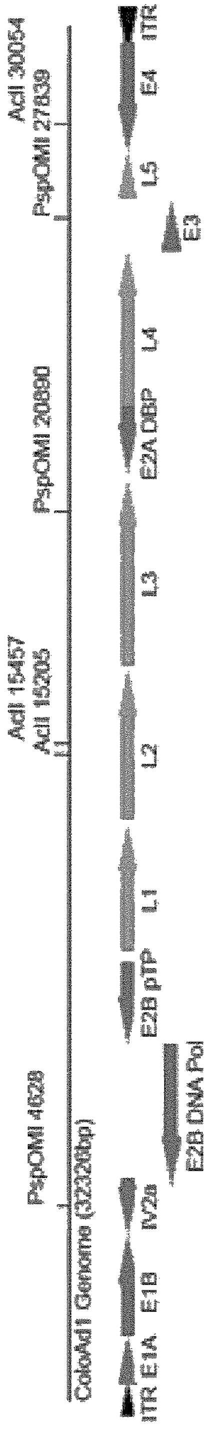
FIG. 9 shows a map of ColoAd1 detailing PspOMI and AclI restriction sites.

Two of the unique (native) restriction sites (PspOMI and AclI) flank the fibre (L5) gene at positions 4634 and 6851 respectively in the ColoAd1 Shuttle Vector. These correspond to the original PspOMI and AclI that flank the fibre (L5) gene in the ColoAd1 genome at positions 27839 and 30065 (FIG. 9). In the ColoAd1 shuttle vector these sites permit DNA sequences in this region to be excised and replaced with a modified or different sequence, or have a DNA sequence inserted within them as a simple addition.

Figure 3:
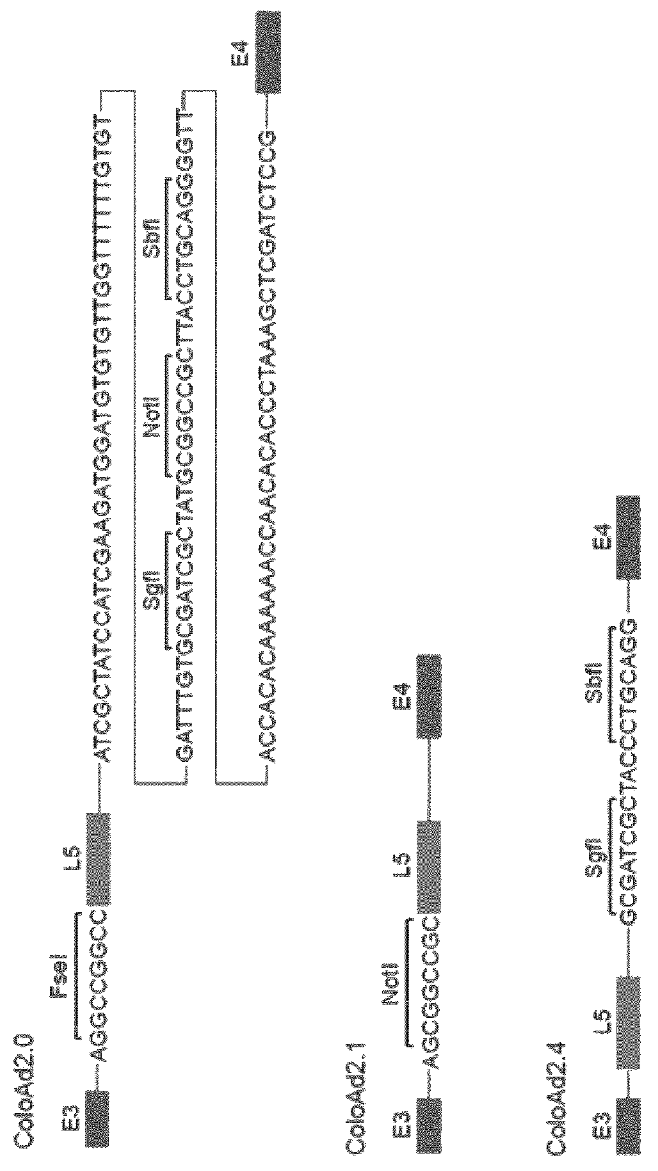
FIG. 3 shows specific alterations in ColoAd1 genome sequence in ColoAd2.0, ColoAd2.1 and ColoAd2.4 plasmids. All base pairs shown in black are additional to the ColoAd1 genome sequence. The sequences and names of the specific restriction enzymes are indicated. The nucleotide sequence written out in FIG. 3 between E3 and L5 of ColoAd2.0 is SEQ ID NO: 45. The nucleotide sequence written out in FIG. 3 between L5 and E4 of ColoAd2.0 is SEQ ID NO: 44. The nucleotide sequence written out in FIG. 3 between E3 and L5 of ColoAd2.1 is SEQ ID NO: 19. The nucleotide sequence written out in FIG. 3 between L5 and E4 of ColoAd2.4 is SEQ ID NO: 29.

The ColoAd2.4 Shuttle vector was generated from the ColoAd1 shuttle vector by replacement of the DNA sequence between the PspOMI and AclI restriction sites with a synthetic DNA fragment. The synthetic DNA fragment sequence was identical to the sequence it was replacing in the ColoAd1 Shuttle Vector except that it contained an additional 19 bp downstream of the fibre gene (GCGATCGCTACCCTGCAGG—SEQ ID NO.29, FIG. 3). These additional bases included new original SgfI and SbfI restriction sites (FIG. 17).

The synthetic DNA fragment flanked by PspOMI and AclI sites was ordered from MWG Eurofins (FIG. 18, SEQ ID NO. 27)). The synthetic fragment was supplied in a 5.17 kb AmpR pBluescript II SK plasmid.

The ColoAd1 shuttle vector and the pBluescript plasmid containing the synthetic fragment were digested for 1 hour at 37° C. in the reaction detailed in Table 15:

| Reagent | Volume (insert/vector) (μl) | Supplier |
|---|---|---|
| DNA (pBSK plasmid/ColoAd1 shuttle vector) | 4/10 | |
| AclI | 0.4 | NEB R0598S |
| PspOMI | 0.2 | NEB R0653S |
| Buffer 4 | 2 | NEB R0558S |
| BSA | 2 | NEB B9001S |
| Nuclease free water | 5.4/11.3 | Fisher Scientific (BPE 2484-100) |

Both the digested shuttle vector and synthetic fragment were separated on a 0.8% agarose gel and the fragments of appropriate size were gel purified and eluted in 400 of nuclease free water.

The synthetic fragment was ligated into the ColoAd1 shuttle vector using a 3:1 ligation ratio of insert to shuttle vector at volumes of 3 μl:1 μl with 1× Ligase Buffer and 1 μl T4 DNA ligase in a 10 μl reaction for 1 hour at RT.

2 μl of the ligation mixture was transformed by heatshock at 42° C. into XL-1 Blue cells according to the manufacturer's protocol. Following transformation, 5 colonies were picked from the LB kanamycin plate and were cultured overnight in 3 ml LB Broth containing Kanamycin, at 250 rpm, 37° C. Minipreps were performed for each culture according to the manufacturer's protocol and the purified DNA was eluted in 40 μl buffer.

To confirm the construction of the ColoAd2.4 Shuttle vector containing the original restriction sites, SbfI and SgfI, restriction enzyme analysis was performed for each of the 5 samples. Restriction digests with EcoRV and SbfI were set up as detailed in Table 16 below:

| Reagent | Volume (μl) | Supplier |
|---|---|---|
| DNA | 3 | |
| EcoRV HF | 0.2 | NEB R3195S |
| SbfI HF | 0.2 | NEB R3642L |
| BSA | 2 | NEB B9001S |
| NEBuffer 4 | 2 | NEB R0558S |
| Nuclease free water | 14.6 | Fisher Scientific (BPE 2484-100) |

All 5 of the digests produced correctly sized fragments: bands of 3 kb and 9 kb (FIG. 19).

The putative ColoAd2.4 shuttle vector #5 was amplified in bacteria from a glycerol stock and the DNA harvested and purified by maxiprep. This construct #5 was sequenced confirming successful construction of the ColoAd2.4 shuttle vector (SEQ ID No.26).

Example 3 Construction of the ColoAd2.0 Shuttle Vector

The ColoAd2.0 Shuttle Vector (SEQ ID NO: 15, FIG. 20) was generated from the ColoAd1 Shuttle Vector constructed in Example 1. The methods employed to generate the ColoAd2.0 Shuttle Vector were identical to those used to generate the ColoAd2.4 Shuttle Vector; using ligation of a synthetic DNA fragment between the PspOMI and AclI restriction sites detailed in Example 2

The synthetic DNA fragment sequence used to construct the ColoAd2.0 shuttle vector was similar to the sequence it was replacing in the ColoAd1 Shuttle Vector except it contained an additional 9 bp upstream of the Fibre (L5) gene, comprising a FseI original restriction site, and an additional 123 bp downstream of the fibre gene, comprising two polyadenylation sequences and SgfI, NotI and SbfI original restrictions sites (SEQ ID NO: 16, FIG. 21)

The construction of the ColoAd2.0 Shuttle Vector was confirmed by a panel of restriction digests with the enzymes FseI, AscI, NotI, SbfI or PspOMI 1 hr, 37° C. as detailed by the mixes in Table 17:

| Reagent | Volume (µl) | Supplier |
|---|---|---|
| DNA | 3 | |
| Enzyme 1 (FseI, PspOMI) | 0.2 | NEB R0588S, NEB R0653S |
| Enzyme 2 (SbfI, AscI, NotI) | 0.2 | NEB R3642S, NEB R0558S, NEB R3189S |
| BSA | 2 | NEB B9001S |
| NEBuffer 4 | 2 | NEB R0558S |
| Nuclease free water | 14.6 | Fisher Scientific (BPE 2484-100) |

2 µl of each digest was separated on a 1% agarose gel. All the constructs showed the correct banding patterns for each digest (FIG. 22). ColoAd2.0 Shuttle Vector construct #4 was selected and sequenced which confirmed successful construction of the ColoAd2.0 Shuttle Vector (SEQ ID NO: 15)

Example 4 Construction of the ColoAd2.1 Shuttle Vector

The ColoAd2.1 Shuttle vector (SEQ ID NO: 17, FIG. 23) was generated from the ColoAd1 shuttle vector (produced in Example 1) by replacement of the DNA sequence between the PspOMI and AclI restriction sites with a DNA fragment generated by two PCR reactions (SEQ ID NO: 18). The DNA fragment produced was identical to the sequence it was replacing in the ColoAd1 Shuttle Vector except it contained an additional 9 bp upstream of the fibre gene (AGCGGCCGC—SEQ ID NO: 19, FIG. 3). These additional bases include an original NotI restriction site (FIG. 24C).

To introduce the NotI restriction site by PCR into the PspOMI-AclI flanked sequence, 2 PCR reactions were required. One PCR (PCR 1) that generated a fragment including the 5' PspOMI restriction site and an introduced 3' NotI site (FIG. 24A) and a second (PCR 2) that generated a fragment including an introduced 5' NotI site and the 3' AclI site (FIG. 24B). Ligation of these PCR products at the NotI site generated the ColoAd2.0 DNA fragment (FIG. 24C) used in ColoAd2.0 Shuttle Vector construction.

The primers used for the two PCR reactions are shown in Table 18:

| Primer ref number | Primer name | Sequence |
|---|---|---|
| 0274 (SEQ ID NO. 20) | Bam-Not A Fwd | TTCGGATCCGGGCCCATACTAGTCTTGC |
| 0275 (SEQ ID NO. 21) | Bam-Not A Rev | CATGCGGCCGCTCTGGGAAGAAAGACATGAAGA |
| 0276 (SEQ ID NO. 22) | Not-EcoRI A Fwd | TATGCGGCCGCATGACCAAGAGAGTCCG |
| 0277 (SEQ ID NO. 23) | Not-EcoRI A Rev | TGCGAATTCAACGTTGTCCATGGTACAGAC |

PCR 1 was performed on the ColoAd1 genome template DNA using primers 0274 (SEQ ID NO: 20) and 0275 (SEQ ID NO: 21). A 50 µl reaction volume was used for the PCR 1 reaction, according to Table 19 below and a schematic of the PCR 1 product is shown in FIG. 24A (SEQ ID NO: 24).

TABLE 19

| Reagent | Volume (µl) | Supplier |
|---|---|---|
| Phusion PCR Mix | 25 | NEB MO531S |
| Primer 0274 (SEQ ID NO: 20) (10 µM) | 2.5 | Sigma |
| Primer 0275 (SEQ ID NO: 21) (10 µM) | 2.5 | Sigma |
| DNA (ColoAd1) | 1 | Ark Therapeutics |
| Nuclease Free Water | 19 | Fisher Scientific (BPE 2484-100) |

PCR 2 was performed on the ColoAd1 genome template DNA using primers 0276 (SEQ ID NO: 22) and 0277 (SEQ ID NO.23). A 50 µl reaction volume was used for the PCR 2 reaction, according to Table 20 below and a schematic of the PCR 2 product is shown in FIG. 24B (SEQ ID NO: 25)

TABLE 20

| Reagent | Volume (µl) | Supplier |
|---|---|---|
| Phusion PCR Mix | 25 | NEB MO531S |
| Primer 0276 (SEQ ID NO. 22) (10 µM) | 2.5 | Sigma |
| Primer 0277 (SEQ ID NO. 23) (10 µM) | 2.5 | Sigma |
| DNA (ColoAd1) | 1 | Ark Therapeutics |
| Nuclease Free Water | 19 | Fisher Scientific (BPE 2484-100) |

The PCR reactions were both carried out according to the programme detailed in Table 21:

| Step no. | Stage | Temp (° C.) | Time (Secs) |
|---|---|---|---|
| Step 1 | Initial Denaturation | 98 | 60 |
| Step 2 | Denaturation | 98 | 8 |
| Step 3 | Annealing | 60 | 20 |

-continued

| Step no. | Stage | Temp (° C.) | Time (Secs) |
|---|---|---|---|
| Step 4 | Extension | 72 | 90 |
| Step 5 | Final Extension | 72 | 300 |
| Step 6 | Hold | 4 | Hold |

30 cycles of amplification were carried out: [Step 1]×1, [Step 2, Step 3, Step 4]×30, [Step 5]×1.

The entire volume of the PCR products were purified by Spin Column Method according to the manufacturer's protocol and eluted into 40 μl of Elution Buffer.

The PCR 1 product was then digested with BamHI and NotI (Table 22) and a cloning vector was also digested using BglII and NotI (see Table 23) for 1 hr, 37° C.

TABLE 22

| PCR product: | | |
|---|---|---|
| Reagent | Volume (μl) | Supplier |
| DNA (PCR product) | 20 | |
| Buffer 4 | 5 | NEB B7004S |
| BamHI | 0.2 | NEB R0136S |
| NotI | 0.2 | NEB R3189S |
| Nuclease Free Water | 19.6 | Fisher Scientific (BPE 2484-100) |

TABLE 23

| Vector: | | |
|---|---|---|
| Reagent | Volume (μl) | Supplier |
| DNA | 5 | |
| Buffer 4 | 2 | NEB R7004S |
| BglII | 0.2 | NEB R0144S |
| NotI | 0.2 | NEB R3189S |
| Nuclease Free Water | 10.6 | Fisher Scientific (BPE 2484-100) |

The digested vector and PCR 1 product were separated on a 0.8% agarose gel and the fragments of appropriate size were gel purified and eluted in 40 μl of nuclease free water.

The PCR 1 product was ligated into the vector using a 3:1 ligation ratio of insert to vector at volumes of 10 μl:1 μl with 1× Ligase Buffer and 1 μl T4 DNA ligase in a 20 μl reaction for 1 hour at RT.

6 μl of the ligation mixture was transformed by heat shock at 42° C. into XL-1 Blue cells according to the manufacturer's protocol. Following transformation, 5 colonies were picked from the LB kanamycin plate and were cultured overnight in 3 ml LB Broth containing Kanamycin, at 250 rpm, 37° C. Minipreps were performed for each culture according to the manufacturer's protocol and the purified DNA was eluted in 40 μl buffer.

To confirm the vector contained the PCR 1 product, restriction enzyme analysis was performed for each of the 5 samples. Restriction digests with SpeI and AscI were set up for 1 hr, 37° C. as detailed in

TABLE 24

| Reagent | Volume (μl) | Supplier |
|---|---|---|
| DNA (PCR product) | 20 | |
| Buffer 4 | 5 | NEB B7004S |
| SpeI | 0.2 | NEB R3133S |
| AscI | 0.2 | NEB R0558S |
| Nuclease Free Water | 19.6 | Fisher Scientific (BPE 2484-100) |

All 5 of the digests produced correctly sized fragments: bands of 1.5 kb and 4 kb.

The PCR 2 product and the newly generated vector containing the PCR 1 product were digested with NotI and EcoRI, 1 hr, 37° C., as detailed in Table 25:

| Reagent | Volume (μl) | Supplier |
|---|---|---|
| DNA (PCR product) | 20 | |
| Buffer 4 | 5 | NEB B7004S |
| EcoRI | 0.2 | NEB R0101S |
| NotI | 0.2 | NEB 3189S |
| Nuclease Free Water | 19.6 | Fisher Scientific (BPE 2484-100) |

The digested vector containing the PCR 1 fragment and PCR 2 product were separated on a 0.8% agarose gel and the fragments of appropriate size were gel purified and eluted in 40 μl of nuclease free water.

The PCR 2 product was ligated into the vector using a 3:1 ligation ratio of insert to vector at volumes of 10 μl:1 μl with 1× Ligase Buffer and 1 μl T4 DNA ligase in a 20 μl reaction for 1 hour at RT.

6 μl of the ligation mixture was transformed by heat shock at 42° C. into XL-1 Blue cells according to the manufacturer's protocol. Following transformation, 5 colonies were picked from the LB kanamycin plate and were cultured overnight in 3 ml LB Broth containing Kanamycin, at 250 rpm, 37° C. Minipreps were performed for each culture according to the manufacturer's protocol and the purified DNA was eluted in 40 μl buffer.

To confirm the vector contained the DNA fragment consisting of both PCR1 and PCR2 products, restriction enzyme analysis was performed for each of the 5 samples. Restriction digests with PspOMI and AclI were set up for 1 hr, 37° C. as detailed in Table 26:

| Reagent | Volume (μl) | Supplier |
|---|---|---|
| DNA (PCR product) | 20 | |
| Buffer 4 | 5 | NEB B7004S |
| PspOMI | 0.2 | NEB R0653S |
| AclI | 0.2 | NEB R0598S |
| Nuclease Free Water | 19.6 | Fisher Scientific (BPE 2484-100) |

All 5 of the digests produced correctly sized fragments: bands of 2.3 kb and 3.15 kb. To confirm the sequence of the DNA fragment between the PspOMI and AclI sites in the vector was correct the sample #5 was sequenced (SEQ ID NO. 18).

The ColoAd2.1 Shuttle Vector was then generated from the ColoAd1 Shuttle Vector constructed in Example 1. The methods employed to ligate the DNA fragment generated by the 2 PCR reactions into the ColoAd1 Shuttle Vector are identical to those ligate the synthetic DNA fragment to produce the ColoAd2.4 Shuttle Vector in Example 2.

The construction of the ColoAd2.1 Shuttle Vector was confirmed by restriction digest with the enzymes NotI and AscI for 1 hr, 37° C. as detailed by the mixes in Table 27:

| Reagent | Volume (μl) | Supplier |
|---|---|---|
| DNA (PCR product) | 20 | |
| Buffer 4 | 5 | NEB B7004S |
| AscI | 0.2 | NEB R0558S |
| NotI | 0.2 | NEB R3189S |
| Nuclease Free Water | 19.6 | Fisher Scientific (BPE 2484-100) |

2 μl of each digest was separated on a 1% agarose gel, all constructs show the correct banding patterns corresponding to the ColoAd2.1 Shuttle Vector (FIG. 25). ColoAd2.1 Shuttle Vector Sample #4 was selected and sequenced, confirming successful construction of the ColoAd2.1 Shuttle Vector (SEQ ID NO. 17).

Example 5 Construction of the ColoAd2.4, ColoAd2.0 or ColoAd2.1 Plasmids by Homologous Recombination ColoAd2.0 (SEQ ID NO.30), ColoAd2.4 (SEQ ID NO.28) and ColoAd2.1 (SEQ ID NO.31) plasmids were generated from the ColoAd2.0, ColoAd2.4 and ColoAd2.1 Shuttle Vectors by homologous recombination. A schematic overview of the methods is provided in FIG. 5.

The PspOMI site in the ColoAd2.0, ColoAd2.4 and ColoAd2.1 shuttle vectors permitted the shuttle vectors to be linearised for homologous recombination with the ColoAd1 genome in electrocompetent *E. coli*

The ColoAd2.4 shuttle vector (SEQ ID NO.26) (68.6 ng/μl) was digested with PspOMI for 1 hour, 37° C. using the following reaction:

| Reagent | Volume (μl) | Supplier |
|---|---|---|
| DNA (PCR product) | 25 (x2) | |
| Buffer 4 | 5 | NEB B7004S |
| PspOMI | 1 | NEB R0598S |
| BSA | 5 | B9001S |
| Nuclease Free Water | 19 | Fisher Scientific (BPE 2484-100) |

The 50 μl digest was treated with 1 μl CIP (Calf Alkaline Phosphatase) for 1 hour at 37° C.

The digests were pooled and purified on a Sigma Genelute Miniprep column, eluting in 40 μl NFW. Recombinations were carried out with 3.5 μl (23.4 ng/μl) ColoAd2.4 shuttle vector and 1.5 μl (36 ng/μl) of ColoAd1 in 40 μl of electrocompetent BJ5183 cells (Agilent). A negative control was also carried out with 3.5 μl of the linearised vector (ColoAd2.4 vector) in 40 μl BJ5183 cells. Recombinations were performed by electroporation according to manufacturer's protocol (#200154 Agilent).

Figure 27:
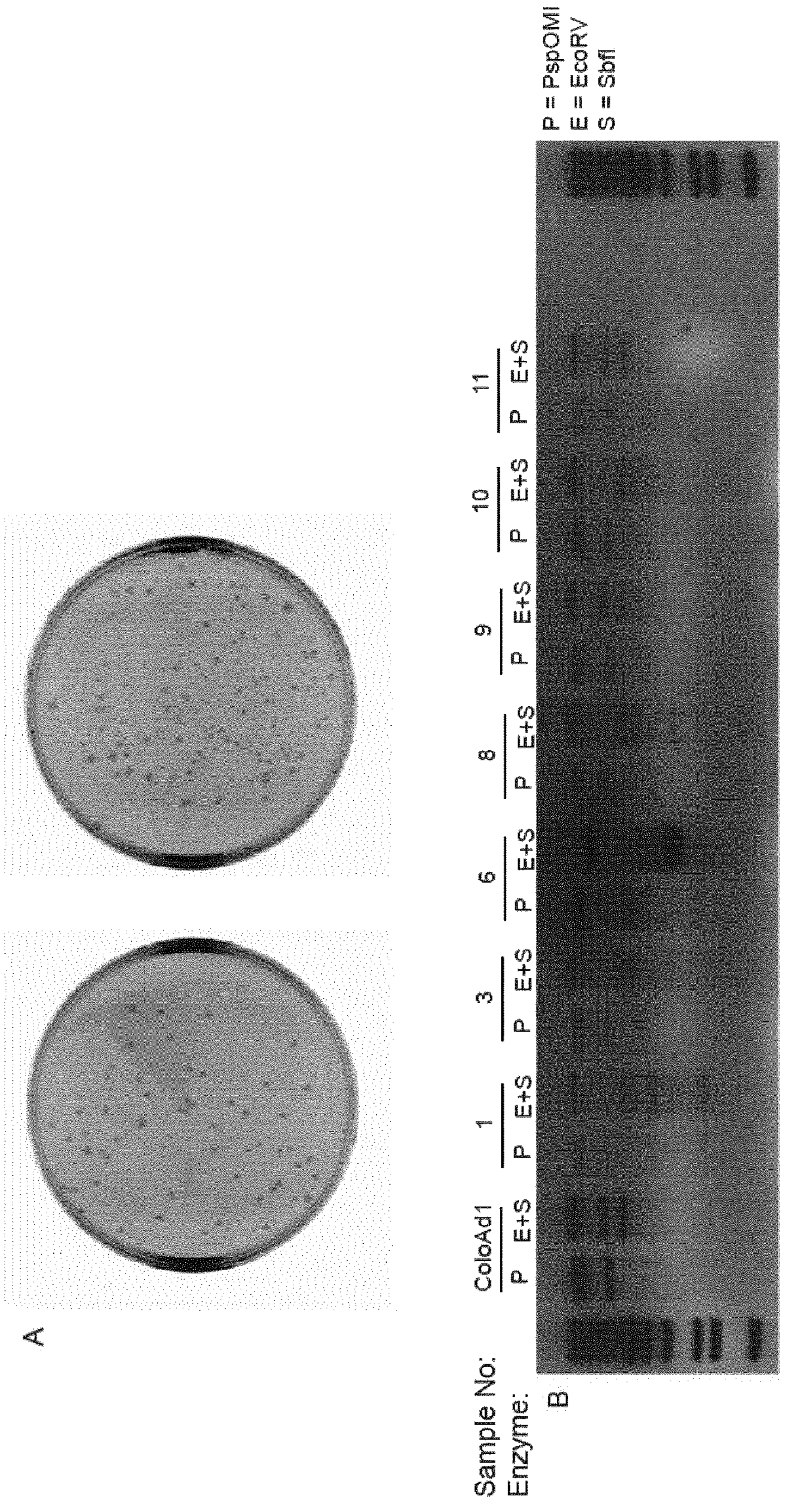

5 μl of the cultures were diluted and spread on LB agar+Kanamycin and incubated overnight at 37° C. The negative control showed few normal sized colonies on the LB+Kan plates, while the recombination plates showed many tiny colonies and a few large or medium colonies (FIG. 27A). From the experimental plates 48 colonies were picked and inoculated into 3 ml LB Broth+Kan overnight at 37° C., 250 rpm.

The DNA was purified from the bacteria by miniprep according to the manufacturer's protocol and was eluted in 40 μl nuclease free water.

To determine the presence of recombinants in the DNA samples, the candidates were digested with EcoRV and SbfI using the following reaction Table 29:

| Reagent | Volume (μl) | Supplier |
|---|---|---|
| DNA | 12 | |
| Buffer 4 | 2 | NEB B7004S |
| BSA | 2 | NEB B9001S |
| EcoRV | 0.2 | NEB R3195S |
| SbfI Hi Fi | 0.2 | NEB B7004S |
| Nuclease free water | 3.6 | Fisher Scientific (BPE 2484-100) |

The digests were run on a 0.8% agarose gel for 1 hour at 150V (FIG. 27B).

Recombinants #3, #8 and #10 showed the correct bands following EcoRV/SbfI digestions and 2 μl of each were transformed into 50 μl XL-1 Blue cells according to manufacturer's protocol. 50 μl of cells were plated on LB and Kanamycin plates and incubated overnight at 37° C.

From the #8 plates, 7 colonies were picked and grown in 3 ml LB broth with Kanamycin overnight at 37° C., 220 rpm. Minipreps were performed on the recombinant clones according to the manufacturer's protocol and DNA was eluted in 40 μl NFW. Diagnostic restriction enzyme digests were set up at 37° C. for 1 hour using the following digestion reactions Table 30:

| Reagent | Volume (μl) | Supplier |
|---|---|---|
| DNA | 2 | |
| Buffer 4 | 2 | NEB B7004S |
| BSA | 2 | NEB B9001S |
| EcoRV | 0.2 | NEB R3195S |
| SbfI-HF | 0.2 | NEB B7004S |
| Nuclease free water | 13.6 | Fisher Scientific (BPE 2484-100) |

TABLE 31

| Reagent | Volume (μl) | Supplier |
|---|---|---|
| DNA | 2 | |
| PspOMI | 0.2 | NEB R0598S |
| Buffer 4 | 5 | NEB R0558S |
| Nuclease free water | 15.6 | Fisher Scientific (BPE 2484-100) |

The digests were run on a 0.8% agarose gel (FIG. 28).

Of the constructs digested Recombinant ColoAd2.4 #4 plasmid had the correct restriction pattern. This plasmid was therefore amplified from a glycerol stock and the DNA was purified by maxiprep and sequenced (SEQ ID NO.28). This confirmed successful production of the ColoAd2.4 plasmid (FIG. 26). ColoAd2.0 (SEQ ID NO.30), ColoAd2.4 (SEQ ID NO.28) and ColoAd2.1 (SEQ ID NO.31) plasmids shown in FIG. 2 were all successfully constructed using the above method All plasmids were sequenced to confirm no unwanted changes had occurred in the ColoAd1 genome sequence.

Example 6 Failed Two-Step Ligation of the Shuttle Vector

20 μl of the ColoAd1 5' arm and 3' arm PCR products described in Example 1 were digested by PspOMI at 37° C. for 2 hrs as detailed below Table 32:

| Reagent | Volume (μl) | Supplier |
|---|---|---|
| DNA (3' and 5' arm PCR products) | 20 | |

-continued

| Reagent | Volume (µl) | Supplier |
|---|---|---|
| Buffer 4 | 4 | NEB B7004S |
| PspOMI | 1.5 | NEB R0653S |
| Nuclease Free Water | 14.5 | Fisher Scientific (BPE 2484-100) |

The digests were separated on a 0.8% agarose gel, gel purified and eluted in 30 µl of elution buffer. The entire volume of eluted product was used for ligation reactions.

The 5' arm and 3' arm (~4.6 kb and ~4.5 kb) fragments were ligated at a 1:1 ratio using volumes of 10 µl (low) or 25 µl (high) at RT for 2.5 hrs. Table 33:

| 10:10 mix | 25:25 Mix | |
|---|---|---|
| 10 µl 5' arm DNA | 25 µl 5' arm DNA | |
| 10 µl 3' arm DNA | 25 µl 3' arm DNA | |
| 2 µl T4 DNA ligase | 3 µl T4 DNA ligase | NEB M0202S |
| 4 µl Ligase Buffer | 6 µl Ligase Buffer | NEB B0202S |

The ligation reactions were heat inactivated for 5 mins at 70° C. and two PCR5 were performed on each set of ligations using Primer 0199 (SEQ ID NO.6) or Primer 0198 (SEQ ID NO.5) to amplify a ~9.1 kb fragment.

Figure 29:
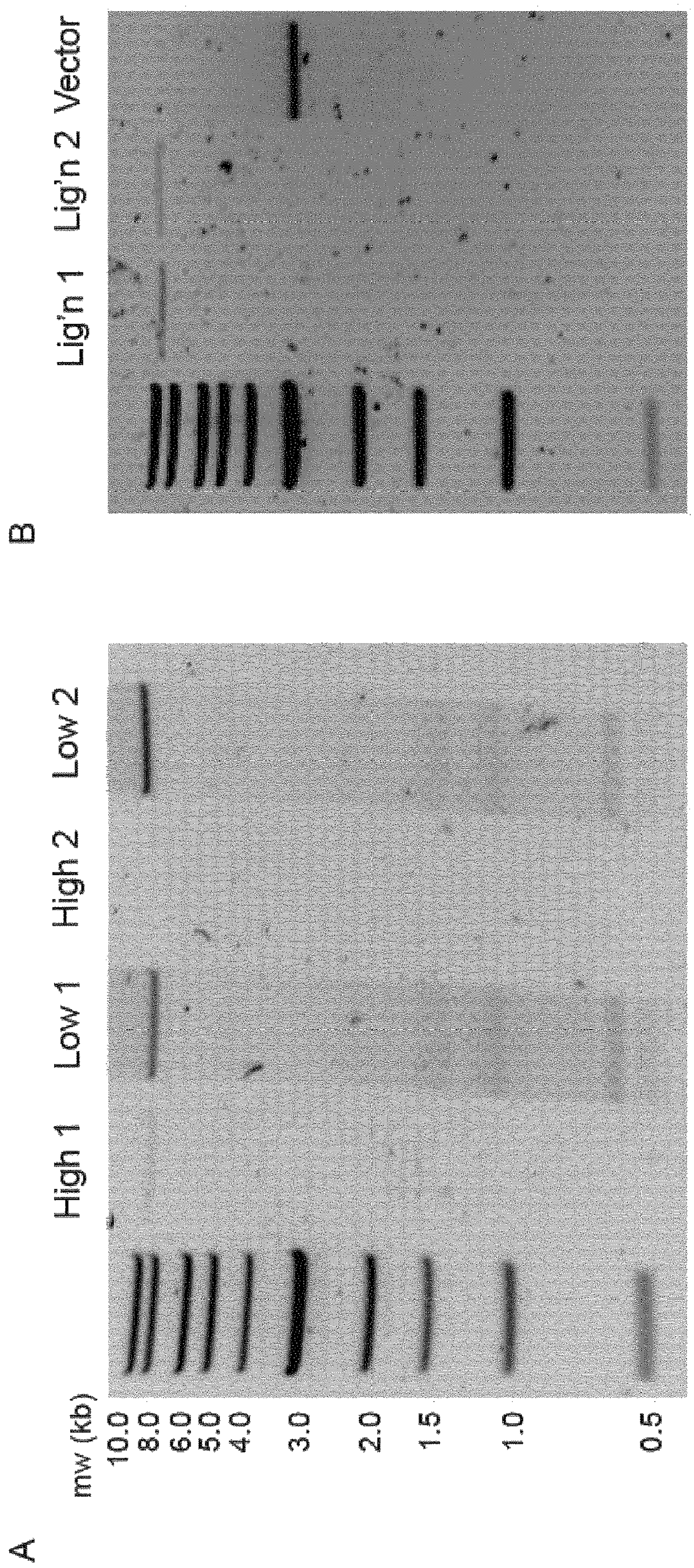

1 µl of each PCR product was run on a 0.8% agarose gel (FIG. 29A).

The total volume of PCR products following low volume ligation were separated on a 0.8% agarose gel, gel purified and eluted into 40 µl elution buffer.

The ligated PCR 9 kb product and previously PCR amplified ~3 kb p15A-Kan vector were restriction digested with enzyme AscI for 2 hrs at 37° C. using the following mix:

TABLE 34

| Reagent | Volume (µl) | Supplier |
|---|---|---|
| DNA (9 kb ligations/ p15a-Kan vector) | 20 | |
| Buffer 4 | 4 | NEB B7004S |
| AscI | 2 | NEB R0558S |
| Nuclease free water | 10 | Fisher Scientific (BPE 2484-100) |

The AscI digested ~9 kb fragments were heat inactivated at 65° C. for 20 mins and the AscI digested p15a KAN vector was treated with 1 µl CIP for 1 hr at 37° C.

1 µl of the digested products were run on a 1% agarose gel to assess relative DNA concentrations (FIG. 29B).

The entire volume of each product was then purified by Spin Column method and eluted in 40 µl elution buffer.

A ligation between the ~9 kb fragment (5'arm-3'arm) and the p15A-Kan vector was performed using 2 µl of T4 DNA Ligase and 4 µl Ligase Buffer at the following ratios for 1.5 hrs at RT:

1:1 (5 µl); 1:2 (2 µl:4 µl); 1:3 (2 µl:6 µl); 1:3 (4 µl:12 µl); and 1:3 (3 µl:9 µl)

The entire volume of each ligation mix was transformed by heatshock into 50 µl of XL-10 Gold Ultracompetent cells according to the manufacturer's protocol (Stratagene #200314).

500 µl of each culture was spread on LB+kanamycin plates and incubated overnight at 37° C. Colonies were present on the plates and were amplified in LB Broth, 37° C., 250 rpm. The DNA was purified from the bacteria by miniprep, according to the manufacturer's protocol.

The purified DNA was analysed for the presence of the ColoAd1 Shuttle Vector by diagnostic PCR and restriction digest methods identical to those detailed in Example 1.

For correctly sized and orientated constructs diagnostic PCR was expected to produce 1.3 kb, 1.4 kb and 1.1 kb bands and restriction digest was expected to yield a single ~12 kb band for PspOMI and ~3 kb band and ~4.7 kb bands for PspOMI/AscI. None of the samples showed the correct bands by either diagnostic method (FIG. 16).

Example 7 Construction of a ColoAd2.4 Plasmid Containing a Reporter Transgene Cassette (pNG-62)

The ColoAd2.4 plasmid generated in Example 5 was used to construct a plasmid named pNG-62 (SEQ ID NO. 35, FIG. 30), which contained a reporter gene transgene cassette between the ColoAd2.4 plasmid unique restriction sites SgfI and SbfI. The transgene cassette consisted of a branched splice acceptor sequence (bSA), a fluorescent reporter gene, green fluorescent protein (GFP) and a SV40 late polyA sequence (PA).

1) Construction of the transgene cassette

A cloning vector that contained the GFP sequence with a 3' SV40 late polyA sequence (mpSF-CMV-GFP-PA) was used as a PCR template for construction of the transgene cassette.

Figure 31:
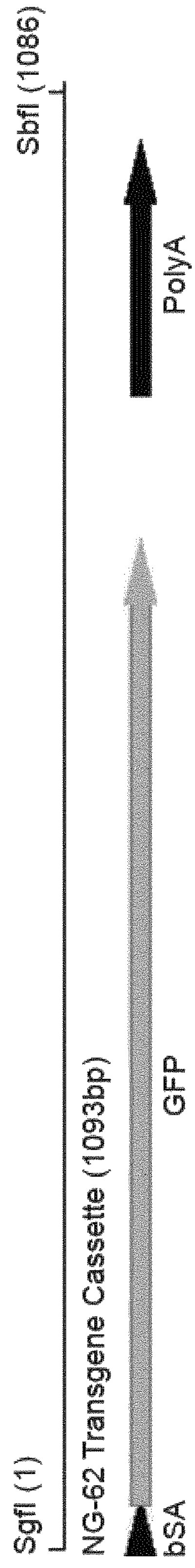

A branched splice acceptor (bSA) and KOZAK sequence 5'-TGCTAATCTTCCTTTCTCTCTTCAGGCCGCC-3' (SEQ ID NO. 36) was added to the 5' end of the GFP gene by PCR. The PCR primers also introduced a 5' SgfI site before the start of the bSA sequence and a 3' SbfI site after the SV40 polyA sequence to give the transgene cassette PCR product (FIG. 31, SEQ ID NO. 37). The PCR primers used to amplify the PCR product are detailed in Table 35:

| Reference number | Primer name | Sequence |
|---|---|---|
| 0350 (SEQ ID NO: 39) | GFP Sgf bSA Fwd | TATGCGATCGCTGCTAATCCTTTCTCTCTTCAGGCCA CCATGGTGAGCAAGGGC |
| 0323 (SEQ ID NO.40) | Luc Sbf PA Rev | CTGAAGAGAGAAACTACCTGCAGGACCACATTTGTA GAGGTTTTAC |

A 50 µl reaction volume was used for the PCR reaction detailed in Table 36:

| Reagent | Volume | Supplier |
|---|---|---|
| DNA | 1 µl | |
| PCR phusion mix | 25 µl | NEB MO531S |
| Forward primer - 0350 | 2.5 µl | Mwg Eurofins |
| Reverse primer - 0323 | 2.5 µl | Mwg Eurofins |
| Nuclease free water | 19 µl | Fisher Scientific (BPE 2484-100) |

PCR amplification was carried out according to the programme in Table 37:

| Cycles | Step number | Stage | Temp (° C.) | Time (Secs) |
|---|---|---|---|---|
| 1 | Step 1 | Initial Denaturation | 98 | 60 |
| 10 | Step 2 | Denaturation | 98 | 20 |
| | Step 3 | Annealing | 57 | 30 |
| | Step 4 | Extension | 72 | 60 |
| 20 | Step 5 | Denaturation | 98 | 20 |
| | Step 6 | Annealing | 65 | 30 |
| | Step 7 | Extension | 72 | 60 |
| 1 | Step 8 | Final Extension | 72 | 300 |
| | Step 9 | Hold | 4 | Hold |

The PCR product was purified by spin column eluting in 40 μl of NFW. The PCR product and the sub-cloning vector containing SgfI and SbfI restriction sites were digested with the enzymes SgfI and SbfI (Table 38) for 1 hr at 37° C.

TABLE 38

| Reagent | Volume | Supplier |
|---|---|---|
| PCR product/vector | 20/4 μl | |
| SgfI | 2 μl | |
| SbfI | 1 μl | |
| BSA | 5/2 μl | NEB B9001S |
| NEBuffer 4 | 5/2 μl | NEB R0558S |
| Nuclease free water | 17/9 μl | Fisher Scientific (BPE 2484-100) |

The digested products were separated on a 1% agarose gel and the fragments of appropriate size were gel purified and eluted in 40 μl of nuclease free water.

The digested, purified PCR product was ligated into the linearised vector using a 3:1 ligation ratio of insert to vector at volumes of 3 μl:1 μl with 1× ligase buffer and 1 μl T4 DNA ligase in a 10 μl reaction for 1 hr at RT.

1 μl of the ligation reaction was transformed into 50 μl of XL Gold cells and 100 μl spread on LB+ampicillin (100 μg/ml) plates. After overnight growth >50 colonies were present on the culture plates. 5 colonies were picked and cultured overnight in 3 ml LB Broth containing ampicillin. DNA was purified by miniprep and eluted in 40 μl buffer.

To confirm the presence of the transgene cassette in the vector the constructs were diagnostically digested with SgfI and SbfI restriction enzymes Table 39:

| Reagent | Volume (μl) | Supplier |
|---|---|---|
| DNA (PCR product) | 20 | |
| Buffer 4 | 5 | NEB B7004S |
| SgfI | 0.2 | NEB R0598S |
| SbfI | 0.2 | |
| Nuclease Free Water | 19.6 | Fisher Scientific (BPE 2484-100) |

Figure 32:
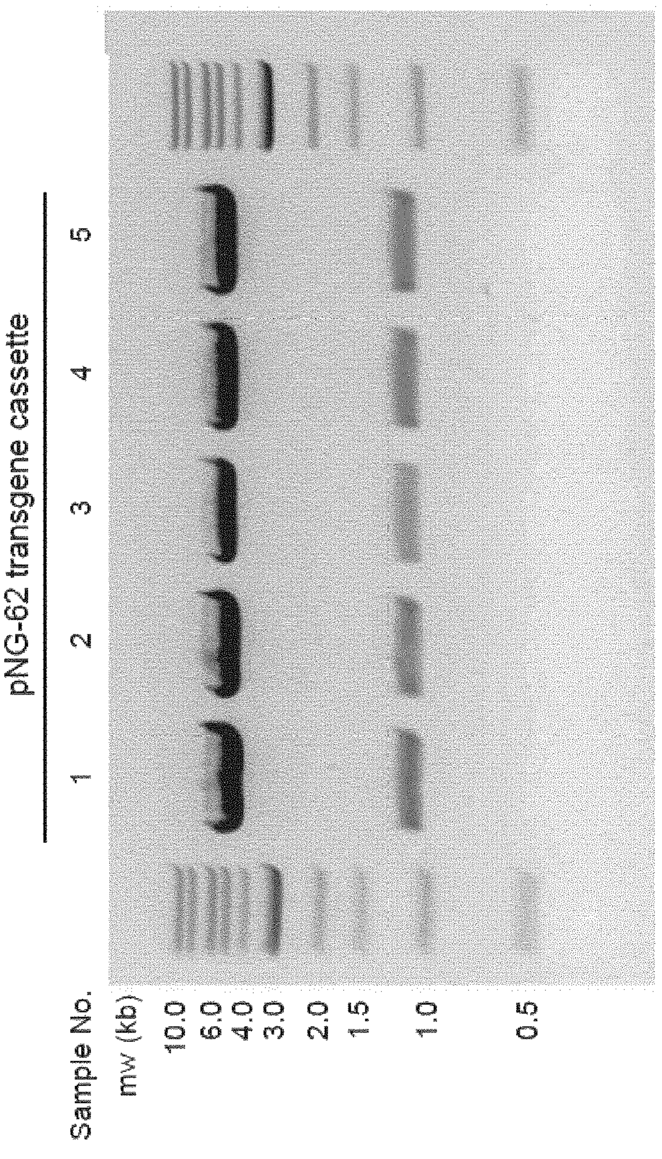

All 5 constructs produced correctly sized fragments from the digests: bands of 1.1 kb and 4.7 kb (FIG. 32). Construct #1 was therefore sequenced and confirmed successful construction of the GFP transgene cassette (FIG. 31, SEQ ID NO. 37).

2) Construction of plasmid NG-62

Construct #1 that contained the GFP transgene cassette (576 ng/μl) and ColoAd2.4 plasmid (583 ng/μl) were digested with SgfI and SbfI for 2 hours at 37° C. using the reaction shown in Table 40:

| Reagent | Volume (μl) | Supplier |
|---|---|---|
| DNA (construct 1/ ColoAd 2.4 plasmid) | 5 (x2) | |
| SgfI | 2 | NEB R0630S |
| SbfI | 1.5 | NEB R3642S |
| Buffer 4 | 2 | NEB B7004S |
| BSA | 2 | NEB B9001S |
| Nuclease free water | 7.5 | Fisher Scientific (BPE 2484-100) |

The digests were separated on a 0.8% agarose gel and the fragments of appropriate size were excised from the gel. The ColoAd2.4 plasmid was then purified using the QIAEX II kit (QIAGEN) and the GFP transgene cassette was purified using the quick gel extraction kit (QIAGEN).

The transgene cassette (40 ng/μl) was ligated into the ColoAd2.4 plasmid (18 ng/μl) using either a 1.5:1 ligation ratio of insert to vector (2.25 μl:3.7 μl) or a 2:1 ligation ratio (3 μl:4 μl). The reactions were carried out with 1× Ligase Buffer and 1 μl T4 DNA ligase in a 10 μl reaction volume. The ligation was carried out for 16 hrs at 16° C.

4 μl of the ligation mixture was transformed into 50 μl XL-Blue cells according to the manufacturer's protocol (Agilent) and the entire transformation volume was spread on LB agar plates containing kanamycin. After overnight growth all colonies were picked from the plates and were cultured overnight in 3 ml LB Broth containing Kanamycin, at 250 rpm, 37° C.

DNA was purified by miniprep and was eluted in 40 μl buffer.

To determine if pNG-62 plasmid had been generated, the constructs were screened by restriction digest using the enzymes NheI and EcoRV as detailed in Table 41:

| Reagent | Volume (μl) | Supplier |
|---|---|---|
| DNA | 2 | |
| NheI | 0.6 | NEB R0131S |
| EcoRV-HF | 0.4 | NEB R3159S |
| Buffer 4 | 2 | NEB R0558S |
| BSA | 2 | NEB B9001S |
| Nuclease free water | 13 | Fisher Scientific (BPE 2484-100) |

The digest products were separated on a 0.8% agarose gel. Of the constructs screened numbers 1, 2 & 3 from 1.5:1 ratio ligation and 1, 2 & 4 from the 2:1 ratio ligation showed band sizes that correspond to the predicted pattern of 12.3 kb, 9.7 kb, 5.5 kb and 3.1 kb of the plasmid pNG-62 (FIG. 33A).

The putative pNG-62 constructs #2 (1.5:1) and #1 (2:1) were further diagnostically restriction digested with the enzyme BglII or the enzymes NheI and EcoRV (FIG. 33B) and then sequenced. This confirmed successful construction of the plasmid pNG-62 (SEQ ID NO 35, FIG. 30).

Example 8 NG-62 Virus Production and Transgene Expression

The plasmid pNG-62 generated in Example 7 was linearised and used to produce viable ColoAd1 virus particles containing the ColoAd1 genome with a reporter gene (GFP) transgene cassette inserted downstream of the fibre (L5) gene between introduced SgfI and SbfI restriction sites.

The plasmid pNG-62 (685 ng/μl) was linearised to produce the NG-62 virus genome (SEQ ID NO. 38) by restriction digest with the enzyme AscI. The restriction digest reaction was set up according to table 42 and carried out for 2 hrs, 37° C.

TABLE 42

| Reagent | Volume (μl) | Supplier |
|---|---|---|
| pNG-62 DNA (~7 μg) | 10 | |
| AscI | 2.5 | NEB R0558S |
| Buffer 4 | 5 | NEB B7004S |
| Nuclease free water | 32.5 | Fisher Scientific (BPE 2484-100) |

Digested pNG-62 DNA was diluted with 50 μl nuclease-free water and then purified by phenol/chloroform extraction. The extracted NG-62 DNA was then precipitated for 16 hrs, −20° C. in 300 μl>95% molecular biology grade ethanol and 10 μl 3M Sodium Acetate.

The precipitated DNA was pelleted by centrifuging at 14000 rpm, 5 mins and was washed in 500 μl 70% ethanol, before centrifuging again, 14000 rpm, 5 mins. The clean DNA pellet was air dried, resuspended in 500 μl OptiMEM containing 15 μl lipofectamine transfection reagent and incubated for 30 mins, RT. The transfection mixture was then added drop wise to a T-25 flask containing Hek293 cells grown to 70% confluency. After incubation of the cells with the transfection mix for 2 hrs at 37° C., 5% $CO_2$ 4 mls of cell media (DMEM high glucose with glutamine supplemented with 2% FBS) was added to the cells and the flasks was incubated 37° C., 5% $CO_2$.

The transfected Hek293 cells were monitored every 24 hrs and were supplemented with additional media every 48-72 hrs. The production of virus was monitored by observation of a significant cytopathic effect (CPE) in the cell monolayer. Once CPE was observed the virus was harvested from Hek293 cells by three freeze-thaw cycles. The harvested NG-62 virus was used to infect AD293 cells and confirmed viable virus production by observation of significant CPE in the cell monolayer 24 hrs and 48 hrs post-infection (FIG. 34A). The productive expression of GFP transgene from the virus was also confirmed in the infected AD293 cells by immunofluorescence imaging (FIG. 34B).

REFERENCES

Shenk, (2001) "Adenoviridae: The Viruses and Their Replication," in Fields Virology, Vol. 2, Fourth Edition, Knipe, ea., Lippincott, Williams & Wilkins, pp. 2265-2267

Jin et al (2004) "Identification of novel insertion sites in the Ad5 genome that utilize the Ad splicing machinery for therapeutic gene expression" Molecular Therapy Vol. 12(6) pp 1052-63.

Cheever M. J. et al, The prioritization of cancer antigens: a National Cancer Institute pilot project for the acceleration of translational research. *Clin Cancer Res* 2009; 15:5323-5337

We claim:

1. A method of preparing a shuttle vector comprising a selection marker gene and a low copy bacterial replication origin, and an adenovirus genome comprising a 5' ITR, a 3' ITR, and an L5 gene; said method comprising the steps:

a) preparing an adenovirus shuttle vector comprising the following three fragments:

i) a vector fragment comprising a selection marker gene and a low copy bacterial replication origin, wherein the 5' end of the vector fragment starts with a first restriction enzyme site and terminates at the 3' end of the vector fragment in a second restriction enzyme site, ii) a 5'-arm comprising the 5' end of the adenovirus genome including the 5' ITR, wherein the 5' end of the 5' arm starts with a second restriction enzyme site and terminates at the 3' end of the 5' arm with a third restriction enzyme site, iii) a 3'-arm comprising the 3' end of the adenovirus genome including the 3' ITR and the L5 gene, wherein the 5' end of the 3' arm starts with a third restriction enzyme site and terminates at the 3' end of the 3' arm with a first restriction enzyme site, by ligating equal proportions of the three fragments in a one-step three-way ligation to join:

the 3' end of the 3' arm (fragment iii) to the 5' end of the vector fragment (fragment i) at the first restriction enzyme site, the 3' end of the vector fragment (fragment i) to the 5' end of the 5' arm (fragment ii) at the second restriction enzyme site, and the 3' end of the 5' arm (fragment ii) to the 5' end of the 3' arm (fragment iii) at the third restriction enzyme site, to form a circularised shuttle vector arranged as a first restriction enzyme site followed by a vector fragment followed by a second restriction enzyme site followed by a 5' arm, followed by a third restriction enzyme site followed by a 3' arm, and b) introducing at least one original restriction site and/or a transgene into the shuttle vector in a location between the L5 gene and an E3 site, between the L5 gene and an E4 site, or both between the L5 gene and an E3 site and also between the L5 gene and an E4 site.

2. The method of claim 1, wherein the 5' arm comprises about 2.4 to 4.7 kb of the 5' end of an adenovirus genome.

3. The method of claim 1, wherein the 3' arm comprises about 3.3 to 4.8 kb of the 3' end of an adenovirus genome.

4. The method of claim 1, wherein the one-step three-way ligation is performed for at least 50 minutes.

5. The method of claim 1, wherein the one-step three-way ligation is performed at approximately room temperature.

6. The method of claim 1, wherein the original restriction site is independently selected from FseI, NotI, SbfI and SgfI.

7. The method of claim 1, wherein the first and second restriction enzyme sites are the same.

8. The method of claim 1, wherein the vector fragment is dephosphorylated.

9. The method of claim 1, wherein the replication origin is p15A.

10. The method of claim 1, wherein the selection marker gene is KanR.

11. The method of claim 1, wherein the adenovirus genome is from an adenovirus capable of replication.

12. A method of preparing a plasmid, comprising the steps a) and b) of the method of claim 1, and further comprising a step c) performing homologous recombination between the shuttle vector of step a) or step b) and an adenovirus genome to form a plasmid.

13. The method of claim 12, wherein step c) is performed at a shuttle vector to adenovirus genome ratio of 3.5:1.5.

14. The method of claim 13, wherein step c) is performed in electrocompetent BJ5183 cells.

15. The method of claim 12, wherein the adenovirus genome is selected from EnAd, OvAd1, OvAd2, Ad3, Ad5 and Ad11.

16. A method of generating an adenovirus, comprising the steps a) to c) of the method of claim 12, and further comprising the step of expressing the plasmid in a host cell.

17. The method of claim 5, wherein the one-step three-way ligation is performed at a temperature of 20 to 25° C.

18. The method of claim 16, wherein the adenovirus is a replication capable adenovirus.

* * * * *

SEQUENCE LISTING

```
<160> NUMBER OF SEQ ID NOS: 45

<210> SEQ ID NO 1
<211> LENGTH: 32322
<212> TYPE: DNA
<213> ORGANISM: Artificial Sequence
<220> FEATURE:
<223> OTHER INFORMATION: ColoAd1 genome

<400> SEQUENCE: 1

tatctatata atatacctta tagatggaat ggtgccaata tgtaaatgag gtgattttaa      60

aaagtgtgga tcgtgtggtg attggctgtg gggttaacgg ctaaaagggg cggtgcgacc     120

gtgggaaaat gacgttttgt gggggtggag tttttttgca agttgtcgcg ggaaatgtga     180

cgcataaaaa ggcttttttc tcacggaact acttagtttt cccacggtat ttaacaggaa     240

atgaggtagt tttgaccgga tgcaagtgaa aattgttgat tttcgcgcga aaactgaatg     300

aggaagtgtt tttctgaata atgtggtatt tatggcaggg tggagtattt gttcagggcc     360

aggtagactt tgacccatta cgtggaggtt tcgattaccg tgtttttttac ctgaatttcc    420

gcgtaccgtg tcaaagtctt ctgtttttac gtaggtgtca gctgatcgct agggtattta     480

tacctcaggg tttgtgtcaa gaggccactc ttgagtgcca gcgagaagag ttttctcctc     540

tgcgccggca gtttaataat aaaaaaatga gagatttgcg atttctgcct caggaaataa     600

tctctgctga gactggaaat gaaatattgg agcttgtggt gcacgccctg atgggagacg     660

atccggagcc acctgtgcag ctttttgagc ctcctacgct tcaggaactg tatgatttag     720

aggtagaggg atcggaggat tctaatgagg aagctgtaaa tggctttttt accgattcta     780

tgcttttagc tgctaatgaa gggttagaat tagatccgcc tttggacact tttgatactc     840

caggggtaat tgtggaaagc ggtacaggtg taagaaaatt acctgatttg agttccgtgg     900

actgtgattt gcactgctat gaagacgggt ttcctccgag tgatgaggag gaccatgaaa     960

aggagcagtc catgcagact gcagcgggtg agggagtgaa ggctgccaat gttggttttc    1020
```

```
agttggattg cccggagctt cctggacatg gctgtaagtc ttgtgaattt cacaggaaaa   1080
atactggagt aaaggaactg ttatgttcgc tttgttatat gagaacgcac tgccacttta   1140
tttacagtaa gtgtgtttaa gttaaaattt aaaggaatat gctgtttttc acatgtatat   1200
tgagtgtgag ttttgtgctt cttattatag gtcctgtgtc tgatgctgat gaatcaccat   1260
ctcctgattc tactacctca cctcctgaga ttcaagcacc tgttcctgtg gacgtgcgca   1320
agcccattcc tgtgaagctt aagcctggga aacgtccagc agtggaaaaa cttgaggact   1380
tgttacaggg tggggacgga cctttggact tgagtacacg gaaacgtcca agacaataag   1440
tgttccatat ccgtgtttac ttaaggtgac gtcaatattt gtgtgacagt gcaatgtaat   1500
aaaaatatgt taactgttca ctggttttta ttgctttttg ggcggggact caggtatata   1560
agtagaagca gacctgtgtg gttagctcat aggagctggc tttcatccat ggaggtttgg   1620
gccattttgg aagaccttag gaagactagg caactgttag agaacgcttc ggacggagtc   1680
tccggttttt ggagattctg gttcgctagt gaattagcta gggtagtttt taggataaaa   1740
caggactata aacaagaatt tgaaaagttg ttggtagatt gcccaggact tttgaagct    1800
cttaatttgg gccatcaggt tcactttaaa gaaaaagttt tatcagtttt agacttttca   1860
accccaggta gaactgctgc tgctgtggct tttcttactt ttatattaga taaatggatc   1920
ccgcagactc atttcagcag ggatacgtt ttggatttca tagccacagc attgtggaga    1980
acatggaagg ttcgcaagat gaggacaatc ttaggttact ggccagtgca gcctttgggt   2040
gtagcgggaa tcctgaggca tccaccggtc atgccagcgg ttctggagga ggaacagcaa   2100
gaggacaacc cgagagccgg cctggaccct ccagtggagg aggcggagta gctgacttgt   2160
ctcctgaact gcaacgggtg cttactggat ctacgtccac tggacgggat aggggcgtta   2220
agagggagag ggcatctagt ggtactgatg ctagatctga gttggcttta agtttaatga   2280
gtcgcagacg tcctgaaacc atttggtggc atgaggttca gaaagaggga agggatgaag   2340
tttctgtatt gcaggagaaa tattcactgg aacaggtgaa aacatgttgg ttggagcctg   2400
aggatgattg ggaggtggcc attaaaaatt atgccaagat agctttgagg cctgataaac   2460
agtataagat tactagacgg attaatatcc ggaatgcttg ttacatatct ggaaatgggg   2520
ctgaggtggt aatagatact caagacaagg cagttattag atgctgcatg atggatatgt   2580
ggcctggggt agtcggtatg gaagcagtaa cttttgtaaa tgttaagttt aggggagatg   2640
gttataatgg aatagtgttt atggccaata ccaaacttat attgcatggt tgtagctttt   2700
ttggtttcaa caatacctgt gtagatgcct ggggacaggt tagtgtacgg ggatgtagtt   2760
tctatgcgtg ttggattgcc acagctggca gaaccaagag tcaattgtct ctgaagaaat   2820
gcatatttca aagatgtaac ctgggcattc tgaatgaagg cgaagcaagg gtccgccact   2880
gcgcttctac agatactgga tgttttattt tgattaaggg aaatgccagc gtaaagcata   2940
acatgatttg cggtgcttcc gatgagaggc cttatcaaat gctcacttgt gctggtgggc   3000
attgtaatat gctggctact gtgcatattg tttcccatca acgcaaaaaa tggcctgttt   3060
ttgatcacaa tgtgatgacg aagtgtacca tgcatgcagg tgggcgtaga ggaatgttta   3120
tgccttacca gtgtaacatg aatcatgtga aagtgttgtt ggaaccagat gccttttcca   3180
gaatgagcct aacaggaatt tttgacatga acatgcaaat ctggaagatc ctgaggtatg   3240
atgatacgag atcgagggta cgcgcatgcg aatgcggagg caagcatgcc aggttccagc   3300
cggtgtgtgt agatgtgact gaagatctca gaccggatca tttggttatt gcccgcactg   3360
```

-continued

```
gagcagagtt cggatccagt ggagaagaaa ctgactaagg tgagtattgg gaaaactttg   3420
gggtgggatt ttcagatgga cagattgagt aaaaatttgt tttttctgtc ttgcagctgt   3480
catgagtgga aacgcttctt ttaagggggg agtcttcagc ccttatctga cagggcgtct   3540
cccatcctgg gcaggagttc gtcagaatgt tatgggatct actgtggatg gaagacccgt   3600
ccaacccgcc aattcttcaa cgctgaccta tgctacttta agttcttcac ctttggacgc   3660
agctgcagct gccgccgccg cttctgttgc cgctaacact gtgcttggaa tgggttacta   3720
tggaagcatc atggctaatt ccacttcctc taataaccct tctaccctga ctcaggacaa   3780
gttacttgtc cttttggccc agctggaggc tttgacccaa cgtctgggtg aactttctca   3840
gcaggtggtc gagttgcgag tacaaactga gtctgctgtc ggcacggcaa agtctaaata   3900
aaaaaatccc agaatcaatg aataaataaa caagcttgtt gttgatttaa aatcaagtgt   3960
ttttatttca tttttcgcgc acggtatgcc ctagaccacc gatctctatc attgagaact   4020
cggtggattt tttccaggat cctatagagg tgggattgaa tgtttagata catgggcatt   4080
aggccgtctt tggggtggag atagctccat tgaagggatt catgctccgg ggtagtgttg   4140
taaatcaccc agtcataaca aggtcgcagt gcatggtgtt gcacaatatc ttttagaagt   4200
aggctgattg ccacagataa gcccttggtg taggtgttta caaaccggtt gagctgggat   4260
gggtgcattc ggggtgaaat tatgtgcatt ttggattgga tttttaagtt ggcaatattg   4320
ccgccaagat cccgtcttgg gttcatgtta tgaaggacca ccaagacggt gtatccggta   4380
catttaggaa atttatcgtg cagcttggat ggaaaagcgt ggaaaaattt ggagacaccc   4440
ttgtgtcctc caagattttc catgcactca tccatgataa tagcaatggg gccgtgggca   4500
gcggcgcggg caaacacgtt ccgtgggtct gacacatcat agttatgttc ctgagttaaa   4560
tcatcataag ccattttaat gaatttgggg cggagagtac cagattgggg tatgaatgtt   4620
ccttcgggcc ccggagcata gttcccctca cagatttgca tttcccaagc tttcagttcc   4680
gagggtggaa tcatgtccac ctgggggggct atgaaaaaca ccgtttctgg ggcgggggtg   4740
attaattgtg atgatagcaa atttctgagc aattgagatt tgccacatcc ggtggggcca   4800
taaatgattc cgattacggg ttgcaggtgg tagtttaggg aacggcaact gccgtcttct   4860
cgaagcaagg gggccacctc gttcatcatt tcccttacat gcatattttc ccgcaccaaa   4920
tccattagga ggcgctctcc tcctagtgat agaagttctt gtagtgagga aaagtttttc   4980
agcggtttca gaccgtcagc catgggcatt ttggagagag tttgctgcaa aagttctagt   5040
ctgttccaca gttcagtgat gtgttctatg gcatctcgat ccagcagacc tcctcgtttc   5100
gcgggtttgg acggctcctg gaatagggta tgagacgatg ggcgtccagc gctgccaggg   5160
ttcggtcctt ccagggtctc agtgttcgag tcagggttgt ttccgtcaca gtgaaggggt   5220
gtgcgcctgc ttgggcgctt gccagggtgc gcttcagact catcctgctg gtcgaaaact   5280
tctgtcgctt ggcgccctgt atgtcggcca agtagcagtt taccatgagt tcgtagttga   5340
gcgcctcggc tgcgtggcct ttggcgcgga gcttaccttt ggaagttttc ttgcataccg   5400
ggcagtatag gcatttcagc gcatacaact tgggcgcaag gaaaacggat tctggggagt   5460
atgcatctgc gccgcaggag gcgcaaacag tttcacattc caccagccag gttaaatccg   5520
gttcattggg gtcaaaaaca agttttccgc catatttttt gatgcgtttc ttacctttgg   5580
tctccatgag ttcgtgtcct cgttgagtga caaacaggct gtccgtgtcc ccgtagactg   5640
attttacagg cctcttctcc agtggagtgc ctcggtcttc ttcgtacagg aactctgacc   5700
actctgatac aaaggcgcgc gtccaggcca gcacaaagga ggctatgtgg gaggggtagc   5760
```

```
gatcgttgtc aaccaggggg tccacctttt ccaaagtatg caaacacatg tcaccctctt   5820
caacatccag gaatgtgatt ggcttgtagg tgtatttcac gtgacctggg gtccccgctg   5880
ggggggtata aaagggggcg gttctttgct cttcctcact gtcttccgga tcgctgtcca   5940
ggaacgtcag ctgttggggt aggtattccc tctcgaaggc gggcatgacc tctgcactca   6000
ggttgtcagt ttctaagaac gaggaggatt tgatattgac agtgccggtt gagatgcctt   6060
tcatgaggtt ttcgtccatc tggtcagaaa acacaatttt tttattgtca agtttggtgg   6120
caaatgatcc atacagggcg ttggataaaa gtttggcaat ggatcgcatg gtttggttct   6180
tttccttgtc cgcgcgctct ttggcggcga tgttgagttg gacatactcg cgtgccaggc   6240
acttccattc ggggaagata gttgttaatt catctggcac gattctcact tgccaccctc   6300
gattatgcaa ggtaattaaa tccacactgg tggccacctc gcctcgaagg ggttcattgg   6360
tccaacagag cctacctcct ttcctagaac agaaaggggg aagtgggtct agcataagtt   6420
catcgggagg gtctgcatcc atggtaaaga ttcccggaag taaatcctta tcaaaatagc   6480
tgatgggagt ggggtcatct aaggccattt gccattctcg agctgccagt gcgcgctcat   6540
atgggttaag ggactgccc catggcatgg gatgggtgag tgcagaggca tacatgccac   6600
agatgtcata gacgtagatg ggatcctcaa agatgcctat gtaggttgga tagcatcgcc   6660
cccctctgat acttgctcgc acatagtcat atagttcatg tgatggcgct agcagccccg   6720
gacccaagtt ggtgcgattg ggtttttctg ttctgtagac gatctggcga aagatggcgt   6780
gagaattgga agagatggtg ggtctttgaa aaatgttgaa atgggcatga ggtagaccta   6840
cagagtctct gacaaagtgg gcataagatt cttgaagctt ggttaccagt tcggcggtga   6900
caagtacgtc tagggcgcag tagtcaagtg tttcttgaat gatgtcataa cctggttggt   6960
ttttctttc ccacagttcg cggttgagaa ggtattcttc gcgatccttc cagtactctt   7020
ctagcggaaa cccgtctttg tctgcacggt aagatcctag catgtagaac tgattaactg   7080
ccttgtaagg gcagcagccc ttctctacgg gtagagagta tgcttgagca gcttttcgta   7140
gcgaagcgtg agtaagggca aaggtgtctc tgaccatgac tttgaggaat tggtatttga   7200
agtcgatgtc gtcacaggct ccctgttccc agagttggaa gtctacccgt ttcttgtagg   7260
cggggttggg caaagcgaaa gtaacatcat tgaagagaat cttgccggcc ctgggcatga   7320
aattgcgagt gatgcgaaaa ggctgtggta cttccgctcg gttattgata acctgggcag   7380
ctaggacgat ctcgtcgaaa ccgttgatgt tgtgtcctac gatgtataat tctatgaaac   7440
gcggcgtgcc tctgacgtga ggtagcttac tgagctcatc aaaggttagg tctgtggggt   7500
cagataaggc gtagtgttcg agagcccatt cgtgcaggtg aggattcgct ttaaggaagg   7560
aggaccagag gtccactgcc agtgctgttt gtaactggtc ccggtactga cgaaaatgcc   7620
gtccgactgc cattttttct ggggtgacgc aatagaaggt ttgggggtcc tgccgccagc   7680
gatcccactt gagttttatg gcgaggtcat aggcgatgtt gacgagccgc tggtctccag   7740
agagtttcat gaccagcatg aaggggatta gctgcttgcc aaaggacccc atccaggtgt   7800
aggtttccac atcgtaggtg agaaagagcc tttctgtgcg aggatgagag ccaatcggga   7860
agaactggat ctcctgccac cagttggagg aatggctgtt gatgtgatgg aagtagaact   7920
ccctgcgacg cgccgagcat tcatgcttgt gcttgtacag acggccgcag tagtcgcagc   7980
gttgcacggg ttgtatctcg tgaatgagtt gtacctggct tcccttgacg agaaatttca   8040
gtgggaagcc gaggcctggc gattgtatct cgtgctttac tatgttgtct gcatcggcct   8100
```

-continued

```
gttcatcttc tgtctcgatg gtggtcatgc tgacgagccc tcgcgggagg caagtccaga   8160
cctcggcgcg gcaggggcgg agctcgagga cgagagcgcg caggctggag ctgtccaggg   8220
tcctgagacg ctgcggactc aggttagtag gcagtgtcag gagattaact tgcatgatct   8280
tttggagggc gtgcgggagg ttcagatagt acttgatctc aacgggtccg ttggtggaga   8340
tgtcgatggc ttgcagggtt ccgtgtccct tgggcgctac caccgtgccc ttgtttttca   8400
ttttggacgg cggtggctct gttgcttctt gcatgtttag aagcggtgtc gagggcgcgc   8460
accgggcggc aggggcggct cgggacccgg cggcatggct ggcagtggta cgtcggcgcc   8520
gcgcgcgggt aggttctggt actgcgccct gagaagactc gcatgcgcga cgacgcggcg   8580
gttgacatcc tggatctgac gcctctgggt gaaagctacc ggccccgtga gcttgaacct   8640
gaaagagagt tcaacagaat caatctcggt atcgttgacg gcggcttgcc taaggatttc   8700
ttgcacgtca ccagagttgt cctggtaggc gatctccgcc atgaactgct cgatctcttc   8760
ctcttgaaga tctccgcggc ccgctctctc gacggtggcc gcgaggtcgt tggagatgcg   8820
cccaatgagt tgagagaatg cattcatgcc cgcctcgttc cagacgcggc tgtagaccac   8880
ggcccccacg ggatctctcg cgcgcatgac cacctgggcg aggttgagct ccacgtggcg   8940
ggtgaagacc gcatagttgc ataggcgctg gaaaaggtag ttgagtgtgg tggcgatgtg   9000
ctcggtgacg aagaaataca tgatccatcg tctcagcggc atctcgctga catcgcccag   9060
agcttccaag cgctccatgg cctcgtagaa gtccacggca aaattaaaaa actgggagtt   9120
tcgcgcggac acggtcaact cctcttccag aagacggata agttcggcga tggtggtgcg   9180
cacctcgcgc tcgaaagccc ctgggatttc ttcctcaatc tcttcttctt ccactaacat   9240
ctcttcctct tcaggtgggg ctgcaggagg agggggaacg cggcgacgcc ggcggcgcac   9300
gggcagacgg tcgatgaatc tttcaatgac ctctccgcgg cggcggcgca tggtttcagt   9360
gacggcgcgg ccgttctcgc gcggtcgcag agtaaaaaca ccgccgcgca tctccttaaa   9420
gtggtgactg ggaggttctc cgtttgggag ggagagggcg ctgattatac attttattaa   9480
ttggcccgta gggactgcac gcagagatct gatcgtgtca agatccacgg gatctgaaaa   9540
cctttcgacg aaagcgtcta accagtcaca gtcacaaggt aggctgagta cggcttcttg   9600
tgggcggggg tggttatgtg ttcggtctgg gtcttctgtt tcttcttcat ctcgggaagg   9660
tgagacgatg ctgctggtga tgaaattaaa gtaggcagtt ctaagacggc ggatggtggc   9720
gaggagcacc aggtctttgg gtccggcttg ctggatacgc aggcgattgg ccattcccca   9780
agcattatcc tgacatctag caagatcttt gtagtagtct tgcatgagcc gttctacggg   9840
cacttcttcc tcacccgttc tgccatgcat acgtgtgagt ccaaatccgc gcattggttg   9900
taccagtgcc aagtcagcta cgactctttc ggcgaggatg gcttgctgta cttgggtaag   9960
ggtggcttga aagtcatcaa aatccacaaa gcggtggtaa gctcctgtat taatggtgta  10020
agcacagttg gccatgactg accagttaac tgtctggtga ccagggcgca cgagctcggt  10080
gtatttaagg cgcgaatagg cgcgggtgtc aaagatgtaa tcgttgcagg tgcgcaccag  10140
atactggtac cctataagaa aatgcggcgg tggttggcgg tagagaggcc atcgttctgt  10200
agctggagcg ccaggggcga ggtcttccaa cataaggcgg tgatagccgt agatgtacct  10260
ggacatccag gtgattcctg cggcggtagt agaagcccga ggaaactcgc gtacgcggtt  10320
ccaaatgttg cgtagcggca tgaagtagtt cattgtaggc acggtttgac cagtgaggcg  10380
cgcgcagtca ttgatgctct atagacacgg agaaaatgaa agcgttcagc gactcgactc  10440
cgtagcctgg aggaacgtga acgggttggg tcgcggtgta ccccggttcg agacttgtac  10500
```

-continued

```
tcgagccggc cggagccgcg gctaacgtgg tattggcact cccgtctcga cccagcctac  10560
aaaaatccag gatacggaat cgagtcgttt tgctggtttc cgaatggcag ggaagtgagt  10620
cctatttttt ttttttgccg ctcagatgca tcccgtgctg cgacagatgc gcccccaaca  10680
acagcccccc tcgcagcagc agcagcagca atcacaaaag gctgtccctg caactactgc  10740
aactgccgcc gtgagcggtg cgggacagcc cgcctatgat ctggacttgg aagagggcga  10800
aggactggca cgtctaggtg cgccttcacc cgagcggcat ccgcgagttc aactgaaaaa  10860
agattctcgc gaggcgtatg tgccccaaca gaacctattt agagacagaa gcggcgagga  10920
gccggaggag atgcgagctt cccgctttaa cgcgggtcgt gagctgcgtc acggtttgga  10980
ccgaagacga gtgttgcggg acgaggattt cgaagttgat gaaatgacag ggatcagtcc  11040
tgccagggca cacgtggctg cagccaacct tgtatcggct tacgagcaga cagtaaagga  11100
agagcgtaac ttccaaaagt cttttaataa tcatgtgcga accctgattg cccgcgaaga  11160
agttaccctt ggtttgatgc atttgtggga tttgatggaa gctatcattc agaaccctac  11220
tagcaaacct ctgaccgccc agctgtttct ggtggtgcaa cacagcagag acaatgaggc  11280
tttcagagag gcgctgctga acatcaccga acccgagggg agatggttgt atgatcttat  11340
caacattcta cagagtatca tagtgcagga gcggagcctg ggcctggccg agaaggtggc  11400
tgccatcaat tactcggttt tgagcttggg aaaatattac gctcgcaaaa tctacaagac  11460
tccatacgtt cccatagaca aggaggtgaa gatagatggg ttctacatgc gcatgacgct  11520
caaggtcttg accctgagcg atgatcttgg ggtgtatcgc aatgacagaa tgcatcgcgc  11580
ggttagcgcc agcaggaggc gcgagttaag cgacagggaa ctgatgcaca gtttgcaaag  11640
agctctgact ggagctggaa ccgagggtga gaattacttc gacatgggag ctgacttgca  11700
gtggcagcct agtcgcaggg ctctgagcgc cgcgacggca ggatgtgagc ttccttacat  11760
agaagaggcg gatgaaggcg aggaggaaga gggcgagtac ttggaagact gatggcacaa  11820
cccgtgtttt ttgctagatg gaacagcaag caccggatcc cgcaatgcgg gcggcgctgc  11880
agagccagcc gtccggcatt aactcctcgg acgattggac ccaggccatg caacgtatca  11940
tggcgttgac gactcgcaac cccgaagcct ttagacagca accccaggcc aaccgtctat  12000
cggccatcat ggaagctgta gtgccttccc gctctaatcc cactcatgag aaggtcctgg  12060
ccatcgtgaa cgcgttggtg gagaacaaag ctattcgtcc agatgaggcc ggactggtat  12120
acaacgctct cttagaacgc gtggctcgct acaacagtag caatgtgcaa accaatttgg  12180
accgtatgat aacagatgta cgcgaagccg tgtctcagcg cgaaaggttc cagcgtgatg  12240
ccaacctggg ttcgctggtg gcgttaaatg ctttcttgag tactcagcct gctaatgtgc  12300
cgcgtggtca acaggattat actaactttt taagtgcttt gagactgatg gtatcagaag  12360
tacctcagag cgaagtgtat cagtccggtc ctgattactt ctttcagact agcagacagg  12420
gcttgcagac ggtaaatctg agccaagctt ttaaaaacct taaaggtttg tggggagtgc  12480
atgccccggt aggagaaaga gcaaccgtgt ctagcttgtt aactccgaac tcccgcctat  12540
tattactgtt ggtagctcct ttcaccgaca gcggtagcat cgaccgtaat tcctatttgg  12600
gttacctact aaacctgtat cgcgaagcca tagggcaaag tcaggtggac gagcagacct  12660
atcaagaaat tacccaagtc agtcgcgctt tgggacagga agacactggc agtttggaag  12720
ccactctgaa cttcttgctt accaatcggt ctcaaaagat ccctcctcaa tatgctctta  12780
ctgcggagga ggagaggatc cttagatatg tgcagcagag cgtgggattg tttctgatgc  12840
```

```
aagagggggc aactccgact gcagcactgg acatgacagc gcgaaatatg gagcccagca  12900
tgtatgccag taaccgacct ttcattaaca aactgctgga ctacttgcac agagctgccg  12960
ctatgaactc tgattatttc accaatgcca tcttaaaccc gcactggctg cccccacctg  13020
gtttctacac gggcgaatat gacatgcccg accctaatga cggatttctg tgggacgacg  13080
tggacagcga tgttttttca cctctttctg atcatcgcac gtggaaaaag gaaggcggcg  13140
atagaatgca ttcttctgca tcgctgtccg gggtcatggg tgctaccgcg gctgagcccg  13200
agtctgcaag tccttttcct agtctaccct tttctctaca cagtgtacgt agcagcgaag  13260
tgggtagaat aagtcgcccg agtttaatgg gcgaagagga gtatctaaac gattccttgc  13320
tcagaccggc aagagaaaaa aatttcccaa acaatggaat agaaagtttg gtggataaaa  13380
tgagtagatg gaagacttat gctcaggatc acagagacga gcctgggatc atggggatta  13440
caagtagagc gagccgtaga cgccagcgcc atgacagaca gaggggtctt gtgtgggacg  13500
atgaggattc ggccgatgat agcagcgtgc tggacttggg tgggagagga aggggcaacc  13560
cgtttgctca tttgcgccct cgcttgggtg gtatgttgta aaaaaaaata aaaaaaaaac  13620
tcaccaaggc catggcgacg agcgtacgtt cgttcttctt tattatctgt gtctagtata  13680
atgaggcgag tcgtgctagg cggagcggtg gtgtatccgg agggtcctcc tccttcgtac  13740
gagagcgtga tgcagcagca gcaggcgacg gcggtgatgc aatccccact ggaggctccc  13800
tttgtgcctc cgcgatacct ggcacctacg gagggcagaa acagcattcg ttattcggaa  13860
ctggcacctc agtacgatac caccaggttg tatctggtgg acaacaagtc ggcggacatt  13920
gcttctctga actatcagaa tgaccacagc aacttcttga ccacggtggt gcaaaacaat  13980
gactttaccc ctacggaagc cagcacccag accattaact ttgatgaacg atcgcggtgg  14040
ggcggtcagc taaagaccat catgcatact aacatgccaa acgtgaacga gtatatgttt  14100
agtaacaagt tcaaagcgcg tgtgatggtg tccagaaaac ctcccgacgg tgctgcagtt  14160
ggggatactt atgatcacaa gcaggatatt ttgaaatatg agtggttcga gtttactttg  14220
ccagaaggca acttttcagt tactatgact attgatttga tgaacaatgc catcatagat  14280
aattacttga aagtgggtag acagaatgga gtgcttgaaa gtgacattgg tgttaagttc  14340
gacaccagga acttcaagct gggatgggat cccgaaacca agttgatcat gcctggagtg  14400
tatacgtatg aagccttcca tcctgacatt gtcttactgc ctggctgcgg agtggatttt  14460
accgagagtc gtttgagcaa ccttcttggt atcagaaaaa aacagccatt tcaagagggt  14520
tttaagattt tgtatgaaga tttagaaggt ggtaatattc cggccctctt ggatgtagat  14580
gcctatgaga acagtaagaa agaacaaaaa gccaaaatag aagctgctac agctgctgca  14640
gaagctaagg caaacatagt tgccagcgac tctacaaggg ttgctaacgc tggagaggtc  14700
agaggagaca attttgcgcc aacacctgtt ccgactgcag aatcattatt ggccgatgtg  14760
tctgaaggaa cggacgtgaa actcactatt caacctgtag aaaaagatag taagaataga  14820
agctataatg tgttggaaga caaaatcaac acagcctatc gcagttggta tctttcgtac  14880
aattatggcg atcccgaaaa aggagtgcgt tcctggacat tgctcaccac ctcagatgtc  14940
acctgcggag cagagcaggt ctactggtcg cttccagaca tgatgaagga tcctgtcact  15000
ttccgctcca ctagacaagt cagtaactac cctgtggtgg gtgcagagct tatgcccgtc  15060
ttctcaaaga gcttctacaa cgaacaagct gtgtactccc agcagctccg ccagtccacc  15120
tcgcttacgc acgtcttcaa ccgctttcct gagaaccaga ttttaatccg tccgccggcg  15180
cccaccatta ccaccgtcag tgaaaacgtt cctgctctca cagatcacgg gaccctgccg  15240
```

```
ttgcgcagca gtatccgggg agtccaacgt gtgaccgtta ctgacgccag acgccgcacc  15300
tgtccctacg tgtacaaggc actgggcata gtcgcaccgc gcgtcctttc aagccgcact  15360
ttctaaaaaa aaaaaaaatg tccattctta tctcgcccag taataacacc ggttggggtc  15420
tgcgcgctcc aagcaagatg tacggaggcg cacgcaaacg ttctacccaa catcctgtcc  15480
gtgttcgcgg acattttcgc gctccatggg gcgccctcaa gggccgcact cgcgttcgaa  15540
ccaccgtcga tgatgtaatc gatcaggtgg ttgccgacgc ccgtaattat actcctactg  15600
cgcctacatc tactgtggat gcagttattg acagtgtagt ggctgacgct cgcaactatg  15660
ctcgacgtaa gagccggcga aggcgcattg ccagacgcca ccgagctacc actgccatgc  15720
gagccgcaag agctctgcta cgaagagcta gacgcgtggg gcgaagagcc atgcttaggg  15780
cggccagacg tgcagcttcg ggcgccagcg ccggcaggtc ccgcaggcaa gcagccgctg  15840
tcgcagcggc gactattgcc gacatggccc aatcgcgaag aggcaatgta tactgggtgc  15900
gtgacgctgc caccggtcaa cgtgtacccg tgcgcacccg tcccccctcgc acttagaaga  15960
tactgagcag tctccgatgt tgtgtcccag cggcgaggat gtccaagcgc aaatacaagg  16020
aagaaatgct gcaggttatc gcacctgaag tctacggcca accgttgaag gatgaaaaaa  16080
aaccccgcaa aatcaagcgg gttaaaaagg acaaaaaaga agaggaagat ggcgatgatg  16140
ggctggcgga gtttgtgcgc gagtttgccc cacggcgacg cgtgcaatgg cgtgggcgca  16200
aagttcgaca tgtgttgaga cctggaactt cggtggtctt tacacccggc gagcgttcaa  16260
gcgctacttt taagcgttcc tatgatgagg tgtacgggga tgatgatatt cttgagcagg  16320
cggctgaccg attaggcgag tttgcttatg gcaagcgtag tagaataact tccaaggatg  16380
agacagtgtc gataccccttg gatcatggaa atcccacccc tagtcttaaa ccggtcactt  16440
tgcagcaagt gttacccgta actccgcgaa caggtgttaa acgcgaaggt gaagatttgt  16500
atcccactat gcaactgatg gtacccaaac gccagaagtt ggaggacgtt ttggagaaag  16560
taaaagtgga tccagatatt caacctgagg ttaaagtgag acccattaag caggtagcgc  16620
ctggtctggg ggtacaaact gtagacatta agattcccac tgaaagtatg gaagtgcaaa  16680
ctgaacccgc aaagcctact gccacctcca ctgaagtgca aacggatcca tggatgccca  16740
tgcctattac aactgacgcc gccggtccca ctcgaagatc ccgacgaaag tacggtccag  16800
caagtctgtt gatgcccaat tatgttgtac acccatctat tattcctact cctggttacc  16860
gaggcactcg ctactatcgc agccgaaaca gtacctcccg ccgtcgccgc aagacacctg  16920
caaatcgcag tcgtcgccgt agacgcacaa gcaaaccgac tcccggcgcc ctggtgcggc  16980
aagtgtaccg caatggtagt gcggaacctt tgacactgcc gcgtgcgcgt taccatccga  17040
gtatcatcac ttaatcaatg ttgccgctgc ctccttgcag atatggccct cacttgtcgc  17100
cttcgcgttc ccatcactgg ttaccgagga agaaactcgc gccgtagaag agggatgttg  17160
ggacgcggaa tgcgacgcta caggcgacgg cgtgctatcc gcaagcaatt gcggggtggt  17220
tttttaccag ccttaattcc aattatcgct gctgcaattg gcgcgatacc aggcatagct  17280
tccgtggcgg ttcaggcctc gcaacgacat tgacattgga aaaaaacgta taaataaaaa  17340
aaaaaaaata caatggactc tgacactcct ggtcctgtga ctatgttttc ttagagatgg  17400
aagacatcaa tttttcatcc ttggctccgc gacacggcac gaagccgtac atgggcacct  17460
ggagcgacat cggcacgagc caactgaacg ggggcgcctt caattggagc agtatctgga  17520
gcgggcttaa aaattttggc tcaaccataa aaacatacgg gaacaaagct tggaacagca  17580
```

gtacaggaca ggcgcttaga aataaactta aagaccagaa cttccaacaa aaagtagtcg 17640
atgggatagc ttccggcatc aatggagtgg tagatttggc taaccaggct gtgcagaaaa 17700
agataaacag tcgtttggac ccgccgccag caaccccagg tgaaatgcaa gtggaggaag 17760
aaattcctcc gccagaaaaa cgaggcgaca agcgtccgcg tcccgatttg gaagagacgc 17820
tggtgacgcg cgtagatgaa ccgccttctt atgaggaagc aacgaagctt ggaatgccca 17880
ccactagacc gatagcccca atggccaccg gggtgatgaa accttctcag ttgcatcgac 17940
ccgtcacctt ggatttgccc cctccccctg ctgctactgc tgtacccgct tctaagcctg 18000
tcgctgcccc gaaaccagtc gccgtagcca ggtcacgtcc cgggggcgct cctcgtccaa 18060
atgcgcactg gcaaaatact ctgaacagca tcgtgggtct aggcgtgcaa agtgtaaaac 18120
gccgtcgctg cttttaatta aatatggagt agcgcttaac ttgcctatct gtgtatatgt 18180
gtcattacac gccgtcacag cagcagagga aaaaaggaag aggtcgtgcg tcgacgctga 18240
gttactttca agatggccac cccatcgatg ctgccccaat gggcatacat gcacatcgcc 18300
ggacaggatg cttcggagta cctgagtccg ggtctggtgc agttcgcccg cgccacagac 18360
acctacttca atctgggaaa taagtttaga aatcccaccg tagcgccgac ccacgatgtg 18420
accaccgacc gtagccagcg gctcatgttg cgcttcgtgc ccgttgaccg ggaggacaat 18480
acatactctt acaaagtgcg gtacaccctg gccgtgggcg acaacagagt gctggatatg 18540
gccagcacgt tctttgacat taggggtgtg ttggacagag gtcccagttt caaaccctat 18600
tctggtacgg cttacaactc cctggctcct aaaggcgctc caaatacatc tcagtggatt 18660
gcagaaggtg taaaaaatac aactggtgag gaacacgtaa cagaagagga aaccaatact 18720
actacttaca cttttggcaa tgctcctgta aaagctgaag ctgaaattac aaaagaagga 18780
ctcccagtag gtttggaagt ttcagatgaa gaaagtaaac cgatttatgc tgataaaaca 18840
tatcagccag aacctcagct gggagatgaa acttggactg accttgatgg aaaaaaccgaa 18900
aagtatggag gcagggctct caaacccgat actaagatga aaccatgcta cgggtccttt 18960
gccaaaccta ctaatgtgaa aggcggtcag gcaaaacaaa aaacaacgga gcagccaaat 19020
cagaaagtcg aatatgatat cgacatggag ttttttgatg cggcatcgca gaaaacaaac 19080
ttaagtccta aaattgtcat gtatgcagaa aatgtaaatt tggaaactcc agacactcat 19140
gtagtgtaca aacctggaac agaagacaca agttccgaag ctaatttggg acaacaatct 19200
atgcccaaca gacccaacta cattggcttc agagataact ttattggact tatgtactat 19260
aacagtactg gtaacatggg ggtgctggct ggtcaagcgt ctcagttaaa tgcagtggtt 19320
gacttgcagg acagaaacac agaactttct taccaactct tgcttgactc tctgggcgac 19380
agaaccagat actttagcat gtggaatcag gctgtggaca gttatgatcc tgatgtacgt 19440
gttattgaaa atcatggtgt ggaagatgaa cttcccaact actgttttcc actggacggc 19500
ataggtgttc caacaaccag ttacaaatca atagttccaa atggagacaa tgcgcctaat 19560
tggaaggaac ctgaagtaaa tggaacaagt gagatcggac agggtaattt gtttgccatg 19620
gaaattaacc ttcaagccaa tctatggcga agtttccttt attccaatgt ggctctatat 19680
ctcccagact cgtacaaata caccccgtcc aatgtcactc ttccagaaaa caaaaacacc 19740
tacgactaca tgaacgggcg ggtggtgccg ccatctctag tagacaccta tgtgaacatt 19800
ggtgccaggt ggtctctgga tgccatggac aatgtcaacc cattcaacca ccaccgtaac 19860
gctggcttgc gttaccgatc catgcttctg ggtaacggac gttatgtgcc tttccacata 19920
caagtgcctc aaaaattctt cgctgttaaa aacctgctgc ttctcccagg ctcctacact 19980

-continued

```
tatgagtgga actttaggaa ggatgtgaac atggttctac agagttccct cggtaacgac  20040
ctgcgggtag atggcgccag catcagtttc acgagcatca acctctatgc tactttttc   20100
cccatggctc acaacaccgc ttccaccctt gaagccatgc tgcggaatga caccaatgat  20160
cagtcattca acgactacct atctgcagct aacatgctct accccattcc tgccaatgca  20220
accaatattc ccatttccat tccttctcgc aactgggcgg ctttcagagg ctggtcattt  20280
accagactga aaaccaaaga aactccctct ttggggtctg gatttgaccc ctactttgtc  20340
tattctggtt ctattcccta cctggatggt accttctacc tgaaccacac ttttaagaag  20400
gtttccatca tgtttgactc ttcagtgagc tggcctggaa atgacaggtt actatctcct  20460
aacgaatttg aaataaagcg cactgtggat ggcgaaggct acaacgtagc ccaatgcaac  20520
atgaccaaag actggttctt ggtacagatg ctcgccaact acaacatcgg ctatcagggc  20580
ttctacattc cagaaggata caaagatcgc atgtattcat ttttcagaaa cttccagccc  20640
atgagcaggc aggtggttga tgaggtcaat tacaaagact tcaaggccgt cgccataccc  20700
taccaacaca acaactctgg ctttgtgggt tacatggctc cgaccatgcg ccaaggtcaa  20760
ccctatcccg ctaactatcc ctatccactc attggaacaa ctgccgtaaa tagtgttacg  20820
cagaaaaagt tcttgtgtga cagaaccatg tggcgcatac cgttctcgag caacttcatg  20880
tctatggggg cccttacaga cttgggacag aatatgctct atgccaactc agctcatgct  20940
ctggacatga cctttgaggt ggatcccatg gatgagccca ccctgcttta tcttctcttc  21000
gaagttttcg acgtggtcag agtgcatcag ccacaccgcg gcatcatcga ggcagtctac  21060
ctgcgtacac cgttctcggc cggtaacgct accacgtaag aagcttcttg cttcttgcaa  21120
atagcagctg caaccatggc ctgcggatcc caaaacggct ccagcgagca agagctcaga  21180
gccattgtcc aagacctggg ttgcggaccc tattttttgg gaacctacga taagcgcttc  21240
ccggggttca tggcccccga taagctcgcc tgtgccattg taaatacggc cggacgtgag  21300
acgggggggag agcactggtt ggctttcggt tggaacccac gttctaacac ctgctacctt  21360
tttgatcctt ttggattctc ggatgatcgt ctcaaacaga tttaccagtt tgaatatgag  21420
ggtctcctgc gccgcagcgc tcttgctacc aaggaccgct gtattacgct ggaaaaatct  21480
acccagaccg tgcagggtcc ccgttctgcc gcctgcggac ttttctgctg catgttcctt  21540
cacgcctttg tgcactggcc tgaccgtccc atggacggaa accccaccat gaaattgcta  21600
actggagtgc caaacaacat gcttcattct cctaaagtcc agcccaccct gtgtgacaat  21660
caaaaagcac tctaccattt tcttaatacc cattcgcctt attttcgctc ccatcgtaca  21720
cacatcgaaa gggccactgc gttcgaccgt atggatgttc aataatgact catgtaaaca  21780
acgtgttcaa taaacatcac tttattttt tacatgtatc aaggctctgc attacttatt   21840
tatttacaag tcgaatgggt tctgacgaga atcagaatga cccgcaggca gtgatacgtt  21900
gcggaactga tacttgggtt gccacttgaa ttcgggaatc accaacttgg gaaccggtat  21960
atcgggcagg atgtcactcc acagctttct ggtcagctgc aaagctccaa gcaggtcagg  22020
agccgaaatc ttgaaatcac aattaggacc agtgctttga gcgcgagagt tgcggtacac  22080
cggattgcag cactgaaaca ccatcagcga cggatgtctc acgcttgcca gcacggtggg  22140
atctgcaatc atgcccacat ccagatcttc agcattggca atgctgaacg gggtcatctt  22200
gcaggtctgc ctacccatgg cgggcaccca attaggcttg tggttgcaat cgcagtgcag  22260
ggggatcagt atcatcttgg cctgatcctg tctgattcct ggatacacgg ctctcatgaa  22320
```

agcatcatat tgcttgaaag cctgctgggc tttactaccc tcggtataaa acatcccgca 22380
ggacctgctc gaaaactggt tagctgcaca gccggcatca ttcacacagc agcgggcgtc 22440
attgttagct atttgcacca cacttctgcc ccagcggttt tgggtgattt tggttcgctc 22500
gggattctcc tttaaggctc gttgtccgtt ctcgctggcc acatccatct cgataatctg 22560
ctccttctga atcataatat tgccatgcag gcacttcagc ttgccctcat aatcattgca 22620
gccatgaggc cacaacgcac agcctgtaca ttcccaatta tggtgggcga tctgagaaaa 22680
agaatgtatc attccctgca gaaatcttcc catcatcgtg ctcagtgtct tgtgactagt 22740
gaaagttaac tggatgcctc ggtgctcctc gtttacgtac tggtgacaga tgcgcttgta 22800
ttgttcgtgt tgctcaggca ttagtttaaa agaggttcta agttcgttat ccagcctgta 22860
cttctccatc agcagacaca tcacttccat gcctttctcc caagcagaca ccaggggcaa 22920
gctaatcgga ttcttaacag tgcaggcagc agctccttta gccagagggt catctttagc 22980
gatcttctca atgcttcttt tgccatcctt ctcaacgatg cgcacgggcg ggtagctgaa 23040
acccactgct acaagttgcg cctcttctct ttcttcttcg ctgtcttgac tgatgtcttg 23100
catggggata tgtttggtct tccttggctt ctttttgggg ggtatcggag gaggaggact 23160
gtcgctccgt tccggagaca gggaggattg tgacgtttcg ctcaccatta ccaactgact 23220
gtcggtagaa gaacctgacc ccacacggcg acaggtgttt ctcttcgggg gcagaggtgg 23280
aggcgattgc gaagggctgc ggtccgacct ggaaggcgga tgactggcag aacctcttcc 23340
gcgttcgggg gtgtgctccc tgtggcggtc gcttaactga tttccttcgc ggctggccat 23400
tgtgttctcc taggcagaga aacaacagac atggaaactc agccattgct gtcaacatcg 23460
ccacgagtgc catcacatct cgtcctcagc gacgaggaaa aggagcagag cttaagcatt 23520
ccaccgccca gtcctgccac cacctctacc ctagaagata aggaggtcga cgcatctcat 23580
gacatgcaga ataaaaaagc gaaagagtct gagacagaca tcgagcaaga cccgggctat 23640
gtgacaccgg tggaacacga ggaagagttg aaacgctttc tagagagaga ggatgaaaac 23700
tgcccaaaac aacgagcaga taactatcac caagatgctg gaaataggga tcagaacacc 23760
gactacctca tagggcttga cggggaagac gcgctcctta aacatctagc aagacagtcg 23820
ctcatagtca aggatgcatt attggacaga actgaagtgc ccatcagtgt ggaagagctc 23880
agccgcgcct acgagcttaa cctcttttca cctcgtactc cccccaaacg tcagccaaac 23940
ggcacctgcg agccaaatcc tcgcttaaac ttttatccag cttttgctgt gccagaagta 24000
ctggctacct atcacatctt ttttaaaaat caaaaaattc cagtctcctg ccgcgctaat 24060
cgcacccgcg ccgatgccct actcaatctg ggacctggtt cacgcttacc tgatatagct 24120
tccttggaag aggttccaaa gatcttcgag ggtctgggca ataatgagac tcgggccgca 24180
aatgctctgc aaaagggaga aaatggcatg gatgagcatc acagcgttct ggtggaattg 24240
gaaggcgata atgccagact cgcagtactc aagcgaagca tcgaggtcac acacttcgca 24300
tatcccgctg tcaacctgcc ccctaaagtc atgacggcgg tcatggacca gttactcatt 24360
aagcgcgcaa gtcccctttc agaagacatg catgacccag atgcctgtga tgagggtaaa 24420
ccagtggtca gtgatgagca gctaacccga tggctgggca ccgactctcc cagggatttg 24480
gaagagcgtc gcaagcttat gatggccgtg gtgctggtta ccgtagaact agagtgtctc 24540
cgacgtttct ttaccgattc agaaaccttg cgcaaactcg aagagaatct gcactacact 24600
tttagacacg gctttgtgcg gcaggcatgc aagatatcta acgtggaact caccaacctg 24660
gtttcctaca tgggtattct gcatgagaat cgcctaggac aaagcgtgct gcacagcacc 24720

-continued

```
ctgaaggggg aagcccgccg tgattacatc cgcgattgtg tctatctgta cctgtgccac  24780
acgtggcaaa ccggcatggg tgtatggcag caatgtttag aagaacagaa cttgaaagag  24840
cttgacaagc tcttacagaa atctcttaag gttctgtgga cagggttcga cgagcgcacc  24900
gtcgcttccg acctggcaga cctcatcttc ccagagcgtc tcagggttac tttgcgaaac  24960
ggattgcctg actttatgag ccagagcatg cttaacaatt ttcgctcttt catcctggaa  25020
cgctccggta tcctgcccgc cacctgctgc gcactgccct ccgactttgt gcctctcacc  25080
taccgcgagt gccccccgcc gctatggagt cactgctacc tgttccgtct ggccaactat  25140
ctctcctacc actcggatgt gatcgaggat gtgagcggag acggcttgct ggagtgtcac  25200
tgccgctgca atctgtgcac gccccaccgg tccctagctt gcaaccccca gttgatgagc  25260
gaaacccaga taataggcac ctttgaattg caaggcccca gcagccaagg cgatgggtct  25320
tctcctgggc aaagtttaaa actgaccccg ggactgtgga cctccgccta cttgcgcaag  25380
tttgctccgg aagattacca cccctatgaa atcaagttct atgaggacca atcacagcct  25440
ccaaaggccg aactttcggc ctgcgtcatc acccaggggg caattctggc ccaattgcaa  25500
gccatccaaa aatcccgcca agaatttcta ctgaaaaagg gtaagggggt ctaccttgac  25560
ccccagaccg gcgaggaact caacacaagg ttccctcagg atgtcccaac gacgagaaaa  25620
caagaagttg aaggtgcagc cgccgccccc agaagatatg gaggaagatt gggacagtca  25680
ggcagaggag gcggaggagg acagtctgga ggacagtctg gaggaagaca gtttggagga  25740
ggaaaacgag gaggcagagg aggtggaaga agtaaccgcc gacaaacagt tatcctcggc  25800
tgcggagaca agcaacagcg ctaccatctc cgctccgagt cgaggaaccc ggcggcgtcc  25860
cagcagtaga tgggacgaga ccggacgctt cccgaaccca accagcgctt ccaagaccgg  25920
taagaaggat cggcagggat acaagtcctg gcgggggcat aagaatgcca tcatctcctg  25980
cttgcatgag tgcgggggca acatatcctt cacgcggcgc tacttgctat tccaccatgg  26040
ggtgaacttt ccgcgcaatg ttttgcatta ctaccgtcac ctccacagcc cctactatag  26100
ccagcaaatc ccggcagtct cgacagataa agacagcggc ggcgacctcc aacagaaaac  26160
cagcagcggc agttagaaaa tacacaacaa gtgcagcaac aggaggatta aagattacag  26220
ccaacgagcc agcgcaaacc cgagagttaa gaaatcggat ctttccaacc ctgtatgcca  26280
tcttccagca gagtcggggt caagagcagg aactgaaaat aaaaaaccga tctctgcgtt  26340
cgctcaccag aagttgtttg tatcacaaga gcgaagatca acttcagcgc actctcgagg  26400
acgccgaggc tctcttcaac aagtactgcg cgctgactct taaagagtag gcagcgaccg  26460
cgcttattca aaaaaggcgg gaattacatc atcctcgaca tgagtaaaga aattcccacg  26520
ccttacatgt ggagttatca accccaaatg ggattggcgg caggcgcctc ccaggactac  26580
tccacccgca tgaattggct cagcgccggg ccttctatga tttctcgagt taatgatata  26640
cgcgcctacc gaaaccaaat acttttggaa cagtcagctc ttaccaccac gccccgccaa  26700
caccttaatc ccagaaattg gcccgccgcc ctagtgtacc aggaaagtcc cgctcccacc  26760
actgtattac ttcctcgaga cgcccaggcc gaagtccaaa tgactaatgc aggtgcgcag  26820
ttagctggcg gctccaccct atgtcgtcac aggcctcggc ataatataaa acgcctgatg  26880
atcagaggcc gaggtatcca gctcaacgac gagtcggtga gctctccgct tggtctacga  26940
ccagacggaa tctttcagat tgccggctgc gggagatctt ccttcacccc tcgtcaggct  27000
gttctgactt tggaaagttc gtcttcgcaa ccccgctcgg gcggaatcgg gaccgttcaa  27060
```

```
tttgtggagg agtttactcc ctctgtctac ttcaacccct tctccggatc tcctgggcat  27120
tacccggacg agttcatacc gaacttcgac gcgattagcg agtcagtgga cggctacgat  27180
tgatgtctgg tgacgcggct gagctatctc ggctgcgaca tctagaccac tgccgccgct  27240
ttcgctgctt tgcccgggaa ctcattgagt tcatctactt cgaactcccc aaggatcacc  27300
ctcaaggtcc ggcccacgga gtgcggattt ctatcgaagg caaaatagac tctcgcctgc  27360
aacgaatttt ctcccagcgg cccgtgctga tcgagcgaga ccagggaaac accacggttt  27420
ccatctactg catttgtaat caccccggat tgcatgaaag cctttgctgt cttatgtgta  27480
ctgagtttaa taaaaactga attaagactc tcctacggac tgccgcttct tcaacccgga  27540
ttttacaacc agaagaacga aacttttcct gtcgtccagg actctgttaa cttcaccttt  27600
cctactcaca aactagaagc tcaacgacta caccgctttt ccagaagcat tttccctact  27660
aatactactt tcaaaaccgg aggtgagctc caaggtcttc ctacagaaaa cccttgggtg  27720
gaagcgggcc ttgtagtgct aggaattctt gcgggtgggc ttgtgattat tctttgctac  27780
ctatacacac cttgcttcac tttcttagtg gtgttgtggt attggtttaa aaaatggggc  27840
ccatactagt cttgcttgtt ttactttcgc ttttggaacc gggttctgcc aattacgatc  27900
catgtctaga cttcgaccca gaaaactgca cacttacttt tgcacccgac acaagccgca  27960
tctgtggagt tcatcgcctc tcttacgaac ttggccccca acgacaaaaa tttacctgca  28020
tggtgggaat caaccccata gttatcaccc agcaaagtgg agatactaag ggttgcattc  28080
actgctcctg cgattccatc gagtgcacct acaccctgct gaagacccta tgcggcctaa  28140
gagacctgct accaatgaat taaaaaatga ttaataaaaa atcacttact tgaaatcagc  28200
aataaggtct ctgttgaaat tttctcccag cagcacctca cttccctctt cccaactctg  28260
gtattctaaa ccccgttcag cggcatactt tctccatact ttaaagggga tgtcaaattt  28320
tagctcctct cctgtaccca caatcttcat gtctttcttc ccagatgacc aagagagtcc  28380
ggctcagtga ctccttcaac cctgtctacc cctatgaaga tgaaagcacc tcccaacacc  28440
cctttataaa cccagggttt atttccccaa atggcttcac acaaagccca aacggagttc  28500
ttactttaaa atgtttaacc ccactaacaa ccacaggcgg atctctacag ctaaaagtgg  28560
gagggggact tacagtggat gacaccaacg gtttttttgaa agaaaacata agtgccacca  28620
caccactcgt taagactggt cactctatag gtttaccact aggagccgga ttgggaacga  28680
atgaaaataa actttgtatc aaattaggac aaggacttac attcaattca aacaacattt  28740
gcattgatga caatattaac accttatgga caggagtcaa ccccaccgaa gccaactgtc  28800
aaatcatgaa ctccagtgaa tctaatgatt gcaaattaat tctaacacta gttaaaactg  28860
gagcactagt cactgcattt gtttatgtta taggagtatc taacaatttt aatatgctaa  28920
ctacacacag aaatataaat tttactgcag agctgttttt cgattctact ggtaatttac  28980
taactagact ctcatccctc aaaactccac ttaatcataa atcaggacaa aacatggcta  29040
ctggtgccat tactaatgct aaaggtttca tgcccagcac gactgcctat cctttcaatg  29100
ataattctag agaaaaagaa aactacattt acggaacttg ttactacaca gctagtgatc  29160
gcactgcttt tcccattgac atatctgtca tgcttaaccg aagagcaata aatgacgaga  29220
catcatattg tattcgtata acttggtcct ggaacacagg agatgcccca gaggtgcaaa  29280
cctctgctac aaccctagtc acctccccat ttacctttta ctacatcaga gaagacgact  29340
gacaaataaa gtttaacttg tttatttgaa aatcaattca caaaatccga gtagttattt  29400
tgcctccccc ttcccattta acagaataca ccaatctctc cccacgcaca gctttaaaca  29460
```

-continued

```
tttggatacc attagatata gacatggttt tagattccac attccaaaca gtttcagagc  29520
gagccaatct ggggtcagtg atagataaaa atccatcggg atagtctttt aaagcgcttt  29580
cacagtccaa ctgctgcgga tgcgactccg gagtctggat cacggtcatc tggaagaaga  29640
acgatgggaa tcataatccg aaaacggtat cggacgattg tgtctcatca aacccacaag  29700
cagccgctgt ctgcgtcgct ccgtgcgact gctgtttatg ggatcagggt ccacagtgtc  29760
ctgaagcatg attttaatag cccttaacat caactttctg gtgcgatgcg cgcagcaacg  29820
cattctgatt tcactcaaat ctttgcagta ggtacaacac attattacaa tattgtttaa  29880
taaaccataa ttaaaagcgc tccagccaaa actcatatct gatataatcg cccctgcatg  29940
accatcatac caaagtttaa tataaattaa atgacgttcc ctcaaaaaca cactacccac  30000
atacatgatc tcttttggca tgtgcatatt aacaatctgt ctgtaccatg gacaacgttg  30060
gttaatcatg caacccaata taaccttccg gaaccacact gccaacaccg ctcccccagc  30120
catgcattga agtgaaccct gctgattaca atgacaatga agaacccaat tctctcgacc  30180
gtgaatcact tgagaatgaa aaatatctat agtggcacaa catagacata aatgcatgca  30240
tcttctcata atttttaact cctcaggatt tagaaacata tcccagggaa taggaagctc  30300
ttgcagaaca gtaaagctgg cagaacaagg aagaccacga acacaactta cactatgcat  30360
agtcatagta tcacaatctg gcaacagcgg gtggtcttca gtcatagaag ctcgggtttc  30420
attttcctca caacgtggta actgggctct ggtgtaaggg tgatgtctgg cgcatgatgt  30480
cgagcgtgcg cgcaaccttg tcataatgga gttgcttcct gacattctcg tattttgtat  30540
agcaaaacgc ggccctggca gaacacactc ttcttcgcct tctatcctgc cgcttagcgt  30600
gttccgtgtg atagttcaag tacaaccaca ctcttaagtt ggtcaaaaga atgctggctt  30660
cagttgtaat caaaactcca tcgcatctaa tcgttctgag gaaatcatcc aagcaatgca  30720
actggattgt gtttcaagca ggagaggaga gggaagagac ggaagaacca tgttaatttt  30780
tattccaaac gatctcgcag tacttcaaat tgtagatcgc gcagatggca tctctcgccc  30840
ccactgtgtt ggtgaaaaag cacagctaga tcaaaagaaa tgcgattttc aaggtgctca  30900
acggtggctt ccagcaaagc ctccacgcgc acatccaaga acaaaagaat accaaaagaa  30960
ggagcatttt ctaactcctc aatcatcata ttacattcct gcaccattcc cagataattt  31020
tcagctttcc agccttgaat tattcgtgtc agttcttgtg gtaaatccaa tccacacatt  31080
acaaacaggt cccggagggc gccctccacc accattctta aacacaccct cataatgaca  31140
aaatatcttg ctcctgtgtc acctgtagcg aattgagaat ggcaacatca attgacatgc  31200
ccttggctct aagttcttct ttaagttcta gttgtaaaaa ctctctcata ttatcaccaa  31260
actgcttagc cagaagcccc ccgggaacaa gagcagggga cgctacagtg cagtacaagc  31320
gcagacctcc ccaattggct ccagcaaaaa caagattgga ataagcatat tgggaaccgc  31380
cagtaatatc atcgaagttg ctggaaatat aatcaggcag agtttcttgt aaaaattgaa  31440
taaaagaaaa atttgccaaa aaaacattca aaacctctgg gatgcaaatg caataggtta  31500
ccgcgctgcg ctccaacatt gttagttttg aattagtctg caaaaataaa aaaaaaaaca  31560
agcgtcatat catagtagcc tgacgaacag atggataaat cagtctttcc atcacaagac  31620
aagccacagg gtctccagct cgaccctcgt aaaacctgtc atcatgatta aacaacagca  31680
ccgaaagttc ctcgcggtga ccagcatgaa taattcttga tgaagcatac aatccagaca  31740
tgttagcatc agttaacgag aaaaaacagc caacatagcc tttgggtata attatgctta  31800
```

atcgtaagta tagcaaagcc acccctcgcg gatacaaagt aaaaggcaca ggagaataaa 31860
aaatataatt atttctctgc tgctgttcag gcaacgtcgc cccggtcccc tctaaataca 31920
catacaaagc ctcatcagcc atggcttacc agacaaagta cagcgggcac acaaagcaca 31980
agctctaaag tgactctcca acctctccac aatatatata tacacaagcc ctaaactgac 32040
gtaatgggag taaagtgtaa aaaatcccgc caaacccaac acacaccccg aaactgcgtc 32100
accagggaaa agtacagttt cacttccgca atcccaacag gcgtaacttc ctctttctca 32160
cggtacgtga tatcccacta acttgcaacg tcattttccc acggtcgcac cgcccctttt 32220
agccgttaac cccacagcca atcaccacac gatccacact ttttaaaatc acctcattta 32280
catattggca ccattccatc tataaggtat attatataga ta 32322

<210> SEQ ID NO 2
<211> LENGTH: 11978
<212> TYPE: DNA
<213> ORGANISM: Artificial Sequence
<220> FEATURE:
<223> OTHER INFORMATION: ColoAd1 shuttle vector

<400> SEQUENCE: 2
ggcgcgccta tctatataat ataccttata gatggaatgg tgccaatatg taaatgaggt 60
gattttaaaa agtgtggatc gtgtggtgat tggctgtggg gttaacggct aaaaggggcg 120
gtgcgaccgt gggaaaatga cgttttgtgg gggtggagtt tttttgcaag ttgtcgcggg 180
aaatgtgacg cataaaaagg ctttttttctc acggaactac ttagttttcc cacggtattt 240
aacaggaaat gaggtagttt tgaccggatg caagtgaaaa ttgttgattt tcgcgcgaaa 300
actgaatgag gaagtgtttt tctgaataat gtggtattta tggcagggtg gagtatttgt 360
tcagggccag gtagactttg acccattacg tggaggtttc gattaccgtg tttttttacct 420 gaatttccgc gtaccgtgtc aaagtcttct gtttttacgt aggtgtcagc tgatcgctag 480
ggtatttata cctcagggtt tgtgtcaaga ggccactctt gagtgccagc gagaagagtt 540
ttctcctctg cgccggcagt ttaataataa aaaaatgaga gatttgcgat ttctgcctca 600
ggaaataatc tctgctgaga ctggaaatga aatattggag cttgtggtgc acgccctgat 660
gggagacgat ccggagccac ctgtgcagct ttttgagcct cctacgcttc aggaactgta 720
tgatttagag gtagagggat cggaggattc taatgaggaa gctgtaaatg gctttttttac 780 cgattctatg cttttagctg ctaatgaagg gttagaatta gatccgcctt tggacacttt 840
tgatactcca ggggtaattg tggaaagcgg tacaggtgta agaaaattac ctgatttgag 900
ttccgtggac tgtgatttgc actgctatga agacgggttt cctccgagtg atgaggagga 960
ccatgaaaag gagcagtcca tgcagactgc agcgggtgag ggagtgaagg ctgccaatgt 1020
tggttttcag ttggattgcc cggagcttcc tggacatggc tgtaagtctt gtgaatttca 1080
caggaaaaat actggagtaa aggaactgtt atgttcgctt tgttatatga gaacgcactg 1140
ccactttatt tacagtaagt gtgtttaagt taaaatttaa aggaatatgc tgtttttcac 1200
atgtatattg agtgtgagtt ttgtgcttct tattataggt cctgtgtctg atgctgatga 1260
atcaccatct cctgattcta ctacctcacc tcctgagatt caagcacctg ttcctgtgga 1320
cgtgcgcaag cccattcctg tgaagcttaa gcctgggaaa cgtccagcag tggaaaaact 1380
tgaggacttg ttacagggtg gggacggacc tttggacttg agtacacgga aacgtccaag 1440
acaataagtg ttccatatcc gtgtttactt aaggtgacgt caatatttgt gtgacagtgc 1500
aatgtaataa aaatatgtta actgttcact ggtttttatt gctttttggg cggggactca 1560

-continued

```
ggtatataag tagaagcaga cctgtgtggt tagctcatag gagctggctt tcatccatgg   1620
aggtttgggc cattttggaa gaccttagga agactaggca actgttagag aacgcttcgg   1680
acggagtctc cggtttttgg agattctggt tcgctagtga attagctagg gtagttttta   1740
ggataaaaca ggactataaa caagaatttg aaaagttgtt ggtagattgc ccaggacttt   1800
ttgaagctct taatttgggc catcaggttc actttaaaga aaaagtttta tcagttttag   1860
acttttcaac cccaggtaga actgctgctg ctgtggcttt tcttactttt atattagata   1920
aatggatccc gcagactcat ttcagcaggg gatacgtttt ggatttcata gccacagcat   1980
tgtggagaac atggaaggtt cgcaagatga ggacaatctt aggttactgg ccagtgcagc   2040
ctttgggtgt agcgggaatc ctgaggcatc caccggtcat gccagcggtt ctggaggagg   2100
aacagcaaga ggacaacccg agagccggcc tggaccctcc agtggaggag gcggagtagc   2160
tgacttgtct cctgaactgc aacgggtgct tactggatct acgtccactg gacgggatag   2220
gggcgttaag agggagaggg catctagtgg tactgatgct agatctgagt tggctttaag   2280
tttaatgagt cgcagacgtc ctgaaaccat ttggtggcat gaggttcaga aagagggaag   2340
ggatgaagtt tctgtattgc aggagaaata ttcactggaa caggtgaaaa catgttggtt   2400
ggagcctgag gatgattggg aggtggccat taaaaattat gccaagatag ctttgaggcc   2460
tgataaacag tataagatta ctagacggat taatatccgg aatgcttgtt acatatctgg   2520
aaatggggct gaggtggtaa tagatactca agacaaggca gttattagat gctgcatgat   2580
ggatatgtgg cctggggtag tcggtatgga agcagtaact tttgtaaatg ttaagtttag   2640
gggagatggt tataatggaa tagtgtttat ggccaatacc aaacttatat tgcatggttg   2700
tagctttttt ggtttcaaca atacctgtgt agatgcctgg ggacaggtta gtgtacgggg   2760
atgtagtttc tatgcgtgtt ggattgccac agctggcaga accaagagtc aattgtctct   2820
gaagaaatgc atatttcaaa gatgtaacct gggcattctg aatgaaggcg aagcaagggt   2880
ccgccactgc gcttctacag atactggatg ttttattttg attaagggaa atgccagcgt   2940
aaagcataac atgatttgcg gtgcttccga tgagaggcct tatcaaatgc tcacttgtgc   3000
tggtgggcat tgtaatatgc tggctactgt gcatattgtt tcccatcaac gcaaaaaatg   3060
gcctgttttt gatcacaatg tgatgacgaa gtgtaccatg catgcaggtg ggcgtagagg   3120
aatgtttatg ccttaccagt gtaacatgaa tcatgtgaaa gtgttgttgg aaccagatgc   3180
cttttccaga atgagcctaa caggaatttt tgacatgaac atgcaaatct ggaagatcct   3240
gaggtatgat gatacgagat cgagggtacg cgcatgcgaa tgcggaggca agcatgccag   3300
gttccagccg gtgtgtgtag atgtgactga agatctcaga ccggatcatt tggttattgc   3360
ccgcactgga gcagagttcg gatccagtgg agaagaaact gactaaggtg agtattggga   3420
aaactttggg gtgggatttt cagatggaca gattgagtaa aaatttgttt tttctgtctt   3480
gcagctgtca tgagtggaaa cgcttctttt aagggggggag tcttcagccc ttatctgaca   3540
gggcgtctcc catcctgggc aggagttcgt cagaatgtta tgggatctac tgtggatgga   3600
agacccgtcc aacccgccaa ttcttcaacg ctgacctatg ctactttaag ttcttcacct   3660
ttggacgcag ctgcagctgc cgccgccgct tctgttgccg ctaacactgt gcttggaatg   3720
ggttactatg gaagcatcat ggctaattcc acttcctcta ataacccttc taccctgact   3780
caggacaagt tacttgtcct tttggcccag ctggaggctt tgacccaacg tctgggtgaa   3840
ctttctcagc aggtggtcga gttgcgagta caaactgagt ctgctgtcgg cacggcaaag   3900
```

-continued

```
tctaaataaa aaaatcccag aatcaatgaa taaataaaca agcttgttgt tgatttaaaa   3960
tcaagtgttt ttatttcatt tttcgcgcac ggtatgccct agaccaccga tctctatcat   4020
tgagaactcg gtggattttt tccaggatcc tatagaggtg ggattgaatg tttagataca   4080
tgggcattag gccgtctttg gggtggagat agctccattg aagggattca tgctccgggg   4140
tagtgttgta aatcacccag tcataacaag gtcgcagtgc atggtgttgc acaatatctt   4200
ttagaagtag gctgattgcc acagataagc ccttggtgta ggtgtttaca aaccggttga   4260
gctgggatgg gtgcattcgg ggtgaaatta tgtgcatttt ggattggatt tttaagttgg   4320
caatattgcc gccaagatcc cgtcttgggt tcatgttatg aaggaccacc aagacggtgt   4380
atccggtaca tttaggaaat ttatcgtgca gcttggatgg aaaagcgtgg aaaaatttgg   4440
agacaccctt gtgtcctcca agattttcca tgcactcatc catgataata gcaatggggc   4500
cgtgggcagc ggcgcgggca aacacgttcc gtgggtctga cacatcatag ttatgttcct   4560
gagttaaatc atcataagcc attttaatga atttggggcg gagagtacca gattggggta   4620
tgaatgttcc ttcgggccca tactagtctt gcttgtttta ctttcgcttt tggaaccggg   4680
ttctgccaat tacgatccat gtctagactt cgacccagaa aactgcacac ttacttttgc   4740
acccgacaca agccgcatct gtggagttca tcgcctctct tacgaacttg gcccccaacg   4800
acaaaaattt acctgcatgg tgggaatcaa ccccatagtt atcacccagc aaagtggaga   4860
tactaagggt tgcattcact gctcctgcga ttccatcgag tgcacctaca ccctgctgaa   4920
gaccctatgc ggcctaagag acctgctacc aatgaattaa aaaatgatta ataaaaaatc   4980
acttacttga aatcagcaat aaggtctctg ttgaaatttt ctcccagcag cacctcactt   5040
ccctcttccc aactctggta ttctaaaccc cgttcagcgg catactttct ccatacttta   5100
aaggggatgt caaattttag ctcctctcct gtacccacaa tcttcatgtc tttcttccca   5160
gatgaccaag agagtccggc tcagtgactc cttcaaccct gtctacccct atgaagatga   5220
aagcacctcc caacacccct ttataaaccc agggtttatt tccccaaatg gcttcacaca   5280
aagcccaaac ggagttctta ctttaaaatg tttaacccca ctaacaacca caggcggatc   5340
tctacagcta aaagtgggag ggggacttac agtggatgac accaacggtt ttttgaaaga   5400
aaacataagt gccaccacac cactcgttaa gactggtcac tctataggtt taccactagg   5460
agccggattg ggaacgaatg aaaataaact ttgtatcaaa ttaggacaag gacttacatt   5520
caattcaaac aacatttgca ttgatgacaa tattaacacc ttatggacag gagtcaaccc   5580
caccgaagcc aactgtcaaa tcatgaactc cagtgaatct aatgattgca aattaattct   5640
aacactagtt aaaactggag cactagtcac tgcatttgtt tatgttatag gagtatctaa   5700
caattttaat atgctaacta cacacagaaa tataaatttt actgcagagc tgtttttcga   5760
ttctactggt aatttactaa ctagactctc atccctcaaa actccactta atcataaatc   5820
aggacaaaac atggctactg gtgccattac taatgctaaa ggtttcatgc ccagcacgac   5880
tgcctatcct ttcaatgata attctagaga aaaagaaaac tacatttacg gaacttgtta   5940
ctacacagct agtgatcgca ctgcttttcc cattgacata tctgtcatgc ttaaccgaag   6000
agcaataaat gacgagacat catattgtat tcgtataact tggtcctgga acacaggaga   6060
tgccccagag gtgcaaacct ctgctacaac cctagtcacc tccccattta ccttttacta   6120
catcagagaa gacgactgac aaataaagtt taacttgttt atttgaaaat caattcacaa   6180
aatccgagta gttattttgc ctccccccttc ccatttaaca gaatacacca atctctcccc   6240
acgcacagct ttaaacattt ggataccatt agatatagac atggttttag attccacatt   6300
```

ccaaacagtt tcagagcgag ccaatctggg gtcagtgata gataaaaatc catcgggata 6360
gtcttttaaa gcgctttcac agtccaactg ctgcggatgc gactccggag tctggatcac 6420
ggtcatctgg aagaagaacg atgggaatca taatccgaaa acggtatcgg acgattgtgt 6480
ctcatcaaac ccacaagcag ccgctgtctg cgtcgctccg tgcgactgct gtttatggga 6540
tcagggtcca cagtgtcctg aagcatgatt ttaatagccc ttaacatcaa ctttctggtg 6600
cgatgcgcgc agcaacgcat tctgatttca ctcaaatctt tgcagtaggt acaacacatt 6660
attacaatat tgtttaataa accataatta aaagcgctcc agccaaaact catatctgat 6720
ataatcgccc ctgcatgacc atcataccaa agtttaatat aaattaaatg acgttccctc 6780
aaaaacacac tacccacata catgatctct tttggcatgt gcatattaac aatctgtctg 6840
taccatggac aacgttggtt aatcatgcaa cccaatataa ccttccggaa ccacactgcc 6900
aacaccgctc ccccagccat gcattgaagt gaaccctgct gattacaatg acaatgaaga 6960
acccaattct ctcgaccgtg aatcacttga gaatgaaaaa tatctatagt ggcacaacat 7020
agacataaat gcatgcatct tctcataatt tttaactcct caggatttag aaacatatcc 7080
cagggaatag gaagctcttg cagaacagta aagctggcag aacaaggaag accacgaaca 7140
caacttacac tatgcatagt catagtatca caatctggca acagcgggtg gtcttcagtc 7200
atagaagctc gggtttcatt ttcctcacaa cgtggtaact gggctctggt gtaagggtga 7260
tgtctggcgc atgatgtcga gcgtgcgcgc aaccttgtca taatggagtt gcttcctgac 7320
attctcgtat tttgtatagc aaaacgcggc cctggcagaa cacactcttc ttcgccttct 7380
atcctgccgc ttagcgtgtt ccgtgtgata gttcaagtac aaccacactc ttaagttggt 7440
caaaagaatg ctggcttcag ttgtaatcaa aactccatcg catctaatcg ttctgaggaa 7500
atcatccaag caatgcaact ggattgtgtt tcaagcagga gaggagaggg aagagacgga 7560
agaaccatgt taatttttat tccaaacgat ctcgcagtac ttcaaattgt agatcgcgca 7620
gatggcatct ctcgccccca ctgtgttggt gaaaaagcac agctagatca aaagaaatgc 7680
gattttcaag gtgctcaacg gtggcttcca gcaaagcctc cacgcgcaca tccaagaaca 7740
aaagaatacc aaaagaagga gcattttcta actcctcaat catcatatta cattcctgca 7800
ccattcccag ataattttca gctttccagc cttgaattat tcgtgtcagt tcttgtggta 7860
aatccaatcc acacattaca aacaggtccc ggagggcgcc ctccaccacc attcttaaac 7920
acaccctcat aatgacaaaa tatcttgctc ctgtgtcacc tgtagcgaat tgagaatggc 7980
aacatcaatt gacatgccct tggctctaag ttcttcttta agttctagtt gtaaaaactc 8040
tctcatatta tcaccaaact gcttagccag aagccccccg ggaacaagag caggggacgc 8100
tacagtgcag tacaagcgca gacctcccca attggctcca gcaaaaacaa gattggaata 8160
agcatattgg gaaccgccag taatatcatc gaagttgctg gaaatataat caggcagagt 8220
ttcttgtaaa aattgaataa aagaaaaatt tgccaaaaaa acattcaaaa cctctgggat 8280
gcaaatgcaa taggttaccg cgctgcgctc caacattgtt agttttgaat tagtctgcaa 8340
aaataaaaaa aaaaacaagc gtcatatcat agtagcctga cgaacagatg gataaatcag 8400
tctttccatc acaagacaag ccacagggtc tccagctcga ccctcgtaaa acctgtcatc 8460
atgattaaac aacagcaccg aaagttcctc gcggtgacca gcatgaataa ttcttgatga 8520
agcatacaat ccagacatgt tagcatcagt taacgagaaa aaacagccaa catagccttt 8580
gggtataatt atgcttaatc gtaagtatag caaagccacc cctcgcggat acaaagtaaa 8640
aggcacagga gaataaaaaa tataattatt tctctgctgc tgttcaggca acgtcgcccc 8700
cggtccctct aaatacacat acaaagcctc atcagccatg gcttaccaga caaagtacag 8760
cgggcacaca aagcacaagc tctaaagtga ctctccaacc tctccacaat atatatatac 8820
acaagcccta aactgacgta atgggagtaa agtgtaaaaa atcccgccaa acccaacaca 8880
caccccgaaa ctgcgtcacc agggaaaagt acagtttcac ttccgcaatc ccaacaggcg 8940
taacttcctc tttctcacgg tacgtgatat cccactaact tgcaacgtca ttttcccacg 9000
gtcgcaccgc cccttttagc cgttaacccc acagccaatc accacacgat ccacactttt 9060
taaaatcacc tcatttacat attggcacca ttccatctat aaggtatatt atatagatag 9120
gcgcgccctc tcttaaggta gcatcgggat cgagtccctg agagaacatc ctcaatcccg 9180
atctatcctt agatccgagg aatatcgaaa tcagttacgc tagggataac agggtaatat 9240
agcatcccct cggattgcta tctaccggct cgtcagctat gatctctcga tttcgatcaa 9300
gaaatctcat tggttacctt gggctatcga aaccagtcaa gtcagctact tggcgagatc 9360
gacttgtctg agtttcgact acgctcagaa ttgcgtcagc gcctatcgcc aggtattact 9420
ccaatcccga atatccgagc ctgagagaac atcctcaatc ccgatctatc cttagatccg 9480
aggaatatcg aaatcgttta aatcttttct tgatggtaaa tcattcgaat ataagaatgg 9540
agagacgaat ggggaaacga caaagatgac attctttggt ccttctggtg aggttctcaa 9600
gtttttggtt aatcctgtca acaacttata tcgtatgggg ctgacttcag gtgctacatt 9660
tgaagagata aattgcactg aaatctagta atattttatc tgattaataa gatgatcttc 9720
ttgagatcgt tttggtctgc gcgtaatctc ttgctctgaa aacgaaaaaa ccgccttgca 9780
gggcggtttt tcgaaggttc tctgagctac caactctttg aaccgaggta actggcttgg 9840
cagagcgcag tcaccaaaac ttgtcctttc agtttagcct taaccggcgc atgacttcaa 9900
gactaactct gctaaatcaa ttaccagtgg ctgctgccag tggtgctttt gcatgtcttt 9960
ccgggttgga ctcaagacga tagttaccgg ataaggcgca gcggtcggac tgaacggggg 10020
gttcgtgcat acagtccagc ttggagcgaa ctgcctaccc ggaactgagt gtcaggcgtg 10080
gaatgagaca aacgcggcca taacagcgga atgacaccgg taaaccgaaa ggcaggaaca 10140
ggagagcgca cgagggagcc gccaggggga aacgcctggt atctttatag tcctgtcggg 10200
tttcgccacc actgatttga gcgtcagatt tcgtgatgct tgtcaggggg gcggagccta 10260
tggaaaaacg gctttgccgc ggccctctca cttccctgtt aagtatcttc ctggcatctt 10320
ccaggaaatc tccgccccgt tcgtaagcca tttccgctcg ccgcagtcga acgaccgagc 10380
gtagcgagtc agtgagcgag gaagcggaat atatcctgta tcacatattc tgctgacgca 10440
ccggtgcggc ctttttttctc ctgccacatg aagcacttca ctgacaccct catcagtgcc 10500
aacatagtaa gccagtatac actccgctaa tttaaacgtg gtgtaccgag aacgatcctc 10560
tcagtgcgat ctcgacgatc agtggtattc cgacatatcg ttgcttggca gtcagccagt 10620
cgatcctagc ttgggaccca ggaagtccaa tcgtcagata ttgtactcag cctggtcacg 10680
gcagcgtacc gatctcgtaa ctataacggt cctaaggtag cgaactagat attgatagtc 10740
tgatcggtca acgtataatc gagtcctagc ttttgcaaac atctatcaag agacaggatc 10800
agcaggaggc tttcgcatga ttgaacaaga tggattgcac gcaggttctc cggcggcttg 10860
ggtggagagg ctattcggct atgactgggc acaacagaca atcggctgct ctgatgccgc 10920
cgtgttccgg ctgtcagcgc aggggcgtcc ggttcttttt gtcaagaccg acctgtccgg 10980
tgccctgaat gaactgcaag acgaggcagc gcggctatcg tggctggcga cgacgggcgt 11040

-continued

```
tccttgcgcg gctgtgctcg acgttgtcac tgaagcggga agggactggc tgctattggg    11100
cgaagtgccg gggcaggatc tcctgtcatc tcaccttgct cctgccgaga aagtatccat    11160
catggctgat gcaatgcggc ggctgcatac gcttgatccg gctacctgcc cattcgacca    11220
ccaagcgaaa catcgcatcg agcgagcacg tactcggatg gaagccggtc ttgtcgatca    11280
ggatgatctg gacgaagagc atcaggggct cgcgccagcc gaactgttcg ccaggctcaa    11340
ggcgtctatg cccgacggcg aggatctcgt cgtgacccac ggcgatgcct gcttgccgaa    11400
tatcatggtg gaaaatggcc gcttttctgg attcatcgac tgtggccgtc tgggtgtggc    11460
ggaccgctat caggacatag cgttggctac ccgtgatatt gctgaagagc ttggcggcga    11520
atgggctgac cgcttccttg tgctttacgg tatcgccgcg cccgattcgc agcgcatcgc    11580
cttctatcgc cttcttgacg agttcttctg accgattcta ggtgcattgg cgcagaaaaa    11640
aatgcctgat gcgacgctgc gcgtcttata ctcccacata tgccagattc agcaacggat    11700
acggcttccc caacttgccc acttccatac gtgtcctcct taccagaaat ttatccttaa    11760
ggtccgtaac tataacggtc ctaaggtagc gaatcgacct agctctatcg aatctccctc    11820
gtttcgagct tacgcgaact agcctctggc gatagcatcc gaggggcagg catctatgtc    11880
gggtgcggag aaagaggtaa tgtcaagttc gatctgattg cttggcataa agtccgatgg    11940
ttcgagtaga ctcagttcaa cctctctctt aaggtagc                            11978
```

<210> SEQ ID NO 3
<211> LENGTH: 34
<212> TYPE: DNA
<213> ORGANISM: Artificial Sequence
<220> FEATURE:
<223> OTHER INFORMATION: primer 196

<400> SEQUENCE: 3

```
ttataggcgc gccctctctt aaggtagcat cggg                                 34
```

<210> SEQ ID NO 4
<211> LENGTH: 35
<212> TYPE: DNA
<213> ORGANISM: Artificial Sequence
<220> FEATURE:
<223> OTHER INFORMATION: primer 197

<400> SEQUENCE: 4

```
ttataggcgc gccgctacct taagagagag gttga                                35
```

<210> SEQ ID NO 5
<211> LENGTH: 30
<212> TYPE: DNA
<213> ORGANISM: Artificial Sequence
<220> FEATURE:
<223> OTHER INFORMATION: primer 198

<400> SEQUENCE: 5

```
ttggcggcgc gcctatctat ataatatacc                                      30
```

<210> SEQ ID NO 6
<211> LENGTH: 19
<212> TYPE: DNA
<213> ORGANISM: Artificial Sequence
<220> FEATURE:
<223> OTHER INFORMATION: primer 199

<400> SEQUENCE: 6
ttggcggcgc gcctatcta 19

<210> SEQ ID NO 7
<211> LENGTH: 19
<212> TYPE: DNA
<213> ORGANISM: Artificial Sequence
<220> FEATURE:
<223> OTHER INFORMATION: primer 200

<400> SEQUENCE: 7
aatgcaaatc tgtgagggg 19

<210> SEQ ID NO 8
<211> LENGTH: 22
<212> TYPE: DNA
<213> ORGANISM: Artificial Sequence
<220> FEATURE:
<223> OTHER INFORMATION: primer 201

<400> SEQUENCE: 8
cttagtggtg ttgtggtatt gg 22

<210> SEQ ID NO 9
<211> LENGTH: 19
<212> TYPE: DNA
<213> ORGANISM: Artificial Sequence
<220> FEATURE:
<223> OTHER INFORMATION: primer 202

<400> SEQUENCE: 9
atcgccttct atcgccttc 19

<210> SEQ ID NO 10
<211> LENGTH: 19
<212> TYPE: DNA
<213> ORGANISM: Artificial Sequence
<220> FEATURE:
<223> OTHER INFORMATION: primer 203

<400> SEQUENCE: 10
agcagtgcaa atcacagtc 19

<210> SEQ ID NO 11
<211> LENGTH: 19
<212> TYPE: DNA
<213> ORGANISM: Artificial Sequence
<220> FEATURE:
<223> OTHER INFORMATION: primer 204

<400> SEQUENCE: 11
caaactgagt ctgctgtcg 19

<210> SEQ ID NO 12
<211> LENGTH: 19
<212> TYPE: DNA
<213> ORGANISM: Artificial Sequence
<220> FEATURE:
<223> OTHER INFORMATION: primer 205

<400> SEQUENCE: 12
ataaaggggt gttgggagg 19

<210> SEQ ID NO 13
<211> LENGTH: 20
<212> TYPE: DNA
<213> ORGANISM: Artificial Sequence
<220> FEATURE:
<223> OTHER INFORMATION: primer 206

<400> SEQUENCE: 13
ccctcgtaaa acctgtcatc 20

<210> SEQ ID NO 14
<211> LENGTH: 19
<212> TYPE: DNA
<213> ORGANISM: Artificial Sequence
<220> FEATURE:
<223> OTHER INFORMATION: primer 207

<400> SEQUENCE: 14
cccattcgtc tctccattc 19

<210> SEQ ID NO 15
<211> LENGTH: 12105
<212> TYPE: DNA
<213> ORGANISM: Artificial Sequence
<220> FEATURE:
<223> OTHER INFORMATION: ColoAd2.0 shuttle vector

<400> SEQUENCE: 15
ggcgcgccta tctatataat ataccttata gatggaatgg tgccaatatg taaatgaggt 60
gattttaaaa agtgtggatc gtgtggtgat tggctgtggg gttaacggct aaaaggggcg 120
gtgcgaccgt gggaaaatga cgttttgtgg gggtggagtt tttttgcaag ttgtcgcggg 180
aaatgtgacg cataaaaagg ctttttttctc acggaactac ttagttttcc cacggtattt 240
aacaggaaat gaggtagttt tgaccggatg caagtgaaaa ttgttgattt tcgcgcgaaa 300
actgaatgag gaagtgtttt tctgaataat gtggtattta tggcagggtg gagtatttgt 360
tcagggccag gtagactttg acccattacg tggaggtttc gattaccgtg tttttttacct 420 gaatttccgc gtaccgtgtc aaagtcttct gtttttacgt aggtgtcagc tgatcgctag 480
ggtatttata cctcagggtt tgtgtcaaga ggccactctt gagtgccagc gagaagagtt 540
ttctcctctg cgccggcagt ttaataataa aaaaatgaga gatttgcgat ttctgcctca 600
ggaaataatc tctgctgaga ctggaaatga aatattggag cttgtggtgc acgccctgat 660
gggagacgat ccggagccac ctgtgcagct ttttgagcct cctacgcttc aggaactgta 720
tgatttagag gtagagggat cggaggattc taatgaggaa gctgtaaatg gctttttttac 780 cgattctatg cttttagctg ctaatgaagg gttagaatta gatccgcctt tggacacttt 840
tgatactcca ggggtaattg tggaaagcgg tacaggtgta agaaaattac ctgatttgag 900
ttccgtggac tgtgatttgc actgctatga agacgggttt cctccgagtg atgaggagga 960
ccatgaaaag gagcagtcca tgcagactgc agcgggtgag ggagtgaagg ctgccaatgt 1020
tggttttcag ttggattgcc cggagcttcc tggacatggc tgtaagtctt gtgaatttca 1080
caggaaaaat actggagtaa aggaactgtt atgttcgctt tgttatatga gaacgcactg 1140
ccactttatt tacagtaagt gtgtttaagt taaaatttaa aggaatatgc tgtttttcac 1200
atgtatattg agtgtgagtt ttgtgcttct tattataggt cctgtgtctg atgctgatga 1260
atcaccatct cctgattcta ctacctcacc tcctgagatt caagcacctg ttcctgtgga 1320
cgtgcgcaag cccattcctg tgaagcttaa gcctgggaaa cgtccagcag tggaaaaact 1380
tgaggacttg ttacagggtg gggacggacc tttggacttg agtacacgga aacgtccaag 1440
acaataagtg ttccatatcc gtgtttactt aaggtgacgt caatatttgt gtgacagtgc 1500
aatgtaataa aaatatgtta actgttcact ggtttttatt gctttttggg cggggactca 1560
ggtatataag tagaagcaga cctgtgtggt tagctcatag gagctggctt tcatccatgg 1620
aggtttgggc cattttggaa gaccttagga agactaggca actgttagag aacgcttcgg 1680
acggagtctc cggtttttgg agattctggt tcgctagtga attagctagg gtagttttta 1740
ggataaaaca ggactataaa caagaatttg aaaagttgtt ggtagattgc ccaggacttt 1800
ttgaagctct taatttgggc catcaggttc actttaaaga aaaagtttta tcagttttag 1860
acttttcaac cccaggtaga actgctgctg ctgtggcttt tcttactttt atattagata 1920
aatggatccc gcagactcat ttcagcaggg gatacgtttt ggatttcata gccacagcat 1980
tgtggagaac atggaaggtt cgcaagatga ggacaatctt aggttactgg ccagtgcagc 2040
ctttgggtgt agcgggaatc ctgaggcatc caccggtcat gccagcggtt ctggaggagg 2100
aacagcaaga ggacaacccg agagccggcc tggaccctcc agtggaggag gcggagtagc 2160
tgacttgtct cctgaactgc aacgggtgct tactggatct acgtccactg gacgggatag 2220
gggcgttaag agggagaggg catctagtgg tactgatgct agatctgagt tggctttaag 2280
tttaatgagt cgcagacgtc ctgaaaccat ttggtggcat gaggttcaga aagagggaag 2340
ggatgaagtt tctgtattgc aggagaaata ttcactggaa caggtgaaaa catgttggtt 2400
ggagcctgag gatgattggg aggtggccat taaaaattat gccaagatag ctttgaggcc 2460
tgataaacag tataagatta ctagacggat taatatccgg aatgcttgtt acatatctgg 2520
aaatggggct gaggtggtaa tagatactca agacaaggca gttattagat gctgcatgat 2580
ggatatgtgg cctggggtag tcggtatgga agcagtaact tttgtaaatg ttaagtttag 2640
gggagatggt tataatggaa tagtgtttat ggccaatacc aaacttatat tgcatggttg 2700
tagctttttt ggtttcaaca atacctgtgt agatgcctgg ggacaggtta gtgtacgggg 2760
atgtagtttc tatgcgtgtt ggattgccac agctggcaga accaagagtc aattgtctct 2820
gaagaaatgc atatttcaaa gatgtaacct gggcattctg aatgaaggcg aagcaagggt 2880
ccgccactgc gcttctacag atactggatg ttttattttg attaagggaa atgccagcgt 2940
aaagcataac atgatttgcg gtgcttccga tgagaggcct tatcaaatgc tcacttgtgc 3000
tggtgggcat tgtaatatgc tggctactgt gcatattgtt tcccatcaac gcaaaaaatg 3060
gcctgttttt gatcacaatg tgatgacgaa gtgtaccatg catgcaggtg ggcgtagagg 3120
aatgtttatg ccttaccagt gtaacatgaa tcatgtgaaa gtgttgttgg aaccagatgc 3180
cttttccaga atgagcctaa caggaatttt tgacatgaac atgcaaatct ggaagatcct 3240
gaggtatgat gatacgagat cgagggtacg cgcatgcgaa tgcggaggca agcatgccag 3300
gttccagccg gtgtgtgtag atgtgactga agatctcaga ccggatcatt tggttattgc 3360
ccgcactgga gcagagttcg gatccagtgg agaagaaact gactaaggtg agtattggga 3420
aaactttggg gtgggatttt cagatggaca gattgagtaa aaatttgttt tttctgtctt 3480
gcagctgtca tgagtggaaa cgcttctttt aagggggggag tcttcagccc ttatctgaca 3540
gggcgtctcc catcctgggc aggagttcgt cagaatgtta tgggatctac tgtggatgga 3600
agacccgtcc aacccgccaa ttcttcaacg ctgacctatg ctactttaag ttcttcacct 3660
ttggacgcag ctgcagctgc cgccgccgct tctgttgccg ctaacactgt gcttggaatg 3720
ggttactatg gaagcatcat ggctaattcc acttcctcta ataacccttc taccctgact 3780
caggacaagt tacttgtcct tttggcccag ctggaggctt tgacccaacg tctgggtgaa 3840
ctttctcagc aggtggtcga gttgcgagta caaactgagt ctgctgtcgg cacggcaaag 3900

```
tctaaataaa aaaatcccag aatcaatgaa taaataaaca agcttgttgt tgatttaaaa   3960
tcaagtgttt ttatttcatt tttcgcgcac ggtatgccct agaccaccga tctctatcat   4020
tgagaactcg gtggattttt tccaggatcc tatagaggtg ggattgaatg tttagataca   4080
tgggcattag gccgtctttg ggtggagat agctccattg aagggattca tgctccgggg    4140
tagtgttgta aatcacccag tcataacaag gtcgcagtgc atggtgttgc acaatatctt   4200
ttagaagtag gctgattgcc acagataagc ccttggtgta ggtgtttaca aaccggttga   4260
gctgggatgg gtgcattcgg ggtgaaatta tgtgcatttt ggattggatt tttaagttgg   4320
caatattgcc gccaagatcc cgtcttgggt tcatgttatg aaggaccacc aagacggtgt   4380
atccggtaca tttaggaaat ttatcgtgca gcttggatgg aaaagcgtgg aaaaatttgg   4440
agacaccctt gtgtcctcca agattttcca tgcactcatc catgataata gcaatggggc   4500
cgtgggcagc ggcgcgggca aacacgttcc gtgggtctga cacatcatag ttatgttcct   4560
gagttaaatc atcataagcc attttaatga atttggggcg gagagtacca gattggggta   4620
tgaatgttcc ttcgggccca tactagtctt gcttgtttta ctttcgcttt tggaaccggg   4680
ttctgccaat tacgatccat gtctagactt cgacccagaa aactgcacac ttacttttgc   4740
acccgacaca agccgcatct gtggagttca tcgcctctct tacgaacttg gcccccaacg   4800
acaaaaattt acctgcatgg tgggaatcaa ccccatagtt atcacccagc aaagtggaga   4860
tactaagggt tgcattcact gctcctgcga ttccatcgag tgcacctaca ccctgctgaa   4920
gaccctatgc ggcctaagag acctgctacc aatgaattaa aaaatgatta ataaaaaatc   4980
acttacttga aatcagcaat aaggtctctg ttgaaatttt ctcccagcag cacctcactt   5040
ccctcttccc aactctggta ttctaaaccc cgttcagcgg catactttct ccatacttta   5100
aaggggatgt caaattttag ctcctctcct gtacccacaa tcttcatgtc tttcttccca   5160
gtggccggcc atgaccaaga gagtccggct cagtgactcc ttcaaccctg tctacccta    5220
tgaagatgaa agcacctccc aacacccctt tataaaccca gggtttattt ccccaaatgg   5280
cttcacacaa agcccaaacg gagttcttac tttaaaatgt ttaaccccac taacaaccac   5340
aggcggatct ctacagctaa aagtgggagg gggacttaca gtggatgaca ccaacggttt   5400
tttgaaagaa aacataagtg ccaccacacc actcgttaag actggtcact ctataggttt   5460
accactagga gccggattgg gaacgaatga aaataaactt tgtatcaaat taggacaagg   5520
acttacattc aattcaaaca acatttgcat tgatgacaat attaacacct tatggacagg   5580
agtcaacccc accgaagcca actgtcaaat catgaactcc agtgaatcta atgattgcaa   5640
attaattcta acactagtta aaactggagc actagtcact gcatttgttt atgttatagg   5700
agtatctaac aattttaata tgctaactac acacagaaat ataaatttta ctgcagagct   5760
gtttttcgat tctactggta atttactaac tagactctca tccctcaaaa ctccacttaa   5820
tcataaatca ggacaaaaca tggctactgg tgccattact aatgctaaag gtttcatgcc   5880
cagcacgact gcctatcctt tcaatgataa ttctagagaa aaagaaaact acatttacgg   5940
aacttgttac tacacagcta gtgatcgcac tgcttttccc attgacatat ctgtcatgct   6000
taaccgaaga gcaataaatg acgagacatc atattgtatt cgtataactt ggtcctggaa   6060
cacaggagat gccccagagg tgcaaacctc tgctacaacc ctagtcacct ccccatttac   6120
cttttactac atcagagaag acgactgaca aataaaatcg ctatccatcg aagatggatg   6180
tgtgttggtt ttttgtgtga tttgtgcgat cgctatgcgg ccgcttacct gcaggggtta   6240
```

```
ccacacaaaa aaccaacaca ccctaaagct cgatctccga cttgtttatt tgaaaatcaa   6300
ttcacaaaat ccgagtagtt attttgcctc ccccttccca tttaacagaa tacaccaatc   6360
tctccccacg cacagcttta aacatttgga taccattaga tatagacatg gttttagatt   6420
ccacattcca aacagtttca gagcgagcca atctggggtc agtgatagat aaaaatccat   6480
cgggatagtc ttttaaagcg ctttcacagt ccaactgctg cggatgcgac tccggagtct   6540
ggatcacggt catctggaag aagaacgatg ggaatcataa tccgaaaacg gtatcggacg   6600
attgtgtctc atcaaaccca caagcagccg ctgtctgcgt cgctccgtgc gactgctgtt   6660
tatgggatca gggtccacag tgtcctgaag catgatttta atagccctta acatcaactt   6720
tctggtgcga tgcgcgcagc aacgcattct gatttcactc aaatctttgc agtaggtaca   6780
acacattatt acaatattgt ttaataaacc ataattaaaa gcgctccagc caaaactcat   6840
atctgatata atcgcccctg catgaccatc ataccaaagt ttaatataaa ttaaatgacg   6900
ttccctcaaa aacacactac ccacatacat gatctctttt ggcatgtgca tattaacaat   6960
ctgtctgtac catggacaac gttggttaat catgcaaccc aatataacct tccggaacca   7020
cactgccaac accgctcccc cagccatgca ttgaagtgaa ccctgctgat tacaatgaca   7080
atgaagaacc caattctctc gaccgtgaat cacttgagaa tgaaaaatat ctatagtggc   7140
acaacataga cataaatgca tgcatcttct cataattttt aactcctcag gatttagaaa   7200
catatcccag ggaataggaa gctcttgcag aacagtaaag ctggcagaac aaggaagacc   7260
acgaacacaa cttacactat gcatagtcat agtatcacaa tctggcaaca gcgggtggtc   7320
ttcagtcata gaagctcggg tttcattttc ctcacaacgt ggtaactggg ctctggtgta   7380
agggtgatgt ctggcgcatg atgtcgagcg tgcgcgcaac cttgtcataa tggagttgct   7440
tcctgacatt ctcgtatttt gtatagcaaa acgcggccct ggcagaacac actcttcttc   7500
gccttctatc ctgccgctta gcgtgttccg tgtgatagtt caagtacaac cacactctta   7560
agttggtcaa aagaatgctg gcttcagttg taatcaaaac tccatcgcat ctaatcgttc   7620
tgaggaaatc atccaagcaa tgcaactgga ttgtgtttca agcaggagag gagagggaag   7680
agacggaaga accatgttaa tttttattcc aaacgatctc gcagtacttc aaattgtaga   7740
tcgcgcagat ggcatctctc gcccccactg tgttggtgaa aaagcacagc tagatcaaaa   7800
gaaatgcgat tttcaaggtg ctcaacggtg gcttccagca aagcctccac gcgcacatcc   7860
aagaacaaaa gaataccaaa agaaggagca ttttctaact cctcaatcat catattacat   7920
tcctgcacca ttcccagata attttcagct ttccagcctt gaattattcg tgtcagttct   7980
tgtggtaaat ccaatccaca cattacaaac aggtcccgga gggcgccctc caccaccatt   8040
cttaaacaca ccctcataat gacaaaatat cttgctcctg tgtcacctgt agcgaattga   8100
gaatggcaac atcaattgac atgcccttgg ctctaagttc ttctttaagt tctagttgta   8160
aaaactctct catattatca ccaaactgct tagccagaag ccccccggga acaagagcag   8220
gggacgctac agtgcagtac aagcgcagac ctccccaatt ggctccagca aaaacaagat   8280
tggaataagc atattgggaa ccgccagtaa tatcatcgaa gttgctggaa atataatcag   8340
gcagagtttc ttgtaaaaat tgaataaaag aaaaatttgc caaaaaaaca ttcaaaacct   8400
ctgggatgca aatgcaatag gttaccgcgc tgcgctccaa cattgttagt tttgaattag   8460
tctgcaaaaa taaaaaaaaa aacaagcgtc atatcatagt agcctgacga acagatggat   8520
aaatcagtct ttccatcaca agacaagcca cagggtctcc agctcgaccc tcgtaaaacc   8580
tgtcatcatg attaaacaac agcaccgaaa gttcctcgcg gtgaccagca tgaataattc   8640
```

```
ttgatgaagc atacaatcca gacatgttag catcagttaa cgagaaaaaa cagccaacat   8700
agcctttggg tataattatg cttaatcgta agtatagcaa agccacccct cgcggataca   8760
aagtaaaagg cacaggagaa taaaaaatat aattatttct ctgctgctgt tcaggcaacg   8820
tcgcccccgg tccctctaaa tacacataca aagcctcatc agccatggct taccagacaa   8880
agtacagcgg gcacacaaag cacaagctct aaagtgactc tccaacctct ccacaatata   8940
tatatacaca agccctaaac tgacgtaatg ggagtaaagt gtaaaaaatc ccgccaaacc   9000
caacacacac cccgaaactg cgtcaccagg gaaaagtaca gtttcacttc cgcaatccca   9060
acaggcgtaa cttcctcttt ctcacggtac gtgatatccc actaacttgc aacgtcattt   9120
tcccacggtc gcaccgcccc ttttagccgt taaccccaca gccaatcacc acacgatcca   9180
cactttttaa aatcacctca tttacatatt ggcaccattc catctataag gtatattata   9240
tagataggcg cgccctctct taaggtagca tcgggatcga gtccctgaga gaacatcctc   9300
aatcccgatc tatccttaga tccgaggaat atcgaaatca gttacgctag ggataacagg   9360
gtaatatagc atcccctcgg attgctatct accggctcgt cagctatgat ctctcgattt   9420
cgatcaagaa atctcattgg ttaccttggg ctatcgaaac cagtcaagtc agctacttgg   9480
cgagatcgac ttgtctgagt ttcgactacg ctcagaattg cgtcagcgcc tatcgccagg   9540
tattactcca atcccgaata tccgagcctg agagaacatc ctcaatcccg atctatcctt   9600
agatccgagg aatatcgaaa tcgtttaaat cttttcttga tggtaaatca ttcgaatata   9660
agaatggaga gacgaatggg gaaacgacaa agatgacatt ctttggtcct tctggtgagg   9720
ttctcaagtt tttggttaat cctgtcaaca acttatatcg tatggggctg acttcaggtg   9780
ctacatttga agagataaat tgcactgaaa tctagtaata ttttatctga ttaataagat   9840
gatcttcttg agatcgtttt ggtctgcgcg taatctcttg ctctgaaaac gaaaaaaccg   9900
ccttgcaggg cggtttttcg aaggttctct gagctaccaa ctctttgaac cgaggtaact   9960
ggcttggcag agcgcagtca ccaaaacttg tcctttcagt ttagccttaa ccggcgcatg  10020
acttcaagac taactctgct aaatcaatta ccagtggctg ctgccagtgg tgcttttgca  10080
tgtctttccg ggttggactc aagacgatag ttaccggata aggcgcagcg gtcggactga  10140
acggggggtt cgtgcataca gtccagcttg gagcgaactg cctacccgga actgagtgtc  10200
aggcgtggaa tgagacaaac gcggccataa cagcggaatg acaccggtaa accgaaaggc  10260
aggaacagga gagcgcacga gggagccgcc agggggaaac gcctggtatc tttatagtcc  10320
tgtcgggttt cgccaccact gatttgagcg tcagatttcg tgatgcttgt caggggggcg  10380
gagcctatgg aaaaacggct ttgccgcggc cctctcactt ccctgttaag tatcttcctg  10440
gcatcttcca ggaaatctcc gccccgttcg taagccattt ccgctcgccg cagtcgaacg  10500
accgagcgta gcgagtcagt gagcgaggaa gcggaatata tcctgtatca catattctgc  10560
tgacgcaccg gtgcggcctt ttttctcctg ccacatgaag cacttcactg acaccctcat  10620
cagtgccaac atagtaagcc agtatacact ccgctaattt aaacgtggtg taccgagaac  10680
gatcctctca gtgcgatctc gacgatcagt ggtattccga catatcgttg cttggcagtc  10740
agccagtcga tcctagcttg ggacccagga agtccaatcg tcagatattg tactcagcct  10800
ggtcacggca gcgtaccgat ctcgtaacta taacggtcct aaggtagcga actagatatt  10860
gatagtctga tcggtcaacg tataatcgag tcctagcttt tgcaaacatc tatcaagaga  10920
caggatcagc aggaggcttt cgcatgattg aacaagatgg attgcacgca ggttctccgg  10980
```

```
cggcttgggt ggagaggcta ttcggctatg actgggcaca acagacaatc ggctgctctg  11040

atgccgccgt gttccggctg tcagcgcagg ggcgtccggt tctttttgtc aagaccgacc  11100

tgtccggtgc cctgaatgaa ctgcaagacg aggcagcgcg gctatcgtgg ctggcgacga  11160

cgggcgttcc ttgcgcggct gtgctcgacg ttgtcactga agcgggaagg gactggctgc  11220

tattgggcga agtgccgggg caggatctcc tgtcatctca ccttgctcct gccgagaaag  11280

tatccatcat ggctgatgca atgcggcggc tgcatacgct tgatccggct acctgcccat  11340

tcgaccacca agcgaaacat cgcatcgagc gagcacgtac tcggatggaa gccggtcttg  11400

tcgatcagga tgatctggac gaagagcatc aggggctcgc gccagccgaa ctgttcgcca  11460

ggctcaaggc gtctatgccc gacggcgagg atctcgtcgt gacccacggc gatgcctgct  11520

tgccgaatat catggtggaa aatggccgct tttctggatt catcgactgt ggccgtctgg  11580

gtgtggcgga ccgctatcag gacatagcgt tggctacccg tgatattgct gaagagcttg  11640

gcggcgaatg ggctgaccgc ttccttgtgc tttacggtat cgccgcgccc gattcgcagc  11700

gcatcgcctt ctatcgcctt cttgacgagt tcttctgacc gattctaggt gcattggcgc  11760

agaaaaaaat gcctgatgcg acgctgcgcg tcttatactc ccacatatgc cagattcagc  11820

aacggatacg gcttccccaa cttgcccact tccatacgtg tcctccttac cagaaattta  11880

tccttaaggt ccgtaactat aacggtccta aggtagcgaa tcgacctagc tctatcgaat  11940

ctccctcgtt tcgagcttac gcgaactagc ctctggcgat agcatccgag ggcaggcat   12000

ctatgtcggg tgcggagaaa gaggtaatgt caagttcgat ctgattgctt ggcataaagt  12060

ccgatggttc gagtagactc agttcaacct ctctcttaag gtagc                  12105
```

<210> SEQ ID NO 16
<211> LENGTH: 2350
<212> TYPE: DNA
<213> ORGANISM: Artificial Sequence
<220> FEATURE:
<223> OTHER INFORMATION: ColoAd2.0 synthetic fragment

<400> SEQUENCE: 16

```
gggcccatac tagtcttgct tgttttactt tcgcttttgg aaccgggttc tgccaattac     60

gatccatgtc tagacttcga cccagaaaac tgcacactta cttttgcacc cgacacaagc    120

cgcatctgtg gagttcatcg cctctcttac gaacttggcc cccaacgaca aaaatttacc    180

tgcatggtgg gaatcaaccc catagttatc acccagcaaa gtggagatac taagggttgc    240

attcactgct cctgcgattc catcgagtgc acctacaccc tgctgaagac cctatgcggc    300

ctaagagacc tgctaccaat gaattaaaaa atgattaata aaaaatcact tacttgaaat    360

cagcaataag gtctctgttg aaattttctc ccagcagcac ctcacttccc tcttcccaac    420

tctggtattc taaaccccgt tcagcggcat actttctcca tactttaaag gggatgtcaa    480

attttagctc ctctcctgta cccacaatct tcatgtcttt cttcccagtg gccggccatg    540

accaagagag tccggctcag tgactccttc aaccctgtct acccctatga agatgaaagc    600

acctcccaac accccttat aaacccaggg tttatttccc caaatggctt cacacaaagc     660

ccaaacggag ttcttacttt aaaatgttta accccactaa caaccacagg cggatctcta    720

cagctaaaag tgggaggggg acttacagtg gatgacacca acggtttttt gaaagaaaac    780

ataagtgcca ccacaccact cgttaagact ggtcactcta taggtttacc actaggagcc    840

ggattgggaa cgaatgaaaa taaactttgt atcaaattag gacaaggact tacattcaat    900

tcaaacaaca tttgcattga tgacaatatt aacaccttat ggacaggagt caaccccacc    960
```

gaagccaact gtcaaatcat gaactccagt gaatctaatg attgcaaatt aattctaaca 1020
ctagttaaaa ctggagcact agtcactgca tttgtttatg ttataggagt atctaacaat 1080
tttaatatgc taactacaca cagaaatata aattttactg cagagctgtt tttcgattct 1140
actggtaatt tactaactag actctcatcc ctcaaaactc cacttaatca taaatcagga 1200
caaaacatgg ctactggtgc cattactaat gctaaaggtt tcatgcccag cacgactgcc 1260
tatcctttca atgataattc tagagaaaaa gaaaactaca tttacggaac ttgttactac 1320
acagctagtg atcgcactgc ttttcccatt gacatatctg tcatgcttaa ccgaagagca 1380
ataaatgacg agacatcata ttgtattcgt ataacttggt cctggaacac aggagatgcc 1440
ccagaggtgc aaacctctgc tacaacccta gtcacctccc catttacctt ttactacatc 1500
agagaagacg actgacaaat aaaatcgcta tccatcgaag atggatgtgt gttggttttt 1560
tgtgtgattt gtgcgatcgc tatgcggccg cttacctgca ggggttacca cacaaaaaac 1620
caacacaccc taaagctcga tctccgactt gtttatttga aaatcaattc acaaaatccg 1680
agtagttatt ttgcctcccc cttcccattt aacagaatac accaatctct ccccacgcac 1740
agctttaaac atttggatac cattagatat agacatggtt ttagattcca cattccaaac 1800
agtttcagag cgagccaatc tggggtcagt gatagataaa aatccatcgg gatagtcttt 1860
taaagcgctt tcacagtcca actgctgcgg atgcgactcc ggagtctgga tcacggtcat 1920
ctggaagaag aacgatggga atcataatcc gaaaacggta tcggacgatt gtgtctcatc 1980
aaacccacaa gcagccgctg tctgcgtcgc tccgtgcgac tgctgtttat gggatcaggg 2040
tccacagtgt cctgaagcat gattttaata gcccttaaca tcaactttct ggtgcgatgc 2100
gcgcagcaac gcattctgat ttcactcaaa tctttgcagt aggtacaaca cattattaca 2160
atattgttta ataaaccata attaaaagcg ctccagccaa aactcatatc tgatataatc 2220
gcccctgcat gaccatcata ccaaagttta atataaatta aatgacgttc cctcaaaaac 2280
acactaccca catacatgat ctcttttggc atgtgcatat taacaatctg tctgtaccat 2340
ggacaacgtt 2350

<210> SEQ ID NO 17
<211> LENGTH: 11987
<212> TYPE: DNA
<213> ORGANISM: Artificial Sequence
<220> FEATURE:
<223> OTHER INFORMATION: ColoAd2.1 shuttle vector

<400> SEQUENCE: 17
ggcgcgccta tctatataat ataccttata gatggaatgg tgccaatatg taaatgaggt 60
gattttaaaa agtgtggatc gtgtggtgat tggctgtggg gttaacggct aaaaggggcg 120
gtgcgaccgt gggaaaatga cgttttgtgg gggtggagtt tttttgcaag ttgtcgcggg 180
aaatgtgacg cataaaaagg ctttttttctc acggaactac ttagttttcc cacggtattt 240
aacaggaaat gaggtagttt tgaccggatg caagtgaaaa ttgttgattt tcgcgcgaaa 300
actgaatgag gaagtgtttt tctgaataat gtggtattta tggcagggtg gagtatttgt 360
tcagggccag gtagactttg acccattacg tggaggtttc gattaccgtg ttttttacct 420
gaatttccgc gtaccgtgtc aaagtcttct gtttttacgt aggtgtcagc tgatcgctag 480
ggtatttata cctcagggtt tgtgtcaaga ggccactctt gagtgccagc gagaagagtt 540
ttctcctctg cgccggcagt ttaataataa aaaaatgaga gatttgcgat ttctgcctca 600

-continued

```
ggaaataatc tctgctgaga ctggaaatga aatattggag cttgtggtgc acgccctgat    660
gggagacgat ccggagccac ctgtgcagct ttttgagcct cctacgcttc aggaactgta    720
tgatttagag gtagagggat cggaggattc taatgaggaa gctgtaaatg gcttttttac    780
cgattctatg cttttagctg ctaatgaagg gttagaatta gatccgcctt tggacacttt    840
tgatactcca ggggtaattg tggaaagcgg tacaggtgta agaaaattac ctgatttgag    900
ttccgtggac tgtgatttgc actgctatga agacgggttt cctccgagtg atgaggagga    960
ccatgaaaag gagcagtcca tgcagactgc agcgggtgag ggagtgaagg ctgccaatgt   1020
tggttttcag ttggattgcc cggagcttcc tggacatggc tgtaagtctt gtgaatttca   1080
caggaaaaat actggagtaa aggaactgtt atgttcgctt tgttatatga gaacgcactg   1140
ccactttatt tacagtaagt gtgtttaagt taaaatttaa aggaatatgc tgtttttcac   1200
atgtatattg agtgtgagtt ttgtgcttct tattataggt cctgtgtctg atgctgatga   1260
atcaccatct cctgattcta ctacctcacc tcctgagatt caagcacctg ttcctgtgga   1320
cgtgcgcaag cccattcctg tgaagcttaa gcctgggaaa cgtccagcag tggaaaaact   1380
tgaggacttg ttacagggtg gggacggacc tttggacttg agtacacgga aacgtccaag   1440
acaataagtg ttccatatcc gtgtttactt aaggtgacgt caatatttgt gtgacagtgc   1500
aatgtaataa aaatatgtta actgttcact ggtttttatt gctttttggg cggggactca   1560
ggtatataag tagaagcaga cctgtgtggt tagctcatag gagctggctt tcatccatgg   1620
aggtttgggc cattttggaa gaccttagga agactaggca actgttagag aacgcttcgg   1680
acggagtctc cggtttttgg agattctggt tcgctagtga attagctagg gtagttttta   1740
ggataaaaca ggactataaa caagaatttg aaaagttgtt ggtagattgc ccaggacttt   1800
ttgaagctct taatttgggc catcaggttc actttaaaga aaaagtttta tcagttttag   1860
acttttcaac cccaggtaga actgctgctg ctgtggcttt tcttactttt atattagata   1920
aatggatccc gcagactcat ttcagcaggg gatacgtttt ggatttcata gccacagcat   1980
tgtggagaac atggaaggtt cgcaagatga ggacaatctt aggttactgg ccagtgcagc   2040
ctttgggtgt agcgggaatc ctgaggcatc caccggtcat gccagcggtt ctggaggagg   2100
aacagcaaga ggacaacccg agagccggcc tggaccctcc agtggaggag gcggagtagc   2160
tgacttgtct cctgaactgc aacgggtgct tactggatct acgtccactg gacgggatag   2220
gggcgttaag agggagaggg catctagtgg tactgatgct agatctgagt tggctttaag   2280
tttaatgagt cgcagacgtc ctgaaaccat ttggtggcat gaggttcaga aagagggaag   2340
ggatgaagtt tctgtattgc aggagaaata ttcactggaa caggtgaaaa catgttggtt   2400
ggagcctgag gatgattggg aggtggccat taaaaattat gccaagatag ctttgaggcc   2460
tgataaacag tataagatta ctagacggat taatatccgg aatgcttgtt acatatctgg   2520
aaatggggct gaggtggtaa tagatactca agacaaggca gttattagat gctgcatgat   2580
ggatatgtgg cctggggtag tcggtatgga agcagtaact tttgtaaatg ttaagtttag   2640
gggagatggt tataatggaa tagtgtttat ggccaatacc aaacttatat tgcatggttg   2700
tagctttttt ggtttcaaca atacctgtgt agatgcctgg ggacaggtta gtgtacgggg   2760
atgtagtttc tatgcgtgtt ggattgccac agctggcaga accaagagtc aattgtctct   2820
gaagaaatgc atatttcaaa gatgtaacct gggcattctg aatgaaggcg aagcaagggt   2880
ccgccactgc gcttctacag atactggatg ttttattttg attaagggaa atgccagcgt   2940
aaagcataac atgatttgcg gtgcttccga tgagaggcct tatcaaatgc tcacttgtgc   3000
```

```
tggtgggcat tgtaatatgc tggctactgt gcatattgtt tcccatcaac gcaaaaaatg   3060
gcctgttttt gatcacaatg tgatgacgaa gtgtaccatg catgcaggtg ggcgtagagg   3120
aatgtttatg ccttaccagt gtaacatgaa tcatgtgaaa gtgttgttgg aaccagatgc   3180
cttttccaga atgagcctaa caggaatttt tgacatgaac atgcaaatct ggaagatcct   3240
gaggtatgat gatacgagat cgagggtacg cgcatgcgaa tgcggaggca agcatgccag   3300
gttccagccg gtgtgtgtag atgtgactga agatctcaga ccggatcatt tggttattgc   3360
ccgcactgga gcagagttcg gatccagtgg agaagaaact gactaaggtg agtattggga   3420
aaactttggg gtgggatttt cagatggaca gattgagtaa aaatttgttt tttctgtctt   3480
gcagctgtca tgagtggaaa cgcttctttt aaggggggag tcttcagccc ttatctgaca   3540
gggcgtctcc catcctgggc aggagttcgt cagaatgtta tgggatctac tgtggatgga   3600
agacccgtcc aacccgccaa ttcttcaacg ctgacctatg ctactttaag ttcttcacct   3660
ttggacgcag ctgcagctgc cgccgccgct tctgttgccg ctaacactgt gcttggaatg   3720
ggttactatg gaagcatcat ggctaattcc acttcctcta ataacccttc taccctgact   3780
caggacaagt tacttgtcct tttggcccag ctggaggctt tgacccaacg tctgggtgaa   3840
ctttctcagc aggtggtcga gttgcgagta caaactgagt ctgctgtcgg cacggcaaag   3900
tctaaataaa aaaatcccag aatcaatgaa taaataaaca agcttgttgt tgatttaaaa   3960
tcaagtgttt ttatttcatt tttcgcgcac ggtatgccct agaccaccga tctctatcat   4020
tgagaactcg gtggattttt tccaggatcc tatagaggtg ggattgaatg tttagataca   4080
tgggcattag gccgtctttg gggtggagat agctccattg aagggattca tgctccgggg   4140
tagtgttgta aatcacccag tcataacaag gtcgcagtgc atggtgttgc acaatatctt   4200
ttagaagtag gctgattgcc acagataagc ccttggtgta ggtgtttaca aaccggttga   4260
gctgggatgg gtgcattcgg ggtgaaatta tgtgcatttt ggattggatt tttaagttgg   4320
caatattgcc gccaagatcc cgtcttgggt tcatgttatg aaggaccacc aagacggtgt   4380
atccggtaca tttaggaaat ttatcgtgca gcttggatgg aaaagcgtgg aaaaatttgg   4440
agacaccctt gtgtcctcca agattttcca tgcactcatc catgataata gcaatggggc   4500
cgtgggcagc ggcgcgggca aacacgttcc gtgggtctga cacatcatag ttatgttcct   4560
gagttaaatc atcataagcc attttaatga atttggggcg gagagtacca gattggggta   4620
tgaatgttcc ttcgggccca tactagtctt gcttgtttta ctttcgcttt tggaaccggg   4680
ttctgccaat tacgatccat gtctagactt cgacccagaa aactgcacac ttacttttgc   4740
acccgacaca agccgcatct gtggagttca tcgcctctct tacgaacttg gcccccaacg   4800
acaaaaattt acctgcatgg tgggaatcaa ccccatagtt atcacccagc aaagtggaga   4860
tactaagggt tgcattcact gctcctgcga ttccatcgag tgcacctaca ccctgctgaa   4920
gaccctatgc ggcctaagag acctgctacc aatgaattaa aaaatgatta ataaaaaatc   4980
acttacttga aatcagcaat aaggtctctg ttgaaatttt ctcccagcag cacctcactt   5040
ccctcttccc aactctggta ttctaaaccc cgttcagcgg catactttct ccatacttta   5100
aaggggatgt caaattttag ctcctctcct gtacccacaa tcttcatgtc tttcttccca   5160
gagcggccgc atgaccaaga gagtccggct cagtgactcc ttcaaccctg tctacccccta  5220
tgaagatgaa agcacctccc aacacccctt tataaaccca gggtttattt ccccaaatgg   5280
cttcacacaa agcccaaacg gagttcttac tttaaaatgt ttaaccccac taacaaccac   5340
```

```
aggcggatct ctacagctaa aagtgggagg gggacttaca gtggatgaca ccaacggttt   5400
tttgaaagaa aacataagtg ccaccacacc actcgttaag actggtcact ctataggttt   5460
accactagga gccggattgg gaacgaatga aaataaactt tgtatcaaat taggacaagg   5520
acttacattc aattcaaaca acatttgcat tgatgacaat attaacacct tatggacagg   5580
agtcaacccc accgaagcca actgtcaaat catgaactcc agtgaatcta atgattgcaa   5640
attaattcta acactagtta aaactggagc actagtcact gcatttgttt atgttatagg   5700
agtatctaac aattttaata tgctaactac acacagaaat ataaatttta ctgcagagct   5760
gtttttcgat tctactggta atttactaac tagactctca tccctcaaaa ctccacttaa   5820
tcataaatca ggacaaaaca tggctactgg tgccattact aatgctaaag gtttcatgcc   5880
cagcacgact gcctatcctt tcaatgataa ttctagagaa aaagaaaact acatttacgg   5940
aacttgttac tacacagcta gtgatcgcac tgcttttccc attgacatat ctgtcatgct   6000
taaccgaaga gcaataaatg acgagacatc atattgtatt cgtataactt ggtcctggaa   6060
cacaggagat gccccagagg tgcaaacctc tgctacaacc ctagtcacct ccccatttac   6120
cttttactac atcagagaag acgactgaca aataaagttt aacttgttta tttgaaaatc   6180
aattcacaaa atccgagtag ttattttgcc tccccccttcc catttaacag aatacaccaa   6240
tctctcccca cgcacagctt taaacatttg gataccatta gatatagaca tggttttaga   6300
ttccacattc caaacagttt cagagcgagc caatctgggg tcagtgatag ataaaaaatcc   6360
atcgggatag tcttttaaag cgctttcaca gtccaactgc tgcggatgcg actccggagt   6420
ctggatcacg gtcatctgga agaagaacga tgggaatcat aatccgaaaa cggtatcgga   6480
cgattgtgtc tcatcaaacc cacaagcagc cgctgtctgc gtcgctccgt gcgactgctg   6540
tttatgggat cagggtccac agtgtcctga agcatgattt taatagccct taacatcaac   6600
tttctggtgc gatgcgcgca gcaacgcatt ctgatttcac tcaaatcttt gcagtaggta   6660
caacacatta ttacaatatt gtttaataaa ccataattaa aagcgctcca gccaaaactc   6720
atatctgata taatcgcccc tgcatgacca tcataccaaa gtttaatata aattaaatga   6780
cgttccctca aaaacacact acccacatac atgatctctt ttggcatgtg catattaaca   6840
atctgtctgt accatggaca acgttggtta atcatgcaac ccaatataac cttccggaac   6900
cacactgcca acaccgctcc cccagccatg cattgaagtg aaccctgctg attacaatga   6960
caatgaagaa cccaattctc tcgaccgtga atcacttgag aatgaaaaat atctatagtg   7020
gcacaacata gacataaatg catgcatctt ctcataattt ttaactcctc aggatttaga   7080
aacatatccc agggaatagg aagctcttgc agaacagtaa agctggcaga acaaggaaga   7140
ccacgaacac aacttacact atgcatagtc atagtatcac aatctggcaa cagcgggtgg   7200
tcttcagtca tagaagctcg ggtttcattt tcctcacaac gtggtaactg ggctctggtg   7260
taagggtgat gtctggcgca tgatgtcgag cgtgcgcgca accttgtcat aatggagttg   7320
cttcctgaca ttctcgtatt ttgtatagca aaacgcggcc ctggcagaac acactcttct   7380
tcgccttcta tcctgccgct tagcgtgttc cgtgtgatag ttcaagtaca accacactct   7440
taagttggtc aaaagaatgc tggcttcagt tgtaatcaaa actccatcgc atctaatcgt   7500
tctgaggaaa tcatccaagc aatgcaactg gattgtgttt caagcaggag aggagaggga   7560
agagacggaa gaaccatgtt aatttttatt ccaaacgatc tcgcagtact tcaaattgta   7620
gatcgcgcag atggcatctc tcgcccccac tgtgttggtg aaaaagcaca gctagatcaa   7680
aagaaatgcg attttcaagg tgctcaacgg tggcttccag caaagcctcc acgcgcacat   7740
```

```
ccaagaacaa aagaatacca aaagaaggag cattttctaa ctcctcaatc atcatattac   7800
attcctgcac cattcccaga taattttcag ctttccagcc ttgaattatt cgtgtcagtt   7860
cttgtggtaa atccaatcca cacattacaa acaggtcccg gagggcgccc tccaccacca   7920
ttcttaaaca caccctcata atgacaaaat atcttgctcc tgtgtcacct gtagcgaatt   7980
gagaatggca acatcaattg acatgccctt ggctctaagt tcttctttaa gttctagttg   8040
taaaaactct ctcatattat caccaaactg cttagccaga agcccccgg gaacaagagc    8100
aggggacgct acagtgcagt acaagcgcag acctccccaa ttggctccag caaaaacaag   8160
attggaataa gcatattggg aaccgccagt aatatcatcg aagttgctgg aaatataatc   8220
aggcagagtt tcttgtaaaa attgaataaa agaaaaattt gccaaaaaaa cattcaaaac   8280
ctctgggatg caaatgcaat aggttaccgc gctgcgctcc aacattgtta gttttgaatt   8340
agtctgcaaa aataaaaaaa aaaacaagcg tcatatcata gtagcctgac gaacagatgg   8400
ataaatcagt ctttccatca caagacaagc cacagggtct ccagctcgac cctcgtaaaa   8460
cctgtcatca tgattaaaca acagcaccga aagttcctcg cggtgaccag catgaataat   8520
tcttgatgaa gcatacaatc cagacatgtt agcatcagtt aacgagaaaa aacagccaac   8580
atagcctttg ggtataatta tgcttaatcg taagtatagc aaagccaccc ctcgcggata   8640
caaagtaaaa ggcacaggag aataaaaaat ataattattt ctctgctgct gttcaggcaa   8700
cgtcgccccc ggtccctcta aatacacata caaagcctca tcagccatgg cttaccagac   8760
aaagtacagc gggcacacaa agcacaagct ctaaagtgac tctccaacct ctccacaata   8820
tatatataca caagccctaa actgacgtaa tgggagtaaa gtgtaaaaaa tcccgccaaa   8880
cccaacacac accccgaaac tgcgtcacca gggaaaagta cagtttcact tccgcaatcc   8940
caacaggcgt aacttcctct ttctcacggt acgtgatatc ccactaactt gcaacgtcat   9000
tttcccacgg tcgcaccgcc ccttttagcc gttaacccca cagccaatca ccacacgatc   9060
cacacttttt aaaatcacct catttacata ttggcaccat tccatctata aggtatatta   9120
tatagatagg cgcgccctct cttaaggtag catcgggatc gagtccctga gagaacatcc   9180
tcaatcccga tctatcctta gatccgagga atatcgaaat cagttacgct agggataaca   9240
gggtaatata gcatcccctc ggattgctat ctaccggctc gtcagctatg atctctcgat   9300
ttcgatcaag aaatctcatt ggttaccttg ggctatcgaa accagtcaag tcagctactt   9360
ggcgagatcg acttgtctga gtttcgacta cgctcagaat tgcgtcagcg cctatcgcca   9420
ggtattactc caatcccgaa tatccgagcc tgagagaaca tcctcaatcc cgatctatcc   9480
ttagatccga ggaatatcga aatcgtttaa atcttttctt gatggtaaat cattcgaata   9540
taagaatgga gagacgaatg ggaaacgac  aaagatgaca ttctttggtc cttctggtga   9600
ggttctcaag tttttggtta atcctgtcaa caacttatat cgtatggggc tgacttcagg   9660
tgctacattt gaagagataa attgcactga aatctagtaa tattttatct gattaataag   9720
atgatcttct tgagatcgtt ttggtctgcg cgtaatctct tgctctgaaa acgaaaaaac   9780
cgccttgcag ggcggttttt cgaaggttct ctgagctacc aactctttga accgaggtaa   9840
ctggcttggc agagcgcagt caccaaaact tgtcctttca gtttagcctt aaccggcgca   9900
tgacttcaag actaactctg ctaaatcaat taccagtggc tgctgccagt ggtgcttttg   9960
catgtctttc cgggttggac tcaagacgat agttaccgga taaggcgcag cggtcggact  10020
gaacgggggg ttcgtgcata cagtccagct tggagcgaac tgcctacccg gaactgagtg  10080
```

```
tcaggcgtgg aatgagacaa acgcggccat aacagcggaa tgacaccggt aaaccgaaag  10140
gcaggaacag gagagcgcac gagggagccg ccagggggaa acgcctggta tctttatagt  10200
cctgtcgggt ttcgccacca ctgatttgag cgtcagattt cgtgatgctt gtcagggggg  10260
cggagcctat ggaaaaacgg ctttgccgcg gccctctcac ttccctgtta agtatcttcc  10320
tggcatcttc caggaaatct ccgccccgtt cgtaagccat ttccgctcgc cgcagtcgaa  10380
cgaccgagcg tagcgagtca gtgagcgagg aagcggaata tatcctgtat cacatattct  10440
gctgacgcac cggtgcggcc tttttctcc tgccacatga agcacttcac tgacaccctc  10500
atcagtgcca acatagtaag ccagtataca ctccgctaat ttaaacgtgg tgtaccgaga  10560
acgatcctct cagtgcgatc tcgacgatca gtggtattcc gacatatcgt tgcttggcag  10620
tcagccagtc gatcctagct tgggacccag gaagtccaat cgtcagatat tgtactcagc  10680
ctggtcacgg cagcgtaccg atctcgtaac tataacggtc ctaaggtagc gaactagata  10740
ttgatagtct gatcggtcaa cgtataatcg agtcctagct tttgcaaaca tctatcaaga  10800
gacaggatca gcaggaggct ttcgcatgat tgaacaagat ggattgcacg caggttctcc  10860
ggcggcttgg gtggagaggc tattcggcta tgactgggca caacagacaa tcggctgctc  10920
tgatgccgcc gtgttccggc tgtcagcgca ggggcgtccg gttctttttg tcaagaccga  10980
cctgtccggt gccctgaatg aactgcaaga cgaggcagcg cggctatcgt ggctggcgac  11040
gacgggcgtt ccttgcgcgg ctgtgctcga cgttgtcact gaagcgggaa gggactggct  11100
gctattgggc gaagtgccgg ggcaggatct cctgtcatct caccttgctc ctgccgagaa  11160
agtatccatc atggctgatg caatgcggcg gctgcatacg cttgatccgg ctacctgccc  11220
attcgaccac caagcgaaac atcgcatcga gcgagcacgt actcggatgg aagccggtct  11280
tgtcgatcag gatgatctgg acgaagagca tcaggggctc gcgccagccg aactgttcgc  11340
caggctcaag gcgtctatgc ccgacggcga ggatctcgtc gtgacccacg gcgatgcctg  11400
cttgccgaat atcatggtgg aaaatggccg cttttctgga ttcatcgact gtggccgtct  11460
gggtgtggcg gaccgctatc aggacatagc gttggctacc cgtgatattg ctgaagagct  11520
tggcggcgaa tgggctgacc gcttccttgt gctttacggt atcgccgcgc ccgattcgca  11580
gcgcatcgcc ttctatcgcc ttcttgacga gttcttctga ccgattctag gtgcattggc  11640
gcagaaaaaa atgcctgatg cgacgctgcg cgtcttatac tcccacatat gccagattca  11700
gcaacggata cggcttcccc aacttgccca cttccatacg tgtcctcctt accagaaatt  11760
tatccttaag gtccgtaact ataacggtcc taaggtagcg aatcgaccta gctctatcga  11820
atctccctcg tttcgagctt acgcgaacta gcctctggcg atagcatccg aggggcaggc  11880
atctatgtcg ggtgcggaga aagaggtaat gtcaagttcg atctgattgc ttggcataaa  11940
gtccgatggt tcgagtagac tcagttcaac ctctctctta aggtagc               11987
```

```
<210> SEQ ID NO 18
<211> LENGTH: 2232
<212> TYPE: DNA
<213> ORGANISM: Artificial Sequence
<220> FEATURE:
<223> OTHER INFORMATION: - ColoAd2.1 DNA (PCR) fragment

<400> SEQUENCE: 18

gggcccatac tagtcttgct tgttttactt tcgcttttgg aaccgggttc tgccaattac     60
gatccatgtc tagacttcga cccagaaaac tgcacactta cttttgcacc cgacacaagc    120
cgcatctgtg gagttcatcg cctctcttac gaacttggcc cccaacgaca aaaatttacc    180
```

```
tgcatggtgg gaatcaaccc catagttatc acccagcaaa gtggagatac taagggttgc    240
attcactgct cctgcgattc catcgagtgc acctacaccc tgctgaagac cctatgcggc    300
ctaagagacc tgctaccaat gaattaaaaa atgattaata aaaaatcact tacttgaaat    360
cagcaataag gtctctgttg aaattttctc ccagcagcac ctcacttccc tcttcccaac    420
tctggtattc taaaccccgt tcagcggcat actttctcca tactttaaag ggatgtcaa     480
attttagctc ctctcctgta cccacaatct tcatgtcttt cttcccagag cggccgcatg    540
accaagagag tccggctcag tgactccttc aaccctgtct acccctatga agatgaaagc    600
acctcccaac accccttat aaacccaggg tttatttccc caaatggctt cacacaaagc     660
ccaaacggag ttcttacttt aaaatgttta accccactaa caaccacagg cggatctcta    720
cagctaaaag tgggaggggg acttacagtg gatgacacca acggtttttt gaaagaaaac    780
ataagtgcca ccacaccact cgttaagact ggtcactcta taggtttacc actaggagcc    840
ggattgggaa cgaatgaaaa taaactttgt atcaaattag gacaaggact tacattcaat    900
tcaaacaaca tttgcattga tgacaatatt aacaccttat ggacaggagt caaccccacc    960
gaagccaact gtcaaatcat gaactccagt gaatctaatg attgcaaatt aattctaaca   1020
ctagttaaaa ctggagcact agtcactgca tttgtttatg ttataggagt atctaacaat   1080
tttaatatgc taactacaca cagaaatata aattttactg cagagctgtt tttcgattct   1140
actggtaatt tactaactag actctcatcc ctcaaaactc cacttaatca taaatcagga   1200
caaaacatgg ctactggtgc cattactaat gctaaaggtt tcatgcccag cacgactgcc   1260
tatcctttca atgataattc tagagaaaaa gaaaactaca tttacggaac ttgttactac   1320
acagctagtg atcgcactgc ttttcccatt gacatatctg tcatgcttaa ccgaagagca   1380
ataaatgacg agacatcata ttgtattcgt ataacttggt cctggaacac aggagatgcc   1440
ccagaggtgc aaacctctgc tacaacccta gtcacctccc catttacctt ttactacatc   1500
agagaagacg actgacaaat aaagtttaac ttgtttattt gaaaatcaat tcacaaaatc   1560
cgagtagtta ttttgcctcc cccttcccat ttaacagaat acaccaatct ctccccacgc   1620
acagctttaa acatttggat accattagat atagacatgg ttttagattc cacattccaa   1680
acagtttcag agcgagccaa tctggggtca gtgatagata aaaatccatc gggatagtct   1740
tttaaagcgc tttcacagtc caactgctgc ggatgcgact ccggagtctg gatcacggtc   1800
atctggaaga agaacgatgg gaatcataat ccgaaaacgg tatcggacga ttgtgtctca   1860
tcaaacccac aagcagccgc tgtctgcgtc gctccgtgcg actgctgttt atgggatcag   1920
ggtccacagt gtcctgaagc atgattttaa tagcccttaa catcaacttt ctggtgcgat   1980
gcgcgcagca acgcattctg atttcactca aatctttgca gtaggtacaa cacattatta   2040
caatattgtt taataaacca taattaaaag cgctccagcc aaaactcata tctgatataa   2100
tcgcccctgc atgaccatca taccaaagtt taatataaat taaatgacgt tccctcaaaa   2160
acacactacc cacatacatg atctcttttg gcatgtgcat attaacaatc tgtctgtacc   2220
atggacaacg tt                                                       2232
```

<210> SEQ ID NO 19
<211> LENGTH: 9
<212> TYPE: DNA
<213> ORGANISM: Artificial Sequence
<220> FEATURE:
<223> OTHER INFORMATION: 9bp insert ColoAd2.1

<400> SEQUENCE: 19 agcggccgc 9

<210> SEQ ID NO 20
<211> LENGTH: 28
<212> TYPE: DNA
<213> ORGANISM: Artificial Sequence
<220> FEATURE:
<223> OTHER INFORMATION: primer 274

<400> SEQUENCE: 20
ttcggatccg ggcccatact agtcttgc 28

<210> SEQ ID NO 21
<211> LENGTH: 33
<212> TYPE: DNA
<213> ORGANISM: Artificial Sequence
<220> FEATURE:
<223> OTHER INFORMATION: primer 275

<400> SEQUENCE: 21
catgcggccg ctctgggaag aaagacatga aga 33

<210> SEQ ID NO 22
<211> LENGTH: 28
<212> TYPE: DNA
<213> ORGANISM: Artificial Sequence
<220> FEATURE:
<223> OTHER INFORMATION: primer 276

<400> SEQUENCE: 22
tatgcggccg catgaccaag agagtccg 28

<210> SEQ ID NO 23
<211> LENGTH: 30
<212> TYPE: DNA
<213> ORGANISM: Artificial Sequence
<220> FEATURE:
<223> OTHER INFORMATION: primer 277

<400> SEQUENCE: 23
tgcgaattca acgttgtcca tggtacagac 30

<210> SEQ ID NO 24
<211> LENGTH: 543
<212> TYPE: DNA
<213> ORGANISM: Artificial Sequence
<220> FEATURE:
<223> OTHER INFORMATION: ColoAd2.1 PCR 1 fragment

<400> SEQUENCE: 24
ggatccgggc ccatactagt cttgcttgtt ttactttcgc ttttggaacc gggttctgcc 60
aattacgatc catgtctaga cttcgaccca gaaaactgca cacttacttt tgcacccgac 120
acaagccgca tctgtggagt tcatcgcctc tcttacgaac ttggccccca acgacaaaaa 180
tttacctgca tggtgggaat caaccccata gttatcaccc agcaaagtgg agatactaag 240
ggttgcattc actgctcctg cgattccatc gagtgcacct acaccctgct gaagacccta 300
tgcggcctaa gagacctgct accaatgaat taaaaaatga ttaataaaaa atcacttact 360
tgaaatcagc aataaggtct ctgttgaaat tttctcccag cagcacctca cttccctctt 420
cccaactctg gtattctaaa ccccgttcag cggcatactt tctccatact ttaaagggga 480
tgtcaaattt tagctcctct cctgtaccca caatcttcat gtctttcttc ccagagcggc 540

```
cgc                                                                543

<210> SEQ ID NO 25
<211> LENGTH: 1709
<212> TYPE: DNA
<213> ORGANISM: Artificial Sequence
<220> FEATURE:
<223> OTHER INFORMATION: ColoAd2.1 PCR 2 fragment

<400> SEQUENCE: 25

gcggccgcat gaccaagaga gtccggctca gtgactcctt caaccctgtc tacccctatg     60

aagatgaaag cacctcccaa caccccttta taaacccagg gtttatttcc ccaaatggct    120

tcacacaaag cccaaacgga gttcttactt taaaatgttt aaccccacta acaaccacag    180

gcggatctct acagctaaaa gtgggagggg gacttacagt ggatgacacc aacggttttt    240

tgaaagaaaa cataagtgcc accacaccac tcgttaagac tggtcactct ataggtttac    300

cactaggagc cggattggga acgaatgaaa ataaactttg tatcaaatta ggacaaggac    360

ttacattcaa ttcaaacaac atttgcattg atgacaatat taacacctta tggacaggag    420

tcaaccccac cgaagccaac tgtcaaatca tgaactccag tgaatctaat gattgcaaat    480

taattctaac actagttaaa actggagcac tagtcactgc atttgtttat gttataggag    540

tatctaacaa ttttaatatg ctaactacac acagaaatat aaattttact gcagagctgt    600

ttttcgattc tactggtaat ttactaacta gactctcatc cctcaaaact ccacttaatc    660

ataaatcagg acaaaacatg gctactggtg ccattactaa tgctaaaggt ttcatgccca    720

gcacgactgc ctatcctttc aatgataatt ctagagaaaa agaaaactac atttacggaa    780

cttgttacta cacagctagt gatcgcactg cttttcccat tgacatatct gtcatgctta    840

accgaagagc aataaatgac gagacatcat attgtattcg tataacttgg tcctggaaca    900

caggagatgc cccagaggtg caaacctctg ctacaaccct agtcacctcc ccatttacct    960

tttactacat cagagaagac gactgacaaa taaagtttaa cttgtttatt tgaaaatcaa   1020

ttcacaaaat ccgagtagtt attttgcctc ccccttccca tttaacagaa tacaccaatc   1080

tctccccacg cacagcttta aacatttgga taccattaga tatagacatg gttttagatt   1140

ccacattcca aacagtttca gagcgagcca atctggggtc agtgatagat aaaaatccat   1200

cgggatagtc ttttaaagcg ctttcacagt ccaactgctg cggatgcgac tccggagtct   1260

ggatcacggt catctggaag aagaacgatg ggaatcataa tccgaaaacg gtatcggacg   1320

attgtgtctc atcaaaccca caagcagccg ctgtctgcgt cgctccgtgc gactgctgtt   1380

tatgggatca gggtccacag tgtcctgaag catgatttta atagccctta acatcaactt   1440

tctggtgcga tgcgcgcagc aacgcattct gatttcactc aaatctttgc agtaggtaca   1500

acacattatt acaatattgt ttaataaacc ataattaaaa gcgctccagc caaaactcat   1560

atctgatata atcgcccctg catgaccatc ataccaaagt ttaatataaa ttaaatgacg   1620

ttccctcaaa aacacactac ccacatacat gatctctttt ggcatgtgca tattaacaat   1680

ctgtctgtac catggacaac gttgaattc                                    1709

<210> SEQ ID NO 26
<211> LENGTH: 11997
<212> TYPE: DNA
<213> ORGANISM: Artificial Sequence
<220> FEATURE:
<223> OTHER INFORMATION: ColoAd2.4 shuttle vector
```

<400> SEQUENCE: 26

```
ggcgcgccta tctatataat ataccttata gatggaatgg tgccaatatg taaatgaggt     60
gattttaaaa agtgtggatc gtgtggtgat tggctgtggg gttaacggct aaaaggggcg    120
gtgcgaccgt gggaaaatga cgttttgtgg gggtggagtt tttttgcaag ttgtcgcggg    180
aaatgtgacg cataaaaagg ctttttttctc acggaactac ttagttttcc cacggtattt    240
aacaggaaat gaggtagttt tgaccggatg caagtgaaaa ttgttgattt tcgcgcgaaa    300
actgaatgag gaagtgtttt tctgaataat gtggtattta tggcagggtg gagtatttgt    360
tcagggccag gtagactttg acccattacg tggaggtttc gattaccgtg tttttttacct    420
gaatttccgc gtaccgtgtc aaagtcttct gtttttacgt aggtgtcagc tgatcgctag    480
ggtatttata cctcagggtt tgtgtcaaga ggccactctt gagtgccagc gagaagagtt    540
ttctcctctg cgccggcagt ttaataataa aaaaatgaga gatttgcgat ttctgcctca    600
ggaaataatc tctgctgaga ctggaaatga aatattggag cttgtggtgc acgccctgat    660
gggagacgat ccggagccac ctgtgcagct tttgagcct cctacgcttc aggaactgta    720
tgatttagag gtagagggat cggaggattc taatgaggaa gctgtaaatg gctttttttac    780
cgattctatg cttttagctg ctaatgaagg gttagaatta gatccgcctt tggacacttt    840
tgatactcca ggggtaattg tggaaagcgg tacaggtgta agaaaattac ctgatttgag    900
ttccgtggac tgtgatttgc actgctatga agacgggttt cctccgagtg atgaggagga    960
ccatgaaaag gagcagtcca tgcagactgc agcgggtgag ggagtgaagg ctgccaatgt   1020
tggttttcag ttggattgcc cggagcttcc tggacatggc tgtaagtctt gtgaatttca   1080
caggaaaaat actggagtaa aggaactgtt atgttcgctt tgttatatga gaacgcactg   1140
ccactttatt tacagtaagt gtgtttaagt taaaatttaa aggaatatgc tgtttttcac   1200
atgtatattg agtgtgagtt ttgtgcttct tattataggt cctgtgtctg atgctgatga   1260
atcaccatct cctgattcta ctacctcacc tcctgagatt caagcacctg ttcctgtgga   1320
cgtgcgcaag cccattcctg tgaagcttaa gcctgggaaa cgtccagcag tggaaaaact   1380
tgaggacttg ttacagggtg gggacggacc tttggacttg agtacacgga aacgtccaag   1440
acaataagtg ttccatatcc gtgtttactt aaggtgacgt caatatttgt gtgacagtgc   1500
aatgtaataa aaatatgtta actgttcact ggtttttatt gctttttggg cggggactca   1560
ggtatataag tagaagcaga cctgtgtggt tagctcatag gagctggctt tcatccatgg   1620
aggtttgggc cattttggaa gaccttagga agactaggca actgttagag aacgcttcgg   1680
acggagtctc cggtttttgg agattctggt tcgctagtga attagctagg gtagttttta   1740
ggataaaaca ggactataaa caagaatttg aaaagttgtt ggtagattgc ccaggacttt   1800
ttgaagctct taatttgggc catcaggttc actttaaaga aaaagtttta tcagttttag   1860
acttttcaac cccaggtaga actgctgctg ctgtggcttt tcttactttt atattagata   1920
aatggatccc gcagactcat ttcagcaggg gatacgtttt ggatttcata gccacagcat   1980
tgtggagaac atggaaggtt cgcaagatga ggacaatctt aggttactgg ccagtgcagc   2040
ctttgggtgt agcgggaatc ctgaggcatc caccggtcat gccagcggtt ctggaggagg   2100
aacagcaaga ggacaacccg agagccggcc tggaccctcc agtggaggag gcggagtagc   2160
tgacttgtct cctgaactgc aacgggtgct tactggatct acgtccactg gacgggatag   2220
gggcgttaag agggagaggg catctagtgg tactgatgct agatctgagt tggctttaag   2280
tttaatgagt cgcagacgtc ctgaaaccat ttggtggcat gaggttcaga aagagggaag   2340
```

ggatgaagtt tctgtattgc aggagaaata ttcactggaa caggtgaaaa catgttggtt 2400
ggagcctgag gatgattggg aggtggccat taaaaattat gccaagatag ctttgaggcc 2460
tgataaacag tataagatta ctagacggat taatatccgg aatgcttgtt acatatctgg 2520
aaatggggct gaggtggtaa tagatactca agacaaggca gttattagat gctgcatgat 2580
ggatatgtgg cctggggtag tcggtatgga agcagtaact tttgtaaatg ttaagtttag 2640
gggagatggt tataatggaa tagtgtttat ggccaatacc aaacttatat tgcatggttg 2700
tagctttttt ggtttcaaca atacctgtgt agatgcctgg ggacaggtta gtgtacgggg 2760
atgtagtttc tatgcgtgtt ggattgccac agctggcaga accaagagtc aattgtctct 2820
gaagaaatgc atatttcaaa gatgtaacct gggcattctg aatgaaggcg aagcaagggt 2880
ccgccactgc gcttctacag atactggatg ttttattttg attaagggaa atgccagcgt 2940
aaagcataac atgatttgcg gtgcttccga tgagaggcct tatcaaatgc tcacttgtgc 3000
tggtgggcat tgtaatatgc tggctactgt gcatattgtt tcccatcaac gcaaaaaatg 3060
gcctgttttt gatcacaatg tgatgacgaa gtgtaccatg catgcaggtg ggcgtagagg 3120
aatgtttatg ccttaccagt gtaacatgaa tcatgtgaaa gtgttgttgg aaccagatgc 3180
cttttccaga atgagcctaa caggaatttt tgacatgaac atgcaaatct ggaagatcct 3240
gaggtatgat gatacgagat cgagggtacg cgcatgcgaa tgcggaggca agcatgccag 3300
gttccagccg gtgtgtgtag atgtgactga agatctcaga ccggatcatt tggttattgc 3360
ccgcactgga gcagagttcg gatccagtgg agaagaaact gactaaggtg agtattggga 3420
aaactttggg gtgggatttt cagatggaca gattgagtaa aaatttgttt tttctgtctt 3480
gcagctgtca tgagtggaaa cgcttctttt aagggggggag tcttcagccc ttatctgaca 3540
gggcgtctcc catcctgggc aggagttcgt cagaatgtta tgggatctac tgtggatgga 3600
agacccgtcc aacccgccaa ttcttcaacg ctgacctatg ctactttaag ttcttcacct 3660
ttggacgcag ctgcagctgc cgccgccgct tctgttgccg ctaacactgt gcttggaatg 3720
ggttactatg gaagcatcat ggctaattcc acttcctcta ataacccttc taccctgact 3780
caggacaagt tacttgtcct tttggcccag ctggaggctt tgacccaacg tctgggtgaa 3840
ctttctcagc aggtggtcga gttgcgagta caaactgagt ctgctgtcgg cacggcaaag 3900
tctaaataaa aaaatcccag aatcaatgaa taaataaaca agcttgttgt tgatttaaaa 3960
tcaagtgttt ttatttcatt tttcgcgcac ggtatgccct agaccaccga tctctatcat 4020
tgagaactcg gtggattttt tccaggatcc tatagaggtg ggattgaatg tttagataca 4080
tgggcattag gccgtctttg gggtggagat agctccattg aagggattca tgctccgggg 4140
tagtgttgta aatcacccag tcataacaag gtcgcagtgc atggtgttgc acaatatctt 4200
ttagaagtag gctgattgcc acagataagc ccttggtgta ggtgtttaca aaccggttga 4260
gctgggatgg gtgcattcgg ggtgaaatta tgtgcatttt ggattggatt tttaagttgg 4320
caatattgcc gccaagatcc cgtcttgggt tcatgttatg aaggaccacc aagacggtgt 4380
atccggtaca tttaggaaat ttatcgtgca gcttggatgg aaaagcgtgg aaaaatttgg 4440
agacaccctt gtgtcctcca agattttcca tgcactcatc catgataata gcaatggggc 4500
cgtgggcagc ggcgcgggca aacacgttcc gtgggtctga cacatcatag ttatgttcct 4560
gagttaaatc atcataagcc attttaatga atttggggcg gagagtacca gattggggta 4620
tgaatgttcc ttcgggccca tactagtctt gcttgtttta ctttcgcttt tggaaccggg 4680

```
ttctgccaat tacgatccat gtctagactt cgacccagaa aactgcacac ttacttttgc   4740

acccgacaca agccgcatct gtggagttca tcgcctctct tacgaacttg gcccccaacg   4800

acaaaaattt acctgcatgg tgggaatcaa ccccatagtt atcacccagc aaagtggaga   4860

tactaagggt tgcattcact gctcctgcga ttccatcgag tgcacctaca ccctgctgaa   4920

gaccctatgc ggcctaagag acctgctacc aatgaattaa aaaatgatta ataaaaaatc   4980

acttacttga aatcagcaat aaggtctctg ttgaaatttt ctcccagcag cacctcactt   5040

ccctcttccc aactctggta ttctaaaccc cgttcagcgg catactttct ccatacttta   5100

aaggggatgt caaattttag ctcctctcct gtacccacaa tcttcatgtc tttcttccca   5160

gatgaccaag agagtccggc tcagtgactc cttcaaccct gtctacccct atgaagatga   5220

aagcacctcc caacacccct ttataaaccc agggtttatt tccccaaatg gcttcacaca   5280

aagcccaaac ggagttctta ctttaaaatg tttaacccca ctaacaacca caggcggatc   5340

tctacagcta aaagtgggag gggacttac agtggatgac accaacggtt ttttgaaaga   5400

aaacataagt gccaccacac cactcgttaa gactggtcac tctataggtt taccactagg   5460

agccggattg ggaacgaatg aaaataaact ttgtatcaaa ttaggacaag gacttacatt   5520

caattcaaac aacatttgca ttgatgacaa tattaacacc ttatggacag gagtcaaccc   5580

caccgaagcc aactgtcaaa tcatgaactc cagtgaatct aatgattgca aattaattct   5640

aacactagtt aaaactggag cactagtcac tgcatttgtt tatgttatag gagtatctaa   5700

caattttaat atgctaacta cacacagaaa tataaatttt actgcagagc tgtttttcga   5760

ttctactggt aatttactaa ctagactctc atccctcaaa actccactta atcataaatc   5820

aggacaaaac atggctactg gtgccattac taatgctaaa ggtttcatgc ccagcacgac   5880

tgcctatcct ttcaatgata attctagaga aaaagaaaac tacatttacg gaacttgtta   5940

ctacacagct agtgatcgca ctgcttttcc cattgacata tctgtcatgc ttaaccgaag   6000

agcaataaat gacgagacat catattgtat tcgtataact tggtcctgga acacaggaga   6060

tgccccagag gtgcaaacct ctgctacaac cctagtcacc tccccattta cctttacta   6120

catcagagaa gacgactgac aaataaagtt tgcgatcgct accctgcagg aacttgttta   6180

tttgaaaatc aattcacaaa atccgagtag ttattttgcc tccccttcc catttaacag   6240

aatacaccaa tctctcccca cgcacagctt taaacatttg gataccatta gatatagaca   6300

tggttttaga ttccacattc caaacagttt cagagcgagc caatctgggg tcagtgatag   6360

ataaaaatcc atcgggatag tcttttaaag cgctttcaca gtccaactgc tgcggatgcg   6420

actccggagt ctggatcacg gtcatctgga agaagaacga tgggaatcat aatccgaaaa   6480

cggtatcgga cgattgtgtc tcatcaaacc cacaagcagc cgctgtctgc gtcgctccgt   6540

gcgactgctg tttatgggat cagggtccac agtgtcctga agcatgattt taatagccct   6600

taacatcaac tttctggtgc gatgcgcgca gcaacgcatt ctgatttcac tcaaatcttt   6660

gcagtaggta caacacatta ttacaatatt gtttaataaa ccataattaa aagcgctcca   6720

gccaaaactc atatctgata taatcgcccc tgcatgacca tcataccaaa gtttaatata   6780

aattaaatga cgttccctca aaaacacact acccacatac atgatctctt ttggcatgtg   6840

catattaaca atctgtctgt accatggaca acgttggtta atcatgcaac ccaatataac   6900

cttccggaac cacactgcca acaccgctcc cccagccatg cattgaagtg aaccctgctg   6960

attacaatga caatgaagaa cccaattctc tcgaccgtga atcacttgag aatgaaaaat   7020

atctatagtg gcacaacata gacataaatg catgcatctt ctcataattt ttaactcctc   7080
```

-continued

```
aggatttaga aacatatccc agggaatagg aagctcttgc agaacagtaa agctggcaga   7140
acaaggaaga ccacgaacac aacttacact atgcatagtc atagtatcac aatctggcaa   7200
cagcgggtgg tcttcagtca tagaagctcg ggtttcattt tcctcacaac gtggtaactg   7260
ggctctggtg taagggtgat gtctggcgca tgatgtcgag cgtgcgcgca accttgtcat   7320
aatggagttg cttcctgaca ttctcgtatt ttgtatagca aaacgcggcc ctggcagaac   7380
acactcttct tcgccttcta tcctgccgct tagcgtgttc cgtgtgatag ttcaagtaca   7440
accacactct taagttggtc aaaagaatgc tggcttcagt tgtaatcaaa actccatcgc   7500
atctaatcgt tctgaggaaa tcatccaagc aatgcaactg gattgtgttt caagcaggag   7560
aggagaggga agagacggaa gaaccatgtt aatttttatt ccaaacgatc tcgcagtact   7620
tcaaattgta gatcgcgcag atggcatctc tcgcccccac tgtgttggtg aaaaagcaca   7680
gctagatcaa aagaaatgcg attttcaagg tgctcaacgg tggcttccag caaagcctcc   7740
acgcgcacat ccaagaacaa aagaatacca aaagaaggag cattttctaa ctcctcaatc   7800
atcatattac attcctgcac cattcccaga taattttcag ctttccagcc ttgaattatt   7860
cgtgtcagtt cttgtggtaa atccaatcca cacattacaa acaggtcccg gagggcgccc   7920
tccaccacca ttcttaaaca caccctcata atgacaaaat atcttgctcc tgtgtcacct   7980
gtagcgaatt gagaatggca acatcaattg acatgccctt ggctctaagt tcttctttaa   8040
gttctagttg taaaaactct ctcatattat caccaaactg cttagccaga agccccccgg   8100
gaacaagagc aggggacgct acagtgcagt acaagcgcag acctccccaa ttggctccag   8160
caaaaacaag attggaataa gcatattggg aaccgccagt aatatcatcg aagttgctgg   8220
aaatataatc aggcagagtt tcttgtaaaa attgaataaa agaaaaattt gccaaaaaaa   8280
cattcaaaac ctctgggatg caaatgcaat aggttaccgc gctgcgctcc aacattgtta   8340
gttttgaatt agtctgcaaa aataaaaaaa aaaacaagcg tcatatcata gtagcctgac   8400
gaacagatgg ataaatcagt ctttccatca caagacaagc cacagggtct ccagctcgac   8460
cctcgtaaaa cctgtcatca tgattaaaca acagcaccga aagttcctcg cggtgaccag   8520
catgaataat tcttgatgaa gcatacaatc cagacatgtt agcatcagtt aacgagaaaa   8580
aacagccaac atagcctttg ggtataatta tgcttaatcg taagtatagc aaagccaccc   8640
ctcgcggata caaagtaaaa ggcacaggag aataaaaaat ataattattt ctctgctgct   8700
gttcaggcaa cgtcgccccc ggtccctcta aatacacata caaagcctca tcagccatgg   8760
cttaccagac aaagtacagc gggcacacaa agcacaagct ctaaagtgac tctccaacct   8820
ctccacaata tatatataca caagccctaa actgacgtaa tgggagtaaa gtgtaaaaaa   8880
tcccgccaaa cccaacacac accccgaaac tgcgtcacca gggaaaagta cagtttcact   8940
tccgcaatcc caacaggcgt aacttcctct ttctcacggt acgtgatatc ccactaactt   9000
gcaacgtcat tttcccacgg tcgcaccgcc ccttttagcc gttaacccca cagccaatca   9060
ccacacgatc cacacttttt aaaatcacct catttacata ttggcaccat tccatctata   9120
aggtatatta tatagatagg cgcgccctct cttaaggtag catcgggatc gagtccctga   9180
gagaacatcc tcaatcccga tctatcctta gatccgagga atatcgaaat cagttacgct   9240
agggataaca gggtaatata gcatcccctc ggattgctat ctaccggctc gtcagctatg   9300
atctctcgat ttcgatcaag aaatctcatt ggttaccttg ggctatcgaa accagtcaag   9360
tcagctactt ggcgagatcg acttgtctga gtttcgacta cgctcagaat tgcgtcagcg   9420
```

```
cctatcgcca ggtattactc caatcccgaa tatccgagcc tgagagaaca tcctcaatcc   9480
cgatctatcc ttagatccga ggaatatcga aatcgtttaa atcttttctt gatggtaaat   9540
cattcgaata taagaatgga gagacgaatg gggaaacgac aaagatgaca ttctttggtc   9600
cttctggtga ggttctcaag tttttggtta atcctgtcaa caacttatat cgtatggggc   9660
tgacttcagg tgctacattt gaagagataa attgcactga aatctagtaa tattttatct   9720
gattaataag atgatcttct tgagatcgtt ttggtctgcg cgtaatctct tgctctgaaa   9780
acgaaaaaac cgccttgcag ggcggttttt cgaaggttct ctgagctacc aactctttga   9840
accgaggtaa ctggcttggc agagcgcagt caccaaaact tgtcctttca gtttagcctt   9900
aaccggcgca tgacttcaag actaactctg ctaaatcaat taccagtggc tgctgccagt   9960
ggtgcttttg catgtctttc cgggttggac tcaagacgat agttaccgga taaggcgcag  10020
cggtcggact gaacgggggg ttcgtgcata cagtccagct tggagcgaac tgcctacccg  10080
gaactgagtg tcaggcgtgg aatgagacaa acgcggccat aacagcggaa tgacaccggt  10140
aaaccgaaag gcaggaacag gagagcgcac gagggagccg ccagggggaa acgcctggta  10200
tctttatagt cctgtcgggt ttcgccacca ctgatttgag cgtcagattt cgtgatgctt  10260
gtcagggggg cggagcctat ggaaaaacgg ctttgccgcg gccctctcac ttccctgtta  10320
agtatcttcc tggcatcttc caggaaatct ccgccccgtt cgtaagccat ttccgctcgc  10380
cgcagtcgaa cgaccgagcg tagcgagtca gtgagcgagg aagcggaata tatcctgtat  10440
cacatattct gctgacgcac cggtgcggcc tttttctcc tgccacatga agcacttcac  10500
tgacaccctc atcagtgcca acatagtaag ccagtataca ctccgctaat ttaaacgtgg  10560
tgtaccgaga acgatcctct cagtgcgatc tcgacgatca gtggtattcc gacatatcgt  10620
tgcttggcag tcagccagtc gatcctagct tgggacccag gaagtccaat cgtcagatat  10680
tgtactcagc ctggtcacgg cagcgtaccg atctcgtaac tataacggtc ctaaggtagc  10740
gaactagata ttgatagtct gatcggtcaa cgtataatcg agtcctagct tttgcaaaca  10800
tctatcaaga gacaggatca gcaggaggct ttcgcatgat tgaacaagat ggattgcacg  10860
caggttctcc ggcggcttgg gtggagaggc tattcggcta tgactgggca caacagacaa  10920
tcggctgctc tgatgccgcc gtgttccggc tgtcagcgca ggggcgtccg gttctttttg  10980
tcaagaccga cctgtccggt gccctgaatg aactgcaaga cgaggcagcg cggctatcgt  11040
ggctggcgac gacgggcgtt ccttgcgcgg ctgtgctcga cgttgtcact gaagcgggaa  11100
gggactggct gctattgggc gaagtgccgg ggcaggatct cctgtcatct caccttgctc  11160
ctgccgagaa agtatccatc atggctgatg caatgcggcg gctgcatacg cttgatccgg  11220
ctacctgccc attcgaccac caagcgaaac atcgcatcga gcgagcacgt actcggatgg  11280
aagccggtct tgtcgatcag gatgatctgg acgaagagca tcaggggctc gcgccagccg  11340
aactgttcgc caggctcaag gcgtctatgc ccgacggcga ggatctcgtc gtgacccacg  11400
gcgatgcctg cttgccgaat atcatggtgg aaaatggccg cttttctgga ttcatcgact  11460
gtggccgtct gggtgtggcg gaccgctatc aggacatagc gttggctacc cgtgatattg  11520
ctgaagagct tggcggcgaa tgggctgacc gcttccttgt gctttacggt atcgccgcgc  11580
ccgattcgca gcgcatcgcc ttctatcgcc ttcttgacga gttcttctga ccgattctag  11640
gtgcattggc gcagaaaaaa atgcctgatg cgacgctgcg cgtcttatac tcccacatat  11700
gccagattca gcaacggata cggcttcccc aacttgccca cttccatacg tgtcctcctt  11760
accagaaatt tatccttaag gtccgtaact ataacggtcc taaggtagcg aatcgaccta  11820
```

```
gctctatcga atctccctcg tttcgagctt acgcgaacta gcctctggcg atagcatccg  11880

aggggcaggc atctatgtcg ggtgcggaga aagaggtaat gtcaagttcg atctgattgc  11940

ttggcataaa gtccgatggt tcgagtagac tcagttcaac ctctctctta aggtagc     11997
```

<210> SEQ ID NO 27
<211> LENGTH: 2242
<212> TYPE: DNA
<213> ORGANISM: Artificial Sequence
<220> FEATURE:
<223> OTHER INFORMATION: ColoAd2.4 synthetic fragment

<400> SEQUENCE: 27

```
gggcccatac tagtcttgct tgttttactt tcgcttttgg aaccgggttc tgccaattac     60

gatccatgtc tagacttcga cccagaaaac tgcacactta cttttgcacc cgacacaagc    120

cgcatctgtg gagttcatcg cctctcttac gaacttggcc cccaacgaca aaaatttacc    180

tgcatggtgg gaatcaaccc catagttatc acccagcaaa gtggagatac taagggttgc    240

attcactgct cctgcgattc catcgagtgc acctacaccc tgctgaagac cctatgcggc    300

ctaagagacc tgctaccaat gaattaaaaa atgattaata aaaaatcact tacttgaaat    360

cagcaataag gtctctgttg aaattttctc ccagcagcac ctcacttccc tcttcccaac    420

tctggtattc taaaccccgt tcagcggcat actttctcca tactttaaag gggatgtcaa    480

atttagctcc tctcctgta cccacaatct tcatgtcttt cttcccagat gaccaagaga     540

gtccggctca gtgactcctt caaccctgtc tacccctatg aagatgaaag cacctcccaa    600

cacccettta taaacccagg gtttatttcc ccaaatggct tcacacaaag cccaaacgga    660

gttcttactt taaaatgttt aaccccacta acaaccacag gcggatctct acagctaaaa    720

gtgggagggg gacttacagt ggatgacacc aacggttttt tgaaagaaaa cataagtgcc    780

accacaccac tcgttaagac tggtcactct ataggtttac cactaggagc cggattggga    840

acgaatgaaa ataaactttg tatcaaatta ggacaaggac ttacattcaa ttcaaacaac    900

atttgcattg atgacaatat taacacctta tggacaggag tcaaccccac cgaagccaac    960

tgtcaaatca tgaactccag tgaatctaat gattgcaaat taattctaac actagttaaa   1020

actggagcac tagtcactgc atttgtttat gttataggag tatctaacaa ttttaatatg   1080

ctaactacac acagaaatat aaattttact gcagagctgt tttcgattc tactggtaat    1140

ttactaacta gactctcatc cctcaaaact ccacttaatc ataaatcagg acaaaacatg   1200

gctactggtg ccattactaa tgctaaaggt ttcatgccca gcacgactgc ctatcctttc   1260

aatgataatt ctagagaaaa agaaaactac atttacggaa cttgttacta cacagctagt   1320

gatcgcactg cttttcccat tgacatatct gtcatgctta accgaagagc aataaatgac   1380

gagacatcat attgtattcg tataacttgg tcctggaaca caggagatgc cccagaggtg   1440

caaacctctg ctacaaccct agtcacctcc ccatttacct tttactacat cagagaagac   1500

gactgacaaa taaagtttgc gatcgctacc ctgcaggaac ttgtttattt gaaaatcaat   1560

tcacaaaatc cgagtagtta ttttgcctcc cccttcccat ttaacagaat acaccaatct   1620

ctccccacgc acagctttaa acatttggat accattagat atagacatgg ttttagattc   1680

cacattccaa acagtttcag agcgagccaa tctggggtca gtgatagata aaaatccatc   1740

gggatagtct tttaaagcgc tttcacagtc caactgctgc ggatgcgact ccggagtctg   1800

gatcacggtc atctggaaga agaacgatgg gaatcataat ccgaaaacgg tatcggacga   1860
```

ttgtgtctca tcaaacccac aagcagccgc tgtctgcgtc gctccgtgcg actgctgttt 1920
atgggatcag ggtccacagt gtcctgaagc atgattttaa tagcccttaa catcaacttt 1980
ctggtgcgat gcgcgcagca acgcattctg atttcactca aatctttgca gtaggtacaa 2040
cacattatta caatattgtt taataaacca taattaaaag cgctccagcc aaaactcata 2100
tctgatataa tcgcccctgc atgaccatca taccaaagtt taatataaat taaatgacgt 2160
tccctcaaaa acacactacc cacatacatg atctcttttg gcatgtgcat attaacaatc 2220
tgtctgtacc atggacaacg tt 2242

<210> SEQ ID NO 28
<211> LENGTH: 35208
<212> TYPE: DNA
<213> ORGANISM: Artificial Sequence
<220> FEATURE:
<223> OTHER INFORMATION: ColoAd2.4 plasmid

<400> SEQUENCE: 28
ggcgcgccta tctatataat ataccttata gatggaatgg tgccaatatg taaatgaggt 60
gattttaaaa agtgtggatc gtgtggtgat tggctgtggg gttaacggct aaaaggggcg 120
gtgcgaccgt gggaaaatga cgttttgtgg gggtggagtt tttttgcaag ttgtcgcggg 180
aaatgtgacg cataaaaagg ctttttttctc acggaactac ttagttttcc cacggtattt 240
aacaggaaat gaggtagttt tgaccggatg caagtgaaaa ttgttgattt tcgcgcgaaa 300
actgaatgag gaagtgtttt tctgaataat gtggtattta tggcagggtg gagtatttgt 360
tcagggccag gtagactttg acccattacg tggaggtttc gattaccgtg tttttttacct 420 gaatttccgc gtaccgtgtc aaagtcttct gtttttacgt aggtgtcagc tgatcgctag 480
ggtatttata cctcagggtt tgtgtcaaga ggccactctt gagtgccagc gagaagagtt 540
ttctcctctg cgccggcagt ttaataataa aaaaatgaga gatttgcgat ttctgcctca 600
ggaaataatc tctgctgaga ctggaaatga aatattggag cttgtggtgc acgccctgat 660
gggagacgat ccggagccac ctgtgcagct ttttgagcct cctacgcttc aggaactgta 720
tgatttagag gtagagggat cggaggattc taatgaggaa gctgtaaatg gcttttttac 780
cgattctatg cttttagctg ctaatgaagg gttagaatta gatccgcctt tggacacttt 840
tgatactcca ggggtaattg tggaaagcgg tacaggtgta agaaaattac ctgatttgag 900
ttccgtggac tgtgatttgc actgctatga agacgggttt cctccgagtg atgaggagga 960
ccatgaaaag gagcagtcca tgcagactgc agcgggtgag ggagtgaagg ctgccaatgt 1020
tggttttcag ttggattgcc cggagcttcc tggacatggc tgtaagtctt gtgaatttca 1080
caggaaaaat actggagtaa aggaactgtt atgttcgctt tgttatatga gaacgcactg 1140
ccactttatt tacagtaagt gtgtttaagt taaaatttaa aggaatatgc tgtttttcac 1200
atgtatattg agtgtgagtt ttgtgcttct tattataggt cctgtgtctg atgctgatga 1260
atcaccatct cctgattcta ctacctcacc tcctgagatt caagcacctg ttcctgtgga 1320
cgtgcgcaag cccattcctg tgaagcttaa gcctgggaaa cgtccagcag tggaaaaact 1380
tgaggacttg ttacagggtg gggacggacc tttggacttg agtacacgga aacgtccaag 1440
acaataagtg ttccatatcc gtgtttactt aaggtgacgt caatatttgt gtgacagtgc 1500
aatgtaataa aaatatgtta actgttcact ggtttttatt gctttttggg cggggactca 1560
ggtatataag tagaagcaga cctgtgtggt tagctcatag gagctggctt tcatccatgg 1620
aggtttgggc cattttggaa gaccttagga agactaggca actgttagag aacgcttcgg 1680
acggagtctc cggtttttgg agattctggt tcgctagtga attagctagg gtagttttta 1740
ggataaaaca ggactataaa caagaatttg aaaagttgtt ggtagattgc ccaggacttt 1800
ttgaagctct taatttgggc catcaggttc actttaaaga aaaagtttta tcagttttag 1860
acttttcaac cccaggtaga actgctgctg ctgtggcttt tcttactttt atattagata 1920
aatggatccc gcagactcat ttcagcaggg gatacgtttt ggatttcata gccacagcat 1980
tgtggagaac atggaaggtt cgcaagatga ggacaatctt aggttactgg ccagtgcagc 2040
ctttgggtgt agcgggaatc ctgaggcatc caccggtcat gccagcggtt ctggaggagg 2100
aacagcaaga ggacaacccg agagccggcc tggaccctcc agtggaggag gcggagtagc 2160
tgacttgtct cctgaactgc aacgggtgct tactggatct acgtccactg gacgggatag 2220
gggcgttaag agggagaggg catctagtgg tactgatgct agatctgagt tggctttaag 2280
tttaatgagt cgcagacgtc ctgaaaccat ttggtggcat gaggttcaga aagagggaag 2340
ggatgaagtt tctgtattgc aggagaaata ttcactggaa caggtgaaaa catgttggtt 2400
ggagcctgag gatgattggg aggtggccat taaaaattat gccaagatag ctttgaggcc 2460
tgataaacag tataagatta ctagacggat taatatccgg aatgcttgtt acatatctgg 2520
aaatggggct gaggtggtaa tagatactca agacaaggca gttattagat gctgcatgat 2580
ggatatgtgg cctggggtag tcggtatgga agcagtaact tttgtaaatg ttaagtttag 2640
gggagatggt tataatggaa tagtgtttat ggccaatacc aaacttatat tgcatggttg 2700
tagctttttt ggtttcaaca atacctgtgt agatgcctgg ggacaggtta gtgtacgggg 2760
atgtagtttc tatgcgtgtt ggattgccac agctggcaga accaagagtc aattgtctct 2820
gaagaaatgc atatttcaaa gatgtaacct gggcattctg aatgaaggcg aagcaagggt 2880
ccgccactgc gcttctacag atactggatg ttttattttg attaagggaa atgccagcgt 2940
aaagcataac atgatttgcg gtgcttccga tgagaggcct tatcaaatgc tcacttgtgc 3000
tggtgggcat tgtaatatgc tggctactgt gcatattgtt tcccatcaac gcaaaaaatg 3060
gcctgttttt gatcacaatg tgatgacgaa gtgtaccatg catgcaggtg ggcgtagagg 3120
aatgtttatg ccttaccagt gtaacatgaa tcatgtgaaa gtgttgttgg aaccagatgc 3180
cttttccaga atgagcctaa caggaatttt tgacatgaac atgcaaatct ggaagatcct 3240
gaggtatgat gatacgagat cgagggtacg cgcatgcgaa tgcggaggca agcatgccag 3300
gttccagccg gtgtgtgtag atgtgactga agatctcaga ccggatcatt tggttattgc 3360
ccgcactgga gcagagttcg gatccagtgg agaagaaact gactaaggtg agtattggga 3420
aaactttggg gtgggatttt cagatggaca gattgagtaa aaatttgttt tttctgtctt 3480
gcagctgtca tgagtggaaa cgcttctttt aagggggggag tcttcagccc ttatctgaca 3540
gggcgtctcc catcctgggc aggagttcgt cagaatgtta tgggatctac tgtggatgga 3600
agacccgtcc aacccgccaa ttcttcaacg ctgacctatg ctactttaag ttcttcacct 3660
ttggacgcag ctgcagctgc cgccgccgct tctgttgccg ctaacactgt gcttggaatg 3720
ggttactatg gaagcatcat ggctaattcc acttcctcta ataacccttc taccctgact 3780
caggacaagt tacttgtcct tttggcccag ctggaggctt tgacccaacg tctgggtgaa 3840
ctttctcagc aggtggtcga gttgcgagta caaactgagt ctgctgtcgg cacggcaaag 3900
tctaaataaa aaaatcccag aatcaatgaa taaataaaca agcttgttgt tgatttaaaa 3960
tcaagtgttt ttatttcatt tttcgcgcac ggtatgccct agaccaccga tctctatcat 4020

-continued

```
tgagaactcg gtggattttt tccaggatcc tatagaggtg ggattgaatg tttagataca   4080
tgggcattag gccgtctttg gggtggagat agctccattg aagggattca tgctccgggg   4140
tagtgttgta aatcacccag tcataacaag gtcgcagtgc atggtgttgc acaatatctt   4200
ttagaagtag gctgattgcc acagataagc ccttggtgta ggtgtttaca aaccggttga   4260
gctgggatgg gtgcattcgg ggtgaaatta tgtgcatttt ggattggatt tttaagttgg   4320
caatattgcc gccaagatcc cgtcttgggt tcatgttatg aaggaccacc aagacggtgt   4380
atccggtaca tttaggaaat ttatcgtgca gcttggatgg aaaagcgtgg aaaaatttgg   4440
agacaccctt gtgtcctcca agattttcca tgcactcatc catgataata gcaatggggc   4500
cgtgggcagc ggcgcgggca aacacgttcc gtgggtctga cacatcatag ttatgttcct   4560
gagttaaatc atcataagcc attttaatga atttggggcg gagagtacca gattggggta   4620
tgaatgttcc ttcgggcccc ggagcatagt tcccctcaca gatttgcatt tcccaagctt   4680
tcagttccga gggtggaatc atgtccacct ggggggctat gaaaaacacc gtttctgggg   4740
cgggggtgat taattgtgat gatagcaaat ttctgagcaa ttgagatttg ccacatccgg   4800
tggggccata aatgattccg attacgggtt gcaggtggta gtttagggaa cggcaactgc   4860
cgtcttctcg aagcaagggg gccacctcgt tcatcatttc ccttacatgc atattttccc   4920
gcaccaaatc cattaggagg cgctctcctc ctagtgatag aagttcttgt agtgaggaaa   4980
agtttttcag cggtttcaga ccgtcagcca tgggcatttt ggagagagtt tgctgcaaaa   5040
gttctagtct gttccacagt tcagtgatgt gttctatggc atctcgatcc agcagacctc   5100
ctcgtttcgc gggtttggac ggctcctgga atagggtatg agacgatggg cgtccagcgc   5160
tgccagggtt cggtccttcc agggtctcag tgttcgagtc agggttgttt ccgtcacagt   5220
gaaggggtgt gcgcctgctt gggcgcttgc cagggtgcgc ttcagactca tcctgctggt   5280
cgaaaacttc tgtcgcttgg cgccctgtat gtcggccaag tagcagttta ccatgagttc   5340
gtagttgagc gcctcggctg cgtggccttt ggcgcggagc ttacctttgg aagttttctt   5400
gcataccggg cagtataggc atttcagcgc atacaacttg ggcgcaagga aaacggattc   5460
tggggagtat gcatctgcgc cgcaggaggc gcaaacagtt tcacattcca ccagccaggt   5520
taaatccggt tcattggggt caaaaacaag ttttccgcca tatttttga tgcgtttctt    5580
acctttggtc tccatgagtt cgtgtcctcg ttgagtgaca aacaggctgt ccgtgtcccc   5640
gtagactgat tttacaggcc tcttctccag tggagtgcct cggtcttctt cgtacaggaa   5700
ctctgaccac tctgatacaa aggcgcgcgt ccaggccagc acaaaggagg ctatgtggga   5760
ggggtagcga tcgttgtcaa ccagggggtc cacctttttcc aaagtatgca aacacatgtc  5820
accctcttca acatccagga atgtgattgg cttgtaggtg tatttcacgt gacctggggt   5880
ccccgctggg ggggtataaa agggggcggt tctttgctct tcctcactgt cttccggatc   5940
gctgtccagg aacgtcagct gttggggtag gtattccctc tcgaaggcgg gcatgacctc   6000
tgcactcagg ttgtcagttt ctaagaacga ggaggatttg atattgacag tgccggttga   6060
gatgcctttc atgaggtttt cgtccatctg gtcagaaaac acaatttttt tattgtcaag   6120
tttggtggca aatgatccat acagggcgtt ggataaaagt ttggcaatgg atcgcatggt   6180
ttggttcttt tccttgtccg cgcgctcttt ggcggcgatg ttgagttgga catactcgcg   6240
tgccaggcac ttccattcgg ggaagatagt tgttaattca tctggcacga ttctcacttg   6300
ccaccctcga ttatgcaagg taattaaatc cacactggtg gccacctcgc ctcgaagggg   6360
ttcattggtc caacagagcc tacctccttt cctagaacag aaagggggaa gtgggtctag   6420
```

```
cataagttca tcgggagggt ctgcatccat ggtaaagatt cccggaagta aatccttatc   6480
aaaatagctg atgggagtgg ggtcatctaa ggccatttgc cattctcgag ctgccagtgc   6540
gcgctcatat gggttaaggg gactgcccca tggcatggga tgggtgagtg cagaggcata   6600
catgccacag atgtcataga cgtagatggg atcctcaaag atgcctatgt aggttggata   6660
gcatcgcccc cctctgatac ttgctcgcac atagtcatat agttcatgtg atggcgctag   6720
cagccccgga cccaagttgg tgcgattggg tttttctgtt ctgtagacga tctggcgaaa   6780
gatggcgtga gaattggaag agatggtggg tctttgaaaa atgttgaaat gggcatgagg   6840
tagacctaca gagtctctga caaagtgggc ataagattct tgaagcttgg ttaccagttc   6900
ggcggtgaca agtacgtcta gggcgcagta gtcaagtgtt tcttgaatga tgtcataacc   6960
tggttggttt ttcttttccc acagttcgcg gttgagaagg tattcttcgc gatccttcca   7020
gtactcttct agcggaaacc cgtctttgtc tgcacggtaa gatcctagca tgtagaactg   7080
attaactgcc ttgtaagggc agcagccctt ctctacgggt agagagtatg cttgagcagc   7140
ttttcgtagc gaagcgtgag taagggcaaa ggtgtctctg accatgactt tgaggaattg   7200
gtatttgaag tcgatgtcgt cacaggctcc ctgttcccag agttggaagt ctacccgttt   7260
cttgtaggcg ggttgggca aagcgaaagt aacatcattg aagagaatct tgccggccct    7320
gggcatgaaa ttgcgagtga tgcgaaaagg ctgtggtact tccgctcggt tattgataac   7380
ctgggcagct aggacgatct cgtcgaaacc gttgatgttg tgtcctacga tgtataattc   7440
tatgaaacgc ggcgtgcctc tgacgtgagg tagcttactg agctcatcaa aggttaggtc   7500
tgtggggtca gataaggcgt agtgttcgag agcccattcg tgcaggtgag gattcgcttt   7560
aaggaaggag gaccagaggt ccactgccag tgctgtttgt aactggtccc ggtactgacg   7620
aaaatgccgt ccgactgcca ttttttctgg ggtgacgcaa tagaaggttt gggggtcctg   7680
ccgccagcga tcccacttga gttttatggc gaggtcatag gcgatgttga cgagccgctg   7740
gtctccagag agtttcatga ccagcatgaa ggggattagc tgcttgccaa aggaccccat   7800
ccaggtgtag gtttccacat cgtaggtgag aaagagcctt tctgtgcgag gatgagagcc   7860
aatcgggaag aactggatct cctgccacca gttggaggaa tggctgttga tgtgatggaa   7920
gtagaactcc ctgcgacgcg ccgagcattc atgcttgtgc ttgtacagac ggccgcagta   7980
gtcgcagcgt tgcacgggtt gtatctcgtg aatgagttgt acctggcttc ccttgacgag   8040
aaatttcagt gggaagccga ggcctggcga ttgtatctcg tgctttacta tgttgtctgc   8100
atcggcctgt tcatcttctg tctcgatggt ggtcatgctg acgagccctc gcgggaggca   8160
agtccagacc tcggcgcggc aggggcggag ctcgaggacg agagcgcgca ggctggagct   8220
gtccagggtc ctgagacgct gcggactcag gttagtaggc agtgtcagga gattaacttg   8280
catgatcttt tggagggcgt gcgggaggtt cagatagtac ttgatctcaa cgggtccgtt   8340
ggtggagatg tcgatggctt gcagggttcc gtgtcccttg ggcgctacca ccgtgccctt   8400
gtttttcatt ttggacggcg gtggctctgt tgcttcttgc atgtttagaa gcggtgtcga   8460
gggcgcgcac cgggcggcag gggcggctcg ggacccggcg gcatggctgg cagtggtacg   8520
tcggcgccgc gcgcgggtag gttctggtac tgcgccctga gaagactcgc atgcgcgacg   8580
acgcggcggt tgacatcctg gatctgacgc ctctgggtga aagctaccgg ccccgtgagc   8640
ttgaacctga aagagagttc aacagaatca atctcggtat cgttgacggc ggcttgccta   8700
aggatttctt gcacgtcacc agagttgtcc tggtaggcga tctccgccat gaactgctcg   8760
```

-continued

```
atctcttcct cttgaagatc tccgcggccc gctctctcga cggtggccgc gaggtcgttg   8820
gagatgcgcc caatgagttg agagaatgca ttcatgcccg cctcgttcca gacgcggctg   8880
tagaccacgg cccccacggg atctctcgcg cgcatgacca cctgggcgag gttgagctcc   8940
acgtggcggg tgaagaccgc atagttgcat aggcgctgga aaaggtagtt gagtgtggtg   9000
gcgatgtgct cggtgacgaa gaaatacatg atccatcgtc tcagcggcat ctcgctgaca   9060
tcgcccagag cttccaagcg ctccatggcc tcgtagaagt ccacggcaaa attaaaaaac   9120
tgggagtttc gcgcggacac ggtcaactcc tcttccagaa gacggataag ttcggcgatg   9180
gtggtgcgca cctcgcgctc gaaagcccct gggatttctt cctcaatctc ttcttcttcc   9240
actaacatct cttcctcttc aggtggggct gcaggaggag ggggaacgcg gcgacgccgg   9300
cggcgcacgg gcagacggtc gatgaatctt tcaatgacct ctccgcggcg gcggcgcatg   9360
gtttcagtga cggcgcggcc gttctcgcgc ggtcgcagag taaaaacacc gccgcgcatc   9420
tccttaaagt ggtgactggg aggttctccg tttgggaggg agagggcgct gattatacat   9480
tttattaatt ggcccgtagg gactgcacgc agagatctga tcgtgtcaag atccacggga   9540
tctgaaaacc tttcgacgaa agcgtctaac cagtcacagt cacaaggtag gctgagtacg   9600
gcttcttgtg ggcgggggtg gttatgtgtt cggtctgggt cttctgtttc ttcttcatct   9660
cgggaaggtg agacgatgct gctggtgatg aaattaaagt aggcagttct aagacggcgg   9720
atggtggcga ggagcaccag gtctttgggt ccggcttgct ggatacgcag gcgattggcc   9780
attccccaag cattatcctg acatctagca agatctttgt agtagtcttg catgagccgt   9840
tctacgggca cttcttcctc acccgttctg ccatgcatac gtgtgagtcc aaatccgcgc   9900
attggttgta ccagtgccaa gtcagctacg actctttcgg cgaggatggc ttgctgtact   9960
tgggtaaggg tggcttgaaa gtcatcaaaa tccacaaagc ggtggtaagc tcctgtatta  10020
atggtgtaag cacagttggc catgactgac cagttaactg tctggtgacc agggcgcacg  10080
agctcggtgt atttaaggcg cgaataggcg cgggtgtcaa agatgtaatc gttgcaggtg  10140
cgcaccagat actggtaccc tataagaaaa tgcggcggtg gttggcggta gagaggccat  10200
cgttctgtag ctggagcgcc aggggcgagg tcttccaaca taaggcggtg atagccgtag  10260
atgtacctgg acatccaggt gattcctgcg gcggtagtag aagcccgagg aaactcgcgt  10320
acgcggttcc aaatgttgcg tagcggcatg aagtagttca ttgtaggcac ggtttgacca  10380
gtgaggcgcg cgcagtcatt gatgctctat agacacggag aaaatgaaag cgttcagcga  10440
ctcgactccg tagcctggag gaacgtgaac gggttgggtc gcggtgtacc ccggttcgag  10500
acttgtactc gagccggccg gagccgcggc taacgtggta ttggcactcc cgtctcgacc  10560
cagcctacaa aaatccagga tacggaatcg agtcgttttg ctggtttccg aatggcaggg  10620
aagtgagtcc tatttttttt ttttgccgct cagatgcatc ccgtgctgcg acagatgcgc  10680
ccccaacaac agcccccctc gcagcagcag cagcagcaat cacaaaaggc tgtccctgca  10740
actactgcaa ctgccgccgt gagcggtgcg ggacagcccg cctatgatct ggacttggaa  10800
gagggcgaag gactggcacg tctaggtgcg ccttcacccg agcggcatcc gcgagttcaa  10860
ctgaaaaaag attctcgcga ggcgtatgtg ccccaacaga acctatttag agacagaagc  10920
ggcgaggagc cggaggagat gcgagcttcc cgctttaacg cgggtcgtga gctgcgtcac  10980
ggtttggacc gaagacgagt gttgcgggac gaggatttcg aagttgatga aatgacaggg  11040
atcagtcctg ccagggcaca cgtggctgca gccaaccttg tatcggctta cgagcagaca  11100
gtaaaggaag agcgtaactt ccaaaagtct tttaataatc atgtgcgaac cctgattgcc  11160
```

-continued

```
cgcgaagaag ttacccttgg tttgatgcat ttgtgggatt tgatggaagc tatcattcag  11220
aaccctacta gcaaacctct gaccgcccag ctgtttctgg tggtgcaaca cagcagagac  11280
aatgaggctt tcagagaggc gctgctgaac atcaccgaac ccgaggggag atggttgtat  11340
gatcttatca acattctaca gagtatcata gtgcaggagc ggagcctggg cctggccgag  11400
aaggtggctg ccatcaatta ctcggttttg agcttgggaa aatattacgc tcgcaaaatc  11460
tacaagactc catacgttcc catagacaag gaggtgaaga tagatgggtt ctacatgcgc  11520
atgacgctca aggtcttgac cctgagcgat gatcttgggg tgtatcgcaa tgacagaatg  11580
catcgcgcgg ttagcgccag caggaggcgc gagttaagcg acagggaact gatgcacagt  11640
ttgcaaagag ctctgactgg agctggaacc gagggtgaga attacttcga catgggagct  11700
gacttgcagt ggcagcctag tcgcagggct ctgagcgccg cgacggcagg atgtgagctt  11760
ccttacatag aagaggcgga tgaaggcgag gaggaagagg gcgagtactt ggaagactga  11820
tggcacaacc cgtgtttttt gctagatgga acagcaagca ccggatcccg caatgcgggc  11880
ggcgctgcag agccagccgt ccggcattaa ctcctcggac gattggaccc aggccatgca  11940
acgtatcatg gcgttgacga ctcgcaaccc cgaagccttt agacagcaac cccaggccaa  12000
ccgtctatcg gccatcatgg aagctgtagt gccttcccgc tctaatccca ctcatgagaa  12060
ggtcctggcc atcgtgaacg cgttggtgga gaacaaagct attcgtccag atgaggccgg  12120
actggtatac aacgctctct tagaacgcgt ggctcgctac aacagtagca atgtgcaaac  12180
caatttggac cgtatgataa cagatgtacg cgaagccgtg tctcagcgcg aaaggttcca  12240
gcgtgatgcc aacctgggtt cgctggtggc gttaaatgct ttcttgagta ctcagcctgc  12300
taatgtgccg cgtggtcaac aggattatac taacttttta agtgctttga gactgatggt  12360
atcagaagta cctcagagcg aagtgtatca gtccggtcct gattacttct ttcagactag  12420
cagacagggc ttgcagacgg taaatctgag ccaagctttt aaaaacctta aaggtttgtg  12480
gggagtgcat gccccggtag gagaaagagc aaccgtgtct agcttgttaa ctccgaactc  12540
ccgcctatta ttactgttgg tagctccttt caccgacagc ggtagcatcg accgtaattc  12600
ctatttgggt tacctactaa acctgtatcg cgaagccata gggcaaagtc aggtggacga  12660
gcagacctat caagaaatta cccaagtcag tcgcgctttg ggacaggaag acactggcag  12720
tttggaagcc actctgaact tcttgcttac caatcggtct caaaagatcc ctcctcaata  12780
tgctcttact gcggaggagg agaggatcct tagatatgtg cagcagagcg tgggattgtt  12840
tctgatgcaa gagggggcaa ctccgactgc agcactggac atgacagcgc gaaatatgga  12900
gcccagcatg tatgccagta accgaccttt cattaacaaa ctgctggact acttgcacag  12960
agctgccgct atgaactctg attatttcac caatgccatc ttaaacccgc actggctgcc  13020
cccacctggt ttctacacgg gcgaatatga catgcccgac cctaatgacg gatttctgtg  13080
ggacgacgtg gacagcgatg ttttttcacc tctttctgat catcgcacgt ggaaaaagga  13140
aggcggcgat agaatgcatt cttctgcatc gctgtccggg gtcatgggtg ctaccgcggc  13200
tgagcccgag tctgcaagtc cttttcctag tctacccttt tctctacaca gtgtacgtag  13260
cagcgaagtg ggtagaataa gtcgcccgag tttaatgggc gaagaggagt atctaaacga  13320
ttccttgctc agaccggcaa gagaaaaaaa tttcccaaac aatggaatag aaagtttggt  13380
ggataaaatg agtagatgga agacttatgc tcaggatcac agagacgagc ctgggatcat  13440
ggggattaca agtagagcga gccgtagacg ccagcgccat gacagacaga ggggtcttgt  13500
```

```
gtgggacgat gaggattcgg ccgatgatag cagcgtgctg gacttgggtg ggagaggaag  13560
gggcaacccg tttgctcatt tgcgccctcg cttgggtggt atgttgtaaa aaaaaataaa  13620
aaaaaaactc accaaggcca tggcgacgag cgtacgttcg ttcttcttta ttatctgtgt  13680
ctagtataat gaggcgagtc gtgctaggcg gagcggtggt gtatccggag ggtcctcctc  13740
cttcgtacga gagcgtgatg cagcagcagc aggcgacggc ggtgatgcaa tccccactgg  13800
aggctccctt tgtgcctccg cgatacctgg cacctacgga gggcagaaac agcattcgtt  13860
attcggaact ggcacctcag tacgatacca ccaggttgta tctggtggac aacaagtcgg  13920
cggacattgc ttctctgaac tatcagaatg accacagcaa cttcttgacc acggtggtgc  13980
aaaacaatga ctttacccct acggaagcca gcacccagac cattaacttt gatgaacgat  14040
cgcggtgggg cggtcagcta aagaccatca tgcatactaa catgccaaac gtgaacgagt  14100
atatgtttag taacaagttc aaagcgcgtg tgatggtgtc cagaaaacct cccgacggtg  14160
ctgcagttgg ggatacttat gatcacaagc aggatatttt gaaatatgag tggttcgagt  14220
ttactttgcc agaaggcaac ttttcagtta ctatgactat tgatttgatg aacaatgcca  14280
tcatagataa ttacttgaaa gtgggtagac agaatggagt gcttgaaagt gacattggtg  14340
ttaagttcga caccaggaac ttcaagctgg gatgggatcc cgaaaccaag ttgatcatgc  14400
ctggagtgta tacgtatgaa gccttccatc ctgacattgt cttactgcct ggctgcggag  14460
tggattttac cgagagtcgt ttgagcaacc ttcttggtat cagaaaaaaa cagccatttc  14520
aagagggttt taagattttg tatgaagatt tagaaggtgg taatattccg gccctcttgg  14580
atgtagatgc ctatgagaac agtaagaaag aacaaaaagc caaaatagaa gctgctacag  14640
ctgctgcaga agctaaggca aacatagttg ccagcgactc tacaagggtt gctaacgctg  14700
gagaggtcag aggagacaat tttgcgccaa cacctgttcc gactgcagaa tcattattgg  14760
ccgatgtgtc tgaaggaacg gacgtgaaac tcactattca acctgtagaa aaagatagta  14820
agaatagaag ctataatgtg ttggaagaca aaatcaacac agcctatcgc agttggtatc  14880
tttcgtacaa ttatggcgat cccgaaaaag gagtgcgttc ctggacattg ctcaccacct  14940
cagatgtcac ctgcggagca gagcaggtct actggtcgct tccagacatg atgaaggatc  15000
ctgtcacttt ccgctccact agacaagtca gtaactaccc tgtggtgggt gcagagctta  15060
tgcccgtctt ctcaaagagc ttctacaacg aacaagctgt gtactcccag cagctccgcc  15120
agtccacctc gcttacgcac gtcttcaacc gctttcctga gaaccagatt ttaatccgtc  15180
cgccggcgcc caccattacc accgtcagtg aaaacgttcc tgctctcaca gatcacggga  15240
ccctgccgtt gcgcagcagt atccggggag tccaacgtgt gaccgttact gacgccagac  15300
gccgcacctg tccctacgtg tacaaggcac tgggcatagt cgcaccgcgc gtcctttcaa  15360
gccgcacttt ctaaaaaaaa aaaaaatgtc cattcttatc tcgcccagta ataacaccgg  15420
ttggggtctg cgcgctccaa gcaagatgta cggaggcgca cgcaaacgtt ctacccaaca  15480
tcctgtccgt gttcgcggac attttcgcgc tccatggggc gccctcaagg gccgcactcg  15540
cgttcgaacc accgtcgatg atgtaatcga tcaggtggtt gccgacgccc gtaattatac  15600
tcctactgcg cctacatcta ctgtggatgc agttattgac agtgtagtgg ctgacgctcg  15660
caactatgct cgacgtaaga gccggcgaag gcgcattgcc agacgccacc gagctaccac  15720
tgccatgcga gccgcaagag ctctgctacg aagagctaga cgcgtggggc gaagagccat  15780
gcttagggcg gccagacgtg cagcttcggg cgccagcgcc ggcaggtccc gcaggcaagc  15840
agccgctgtc gcagcggcga ctattgccga catggcccaa tcgcgaagag gcaatgtata  15900
```

```
ctgggtgcgt gacgctgcca ccggtcaacg tgtacccgtg cgcacccgtc cccctcgcac  15960
ttagaagata ctgagcagtc tccgatgttg tgtcccagcg gcgaggatgt ccaagcgcaa  16020
atacaaggaa gaaatgctgc aggttatcgc acctgaagtc tacggccaac cgttgaagga  16080
tgaaaaaaaa ccccgcaaaa tcaagcgggt taaaaaggac aaaaaagaag aggaagatgg  16140
cgatgatggg ctggcggagt ttgtgcgcga gtttgcccca cggcgacgcg tgcaatggcg  16200
tgggcgcaaa gttcgacatg tgttgagacc tggaacttcg gtggtcttta cacccggcga  16260
gcgttcaagc gctactttta agcgttccta tgatgaggtg tacggggatg atgatattct  16320
tgagcaggcg gctgaccgat taggcgagtt tgcttatggc aagcgtagta gaataacttc  16380
caaggatgag acagtgtcga tacccttgga tcatggaaat cccaccccta gtcttaaacc  16440
ggtcactttg cagcaagtgt tacccgtaac tccgcgaaca ggtgttaaac gcgaaggtga  16500
agatttgtat cccactatgc aactgatggt acccaaacgc cagaagttgg aggacgtttt  16560
ggagaaagta aaagtggatc cagatattca acctgaggtt aaagtgagac ccattaagca  16620
ggtagcgcct ggtctggggg tacaaactgt agacattaag attcccactg aaagtatgga  16680
agtgcaaact gaacccgcaa agcctactgc cacctccact gaagtgcaaa cggatccatg  16740
gatgcccatg cctattacaa ctgacgccgc cggtcccact cgaagatccc gacgaaagta  16800
cggtccagca agtctgttga tgcccaatta tgttgtacac ccatctatta ttcctactcc  16860
tggttaccga ggcactcgct actatcgcag ccgaaacagt acctcccgcc gtcgccgcaa  16920
gacacctgca aatcgcagtc gtcgccgtag acgcacaagc aaaccgactc ccggcgccct  16980
ggtgcggcaa gtgtaccgca atggtagtgc ggaacctttg acactgccgc gtgcgcgtta  17040
ccatccgagt atcatcactt aatcaatgtt gccgctgcct ccttgcagat atggccctca  17100
cttgtcgcct tcgcgttccc atcactggtt accgaggaag aaactcgcgc cgtagaagag  17160
ggatgttggg acgcggaatg cgacgctaca ggcgacggcg tgctatccgc aagcaattgc  17220
ggggtggttt tttaccagcc ttaattccaa ttatcgctgc tgcaattggc gcgataccag  17280
gcatagcttc cgtggcggtt caggcctcgc aacgacattg acattggaaa aaaacgtata  17340
aataaaaaaa aaaaaataca atggactctg acactcctgg tcctgtgact atgttttctt  17400
agagatggaa gacatcaatt tttcatcctt ggctccgcga cacggcacga agccgtacat  17460
gggcacctgg agcgacatcg gcacgagcca actgaacggg ggcgccttca attggagcag  17520
tatctggagc gggcttaaaa attttggctc aaccataaaa acatacggga acaaagcttg  17580
gaacagcagt acaggacagg cgcttagaaa taaacttaaa gaccagaact tccaacaaaa  17640
agtagtcgat gggatagctt ccggcatcaa tggagtggta gatttggcta accaggctgt  17700
gcagaaaaag ataaacagtc gtttggaccc gccgccagca accccaggtg aaatgcaagt  17760
ggaggaagaa attcctccgc cagaaaaacg aggcgacaag cgtccgcgtc ccgatttgga  17820
agagacgctg gtgacgcgcg tagatgaacc gccttcttat gaggaagcaa cgaagcttgg  17880
aatgcccacc actagaccga tagccccaat ggccaccggg gtgatgaaac cttctcagtt  17940
gcatcgaccc gtcaccttgg atttgccccc tccccctgct gctactgctg tacccgcttc  18000
taagcctgtc gctgccccga aaccagtcgc cgtagccagg tcacgtcccg gggcgctcc  18060
tcgtccaaat gcgcactggc aaaatactct gaacagcatc gtgggtctag gcgtgcaaag  18120
tgtaaaacgc cgtcgctgct tttaattaaa tatggagtag cgcttaactt gcctatctgt  18180
gtatatgtgt cattacacgc cgtcacagca gcagaggaaa aaaggaagag gtcgtgcgtc  18240
```

-continued

```
gacgctgagt tactttcaag atggccaccc catcgatgct gccccaatgg gcatacatgc  18300
acatcgccgg acaggatgct tcggagtacc tgagtccggg tctggtgcag ttcgcccgcg  18360
ccacagacac ctacttcaat ctgggaaata agtttagaaa tcccaccgta gcgccgaccc  18420
acgatgtgac caccgaccgt agccagcggc tcatgttgcg cttcgtgccc gttgaccggg  18480
aggacaatac atactcttac aaagtgcggt acaccctggc cgtgggcgac aacagagtgc  18540
tggatatggc cagcacgttc tttgacatta ggggtgtgtt ggacagaggt cccagtttca  18600
aaccctattc tggtacggct tacaactccc tggctcctaa aggcgctcca aatacatctc  18660
agtggattgc agaaggtgta aaaaatacaa ctggtgagga acacgtaaca gaagaggaaa  18720
ccaatactac tacttacact tttggcaatg ctcctgtaaa agctgaagct gaaattacaa  18780
aagaaggact cccagtaggt ttggaagttt cagatgaaga aagtaaaccg atttatgctg  18840
ataaaacata tcagccagaa cctcagctgg gagatgaaac ttggactgac cttgatggaa  18900
aaaccgaaaa gtatggaggc agggctctca aacccgatac taagatgaaa ccatgctacg  18960
ggtcctttgc caaacctact aatgtgaaag gcggtcaggc aaaacaaaaa acaacggagc  19020
agccaaatca gaaagtcgaa tatgatatcg acatggagtt ttttgatgcg gcatcgcaga  19080
aaacaaactt aagtcctaaa attgtcatgt atgcagaaaa tgtaaatttg gaaactccag  19140
acactcatgt agtgtacaaa cctggaacag aagacacaag ttccgaagct aatttgggac  19200
aacaatctat gcccaacaga cccaactaca ttggcttcag agataacttt attggactta  19260
tgtactataa cagtactggt aacatggggg tgctggctgg tcaagcgtct cagttaaatg  19320
cagtggttga cttgcaggac agaaacacag aactttctta ccaactcttg cttgactctc  19380
tgggcgacag aaccagatac tttagcatgt ggaatcaggc tgtggacagt tatgatcctg  19440
atgtacgtgt tattgaaaat catggtgtgg aagatgaact tcccaactac tgtttttccac  19500
tggacggcat aggtgttcca acaaccagtt acaaatcaat agttccaaat ggagacaatg  19560
cgcctaattg gaaggaacct gaagtaaatg gaacaagtga gatcggacag ggtaatttgt  19620
ttgccatgga aattaacctt caagccaatc tatggcgaag tttcctttat tccaatgtgg  19680
ctctatatct cccagactcg tacaaataca ccccgtccaa tgtcactctt ccagaaaaca  19740
aaaacaccta cgactacatg aacgggcggg tggtgccgcc atctctagta gacacctatg  19800
tgaacattgg tgccaggtgg tctctggatg ccatggacaa tgtcaaccca ttcaaccacc  19860
accgtaacgc tggcttgcgt taccgatcca tgcttctggg taacggacgt tatgtgcctt  19920
tccacataca agtgcctcaa aaattcttcg ctgttaaaaa cctgctgctt ctcccaggct  19980
cctacactta tgagtggaac tttaggaagg atgtgaacat ggttctacag agttccctcg  20040
gtaacgacct gcgggtagat ggcgccagca tcagtttcac gagcatcaac ctctatgcta  20100
ctttttttccc catggctcac aacaccgctt ccaccccttga agccatgctg cggaatgaca  20160
ccaatgatca gtcattcaac gactacctat ctgcagctaa catgctctac cccattcctg  20220
ccaatgcaac caatattccc atttccattc cttctcgcaa ctgggcggct ttcagaggct  20280
ggtcatttac cagactgaaa accaaagaaa ctccctcttt ggggtctgga tttgacccct  20340
actttgtcta ttctggttct attccctacc tggatggtac cttctacctg aaccacactt  20400
ttaagaaggt ttccatcatg tttgactctt cagtgagctg gcctggaaat gacaggttac  20460
tatctcctaa cgaatttgaa ataaagcgca ctgtggatgg cgaaggctac aacgtagccc  20520
aatgcaacat gaccaaagac tggttcttgg tacagatgct cgccaactac aacatcggct  20580
atcagggctt ctacattcca gaaggataca aagatcgcat gtattcattt ttcagaaact  20640
```

```
tccagcccat gagcaggcag gtggttgatg aggtcaatta caaagacttc aaggccgtcg  20700
ccatacccta ccaacacaac aactctggct ttgtgggtta catggctccg accatgcgcc  20760
aaggtcaacc ctatcccgct aactatccct atccactcat tggaacaact gccgtaaata  20820
gtgttacgca gaaaaagttc ttgtgtgaca gaaccatgtg gcgcataccg ttctcgagca  20880
acttcatgtc tatgggggcc cttacagact tgggacagaa tatgctctat gccaactcag  20940
ctcatgctct ggacatgacc tttgaggtgg atcccatgga tgagcccacc ctgctttatc  21000
ttctcttcga agttttcgac gtggtcagag tgcatcagcc acaccgcggc atcatcgagg  21060
cagtctacct gcgtacaccg ttctcggccg gtaacgctac cacgtaagaa gcttcttgct  21120
tcttgcaaat agcagctgca accatggcct gcggatccca aaacggctcc agcgagcaag  21180
agctcagagc cattgtccaa gacctgggtt gcggaccccta tttttggga acctacgata  21240
agcgcttccc ggggttcatg gcccccgata agctcgcctg tgccattgta aatacggccg  21300
gacgtgagac ggggggagag cactggttgg ctttcggttg gaacccacgt tctaacacct  21360
gctacctttt tgatcctttt ggattctcgg atgatcgtct caaacagatt taccagtttg  21420
aatatgaggg tctcctgcgc cgcagcgctc ttgctaccaa ggaccgctgt attacgctgg  21480
aaaaatctac ccagaccgtg cagggtcccc gttctgccgc ctgcggactt ttctgctgca  21540
tgttccttca cgcctttgtg cactggcctg accgtcccat ggacggaaac cccaccatga  21600
aattgctaac tggagtgcca aacaacatgc ttcattctcc taaagtccag cccaccctgt  21660
gtgacaatca aaaagcactc taccattttc ttaataccca ttcgccttat tttcgctccc  21720
atcgtacaca catcgaaagg gccactgcgt tcgaccgtat ggatgttcaa taatgactca  21780
tgtaaacaac gtgttcaata aacatcactt tattttttta catgtatcaa ggctctgcat  21840
tacttattta tttacaagtc gaatgggttc tgacgagaat cagaatgacc cgcaggcagt  21900
gatacgttgc ggaactgata cttgggttgc cacttgaatt cgggaatcac caacttggga  21960
accggtatat cgggcaggat gtcactccac agctttctgg tcagctgcaa agctccaagc  22020
aggtcaggag ccgaaatctt gaaatcacaa ttaggaccag tgctttgagc gcgagagttg  22080
cggtacaccg gattgcagca ctgaaacacc atcagcgacg gatgtctcac gcttgccagc  22140
acggtgggat ctgcaatcat gcccacatcc agatcttcag cattggcaat gctgaacggg  22200
gtcatcttgc aggtctgcct acccatggcg ggcacccaat taggcttgtg gttgcaatcg  22260
cagtgcaggg ggatcagtat catcttggcc tgatcctgtc tgattcctgg atacacggct  22320
ctcatgaaag catcatattg cttgaaagcc tgctgggctt tactaccctc ggtataaaac  22380
atcccgcagg acctgctcga aaactggtta gctgcacagc cggcatcatt cacacagcag  22440
cgggcgtcat tgttagctat ttgcaccaca cttctgcccc agcggttttg ggtgattttg  22500
gttcgctcgg gattctcctt taaggctcgt tgtccgttct cgctggccac atccatctcg  22560
ataatctgct ccttctgaat cataatattg ccatgcaggc acttcagctt gccctcataa  22620
tcattgcagc catgaggcca caacgcacag cctgtacatt cccaattatg gtgggcgatc  22680
tgagaaaaag aatgtatcat tccctgcaga aatcttccca tcatcgtgct cagtgtcttg  22740
tgactagtga aagttaactg gatgcctcgg tgctcctcgt ttacgtactg gtgacagatg  22800
cgcttgtatt gttcgtgttg ctcaggcatt agtttaaaag aggttctaag ttcgttatcc  22860
agcctgtact tctccatcag cagacacatc acttccatgc ctttctccca agcagacacc  22920
aggggcaagc taatcggatt cttaacagtg caggcagcag ctcctttagc cagagggtca  22980
```

-continued

```
tctttagcga tcttctcaat gcttcttttg ccatccttct caacgatgcg cacgggcggg  23040
tagctgaaac ccactgctac aagttgcgcc tcttctcttt cttcttcgct gtcttgactg  23100
atgtcttgca tggggatatg tttggtcttc cttggcttct ttttgggggg tatcggagga  23160
ggaggactgt cgctccgttc cggagacagg gaggattgtg acgtttcgct caccattacc  23220
aactgactgt cggtagaaga acctgacccc acacggcgac aggtgtttct cttcgggggc  23280
agaggtggag gcgattgcga agggctgcgg tccgacctgg aaggcggatg actggcagaa  23340
ccccttccgc gttcgggggt gtgctccctg tggcggtcgc ttaactgatt tccttcgcgg  23400
ctggccattg tgttctccta ggcagagaaa caacagacat ggaaactcag ccattgctgt  23460
caacatcgcc acgagtgcca tcacatctcg tcctcagcga cgaggaaaag gagcagagct  23520
taagcattcc accgcccagt cctgccacca cctctaccct agaagataag gaggtcgacg  23580
catctcatga catgcagaat aaaaaagcga aagagtctga gacagacatc gagcaagacc  23640
cgggctatgt gacaccggtg gaacacgagg aagagttgaa acgctttcta gagagagagg  23700
atgaaaactg cccaaaacaa cgagcagata actatcacca agatgctgga aatagggatc  23760
agaacaccga ctacctcata gggcttgacg gggaagacgc gctccttaaa catctagcaa  23820
gacagtcgct catagtcaag gatgcattat tggacagaac tgaagtgccc atcagtgtgg  23880
aagagctcag ccgcgcctac gagcttaacc tcttttcacc tcgtactccc cccaaacgtc  23940
agccaaacgg cacctgcgag ccaaatcctc gcttaaactt ttatccagct tttgctgtgc  24000
cagaagtact ggctacctat cacatctttt ttaaaaatca aaaaattcca gtctcctgcc  24060
gcgctaatcg cacccgcgcc gatgccctac tcaatctggg acctggttca cgcttacctg  24120
atatagcttc cttggaagag gttccaaaga tcttcgaggg tctgggcaat aatgagactc  24180
gggccgcaaa tgctctgcaa aagggagaaa atggcatgga tgagcatcac agcgttctgg  24240
tggaattgga aggcgataat gccagactcg cagtactcaa gcgaagcatc gaggtcacac  24300
acttcgcata tcccgctgtc aacctgcccc ctaaagtcat gacggcggtc atggaccagt  24360
tactcattaa gcgcgcaagt ccccctttcag aagacatgca tgacccagat gcctgtgatg  24420
agggtaaacc agtggtcagt gatgagcagc taacccgatg gctgggcacc gactctccca  24480
gggatttgga agagcgtcgc aagcttatga tggccgtggt gctggttacc gtagaactag  24540
agtgtctccg acgtttcttt accgattcag aaaccttgcg caaactcgaa gagaatctgc  24600
actacacttt tagacacggc tttgtgcggc aggcatgcaa gatatctaac gtggaactca  24660
ccaacctggt ttcctacatg ggtattctgc atgagaatcg cctaggacaa agcgtgctgc  24720
acagcaccct gaagggggaa gcccgccgtg attacatccg cgattgtgtc tatctgtacc  24780
tgtgccacac gtggcaaacc ggcatgggtg tatggcagca atgtttagaa gaacagaact  24840
tgaaagagct tgacaagctc ttacagaaat ctcttaaggt tctgtggaca gggttcgacg  24900
agcgcaccgt cgcttccgac ctggcagacc tcatcttccc agagcgtctc agggttactt  24960
tgcgaaacgg attgcctgac tttatgagcc agagcatgct taacaatttt cgctctttca  25020
tcctggaacg ctccggtatc ctgcccgcca cctgctgcgc actgccctcc gactttgtgc  25080
ctctcaccta ccgcgagtgc ccccgccgc tatggagtca ctgctacctg ttccgtctgg  25140
ccaactatct ctcctaccac tcggatgtga tcgaggatgt gagcggagac ggcttgctgg  25200
agtgtcactg ccgctgcaat ctgtgcacgc cccaccggtc cctagcttgc aacccccagt  25260
tgatgagcga aacccagata ataggcacct ttgaattgca aggccccagc agccaaggcg  25320
atgggtcttc tcctgggcaa agtttaaaac tgaccccggg actgtggacc tccgcctact  25380
```

```
tgcgcaagtt tgctccggaa gattaccacc cctatgaaat caagttctat gaggaccaat  25440
cacagcctcc aaaggccgaa ctttcggcct gcgtcatcac ccaggggca attctggccc  25500
aattgcaagc catccaaaaa tcccgccaag aatttctact gaaaaagggt aaggggggtct  25560
accttgaccc ccagaccggc gaggaactca acacaaggtt ccctcaggat gtcccaacga  25620
cgagaaaaca agaagttgaa ggtgcagccg ccgcccccag aagatatgga ggaagattgg  25680
gacagtcagg cagaggaggc ggaggaggac agtctggagg acagtctgga ggaagacagt  25740
ttggaggagg aaaacgagga ggcagaggag gtggaagaag taaccgccga caaacagtta  25800
tcctcggctg cggagacaag caacagcgct accatctccg ctccgagtcg aggaacccgg  25860
cggcgtccca gcagtagatg ggacgagacc ggacgcttcc cgaacccaac cagcgcttcc  25920
aagaccggta agaaggatcg gcagggatac aagtcctggc gggggcataa gaatgccatc  25980
atctcctgct tgcatgagtg cgggggcaac atatccttca cgcggcgcta cttgctattc  26040
caccatgggg tgaactttcc gcgcaatgtt ttgcattact accgtcacct ccacagcccc  26100
tactatagcc agcaaatccc ggcagtctcg acagataaag acagcggcgg cgacctccaa  26160
cagaaaacca gcagcggcag ttagaaaata cacaacaagt gcagcaacag gaggattaaa  26220
gattacagcc aacgagccag cgcaaacccg agagttaaga aatcggatct ttccaaccct  26280
gtatgccatc ttccagcaga gtcggggtca agagcaggaa ctgaaaataa aaaaccgatc  26340
tctgcgttcg ctcaccagaa gttgtttgta tcacaagagc gaagatcaac ttcagcgcac  26400
tctcgaggac gccgaggctc tcttcaacaa gtactgcgcg ctgactctta aagagtaggc  26460
agcgaccgcg cttattcaaa aaaggcggga attacatcat cctcgacatg agtaaagaaa  26520
ttcccacgcc ttacatgtgg agttatcaac cccaaatggg attggcggca ggcgcctccc  26580
aggactactc cacccgcatg aattggctca gcgccgggcc ttctatgatt tctcgagtta  26640
atgatatacg cgcctaccga aaccaaatac ttttggaaca gtcagctctt accaccacgc  26700
cccgccaaca ccttaatccc agaaattggc ccgccgccct agtgtaccag gaaagtcccg  26760
ctcccaccac tgtattactt cctcgagacg cccaggccga agtccaaatg actaatgcag  26820
gtgcgcagtt agctggcggc tccaccctat gtcgtcacag gcctcggcat aatataaaac  26880
gcctgatgat cagaggccga ggtatccagc tcaacgacga gtcggtgagc tctccgcttg  26940
gtctacgacc agacggaatc tttcagattg ccggctgcgg gagatcttcc ttcacccctc  27000
gtcaggctgt tctgactttg gaaagttcgt cttcgcaacc ccgctcgggc ggaatcggga  27060
ccgttcaatt tgtggaggag tttactccct ctgtctactt caacccctc tccggatctc  27120
ctgggcatta cccggacgag ttcataccga acttcgacgc gattagcgag tcagtggacg  27180
gctacgattg atgtctggtg acgcggctga gctatctcgg ctgcgacatc tagaccactg  27240
ccgccgcttt cgctgctttg cccgggaact cattgagttc atctacttcg aactccccaa  27300
ggatcaccct caaggtccgg cccacggagt gcggatttct atcgaaggca aaatagactc  27360
tcgcctgcaa cgaattttct cccagcggcc cgtgctgatc gagcgagacc agggaaacac  27420
cacggtttcc atctactgca tttgtaatca ccccggattg catgaaagcc tttgctgtct  27480
tatgtgtact gagtttaata aaaactgaat taagactctc ctacggactg ccgcttcttc  27540
aacccggatt ttacaaccag aagaacgaaa cttttcctgt cgtccaggac tctgttaact  27600
tcacctttcc tactcacaaa ctagaagctc aacgactaca ccgcttttcc agaagcattt  27660
tccctactaa tactactttc aaaaccggag gtgagctcca aggtcttcct acagaaaacc  27720
```

-continued

```
cttgggtgga agcgggcctt gtagtgctag gaattcttgc gggtgggctt gtgattattc  27780
tttgctacct atacacacct tgcttcactt tcttagtggt gttgtggtat tggtttaaaa  27840
aatggggccc atactagtct tgcttgtttt actttcgctt ttggaaccgg gttctgccaa  27900
ttacgatcca tgtctagact tcgacccaga aaactgcaca cttacttttg cacccgacac  27960
aagccgcatc tgtggagttc atcgcctctc ttacgaactt ggcccccaac gacaaaaatt  28020
tacctgcatg gtgggaatca accccatagt tatcacccag caaagtggag atactaaggg  28080
ttgcattcac tgctcctgcg attccatcga gtgcacctac accctgctga agaccctatg  28140
cggcctaaga gacctgctac caatgaatta aaaaatgatt aataaaaaat cacttacttg  28200
aaatcagcaa taaggtctct gttgaaattt tctcccagca gcacctcact tccctcttcc  28260
caactctggt attctaaacc ccgttcagcg gcatactttc tccatacttt aaaggggatg  28320
tcaaatttta gctcctctcc tgtacccaca atcttcatgt ctttcttccc agatgaccaa  28380
gagagtccgg ctcagtgact ccttcaaccc tgtctacccc tatgaagatg aaagcacctc  28440
ccaacacccc tttataaacc cagggtttat ttccccaaat ggcttcacac aaagcccaaa  28500
cggagttctt actttaaaat gtttaacccc actaacaacc acaggcggat ctctacagct  28560
aaaagtggga gggggactta cagtggatga caccaacggt tttttgaaag aaaacataag  28620
tgccaccaca ccactcgtta agactggtca ctctataggt ttaccactag gagccggatt  28680
gggaacgaat gaaaataaac tttgtatcaa attaggacaa ggacttacat tcaattcaaa  28740
caacatttgc attgatgaca atattaacac cttatggaca ggagtcaacc ccaccgaagc  28800
caactgtcaa atcatgaact ccagtgaatc taatgattgc aaattaattc taacactagt  28860
taaaactgga gcactagtca ctgcatttgt ttatgttata ggagtatcta acaattttaa  28920
tatgctaact acacacagaa atataaattt tactgcagag ctgtttttcg attctactgg  28980
taatttacta actagactct catccctcaa aactccactt aatcataaat caggacaaaa  29040
catggctact ggtgccatta ctaatgctaa aggtttcatg cccagcacga ctgcctatcc  29100
tttcaatgat aattctagag aaaaagaaaa ctacatttac ggaacttgtt actacacagc  29160
tagtgatcgc actgcttttc ccattgacat atctgtcatg cttaaccgaa gagcaataaa  29220
tgacgagaca tcatattgta ttcgtataac ttggtcctgg aacacaggag atgccccaga  29280
ggtgcaaacc tctgctacaa ccctagtcac ctccccattt accttttact acatcagaga  29340
agacgactga caaataaagt ttgcgatcgc taccctgcag gaacttgttt atttgaaaat  29400
caattcacaa aatccgagta gttattttgc ctccccccttc ccatttaaca gaatacacca  29460
atctctcccc acgcacagct ttaaacattt ggataccatt agatatagac atggttttag  29520
attccacatt ccaaacagtt tcagagcgag ccaatctggg gtcagtgata gataaaaatc  29580
catcgggata gtcttttaaa gcgctttcac agtccaactg ctgcggatgc gactccggag  29640
tctggatcac ggtcatctgg aagaagaacg atgggaatca taatccgaaa acggtatcgg  29700
acgattgtgt ctcatcaaac ccacaagcag ccgctgtctg cgtcgctccg tgcgactgct  29760
gtttatggga tcagggtcca cagtgtcctg aagcatgatt ttaatagccc ttaacatcaa  29820
ctttctggtg cgatgcgcgc agcaacgcat tctgatttca ctcaaatctt tgcagtaggt  29880
acaacacatt attacaatat tgtttaataa accataatta aaagcgctcc agccaaaact  29940
catatctgat ataatcgccc ctgcatgacc atcataccaa agtttaatat aaattaaatg  30000
acgttccctc aaaaacacac tacccacata catgatctct tttggcatgt gcatattaac  30060
aatctgtctg taccatggac aacgttggtt aatcatgcaa cccaatataa ccttccggaa  30120
```

```
ccacactgcc aacaccgctc ccccagccat gcattgaagt gaaccctgct gattacaatg  30180
acaatgaaga acccaattct ctcgaccgtg aatcacttga gaatgaaaaa tatctatagt  30240
ggcacaacat agacataaat gcatgcatct tctcataatt tttaactcct caggatttag  30300
aaacatatcc cagggaatag gaagctcttg cagaacagta aagctggcag aacaaggaag  30360
accacgaaca caacttacac tatgcatagt catagtatca caatctggca acagcgggtg  30420
gtcttcagtc atagaagctc gggtttcatt ttcctcacaa cgtggtaact gggctctggt  30480
gtaagggtga tgtctggcgc atgatgtcga gcgtgcgcgc aaccttgtca taatggagtt  30540
gcttcctgac attctcgtat tttgtatagc aaaacgcggc cctggcagaa cacactcttc  30600
ttcgccttct atcctgccgc ttagcgtgtt ccgtgtgata gttcaagtac aaccacactc  30660
ttaagttggt caaaagaatg ctggcttcag ttgtaatcaa aactccatcg catctaatcg  30720
ttctgaggaa atcatccaag caatgcaact ggattgtgtt tcaagcagga gaggagaggg  30780
aagagacgga agaaccatgt taattttat tccaaacgat ctcgcagtac ttcaaattgt  30840
agatcgcgca gatggcatct ctcgccccca ctgtgttggt gaaaaagcac agctagatca  30900
aaagaaatgc gattttcaag gtgctcaacg gtggcttcca gcaaagcctc cacgcgcaca  30960
tccaagaaca aaagaatacc aaaagaagga gcattttcta actcctcaat catcatatta  31020
cattcctgca ccattcccag ataattttca gctttccagc cttgaattat tcgtgtcagt  31080
tcttgtggta aatccaatcc acacattaca aacaggtccc ggagggcgcc ctccaccacc  31140
attcttaaac acaccctcat aatgacaaaa tatcttgctc ctgtgtcacc tgtagcgaat  31200
tgagaatggc aacatcaatt gacatgccct tggctctaag ttcttcttta agttctagtt  31260
gtaaaaactc tctcatatta tcaccaaact gcttagccag aagccccccg ggaacaagag  31320
caggggacgc tacagtgcag tacaagcgca gacctcccca attggctcca gcaaaaacaa  31380
gattggaata agcatattgg gaaccgccag taatatcatc gaagttgctg gaaatataat  31440
caggcagagt ttcttgtaaa aattgaataa aagaaaaatt tgccaaaaaa acattcaaaa  31500
cctctgggat gcaaatgcaa taggttaccg cgctgcgctc caacattgtt agttttgaat  31560
tagtctgcaa aaataaaaaa aaaaacaagc gtcatatcat agtagcctga cgaacagatg  31620
gataaatcag tctttccatc acaagacaag ccacagggtc tccagctcga ccctcgtaaa  31680
acctgtcatc atgattaaac aacagcaccg aaagttcctc gcggtgacca gcatgaataa  31740
ttcttgatga agcatacaat ccagacatgt tagcatcagt taacgagaaa aaacagccaa  31800
catagccttt gggtataatt atgcttaatc gtaagtatag caaagccacc cctcgcggat  31860
acaaagtaaa aggcacagga gaataaaaaa tataattatt tctctgctgc tgttcaggca  31920
acgtcgcccc cggtccctct aaatacacat acaaagcctc atcagccatg gcttaccaga  31980
caaagtacag cgggcacaca aagcacaagc tctaaagtga ctctccaacc tctccacaat  32040
atatatatac acaagcccta aactgacgta atgggagtaa agtgtaaaaa atcccgccaa  32100
acccaacaca caccccgaaa ctgcgtcacc agggaaaagt acagtttcac ttccgcaatc  32160
ccaacaggcg taacttcctc tttctcacgg tacgtgatat cccactaact tgcaacgtca  32220
ttttcccacg gtcgcaccgc cccttttagc cgttaacccc acagccaatc accacacgat  32280
ccacactttt taaaatcacc tcatttacat attggcacca ttccatctat aaggtatatt  32340
atatagatag gcgcgccctc tcttaaggta gcatcgggat cgagtccctg agagaacatc  32400
ctcaatcccg atctatcctt agatccgagg aatatcgaaa tcagttacgc tagggataac  32460
```

-continued agggtaatat agcatcccct cggattgcta tctaccggct cgtcagctat gatctctcga 32520
tttcgatcaa gaaatctcat tggttacctt gggctatcga aaccagtcaa gtcagctact 32580
tggcgagatc gacttgtctg agtttcgact acgctcagaa ttgcgtcagc gcctatcgcc 32640
aggtattact ccaatcccga atatccgagc ctgagagaac atcctcaatc ccgatctatc 32700
cttagatccg aggaatatcg aaatcgttta aatcttttct tgatggtaaa tcattcgaat 32760
ataagaatgg agagacgaat ggggaaacga caaagatgac attctttggt ccttctggtg 32820
aggttctcaa gtttttggtt aatcctgtca acaacttata tcgtatgggg ctgacttcag 32880
gtgctacatt tgaagagata aattgcactg aaatctagta atattttatc tgattaataa 32940
gatgatcttc ttgagatcgt tttggtctgc gcgtaatctc ttgctctgaa aacgaaaaaa 33000
ccgccttgca gggcggtttt tcgaaggttc tctgagctac caactctttg aaccgaggta 33060
actggcttgg cagagcgcag tcaccaaaac ttgtcctttc agtttagcct taaccggcgc 33120
atgacttcaa gactaactct gctaaatcaa ttaccagtgg ctgctgccag tggtgctttt 33180
gcatgtcttt ccgggttgga ctcaagacga tagttaccgg ataaggcgca gcggtcggac 33240
tgaacggggg gttcgtgcat acagtccagc ttggagcgaa ctgcctaccc ggaactgagt 33300
gtcaggcgtg gaatgagaca aacgcggcca taacagcgga atgacaccgg taaaccgaaa 33360
ggcaggaaca ggagagcgca cgagggagcc gccagggggga aacgcctggt atctttatag 33420
tcctgtcggg tttcgccacc actgatttga gcgtcagatt tcgtgatgct tgtcaggggg 33480
gcggagccta tggaaaaacg gctttgccgc ggccctctca cttccctgtt aagtatcttc 33540
ctggcatctt ccaggaaatc tccgccccgt tcgtaagcca tttccgctcg ccgcagtcga 33600
acgaccgagc gtagcgagtc agtgagcgag gaagcggaat atatcctgta tcacatattc 33660
tgctgacgca ccggtgcggc ctttttttctc ctgccacatg aagcacttca ctgacaccct 33720
catcagtgcc aacatagtaa gccagtatac actccgctaa tttaaacgtg gtgtaccgag 33780
aacgatcctc tcagtgcgat ctcgacgatc agtggtattc cgacatatcg ttgcttggca 33840
gtcagccagt cgatcctagc ttgggaccca ggaagtccaa tcgtcagata ttgtactcag 33900
cctggtcacg gcagcgtacc gatctcgtaa ctataacggt cctaaggtag cgaactagat 33960
attgatagtc tgatcggtca acgtataatc gagtcctagc ttttgcaaac atctatcaag 34020
agacaggatc agcaggaggc tttcgcatga ttgaacaaga tggattgcac gcaggttctc 34080
cggcggcttg ggtggagagg ctattcggct atgactgggc acaacagaca atcggctgct 34140
ctgatgccgc cgtgttccgg ctgtcagcgc aggggcgtcc ggttcttttt gtcaagaccg 34200
acctgtccgg tgccctgaat gaactgcaag acgaggcagc gcggctatcg tggctggcga 34260
cgacgggcgt tccttgcgcg gctgtgctcg acgttgtcac tgaagcggga agggactggc 34320
tgctattggg cgaagtgccg gggcaggatc tcctgtcatc tcaccttgct cctgccgaga 34380
aagtatccat catggctgat gcaatgcggc ggctgcatac gcttgatccg gctacctgcc 34440
cattcgacca ccaagcgaaa catcgcatcg agcgagcacg tactcggatg gaagccggtc 34500
ttgtcgatca ggatgatctg gacgaagagc atcaggggct cgcgccagcc gaactgttcg 34560
ccaggctcaa ggcgtctatg cccgacggcg aggatctcgt cgtgacccac ggcgatgcct 34620
gcttgccgaa tatcatggtg gaaaatggcc gcttttctgg attcatcgac tgtggccgtc 34680
tgggtgtggc ggaccgctat caggacatag cgttggctac ccgtgatatt gctgaagagc 34740
ttggcggcga atgggctgac cgcttccttg tgctttacgg tatcgccgcg cccgattcgc 34800
agcgcatcgc cttctatcgc cttcttgacg agttcttctg accgattcta ggtgcattgg 34860
cgcagaaaaa aatgcctgat gcgacgctgc gcgtcttata ctcccacata tgccagattc 34920
agcaacggat acggcttccc caacttgccc acttccatac gtgtcctcct taccagaaat 34980
ttatccttaa ggtccgtaac tataacggtc ctaaggtagc gaatcgacct agctctatcg 35040
aatctccctc gtttcgagct tacgcgaact agcctctggc gatagcatcc gaggggcagg 35100
catctatgtc gggtgcggag aaagaggtaa tgtcaagttc gatctgattg cttggcataa 35160
agtccgatgg ttcgagtaga ctcagttcaa cctctctctt aaggtagc 35208

<210> SEQ ID NO 29
<211> LENGTH: 19
<212> TYPE: DNA
<213> ORGANISM: Artificial Sequence
<220> FEATURE:
<223> OTHER INFORMATION: 19bp insert ColoAd2.4

<400> SEQUENCE: 29
gcgatcgcta ccctgcagg 19

<210> SEQ ID NO 30
<211> LENGTH: 35316
<212> TYPE: DNA
<213> ORGANISM: Artificial Sequence
<220> FEATURE:
<223> OTHER INFORMATION: ColoAd2.0 Plasmid

<400> SEQUENCE: 30
ggcgcgccta tctatataat ataccttata gatggaatgg tgccaatatg taaatgaggt 60
gattttaaaa agtgtggatc gtgtggtgat tggctgtggg gttaacggct aaaaggggcg 120
gtgcgaccgt gggaaaatga cgttttgtgg gggtggagtt tttttgcaag ttgtcgcggg 180
aaatgtgacg cataaaaagg ctttttttctc acggaactac ttagttttcc cacggtattt 240
aacaggaaat gaggtagttt tgaccggatg caagtgaaaa ttgttgattt tcgcgcgaaa 300
actgaatgag gaagtgtttt tctgaataat gtggtattta tggcagggtg gagtatttgt 360
tcagggccag gtagactttg acccattacg tggaggtttc gattaccgtg tttttttacct 420 gaatttccgc gtaccgtgtc aaagtcttct gtttttacgt aggtgtcagc tgatcgctag 480
ggtatttata cctcagggtt tgtgtcaaga ggccactctt gagtgccagc gagaagagtt 540
ttctcctctg cgccggcagt ttaataataa aaaaatgaga gatttgcgat ttctgcctca 600
ggaaataatc tctgctgaga ctggaaatga aatattggag cttgtggtgc acgccctgat 660
gggagacgat ccggagccac ctgtgcagct ttttgagcct cctacgcttc aggaactgta 720
tgatttagag gtagagggat cggaggattc taatgaggaa gctgtaaatg gcttttttac 780
cgattctatg cttttagctg ctaatgaagg gttagaatta gatccgcctt tggacacttt 840
tgatactcca ggggtaattg tggaaagcgg tacaggtgta agaaaattac ctgatttgag 900
ttccgtggac tgtgatttgc actgctatga agacgggttt cctccgagtg atgaggagga 960
ccatgaaaag gagcagtcca tgcagactgc agcgggtgag ggagtgaagg ctgccaatgt 1020
tggttttcag ttggattgcc cggagcttcc tggacatggc tgtaagtctt gtgaatttca 1080
caggaaaaat actggagtaa aggaactgtt atgttcgctt tgttatatga gaacgcactg 1140
ccactttatt tacagtaagt gtgtttaagt taaaatttaa aggaatatgc tgtttttcac 1200
atgtatattg agtgtgagtt ttgtgcttct tattataggt cctgtgtctg atgctgatga 1260
atcaccatct cctgattcta ctacctcacc tcctgagatt caagcacctg ttcctgtgga 1320

-continued

```
cgtgcgcaag cccattcctg tgaagcttaa gcctgggaaa cgtccagcag tggaaaaact   1380
tgaggacttg ttacagggtg gggacggacc tttggacttg agtacacgga aacgtccaag   1440
acaataagtg ttccatatcc gtgtttactt aaggtgacgt caatatttgt gtgacagtgc   1500
aatgtaataa aaatatgtta actgttcact ggtttttatt gctttttggg cggggactca   1560
ggtatataag tagaagcaga cctgtgtggt tagctcatag gagctggctt tcatccatgg   1620
aggtttgggc cattttggaa gaccttagga agactaggca actgttagag aacgcttcgg   1680
acggagtctc cggtttttgg agattctggt tcgctagtga attagctagg gtagttttta   1740
ggataaaaca ggactataaa caagaatttg aaaagttgtt ggtagattgc ccaggacttt   1800
ttgaagctct taatttgggc catcaggttc actttaaaga aaaagtttta tcagttttag   1860
acttttcaac cccaggtaga actgctgctg ctgtggcttt tcttactttt atattagata   1920
aatggatccc gcagactcat ttcagcaggg gatacgtttt ggatttcata gccacagcat   1980
tgtggagaac atggaaggtt cgcaagatga ggacaatctt aggttactgg ccagtgcagc   2040
ctttgggtgt agcgggaatc ctgaggcatc caccggtcat gccagcggtt ctggaggagg   2100
aacagcaaga ggacaacccg agagccggcc tggaccctcc agtggaggag gcggagtagc   2160
tgacttgtct cctgaactgc aacgggtgct tactggatct acgtccactg gacgggatag   2220
gggcgttaag agggagaggg catctagtgg tactgatgct agatctgagt tggctttaag   2280
tttaatgagt cgcagacgtc ctgaaaccat ttggtggcat gaggttcaga aagagggaag   2340
ggatgaagtt tctgtattgc aggagaaata ttcactggaa caggtgaaaa catgttggtt   2400
ggagcctgag gatgattggg aggtggccat taaaaattat gccaagatag ctttgaggcc   2460
tgataaacag tataagatta ctagacggat taatatccgg aatgcttgtt acatatctgg   2520
aaatggggct gaggtggtaa tagatactca agacaaggca gttattagat gctgcatgat   2580
ggatatgtgg cctggggtag tcggtatgga agcagtaact tttgtaaatg ttaagtttag   2640
gggagatggt tataatggaa tagtgtttat ggccaatacc aaacttatat tgcatggttg   2700
tagctttttt ggtttcaaca atacctgtgt agatgcctgg ggacaggtta gtgtacgggg   2760
atgtagtttc tatgcgtgtt ggattgccac agctggcaga accaagagtc aattgtctct   2820
gaagaaatgc atatttcaaa gatgtaacct gggcattctg aatgaaggcg aagcaagggt   2880
ccgccactgc gcttctacag atactggatg ttttattttg attaagggaa atgccagcgt   2940
aaagcataac atgatttgcg gtgcttccga tgagaggcct tatcaaatgc tcacttgtgc   3000
tggtgggcat tgtaatatgc tggctactgt gcatattgtt tcccatcaac gcaaaaaatg   3060
gcctgttttt gatcacaatg tgatgacgaa gtgtaccatg catgcaggtg ggcgtagagg   3120
aatgtttatg ccttaccagt gtaacatgaa tcatgtgaaa gtgttgttgg aaccagatgc   3180
cttttccaga atgagcctaa caggaatttt tgacatgaac atgcaaatct ggaagatcct   3240
gaggtatgat gatacgagat cgagggtacg cgcatgcgaa tgcggaggca agcatgccag   3300
gttccagccg gtgtgtgtag atgtgactga agatctcaga ccggatcatt tggttattgc   3360
ccgcactgga gcagagttcg gatccagtgg agaagaaact gactaaggtg agtattggga   3420
aaactttggg gtgggatttt cagatggaca gattgagtaa aaatttgttt tttctgtctt   3480
gcagctgtca tgagtggaaa cgcttctttt aagggggggag tcttcagccc ttatctgaca   3540
gggcgtctcc catcctgggc aggagttcgt cagaatgtta tgggatctac tgtggatgga   3600
agacccgtcc aacccgccaa ttcttcaacg ctgacctatg ctactttaag ttcttcacct   3660
ttggacgcag ctgcagctgc cgccgccgct tctgttgccg ctaacactgt gcttggaatg   3720
```

```
ggttactatg gaagcatcat ggctaattcc acttcctcta ataacccttc taccctgact   3780
caggacaagt tacttgtcct tttggcccag ctggaggctt tgacccaacg tctgggtgaa   3840
ctttctcagc aggtggtcga gttgcgagta caaactgagt ctgctgtcgg cacggcaaag   3900
tctaaataaa aaaatcccag aatcaatgaa taaataaaca agcttgttgt tgatttaaaa   3960
tcaagtgttt ttatttcatt tttcgcgcac ggtatgccct agaccaccga tctctatcat   4020
tgagaactcg gtggattttt tccaggatcc tatagaggtg ggattgaatg tttagataca   4080
tgggcattag gccgtctttg ggtggagat agctccattg aagggattca tgctccgggg   4140
tagtgttgta aatcacccag tcataacaag gtcgcagtgc atggtgttgc acaatatctt   4200
ttagaagtag gctgattgcc acagataagc ccttggtgta ggtgtttaca aaccggttga   4260
gctgggatgg gtgcattcgg ggtgaaatta tgtgcatttt ggattggatt tttaagttgg   4320
caatattgcc gccaagatcc cgtcttgggt tcatgttatg aaggaccacc aagacggtgt   4380
atccggtaca tttaggaaat ttatcgtgca gcttggatgg aaaagcgtgg aaaaatttgg   4440
agacaccctt gtgtcctcca agattttcca tgcactcatc catgataata gcaatggggc   4500
cgtgggcagc ggcgcgggca aacacgttcc gtgggtctga cacatcatag ttatgttcct   4560
gagttaaatc atcataagcc attttaatga atttggggcg gagagtacca gattggggta   4620
tgaatgttcc ttcgggcccc ggagcatagt tcccctcaca gatttgcatt tcccaagctt   4680
tcagttccga gggtggaatc atgtccacct ggggggctat gaaaaacacc gtttctgggg   4740
cgggggtgat taattgtgat gatagcaaat ttctgagcaa ttgagatttg ccacatccgg   4800
tggggccata aatgattccg attacgggtt gcaggtggta gtttagggaa cggcaactgc   4860
cgtcttctcg aagcaagggg gccacctcgt tcatcatttc ccttacatgc atattttccc   4920
gcaccaaatc cattaggagg cgctctcctc ctagtgatag aagttcttgt agtgaggaaa   4980
agtttttcag cggtttcaga ccgtcagcca tgggcatttt ggagagagtt tgctgcaaaa   5040
gttctagtct gttccacagt tcagtgatgt gttctatggc atctcgatcc agcagacctc   5100
ctcgtttcgc gggtttggac ggctcctgga atagggtatg agacgatggg cgtccagcgc   5160
tgccagggtt cggtccttcc agggtctcag tgttcgagtc agggttgttt ccgtcacagt   5220
gaaggggtgt gcgcctgctt gggcgcttgc cagggtgcgc ttcagactca tcctgctggt   5280
cgaaaacttc tgtcgcttgg cgccctgtat gtcggccaag tagcagttta ccatgagttc   5340
gtagttgagc gcctcggctg cgtggccttt ggcgcggagc ttacctttgg aagttttctt   5400
gcataccggg cagtataggc atttcagcgc atacaacttg ggcgcaagga aaacggattc   5460
tggggagtat gcatctgcgc cgcaggaggc gcaaacagtt tcacattcca ccagccaggt   5520
taaatccggt tcattggggt caaaaacaag ttttccgcca tatttttga tgcgtttctt   5580
acctttggtc tccatgagtt cgtgtcctcg ttgagtgaca aacaggctgt ccgtgtcccc   5640
gtagactgat tttacaggcc tcttctccag tggagtgcct cggtcttctt cgtacaggaa   5700
ctctgaccac tctgatacaa aggcgcgcgt ccaggccagc acaaaggagg ctatgtggga   5760
ggggtagcga tcgttgtcaa ccagggggtc caccttttcc aaagtatgca aacacatgtc   5820
accctcttca acatccagga atgtgattgg cttgtaggtg tatttcacgt gacctggggt   5880
ccccgctggg ggggtataaa agggggcggt tctttgctct tcctcactgt cttccggatc   5940
gctgtccagg aacgtcagct gttggggtag gtattccctc tcgaaggcgg gcatgacctc   6000
tgcactcagg ttgtcagttt ctaagaacga ggaggatttg atattgacag tgccggttga   6060
```

-continued

```
gatgcctttc atgaggtttt cgtccatctg gtcagaaaac acaatttttt tattgtcaag   6120
tttggtggca aatgatccat acagggcgtt ggataaaagt ttggcaatgg atcgcatggt   6180
ttggttcttt tccttgtccg cgcgctcttt ggcggcgatg ttgagttgga catactcgcg   6240
tgccaggcac ttccattcgg ggaagatagt tgttaattca tctggcacga ttctcacttg   6300
ccaccctcga ttatgcaagg taattaaatc cacactggtg gccacctcgc ctcgaagggg   6360
ttcattggtc caacagagcc tacctccttt cctagaacag aaagggggaa gtgggtctag   6420
cataagttca tcgggagggt ctgcatccat ggtaaagatt cccggaagta aatccttatc   6480
aaaatagctg atgggagtgg ggtcatctaa ggccatttgc cattctcgag ctgccagtgc   6540
gcgctcatat gggttaaggg gactgcccca tggcatggga tgggtgagtg cagaggcata   6600
catgccacag atgtcataga cgtagatggg atcctcaaag atgcctatgt aggttggata   6660
gcatcgcccc cctctgatac ttgctcgcac atagtcatat agttcatgtg atggcgctag   6720
cagccccgga cccaagttgg tgcgattggg tttttctgtt ctgtagacga tctggcgaaa   6780
gatggcgtga gaattggaag agatggtggg tctttgaaaa atgttgaaat gggcatgagg   6840
tagacctaca gagtctctga caaagtgggc ataagattct tgaagcttgg ttaccagttc   6900
ggcggtgaca agtacgtcta gggcgcagta gtcaagtgtt tcttgaatga tgtcataacc   6960
tggttggttt ttcttttccc acagttcgcg gttgagaagg tattcttcgc gatccttcca   7020
gtactcttct agcggaaacc cgtctttgtc tgcacggtaa gatcctagca tgtagaactg   7080
attaactgcc ttgtaagggc agcagccctt ctctacgggt agagagtatg cttgagcagc   7140
ttttcgtagc gaagcgtgag taagggcaaa ggtgtctctg accatgactt tgaggaattg   7200
gtatttgaag tcgatgtcgt cacaggctcc ctgttcccag agttggaagt ctacccgttt   7260
cttgtaggcg gggttgggca aagcgaaagt aacatcattg aagagaatct tgccggccct   7320
gggcatgaaa ttgcgagtga tgcgaaaagg ctgtggtact tccgctcggt tattgataac   7380
ctgggcagct aggacgatct cgtcgaaacc gttgatgttg tgtcctacga tgtataattc   7440
tatgaaacgc ggcgtgcctc tgacgtgagg tagcttactg agctcatcaa aggttaggtc   7500
tgtggggtca gataaggcgt agtgttcgag agcccattcg tgcaggtgag gattcgcttt   7560
aaggaaggag gaccagaggt ccactgccag tgctgtttgt aactggtccc ggtactgacg   7620
aaaatgccgt ccgactgcca ttttttctgg ggtgacgcaa tagaaggttt gggggtcctg   7680
ccgccagcga tcccacttga gttttatggc gaggtcatag gcgatgttga cgagccgctg   7740
gtctccagag agtttcatga ccagcatgaa ggggattagc tgcttgccaa aggaccccat   7800
ccaggtgtag gtttccacat cgtaggtgag aaagagcctt tctgtgcgag gatgagagcc   7860
aatcgggaag aactggatct cctgccacca gttggaggaa tggctgttga tgtgatggaa   7920
gtagaactcc ctgcgacgcg ccgagcattc atgcttgtgc ttgtacagac ggccgcagta   7980
gtcgcagcgt tgcacgggtt gtatctcgtg aatgagttgt acctggcttc ccttgacgag   8040
aaatttcagt gggaagccga ggcctggcga ttgtatctcg tgctttacta tgttgtctgc   8100
atcggcctgt tcatcttctg tctcgatggt ggtcatgctg acgagccctc gcgggaggca   8160
agtccagacc tcggcgcggc aggggcggag ctcgaggacg agagcgcgca ggctggagct   8220
gtccagggtc ctgagacgct gcggactcag gttagtaggc agtgtcagga gattaacttg   8280
catgatcttt tggagggcgt gcgggaggtt cagatagtac ttgatctcaa cgggtccgtt   8340
ggtggagatg tcgatggctt gcagggttcc gtgtcccttg ggcgctacca ccgtgccctt   8400
gtttttcatt ttggacggcg gtggctctgt tgcttcttgc atgtttagaa gcggtgtcga   8460
```

gggcgcgcac cgggcggcag gggcggctcg ggacccggcg gcatggctgg cagtggtacg 8520
tcggcgccgc gcgcgggtag gttctggtac tgcgccctga gaagactcgc atgcgcgacg 8580
acgcggcggt tgacatcctg gatctgacgc ctctgggtga aagctaccgg ccccgtgagc 8640
ttgaacctga aagagagttc aacagaatca atctcggtat cgttgacggc ggcttgccta 8700
aggatttctt gcacgtcacc agagttgtcc tggtaggcga tctccgccat gaactgctcg 8760
atctcttcct cttgaagatc tccgcggccc gctctctcga cggtggccgc gaggtcgttg 8820
gagatgcgcc caatgagttg agagaatgca ttcatgcccg cctcgttcca gacgcggctg 8880
tagaccacgg cccccacggg atctctcgcg cgcatgacca cctgggcgag gttgagctcc 8940
acgtggcggg tgaagaccgc atagttgcat aggcgctgga aaaggtagtt gagtgtggtg 9000
gcgatgtgct cggtgacgaa gaaatacatg atccatcgtc tcagcggcat ctcgctgaca 9060
tcgcccagag cttccaagcg ctccatggcc tcgtagaagt ccacggcaaa attaaaaaac 9120
tgggagtttc gcgcggacac ggtcaactcc tcttccagaa gacggataag ttcggcgatg 9180
gtggtgcgca cctcgcgctc gaaagcccct gggatttctt cctcaatctc ttcttcttcc 9240
actaacatct cttcctcttc aggtggggct gcaggaggag ggggaacgcg gcgacgccgg 9300
cggcgcacgg gcagacggtc gatgaatctt tcaatgacct ctccgcggcg gcggcgcatg 9360
gtttcagtga cggcgcggcc gttctcgcgc ggtcgcagag taaaaacacc gccgcgcatc 9420
tccttaaagt ggtgactggg aggttctccg tttgggaggg agagggcgct gattatacat 9480
tttattaatt ggcccgtagg gactgcacgc agagatctga tcgtgtcaag atccacggga 9540
tctgaaaacc tttcgacgaa agcgtctaac cagtcacagt cacaaggtag gctgagtacg 9600
gcttcttgtg ggcgggggtg gttatgtgtt cggtctgggt cttctgtttc ttcttcatct 9660
cgggaaggtg agacgatgct gctggtgatg aaattaaagt aggcagttct aagacggcgg 9720
atggtggcga ggagcaccag gtctttgggt ccggcttgct ggatacgcag gcgattggcc 9780
attccccaag cattatcctg acatctagca agatctttgt agtagtcttg catgagccgt 9840
tctacgggca cttcttcctc acccgttctg ccatgcatac gtgtgagtcc aaatccgcgc 9900
attggttgta ccagtgccaa gtcagctacg actctttcgg cgaggatggc ttgctgtact 9960
tgggtaaggg tggcttgaaa gtcatcaaaa tccacaaagc ggtggtaagc tcctgtatta 10020
atggtgtaag cacagttggc catgactgac cagttaactg tctggtgacc agggcgcacg 10080
agctcggtgt atttaaggcg cgaataggcg cgggtgtcaa agatgtaatc gttgcaggtg 10140
cgcaccagat actggtaccc tataagaaaa tgcggcggtg gttggcggta gagaggccat 10200
cgttctgtag ctggagcgcc aggggcgagg tcttccaaca taaggcggtg atagccgtag 10260
atgtacctgg acatccaggt gattcctgcg gcggtagtag aagcccgagg aaactcgcgt 10320
acgcggttcc aaatgttgcg tagcggcatg aagtagttca ttgtaggcac ggtttgacca 10380
gtgaggcgcg cgcagtcatt gatgctctat agacacggag aaaatgaaag cgttcagcga 10440
ctcgactccg tagcctggag gaacgtgaac gggttgggtc gcggtgtacc ccggttcgag 10500
acttgtactc gagccggccg gagccgcggc taacgtggta ttggcactcc cgtctcgacc 10560
cagcctacaa aaatccagga tacggaatcg agtcgttttg ctggtttccg aatggcaggg 10620
aagtgagtcc tatttttttt ttttgccgct cagatgcatc ccgtgctgcg acagatgcgc 10680
ccccaacaac agccccccctc gcagcagcag cagcagcaat cacaaaaggc tgtccctgca 10740
actactgcaa ctgccgccgt gagcggtgcg ggacagcccg cctatgatct ggacttggaa 10800

-continued

```
gagggcgaag gactggcacg tctaggtgcg ccttcacccg agcggcatcc gcgagttcaa  10860
ctgaaaaaag attctcgcga ggcgtatgtg ccccaacaga acctatttag agacagaagc  10920
ggcgaggagc cggaggagat gcgagcttcc cgctttaacg cgggtcgtga gctgcgtcac  10980
ggtttggacc gaagacgagt gttgcgggac gaggatttcg aagttgatga aatgacaggg  11040
atcagtcctg ccagggcaca cgtggctgca gccaaccttg tatcggctta cgagcagaca  11100
gtaaaggaag agcgtaactt ccaaaagtct tttaataatc atgtgcgaac cctgattgcc  11160
cgcgaagaag ttacccttgg tttgatgcat ttgtgggatt tgatggaagc tatcattcag  11220
aaccctacta gcaaacctct gaccgcccag ctgtttctgg tggtgcaaca cagcagagac  11280
aatgaggctt tcagagaggc gctgctgaac atcaccgaac ccgaggggag atggttgtat  11340
gatcttatca acattctaca gagtatcata gtgcaggagc ggagcctggg cctggccgag  11400
aaggtggctg ccatcaatta ctcggttttg agcttgggaa aatattacgc tcgcaaaatc  11460
tacaagactc catacgttcc catagacaag gaggtgaaga tagatgggtt ctacatgcgc  11520
atgacgctca aggtcttgac cctgagcgat gatcttgggg tgtatcgcaa tgacagaatg  11580
catcgcgcgg ttagcgccag caggaggcgc gagttaagcg acagggaact gatgcacagt  11640
ttgcaaagag ctctgactgg agctggaacc gagggtgaga attacttcga catgggagct  11700
gacttgcagt ggcagcctag tcgcagggct ctgagcgccg cgacggcagg atgtgagctt  11760
ccttacatag aagaggcgga tgaaggcgag gaggaagagg gcgagtactt ggaagactga  11820
tggcacaacc cgtgtttttt gctagatgga acagcaagca ccggatcccg caatgcgggc  11880
ggcgctgcag agccagccgt ccggcattaa ctcctcggac gattggaccc aggccatgca  11940
acgtatcatg gcgttgacga ctcgcaaccc cgaagccttt agacagcaac cccaggccaa  12000
ccgtctatcg gccatcatgg aagctgtagt gccttcccgc tctaatccca ctcatgagaa  12060
ggtcctggcc atcgtgaacg cgttggtgga gaacaaagct attcgtccag atgaggccgg  12120
actggtatac aacgctctct tagaacgcgt ggctcgctac aacagtagca atgtgcaaac  12180
caatttggac cgtatgataa cagatgtacg cgaagccgtg tctcagcgcg aaaggttcca  12240
gcgtgatgcc aacctgggtt cgctggtggc gttaaatgct ttcttgagta ctcagcctgc  12300
taatgtgccg cgtggtcaac aggattatac taacttttta agtgctttga gactgatggt  12360
atcagaagta cctcagagcg aagtgtatca gtccggtcct gattacttct ttcagactag  12420
cagacagggc ttgcagacgg taaatctgag ccaagctttt aaaaacctta aaggtttgtg  12480
gggagtgcat gccccggtag gagaaagagc aaccgtgtct agcttgttaa ctccgaactc  12540
ccgcctatta ttactgttgg tagctccttt caccgacagc ggtagcatcg accgtaattc  12600
ctatttgggt tacctactaa acctgtatcg cgaagccata gggcaaagtc aggtggacga  12660
gcagacctat caagaaatta cccaagtcag tcgcgctttg ggacaggaag acactggcag  12720
tttggaagcc actctgaact tcttgcttac caatcggtct caaaagatcc ctcctcaata  12780
tgctcttact gcggaggagg agaggatcct tagatatgtg cagcagagcg tgggattgtt  12840
tctgatgcaa gagggggcaa ctccgactgc agcactggac atgacagcgc gaaatatgga  12900
gcccagcatg tatgccagta accgaccttt cattaacaaa ctgctggact acttgcacag  12960
agctgccgct atgaactctg attatttcac caatgccatc ttaaacccgc actggctgcc  13020
cccacctggt ttctacacgg gcgaatatga catgcccgac cctaatgacg gatttctgtg  13080
ggacgacgtg gacagcgatg ttttttcacc tctttctgat catcgcacgt ggaaaaagga  13140
aggcggcgat agaatgcatt cttctgcatc gctgtccggg gtcatgggtg ctaccgcggc  13200
```

tgagcccgag tctgcaagtc cttttcctag tctacccttt tctctacaca gtgtacgtag 13260
cagcgaagtg ggtagaataa gtcgcccgag tttaatgggc gaagaggagt atctaaacga 13320
ttccttgctc agaccggcaa gagaaaaaaa tttcccaaac aatggaatag aaagtttggt 13380
ggataaaatg agtagatgga agacttatgc tcaggatcac agagacgagc ctgggatcat 13440
ggggattaca agtagagcga gccgtagacg ccagcgccat gacagacaga ggggtcttgt 13500
gtgggacgat gaggattcgg ccgatgatag cagcgtgctg gacttgggtg ggagaggaag 13560
gggcaacccg tttgctcatt tgcgccctcg cttgggtggt atgttgtaaa aaaaaataaa 13620
aaaaaaactc accaaggcca tggcgacgag cgtacgttcg ttcttcttta ttatctgtgt 13680
ctagtataat gaggcgagtc gtgctaggcg gagcggtggt gtatccggag ggtcctcctc 13740
cttcgtacga gagcgtgatg cagcagcagc aggcgacggc ggtgatgcaa tccccactgg 13800
aggctccctt tgtgcctccg cgatacctgg cacctacgga gggcagaaac agcattcgtt 13860
attcggaact ggcacctcag tacgatacca ccaggttgta tctggtggac aacaagtcgg 13920
cggacattgc ttctctgaac tatcagaatg accacagcaa cttcttgacc acggtggtgc 13980
aaaacaatga ctttacccct acggaagcca gcacccagac cattaacttt gatgaacgat 14040
cgcggtgggg cggtcagcta aagaccatca tgcatactaa catgccaaac gtgaacgagt 14100
atatgtttag taacaagttc aaagcgcgtg tgatggtgtc cagaaaacct cccgacggtg 14160
ctgcagttgg ggatacttat gatcacaagc aggatatttt gaaatatgag tggttcgagt 14220
ttactttgcc agaaggcaac ttttcagtta ctatgactat tgatttgatg aacaatgcca 14280
tcatagataa ttacttgaaa gtgggtagac agaatggagt gcttgaaagt gacattggtg 14340
ttaagttcga caccaggaac ttcaagctgg gatgggatcc cgaaaccaag ttgatcatgc 14400
ctggagtgta tacgtatgaa gccttccatc ctgacattgt cttactgcct ggctgcggag 14460
tggattttac cgagagtcgt ttgagcaacc ttcttggtat cagaaaaaaa cagccatttc 14520
aagagggttt taagattttg tatgaagatt tagaaggtgg taatattccg gccctcttgg 14580
atgtagatgc ctatgagaac agtaagaaag aacaaaaagc caaaatagaa gctgctacag 14640
ctgctgcaga agctaaggca aacatagttg ccagcgactc tacaagggtt gctaacgctg 14700
gagaggtcag aggagacaat tttgcgccaa cacctgttcc gactgcagaa tcattattgg 14760
ccgatgtgtc tgaaggaacg gacgtgaaac tcactattca acctgtagaa aaagatagta 14820
agaatagaag ctataatgtg ttggaagaca aaatcaacac agcctatcgc agttggtatc 14880
tttcgtacaa ttatggcgat cccgaaaaag gagtgcgttc ctggacattg ctcaccacct 14940
cagatgtcac ctgcggagca gagcaggtct actggtcgct tccagacatg atgaaggatc 15000
ctgtcacttt ccgctccact agacaagtca gtaactaccc tgtggtgggt gcagagctta 15060
tgcccgtctt ctcaaagagc ttctacaacg aacaagctgt gtactcccag cagctccgcc 15120
agtccacctc gcttacgcac gtcttcaacc gctttcctga gaaccagatt ttaatccgtc 15180
cgccggcgcc caccattacc accgtcagtg aaaacgttcc tgctctcaca gatcacggga 15240
ccctgccgtt gcgcagcagt atccggggag tccaacgtgt gaccgttact gacgccagac 15300
gccgcacctg tccctacgtg tacaaggcac tgggcatagt cgcaccgcgc gtcctttcaa 15360
gccgcacttt ctaaaaaaaa aaaaaatgtc cattcttatc tcgcccagta ataacaccgg 15420
ttggggtctg cgcgctccaa gcaagatgta cggaggcgca cgcaaacgtt ctacccaaca 15480
tcctgtccgt gttcgcggac attttcgcgc tccatggggc gccctcaagg gccgcactcg 15540

-continued

```
cgttcgaacc accgtcgatg atgtaatcga tcaggtggtt gccgacgccc gtaattatac  15600
tcctactgcg cctacatcta ctgtggatgc agttattgac agtgtagtgg ctgacgctcg  15660
caactatgct cgacgtaaga gccggcgaag gcgcattgcc agacgccacc gagctaccac  15720
tgccatgcga gccgcaagag ctctgctacg aagagctaga cgcgtggggc gaagagccat  15780
gcttagggcg gccagacgtg cagcttcggg cgccagcgcc ggcaggtccc gcaggcaagc  15840
agccgctgtc gcagcggcga ctattgccga catggcccaa tcgcgaagag gcaatgtata  15900
ctgggtgcgt gacgctgcca ccggtcaacg tgtacccgtg cgcacccgtc cccctcgcac  15960
ttagaagata ctgagcagtc tccgatgttg tgtcccagcg gcgaggatgt ccaagcgcaa  16020
atacaaggaa gaaatgctgc aggttatcgc acctgaagtc tacggccaac cgttgaagga  16080
tgaaaaaaaa ccccgcaaaa tcaagcgggt taaaaaggac aaaaaagaag aggaagatgg  16140
cgatgatggg ctggcggagt ttgtgcgcga gtttgcccca cggcgacgcg tgcaatggcg  16200
tgggcgcaaa gttcgacatg tgttgagacc tggaacttcg gtggtcttta cacccggcga  16260
gcgttcaagc gctactttta agcgttccta tgatgaggtg tacggggatg atgatattct  16320
tgagcaggcg gctgaccgat taggcgagtt tgcttatggc aagcgtagta gaataacttc  16380
caaggatgag acagtgtcga tacccttgga tcatggaaat cccaccccta gtcttaaacc  16440
ggtcactttg cagcaagtgt tacccgtaac tccgcgaaca ggtgttaaac gcgaaggtga  16500
agatttgtat cccactatgc aactgatggt acccaaacgc cagaagttgg aggacgtttt  16560
ggagaaagta aaagtggatc cagatattca acctgaggtt aaagtgagac ccattaagca  16620
ggtagcgcct ggtctggggg tacaaactgt agacattaag attcccactg aaagtatgga  16680
agtgcaaact gaacccgcaa agcctactgc cacctccact gaagtgcaaa cggatccatg  16740
gatgcccatg cctattacaa ctgacgccgc cggtcccact cgaagatccc gacgaaagta  16800
cggtccagca agtctgttga tgcccaatta tgttgtacac ccatctatta ttcctactcc  16860
tggttaccga ggcactcgct actatcgcag ccgaaacagt acctcccgcc gtcgccgcaa  16920
gacacctgca aatcgcagtc gtcgccgtag acgcacaagc aaaccgactc ccggcgccct  16980
ggtgcggcaa gtgtaccgca atggtagtgc ggaacctttg acactgccgc gtgcgcgtta  17040
ccatccgagt atcatcactt aatcaatgtt gccgctgcct ccttgcagat atggccctca  17100
cttgtcgcct tcgcgttccc atcactggtt accgaggaag aaactcgcgc cgtagaagag  17160
ggatgttggg acgcggaatg cgacgctaca ggcgacggcg tgctatccgc aagcaattgc  17220
ggggtggttt tttaccagcc ttaattccaa ttatcgctgc tgcaattggc gcgataccag  17280
gcatagcttc cgtggcggtt caggcctcgc aacgacattg acattggaaa aaaacgtata  17340
aataaaaaaa aaaaaataca atggactctg acactcctgg tcctgtgact atgttttctt  17400
agagatggaa gacatcaatt tttcatcctt ggctccgcga cacggcacga agccgtacat  17460
gggcacctgg agcgacatcg gcacgagcca actgaacggg ggcgccttca attggagcag  17520
tatctggagc gggcttaaaa attttggctc aaccataaaa acatacggga acaaagcttg  17580
gaacagcagt acaggacagg cgcttagaaa taaacttaaa gaccagaact tccaacaaaa  17640
agtagtcgat gggatagctt ccggcatcaa tggagtggta gatttggcta accaggctgt  17700
gcagaaaaag ataaacagtc gtttggaccc gccgccagca accccaggtg aaatgcaagt  17760
ggaggaagaa attcctccgc cagaaaaacg aggcgacaag cgtccgcgtc ccgatttgga  17820
agagacgctg gtgacgcgcg tagatgaacc gccttcttat gaggaagcaa cgaagcttgg  17880
aatgcccacc actagaccga tagccccaat ggccaccggg gtgatgaaac cttctcagtt  17940
```

```
gcatcgaccc gtcaccttgg atttgccccc tccccctgct gctactgctg tacccgcttc  18000
taagcctgtc gctgccccga aaccagtcgc cgtagccagg tcacgtcccg gggggcgctcc  18060
tcgtccaaat gcgcactggc aaaatactct gaacagcatc gtgggtctag gcgtgcaaag  18120
tgtaaaacgc cgtcgctgct tttaattaaa tatggagtag cgcttaactt gcctatctgt  18180
gtatatgtgt cattacacgc cgtcacagca gcagaggaaa aaaggaagag gtcgtgcgtc  18240
gacgctgagt tactttcaag atggccaccc catcgatgct gccccaatgg gcatacatgc  18300
acatcgccgg acaggatgct tcggagtacc tgagtccggg tctggtgcag ttcgcccgcg  18360
ccacagacac ctacttcaat ctgggaaata agtttagaaa tcccaccgta gcgccgaccc  18420
acgatgtgac caccgaccgt agccagcggc tcatgttgcg cttcgtgccc gttgaccggg  18480
aggacaatac atactcttac aaagtgcggt acaccctggc cgtgggcgac aacagagtgc  18540
tggatatggc cagcacgttc tttgacatta ggggtgtgtt ggacagaggt cccagtttca  18600
aaccctattc tggtacggct tacaactccc tggctcctaa aggcgctcca aatacatctc  18660
agtggattgc agaaggtgta aaaaatacaa ctggtgagga acacgtaaca gaagaggaaa  18720
ccaatactac tacttacact tttggcaatg ctcctgtaaa agctgaagct gaaattacaa  18780
aagaaggact cccagtaggt ttggaagttt cagatgaaga aagtaaaccg atttatgctg  18840
ataaaacata tcagccagaa cctcagctgg gagatgaaac ttggactgac cttgatggaa  18900
aaaccgaaaa gtatggaggc agggctctca aacccgatac taagatgaaa ccatgctacg  18960
ggtcctttgc caaacctact aatgtgaaag gcggtcaggc aaaacaaaaa acaacggagc  19020
agccaaatca gaaagtcgaa tatgatatcg acatggagtt ttttgatgcg gcatcgcaga  19080
aaacaaactt aagtcctaaa attgtcatgt atgcagaaaa tgtaaatttg gaaactccag  19140
acactcatgt agtgtacaaa cctggaacag aagacacaag ttccgaagct aatttgggac  19200
aacaatctat gcccaacaga cccaactaca ttggcttcag agataacttt attggactta  19260
tgtactataa cagtactggt aacatggggg tgctggctgg tcaagcgtct cagttaaatg  19320
cagtggttga cttgcaggac agaaacacag aactttctta ccaactcttg cttgactctc  19380
tgggcgacag aaccagatac tttagcatgt ggaatcaggc tgtggacagt tatgatcctg  19440
atgtacgtgt tattgaaaat catggtgtgg aagatgaact tcccaactac tgttttccac  19500
tggacggcat aggtgttcca acaaccagtt acaaatcaat agttccaaat ggagacaatg  19560
cgcctaattg gaaggaacct gaagtaaatg gaacaagtga gatcggacag ggtaatttgt  19620
ttgccatgga aattaacctt caagccaatc tatggcgaag tttcctttat tccaatgtgg  19680
ctctatatct cccagactcg tacaaataca ccccgtccaa tgtcactctt ccagaaaaca  19740
aaaacaccta cgactacatg aacgggcggg tggtgccgcc atctctagta gacacctatg  19800
tgaacattgg tgccaggtgg tctctggatg ccatggacaa tgtcaaccca ttcaaccacc  19860
accgtaacgc tggcttgcgt taccgatcca tgcttctggg taacggacgt tatgtgcctt  19920
tccacataca agtgcctcaa aaattcttcg ctgttaaaaa cctgctgctt ctcccaggct  19980
cctacactta tgagtggaac tttaggaagg atgtgaacat ggttctacag agttccctcg  20040
gtaacgacct gcgggtagat ggcgccagca tcagtttcac gagcatcaac ctctatgcta  20100
ctttttttccc catggctcac aacaccgctt ccaccccttga agccatgctg cggaatgaca  20160
ccaatgatca gtcattcaac gactacctat ctgcagctaa catgctctac cccattcctg  20220
ccaatgcaac caatattccc atttccattc cttctcgcaa ctgggcggct ttcagaggct  20280
```

ggtcatttac cagactgaaa accaaagaaa ctccctcttt ggggtctgga tttgacccct 20340
actttgtcta ttctggttct attccctacc tggatggtac cttctacctg aaccacactt 20400
ttaagaaggt ttccatcatg tttgactctt cagtgagctg gcctggaaat gacaggttac 20460
tatctcctaa cgaatttgaa ataaagcgca ctgtggatgg cgaaggctac aacgtagccc 20520
aatgcaacat gaccaaagac tggttcttgg tacagatgct cgccaactac aacatcggct 20580
atcagggctt ctacattcca gaaggataca aagatcgcat gtattcattt ttcagaaact 20640
tccagcccat gagcaggcag gtggttgatg aggtcaatta caaagacttc aaggccgtcg 20700
ccatacccta ccaacacaac aactctggct ttgtgggtta catggctccg accatgcgcc 20760
aaggtcaacc ctatcccgct aactatccct atccactcat tggaacaact gccgtaaata 20820
gtgttacgca gaaaaagttc ttgtgtgaca gaaccatgtg gcgcataccg ttctcgagca 20880
acttcatgtc tatgggggcc cttacagact tgggacagaa tatgctctat gccaactcag 20940
ctcatgctct ggacatgacc tttgaggtgg atcccatgga tgagcccacc ctgctttatc 21000
ttctcttcga agtttcgac gtggtcagag tgcatcagcc acaccgcggc atcatcgagg 21060
cagtctacct gcgtacaccg ttctcggccg gtaacgctac cacgtaagaa gcttcttgct 21120
tcttgcaaat agcagctgca accatggcct gcggatccca aaacggctcc agcgagcaag 21180
agctcagagc cattgtccaa gacctgggtt gcggacccta tttttggga acctacgata 21240 agcgcttccc ggggttcatg gcccccgata agctcgcctg tgccattgta aatacggccg 21300
gacgtgagac ggggggagag cactggttgg ctttcggttg gaacccacgt tctaacacct 21360
gctacctttt tgatcctttt ggattctcgg atgatcgtct caaacagatt taccagtttg 21420
aatatgaggg tctcctgcgc cgcagcgctc ttgctaccaa ggaccgctgt attacgctgg 21480
aaaaatctac ccagaccgtg cagggtcccc gttctgccgc ctgcggactt ttctgctgca 21540
tgttccttca cgcctttgtg cactggcctg accgtcccat ggacggaaac cccaccatga 21600
aattgctaac tggagtgcca aacaacatgc ttcattctcc taaagtccag cccaccctgt 21660
gtgacaatca aaaagcactc taccatttc ttaataccca ttcgccttat tttcgctccc 21720
atcgtacaca catcgaaagg gccactgcgt tcgaccgtat ggatgttcaa taatgactca 21780
tgtaaacaac gtgttcaata aacatcactt tattttttta catgtatcaa ggctctgcat 21840
tacttattta tttacaagtc gaatgggttc tgacgagaat cagaatgacc cgcaggcagt 21900
gatacgttgc ggaactgata cttgggttgc cacttgaatt cgggaatcac caacttggga 21960
accggtatat cgggcaggat gtcactccac agctttctgg tcagctgcaa agctccaagc 22020
aggtcaggag ccgaaatctt gaaatcacaa ttaggaccag tgctttgagc gcgagagttg 22080
cggtacaccg gattgcagca ctgaaacacc atcagcgacg gatgtctcac gcttgccagc 22140
acggtgggat ctgcaatcat gcccacatcc agatcttcag cattggcaat gctgaacggg 22200
gtcatcttgc aggtctgcct acccatggcg ggcacccaat taggcttgtg gttgcaatcg 22260
cagtgcaggg ggatcagtat catcttggcc tgatcctgtc tgattcctgg atacacggct 22320
ctcatgaaag catcatattg cttgaaagcc tgctgggctt tactaccctc ggtataaaac 22380
atcccgcagg acctgctcga aaactggtta gctgcacagc cggcatcatt cacacagcag 22440
cgggcgtcat tgttagctat ttgcaccaca cttctgcccc agcggttttg ggtgattttg 22500
gttcgctcgg gattctcctt taaggctcgt tgtccgttct cgctggccac atccatctcg 22560
ataatctgct ccttctgaat cataatattg ccatgcaggc acttcagctt gccctcataa 22620
tcattgcagc catgaggcca caacgcacag cctgtacatt cccaattatg gtgggcgatc 22680

```
tgagaaaaag aatgtatcat tccctgcaga aatcttccca tcatcgtgct cagtgtcttg  22740
tgactagtga aagttaactg gatgcctcgg tgctcctcgt ttacgtactg gtgacagatg  22800
cgcttgtatt gttcgtgttg ctcaggcatt agtttaaaag aggttctaag ttcgttatcc  22860
agcctgtact tctccatcag cagacacatc acttccatgc ctttctccca agcagacacc  22920
aggggcaagc taatcggatt cttaacagtg caggcagcag ctcctttagc cagagggtca  22980
tctttagcga tcttctcaat gcttcttttg ccatccttct caacgatgcg cacgggcggg  23040
tagctgaaac ccactgctac aagttgcgcc tcttctcttt cttcttcgct gtcttgactg  23100
atgtcttgca tggggatatg tttggtcttc cttggcttct ttttgggggg tatcggagga  23160
ggaggactgt cgctccgttc cggagacagg gaggattgtg acgtttcgct caccattacc  23220
aactgactgt cggtagaaga acctgacccc acacggcgac aggtgtttct cttcgggggc  23280
agaggtggag gcgattgcga agggctgcgg tccgacctgg aaggcggatg actggcagaa  23340
ccccttccgc gttcgggggt gtgctccctg tggcggtcgc ttaactgatt tccttcgcgg  23400
ctggccattg tgttctccta ggcagagaaa caacagacat ggaaactcag ccattgctgt  23460
caacatcgcc acgagtgcca tcacatctcg tcctcagcga cgaggaaaag gagcagagct  23520
taagcattcc accgcccagt cctgccacca cctctaccct agaagataag gaggtcgacg  23580
catctcatga catgcagaat aaaaaagcga aagagtctga gacagacatc gagcaagacc  23640
cgggctatgt gacaccggtg gaacacgagg aagagttgaa acgctttcta gagagagagg  23700
atgaaaactg cccaaaacaa cgagcagata actatcacca agatgctgga aatagggatc  23760
agaacaccga ctacctcata gggcttgacg gggaagacgc gctccttaaa catctagcaa  23820
gacagtcgct catagtcaag gatgcattat tggacagaac tgaagtgccc atcagtgtgg  23880
aagagctcag ccgcgcctac gagcttaacc tcttttcacc tcgtactccc cccaaacgtc  23940
agccaaacgg cacctgcgag ccaaatcctc gcttaaactt ttatccagct tttgctgtgc  24000
cagaagtact ggctacctat cacatctttt ttaaaaatca aaaaattcca gtctcctgcc  24060
gcgctaatcg cacccgcgcc gatgccctac tcaatctggg acctggttca cgcttacctg  24120
atatagcttc cttggaagag gttccaaaga tcttcgaggg tctgggcaat aatgagactc  24180
gggccgcaaa tgctctgcaa aagggagaaa atggcatgga tgagcatcac agcgttctgg  24240
tggaattgga aggcgataat gccagactcg cagtactcaa gcgaagcatc gaggtcacac  24300
acttcgcata tcccgctgtc aacctgcccc ctaaagtcat gacggcggtc atggaccagt  24360
tactcattaa gcgcgcaagt cccctttcag aagacatgca tgacccagat gcctgtgatg  24420
agggtaaacc agtggtcagt gatgagcagc taacccgatg gctgggcacc gactctccca  24480
gggatttgga agagcgtcgc aagcttatga tggccgtggt gctggttacc gtagaactag  24540
agtgtctccg acgtttcttt accgattcag aaaccttgcg caaactcgaa gagaatctgc  24600
actacacttt tagacacggc tttgtgcggc aggcatgcaa gatatctaac gtggaactca  24660
ccaacctggt ttcctacatg ggtattctgc atgagaatcg cctaggacaa agcgtgctgc  24720
acagcaccct gaagggggaa gcccgccgtg attacatccg cgattgtgtc tatctgtacc  24780
tgtgccacac gtggcaaacc ggcatgggtg tatggcagca atgtttagaa gaacagaact  24840
tgaaagagct tgacaagctc ttacagaaat ctcttaaggt tctgtggaca gggttcgacg  24900
agcgcaccgt cgcttccgac ctggcagacc tcatcttccc agagcgtctc agggttactt  24960
tgcgaaacgg attgcctgac tttatgagcc agagcatgct taacaatttt cgctctttca  25020
```

tcctggaacg ctccggtatc ctgcccgcca cctgctgcgc actgccctcc gactttgtgc 25080
ctctcaccta ccgcgagtgc cccccgccgc tatggagtca ctgctacctg ttccgtctgg 25140
ccaactatct ctcctaccac tcggatgtga tcgaggatgt gagcggagac ggcttgctgg 25200
agtgtcactg ccgctgcaat ctgtgcacgc cccaccggtc cctagcttgc aacccccagt 25260
tgatgagcga aacccagata ataggcacct ttgaattgca aggccccagc agccaaggcg 25320
atgggtcttc tcctgggcaa agtttaaaac tgaccccggg actgtggacc tccgcctact 25380
tgcgcaagtt tgctccggaa gattaccacc cctatgaaat caagttctat gaggaccaat 25440
cacagcctcc aaaggccgaa ctttcggcct gcgtcatcac ccagggggca attctggccc 25500
aattgcaagc catccaaaaa tcccgccaag aatttctact gaaaaagggt aagggggtct 25560
accttgaccc ccagaccggc gaggaactca acacaaggtt ccctcaggat gtcccaacga 25620
cgagaaaaca agaagttgaa ggtgcagccg ccgcccccag aagatatgga ggaagattgg 25680
gacagtcagg cagaggaggc ggaggaggac agtctggagg acagtctgga ggaagacagt 25740
ttggaggagg aaaacgagga ggcagaggag gtggaagaag taaccgccga caaacagtta 25800
tcctcggctg cggagacaag caacagcgct accatctccg ctccgagtcg aggaacccgg 25860
cggcgtccca gcagtagatg ggacgagacc ggacgcttcc cgaacccaac cagcgcttcc 25920
aagaccggta agaaggatcg gcagggatac aagtcctggc gggggcataa gaatgccatc 25980
atctcctgct tgcatgagtg cgggggcaac atatccttca cgcggcgcta cttgctattc 26040
caccatgggg tgaactttcc gcgcaatgtt ttgcattact accgtcacct ccacagcccc 26100
tactatagcc agcaaatccc ggcagtctcg acagataaag acagcggcgg cgacctccaa 26160
cagaaaacca gcagcggcag ttagaaaata cacaacaagt gcagcaacag gaggattaaa 26220
gattacagcc aacgagccag cgcaaacccg agagttaaga aatcggatct ttccaaccct 26280
gtatgccatc ttccagcaga gtcggggtca agagcaggaa ctgaaaataa aaaaccgatc 26340
tctgcgttcg ctcaccagaa gttgtttgta tcacaagagc gaagatcaac ttcagcgcac 26400
tctcgaggac gccgaggctc tcttcaacaa gtactgcgcg ctgactctta aagagtaggc 26460
agcgaccgcg cttattcaaa aaaggcggga attacatcat cctcgacatg agtaaagaaa 26520
ttcccacgcc ttacatgtgg agttatcaac cccaaatggg attggcggca ggcgcctccc 26580
aggactactc cacccgcatg aattggctca gcgccgggcc ttctatgatt tctcgagtta 26640
atgatatacg cgcctaccga aaccaaatac ttttggaaca gtcagctctt accaccacgc 26700
cccgccaaca ccttaatccc agaaattggc ccgccgccct agtgtaccag gaaagtcccg 26760
ctcccaccac tgtattactt cctcgagacg cccaggccga agtccaaatg actaatgcag 26820
gtgcgcagtt agctggcggc tccaccctat gtcgtcacag gcctcggcat aatataaaac 26880
gcctgatgat cagaggccga ggtatccagc tcaacgacga gtcggtgagc tctccgcttg 26940
gtctacgacc agacggaatc tttcagattg ccggctgcgg gagatcttcc ttcacccctc 27000
gtcaggctgt tctgactttg gaaagttcgt cttcgcaacc ccgctcgggc ggaatcggga 27060
ccgttcaatt tgtggaggag tttactccct ctgtctactt caacccnttc tccggatctc 27120
ctgggcatta cccggacgag ttcataccga acttcgacgc gattagcgag tcagtggacg 27180
gctacgattg atgtctggtg acgcggctga gctatctcgg ctgcgacatc tagaccactg 27240
ccgccgcttt cgctgctttg cccgggaact cattgagttc atctacttcg aactccccaa 27300
ggatcaccct caaggtccgg cccacggagt gcggatttct atcgaaggca aaatagactc 27360
tcgcctgcaa cgaattttct cccagcggcc cgtgctgatc gagcgagacc agggaaacac 27420

```
cacggtttcc atctactgca tttgtaatca ccccggattg catgaaagcc tttgctgtct  27480
tatgtgtact gagtttaata aaaactgaat taagactctc ctacggactg ccgcttcttc  27540
aacccggatt ttacaaccag aagaacgaaa cttttcctgt cgtccaggac tctgttaact  27600
tcacctttcc tactcacaaa ctagaagctc aacgactaca ccgcttttcc agaagcattt  27660
tccctactaa tactactttc aaaaccggag gtgagctcca aggtcttcct acagaaaacc  27720
cttgggtgga agcgggcctt gtagtgctag gaattcttgc gggtgggctt gtgattattc  27780
tttgctacct atacacacct tgcttcactt tcttagtggt gttgtggtat tggtttaaaa  27840
aatggggccc atactagtct tgcttgtttt actttcgctt ttggaaccgg gttctgccaa  27900
ttacgatcca tgtctagact tcgacccaga aaactgcaca cttacttttg cacccgacac  27960
aagccgcatc tgtggagttc atcgcctctc ttacgaactt ggcccccaac gacaaaaatt  28020
tacctgcatg gtgggaatca accccatagt tatcacccag caaagtggag atactaaggg  28080
ttgcattcac tgctcctgcg attccatcga gtgcacctac accctgctga agaccctatg  28140
cggcctaaga gacctgctac caatgaatta aaaaatgatt aataaaaaat cacttacttg  28200
aaatcagcaa taaggtctct gttgaaattt tctcccagca gcacctcact tccctcttcc  28260
caactctggt attctaaacc ccgttcagcg gcatactttc tccatacttt aaaggggatg  28320
tcaaatttta gctcctctcc tgtacccaca atcttcatgt ctttcttccc agtggccggc  28380
catgaccaag agagtccggc tcagtgactc cttcaaccct gtctacccct atgaagatga  28440
aagcacctcc caacacccct ttataaaccc agggtttatt tccccaaatg gcttcacaca  28500
aagcccaaac ggagttctta ctttaaaatg tttaacccca ctaacaacca caggcggatc  28560
tctacagcta aaagtgggag gggacttac agtggatgac accaacggtt ttttgaaaga  28620
aaacataagt gccaccacac cactcgttaa gactggtcac tctataggtt taccactagg  28680
agccggattg ggaacgaatg aaaataaact ttgtatcaaa ttaggacaag gacttacatt  28740
caattcaaac aacatttgca ttgatgacaa tattaacacc ttatggacag gagtcaaccc  28800
caccgaagcc aactgtcaaa tcatgaactc cagtgaatct aatgattgca aattaattct  28860
aacactagtt aaaactggag cactagtcac tgcatttgtt tatgttatag gagtatctaa  28920
caattttaat atgctaacta cacacagaaa tataaatttt actgcagagc tgtttttcga  28980
ttctactggt aatttactaa ctagactctc atccctcaaa actccactta atcataaatc  29040
aggacaaaac atggctactg gtgccattac taatgctaaa ggtttcatgc ccagcacgac  29100
tgcctatcct ttcaatgata attctagaga aaaagaaaac tacatttacg gaacttgtta  29160
ctacacagct agtgatcgca ctgcttttcc cattgacata tctgtcatgc ttaaccgaag  29220
agcaataaat gacgagacat catattgtat tcgtataact tggtcctgga acacaggaga  29280
tgccccagag gtgcaaacct ctgctacaac cctagtcacc tccccattta ccttttacta  29340
catcagagaa gacgactgac aaataaaatc gctatccatc gaagatggat gtgtgttggt  29400
tttttgtgtg atttgtgcga tcgctatgcg gccgcttacc tgcaggggtt accacacaaa  29460
aaaccaacac accctaaagc tcgatctccg acttgtttat ttgaaaatca attcacaaaa  29520
tccgagtagt tattttgcct ccccccttccc atttaacaga atacaccaat ctctccccac  29580
gcacagcttt aaacatttgg ataccattag atatagacat ggttttagat tccacattcc  29640
aaacagtttc agagcgagcc aatctggggt cagtgataga taaaaatcca tcgggatagt  29700
cttttaaagc gctttcacag tccaactgct gcggatgcga ctccggagtc tggatcacgg  29760
```

-continued

```
tcatctggaa gaagaacgat gggaatcata atccgaaaac ggtatcggac gattgtgtct  29820
catcaaaccc acaagcagcc gctgtctgcg tcgctccgtg cgactgctgt ttatgggatc  29880
agggtccaca gtgtcctgaa gcatgatttt aatagccctt aacatcaact ttctggtgcg  29940
atgcgcgcag caacgcattc tgatttcact caaatctttg cagtaggtac aacacattat  30000
tacaatattg tttaataaac cataattaaa agcgctccag ccaaaactca tatctgatat  30060
aatcgcccct gcatgaccat cataccaaag tttaatataa attaaatgac gttccctcaa  30120
aaacacacta cccacataca tgatctcttt tggcatgtgc atattaacaa tctgtctgta  30180
ccatggacaa cgttggttaa tcatgcaacc caatataacc ttccggaacc acactgccaa  30240
caccgctccc ccagccatgc attgaagtga accctgctga ttacaatgac aatgaagaac  30300
ccaattctct cgaccgtgaa tcacttgaga atgaaaaata tctatagtgg cacaacatag  30360
acataaatgc atgcatcttc tcataatttt taactcctca ggatttagaa acatatccca  30420
gggaatagga agctcttgca gaacagtaaa gctggcagaa caaggaagac cacgaacaca  30480
acttacacta tgcatagtca tagtatcaca atctggcaac agcgggtggt cttcagtcat  30540
agaagctcgg gtttcatttt cctcacaacg tggtaactgg gctctggtgt aagggtgatg  30600
tctggcgcat gatgtcgagc gtgcgcgcaa ccttgtcata atggagttgc ttcctgacat  30660
tctcgtattt tgtatagcaa aacgcggccc tggcagaaca cactcttctt cgccttctat  30720
cctgccgctt agcgtgttcc gtgtgatagt tcaagtacaa ccacactctt aagttggtca  30780
aaagaatgct ggcttcagtt gtaatcaaaa ctccatcgca tctaatcgtt ctgaggaaat  30840
catccaagca atgcaactgg attgtgtttc aagcaggaga ggagagggaa gagacggaag  30900
aaccatgtta atttttattc caaacgatct cgcagtactt caaattgtag atcgcgcaga  30960
tggcatctct cgcccccact gtgttggtga aaaagcacag ctagatcaaa agaaatgcga  31020
ttttcaaggt gctcaacggt ggcttccagc aaagcctcca cgcgcacatc caagaacaaa  31080
agaataccaa aagaaggagc attttctaac tcctcaatca tcatattaca ttcctgcacc  31140
attcccagat aattttcagc tttccagcct tgaattattc gtgtcagttc ttgtggtaaa  31200
tccaatccac acattacaaa caggtcccgg agggcgccct ccaccaccat tcttaaacac  31260
accctcataa tgacaaaata tcttgctcct gtgtcacctg tagcgaattg agaatggcaa  31320
catcaattga catgcccttg gctctaagtt cttctttaag ttctagttgt aaaaactctc  31380
tcatattatc accaaactgc ttagccagaa gccccccggg aacaagagca ggggacgcta  31440
cagtgcagta caagcgcaga cctccccaat tggctccagc aaaaacaaga ttggaataag  31500
catattggga accgccagta atatcatcga agttgctgga aatataatca ggcagagttt  31560
cttgtaaaaa ttgaataaaa gaaaaatttg ccaaaaaaac attcaaaacc tctgggatgc  31620
aaatgcaata ggttaccgcg ctgcgctcca acattgttag ttttgaatta gtctgcaaaa  31680
ataaaaaaaa aaacaagcgt catatcatag tagcctgacg aacagatgga taaatcagtc  31740
tttccatcac aagacaagcc acagggtctc cagctcgacc ctcgtaaaac ctgtcatcat  31800
gattaaacaa cagcaccgaa agttcctcgc ggtgaccagc atgaataatt cttgatgaag  31860
catacaatcc agacatgtta gcatcagtta acgagaaaaa acagccaaca tagcctttgg  31920
gtataattat gcttaatcgt aagtatagca aagccacccc tcgcggatac aaagtaaaag  31980
gcacaggaga ataaaaaata taattatttc tctgctgctg ttcaggcaac gtcgcccccg  32040
gtccctctaa atacacatac aaagcctcat cagccatggc ttaccagaca aagtacagcg  32100
ggcacacaaa gcacaagctc taaagtgact ctccaacctc tccacaatat atatatacac  32160
```

```
aagccctaaa ctgacgtaat gggagtaaag tgtaaaaaat cccgccaaac ccaacacaca  32220
ccccgaaact gcgtcaccag ggaaaagtac agtttcactt ccgcaatccc aacaggcgta  32280
acttcctctt tctcacggta cgtgatatcc cactaacttg caacgtcatt ttcccacggt  32340
cgcaccgccc cttttagccg ttaaccccac agccaatcac cacacgatcc acacttttta  32400
aaatcacctc atttacatat tggcaccatt ccatctataa ggtatattat atagataggc  32460
gcgccctctc ttaaggtagc atcgggatcg agtccctgag agaacatcct caatcccgat  32520
ctatccttag atccgaggaa tatcgaaatc agttacgcta gggataacag ggtaatatag  32580
catcccctcg gattgctatc taccggctcg tcagctatga tctctcgatt tcgatcaaga  32640
aatctcattg gttaccttgg gctatcgaaa ccagtcaagt cagctacttg gcgagatcga  32700
cttgtctgag tttcgactac gctcagaatt gcgtcagcgc ctatcgccag gtattactcc  32760
aatcccgaat atccgagcct gagagaacat cctcaatccc gatctatcct tagatccgag  32820
gaatatcgaa atcgtttaaa tcttttcttg atggtaaatc attcgaatat aagaatggag  32880
agacgaatgg ggaaacgaca aagatgacat tctttggtcc ttctggtgag gttctcaagt  32940
ttttggttaa tcctgtcaac aacttatatc gtatggggct gacttcaggt gctacatttg  33000
aagagataaa ttgcactgaa atctagtaat attttatctg attaataaga tgatcttctt  33060
gagatcgttt tggtctgcgc gtaatctctt gctctgaaaa cgaaaaaacc gccttgcagg  33120
gcggtttttc gaaggttctc tgagctacca actctttgaa ccgaggtaac tggcttggca  33180
gagcgcagtc accaaaactt gtcctttcag tttagcctta accggcgcat gacttcaaga  33240
ctaactctgc taaatcaatt accagtggct gctgccagtg gtgcttttgc atgtctttcc  33300
gggttggact caagacgata gttaccggat aaggcgcagc ggtcggactg aacggggggt  33360
tcgtgcatac agtccagctt ggagcgaact gcctacccgg aactgagtgt caggcgtgga  33420
atgagacaaa cgcggccata acagcggaat gacaccggta aaccgaaagg caggaacagg  33480
agagcgcacg agggagccgc cagggggaaa cgcctggtat ctttatagtc ctgtcgggtt  33540
tcgccaccac tgatttgagc gtcagatttc gtgatgcttg tcaggggggc ggagcctatg  33600
gaaaaacggc tttgccgcgg ccctctcact tccctgttaa gtatcttcct ggcatcttcc  33660
aggaaatctc cgccccgttc gtaagccatt tccgctcgcc gcagtcgaac gaccgagcgt  33720
agcgagtcag tgagcgagga agcggaatat atcctgtatc acatattctg ctgacgcacc  33780
ggtgcggcct tttttctcct gccacatgaa gcacttcact gacaccctca tcagtgccaa  33840
catagtaagc cagtatacac tccgctaatt taaacgtggt gtaccgagaa cgatcctctc  33900
agtgcgatct cgacgatcag tggtattccg acatatcgtt gcttggcagt cagccagtcg  33960
atcctagctt gggacccagg aagtccaatc gtcagatatt gtactcagcc tggtcacggc  34020
agcgtaccga tctcgtaact ataacggtcc taaggtagcg aactagatat tgatagtctg  34080
atcggtcaac gtataatcga gtcctagctt ttgcaaacat ctatcaagag acaggatcag  34140
caggaggctt tcgcatgatt gaacaagatg gattgcacgc aggttctccg gcggcttggg  34200
tggagaggct attcggctat gactgggcac aacagacaat cggctgctct gatgccgccg  34260
tgttccggct gtcagcgcag gggcgtccgg ttctttttgt caagaccgac ctgtccggtg  34320
ccctgaatga actgcaagac gaggcagcgc ggctatcgtg gctggcgacg acgggcgttc  34380
cttgcgcggc tgtgctcgac gttgtcactg aagcgggaag ggactggctg ctattgggcg  34440
aagtgccggg gcaggatctc ctgtcatctc accttgctcc tgccgagaaa gtatccatca  34500
```

tggctgatgc aatgcggcgg ctgcatacgc ttgatccggc tacctgccca ttcgaccacc 34560
aagcgaaaca tcgcatcgag cgagcacgta ctcggatgga agccggtctt gtcgatcagg 34620
atgatctgga cgaagagcat caggggctcg cgccagccga actgttcgcc aggctcaagg 34680
cgtctatgcc cgacggcgag gatctcgtcg tgacccacgg cgatgcctgc ttgccgaata 34740
tcatggtgga aaatggccgc ttttctggat tcatcgactg tggccgtctg ggtgtggcgg 34800
accgctatca ggacatagcg ttggctaccc gtgatattgc tgaagagctt ggcggcgaat 34860
gggctgaccg cttccttgtg ctttacggta tcgccgcgcc cgattcgcag cgcatcgcct 34920
tctatcgcct tcttgacgag ttcttctgac cgattctagg tgcattggcg cagaaaaaaa 34980
tgcctgatgc gacgctgcgc gtcttatact cccacatatg ccagattcag caacggatac 35040
ggcttcccca acttgcccac ttccatacgt gtcctcctta ccagaaattt atccttaagg 35100
tccgtaacta taacggtcct aaggtagcga atcgacctag ctctatcgaa tctccctcgt 35160
ttcgagctta cgcgaactag cctctggcga tagcatccga ggggcaggca tctatgtcgg 35220
gtgcggagaa agaggtaatg tcaagttcga tctgattgct tggcataaag tccgatggtt 35280
cgagtagact cagttcaacc tctctcttaa ggtagc 35316

<210> SEQ ID NO 31
<211> LENGTH: 35198
<212> TYPE: DNA
<213> ORGANISM: Artificial Sequence
<220> FEATURE:
<223> OTHER INFORMATION: ColoAd2.1 plasmid

<400> SEQUENCE: 31
ggcgcgccta tctatataat ataccttata gatggaatgg tgccaatatg taaatgaggt 60
gattttaaaa agtgtggatc gtgtggtgat tggctgtggg gttaacggct aaaaggggcg 120
gtgcgaccgt gggaaaatga cgttttgtgg gggtggagtt tttttgcaag ttgtcgcggg 180
aaatgtgacg cataaaaagg ctttttttctc acggaactac ttagttttcc cacggtattt 240
aacaggaaat gaggtagttt tgaccggatg caagtgaaaa ttgttgattt tcgcgcgaaa 300
actgaatgag gaagtgtttt tctgaataat gtggtattta tggcagggtg gagtatttgt 360
tcagggccag gtagactttg acccattacg tggaggtttc gattaccgtg ttttttacct 420
gaatttccgc gtaccgtgtc aaagtcttct gtttttacgt aggtgtcagc tgatcgctag 480
ggtatttata cctcagggtt tgtgtcaaga ggccactctt gagtgccagc gagaagagtt 540
ttctcctctg cgccggcagt ttaataataa aaaaatgaga gatttgcgat ttctgcctca 600
ggaaataatc tctgctgaga ctggaaatga aatattggag cttgtggtgc acgccctgat 660
gggagacgat ccggagccac ctgtgcagct tttgagcct cctacgcttc aggaactgta 720
tgatttagag gtagagggat cggaggattc taatgaggaa gctgtaaatg gcttttttac 780
cgattctatg cttttagctg ctaatgaagg gttagaatta gatccgcctt tggacacttt 840
tgatactcca ggggtaattg tggaaagcgg tacaggtgta agaaaattac ctgatttgag 900
ttccgtggac tgtgatttgc actgctatga agacgggttt cctccgagtg atgaggagga 960
ccatgaaaag gagcagtcca tgcagactgc agcgggtgag ggagtgaagg ctgccaatgt 1020
tggttttcag ttggattgcc cggagcttcc tggacatggc tgtaagtctt gtgaatttca 1080
caggaaaaat actggagtaa aggaactgtt atgttcgctt tgttatatga gaacgcactg 1140
ccactttatt tacagtaagt gtgtttaagt taaaatttaa aggaatatgc tgtttttcac 1200
atgtatattg agtgtgagtt ttgtgcttct tattataggt cctgtgtctg atgctgatga 1260

```
atcaccatct cctgattcta ctacctcacc tcctgagatt caagcacctg ttcctgtgga   1320
cgtgcgcaag cccattcctg tgaagcttaa gcctgggaaa cgtccagcag tggaaaaact   1380
tgaggacttg ttacagggtg gggacggacc tttggacttg agtacacgga aacgtccaag   1440
acaataagtg ttccatatcc gtgtttactt aaggtgacgt caatatttgt gtgacagtgc   1500
aatgtaataa aaatatgtta actgttcact ggtttttatt gctttttggg cggggactca   1560
ggtatataag tagaagcaga cctgtgtggt tagctcatag gagctggctt tcatccatgg   1620
aggtttgggc cattttggaa gaccttagga agactaggca actgttagag aacgcttcgg   1680
acggagtctc cggtttttgg agattctggt tcgctagtga attagctagg gtagttttta   1740
ggataaaaca ggactataaa caagaatttg aaaagttgtt ggtagattgc ccaggacttt   1800
ttgaagctct taatttgggc catcaggttc actttaaaga aaaagtttta tcagttttag   1860
acttttcaac cccaggtaga actgctgctg ctgtggcttt tcttactttt atattagata   1920
aatggatccc gcagactcat ttcagcaggg gatacgtttt ggatttcata gccacagcat   1980
tgtggagaac atggaaggtt cgcaagatga ggacaatctt aggttactgg ccagtgcagc   2040
ctttgggtgt agcgggaatc ctgaggcatc caccggtcat gccagcggtt ctggaggagg   2100
aacagcaaga ggacaacccg agagccggcc tggaccctcc agtggaggag gcggagtagc   2160
tgacttgtct cctgaactgc aacgggtgct tactggatct acgtccactg gacgggatag   2220
gggcgttaag agggagaggg catctagtgg tactgatgct agatctgagt tggctttaag   2280
tttaatgagt cgcagacgtc ctgaaaccat ttggtggcat gaggttcaga aagagggaag   2340
ggatgaagtt tctgtattgc aggagaaata ttcactggaa caggtgaaaa catgttggtt   2400
ggagcctgag gatgattggg aggtggccat taaaaattat gccaagatag ctttgaggcc   2460
tgataaacag tataagatta ctagacggat taatatccgg aatgcttgtt acatatctgg   2520
aaatggggct gaggtggtaa tagatactca agacaaggca gttattagat gctgcatgat   2580
ggatatgtgg cctggggtag tcggtatgga agcagtaact tttgtaaatg ttaagtttag   2640
gggagatggt tataatggaa tagtgtttat ggccaatacc aaacttatat tgcatggttg   2700
tagctttttt ggtttcaaca atacctgtgt agatgcctgg ggacaggtta gtgtacgggg   2760
atgtagtttc tatgcgtgtt ggattgccac agctggcaga accaagagtc aattgtctct   2820
gaagaaatgc atatttcaaa gatgtaacct gggcattctg aatgaaggcg aagcaagggt   2880
ccgccactgc gcttctacag atactggatg ttttattttg attaagggaa atgccagcgt   2940
aaagcataac atgatttgcg gtgcttccga tgagaggcct tatcaaatgc tcacttgtgc   3000
tggtgggcat tgtaatatgc tggctactgt gcatattgtt tcccatcaac gcaaaaaatg   3060
gcctgttttt gatcacaatg tgatgacgaa gtgtaccatg catgcaggtg ggcgtagagg   3120
aatgtttatg ccttaccagt gtaacatgaa tcatgtgaaa gtgttgttgg aaccagatgc   3180
cttttccaga atgagcctaa caggaatttt tgacatgaac atgcaaatct ggaagatcct   3240
gaggtatgat gatacgagat cgagggtacg cgcatgcgaa tgcggaggca agcatgccag   3300
gttccagccg gtgtgtgtag atgtgactga agatctcaga ccggatcatt tggttattgc   3360
ccgcactgga gcagagttcg gatccagtgg agaagaaact gactaaggtg agtattggga   3420
aaactttggg gtgggatttt cagatggaca gattgagtaa aaatttgttt tttctgtctt   3480
gcagctgtca tgagtggaaa cgcttctttt aagggggggag tcttcagccc ttatctgaca   3540
gggcgtctcc catcctgggc aggagttcgt cagaatgtta tgggatctac tgtggatgga   3600
```

```
agacccgtcc aacccgccaa ttcttcaacg ctgacctatg ctactttaag ttcttcacct   3660
ttggacgcag ctgcagctgc cgccgccgct tctgttgccg ctaacactgt gcttggaatg   3720
ggttactatg gaagcatcat ggctaattcc acttcctcta ataacccttc taccctgact   3780
caggacaagt tacttgtcct tttggcccag ctggaggctt tgacccaacg tctgggtgaa   3840
ctttctcagc aggtggtcga gttgcgagta caaactgagt ctgctgtcgg cacggcaaag   3900
tctaaataaa aaaatcccag aatcaatgaa taaataaaca agcttgttgt tgatttaaaa   3960
tcaagtgttt ttatttcatt tttcgcgcac ggtatgccct agaccaccga tctctatcat   4020
tgagaactcg gtggattttt tccaggatcc tatagaggtg ggattgaatg tttagataca   4080
tgggcattag gccgtctttg gggtggagat agctccattg aagggattca tgctccgggg   4140
tagtgttgta aatcacccag tcataacaag gtcgcagtgc atggtgttgc acaatatctt   4200
ttagaagtag gctgattgcc acagataagc ccttggtgta ggtgtttaca aaccggttga   4260
gctgggatgg gtgcattcgg ggtgaaatta tgtgcatttt ggattggatt tttaagttgg   4320
caatattgcc gccaagatcc cgtcttgggt tcatgttatg aaggaccacc aagacggtgt   4380
atccggtaca tttaggaaat ttatcgtgca gcttggatgg aaaagcgtgg aaaaatttgg   4440
agacaccctt gtgtcctcca agattttcca tgcactcatc catgataata gcaatggggc   4500
cgtgggcagc ggcgcgggca aacacgttcc gtgggtctga cacatcatag ttatgttcct   4560
gagttaaatc atcataagcc attttaatga atttggggcg gagagtacca gattggggta   4620
tgaatgttcc ttcgggcccc ggagcatagt tcccctcaca gatttgcatt tcccaagctt   4680
tcagttccga gggtggaatc atgtccacct ggggggctat gaaaaacacc gtttctgggg   4740
cggggggtgat taattgtgat gatagcaaat ttctgagcaa ttgagatttg ccacatccgg   4800
tggggccata aatgattccg attacgggtt gcaggtggta gtttagggaa cggcaactgc   4860
cgtcttctcg aagcaagggg gccacctcgt tcatcatttc ccttacatgc atattttccc   4920
gcaccaaatc cattaggagg cgctctcctc ctagtgatag aagttcttgt agtgaggaaa   4980
agtttttcag cggtttcaga ccgtcagcca tgggcatttt ggagagagtt tgctgcaaaa   5040
gttctagtct gttccacagt tcagtgatgt gttctatggc atctcgatcc agcagacctc   5100
ctcgtttcgc gggtttggac ggctcctgga atagggtatg agacgatggg cgtccagcgc   5160
tgccagggtt cggtccttcc agggtctcag tgttcgagtc agggttgttt ccgtcacagt   5220
gaaggggtgt gcgcctgctt gggcgcttgc cagggtgcgc ttcagactca tcctgctggt   5280
cgaaaacttc tgtcgcttgg cgccctgtat gtcggccaag tagcagttta ccatgagttc   5340
gtagttgagc gcctcggctg cgtggccttt ggcgcggagc ttacctttgg aagttttctt   5400
gcataccggg cagtataggc atttcagcgc atacaacttg ggcgcaagga aaacggattc   5460
tggggagtat gcatctgcgc cgcaggaggc gcaaacagtt tcacattcca ccagccaggt   5520
taaatccggt tcattggggt caaaaacaag ttttccgcca tatttttga tgcgtttctt   5580
acctttggtc tccatgagtt cgtgtcctcg ttgagtgaca aacaggctgt ccgtgtcccc   5640
gtagactgat tttacaggcc tcttctccag tggagtgcct cggtcttctt cgtacaggaa   5700
ctctgaccac tctgatacaa aggcgcgcgt ccaggccagc acaaaggagg ctatgtggga   5760
ggggtagcga tcgttgtcaa ccagggggtc caccttttcc aaagtatgca aacacatgtc   5820
accctcttca acatccagga atgtgattgg cttgtaggtg tatttcacgt gacctggggt   5880
ccccgctggg ggggtataaa agggggcggt tctttgctct tcctcactgt cttccggatc   5940
gctgtccagg aacgtcagct gttggggtag gtattccctc tcgaaggcgg gcatgacctc   6000
```

tgcactcagg ttgtcagttt ctaagaacga ggaggatttg atattgacag tgccggttga 6060
gatgcctttc atgaggtttt cgtccatctg gtcagaaaac acaatttttt tattgtcaag 6120
tttggtggca aatgatccat acagggcgtt ggataaaagt ttggcaatgg atcgcatggt 6180
ttggttcttt tccttgtccg cgcgctcttt ggcggcgatg ttgagttgga catactcgcg 6240
tgccaggcac ttccattcgg ggaagatagt tgttaattca tctggcacga ttctcacttg 6300
ccaccctcga ttatgcaagg taattaaatc cacactggtg gccacctcgc ctcgaagggg 6360
ttcattggtc caacagagcc tacctccttt cctagaacag aaagggggaa gtgggtctag 6420
cataagttca tcgggagggt ctgcatccat ggtaaagatt cccggaagta aatccttatc 6480
aaaatagctg atgggagtgg ggtcatctaa ggccatttgc cattctcgag ctgccagtgc 6540
gcgctcatat gggttaaggg gactgcccca tggcatggga tgggtgagtg cagaggcata 6600
catgccacag atgtcataga cgtagatggg atcctcaaag atgcctatgt aggttggata 6660
gcatcgcccc cctctgatac ttgctcgcac atagtcatat agttcatgtg atggcgctag 6720
cagccccgga cccaagttgg tgcgattggg tttttctgtt ctgtagacga tctggcgaaa 6780
gatggcgtga gaattggaag agatggtggg tctttgaaaa atgttgaaat gggcatgagg 6840
tagacctaca gagtctctga caaagtgggc ataagattct tgaagcttgg ttaccagttc 6900
ggcggtgaca agtacgtcta gggcgcagta gtcaagtgtt tcttgaatga tgtcataacc 6960
tggttggttt ttcttttccc acagttcgcg gttgagaagg tattcttcgc gatccttcca 7020
gtactcttct agcggaaacc cgtctttgtc tgcacggtaa gatcctagca tgtagaactg 7080
attaactgcc ttgtaagggc agcagccctt ctctacgggt agagagtatg cttgagcagc 7140
ttttcgtagc gaagcgtgag taagggcaaa ggtgtctctg accatgactt tgaggaattg 7200
gtatttgaag tcgatgtcgt cacaggctcc ctgttcccag agttggaagt ctacccgttt 7260
cttgtaggcg gggttgggca aagcgaaagt aacatcattg aagagaatct tgccggccct 7320
gggcatgaaa ttgcgagtga tgcgaaaagg ctgtggtact tccgctcggt tattgataac 7380
ctgggcagct aggacgatct cgtcgaaacc gttgatgttg tgtcctacga tgtataattc 7440
tatgaaacgc ggcgtgcctc tgacgtgagg tagcttactg agctcatcaa aggttaggtc 7500
tgtggggtca gataaggcgt agtgttcgag agcccattcg tgcaggtgag gattcgcttt 7560
aaggaaggag gaccagaggt ccactgccag tgctgtttgt aactggtccc ggtactgacg 7620
aaaatgccgt ccgactgcca tttttttctgg ggtgacgcaa tagaaggttt gggggtcctg 7680
ccgccagcga tcccacttga gttttatggc gaggtcatag gcgatgttga cgagccgctg 7740
gtctccagag agtttcatga ccagcatgaa ggggattagc tgcttgccaa aggaccccat 7800
ccaggtgtag gtttccacat cgtaggtgag aaagagcctt tctgtgcgag gatgagagcc 7860
aatcgggaag aactggatct cctgccacca gttggaggaa tggctgttga tgtgatggaa 7920
gtagaactcc ctgcgacgcg ccgagcattc atgcttgtgc ttgtacagac ggccgcagta 7980
gtcgcagcgt tgcacgggtt gtatctcgtg aatgagttgt acctggcttc ccttgacgag 8040
aaatttcagt gggaagccga ggcctggcga ttgtatctcg tgctttacta tgttgtctgc 8100
atcggcctgt tcatcttctg tctcgatggt ggtcatgctg acgagccctc gcgggaggca 8160
agtccagacc tcggcgcggc aggggcggag ctcgaggacg agagcgcgca ggctggagct 8220
gtccagggtc ctgagacgct gcggactcag gttagtaggc agtgtcagga gattaacttg 8280
catgatcttt tggagggcgt gcgggaggtt cagatagtac ttgatctcaa cgggtccgtt 8340

-continued

```
ggtggagatg tcgatggctt gcagggttcc gtgtcccttg ggcgctacca ccgtgccctt   8400
gtttttcatt ttggacggcg gtggctctgt tgcttcttgc atgtttagaa gcggtgtcga   8460
gggcgcgcac cgggcggcag gggcggctcg ggacccggcg gcatggctgg cagtggtacg   8520
tcggcgccgc gcgcgggtag gttctggtac tgcgccctga gaagactcgc atgcgcgacg   8580
acgcggcggt tgacatcctg gatctgacgc ctctgggtga aagctaccgg ccccgtgagc   8640
ttgaacctga aagagagttc aacagaatca atctcggtat cgttgacggc ggcttgccta   8700
aggatttctt gcacgtcacc agagttgtcc tggtaggcga tctccgccat gaactgctcg   8760
atctcttcct cttgaagatc tccgcggccc gctctctcga cggtggccgc gaggtcgttg   8820
gagatgcgcc caatgagttg agagaatgca ttcatgcccg cctcgttcca gacgcggctg   8880
tagaccacgg cccccacggg atctctcgcg cgcatgacca cctgggcgag gttgagctcc   8940
acgtggcggg tgaagaccgc atagttgcat aggcgctgga aaggtagtt gagtgtggtg    9000
gcgatgtgct cggtgacgaa gaaatacatg atccatcgtc tcagcggcat ctcgctgaca   9060
tcgcccagag cttccaagcg ctccatggcc tcgtagaagt ccacggcaaa attaaaaaac   9120
tgggagtttc gcgcggacac ggtcaactcc tcttccagaa gacggataag ttcggcgatg   9180
gtggtgcgca cctcgcgctc gaaagcccct gggatttctt cctcaatctc ttcttcttcc   9240
actaacatct cttcctcttc aggtggggct gcaggaggag gggaacgcg gcgacgccgg    9300
cggcgcacgg gcagacggtc gatgaatctt tcaatgacct ctccgcggcg gcggcgcatg   9360
gtttcagtga cggcgcggcc gttctcgcgc ggtcgcagag taaaaacacc gccgcgcatc   9420
tccttaaagt ggtgactggg aggttctccg tttgggaggg agagggcgct gattatacat   9480
tttattaatt ggcccgtagg gactgcacgc agagatctga tcgtgtcaag atccacggga   9540
tctgaaaacc tttcgacgaa agcgtctaac cagtcacagt cacaaggtag gctgagtacg   9600
gcttcttgtg ggcgggggtg gttatgtgtt cggtctgggt cttctgtttc ttcttcatct   9660
cgggaaggtg agacgatgct gctggtgatg aaattaaagt aggcagttct aagacggcgg   9720
atggtggcga ggagcaccag gtctttgggt ccggcttgct ggatacgcag gcgattggcc   9780
attccccaag cattatcctg acatctagca agatctttgt agtagtcttg catgagccgt   9840
tctacgggca cttcttcctc acccgttctg ccatgcatac gtgtgagtcc aaatccgcgc   9900
attggttgta ccagtgccaa gtcagctacg actctttcgg cgaggatggc ttgctgtact   9960
tgggtaaggg tggcttgaaa gtcatcaaaa tccacaaagc ggtggtaagc tcctgtatta  10020
atggtgtaag cacagttggc catgactgac cagttaactg tctggtgacc agggcgcacg  10080
agctcggtgt atttaaggcg cgaataggcg cgggtgtcaa agatgtaatc gttgcaggtg  10140
cgcaccagat actggtaccc tataagaaaa tgcggcggtg gttggcggta gagaggccat  10200
cgttctgtag ctggagcgcc aggggcgagg tcttccaaca taaggcggtg atagccgtag  10260
atgtacctgg acatccaggt gattcctgcg gcggtagtag aagcccgagg aaactcgcgt  10320
acgcggttcc aaatgttgcg tagcggcatg aagtagttca ttgtaggcac ggtttgacca  10380
gtgaggcgcg cgcagtcatt gatgctctat agacacggag aaaatgaaag cgttcagcga  10440
ctcgactccg tagcctggag gaacgtgaac gggttgggtc gcggtgtacc ccggttcgag  10500
acttgtactc gagccggccg gagccgcggc taacgtggta ttggcactcc cgtctcgacc  10560
cagcctacaa aaatccagga tacggaatcg agtcgttttg ctggtttccg aatggcaggg  10620
aagtgagtcc tatttttttt ttttgccgct cagatgcatc ccgtgctgcg acagatgcgc  10680
ccccaacaac agcccccctc gcagcagcag cagcagcaat cacaaaaggc tgtccctgca  10740
```

-continued

```
actactgcaa ctgccgccgt gagcggtgcg ggacagcccg cctatgatct ggacttggaa  10800
gagggcgaag gactggcacg tctaggtgcg ccttcacccg agcggcatcc gcgagttcaa  10860
ctgaaaaaag attctcgcga ggcgtatgtg ccccaacaga acctatttag agacagaagc  10920
ggcgaggagc cggaggagat gcgagcttcc cgctttaacg cgggtcgtga gctgcgtcac  10980
ggtttggacc gaagacgagt gttgcgggac gaggatttcg aagttgatga aatgacaggg  11040
atcagtcctg ccagggcaca cgtggctgca gccaaccttg tatcggctta cgagcagaca  11100
gtaaaggaag agcgtaactt ccaaaagtct tttaataatc atgtgcgaac cctgattgcc  11160
cgcgaagaag ttacccttgg tttgatgcat ttgtgggatt tgatggaagc tatcattcag  11220
aaccctacta gcaaacctct gaccgcccag ctgtttctgg tggtgcaaca cagcagagac  11280
aatgaggctt tcagagaggc gctgctgaac atcaccgaac ccgaggggag atggttgtat  11340
gatcttatca acattctaca gagtatcata gtgcaggagc ggagcctggg cctggccgag  11400
aaggtggctg ccatcaatta ctcggttttg agcttgggaa aatattacgc tcgcaaaatc  11460
tacaagactc catacgttcc catagacaag gaggtgaaga tagatgggtt ctacatgcgc  11520
atgacgctca aggtcttgac cctgagcgat gatcttgggg tgtatcgcaa tgacagaatg  11580
catcgcgcgg ttagcgccag caggaggcgc gagttaagcg acagggaact gatgcacagt  11640
ttgcaaagag ctctgactgg agctggaacc gagggtgaga attacttcga catgggagct  11700
gacttgcagt ggcagcctag tcgcagggct ctgagcgccg cgacggcagg atgtgagctt  11760
ccttacatag aagaggcgga tgaaggcgag gaggaagagg gcgagtactt ggaagactga  11820
tggcacaacc cgtgtttttt gctagatgga acagcaagca ccggatcccg caatgcgggc  11880
ggcgctgcag agccagccgt ccggcattaa ctcctcggac gattggaccc aggccatgca  11940
acgtatcatg gcgttgacga ctcgcaaccc cgaagccttt agacagcaac cccaggccaa  12000
ccgtctatcg gccatcatgg aagctgtagt gccttcccgc tctaatccca ctcatgagaa  12060
ggtcctggcc atcgtgaacg cgttggtgga gaacaaagct attcgtccag atgaggccgg  12120
actggtatac aacgctctct tagaacgcgt ggctcgctac aacagtagca atgtgcaaac  12180
caatttggac cgtatgataa cagatgtacg cgaagccgtg tctcagcgcg aaaggttcca  12240
gcgtgatgcc aacctgggtt cgctggtggc gttaaatgct ttcttgagta ctcagcctgc  12300
taatgtgccg cgtggtcaac aggattatac taacttttta agtgctttga gactgatggt  12360
atcagaagta cctcagagcg aagtgtatca gtccggtcct gattacttct ttcagactag  12420
cagacagggc ttgcagacgg taaatctgag ccaagctttt aaaaacctta aaggtttgtg  12480
gggagtgcat gccccggtag gagaaagagc aaccgtgtct agcttgttaa ctccgaactc  12540
ccgcctatta ttactgttgg tagctccttt caccgacagc ggtagcatcg accgtaattc  12600
ctatttgggt tacctactaa acctgtatcg cgaagccata gggcaaagtc aggtggacga  12660
gcagacctat caagaaatta cccaagtcag tcgcgctttg ggacaggaag acactggcag  12720
tttggaagcc actctgaact tcttgcttac caatcggtct caaaagatcc ctcctcaata  12780
tgctcttact gcggaggagg agaggatcct tagatatgtg cagcagagcg tgggattgtt  12840
tctgatgcaa gagggggcaa ctccgactgc agcactggac atgacagcgc gaaatatgga  12900
gcccagcatg tatgccagta accgaccttt cattaacaaa ctgctggact acttgcacag  12960
agctgccgct atgaactctg attatttcac caatgccatc ttaaacccgc actggctgcc  13020
cccacctggt ttctacacgg gcgaatatga catgcccgac cctaatgacg gatttctgtg  13080
```

-continued ggacgacgtg gacagcgatg ttttttcacc tctttctgat catcgcacgt ggaaaaagga 13140
aggcggcgat agaatgcatt cttctgcatc gctgtccggg gtcatgggtg ctaccgcggc 13200
tgagcccgag tctgcaagtc cttttcctag tctacccttt tctctacaca gtgtacgtag 13260
cagcgaagtg ggtagaataa gtcgcccgag tttaatgggc gaagaggagt atctaaacga 13320
ttccttgctc agaccggcaa gagaaaaaaa tttcccaaac aatggaatag aaagtttggt 13380
ggataaaatg agtagatgga agacttatgc tcaggatcac agagacgagc ctgggatcat 13440
ggggattaca agtagagcga gccgtagacg ccagcgccat gacagacaga ggggtcttgt 13500
gtgggacgat gaggattcgg ccgatgatag cagcgtgctg gacttgggtg ggagaggaag 13560
gggcaacccg tttgctcatt tgcgccctcg cttgggtggt atgttgtaaa aaaaaataaa 13620
aaaaaaactc accaaggcca tggcgacgag cgtacgttcg ttcttcttta ttatctgtgt 13680
ctagtataat gaggcgagtc gtgctaggcg gagcggtggt gtatccggag ggtcctcctc 13740
cttcgtacga gagcgtgatg cagcagcagc aggcgacggc ggtgatgcaa tccccactgg 13800
aggctccctt tgtgcctccg cgatacctgg cacctacgga gggcagaaac agcattcgtt 13860
attcggaact ggcacctcag tacgatacca ccaggttgta tctggtggac aacaagtcgg 13920
cggacattgc ttctctgaac tatcagaatg accacagcaa cttcttgacc acggtggtgc 13980
aaaacaatga ctttacccct acggaagcca gcacccagac cattaacttt gatgaacgat 14040
cgcggtgggg cggtcagcta aagaccatca tgcatactaa catgccaaac gtgaacgagt 14100
atatgtttag taacaagttc aaagcgcgtg tgatggtgtc cagaaaacct cccgacggtg 14160
ctgcagttgg ggatacttat gatcacaagc aggatatttt gaaatatgag tggttcgagt 14220
ttactttgcc agaaggcaac ttttcagtta ctatgactat tgatttgatg aacaatgcca 14280
tcatagataa ttacttgaaa gtgggtagac agaatggagt gcttgaaagt gacattggtg 14340
ttaagttcga caccaggaac ttcaagctgg gatgggatcc cgaaaccaag ttgatcatgc 14400
ctggagtgta tacgtatgaa gccttccatc ctgacattgt cttactgcct ggctgcggag 14460
tggattttac cgagagtcgt ttgagcaacc ttcttggtat cagaaaaaaa cagccatttc 14520
aagagggttt taagattttg tatgaagatt tagaaggtgg taatattccg gccctcttgg 14580
atgtagatgc ctatgagaac agtaagaaag aacaaaaagc caaaatagaa gctgctacag 14640
ctgctgcaga agctaaggca aacatagttg ccagcgactc tacaagggtt gctaacgctg 14700
gagaggtcag aggagacaat tttgcgccaa cacctgttcc gactgcagaa tcattattgg 14760
ccgatgtgtc tgaaggaacg gacgtgaaac tcactattca acctgtagaa aaagatagta 14820
agaatagaag ctataatgtg ttggaagaca aaatcaacac agcctatcgc agttggtatc 14880
tttcgtacaa ttatggcgat cccgaaaaag gagtgcgttc ctggacattg ctcaccacct 14940
cagatgtcac ctgcggagca gagcaggtct actggtcgct tccagacatg atgaaggatc 15000
ctgtcacttt ccgctccact agacaagtca gtaactaccc tgtggtgggt gcagagctta 15060
tgcccgtctt ctcaaagagc ttctacaacg aacaagctgt gtactcccag cagctccgcc 15120
agtccacctc gcttacgcac gtcttcaacc gctttcctga gaaccagatt ttaatccgtc 15180
cgccggcgcc caccattacc accgtcagtg aaaacgttcc tgctctcaca gatcacggga 15240
ccctgccgtt gcgcagcagt atccggggag tccaacgtgt gaccgttact gacgccagac 15300
gccgcacctg tccctacgtg tacaaggcac tgggcatagt cgcaccgcgc gtcctttcaa 15360
gccgcacttt ctaaaaaaaa aaaaaatgtc cattcttatc tcgcccagta ataacaccgg 15420
ttggggtctg cgcgctccaa gcaagatgta cggaggcgca cgcaaacgtt ctacccaaca 15480

```
tcctgtccgt gttcgcggac attttcgcgc tccatggggc gccctcaagg gccgcactcg  15540
cgttcgaacc accgtcgatg atgtaatcga tcaggtggtt gccgacgccc gtaattatac  15600
tcctactgcg cctacatcta ctgtggatgc agttattgac agtgtagtgg ctgacgctcg  15660
caactatgct cgacgtaaga gccggcgaag gcgcattgcc agacgccacc gagctaccac  15720
tgccatgcga gccgcaagag ctctgctacg aagagctaga cgcgtggggc gaagagccat  15780
gcttagggcg gccagacgtg cagcttcggg cgccagcgcc ggcaggtccc gcaggcaagc  15840
agccgctgtc gcagcggcga ctattgccga catggcccaa tcgcgaagag gcaatgtata  15900
ctgggtgcgt gacgctgcca ccggtcaacg tgtacccgtg cgcacccgtc cccctcgcac  15960
ttagaagata ctgagcagtc tccgatgttg tgtcccagcg gcgaggatgt ccaagcgcaa  16020
atacaaggaa gaaatgctgc aggttatcgc acctgaagtc tacggccaac cgttgaagga  16080
tgaaaaaaaa ccccgcaaaa tcaagcgggt taaaaaggac aaaaaagaag aggaagatgg  16140
cgatgatggg ctggcggagt ttgtgcgcga gtttgcccca cggcgacgcg tgcaatggcg  16200
tgggcgcaaa gttcgacatg tgttgagacc tggaacttcg gtggtcttta cacccggcga  16260
gcgttcaagc gctactttta agcgttccta tgatgaggtg tacggggatg atgatattct  16320
tgagcaggcg gctgaccgat taggcgagtt tgcttatggc aagcgtagta gaataacttc  16380
caaggatgag acagtgtcga taccccttgga tcatggaaat cccaccccta gtcttaaacc  16440
ggtcactttg cagcaagtgt tacccgtaac tccgcgaaca ggtgttaaac gcgaaggtga  16500
agatttgtat cccactatgc aactgatggt acccaaacgc cagaagttgg aggacgtttt  16560
ggagaaagta aaagtggatc cagatattca acctgaggtt aaagtgagac ccattaagca  16620
ggtagcgcct ggtctggggg tacaaactgt agacattaag attcccactg aaagtatgga  16680
agtgcaaact gaacccgcaa agcctactgc cacctccact gaagtgcaaa cggatccatg  16740
gatgcccatg cctattacaa ctgacgccgc cggtcccact cgaagatccc gacgaaagta  16800
cggtccagca agtctgttga tgcccaatta tgttgtacac ccatctatta ttcctactcc  16860
tggttaccga ggcactcgct actatcgcag ccgaaacagt acctcccgcc gtcgccgcaa  16920
gacacctgca aatcgcagtc gtcgccgtag acgcacaagc aaaccgactc ccggcgccct  16980
ggtgcggcaa gtgtaccgca atggtagtgc ggaacctttg acactgccgc gtgcgcgtta  17040
ccatccgagt atcatcactt aatcaatgtt gccgctgcct ccttgcagat atggccctca  17100
cttgtcgcct tcgcgttccc atcactggtt accgaggaag aaactcgcgc cgtagaagag  17160
ggatgttggg acgcggaatg cgacgctaca ggcgacggcg tgctatccgc aagcaattgc  17220
ggggtggttt tttaccagcc ttaattccaa ttatcgctgc tgcaattggc gcgataccag  17280
gcatagcttc cgtggcggtt caggcctcgc aacgacattg acattggaaa aaaacgtata  17340
aataaaaaaa aaaaaataca atggactctg acactcctgg tcctgtgact atgttttctt  17400
agagatggaa gacatcaatt tttcatcctt ggctccgcga cacggcacga agccgtacat  17460
gggcacctgg agcgacatcg gcacgagcca actgaacggg ggcgccttca attggagcag  17520
tatctggagc gggcttaaaa attttggctc aaccataaaa acatacggga acaaagcttg  17580
gaacagcagt acaggacagg cgcttagaaa taaacttaaa gaccagaact tccaacaaaa  17640
agtagtcgat gggatagctt ccggcatcaa tggagtggta gatttggcta accaggctgt  17700
gcagaaaaag ataaacagtc gtttggaccc gccgccagca accccaggtg aaatgcaagt  17760
ggaggaagaa attcctccgc cagaaaaacg aggcgacaag cgtccgcgtc ccgatttgga  17820
```

agagacgctg gtgacgcgcg tagatgaacc gccttcttat gaggaagcaa cgaagcttgg 17880
aatgcccacc actagaccga tagccccaat ggccaccggg gtgatgaaac cttctcagtt 17940
gcatcgaccc gtcaccttgg atttgccccc tccccctgct gctactgctg tacccgcttc 18000
taagcctgtc gctgccccga aaccagtcgc cgtagccagg tcacgtcccg ggggcgctcc 18060
tcgtccaaat gcgcactggc aaaatactct gaacagcatc gtgggtctag gcgtgcaaag 18120
tgtaaaacgc cgtcgctgct tttaattaaa tatggagtag cgcttaactt gcctatctgt 18180
gtatatgtgt cattacacgc cgtcacagca gcagaggaaa aaaggaagag gtcgtgcgtc 18240
gacgctgagt tactttcaag atggccaccc catcgatgct gccccaatgg gcatacatgc 18300
acatcgccgg acaggatgct tcggagtacc tgagtccggg tctggtgcag ttcgcccgcg 18360
ccacagacac ctacttcaat ctgggaaata agtttagaaa tcccaccgta gcgccgaccc 18420
acgatgtgac caccgaccgt agccagcggc tcatgttgcg cttcgtgccc gttgaccggg 18480
aggacaatac atactcttac aaagtgcggt acaccctggc cgtgggcgac aacagagtgc 18540
tggatatggc cagcacgttc tttgacatta ggggtgtgtt ggacagaggt cccagtttca 18600
aaccctattc tggtacggct tacaactccc tggctcctaa aggcgctcca aatacatctc 18660
agtggattgc agaaggtgta aaaaatacaa ctggtgagga acacgtaaca gaagaggaaa 18720
ccaatactac tacttacact tttggcaatg ctcctgtaaa agctgaagct gaaattacaa 18780
aagaaggact cccagtaggt ttggaagttt cagatgaaga aagtaaaccg atttatgctg 18840
ataaaacata tcagccagaa cctcagctgg gagatgaaac ttggactgac cttgatggaa 18900
aaaccgaaaa gtatggaggc agggctctca aacccgatac taagatgaaa ccatgctacg 18960
ggtcctttgc caaacctact aatgtgaaag gcggtcaggc aaaacaaaaa acaacggagc 19020
agccaaatca gaaagtcgaa tatgatatcg acatggagtt ttttgatgcg gcatcgcaga 19080
aaacaaactt aagtcctaaa attgtcatgt atgcagaaaa tgtaaatttg gaaactccag 19140
acactcatgt agtgtacaaa cctggaacag aagacacaag ttccgaagct aatttgggac 19200
aacaatctat gcccaacaga cccaactaca ttggcttcag agataacttt attggactta 19260
tgtactataa cagtactggt aacatggggg tgctggctgg tcaagcgtct cagttaaatg 19320
cagtggttga cttgcaggac agaaacacag aactttctta ccaactcttg cttgactctc 19380
tgggcgacag aaccagatac tttagcatgt ggaatcaggc tgtggacagt tatgatcctg 19440
atgtacgtgt tattgaaaat catggtgtgg aagatgaact tcccaactac tgttttccac 19500
tggacggcat aggtgttcca acaaccagtt acaaatcaat agttccaaat ggagacaatg 19560
cgcctaattg gaaggaacct gaagtaaatg gaacaagtga gatcggacag ggtaatttgt 19620
ttgccatgga aattaacctt caagccaatc tatggcgaag tttcctttat tccaatgtgg 19680
ctctatatct cccagactcg tacaaataca ccccgtccaa tgtcactctt ccagaaaaca 19740
aaaacaccta cgactacatg aacgggcggg tggtgccgcc atctctagta gacacctatg 19800
tgaacattgg tgccaggtgg tctctggatg ccatggacaa tgtcaaccca ttcaaccacc 19860
accgtaacgc tggcttgcgt taccgatcca tgcttctggg taacggacgt tatgtgcctt 19920
tccacataca agtgcctcaa aaattcttcg ctgttaaaaa cctgctgctt ctcccaggct 19980
cctacactta tgagtggaac tttaggaagg atgtgaacat ggttctacag agttccctcg 20040
gtaacgacct gcgggtagat ggcgccagca tcagtttcac gagcatcaac ctctatgcta 20100 ctttttttccc catggctcac aacaccgctt ccacccttga agccatgctg cggaatgaca 20160
ccaatgatca gtcattcaac gactacctat ctgcagctaa catgctctac cccattcctg 20220

-continued

```
ccaatgcaac caatattccc atttccattc cttctcgcaa ctgggcggct ttcagaggct  20280
ggtcatttac cagactgaaa accaaagaaa ctccctcttt ggggtctgga tttgacccct  20340
actttgtcta ttctggttct attccctacc tggatggtac cttctacctg aaccacactt  20400
ttaagaaggt ttccatcatg tttgactctt cagtgagctg gcctggaaat gacaggttac  20460
tatctcctaa cgaatttgaa ataaagcgca ctgtggatgg cgaaggctac aacgtagccc  20520
aatgcaacat gaccaaagac tggttcttgg tacagatgct cgccaactac aacatcggct  20580
atcagggctt ctacattcca gaaggataca aagatcgcat gtattcattt ttcagaaact  20640
tccagcccat gagcaggcag gtggttgatg aggtcaatta caaagacttc aaggccgtcg  20700
ccatacccta ccaacacaac aactctggct ttgtgggtta catggctccg accatgcgcc  20760
aaggtcaacc ctatcccgct aactatccct atccactcat tggaacaact gccgtaaata  20820
gtgttacgca gaaaaagttc ttgtgtgaca gaaccatgtg gcgcataccg ttctcgagca  20880
acttcatgtc tatgggggcc cttacagact tgggacagaa tatgctctat gccaactcag  20940
ctcatgctct ggacatgacc tttgaggtgg atcccatgga tgagcccacc ctgctttatc  21000
ttctcttcga agttttcgac gtggtcagag tgcatcagcc acaccgcggc atcatcgagg  21060
cagtctacct gcgtacaccg ttctcggccg gtaacgctac cacgtaagaa gcttcttgct  21120
tcttgcaaat agcagctgca accatggcct gcggatccca aaacggctcc agcgagcaag  21180
agctcagagc cattgtccaa gacctgggtt gcggaccccta tttttggga acctacgata  21240
agcgcttccc ggggttcatg gcccccgata agctcgcctg tgccattgta aatacggccg  21300
gacgtgagac ggggggagag cactggttgg ctttcggttg gaacccacgt tctaacacct  21360
gctacctttt tgatcctttt ggattctcgg atgatcgtct caaacagatt taccagtttg  21420
aatatgaggg tctcctgcgc cgcagcgctc ttgctaccaa ggaccgctgt attacgctgg  21480
aaaaatctac ccagaccgtg cagggtcccc gttctgccgc ctgcggactt ttctgctgca  21540
tgttccttca cgcctttgtg cactggcctg accgtcccat ggacggaaac cccaccatga  21600
aattgctaac tggagtgcca aacaacatgc ttcattctcc taaagtccag cccaccctgt  21660
gtgacaatca aaaagcactc taccattttc ttaataccca ttcgccttat tttcgctccc  21720
atcgtacaca catcgaaagg gccactgcgt tcgaccgtat ggatgttcaa taatgactca  21780
tgtaaacaac gtgttcaata aacatcactt tattttttta catgtatcaa ggctctgcat  21840
tacttattta tttacaagtc gaatgggttc tgacgagaat cagaatgacc cgcaggcagt  21900
gatacgttgc ggaactgata cttgggttgc cacttgaatt cgggaatcac caacttggga  21960
accggtatat cgggcaggat gtcactccac agctttctgg tcagctgcaa agctccaagc  22020
aggtcaggag ccgaaatctt gaaatcacaa ttaggaccag tgctttgagc gcgagagttg  22080
cggtacaccg gattgcagca ctgaaacacc atcagcgacg gatgtctcac gcttgccagc  22140
acggtgggat ctgcaatcat gcccacatcc agatcttcag cattggcaat gctgaacggg  22200
gtcatcttgc aggtctgcct acccatggcg ggcacccaat taggcttgtg gttgcaatcg  22260
cagtgcaggg ggatcagtat catcttggcc tgatcctgtc tgattcctgg atacacggct  22320
ctcatgaaag catcatattg cttgaaagcc tgctgggctt tactaccctc ggtataaaac  22380
atcccgcagg acctgctcga aaactggtta gctgcacagc cggcatcatt cacacagcag  22440
cgggcgtcat tgttagctat ttgcaccaca cttctgcccc agcggttttg ggtgattttg  22500
gttcgctcgg gattctcctt taaggctcgt tgtccgttct cgctggccac atccatctcg  22560
```

```
ataatctgct ccttctgaat cataatattg ccatgcaggc acttcagctt gccctcataa  22620
tcattgcagc catgaggcca caacgcacag cctgtacatt cccaattatg gtgggcgatc  22680
tgagaaaaag aatgtatcat tccctgcaga aatcttccca tcatcgtgct cagtgtcttg  22740
tgactagtga aagttaactg gatgcctcgg tgctcctcgt ttacgtactg gtgacagatg  22800
cgcttgtatt gttcgtgttg ctcaggcatt agtttaaaag aggttctaag ttcgttatcc  22860
agcctgtact tctccatcag cagacacatc acttccatgc ctttctccca agcagacacc  22920
aggggcaagc taatcggatt cttaacagtg caggcagcag ctcctttagc cagagggtca  22980
tctttagcga tcttctcaat gcttcttttg ccatccttct caacgatgcg cacgggcggg  23040
tagctgaaac ccactgctac aagttgcgcc tcttctcttt cttcttcgct gtcttgactg  23100
atgtcttgca tggggatatg tttggtcttc cttggcttct ttttgggggg tatcggagga  23160
ggaggactgt cgctccgttc cggagacagg gaggattgtg acgtttcgct caccattacc  23220
aactgactgt cggtagaaga acctgacccc acacggcgac aggtgtttct cttcgggggc  23280
agaggtggag gcgattgcga agggctgcgg tccgacctgg aaggcggatg actggcagaa  23340
ccccttccgc gttcgggggt gtgctccctg tggcggtcgc ttaactgatt tccttcgcgg  23400
ctggccattg tgttctccta ggcagagaaa caacagacat ggaaactcag ccattgctgt  23460
caacatcgcc acgagtgcca tcacatctcg tcctcagcga cgaggaaaag gagcagagct  23520
taagcattcc accgcccagt cctgccacca cctctaccct agaagataag gaggtcgacg  23580
catctcatga catgcagaat aaaaaagcga aagagtctga gacagacatc gagcaagacc  23640
cgggctatgt gacaccggtg gaacacgagg aagagttgaa acgctttcta gagagagagg  23700
atgaaaactg cccaaaacaa cgagcagata actatcacca agatgctgga aatagggatc  23760
agaacaccga ctacctcata gggcttgacg gggaagacgc gctccttaaa catctagcaa  23820
gacagtcgct catagtcaag gatgcattat tggacagaac tgaagtgccc atcagtgtgg  23880
aagagctcag ccgcgcctac gagcttaacc tcttttcacc tcgtactccc cccaaacgtc  23940
agccaaacgg cacctgcgag ccaaatcctc gcttaaactt ttatccagct tttgctgtgc  24000
cagaagtact ggctacctat cacatctttt ttaaaaatca aaaaattcca gtctcctgcc  24060
gcgctaatcg cacccgcgcc gatgccctac tcaatctggg acctggttca cgcttacctg  24120
atatagcttc cttggaagag gttccaaaga tcttcgaggg tctgggcaat aatgagactc  24180
gggccgcaaa tgctctgcaa aagggagaaa atggcatgga tgagcatcac agcgttctgg  24240
tggaattgga aggcgataat gccagactcg cagtactcaa gcgaagcatc gaggtcacac  24300
acttcgcata tcccgctgtc aacctgcccc ctaaagtcat gacggcggtc atggaccagt  24360
tactcattaa gcgcgcaagt cccctttcag aagacatgca tgacccagat gcctgtgatg  24420
agggtaaacc agtggtcagt gatgagcagc taacccgatg gctgggcacc gactctccca  24480
gggatttgga agagcgtcgc aagcttatga tggccgtggt gctggttacc gtagaactag  24540
agtgtctccg acgtttcttt accgattcag aaaccttgcg caaactcgaa gagaatctgc  24600
actacacttt tagacacggc tttgtgcggc aggcatgcaa gatatctaac gtggaactca  24660
ccaacctggt ttcctacatg ggtattctgc atgagaatcg cctaggacaa agcgtgctgc  24720
acagcaccct gaagggggaa gcccgccgtg attacatccg cgattgtgtc tatctgtacc  24780
tgtgccacac gtggcaaacc ggcatgggtg tatggcagca atgtttagaa gaacagaact  24840
tgaaagagct tgacaagctc ttacagaaat ctcttaaggt tctgtggaca gggttcgacg  24900
agcgcaccgt cgcttccgac ctggcagacc tcatcttccc agagcgtctc agggttactt  24960
```

```
tgcgaaacgg attgcctgac tttatgagcc agagcatgct taacaatttt cgctctttca  25020
tcctggaacg ctccggtatc ctgcccgcca cctgctgcgc actgccctcc gactttgtgc  25080
ctctcaccta ccgcgagtgc cccccgccgc tatggagtca ctgctacctg ttccgtctgg  25140
ccaactatct ctcctaccac tcggatgtga tcgaggatgt gagcggagac ggcttgctgg  25200
agtgtcactg ccgctgcaat ctgtgcacgc cccaccggtc cctagcttgc aacccccagt  25260
tgatgagcga aacccagata ataggcacct ttgaattgca aggccccagc agccaaggcg  25320
atgggtcttc tcctgggcaa agtttaaaac tgaccccggg actgtggacc tccgcctact  25380
tgcgcaagtt tgctccggaa gattaccacc cctatgaaat caagttctat gaggaccaat  25440
cacagcctcc aaaggccgaa ctttcggcct gcgtcatcac ccagggggca attctggccc  25500
aattgcaagc catccaaaaa tcccgccaag aatttctact gaaaaagggt aagggggtct  25560
accttgaccc ccagaccggc gaggaactca acacaaggtt ccctcaggat gtcccaacga  25620
cgagaaaaca agaagttgaa ggtgcagccg ccgcccccag aagatatgga ggaagattgg  25680
gacagtcagg cagaggaggc ggaggaggac agtctggagg acagtctgga ggaagacagt  25740
ttggaggagg aaaacgagga ggcagaggag gtggaagaag taaccgccga caaacagtta  25800
tcctcggctg cggagacaag caacagcgct accatctccg ctccgagtcg aggaacccgg  25860
cggcgtccca gcagtagatg ggacgagacc ggacgcttcc cgaacccaac cagcgcttcc  25920
aagaccggta agaaggatcg gcagggatac aagtcctggc gggggcataa gaatgccatc  25980
atctcctgct tgcatgagtg cgggggcaac atatccttca cgcggcgcta cttgctattc  26040
caccatgggg tgaactttcc gcgcaatgtt ttgcattact accgtcacct ccacagcccc  26100
tactatagcc agcaaatccc ggcagtctcg acagataaag acagcggcgg cgacctccaa  26160
cagaaaacca gcagcggcag ttagaaaata cacaacaagt gcagcaacag gaggattaaa  26220
gattacagcc aacgagccag cgcaaacccg agagttaaga aatcggatct ttccaaccct  26280
gtatgccatc ttccagcaga gtcggggtca agagcaggaa ctgaaaataa aaaaccgatc  26340
tctgcgttcg ctcaccagaa gttgtttgta tcacaagagc gaagatcaac ttcagcgcac  26400
tctcgaggac gccgaggctc tcttcaacaa gtactgcgcg ctgactctta aagagtaggc  26460
agcgaccgcg cttattcaaa aaaggcggga attacatcat cctcgacatg agtaaagaaa  26520
ttcccacgcc ttacatgtgg agttatcaac cccaaatggg attggcggca ggcgcctccc  26580
aggactactc cacccgcatg aattggctca gcgccgggcc ttctatgatt tctcgagtta  26640
atgatatacg cgcctaccga aaccaaatac ttttggaaca gtcagctctt accaccacgc  26700
cccgccaaca ccttaatccc agaaattggc ccgccgccct agtgtaccag gaaagtcccg  26760
ctcccaccac tgtattactt cctcgagacg cccaggccga agtccaaatg actaatgcag  26820
gtgcgcagtt agctggcggc tccaccctat gtcgtcacag gcctcggcat aatataaaac  26880
gcctgatgat cagaggccga ggtatccagc tcaacgacga gtcggtgagc tctccgcttg  26940
gtctacgacc agacggaatc tttcagattg ccggctgcgg gagatcttcc ttcacccctc  27000
gtcaggctgt tctgactttg gaaagttcgt cttcgcaacc ccgctcgggc ggaatcggga  27060
ccgttcaatt tgtggaggag tttactccct ctgtctactt caacccctc tccggatctc  27120
ctgggcatta cccggacgag ttcataccga acttcgacgc gattagcgag tcagtggacg  27180
gctacgattg atgtctggtg acgcggctga gctatctcgg ctgcgacatc tagaccactg  27240
ccgccgcttt cgctgctttg cccgggaact cattgagttc atctacttcg aactccccaa  27300
```

```
ggatcaccct caaggtccgg cccacggagt gcggatttct atcgaaggca aaatagactc  27360
tcgcctgcaa cgaattttct cccagcggcc cgtgctgatc gagcgagacc agggaaacac  27420
cacggtttcc atctactgca tttgtaatca ccccggattg catgaaagcc tttgctgtct  27480
tatgtgtact gagtttaata aaaactgaat taagactctc ctacggactg ccgcttcttc  27540
aacccggatt ttacaaccag aagaacgaaa cttttcctgt cgtccaggac tctgttaact  27600
tcacctttcc tactcacaaa ctagaagctc aacgactaca ccgcttttcc agaagcattt  27660
tccctactaa tactactttc aaaaccggag gtgagctcca aggtcttcct acagaaaacc  27720
cttgggtgga agcgggcctt gtagtgctag gaattcttgc gggtgggctt gtgattattc  27780
tttgctacct atacacacct tgcttcactt tcttagtggt gttgtggtat tggtttaaaa  27840
aatggggccc atactagtct tgcttgtttt actttcgctt ttggaaccgg gttctgccaa  27900
ttacgatcca tgtctagact tcgacccaga aaactgcaca cttacttttg cacccgacac  27960
aagccgcatc tgtggagttc atcgcctctc ttacgaactt ggcccccaac gacaaaaatt  28020
tacctgcatg gtgggaatca accccatagt tatcacccag caaagtggag atactaaggg  28080
ttgcattcac tgctcctgcg attccatcga gtgcacctac accctgctga agaccctatg  28140
cggcctaaga gacctgctac caatgaatta aaaaatgatt aataaaaaat cacttacttg  28200
aaatcagcaa taaggtctct gttgaaattt tctcccagca gcacctcact tccctcttcc  28260
caactctggt attctaaacc ccgttcagcg gcatactttc tccatacttt aaaggggatg  28320
tcaaatttta gctcctctcc tgtacccaca atcttcatgt ctttcttccc agagcggccg  28380
catgaccaag agagtccggc tcagtgactc cttcaaccct gtctacccct atgaagatga  28440
aagcacctcc caacacccct ttataaaccc agggtttatt tccccaaatg gcttcacaca  28500
aagcccaaac ggagttctta ctttaaaatg tttaacccca ctaacaacca caggcggatc  28560
tctacagcta aaagtgggag ggggacttac agtggatgac accaacggtt ttttgaaaga  28620
aaacataagt gccaccacac cactcgttaa gactggtcac tctataggtt taccactagg  28680
agccggattg ggaacgaatg aaaataaact ttgtatcaaa ttaggacaag gacttacatt  28740
caattcaaac aacatttgca ttgatgacaa tattaacacc ttatggacag gagtcaaccc  28800
caccgaagcc aactgtcaaa tcatgaactc cagtgaatct aatgattgca aattaattct  28860
aacactagtt aaaactggag cactagtcac tgcatttgtt tatgttatag gagtatctaa  28920
caattttaat atgctaacta cacacagaaa tataaatttt actgcagagc tgtttttcga  28980
ttctactggt aatttactaa ctagactctc atccctcaaa actccactta atcataaatc  29040
aggacaaaac atggctactg gtgccattac taatgctaaa ggtttcatgc ccagcacgac  29100
tgcctatcct ttcaatgata attctagaga aaaagaaaac tacatttacg gaacttgtta  29160
ctacacagct agtgatcgca ctgcttttcc cattgacata tctgtcatgc ttaaccgaag  29220
agcaataaat gacgagacat catattgtat tcgtataact tggtcctgga acacaggaga  29280
tgccccagag gtgcaaacct ctgctacaac cctagtcacc tccccattta ccttttacta  29340
catcagagaa gacgactgac aaataaagtt taacttgttt atttgaaaat caattcacaa  29400
aatccgagta gttattttgc ctccccttc ccatttaaca gaatacacca atctctcccc  29460
acgcacagct ttaaacattt ggataccatt agatatagac atggttttag attccacatt  29520
ccaaacagtt tcagagcgag ccaatctggg gtcagtgata gataaaaatc catcgggata  29580
gtcttttaaa gcgctttcac agtccaactg ctgcggatgc gactccggag tctggatcac  29640
ggtcatctgg aagaagaacg atgggaatca taatccgaaa acggtatcgg acgattgtgt  29700
```

ctcatcaaac ccacaagcag ccgctgtctg cgtcgctccg tgcgactgct gtttatggga 29760
tcagggtcca cagtgtcctg aagcatgatt ttaatagccc ttaacatcaa ctttctggtg 29820
cgatgcgcgc agcaacgcat tctgatttca ctcaaatctt tgcagtaggt acaacacatt 29880
attacaatat tgtttaataa accataatta aaagcgctcc agccaaaact catatctgat 29940
ataatcgccc ctgcatgacc atcataccaa agtttaatat aaattaaatg acgttccctc 30000
aaaaacacac tacccacata catgatctct tttggcatgt gcatattaac aatctgtctg 30060
taccatggac aacgttggtt aatcatgcaa cccaatataa ccttccggaa ccacactgcc 30120
aacaccgctc ccccagccat gcattgaagt gaaccctgct gattacaatg acaatgaaga 30180
acccaattct ctcgaccgtg aatcacttga gaatgaaaaa tatctatagt ggcacaacat 30240
agacataaat gcatgcatct tctcataatt tttaactcct caggatttag aaacatatcc 30300
cagggaatag gaagctcttg cagaacagta aagctggcag aacaaggaag accacgaaca 30360
caacttacac tatgcatagt catagtatca caatctggca acagcgggtg gtcttcagtc 30420
atagaagctc gggtttcatt ttcctcacaa cgtggtaact gggctctggt gtaagggtga 30480
tgtctggcgc atgatgtcga gcgtgcgcgc aaccttgtca taatggagtt gcttcctgac 30540
attctcgtat tttgtatagc aaaacgcggc cctggcagaa cacactcttc ttcgccttct 30600
atcctgccgc ttagcgtgtt ccgtgtgata gttcaagtac aaccacactc ttaagttggt 30660
caaaagaatg ctggcttcag ttgtaatcaa aactccatcg catctaatcg ttctgaggaa 30720
atcatccaag caatgcaact ggattgtgtt tcaagcagga gaggagaggg aagagacgga 30780
agaaccatgt taatttttat tccaaacgat ctcgcagtac ttcaaattgt agatcgcgca 30840
gatggcatct ctcgccccca ctgtgttggt gaaaaagcac agctagatca aaagaaatgc 30900
gattttcaag gtgctcaacg gtggcttcca gcaaagcctc cacgcgcaca tccaagaaca 30960
aaagaatacc aaaagaagga gcattttcta actcctcaat catcatatta cattcctgca 31020
ccattcccag ataattttca gctttccagc cttgaattat tcgtgtcagt tcttgtggta 31080
aatccaatcc acacattaca aacaggtccc ggagggcgcc ctccaccacc attcttaaac 31140
acaccctcat aatgacaaaa tatcttgctc ctgtgtcacc tgtagcgaat tgagaatggc 31200
aacatcaatt gacatgccct tggctctaag ttcttcttta agttctagtt gtaaaaactc 31260
tctcatatta tcaccaaact gcttagccag aagccccccg ggaacaagag caggggacgc 31320
tacagtgcag tacaagcgca gacctcccca attggctcca gcaaaaacaa gattggaata 31380
agcatattgg gaaccgccag taatatcatc gaagttgctg gaaatataat caggcagagt 31440
ttcttgtaaa aattgaataa aagaaaaatt tgccaaaaaa acattcaaaa cctctgggat 31500
gcaaatgcaa taggttaccg cgctgcgctc caacattgtt agttttgaat tagtctgcaa 31560
aaataaaaaa aaaaacaagc gtcatatcat agtagcctga cgaacagatg gataaatcag 31620
tctttccatc acaagacaag ccacagggtc tccagctcga ccctcgtaaa acctgtcatc 31680
atgattaaac aacagcaccg aaagttcctc gcggtgacca gcatgaataa ttcttgatga 31740
agcatacaat ccagacatgt tagcatcagt taacgagaaa aaacagccaa catagccttt 31800
gggtataatt atgcttaatc gtaagtatag caaagccacc cctcgcggat acaaagtaaa 31860
aggcacagga gaataaaaaa tataattatt tctctgctgc tgttcaggca acgtcgcccc 31920
cggtccctct aaatacacat acaaagcctc atcagccatg gcttaccaga caaagtacag 31980
cgggcacaca aagcacaagc tctaaagtga ctctccaacc tctccacaat atatatatac 32040

-continued

```
acaagcccta aactgacgta atgggagtaa agtgtaaaaa atcccgccaa acccaacaca  32100
caccccgaaa ctgcgtcacc agggaaaagt acagtttcac ttccgcaatc ccaacaggcg  32160
taacttcctc tttctcacgg tacgtgatat cccactaact tgcaacgtca ttttcccacg  32220
gtcgcaccgc cccttttagc cgttaacccc acagccaatc accacacgat ccacactttt  32280
taaaatcacc tcatttacat attggcacca ttccatctat aaggtatatt atatagatag  32340
gcgcgccctc tcttaaggta gcatcgggat cgagtccctg agagaacatc ctcaatcccg  32400
atctatcctt agatccgagg aatatcgaaa tcagttacgc tagggataac agggtaatat  32460
agcatcccct cggattgcta tctaccggct cgtcagctat gatctctcga tttcgatcaa  32520
gaaatctcat tggttacctt gggctatcga aaccagtcaa gtcagctact tggcgagatc  32580
gacttgtctg agtttcgact acgctcagaa ttgcgtcagc gcctatcgcc aggtattact  32640
ccaatcccga atatccgagc ctgagagaac atcctcaatc ccgatctatc cttagatccg  32700
aggaatatcg aaatcgttta aatcttttct tgatggtaaa tcattcgaat ataagaatgg  32760
agagacgaat ggggaaacga caaagatgac attctttggt ccttctggtg aggttctcaa  32820
gtttttggtt aatcctgtca acaacttata tcgtatgggg ctgacttcag gtgctacatt  32880
tgaagagata aattgcactg aaatctagta atattttatc tgattaataa gatgatcttc  32940
ttgagatcgt tttggtctgc gcgtaatctc ttgctctgaa aacgaaaaaa ccgccttgca  33000
gggcggtttt tcgaaggttc tctgagctac caactctttg aaccgaggta actggcttgg  33060
cagagcgcag tcaccaaaac ttgtcctttc agtttagcct taaccggcgc atgacttcaa  33120
gactaactct gctaaatcaa ttaccagtgg ctgctgccag tggtgctttt gcatgtcttt  33180
ccgggttgga ctcaagacga tagttaccgg ataaggcgca gcggtcggac tgaacggggg  33240
gttcgtgcat acagtccagc ttggagcgaa ctgcctaccc ggaactgagt gtcaggcgtg  33300
gaatgagaca aacgcggcca taacagcgga atgacaccgg taaaccgaaa ggcaggaaca  33360
ggagagcgca cgagggagcc gccaggggga aacgcctggt atctttatag tcctgtcggg  33420
tttcgccacc actgatttga gcgtcagatt tcgtgatgct tgtcaggggg gcggagccta  33480
tggaaaaacg gctttgccgc ggccctctca cttccctgtt aagtatcttc ctggcatctt  33540
ccaggaaatc tccgccccgt tcgtaagcca tttccgctcg ccgcagtcga acgaccgagc  33600
gtagcgagtc agtgagcgag gaagcggaat atatcctgta tcacatattc tgctgacgca  33660
ccggtgcggc ctttttctc ctgccacatg aagcacttca ctgacaccct catcagtgcc  33720
aacatagtaa gccagtatac actccgctaa tttaaacgtg gtgtaccgag aacgatcctc  33780
tcagtgcgat ctcgacgatc agtggtattc cgacatatcg ttgcttggca gtcagccagt  33840
cgatcctagc ttgggaccca ggaagtccaa tcgtcagata ttgtactcag cctggtcacg  33900
gcagcgtacc gatctcgtaa ctataacggt cctaaggtag cgaactagat attgatagtc  33960
tgatcggtca acgtataatc gagtcctagc ttttgcaaac atctatcaag agacaggatc  34020
agcaggaggc tttcgcatga ttgaacaaga tggattgcac gcaggttctc cggcggcttg  34080
ggtggagagg ctattcggct atgactgggc acaacagaca atcggctgct ctgatgccgc  34140
cgtgttccgg ctgtcagcgc aggggcgtcc ggttcttttt gtcaagaccg acctgtccgg  34200
tgccctgaat gaactgcaag acgaggcagc gcggctatcg tggctggcga cgacgggcgt  34260
tccttgcgcg gctgtgctcg acgttgtcac tgaagcggga agggactggc tgctattggg  34320
cgaagtgccg gggcaggatc tcctgtcatc tcaccttgct cctgccgaga aagtatccat  34380
catggctgat gcaatgcggc ggctgcatac gcttgatccg gctacctgcc cattcgacca  34440
```

ccaagcgaaa catcgcatcg agcgagcacg tactcggatg gaagccggtc ttgtcgatca 34500
ggatgatctg gacgaagagc atcaggggct cgcgccagcc gaactgttcg ccaggctcaa 34560
ggcgtctatg cccgacggcg aggatctcgt cgtgacccac ggcgatgcct gcttgccgaa 34620
tatcatggtg gaaaatggcc gcttttctgg attcatcgac tgtggccgtc tgggtgtggc 34680
ggaccgctat caggacatag cgttggctac ccgtgatatt gctgaagagc ttggcggcga 34740
atgggctgac cgcttcctcg tgctttacgg tatcgccgcg cccgattcgc agcgcatcgc 34800
cttctatcgc cttcttgacg agttcttctg accgattcta ggtgcattgg cgcagaaaaa 34860
aatgcctgat gcgacgctgc gcgtcttata ctcccacata tgccagattc agcaacggat 34920
acggcttccc caacttgccc acttccatac gtgtcctcct taccagaaat ttatccttaa 34980
ggtccgtaac tataacggtc ctaaggtagc gaatcgacct agctctatcg aatctccctc 35040
gtttcgagct tacgcgaact agcctctggc gatagcatcc gaggggcagg catctatgtc 35100
gggtgcggag aaagaggtaa tgtcaagttc gatctgattg cttggcataa agtccgatgg 35160
ttcgagtaga ctcagttcaa cctctctctt aaggtagc 35198

<210> SEQ ID NO 32
<211> LENGTH: 32350
<212> TYPE: DNA
<213> ORGANISM: Artificial Sequence
<220> FEATURE:
<223> OTHER INFORMATION: ColoAd2.4 Genome

<400> SEQUENCE: 32
cgcgcctatc tatataatat accttataga tggaatggtg ccaatatgta aatgaggtga 60
ttttaaaaag tgtggatcgt gtggtgattg gctgtggggt taacggctaa aaggggcggt 120
gcgaccgtgg gaaaatgacg ttttgtgggg gtggagtttt tttgcaagtt gtcgcgggaa 180
atgtgacgca taaaaaggct tttttctcac ggaactactt agttttccca cggtatttaa 240
caggaaatga ggtagttttg accggatgca agtgaaaatt gttgattttc gcgcgaaaac 300
tgaatgagga agtgtttttc tgaataatgt ggtatttatg gcagggtgga gtatttgttc 360
agggccaggt agactttgac ccattacgtg gaggtttcga ttaccgtgtt ttttacctga 420
atttccgcgt accgtgtcaa agtcttctgt ttttacgtag gtgtcagctg atcgctaggg 480
tatttatacc tcagggtttg tgtcaagagg ccactcttga gtgccagcga gaagagtttt 540
ctcctctgcg ccggcagttt aataataaaa aaatgagaga tttgcgattt ctgcctcagg 600
aaataatctc tgctgagact ggaaatgaaa tattggagct tgtggtgcac gccctgatgg 660
gagacgatcc ggagccacct gtgcagcttt ttgagcctcc tacgcttcag gaactgtatg 720
atttagaggt agagggatcg gaggattcta atgaggaagc tgtaaatggc ttttttaccg 780
attctatgct tttagctgct aatgaagggt tagaattaga tccgcctttg gacacttttg 840
atactccagg ggtaattgtg gaaagcggta caggtgtaag aaaattacct gatttgagtt 900
ccgtggactg tgatttgcac tgctatgaag acgggtttcc tccgagtgat gaggaggacc 960
atgaaaagga gcagtccatg cagactgcag cgggtgaggg agtgaaggct gccaatgttg 1020
gttttcagtt ggattgcccg gagcttcctg gacatggctg taagtcttgt gaatttcaca 1080
ggaaaaatac tggagtaaag gaactgttat gttcgctttg ttatatgaga acgcactgcc 1140
actttattta cagtaagtgt gtttaagtta aaatttaaag gaatatgctg tttttcacat 1200
gtatattgag tgtgagtttt gtgcttctta ttataggtcc tgtgtctgat gctgatgaat 1260

-continued

```
caccatctcc tgattctact acctcacctc ctgagattca agcacctgtt cctgtggacg   1320
tgcgcaagcc cattcctgtg aagcttaagc ctgggaaacg tccagcagtg gaaaaacttg   1380
aggacttgtt acagggtggg gacggacctt tggacttgag tacacggaaa cgtccaagac   1440
aataagtgtt ccatatccgt gtttacttaa ggtgacgtca atatttgtgt gacagtgcaa   1500
tgtaataaaa atatgttaac tgttcactgg tttttattgc tttttgggcg ggactcagg    1560
tatataagta gaagcagacc tgtgtggtta gctcatagga gctggctttc atccatggag   1620
gtttgggcca ttttggaaga ccttaggaag actaggcaac tgttagagaa cgcttcggac   1680
ggagtctccg gtttttggag attctggttc gctagtgaat tagctagggt agtttttagg   1740
ataaaacagg actataaaca agaatttgaa aagttgttgg tagattgccc aggacttttt   1800
gaagctctta atttgggcca tcaggttcac tttaaagaaa aagttttatc agttttagac   1860
ttttcaaccc caggtagaac tgctgctgct gtggcttttc ttacttttat attagataaa   1920
tggatcccgc agactcattt cagcagggga tacgttttgg atttcatagc cacagcattg   1980
tggagaacat ggaaggttcg caagatgagg acaatcttag gttactggcc agtgcagcct   2040
ttgggtgtag cgggaatcct gaggcatcca ccggtcatgc cagcggttct ggaggaggaa   2100
cagcaagagg acaacccgag agccggcctg gaccctccag tggaggaggc ggagtagctg   2160
acttgtctcc tgaactgcaa cgggtgctta ctggatctac gtccactgga cgggataggg   2220
gcgttaagag ggagagggca tctagtggta ctgatgctag atctgagttg gctttaagtt   2280
taatgagtcg cagacgtcct gaaaccattt ggtggcatga ggttcagaaa gagggaaggg   2340
atgaagtttc tgtattgcag gagaaatatt cactggaaca ggtgaaaaca tgttggttgg   2400
agcctgagga tgattgggag gtggccatta aaaattatgc caagatagct ttgaggcctg   2460
ataaacagta taagattact agacggatta atatccggaa tgcttgttac atatctggaa   2520
atggggctga ggtggtaata gatactcaag acaaggcagt tattagatgc tgcatgatgg   2580
atatgtggcc tggggtagtc ggtatggaag cagtaacttt tgtaaatgtt aagtttaggg   2640
gagatggtta taatggaata gtgtttatgg ccaataccaa acttatattg catggttgta   2700
gctttttttgg tttcaacaat acctgtgtag atgcctgggg acaggttagt gtacggggat  2760
gtagtttcta tgcgtgttgg attgccacag ctggcagaac caagagtcaa ttgtctctga   2820
agaaatgcat atttcaaaga tgtaacctgg gcattctgaa tgaaggcgaa gcaagggtcc   2880
gccactgcgc ttctacagat actggatgtt ttattttgat taagggaaat gccagcgtaa   2940
agcataacat gatttgcggt gcttccgatg agaggcctta tcaaatgctc acttgtgctg   3000
gtgggcattg taatatgctg gctactgtgc atattgtttc ccatcaacgc aaaaaatggc   3060
ctgtttttga tcacaatgtg atgacgaagt gtaccatgca tgcaggtggg cgtagaggaa   3120
tgtttatgcc ttaccagtgt aacatgaatc atgtgaaagt gttgttggaa ccagatgcct   3180
tttccagaat gagcctaaca ggaatttttg acatgaacat gcaaatctgg aagatcctga   3240
ggtatgatga tacgagatcg agggtacgcg catgcgaatg cggaggcaag catgccaggt   3300
tccagccggt gtgtgtagat gtgactgaag atctcagacc ggatcatttg gttattgccc   3360
gcactggagc agagttcgga tccagtggag aagaaactga ctaaggtgag tattgggaaa   3420
actttggggt gggattttca gatggacaga ttgagtaaaa atttgttttt tctgtcttgc   3480
agctgtcatg agtggaaacg cttcttttaa ggggggagtc ttcagccctt atctgacagg   3540
gcgtctccca tcctgggcag gagttcgtca gaatgttatg ggatctactg tggatggaag   3600
acccgtccaa cccgccaatt cttcaacgct gacctatgct actttaagtt cttcaccttt   3660
```

```
ggacgcagct gcagctgccg ccgccgcttc tgttgccgct aacactgtgc ttggaatggg   3720
ttactatgga agcatcatgg ctaattccac ttcctctaat aacccttcta ccctgactca   3780
ggacaagtta cttgtccttt tggcccagct ggaggctttg acccaacgtc tgggtgaact   3840
ttctcagcag gtggtcgagt tgcgagtaca aactgagtct gctgtcggca cggcaaagtc   3900
taaataaaaa aatcccagaa tcaatgaata aataaacaag cttgttgttg atttaaaatc   3960
aagtgttttt atttcatttt tcgcgcacgg tatgccctag accaccgatc tctatcattg   4020
agaactcggt ggattttttc caggatccta tagaggtggg attgaatgtt tagatacatg   4080
ggcattaggc cgtctttggg gtggagatag ctccattgaa gggattcatg ctccggggta   4140
gtgttgtaaa tcacccagtc ataacaaggt cgcagtgcat ggtgttgcac aatatctttt   4200
agaagtaggc tgattgccac agataagccc ttggtgtagg tgtttacaaa ccggttgagc   4260
tgggatgggt gcattcgggg tgaaattatg tgcattttgg attggatttt taagttggca   4320
atattgccgc caagatcccg tcttgggttc atgttatgaa ggaccaccaa gacggtgtat   4380
ccggtacatt taggaaattt atcgtgcagc ttggatggaa aagcgtggaa aaatttggag   4440
acacccttgt gtcctccaag attttccatg cactcatcca tgataatagc aatggggccg   4500
tgggcagcgg cgcgggcaaa cacgttccgt gggtctgaca catcatagtt atgttcctga   4560
gttaaatcat cataagccat tttaatgaat ttggggcgga gagtaccaga ttggggtatg   4620
aatgttcctt cgggccccgg agcatagttc ccctcacaga tttgcatttc ccaagctttc   4680
agttccgagg gtggaatcat gtccacctgg ggggctatga aaaacaccgt ttctggggcg   4740
ggggtgatta attgtgatga tagcaaattt ctgagcaatt gagatttgcc acatccggtg   4800
gggccataaa tgattccgat tacgggttgc aggtggtagt ttagggaacg gcaactgccg   4860
tcttctcgaa gcaagggggc cacctcgttc atcatttccc ttacatgcat attttcccgc   4920
accaaatcca ttaggaggcg ctctcctcct agtgatagaa gttcttgtag tgaggaaaag   4980
tttttcagcg gtttcagacc gtcagccatg ggcattttgg agagagtttg ctgcaaaagt   5040
tctagtctgt tccacagttc agtgatgtgt tctatggcat ctcgatccag cagacctcct   5100
cgtttcgcgg gtttggacgg ctcctggaat agggtatgag acgatgggcg tccagcgctg   5160
ccagggttcg gtccttccag ggtctcagtg ttcgagtcag ggttgtttcc gtcacagtga   5220
aggggtgtgc gcctgcttgg gcgcttgcca gggtgcgctt cagactcatc ctgctggtcg   5280
aaaacttctg tcgcttggcg ccctgtatgt cggccaagta gcagtttacc atgagttcgt   5340
agttgagcgc ctcggctgcg tggcctttgg cgcggagctt acctttggaa gttttcttgc   5400
ataccgggca gtataggcat ttcagcgcat acaacttggg cgcaaggaaa acggattctg   5460
gggagtatgc atctgcgccg caggaggcgc aaacagtttc acattccacc agccaggtta   5520
aatccggttc attggggtca aaaacaagtt ttccgccata ttttttgatg cgtttcttac   5580
ctttggtctc catgagttcg tgtcctcgtt gagtgacaaa caggctgtcc gtgtccccgt   5640
agactgattt tacaggcctc ttctccagtg gagtgcctcg gtcttcttcg tacaggaact   5700
ctgaccactc tgatacaaag gcgcgcgtcc aggccagcac aaaggaggct atgtgggagg   5760
ggtagcgatc gttgtcaacc agggggtcca ccttttccaa agtatgcaaa cacatgtcac   5820
cctcttcaac atccaggaat gtgattggct tgtaggtgta tttcacgtga cctggggtcc   5880
ccgctggggg ggtataaaag gggcggttc tttgctcttc ctcactgtct tccggatcgc   5940
tgtccaggaa cgtcagctgt tggggtaggt attccctctc gaaggcgggc atgacctctg   6000
```

-continued

```
cactcaggtt gtcagtttct aagaacgagg aggatttgat attgacagtg ccggttgaga   6060
tgcctttcat gaggttttcg tccatctggt cagaaaacac aatttttttta ttgtcaagtt   6120
tggtggcaaa tgatccatac agggcgttgg ataaaagttt ggcaatggat cgcatggttt   6180
ggttcttttc cttgtccgcg cgctctttgg cggcgatgtt gagttggaca tactcgcgtg   6240
ccaggcactt ccattcgggg aagatagttg ttaattcatc tggcacgatt ctcacttgcc   6300
accctcgatt atgcaaggta attaaatcca cactggtggc cacctcgcct cgaaggggtt   6360
cattggtcca acagagccta cctcctttcc tagaacagaa agggggaagt gggtctagca   6420
taagttcatc gggagggtct gcatccatgg taaagattcc cggaagtaaa tccttatcaa   6480
aatagctgat gggagtgggg tcatctaagg ccatttgcca ttctcgagct gccagtgcgc   6540
gctcatatgg gttaagggga ctgccccatg gcatgggatg ggtgagtgca gaggcataca   6600
tgccacagat gtcatagacg tagatgggat cctcaaagat gcctatgtag gttggatagc   6660
atcgcccccc tctgatactt gctcgcacat agtcatatag ttcatgtgat ggcgctagca   6720
gccccggacc caagttggtg cgattgggtt tttctgttct gtagacgatc tggcgaaaga   6780
tggcgtgaga attggaagag atggtgggtc tttgaaaaat gttgaaatgg gcatgaggta   6840
gacctacaga gtctctgaca aagtgggcat aagattcttg aagcttggtt accagttcgg   6900
cggtgacaag tacgtctagg gcgcagtagt caagtgtttc ttgaatgatg tcataacctg   6960
gttggttttt cttttcccac agttcgcggt tgagaaggta ttcttcgcga tccttccagt   7020
actcttctag cggaaacccg tctttgtctg cacggtaaga tcctagcatg tagaactgat   7080
taactgcctt gtaagggcag cagcccttct ctacgggtag agagtatgct tgagcagctt   7140
ttcgtagcga agcgtgagta agggcaaagg tgtctctgac catgactttg aggaattggt   7200
atttgaagtc gatgtcgtca caggctccct gttcccagag ttggaagtct acccgtttct   7260
tgtaggcggg gttgggcaaa gcgaaagtaa catcattgaa gagaatcttg ccggccctgg   7320
gcatgaaatt gcgagtgatg cgaaaaggct gtggtacttc cgctcggtta ttgataacct   7380
gggcagctag gacgatctcg tcgaaaccgt tgatgttgtg tcctacgatg tataattcta   7440
tgaaacgcgg cgtgcctctg acgtgaggta gcttactgag ctcatcaaag gttaggtctg   7500
tggggtcaga taaggcgtag tgttcgagag cccattcgtg caggtgagga ttcgctttaa   7560
ggaaggagga ccagaggtcc actgccagtg ctgtttgtaa ctggtcccgg tactgacgaa   7620
aatgccgtcc gactgccatt ttttctgggg tgacgcaata gaaggtttgg gggtcctgcc   7680
gccagcgatc ccacttgagt tttatggcga ggtcataggc gatgttgacg agccgctggt   7740
ctccagagag tttcatgacc agcatgaagg ggattagctg cttgccaaag gaccccatcc   7800
aggtgtaggt ttccacatcg taggtgagaa agagcctttc tgtgcgagga tgagagccaa   7860
tcgggaagaa ctggatctcc tgccaccagt tggaggaatg gctgttgatg tgatggaagt   7920
agaactccct gcgacgcgcc gagcattcat gcttgtgctt gtacagacgg ccgcagtagt   7980
cgcagcgttg cacgggttgt atctcgtgaa tgagttgtac ctggcttccc ttgacgagaa   8040
atttcagtgg gaagccgagg cctggcgatt gtatctcgtg ctttactatg ttgtctgcat   8100
cggcctgttc atcttctgtc tcgatggtgg tcatgctgac gagccctcgc gggaggcaag   8160
tccagacctc ggcgcggcag ggcggagct cgaggacgag agcgcgcagg ctggagctgt   8220
ccagggtcct gagacgctgc ggactcaggt tagtaggcag tgtcaggaga ttaacttgca   8280
tgatcttttg gagggcgtgc gggaggttca gatagtactt gatctcaacg ggtccgttgg   8340
tggagatgtc gatggcttgc agggttccgt gtcccttggg cgctaccacc gtgcccttgt   8400
```

```
ttttcatttt ggacggcggt ggctctgttg cttcttgcat gtttagaagc ggtgtcgagg   8460
gcgcgcaccg ggcggcaggg gcggctcggg acccggcggc atggctggca gtggtacgtc   8520
ggcgccgcgc gcgggtaggt tctggtactg cgccctgaga agactcgcat gcgcgacgac   8580
gcggcggttg acatcctgga tctgacgcct ctgggtgaaa gctaccggcc ccgtgagctt   8640
gaacctgaaa gagagttcaa cagaatcaat ctcggtatcg ttgacggcgg cttgcctaag   8700
gatttcttgc acgtcaccag agttgtcctg gtaggcgatc tccgccatga actgctcgat   8760
ctcttcctct tgaagatctc cgcggcccgc tctctcgacg gtggccgcga ggtcgttgga   8820
gatgcgccca atgagttgag agaatgcatt catgcccgcc tcgttccaga cgcggctgta   8880
gaccacggcc cccacgggat ctctcgcgcg catgaccacc tgggcgaggt tgagctccac   8940
gtggcgggtg aagaccgcat agttgcatag gcgctggaaa aggtagttga gtgtggtggc   9000
gatgtgctcg gtgacgaaga aatacatgat ccatcgtctc agcggcatct cgctgacatc   9060
gcccagagct tccaagcgct ccatggcctc gtagaagtcc acggcaaaat taaaaaactg   9120
ggagtttcgc gcggacacgg tcaactcctc ttccagaaga cggataagtt cggcgatggt   9180
ggtgcgcacc tcgcgctcga aagcccctgg gatttcttcc tcaatctctt cttcttccac   9240
taacatctct tcctcttcag gtggggctgc aggaggaggg ggaacgcggc gacgccggcg   9300
gcgcacgggc agacggtcga tgaatctttc aatgacctct ccgcggcggc ggcgcatggt   9360
ttcagtgacg gcgcggccgt tctcgcgcgg tcgcagagta aaaacaccgc cgcgcatctc   9420
cttaaagtgg tgactgggag gttctccgtt tgggagggag agggcgctga ttatacattt   9480
tattaattgg cccgtaggga ctgcacgcag agatctgatc gtgtcaagat ccacgggatc   9540
tgaaaacctt tcgacgaaag cgtctaacca gtcacagtca caaggtaggc tgagtacggc   9600
ttcttgtggg cgggggtggt tatgtgttcg gtctgggtct tctgtttctt cttcatctcg   9660
ggaaggtgag acgatgctgc tggtgatgaa attaaagtag gcagttctaa gacggcggat   9720
ggtggcgagg agcaccaggt ctttgggtcc ggcttgctgg atacgcaggc gattggccat   9780
tccccaagca ttatcctgac atctagcaag atctttgtag tagtcttgca tgagccgttc   9840
tacgggcact tcttcctcac ccgttctgcc atgcatacgt gtgagtccaa atccgcgcat   9900
tggttgtacc agtgccaagt cagctacgac tctttcggcg aggatggctt gctgtacttg   9960
ggtaagggtg gcttgaaagt catcaaaatc cacaaagcgg tggtaagctc ctgtattaat  10020
ggtgtaagca cagttggcca tgactgacca gttaactgtc tggtgaccag ggcgcacgag  10080
ctcggtgtat ttaaggcgcg aataggcgcg ggtgtcaaag atgtaatcgt tgcaggtgcg  10140
caccagatac tggtacccta taagaaaatg cggcggtggt tggcggtaga gaggccatcg  10200
ttctgtagct ggagcgccag ggcgaggtc ttccaacata aggcggtgat agccgtagat  10260
gtacctggac atccaggtga ttcctgcggc ggtagtagaa gcccgaggaa actcgcgtac  10320
gcggttccaa atgttgcgta gcggcatgaa gtagttcatt gtaggcacgg tttgaccagt  10380
gaggcgcgcg cagtcattga tgctctatag acacggagaa aatgaaagcg ttcagcgact  10440
cgactccgta gcctggagga acgtgaacgg gttgggtcgc ggtgtacccc ggttcgagac  10500
ttgtactcga gccggccgga gccgcggcta acgtggtatt ggcactcccg tctcgaccca  10560
gcctacaaaa atccaggata cggaatcgag tcgttttgct ggtttccgaa tggcagggaa  10620
gtgagtccta tttttttttt ttgccgctca gatgcatccc gtgctgcgac agatgcgccc  10680
ccaacaacag cccccctcgc agcagcagca gcagcaatca caaaaggctg tccctgcaac  10740
```

-continued

```
tactgcaact gccgccgtga gcggtgcggg acagcccgcc tatgatctgg acttggaaga  10800
gggcgaagga ctggcacgtc taggtgcgcc ttcacccgag cggcatccgc gagttcaact  10860
gaaaaaagat tctcgcgagg cgtatgtgcc ccaacagaac ctatttagag acagaagcgg  10920
cgaggagccg gaggagatgc gagcttcccg ctttaacgcg ggtcgtgagc tgcgtcacgg  10980
tttggaccga agacgagtgt tgcgggacga ggatttcgaa gttgatgaaa tgacagggat  11040
cagtcctgcc agggcacacg tggctgcagc caaccttgta tcggcttacg agcagacagt  11100
aaaggaagag cgtaacttcc aaaagtcttt taataatcat gtgcgaaccc tgattgcccg  11160
cgaagaagtt acccttggtt tgatgcattt gtgggatttg atggaagcta tcattcagaa  11220
ccctactagc aaacctctga ccgcccagct gtttctggtg gtgcaacaca gcagagacaa  11280
tgaggctttc agagaggcgc tgctgaacat caccgaaccc gaggggagat ggttgtatga  11340
tcttatcaac attctacaga gtatcatagt gcaggagcgg agcctgggcc tggccgagaa  11400
ggtggctgcc atcaattact cggttttgag cttgggaaaa tattacgctc gcaaaatcta  11460
caagactcca tacgttccca tagacaagga ggtgaagata gatgggttct acatgcgcat  11520
gacgctcaag gtcttgaccc tgagcgatga tcttggggtg tatcgcaatg acagaatgca  11580
tcgcgcggtt agcgccagca ggaggcgcga gttaagcgac agggaactga tgcacagttt  11640
gcaaagagct ctgactggag ctggaaccga gggtgagaat tacttcgaca tgggagctga  11700
cttgcagtgg cagcctagtc gcagggctct gagcgccgcg acggcaggat gtgagcttcc  11760
ttacatagaa gaggcggatg aaggcgagga ggaagagggc gagtacttgg aagactgatg  11820
gcacaacccg tgtttttgc tagatggaac agcaagcacc ggatcccgca atgcgggcgg  11880
cgctgcagag ccagccgtcc ggcattaact cctcggacga ttggacccag gccatgcaac  11940
gtatcatggc gttgacgact cgcaaccccg aagcctttag acagcaaccc caggccaacc  12000
gtctatcggc catcatggaa gctgtagtgc cttcccgctc taatcccact catgagaagg  12060
tcctggccat cgtgaacgcg ttggtggaga acaaagctat tcgtccagat gaggccggac  12120
tggtatacaa cgctctctta gaacgcgtgg ctcgctacaa cagtagcaat gtgcaaacca  12180
atttggaccg tatgataaca gatgtacgcg aagccgtgtc tcagcgcgaa aggttccagc  12240
gtgatgccaa cctgggttcg ctggtggcgt taaatgcttt cttgagtact cagcctgcta  12300
atgtgccgcg tggtcaacag gattatacta actttttaag tgctttgaga ctgatggtat  12360
cagaagtacc tcagagcgaa gtgtatcagt ccggtcctga ttacttcttt cagactagca  12420
gacagggctt gcagacggta aatctgagcc aagcttttaa aaacctttaa aggtttgtgg  12480
ggagtgcatg ccccggtagg agaaagagca accgtgtcta gcttgttaac tccgaactcc  12540
cgcctattat tactgttggt agctcctttc accgacagcg gtagcatcga ccgtaattcc  12600
tatttgggtt acctactaaa cctgtatcgc gaagccatag ggcaaagtca ggtggacgag  12660
cagacctatc aagaaattac ccaagtcagt cgcgctttgg gacaggaaga cactggcagt  12720
ttggaagcca ctctgaactt cttgcttacc aatcggtctc aaaagatccc tcctcaatat  12780
gctcttactg cggaggagga gaggatcctt agatatgtgc agcagagcgt gggattgttt  12840
ctgatgcaag agggggcaac tccgactgca gcactggaca tgacagcgcg aaatatggag  12900
cccagcatgt atgccagtaa ccgacctttc attaacaaac tgctggacta cttgcacaga  12960
gctgccgcta tgaactctga ttatttcacc aatgccatct taaacccgca ctggctgccc  13020
ccacctggtt tctacacggg cgaatatgac atgcccgacc ctaatgacgg atttctgtgg  13080
gacgacgtgg acagcgatgt tttttcacct ctttctgatc atcgcacgtg gaaaaaggaa  13140
```

ggcggcgata gaatgcattc ttctgcatcg ctgtccgggg tcatgggtgc taccgcggct 13200
gagcccgagt ctgcaagtcc ttttcctagt ctaccctttt ctctacacag tgtacgtagc 13260
agcgaagtgg gtagaataag tcgcccgagt ttaatgggcg aagaggagta tctaaacgat 13320
tccttgctca gaccggcaag agaaaaaaat ttcccaaaca atggaataga aagtttggtg 13380
gataaaatga gtagatggaa gacttatgct caggatcaca gagacgagcc tgggatcatg 13440
gggattacaa gtagagcgag ccgtagacgc cagcgccatg acagacagag gggtcttgtg 13500
tgggacgatg aggattcggc cgatgatagc agcgtgctgg acttgggtgg gagaggaagg 13560
ggcaacccgt ttgctcattt gcgccctcgc ttgggtggta tgttgtaaaa aaaaataaaa 13620
aaaaaactca ccaaggccat ggcgacgagc gtacgttcgt tcttctttat tatctgtgtc 13680
tagtataatg aggcgagtcg tgctaggcgg agcggtggtg tatccggagg gtcctcctcc 13740
ttcgtacgag agcgtgatgc agcagcagca ggcgacggcg gtgatgcaat ccccactgga 13800
ggctcccttt gtgcctccgc gatacctggc acctacggag ggcagaaaca gcattcgtta 13860
ttcggaactg gcacctcagt acgataccac caggttgtat ctggtggaca acaagtcggc 13920
ggacattgct tctctgaact atcagaatga ccacagcaac ttcttgacca cggtggtgca 13980
aaacaatgac tttaccccta cggaagccag cacccagacc attaactttg atgaacgatc 14040
gcggtggggc ggtcagctaa agaccatcat gcatactaac atgccaaacg tgaacgagta 14100
tatgtttagt aacaagttca aagcgcgtgt gatggtgtcc agaaaacctc ccgacggtgc 14160
tgcagttggg gatacttatg atcacaagca ggatattttg aaatatgagt ggttcgagtt 14220
tactttgcca gaaggcaact tttcagttac tatgactatt gatttgatga acaatgccat 14280
catagataat tacttgaaag tgggtagaca gaatggagtg cttgaaagtg acattggtgt 14340
taagttcgac accaggaact tcaagctggg atgggatccc gaaaccaagt tgatcatgcc 14400
tggagtgtat acgtatgaag ccttccatcc tgacattgtc ttactgcctg gctgcggagt 14460
ggattttacc gagagtcgtt tgagcaacct tcttggtatc agaaaaaaac agccatttca 14520
agagggtttt aagattttgt atgaagattt agaaggtggt aatattccgg ccctcttgga 14580
tgtagatgcc tatgagaaca gtaagaaaga acaaaaagcc aaaatagaag ctgctacagc 14640
tgctgcagaa gctaaggcaa acatagttgc cagcgactct acaagggttg ctaacgctgg 14700
agaggtcaga ggagacaatt ttgcgccaac acctgttccg actgcagaat cattattggc 14760
cgatgtgtct gaaggaacgg acgtgaaact cactattcaa cctgtagaaa aagatagtaa 14820
gaatagaagc tataatgtgt tggaagacaa aatcaacaca gcctatcgca gttggtatct 14880
ttcgtacaat tatggcgatc ccgaaaaagg agtgcgttcc tggacattgc tcaccacctc 14940
agatgtcacc tgcggagcag agcaggtcta ctggtcgctt ccagacatga tgaaggatcc 15000
tgtcactttc cgctccacta gacaagtcag taactaccct gtggtgggtg cagagcttat 15060
gcccgtcttc tcaaagagct tctacaacga acaagctgtg tactcccagc agctccgcca 15120
gtccacctcg cttacgcacg tcttcaaccg ctttcctgag aaccagattt taatccgtcc 15180
gccggcgccc accattacca ccgtcagtga aaacgttcct gctctcacag atcacgggac 15240
cctgccgttg cgcagcagta tccggggagt ccaacgtgtg accgttactg acgccagacg 15300
ccgcacctgt ccctacgtgt acaaggcact gggcatagtc gcaccgcgcg tcctttcaag 15360
ccgcactttc taaaaaaaaa aaaaatgtcc attcttatct cgcccagtaa taacaccggt 15420
tggggtctgc gcgctccaag caagatgtac ggaggcgcac gcaaacgttc tacccaacat 15480

-continued

```
cctgtccgtg ttcgcggaca ttttcgcgct ccatggggcg ccctcaaggg ccgcactcgc  15540
gttcgaacca ccgtcgatga tgtaatcgat caggtggttg ccgacgcccg taattatact  15600
cctactgcgc ctacatctac tgtggatgca gttattgaca gtgtagtggc tgacgctcgc  15660
aactatgctc gacgtaagag ccggcgaagg cgcattgcca gacgccaccg agctaccact  15720
gccatgcgag ccgcaagagc tctgctacga agagctagac gcgtggggcg aagagccatg  15780
cttagggcgg ccagacgtgc agcttcgggc gccagcgccg gcaggtcccg caggcaagca  15840
gccgctgtcg cagcggcgac tattgccgac atggcccaat cgcgaagagg caatgtatac  15900
tgggtgcgtg acgctgccac cggtcaacgt gtacccgtgc gcacccgtcc ccctcgcact  15960
tagaagatac tgagcagtct ccgatgttgt gtcccagcgg cgaggatgtc caagcgcaaa  16020
tacaaggaag aaatgctgca ggttatcgca cctgaagtct acggccaacc gttgaaggat  16080
gaaaaaaaac cccgcaaaat caagcgggtt aaaaaggaca aaaaagaaga ggaagatggc  16140
gatgatgggc tggcggagtt tgtgcgcgag tttgccccac ggcgacgcgt gcaatggcgt  16200
gggcgcaaag ttcgacatgt gttgagacct ggaacttcgg tggtctttac acccggcgag  16260
cgttcaagcg ctacttttaa gcgttcctat gatgaggtgt acggggatga tgatattctt  16320
gagcaggcgg ctgaccgatt aggcgagttt gcttatggca agcgtagtag aataacttcc  16380
aaggatgaga cagtgtcgat acccttggat catggaaatc ccacccctag tcttaaaccg  16440
gtcactttgc agcaagtgtt acccgtaact ccgcgaacag gtgttaaacg cgaaggtgaa  16500
gatttgtatc ccactatgca actgatggta cccaaacgcc agaagttgga ggacgttttg  16560
gagaaagtaa aagtggatcc agatattcaa cctgaggtta aagtgagacc cattaagcag  16620
gtagcgcctg gtctgggggt acaaactgta gacattaaga ttcccactga aagtatggaa  16680
gtgcaaactg aacccgcaaa gcctactgcc acctccactg aagtgcaaac ggatccatgg  16740
atgcccatgc ctattacaac tgacgccgcc ggtcccactc gaagatcccg acgaaagtac  16800
ggtccagcaa gtctgttgat gcccaattat gttgtacacc catctattat tcctactcct  16860
ggttaccgag gcactcgcta ctatcgcagc cgaaacagta cctcccgccg tcgccgcaag  16920
acacctgcaa atcgcagtcg tcgccgtaga cgcacaagca aaccgactcc cggcgccctg  16980
gtgcggcaag tgtaccgcaa tggtagtgcg gaacctttga cactgccgcg tgcgcgttac  17040
catccgagta tcatcactta atcaatgttg ccgctgcctc cttgcagata tggccctcac  17100
ttgtcgcctt cgcgttccca tcactggtta ccgaggaaga aactcgcgcc gtagaagagg  17160
gatgttggga cgcggaatgc gacgctacag gcgacggcgt gctatccgca agcaattgcg  17220
gggtggtttt ttaccagcct taattccaat tatcgctgct gcaattggcg cgataccagg  17280
catagcttcc gtggcggttc aggcctcgca acgacattga cattggaaaa aaacgtataa  17340
ataaaaaaaa aaaaatacaa tggactctga cactcctggt cctgtgacta tgttttctta  17400
gagatggaag acatcaattt ttcatccttg gctccgcgac acggcacgaa gccgtacatg  17460
ggcacctgga gcgacatcgg cacgagccaa ctgaacgggg gcgccttcaa ttggagcagt  17520
atctggagcg ggcttaaaaa ttttggctca accataaaaa catacgggaa caaagcttgg  17580
aacagcagta caggacaggc gcttagaaat aaacttaaag accagaactt ccaacaaaaa  17640
gtagtcgatg ggatagcttc cggcatcaat ggagtggtag atttggctaa ccaggctgtg  17700
cagaaaaaga taaacagtcg tttggacccg ccgccagcaa ccccaggtga aatgcaagtg  17760
gaggaagaaa ttcctccgcc agaaaaacga ggcgacaagc gtccgcgtcc cgatttggaa  17820
gagacgctgg tgacgcgcgt agatgaaccg ccttcttatg aggaagcaac gaagcttgga  17880
```

-continued

```
atgcccacca ctagaccgat agccccaatg gccaccgggg tgatgaaacc ttctcagttg  17940
catcgacccg tcaccttgga tttgcccccct cccctgctg ctactgctgt acccgcttct  18000
aagcctgtcg ctgccccgaa accagtcgcc gtagccaggt cacgtcccgg gggcgctcct  18060
cgtccaaatg cgcactggca aaatactctg aacagcatcg tgggtctagg cgtgcaaagt  18120
gtaaaacgcc gtcgctgctt ttaattaaat atggagtagc gcttaacttg cctatctgtg  18180
tatatgtgtc attacacgcc gtcacagcag cagaggaaaa aaggaagagg tcgtgcgtcg  18240
acgctgagtt actttcaaga tggccacccc atcgatgctg ccccaatggg catacatgca  18300
catcgccgga caggatgctt cggagtacct gagtccgggt ctggtgcagt tcgcccgcgc  18360
cacagacacc tacttcaatc tgggaaataa gtttagaaat cccaccgtag cgccgaccca  18420
cgatgtgacc accgaccgta gccagcggct catgttgcgc ttcgtgcccg ttgaccggga  18480
ggacaataca tactcttaca aagtgcggta caccctggcc gtgggcgaca acagagtgct  18540
ggatatggcc agcacgttct ttgacattag gggtgtgttg gacagaggtc ccagtttcaa  18600
accctattct ggtacggctt acaactccct ggctcctaaa ggcgctccaa atacatctca  18660
gtggattgca gaaggtgtaa aaaatacaac tggtgaggaa cacgtaacag aagaggaaac  18720
caatactact acttacactt ttggcaatgc tcctgtaaaa gctgaagctg aaattacaaa  18780
agaaggactc ccagtaggtt tggaagtttc agatgaagaa agtaaaccga tttatgctga  18840
taaaacatat cagccagaac ctcagctggg agatgaaact tggactgacc ttgatggaaa  18900
aaccgaaaag tatggaggca gggctctcaa acccgatact aagatgaaac catgctacgg  18960
gtcctttgcc aaacctacta atgtgaaagg cggtcaggca aaacaaaaaa caacggagca  19020
gccaaatcag aaagtcgaat atgatatcga catggagttt tttgatgcgg catcgcagaa  19080
aacaaactta agtcctaaaa ttgtcatgta tgcagaaaat gtaaatttgg aaactccaga  19140
cactcatgta gtgtacaaac ctggaacaga agacacaagt tccgaagcta atttgggaca  19200
acaatctatg cccaacagac ccaactacat tggcttcaga gataacttta ttggacttat  19260
gtactataac agtactggta acatgggggt gctggctggt caagcgtctc agttaaatgc  19320
agtggttgac ttgcaggaca gaaacacaga actttcttac caactcttgc ttgactctct  19380
gggcgacaga accagatact ttagcatgtg gaatcaggct gtggacagtt atgatcctga  19440
tgtacgtgtt attgaaaatc atggtgtgga agatgaactt cccaactact gttttccact  19500
ggacggcata ggtgttccaa caaccagtta caaatcaata gttccaaatg gagacaatgc  19560
gcctaattgg aaggaacctg aagtaaatgg aacaagtgag atcggacagg gtaatttgtt  19620
tgccatggaa attaaccttc aagccaatct atggcgaagt ttcctttatt ccaatgtggc  19680
tctatatctc ccagactcgt acaaatacac cccgtccaat gtcactcttc cagaaaacaa  19740
aaacacctac gactacatga acgggcgggt ggtgccgcca tctctagtag acacctatgt  19800
gaacattggt gccaggtggt ctctggatgc catggacaat gtcaacccat tcaaccacca  19860
ccgtaacgct ggcttgcgtt accgatccat gcttctgggt aacggacgtt atgtgccttt  19920
ccacatacaa gtgcctcaaa aattcttcgc tgttaaaaac ctgctgcttc tcccaggctc  19980
ctacacttat gagtggaact ttaggaagga tgtgaacatg gttctacaga gttccctcgg  20040
taacgacctg cgggtagatg gcgccagcat cagtttcacg agcatcaacc tctatgctac  20100
tttttcccc atggctcaca acaccgcttc cacccttgaa gccatgctgc ggaatgacac  20160
caatgatcag tcattcaacg actacctatc tgcagctaac atgctctacc ccattcctgc  20220
```

caatgcaacc aatattccca tttccattcc ttctcgcaac tgggcggctt tcagaggctg 20280
gtcatttacc agactgaaaa ccaaagaaac tccctctttg gggtctggat ttgaccccta 20340
ctttgtctat tctggttcta ttccctacct ggatggtacc ttctacctga accacacttt 20400
taagaaggtt tccatcatgt ttgactcttc agtgagctgg cctggaaatg acaggttact 20460
atctcctaac gaatttgaaa taaagcgcac tgtggatggc gaaggctaca acgtagccca 20520
atgcaacatg accaaagact ggttcttggt acagatgctc gccaactaca acatcggcta 20580
tcagggcttc tacattccag aaggatacaa agatcgcatg tattcatttt tcagaaactt 20640
ccagcccatg agcaggcagg tggttgatga ggtcaattac aaagacttca aggccgtcgc 20700
cataccctac caacacaaca actctggctt tgtgggttac atggctccga ccatgcgcca 20760
aggtcaaccc tatcccgcta actatcccta tccactcatt ggaacaactg ccgtaaatag 20820
tgttacgcag aaaaagttct tgtgtgacag aaccatgtgg cgcataccgt tctcgagcaa 20880
cttcatgtct atgggggccc ttacagactt gggacagaat atgctctatg ccaactcagc 20940
tcatgctctg gacatgacct ttgaggtgga tcccatggat gagcccaccc tgctttatct 21000
tctcttcgaa gttttcgacg tggtcagagt gcatcagcca caccgcggca tcatcgaggc 21060
agtctacctg cgtacaccgt tctcggccgg taacgctacc acgtaagaag cttcttgctt 21120
cttgcaaata gcagctgcaa ccatggcctg cggatcccaa aacggctcca gcgagcaaga 21180
gctcagagcc attgtccaag acctgggttg cggaccctat tttttgggaa cctacgataa 21240
gcgcttcccg ggtttcatgg cccccgataa gctcgcctgt gccattgtaa atacggccgg 21300
acgtgagacg gggggagagc actggttggc tttcggttgg aacccacgtt ctaacacctg 21360
ctaccttttt gatccttttg gattctcgga tgatcgtctc aaacagattt accagtttga 21420
atatgagggt ctcctgcgcc gcagcgctct tgctaccaag gaccgctgta ttacgctgga 21480
aaaatctacc cagaccgtgc agggtccccg ttctgccgcc tgcggacttt tctgctgcat 21540
gttccttcac gcctttgtgc actggcctga ccgtcccatg gacggaaacc ccaccatgaa 21600
attgctaact ggagtgccaa acaacatgct tcattctcct aaagtccagc ccaccctgtg 21660
tgacaatcaa aaagcactct accattttct taatacccat tcgccttatt ttcgctccca 21720
tcgtacacac atcgaaaggg ccactgcgtt cgaccgtatg gatgttcaat aatgactcat 21780
gtaaacaacg tgttcaataa acatcacttt atttttttac atgtatcaag gctctgcatt 21840
acttatttat ttacaagtcg aatgggttct gacgagaatc agaatgaccc gcaggcagtg 21900
atacgttgcg gaactgatac ttgggttgcc acttgaattc gggaatcacc aacttgggaa 21960
ccggtatatc gggcaggatg tcactccaca gctttctggt cagctgcaaa gctccaagca 22020
ggtcaggagc cgaaatcttg aaatcacaat taggaccagt gctttgagcg cgagagttgc 22080
ggtacaccgg attgcagcac tgaaacacca tcagcgacgg atgtctcacg cttgccagca 22140
cggtgggatc tgcaatcatg cccacatcca gatcttcagc attggcaatg ctgaacgggg 22200
tcatcttgca ggtctgccta cccatggcgg gcacccaatt aggcttgtgg ttgcaatcgc 22260
agtgcagggg gatcagtatc atcttggcct gatcctgtct gattcctgga tacacggctc 22320
tcatgaaagc atcatattgc ttgaaagcct gctgggcttt actaccctcg gtataaaaca 22380
tcccgcagga cctgctcgaa aactggttag ctgcacagcc ggcatcattc acacagcagc 22440
gggcgtcatt gttagctatt tgcaccacac ttctgcccca gcggttttgg gtgattttgg 22500
ttcgctcggg attctccttt aaggctcgtt gtccgttctc gctggccaca tccatctcga 22560
taatctgctc cttctgaatc ataatattgc catgcaggca cttcagcttg ccctcataat 22620
cattgcagcc atgaggccac aacgcacagc ctgtacattc ccaattatgg tgggcgatct 22680
gagaaaaaga atgtatcatt ccctgcagaa atcttcccat catcgtgctc agtgtcttgt 22740
gactagtgaa agttaactgg atgcctcggt gctcctcgtt tacgtactgg tgacagatgc 22800
gcttgtattg ttcgtgttgc tcaggcatta gtttaaaaga ggttctaagt tcgttatcca 22860
gcctgtactt ctccatcagc agacacatca cttccatgcc tttctcccaa gcagacacca 22920
ggggcaagct aatcggattc ttaacagtgc aggcagcagc tcctttagcc agagggtcat 22980
ctttagcgat cttctcaatg cttcttttgc catccttctc aacgatgcgc acgggcgggt 23040
agctgaaacc cactgctaca agttgcgcct cttctctttc ttcttcgctg tcttgactga 23100
tgtcttgcat ggggatatgt ttggtcttcc ttggcttctt tttgggggt atcggaggag 23160
gaggactgtc gctccgttcc ggagacaggg aggattgtga cgtttcgctc accattacca 23220
actgactgtc ggtagaagaa cctgacccca cacggcgaca ggtgtttctc ttcgggggca 23280
gaggtggagg cgattgcgaa gggctgcggt ccgacctgga aggcggatga ctggcagaac 23340
cccttccgcg ttcgggggtg tgctccctgt ggcggtcgct taactgattt ccttcgcggc 23400
tggccattgt gttctcctag gcagagaaac aacagacatg gaaactcagc cattgctgtc 23460
aacatcgcca cgagtgccat cacatctcgt cctcagcgac gaggaaaagg agcagagctt 23520
aagcattcca ccgcccagtc ctgccaccac ctctacccta gaagataagg aggtcgacgc 23580
atctcatgac atgcagaata aaaaagcgaa agagtctgag acagacatcg agcaagaccc 23640
gggctatgtg acaccggtgg aacacgagga agagttgaaa cgctttctag agagagagga 23700
tgaaaactgc ccaaaacaac gagcagataa ctatcaccaa gatgctggaa atagggatca 23760
gaacaccgac tacctcatag ggcttgacgg ggaagacgcg ctccttaaac atctagcaag 23820
acagtcgctc atagtcaagg atgcattatt ggacagaact gaagtgccca tcagtgtgga 23880
agagctcagc cgcgcctacg agcttaacct cttttcacct cgtactcccc ccaaacgtca 23940
gccaaacggc acctgcgagc caaatcctcg cttaaacttt tatccagctt ttgctgtgcc 24000
agaagtactg gctacctatc acatcttttt taaaaatcaa aaaattccag tctcctgccg 24060
cgctaatcgc acccgcgccg atgccctact caatctggga cctggttcac gcttacctga 24120
tatagcttcc ttggaagagg ttccaaagat cttcgagggt ctgggcaata atgagactcg 24180
ggccgcaaat gctctgcaaa agggagaaaa tggcatggat gagcatcaca gcgttctggt 24240
ggaattggaa ggcgataatg ccagactcgc agtactcaag cgaagcatcg aggtcacaca 24300
cttcgcatat cccgctgtca acctgccccc taaagtcatg acggcggtca tggaccagtt 24360
actcattaag cgcgcaagtc ccctttcaga agacatgcat gacccagatg cctgtgatga 24420
gggtaaacca gtggtcagtg atgagcagct aacccgatgg ctgggcaccg actctcccag 24480
ggatttggaa gagcgtcgca agcttatgat ggccgtggtg ctggttaccg tagaactaga 24540
gtgtctccga cgtttcttta ccgattcaga aaccttgcgc aaactcgaag agaatctgca 24600
ctacactttt agacacggct ttgtgcggca ggcatgcaag atatctaacg tggaactcac 24660
caacctggtt tcctacatgg gtattctgca tgagaatcgc ctaggacaaa gcgtgctgca 24720
cagcaccctg aagggggaag cccgccgtga ttacatccgc gattgtgtct atctgtacct 24780
gtgccacacg tggcaaaccg gcatgggtgt atggcagcaa tgtttagaag aacagaactt 24840
gaaagagctt gacaagctct tacagaaatc tcttaaggtt ctgtggacag ggttcgacga 24900
gcgcaccgtc gcttccgacc tggcagacct catcttccca gagcgtctca gggttacttt 24960

```
gcgaaacgga ttgcctgact ttatgagcca gagcatgctt aacaattttc gctctttcat  25020
cctggaacgc tccggtatcc tgcccgccac ctgctgcgca ctgccctccg actttgtgcc  25080
tctcacctac cgcgagtgcc ccccgccgct atggagtcac tgctacctgt tccgtctggc  25140
caactatctc tcctaccact cggatgtgat cgaggatgtg agcggagacg gcttgctgga  25200
gtgtcactgc cgctgcaatc tgtgcacgcc ccaccggtcc ctagcttgca acccccagtt  25260
gatgagcgaa acccagataa taggcacctt tgaattgcaa ggccccagca gccaaggcga  25320
tgggtcttct cctgggcaaa gtttaaaact gaccccggga ctgtggacct ccgcctactt  25380
gcgcaagttt gctccggaag attaccaccc ctatgaaatc aagttctatg aggaccaatc  25440
acagcctcca aaggccgaac tttcggcctg cgtcatcacc cagggggcaa ttctggccca  25500
attgcaagcc atccaaaaat cccgccaaga atttctactg aaaaagggta agggggtcta  25560
ccttgacccc cagaccggcg aggaactcaa cacaaggttc cctcaggatg tcccaacgac  25620
gagaaaacaa gaagttgaag gtgcagccgc cgcccccaga agatatggag gaagattggg  25680
acagtcaggc agaggaggcg gaggaggaca gtctggagga cagtctggag gaagacagtt  25740
tggaggagga aaacgaggag gcagaggagg tggaagaagt aaccgccgac aaacagttat  25800
cctcggctgc ggagacaagc aacagcgcta ccatctccgc tccgagtcga ggaacccggc  25860
ggcgtcccag cagtagatgg gacgagaccg gacgcttccc gaacccaacc agcgcttcca  25920
agaccggtaa gaaggatcgg cagggataca agtcctggcg gggggcataag aatgccatca  25980
tctcctgctt gcatgagtgc gggggcaaca tatccttcac gcggcgctac ttgctattcc  26040
accatggggt gaactttccg cgcaatgttt tgcattacta ccgtcacctc cacagcccct  26100
actatagcca gcaaatcccg gcagtctcga cagataaaga cagcggcggc gacctccaac  26160
agaaaaccag cagcggcagt tagaaaatac acaacaagtg cagcaacagg aggattaaag  26220
attacagcca acgagccagc gcaaacccga gagttaagaa atcggatctt tccaaccctg  26280
tatgccatct tccagcagag tcggggtcaa gagcaggaac tgaaaataaa aaaccgatct  26340
ctgcgttcgc tcaccagaag ttgtttgtat cacaagagcg aagatcaact tcagcgcact  26400
ctcgaggacg ccgaggctct cttcaacaag tactgcgcgc tgactcttaa agagtaggca  26460
gcgaccgcgc ttattcaaaa aaggcgggaa ttacatcatc ctcgacatga gtaaagaaat  26520
tcccacgcct tacatgtgga gttatcaacc ccaaatggga ttggcggcag gcgcctccca  26580
ggactactcc acccgcatga attggctcag cgccgggcct tctatgattt ctcgagttaa  26640
tgatatacgc gcctaccgaa accaaatact tttggaacag tcagctctta ccaccacgcc  26700
ccgccaacac cttaatccca gaaattggcc cgccgcccta gtgtaccagg aaagtcccgc  26760
tcccaccact gtattacttc ctcgagacgc ccaggccgaa gtccaaatga ctaatgcagg  26820
tgcgcagtta gctggcggct ccaccctatg tcgtcacagg cctcggcata atataaaacg  26880
cctgatgatc agaggccgag gtatccagct caacgacgag tcggtgagct ctccgcttgg  26940
tctacgacca gacggaatct ttcagattgc cggctgcggg agatcttcct tcacccctcg  27000
tcaggctgtt ctgactttgg aaagttcgtc ttcgcaaccc cgctcgggcg gaatcgggac  27060
cgttcaattt gtggaggagt ttactccctc tgtctacttc aaccccttct ccggatctcc  27120
tgggcattac ccggacgagt tcataccgaa cttcgacgcg attagcgagt cagtggacgg  27180
ctacgattga tgtctggtga cgcggctgag ctatctcggc tgcgacatct agaccactgc  27240
cgccgctttc gctgctttgc ccgggaactc attgagttca tctacttcga actccccaag  27300
gatcaccctc aaggtccggc ccacggagtg cggatttcta tcgaaggcaa aatagactct  27360
```

```
cgcctgcaac gaattttctc ccagcggccc gtgctgatcg agcgagacca gggaaacacc  27420
acggtttcca tctactgcat ttgtaatcac cccggattgc atgaaagcct ttgctgtctt  27480
atgtgtactg agtttaataa aaactgaatt aagactctcc tacggactgc cgcttcttca  27540
acccggattt tacaaccaga agaacgaaac ttttcctgtc gtccaggact ctgttaactt  27600
cacctttcct actcacaaac tagaagctca acgactacac cgcttttcca gaagcatttt  27660
ccctactaat actactttca aaaccggagg tgagctccaa ggtcttccta cagaaaaccc  27720
ttgggtggaa gcgggccttg tagtgctagg aattcttgcg ggtgggcttg tgattattct  27780
ttgctaccta tacacacctt gcttcacttt cttagtggtg ttgtggtatt ggtttaaaaa  27840
atggggccca tactagtctt gcttgtttta ctttcgcttt tggaaccggg ttctgccaat  27900
tacgatccat gtctagactt cgacccagaa aactgcacac ttacttttgc acccgacaca  27960
agccgcatct gtggagttca tcgcctctct tacgaacttg gcccccaacg acaaaaattt  28020
acctgcatgg tgggaatcaa ccccatagtt atcacccagc aaagtggaga tactaagggt  28080
tgcattcact gctcctgcga ttccatcgag tgcacctaca ccctgctgaa gaccctatgc  28140
ggcctaagag acctgctacc aatgaattaa aaaatgatta ataaaaaatc acttacttga  28200
aatcagcaat aaggtctctg ttgaaatttt ctcccagcag cacctcactt ccctcttccc  28260
aactctggta ttctaaaccc cgttcagcgg catactttct ccatacttta aaggggatgt  28320
caaattttag ctcctctcct gtacccacaa tcttcatgtc tttcttccca gatgaccaag  28380
agagtccggc tcagtgactc cttcaaccct gtctacccct atgaagatga aagcacctcc  28440
caacacccct ttataaaccc agggtttatt tccccaaatg gcttcacaca aagcccaaac  28500
ggagttctta ctttaaaatg tttaacccca ctaacaacca caggcggatc tctacagcta  28560
aaagtgggag gggacttac agtggatgac accaacggtt ttttgaaaga aaacataagt  28620
gccaccacac cactcgttaa gactggtcac tctataggtt taccactagg agccggattg  28680
ggaacgaatg aaaataaact ttgtatcaaa ttaggacaag gacttacatt caattcaaac  28740
aacatttgca ttgatgacaa tattaacacc ttatggacag gagtcaaccc caccgaagcc  28800
aactgtcaaa tcatgaactc cagtgaatct aatgattgca aattaattct aacactagtt  28860
aaaactggag cactagtcac tgcatttgtt tatgttatag gagtatctaa caattttaat  28920
atgctaacta cacacagaaa tataaatttt actgcagagc tgtttttcga ttctactggt  28980
aatttactaa ctagactctc atccctcaaa actccactta atcataaatc aggacaaaac  29040
atggctactg gtgccattac taatgctaaa ggtttcatgc ccagcacgac tgcctatcct  29100
ttcaatgata attctagaga aaaagaaaac tacatttacg gaacttgtta ctacacagct  29160
agtgatcgca ctgcttttcc cattgacata tctgtcatgc ttaaccgaag agcaataaat  29220
gacgagacat catattgtat tcgtataact tggtcctgga acacaggaga tgccccagag  29280
gtgcaaacct ctgctacaac cctagtcacc tccccattta ccttttacta catcagagaa  29340
gacgactgac aaataaagtt tgcgatcgct accctgcagg aacttgttta tttgaaaatc  29400
aattcacaaa atccgagtag ttattttgcc tcccccttcc catttaacag aatacaccaa  29460
tctctcccca cgcacagctt taaacatttg gataccatta gatatagaca tggttttaga  29520
ttccacattc caaacagttt cagagcgagc caatctgggg tcagtgatag ataaaaatcc  29580
atcgggatag tcttttaaag cgctttcaca gtccaactgc tgcggatgcg actccggagt  29640
ctggatcacg gtcatctgga agaagaacga tgggaatcat aatccgaaaa cggtatcgga  29700
```

-continued

```
cgattgtgtc tcatcaaacc cacaagcagc cgctgtctgc gtcgctccgt gcgactgctg  29760
tttatgggat cagggtccac agtgtcctga agcatgattt taatagccct taacatcaac  29820
tttctggtgc gatgcgcgca gcaacgcatt ctgatttcac tcaaatcttt gcagtaggta  29880
caacacatta ttacaatatt gtttaataaa ccataattaa aagcgctcca gccaaaactc  29940
atatctgata taatcgcccc tgcatgacca tcataccaaa gtttaatata aattaaatga  30000
cgttccctca aaaacacact acccacatac atgatctctt ttggcatgtg catattaaca  30060
atctgtctgt accatggaca acgttggtta atcatgcaac ccaatataac cttccggaac  30120
cacactgcca acaccgctcc cccagccatg cattgaagtg aaccctgctg attacaatga  30180
caatgaagaa cccaattctc tcgaccgtga atcacttgag aatgaaaaat atctatagtg  30240
gcacaacata gacataaatg catgcatctt ctcataattt ttaactcctc aggatttaga  30300
aacatatccc agggaatagg aagctcttgc agaacagtaa agctggcaga acaaggaaga  30360
ccacgaacac aacttacact atgcatagtc atagtatcac aatctggcaa cagcgggtgg  30420
tcttcagtca tagaagctcg ggtttcattt tcctcacaac gtggtaactg ggctctggtg  30480
taagggtgat gtctggcgca tgatgtcgag cgtgcgcgca accttgtcat aatggagttg  30540
cttcctgaca ttctcgtatt ttgtatagca aaacgcggcc ctggcagaac acactcttct  30600
tcgccttcta tcctgccgct tagcgtgttc cgtgtgatag ttcaagtaca accacactct  30660
taagttggtc aaaagaatgc tggcttcagt tgtaatcaaa actccatcgc atctaatcgt  30720
tctgaggaaa tcatccaagc aatgcaactg gattgtgttt caagcaggag aggagaggga  30780
agagacggaa gaaccatgtt aatttttatt ccaaacgatc tcgcagtact tcaaattgta  30840
gatcgcgcag atggcatctc tcgcccccac tgtgttggtg aaaaagcaca gctagatcaa  30900
aagaaatgcg attttcaagg tgctcaacgg tggcttccag caaagcctcc acgcgcacat  30960
ccaagaacaa aagaatacca aaagaaggag cattttctaa ctcctcaatc atcatattac  31020
attcctgcac cattcccaga taattttcag ctttccagcc ttgaattatt cgtgtcagtt  31080
cttgtggtaa atccaatcca cacattacaa acaggtcccg gagggcgccc tccaccacca  31140
ttcttaaaca caccctcata atgacaaaat atcttgctcc tgtgtcacct gtagcgaatt  31200
gagaatggca acatcaattg acatgccctt ggctctaagt tcttctttaa gttctagttg  31260
taaaaactct ctcatattat caccaaactg cttagccaga agccccccgg gaacaagagc  31320
aggggacgct acagtgcagt acaagcgcag acctccccaa ttggctccag caaaaacaag  31380
attggaataa gcatattggg aaccgccagt aatatcatcg aagttgctgg aaatataatc  31440
aggcagagtt tcttgtaaaa attgaataaa agaaaaattt gccaaaaaaa cattcaaaac  31500
ctctgggatg caaatgcaat aggttaccgc gctgcgctcc aacattgtta gttttgaatt  31560
agtctgcaaa aataaaaaaa aaaacaagcg tcatatcata gtagcctgac gaacagatgg  31620
ataaatcagt ctttccatca caagacaagc cacagggtct ccagctcgac cctcgtaaaa  31680
cctgtcatca tgattaaaca acagcaccga aagttcctcg cggtgaccag catgaataat  31740
tcttgatgaa gcatacaatc cagacatgtt agcatcagtt aacgagaaaa aacagccaac  31800
atagcctttg ggtataatta tgcttaatcg taagtatagc aaagccaccc ctcgcggata  31860
caaagtaaaa ggcacaggag aataaaaaat ataattattt ctctgctgct gttcaggcaa  31920
cgtcgccccc ggtccctcta aatacacata caaagcctca tcagccatgg cttaccagac  31980
aaagtacagc gggcacacaa agcacaagct ctaaagtgac tctccaacct ctccacaata  32040
tatatataca caagccctaa actgacgtaa tgggagtaaa gtgtaaaaaa tcccgccaaa  32100
```

```
cccaacacac accccgaaac tgcgtcacca gggaaaagta cagtttcact tccgcaatcc  32160

caacaggcgt aacttcctct ttctcacggt acgtgatatc ccactaactt gcaacgtcat  32220

tttcccacgg tcgcaccgcc ccttttagcc gttaacccca cagccaatca ccacacgatc  32280

cacacttttt aaaatcacct catttacata ttggcaccat tccatctata aggtatatta  32340

tatagatagg                                                          32350
```

<210> SEQ ID NO 33
<211> LENGTH: 32458
<212> TYPE: DNA
<213> ORGANISM: Artificial Sequence
<220> FEATURE:
<223> OTHER INFORMATION: ColoAd2.0 genome

<400> SEQUENCE: 33

```
cgcgcctatc tatataatat accttataga tggaatggtg ccaatatgta aatgaggtga     60

ttttaaaaag tgtggatcgt gtggtgattg gctgtggggt taacggctaa aaggggcggt    120

gcgaccgtgg gaaaatgacg ttttgtgggg gtggagtttt tttgcaagtt gtcgcgggaa    180

atgtgacgca taaaaaggct tttttctcac ggaactactt agttttccca cggtatttaa    240

caggaaatga ggtagttttg accggatgca agtgaaaatt gttgattttc gcgcgaaaac    300

tgaatgagga agtgtttttc tgaataatgt ggtatttatg gcagggtgga gtatttgttc    360

agggccaggt agactttgac ccattacgtg gaggtttcga ttaccgtgtt ttttacctga    420

atttccgcgt accgtgtcaa agtcttctgt ttttacgtag gtgtcagctg atcgctaggg    480

tatttatacc tcagggtttg tgtcaagagg ccactcttga gtgccagcga gaagagtttt    540

ctcctctgcg ccggcagttt aataataaaa aaatgagaga tttgcgattt ctgcctcagg    600

aaataatctc tgctgagact ggaaatgaaa tattggagct tgtggtgcac gccctgatgg    660

gagacgatcc ggagccacct gtgcagcttt ttgagcctcc tacgcttcag gaactgtatg    720

atttagaggt agagggatcg gaggattcta atgaggaagc tgtaaatggc tttttttaccg    780

attctatgct tttagctgct aatgaagggt tagaattaga tccgcctttg gacacttttg    840

atactccagg ggtaattgtg gaaagcggta caggtgtaag aaaattacct gatttgagtt    900

ccgtggactg tgatttgcac tgctatgaag acgggtttcc tccgagtgat gaggaggacc    960

atgaaaagga gcagtccatg cagactgcag cgggtgaggg agtgaaggct gccaatgttg   1020

gttttcagtt ggattgcccg gagcttcctg gacatggctg taagtcttgt gaatttcaca   1080

ggaaaaatac tggagtaaag gaactgttat gttcgctttg ttatatgaga acgcactgcc   1140

actttattta cagtaagtgt gtttaagtta aaatttaaag gaatatgctg tttttcacat   1200

gtatattgag tgtgagtttt gtgcttctta ttataggtcc tgtgtctgat gctgatgaat   1260

caccatctcc tgattctact acctcacctc ctgagattca agcacctgtt cctgtggacg   1320

tgcgcaagcc cattcctgtg aagcttaagc ctgggaaacg tccagcagtg gaaaaacttg   1380

aggacttgtt acagggtggg gacggacctt tggacttgag tacacggaaa cgtccaagac   1440

aataagtgtt ccatatccgt gtttacttaa ggtgacgtca atatttgtgt gacagtgcaa   1500

tgtaataaaa atatgttaac tgttcactgg tttttattgc tttttgggcg ggactcagg   1560

tatataagta gaagcagacc tgtgtggtta gctcatagga gctggctttc atccatggag   1620

gtttgggcca ttttggaaga ccttaggaag actaggcaac tgttagagaa cgcttcggac   1680

ggagtctccg gtttttggag attctggttc gctagtgaat tagctagggt agtttttagg   1740
```

-continued

```
ataaaacagg actataaaca agaatttgaa aagttgttgg tagattgccc aggacttttt   1800
gaagctctta atttgggcca tcaggttcac tttaaagaaa aagttttatc agttttagac   1860
ttttcaaccc caggtagaac tgctgctgct gtggcttttc ttacttttat attagataaa   1920
tggatcccgc agactcattt cagcagggga tacgttttgg atttcatagc cacagcattg   1980
tggagaacat ggaaggttcg caagatgagg acaatcttag gttactggcc agtgcagcct   2040
ttgggtgtag cgggaatcct gaggcatcca ccggtcatgc cagcggttct ggaggaggaa   2100
cagcaagagg acaacccgag agccggcctg gaccctccag tggaggaggc ggagtagctg   2160
acttgtctcc tgaactgcaa cgggtgctta ctggatctac gtccactgga cgggataggg   2220
gcgttaagag ggagagggca tctagtggta ctgatgctag atctgagttg gctttaagtt   2280
taatgagtcg cagacgtcct gaaaccattt ggtggcatga ggttcagaaa gagggaaggg   2340
atgaagtttc tgtattgcag gagaaatatt cactggaaca ggtgaaaaca tgttggttgg   2400
agcctgagga tgattgggag gtggccatta aaaattatgc caagatagct ttgaggcctg   2460
ataaacagta taagattact agacggatta atatccggaa tgcttgttac atatctggaa   2520
atggggctga ggtggtaata gatactcaag acaaggcagt tattagatgc tgcatgatgg   2580
atatgtggcc tggggtagtc ggtatggaag cagtaacttt tgtaaatgtt aagtttaggg   2640
gagatggtta taatggaata gtgtttatgg ccaataccaa acttatattg catggttgta   2700
gcttttttgg tttcaacaat acctgtgtag atgcctgggg acaggttagt gtacggggat   2760
gtagtttcta tgcgtgttgg attgccacag ctggcagaac caagagtcaa ttgtctctga   2820
agaaatgcat atttcaaaga tgtaacctgg gcattctgaa tgaaggcgaa gcaagggtcc   2880
gccactgcgc ttctacagat actggatgtt ttattttgat taagggaaat gccagcgtaa   2940
agcataacat gatttgcggt gcttccgatg agaggcctta tcaaatgctc acttgtgctg   3000
gtgggcattg taatatgctg gctactgtgc atattgtttc ccatcaacgc aaaaaatggc   3060
ctgtttttga tcacaatgtg atgacgaagt gtaccatgca tgcaggtggg cgtagaggaa   3120
tgtttatgcc ttaccagtgt aacatgaatc atgtgaaagt gttgttggaa ccagatgcct   3180
tttccagaat gagcctaaca ggaatttttg acatgaacat gcaaatctgg aagatcctga   3240
ggtatgatga tacgagatcg agggtacgcg catgcgaatg cggaggcaag catgccaggt   3300
tccagccggt gtgtgtagat gtgactgaag atctcagacc ggatcatttg gttattgccc   3360
gcactggagc agagttcgga tccagtggag aagaaactga ctaaggtgag tattgggaaa   3420
actttggggt gggattttca gatggacaga ttgagtaaaa atttgttttt tctgtcttgc   3480
agctgtcatg agtggaaacg cttcttttaa ggggggagtc ttcagccctt atctgacagg   3540
gcgtctccca tcctgggcag gagttcgtca gaatgttatg ggatctactg tggatggaag   3600
acccgtccaa cccgccaatt cttcaacgct gacctatgct actttaagtt cttcaccttt   3660
ggacgcagct gcagctgccg ccgccgcttc tgttgccgct aacactgtgc ttggaatggg   3720
ttactatgga agcatcatgg ctaattccac ttcctctaat aacccttcta ccctgactca   3780
ggacaagtta cttgtccttt tggcccagct ggaggctttg acccaacgtc tgggtgaact   3840
ttctcagcag gtggtcgagt tgcgagtaca aactgagtct gctgtcggca cggcaaagtc   3900
taaataaaaa aatcccagaa tcaatgaata aataaacaag cttgttgttg atttaaaatc   3960
aagtgttttt atttcatttt tcgcgcacgg tatgccctag accaccgatc tctatcattg   4020
agaactcggt ggatttttttc caggatccta tagaggtggg attgaatgtt tagatacatg   4080
ggcattaggc cgtctttggg gtggagatag ctccattgaa gggattcatg ctccggggta   4140
```

gtgttgtaaa tcacccagtc ataacaaggt cgcagtgcat ggtgttgcac aatatctttt 4200
agaagtaggc tgattgccac agataagccc ttggtgtagg tgtttacaaa ccggttgagc 4260
tgggatgggt gcattcgggg tgaaattatg tgcattttgg attggatttt taagttggca 4320
atattgccgc caagatcccg tcttgggttc atgttatgaa ggaccaccaa gacggtgtat 4380
ccggtacatt taggaaattt atcgtgcagc ttggatggaa aagcgtggaa aaatttggag 4440
acacccttgt gtcctccaag attttccatg cactcatcca tgataatagc aatggggccg 4500
tgggcagcgg cgcgggcaaa cacgttccgt gggtctgaca catcatagtt atgttcctga 4560
gttaaatcat cataagccat tttaatgaat ttggggcgga gagtaccaga ttggggtatg 4620
aatgttcctt cgggccccgg agcatagttc ccctcacaga tttgcatttc ccaagctttc 4680
agttccgagg gtggaatcat gtccacctgg ggggctatga aaaacaccgt ttctggggcg 4740
ggggtgatta attgtgatga tagcaaattt ctgagcaatt gagatttgcc acatccggtg 4800
gggccataaa tgattccgat tacgggttgc aggtggtagt ttagggaacg gcaactgccg 4860
tcttctcgaa gcaagggggc cacctcgttc atcatttccc ttacatgcat attttcccgc 4920
accaaatcca ttaggaggcg ctctcctcct agtgatagaa gttcttgtag tgaggaaaag 4980
tttttcagcg gtttcagacc gtcagccatg ggcattttgg agagagtttg ctgcaaaagt 5040
tctagtctgt tccacagttc agtgatgtgt tctatggcat ctcgatccag cagacctcct 5100
cgtttcgcgg gtttggacgg ctcctggaat agggtatgag acgatgggcg tccagcgctg 5160
ccagggttcg gtccttccag ggtctcagtg ttcgagtcag ggttgtttcc gtcacagtga 5220
aggggtgtgc gcctgcttgg gcgcttgcca gggtgcgctt cagactcatc ctgctggtcg 5280
aaaacttctg tcgcttggcg ccctgtatgt cggccaagta gcagtttacc atgagttcgt 5340
agttgagcgc ctcggctgcg tggcctttgg cgcggagctt acctttggaa gttttcttgc 5400
ataccgggca gtataggcat ttcagcgcat acaacttggg cgcaaggaaa acggattctg 5460
gggagtatgc atctgcgccg caggaggcgc aaacagtttc acattccacc agccaggtta 5520
aatccggttc attggggtca aaaacaagtt ttccgccata ttttttgatg cgtttcttac 5580
ctttggtctc catgagttcg tgtcctcgtt gagtgacaaa caggctgtcc gtgtccccgt 5640
agactgattt tacaggcctc ttctccagtg gagtgcctcg gtcttcttcg tacaggaact 5700
ctgaccactc tgatacaaag gcgcgcgtcc aggccagcac aaaggaggct atgtgggagg 5760
ggtagcgatc gttgtcaacc agggggtcca ccttttccaa agtatgcaaa cacatgtcac 5820
cctcttcaac atccaggaat gtgattggct tgtaggtgta tttcacgtga cctggggtcc 5880
ccgctggggg ggtataaaag gggcggttc tttgctcttc ctcactgtct tccggatcgc 5940
tgtccaggaa cgtcagctgt tggggtaggt attccctctc gaaggcgggc atgacctctg 6000
cactcaggtt gtcagtttct aagaacgagg aggatttgat attgacagtg ccggttgaga 6060
tgcctttcat gaggttttcg tccatctggt cagaaaacac aatttttta ttgtcaagtt 6120
tggtggcaaa tgatccatac agggcgttgg ataaaagttt ggcaatggat cgcatggttt 6180
ggttcttttc cttgtccgcg cgctctttgg cggcgatgtt gagttggaca tactcgcgtg 6240
ccaggcactt ccattcgggg aagatagttg ttaattcatc tggcacgatt ctcacttgcc 6300
accctcgatt atgcaaggta attaaatcca cactggtggc cacctcgcct cgaaggggtt 6360
cattggtcca acagagccta cctcctttcc tagaacagaa agggggaagt gggtctagca 6420
taagttcatc gggagggtct gcatccatgg taaagattcc cggaagtaaa tccttatcaa 6480

-continued aatagctgat gggagtgggg tcatctaagg ccatttgcca ttctcgagct gccagtgcgc 6540
gctcatatgg gttaagggga ctgccccatg gcatgggatg ggtgagtgca gaggcataca 6600
tgccacagat gtcatagacg tagatgggat cctcaaagat gcctatgtag gttggatagc 6660
atcgcccccc tctgatactt gctcgcacat agtcatatag ttcatgtgat ggcgctagca 6720
gccccggacc caagttggtg cgattgggtt tttctgttct gtagacgatc tggcgaaaga 6780
tggcgtgaga attggaagag atggtgggtc tttgaaaaat gttgaaatgg gcatgaggta 6840
gacctacaga gtctctgaca aagtgggcat aagattcttg aagcttggtt accagttcgg 6900
cggtgacaag tacgtctagg gcgcagtagt caagtgtttc ttgaatgatg tcataacctg 6960
gttggttttt cttttcccac agttcgcggt tgagaaggta ttcttcgcga tccttccagt 7020
actcttctag cggaaacccg tctttgtctg cacggtaaga tcctagcatg tagaactgat 7080
taactgcctt gtaagggcag cagcccttct ctacgggtag agagtatgct tgagcagctt 7140
ttcgtagcga agcgtgagta agggcaaagg tgtctctgac catgactttg aggaattggt 7200
atttgaagtc gatgtcgtca caggctccct gttcccagag ttggaagtct acccgtttct 7260
tgtaggcggg gttgggcaaa gcgaaagtaa catcattgaa gagaatcttg ccggccctgg 7320
gcatgaaatt gcgagtgatg cgaaaaggct gtggtacttc cgctcggtta ttgataacct 7380
gggcagctag gacgatctcg tcgaaaccgt tgatgttgtg tcctacgatg tataattcta 7440
tgaaacgcgg cgtgcctctg acgtgaggta gcttactgag ctcatcaaag gttaggtctg 7500
tggggtcaga taaggcgtag tgttcgagag cccattcgtg caggtgagga ttcgctttaa 7560
ggaaggagga ccagaggtcc actgccagtg ctgtttgtaa ctggtcccgg tactgacgaa 7620
aatgccgtcc gactgccatt ttttctgggg tgacgcaata gaaggtttgg gggtcctgcc 7680
gccagcgatc ccacttgagt tttatggcga ggtcataggc gatgttgacg agccgctggt 7740
ctccagagag tttcatgacc agcatgaagg ggattagctg cttgccaaag gaccccatcc 7800
aggtgtaggt ttccacatcg taggtgagaa agagcctttc tgtgcgagga tgagagccaa 7860
tcgggaagaa ctggatctcc tgccaccagt tggaggaatg gctgttgatg tgatggaagt 7920
agaactccct gcgacgcgcc gagcattcat gcttgtgctt gtacagacgg ccgcagtagt 7980
cgcagcgttg cacgggttgt atctcgtgaa tgagttgtac ctggcttccc ttgacgagaa 8040
atttcagtgg gaagccgagg cctggcgatt gtatctcgtg ctttactatg ttgtctgcat 8100
cggcctgttc atcttctgtc tcgatggtgg tcatgctgac gagccctcgc gggaggcaag 8160
tccagacctc ggcgcggcag ggcggagct cgaggacgag agcgcgcagg ctggagctgt 8220
ccagggtcct gagacgctgc ggactcaggt tagtaggcag tgtcaggaga ttaacttgca 8280
tgatcttttg gagggcgtgc gggaggttca gatagtactt gatctcaacg ggtccgttgg 8340
tggagatgtc gatggcttgc agggttccgt gtcccttggg cgctaccacc gtgcccttgt 8400
ttttcatttt ggacggcggt ggctctgttg cttcttgcat gtttagaagc ggtgtcgagg 8460
gcgcgcaccg ggcggcaggg gcggctcggg acccggcggc atggctggca gtggtacgtc 8520
ggcgccgcgc gcgggtaggt tctggtactg cgccctgaga agactcgcat gcgcgacgac 8580
gcggcggttg acatcctgga tctgacgcct ctgggtgaaa gctaccggcc ccgtgagctt 8640
gaacctgaaa gagagttcaa cagaatcaat ctcggtatcg ttgacggcgg cttgcctaag 8700
gatttcttgc acgtcaccag agttgtcctg gtaggcgatc tccgccatga actgctcgat 8760
ctcttcctct tgaagatctc cgcggcccgc tctctcgacg gtggccgcga ggtcgttgga 8820
gatgcgccca atgagttgag agaatgcatt catgcccgcc tcgttccaga cgcggctgta 8880

```
gaccacggcc cccacgggat ctctcgcgcg catgaccacc tgggcgaggt tgagctccac   8940
gtggcgggtg aagaccgcat agttgcatag gcgctggaaa aggtagttga gtgtggtggc   9000
gatgtgctcg gtgacgaaga aatacatgat ccatcgtctc agcggcatct cgctgacatc   9060
gcccagagct tccaagcgct ccatggcctc gtagaagtcc acggcaaaat taaaaaactg   9120
ggagtttcgc gcggacacgg tcaactcctc ttccagaaga cggataagtt cggcgatggt   9180
ggtgcgcacc tcgcgctcga aagcccctgg gatttcttcc tcaatctctt cttcttccac   9240
taacatctct tcctcttcag gtggggctgc aggaggaggg ggaacgcggc gacgccggcg   9300
gcgcacgggc agacggtcga tgaatctttc aatgacctct ccgcggcggc ggcgcatggt   9360
ttcagtgacg gcgcggccgt tctcgcgcgg tcgcagagta aaaacaccgc cgcgcatctc   9420
cttaaagtgg tgactgggag gttctccgtt tgggagggag agggcgctga ttatacattt   9480
tattaattgg cccgtaggga ctgcacgcag agatctgatc gtgtcaagat ccacgggatc   9540
tgaaaacctt tcgacgaaag cgtctaacca gtcacagtca caaggtaggc tgagtacggc   9600
ttcttgtggg cgggggtggt tatgtgttcg gtctgggtct tctgtttctt cttcatctcg   9660
ggaaggtgag acgatgctgc tggtgatgaa attaaagtag gcagttctaa gacggcggat   9720
ggtggcgagg agcaccaggt ctttgggtcc ggcttgctgg atacgcaggc gattggccat   9780
tccccaagca ttatcctgac atctagcaag atctttgtag tagtcttgca tgagccgttc   9840
tacgggcact tcttcctcac ccgttctgcc atgcatacgt gtgagtccaa atccgcgcat   9900
tggttgtacc agtgccaagt cagctacgac tctttcggcg aggatggctt gctgtacttg   9960
ggtaagggtg gcttgaaagt catcaaaatc cacaaagcgg tggtaagctc ctgtattaat  10020
ggtgtaagca cagttggcca tgactgacca gttaactgtc tggtgaccag ggcgcacgag  10080
ctcggtgtat ttaaggcgcg aataggcgcg ggtgtcaaag atgtaatcgt tgcaggtgcg  10140
caccagatac tggtacccta taagaaaatg cggcggtggt tggcggtaga gaggccatcg  10200
ttctgtagct ggagcgccag ggcgaggtc ttccaacata aggcggtgat agccgtagat  10260
gtacctggac atccaggtga ttcctgcggc ggtagtagaa gcccgaggaa actcgcgtac  10320
gcggttccaa atgttgcgta gcggcatgaa gtagttcatt gtaggcacgg tttgaccagt  10380
gaggcgcgcg cagtcattga tgctctatag acacggagaa aatgaaagcg ttcagcgact  10440
cgactccgta gcctggagga acgtgaacgg gttgggtcgc ggtgtacccc ggttcgagac  10500
ttgtactcga gccggccgga gccgcggcta acgtggtatt ggcactcccg tctcgaccca  10560
gcctacaaaa atccaggata cggaatcgag tcgttttgct ggtttccgaa tggcagggaa  10620
gtgagtccta tttttttttt ttgccgctca gatgcatccc gtgctgcgac agatgcgccc  10680
ccaacaacag ccccccctcgc agcagcagca gcagcaatca caaaaggctg tccctgcaac  10740
tactgcaact gccgccgtga gcggtgcggg acagcccgcc tatgatctgg acttggaaga  10800
gggcgaagga ctggcacgtc taggtgcgcc ttcacccgag cggcatccgc gagttcaact  10860
gaaaaaagat tctcgcgagg cgtatgtgcc ccaacagaac ctatttagag acagaagcgg  10920
cgaggagccg gaggagatgc gagcttcccg ctttaacgcg ggtcgtgagc tgcgtcacgg  10980
tttggaccga agacgagtgt tgcgggacga ggatttcgaa gttgatgaaa tgacagggat  11040
cagtcctgcc agggcacacg tggctgcagc caaccttgta tcggcttacg agcagacagt  11100
aaaggaagag cgtaacttcc aaaagtcttt taataatcat gtgcgaaccc tgattgcccg  11160
cgaagaagtt acccttggtt tgatgcattt gtgggatttg atggaagcta tcattcagaa  11220
```

-continued

```
ccctactagc aaacctctga ccgcccagct gtttctggtg gtgcaacaca gcagagacaa  11280
tgaggctttc agagaggcgc tgctgaacat caccgaaccc gaggggagat ggttgtatga  11340
tcttatcaac attctacaga gtatcatagt gcaggagcgg agcctgggcc tggccgagaa  11400
ggtggctgcc atcaattact cggttttgag cttgggaaaa tattacgctc gcaaaatcta  11460
caagactcca tacgttccca tagacaagga ggtgaagata gatgggttct acatgcgcat  11520
gacgctcaag gtcttgaccc tgagcgatga tcttggggtg tatcgcaatg acagaatgca  11580
tcgcgcggtt agcgccagca ggaggcgcga gttaagcgac agggaactga tgcacagttt  11640
gcaaagagct ctgactggag ctggaaccga gggtgagaat tacttcgaca tgggagctga  11700
cttgcagtgg cagcctagtc gcagggctct gagcgccgcg acggcaggat gtgagcttcc  11760
ttacatagaa gaggcggatg aaggcgagga ggaagagggc gagtacttgg aagactgatg  11820
gcacaacccg tgtttttgc tagatggaac agcaagcacc ggatcccgca atgcgggcgg  11880
cgctgcagag ccagccgtcc ggcattaact cctcggacga ttggacccag gccatgcaac  11940
gtatcatggc gttgacgact cgcaaccccg aagcctttag acagcaaccc caggccaacc  12000
gtctatcggc catcatggaa gctgtagtgc cttcccgctc taatcccact catgagaagg  12060
tcctggccat cgtgaacgcg ttggtggaga acaaagctat tcgtccagat gaggccggac  12120
tggtatacaa cgctctctta gaacgcgtgg ctcgctacaa cagtagcaat gtgcaaacca  12180
atttggaccg tatgataaca gatgtacgcg aagccgtgtc tcagcgcgaa aggttccagc  12240
gtgatgccaa cctgggttcg ctggtggcgt taaatgcttt cttgagtact cagcctgcta  12300
atgtgccgcg tggtcaacag gattatacta actttttaag tgctttgaga ctgatggtat  12360
cagaagtacc tcagagcgaa gtgtatcagt ccggtcctga ttacttcttt cagactagca  12420
gacagggctt gcagacggta aatctgagcc aagcttttaa aaacctttaa aggtttgtgg  12480
ggagtgcatg ccccggtagg agaaagagca accgtgtcta gcttgttaac tccgaactcc  12540
cgcctattat tactgttggt agctcctttc accgacagcg gtagcatcga ccgtaattcc  12600
tatttgggtt acctactaaa cctgtatcgc gaagccatag ggcaaagtca ggtggacgag  12660
cagacctatc aagaaattac ccaagtcagt cgcgctttgg gacaggaaga cactggcagt  12720
ttggaagcca ctctgaactt cttgcttacc aatcggtctc aaaagatccc tcctcaatat  12780
gctcttactg cggaggagga gaggatcctt agatatgtgc agcagagcgt gggattgttt  12840
ctgatgcaag agggggcaac tccgactgca gcactggaca tgacagcgcg aaatatggag  12900
cccagcatgt atgccagtaa ccgacctttc attaacaaac tgctggacta cttgcacaga  12960
gctgccgcta tgaactctga ttatttcacc aatgccatct taaacccgca ctggctgccc  13020
ccacctggtt tctacacggg cgaatatgac atgcccgacc ctaatgacgg atttctgtgg  13080
gacgacgtgg acagcgatgt tttttcacct ctttctgatc atcgcacgtg gaaaaaggaa  13140
ggcggcgata gaatgcattc ttctgcatcg ctgtccgggg tcatgggtgc taccgcggct  13200
gagcccgagt ctgcaagtcc ttttcctagt ctaccctttt ctctacacag tgtacgtagc  13260
agcgaagtgg gtagaataag tcgcccgagt ttaatgggcg aagaggagta tctaaacgat  13320
tccttgctca gaccggcaag agaaaaaaat ttcccaaaca atggaataga aagtttggtg  13380
gataaaatga gtagatggaa gacttatgct caggatcaca gagacgagcc tgggatcatg  13440
gggattacaa gtagagcgag ccgtagacgc cagcgccatg acagacagag gggtcttgtg  13500
tgggacgatg aggattcggc cgatgatagc agcgtgctgg acttgggtgg gagaggaagg  13560
ggcaacccgt ttgctcattt gcgccctcgc ttgggtggta tgttgtaaaa aaaaataaaa  13620
```

aaaaaactca ccaaggccat ggcgacgagc gtacgttcgt tcttctttat tatctgtgtc 13680
tagtataatg aggcgagtcg tgctaggcgg agcggtggtg tatccggagg gtcctcctcc 13740
ttcgtacgag agcgtgatgc agcagcagca ggcgacggcg gtgatgcaat ccccactgga 13800
ggctcccttt gtgcctccgc gatacctggc acctacggag ggcagaaaca gcattcgtta 13860
ttcggaactg gcacctcagt acgataccac caggttgtat ctggtggaca acaagtcggc 13920
ggacattgct tctctgaact atcagaatga ccacagcaac ttcttgacca cggtggtgca 13980
aaacaatgac tttacccta cggaagccag cacccagacc attaactttg atgaacgatc 14040
gcggtggggc ggtcagctaa agaccatcat gcatactaac atgccaaacg tgaacgagta 14100
tatgtttagt aacaagttca aagcgcgtgt gatggtgtcc agaaaacctc ccgacggtgc 14160
tgcagttggg gatacttatg atcacaagca ggatattttg aaatatgagt ggttcgagtt 14220
tactttgcca gaaggcaact tttcagttac tatgactatt gatttgatga acaatgccat 14280
catagataat tacttgaaag tgggtagaca gaatggagtg cttgaaagtg acattggtgt 14340
taagttcgac accaggaact tcaagctggg atgggatccc gaaaccaagt tgatcatgcc 14400
tggagtgtat acgtatgaag ccttccatcc tgacattgtc ttactgcctg gctgcggagt 14460
ggattttacc gagagtcgtt tgagcaacct tcttggtatc agaaaaaaac agccatttca 14520
agagggtttt aagattttgt atgaagattt agaaggtggt aatattccgg ccctcttgga 14580
tgtagatgcc tatgagaaca gtaagaaaga acaaaaagcc aaaatagaag ctgctacagc 14640
tgctgcagaa gctaaggcaa acatagttgc cagcgactct acaagggttg ctaacgctgg 14700
agaggtcaga ggagacaatt ttgcgccaac acctgttccg actgcagaat cattattggc 14760
cgatgtgtct gaaggaacgg acgtgaaact cactattcaa cctgtagaaa aagatagtaa 14820
gaatagaagc tataatgtgt tggaagacaa aatcaacaca gcctatcgca gttggtatct 14880
ttcgtacaat tatggcgatc ccgaaaaagg agtgcgttcc tggacattgc tcaccacctc 14940
agatgtcacc tgcggagcag agcaggtcta ctggtcgctt ccagacatga tgaaggatcc 15000
tgtcactttc cgctccacta gacaagtcag taactaccct gtggtgggtg cagagcttat 15060
gcccgtcttc tcaaagagct tctacaacga acaagctgtg tactcccagc agctccgcca 15120
gtccacctcg cttacgcacg tcttcaaccg ctttcctgag aaccagattt taatccgtcc 15180
gccggcgccc accattacca ccgtcagtga aaacgttcct gctctcacag atcacgggac 15240
cctgccgttg cgcagcagta tccggggagt ccaacgtgtg accgttactg acgccagacg 15300
ccgcacctgt ccctacgtgt acaaggcact gggcatagtc gcaccgcgcg tcctttcaag 15360
ccgcactttc taaaaaaaaa aaaaatgtcc attcttatct cgcccagtaa taacaccggt 15420
tggggtctgc gcgctccaag caagatgtac ggaggcgcac gcaaacgttc tacccaacat 15480
cctgtccgtg ttcgcggaca ttttcgcgct ccatggggcg ccctcaaggg ccgcactcgc 15540
gttcgaacca ccgtcgatga tgtaatcgat caggtggttg ccgacgcccg taattatact 15600
cctactgcgc ctacatctac tgtggatgca gttattgaca gtgtagtggc tgacgctcgc 15660
aactatgctc gacgtaagag ccggcgaagg cgcattgcca gacgccaccg agctaccact 15720
gccatgcgag ccgcaagagc tctgctacga agagctagac gcgtggggcg aagagccatg 15780
cttagggcgg ccagacgtgc agcttcgggc gccagcgccg gcaggtcccg caggcaagca 15840
gccgctgtcg cagcggcgac tattgccgac atggcccaat cgcgaagagg caatgtatac 15900
tgggtgcgtg acgctgccac cggtcaacgt gtacccgtgc gcacccgtcc ccctcgcact 15960
tagaagatac tgagcagtct ccgatgttgt gtcccagcgg cgaggatgtc caagcgcaaa 16020
tacaaggaag aaatgctgca ggttatcgca cctgaagtct acggccaacc gttgaaggat 16080
gaaaaaaaac cccgcaaaat caagcgggtt aaaaaggaca aaaaagaaga ggaagatggc 16140
gatgatgggc tggcggagtt tgtgcgcgag tttgccccac ggcgacgcgt gcaatggcgt 16200
gggcgcaaag ttcgacatgt gttgagacct ggaacttcgg tggtctttac acccggcgag 16260
cgttcaagcg ctacttttaa gcgttcctat gatgaggtgt acggggatga tgatattctt 16320
gagcaggcgg ctgaccgatt aggcgagttt gcttatggca agcgtagtag aataacttcc 16380
aaggatgaga cagtgtcgat acccttggat catggaaatc ccacccctag tcttaaaccg 16440
gtcactttgc agcaagtgtt acccgtaact ccgcgaacag gtgttaaacg cgaaggtgaa 16500
gatttgtatc ccactatgca actgatggta cccaaacgcc agaagttgga ggacgttttg 16560
gagaaagtaa aagtggatcc agatattcaa cctgaggtta aagtgagacc cattaagcag 16620
gtagcgcctg gtctgggggt acaaactgta gacattaaga ttcccactga aagtatggaa 16680
gtgcaaactg aacccgcaaa gcctactgcc acctccactg aagtgcaaac ggatccatgg 16740
atgcccatgc ctattacaac tgacgccgcc ggtcccactc gaagatcccg acgaaagtac 16800
ggtccagcaa gtctgttgat gcccaattat gttgtacacc catctattat tcctactcct 16860
ggttaccgag gcactcgcta ctatcgcagc cgaaacagta cctcccgccg tcgccgcaag 16920
acacctgcaa atcgcagtcg tcgccgtaga cgcacaagca aaccgactcc cggcgccctg 16980
gtgcggcaag tgtaccgcaa tggtagtgcg gaacctttga cactgccgcg tgcgcgttac 17040
catccgagta tcatcactta atcaatgttg ccgctgcctc cttgcagata tggccctcac 17100
ttgtcgcctt cgcgttccca tcactggtta ccgaggaaga aactcgcgcc gtagaagagg 17160
gatgttggga cgcggaatgc gacgctacag gcgacggcgt gctatccgca agcaattgcg 17220
gggtggtttt ttaccagcct taattccaat tatcgctgct gcaattggcg cgataccagg 17280
catagcttcc gtggcggttc aggcctcgca acgacattga cattggaaaa aaacgtataa 17340
ataaaaaaaa aaaaatacaa tggactctga cactcctggt cctgtgacta tgttttctta 17400
gagatggaag acatcaattt ttcatccttg gctccgcgac acggcacgaa gccgtacatg 17460
ggcacctgga gcgacatcgg cacgagccaa ctgaacgggg gcgccttcaa ttggagcagt 17520
atctggagcg ggcttaaaaa ttttggctca accataaaaa catacgggaa caaagcttgg 17580
aacagcagta caggacaggc gcttagaaat aaacttaaag accagaactt ccaacaaaaa 17640
gtagtcgatg ggatagcttc cggcatcaat ggagtggtag atttggctaa ccaggctgtg 17700
cagaaaaaga taaacagtcg tttggacccg ccgccagcaa ccccaggtga aatgcaagtg 17760
gaggaagaaa ttcctccgcc agaaaaacga ggcgacaagc gtccgcgtcc cgatttggaa 17820
gagacgctgg tgacgcgcgt agatgaaccg ccttcttatg aggaagcaac gaagcttgga 17880
atgcccacca ctagaccgat agccccaatg gccaccgggg tgatgaaacc ttctcagttg 17940
catcgacccg tcaccttgga tttgccccct ccccctgctg ctactgctgt acccgcttct 18000
aagcctgtcg ctgccccgaa accagtcgcc gtagccaggt cacgtcccgg gggcgctcct 18060
cgtccaaatg cgcactggca aaatactctg aacagcatcg tgggtctagg cgtgcaaagt 18120
gtaaaacgcc gtcgctgctt ttaattaaat atggagtagc gcttaacttg cctatctgtg 18180
tatatgtgtc attacacgcc gtcacagcag cagaggaaaa aaggaagagg tcgtgcgtcg 18240
acgctgagtt actttcaaga tggccacccc atcgatgctg ccccaatggg catacatgca 18300
catcgccgga caggatgctt cggagtacct gagtccgggt ctggtgcagt tcgcccgcgc 18360

```
cacagacacc tacttcaatc tgggaaataa gtttagaaat cccaccgtag cgccgaccca  18420
cgatgtgacc accgaccgta gccagcggct catgttgcgc ttcgtgcccg ttgaccggga  18480
ggacaataca tactcttaca aagtgcggta caccctggcc gtgggcgaca acagagtgct  18540
ggatatggcc agcacgttct ttgacattag ggtgtgttg gacagaggtc ccagtttcaa  18600
accctattct ggtacggctt acaactccct ggctcctaaa ggcgctccaa atacatctca  18660
gtggattgca gaaggtgtaa aaaatacaac tggtgaggaa cacgtaacag aagaggaaac  18720
caatactact acttacactt ttggcaatgc tcctgtaaaa gctgaagctg aaattacaaa  18780
agaaggactc ccagtaggtt tggaagtttc agatgaagaa agtaaaccga tttatgctga  18840
taaaacatat cagccagaac ctcagctggg agatgaaact tggactgacc ttgatggaaa  18900
aaccgaaaag tatggaggca gggctctcaa acccgatact aagatgaaac catgctacgg  18960
gtcctttgcc aaacctacta atgtgaaagg cggtcaggca aaacaaaaaa caacggagca  19020
gccaaatcag aaagtcgaat atgatatcga catggagttt tttgatgcgg catcgcagaa  19080
aacaaactta agtcctaaaa ttgtcatgta tgcagaaaat gtaaatttgg aaactccaga  19140
cactcatgta gtgtacaaac ctggaacaga agacacaagt tccgaagcta atttgggaca  19200
acaatctatg cccaacagac ccaactacat tggcttcaga gataacttta ttggacttat  19260
gtactataac agtactggta acatgggggt gctggctggt caagcgtctc agttaaatgc  19320
agtggttgac ttgcaggaca gaaacacaga actttcttac caactcttgc ttgactctct  19380
gggcgacaga accagatact ttagcatgtg gaatcaggct gtggacagtt atgatcctga  19440
tgtacgtgtt attgaaaatc atggtgtgga agatgaactt cccaactact gttttccact  19500
ggacggcata ggtgttccaa caaccagtta caaatcaata gttccaaatg gagacaatgc  19560
gcctaattgg aaggaacctg aagtaaatgg aacaagtgag atcggacagg gtaatttgtt  19620
tgccatggaa attaaccttc aagccaatct atggcgaagt ttcctttatt ccaatgtggc  19680
tctatatctc ccagactcgt acaaatacac cccgtccaat gtcactcttc cagaaaacaa  19740
aaacacctac gactacatga acgggcgggt ggtgccgcca tctctagtag acacctatgt  19800
gaacattggt gccaggtggt ctctggatgc catggacaat gtcaacccat tcaaccacca  19860
ccgtaacgct ggcttgcgtt accgatccat gcttctgggt aacggacgtt atgtgccttt  19920
ccacatacaa gtgcctcaaa aattcttcgc tgttaaaaac ctgctgcttc tcccaggctc  19980
ctacacttat gagtggaact ttaggaagga tgtgaacatg gttctacaga gttccctcgg  20040
taacgacctg cgggtagatg gcgccagcat cagtttcacg agcatcaacc tctatgctac  20100
tttttttccc atggctcaca acaccgcttc caccettgaa gccatgctgc ggaatgacac  20160
caatgatcag tcattcaacg actacctatc tgcagctaac atgctctacc ccattcctgc  20220
caatgcaacc aatattccca tttccattcc ttctcgcaac tgggcggctt tcagaggctg  20280
gtcatttacc agactgaaaa ccaaagaaac tccctctttg ggtctggat ttgaccccta  20340
ctttgtctat tctggttcta ttccctacct ggatggtacc ttctacctga accacacttt  20400
taagaaggtt tccatcatgt ttgactcttc agtgagctgg cctggaaatg acaggttact  20460
atctcctaac gaatttgaaa taaagcgcac tgtggatggc gaaggctaca acgtagccca  20520
atgcaacatg accaaagact ggttcttggt acagatgctc gccaactaca acatcggcta  20580
tcagggcttc tacattccag aaggatacaa agatcgcatg tattcatttt tcagaaactt  20640
ccagcccatg agcaggcagg tggttgatga ggtcaattac aaagacttca aggccgtcgc  20700
```

-continued

```
catacctac caacacaaca actctggctt tgtgggttac atggctccga ccatgcgcca  20760
aggtcaaccc tatcccgcta actatcccta tccactcatt ggaacaactg ccgtaaatag  20820
tgttacgcag aaaaagttct tgtgtgacag aaccatgtgg cgcataccgt tctcgagcaa  20880
cttcatgtct atgggggccc ttacagactt gggacagaat atgctctatg ccaactcagc  20940
tcatgctctg gacatgacct ttgaggtgga tcccatggat gagcccaccc tgctttatct  21000
tctcttcgaa gttttcgacg tggtcagagt gcatcagcca caccgcggca tcatcgaggc  21060
agtctacctg cgtacaccgt tctcggccgg taacgctacc acgtaagaag cttcttgctt  21120
cttgcaaata gcagctgcaa ccatggcctg cggatcccaa aacggctcca gcgagcaaga  21180
gctcagagcc attgtccaag acctgggttg cggaccctat tttttgggaa cctacgataa  21240
gcgcttcccg gggttcatgg cccccgataa gctcgcctgt gccattgtaa atacggccgg  21300
acgtgagacg gggggagagc actggttggc tttcggttgg aacccacgtt ctaacacctg  21360
ctaccttttt gatccttttg gattctcgga tgatcgtctc aaacagattt accagtttga  21420
atatgagggt ctcctgcgcc gcagcgctct tgctaccaag gaccgctgta ttacgctgga  21480
aaaatctacc cagaccgtgc agggtccccg ttctgccgcc tgcggacttt tctgctgcat  21540
gttccttcac gcctttgtgc actggcctga ccgtcccatg gacggaaacc ccaccatgaa  21600
attgctaact ggagtgccaa acaacatgct tcattctcct aaagtccagc ccaccctgtg  21660
tgacaatcaa aaagcactct accattttct taatacccat tcgccttatt ttcgctccca  21720
tcgtacacac atcgaaaggg ccactgcgtt cgaccgtatg gatgttcaat aatgactcat  21780
gtaaacaacg tgttcaataa acatcacttt atttttttac atgtatcaag gctctgcatt  21840
acttatttat ttacaagtcg aatgggttct gacgagaatc agaatgaccc gcaggcagtg  21900
atacgttgcg gaactgatac ttgggttgcc acttgaattc gggaatcacc aacttgggaa  21960
ccggtatatc gggcaggatg tcactccaca gctttctggt cagctgcaaa gctccaagca  22020
ggtcaggagc cgaaatcttg aaatcacaat taggaccagt gctttgagcg cgagagttgc  22080
ggtacaccgg attgcagcac tgaaacacca tcagcgacgg atgtctcacg cttgccagca  22140
cggtgggatc tgcaatcatg cccacatcca gatcttcagc attggcaatg ctgaacgggg  22200
tcatcttgca ggtctgccta cccatggcgg gcacccaatt aggcttgtgg ttgcaatcgc  22260
agtgcagggg gatcagtatc atcttggcct gatcctgtct gattcctgga tacacggctc  22320
tcatgaaagc atcatattgc ttgaaagcct gctgggcttt actaccctcg gtataaaaca  22380
tcccgcagga cctgctcgaa aactggttag ctgcacagcc ggcatcattc acacagcagc  22440
gggcgtcatt gttagctatt tgcaccacac ttctgcccca gcggttttgg gtgattttgg  22500
ttcgctcggg attctccttt aaggctcgtt gtccgttctc gctggccaca tccatctcga  22560
taatctgctc cttctgaatc ataatattgc catgcaggca cttcagcttg ccctcataat  22620
cattgcagcc atgaggccac aacgcacagc ctgtacattc ccaattatgg tgggcgatct  22680
gagaaaaaga atgtatcatt ccctgcagaa atcttcccat catcgtgctc agtgtcttgt  22740
gactagtgaa agttaactgg atgcctcggt gctcctcgtt tacgtactgg tgacagatgc  22800
gcttgtattg ttcgtgttgc tcaggcatta gtttaaaaga ggttctaagt tcgttatcca  22860
gcctgtactt ctccatcagc agacacatca cttccatgcc tttctcccaa gcagacacca  22920
ggggcaagct aatcggattc ttaacagtgc aggcagcagc tcctttagcc agagggtcat  22980
ctttagcgat cttctcaatg cttcttttgc catccttctc aacgatgcgc acgggcgggt  23040
agctgaaacc cactgctaca agttgcgcct cttctctttc ttcttcgctg tcttgactga  23100
```

```
tgtcttgcat ggggatatgt ttggtcttcc ttggcttctt tttggggggt atcggaggag  23160
gaggactgtc gctccgttcc ggagacaggg aggattgtga cgtttcgctc accattacca  23220
actgactgtc ggtagaagaa cctgacccca cacggcgaca ggtgtttctc ttcgggggca  23280
gaggtggagg cgattgcgaa gggctgcggt ccgacctgga aggcggatga ctggcagaac  23340
cccttccgcg ttcgggggtg tgctccctgt ggcggtcgct taactgattt ccttcgcggc  23400
tggccattgt gttctcctag gcagagaaac aacagacatg gaaactcagc cattgctgtc  23460
aacatcgcca cgagtgccat cacatctcgt cctcagcgac gaggaaaagg agcagagctt  23520
aagcattcca ccgcccagtc ctgccaccac ctctacccta gaagataagg aggtcgacgc  23580
atctcatgac atgcagaata aaaaagcgaa agagtctgag acagacatcg agcaagaccc  23640
gggctatgtg acaccggtgg aacacgagga agagttgaaa cgctttctag agagagagga  23700
tgaaaactgc ccaaaacaac gagcagataa ctatcaccaa gatgctggaa atagggatca  23760
gaacaccgac tacctcatag ggcttgacgg ggaagacgcg ctccttaaac atctagcaag  23820
acagtcgctc atagtcaagg atgcattatt ggacagaact gaagtgccca tcagtgtgga  23880
agagctcagc cgcgcctacg agcttaacct cttttcacct cgtactcccc ccaaacgtca  23940
gccaaacggc acctgcgagc caaatcctcg cttaaacttt tatccagctt ttgctgtgcc  24000
agaagtactg gctacctatc acatcttttt taaaaatcaa aaaattccag tctcctgccg  24060
cgctaatcgc acccgcgccg atgccctact caatctggga cctggttcac gcttacctga  24120
tatagcttcc ttggaagagg ttccaaagat cttcgagggt ctgggcaata atgagactcg  24180
ggccgcaaat gctctgcaaa agggagaaaa tggcatggat gagcatcaca gcgttctggt  24240
ggaattggaa ggcgataatg ccagactcgc agtactcaag cgaagcatcg aggtcacaca  24300
cttcgcatat cccgctgtca acctgccccc taaagtcatg acggcggtca tggaccagtt  24360
actcattaag cgcgcaagtc ccctttcaga agacatgcat gacccagatg cctgtgatga  24420
gggtaaacca gtggtcagtg atgagcagct aacccgatgg ctgggcaccg actctcccag  24480
ggatttggaa gagcgtcgca agcttatgat ggccgtggtg ctggttaccg tagaactaga  24540
gtgtctccga cgtttcttta ccgattcaga aaccttgcgc aaactcgaag agaatctgca  24600
ctacactttt agacacggct ttgtgcggca ggcatgcaag atatctaacg tggaactcac  24660
caacctggtt tcctacatgg gtattctgca tgagaatcgc ctaggacaaa gcgtgctgca  24720
cagcaccctg aagggggaag cccgccgtga ttacatccgc gattgtgtct atctgtacct  24780
gtgccacacg tggcaaaccg gcatgggtgt atggcagcaa tgtttagaag aacagaactt  24840
gaaagagctt gacaagctct tacagaaatc tcttaaggtt ctgtggacag ggttcgacga  24900
gcgcaccgtc gcttccgacc tggcagacct catcttccca gagcgtctca gggttacttt  24960
gcgaaacgga ttgcctgact ttatgagcca gagcatgctt aacaattttc gctctttcat  25020
cctggaacgc tccggtatcc tgcccgccac ctgctgcgca ctgccctccg actttgtgcc  25080
tctcacctac cgcgagtgcc ccccgccgct atggagtcac tgctacctgt tccgtctggc  25140
caactatctc tcctaccact cggatgtgat cgaggatgtg agcggagacg gcttgctgga  25200
gtgtcactgc cgctgcaatc tgtgcacgcc ccaccggtcc ctagcttgca acccccagtt  25260
gatgagcgaa acccagataa taggcacctt tgaattgcaa ggccccagca gccaaggcga  25320
tgggtcttct cctgggcaaa gtttaaaact gaccccggga ctgtggacct ccgcctactt  25380
gcgcaagttt gctccggaag attaccaccc ctatgaaatc aagttctatg aggaccaatc  25440
```

```
acagcctcca aaggccgaac tttcggcctg cgtcatcacc caggggggcaa ttctggccca 25500
attgcaagcc atccaaaaat cccgccaaga atttctactg aaaaagggta agggggtcta 25560
ccttgacccc cagaccggcg aggaactcaa cacaaggttc cctcaggatg tcccaacgac 25620
gagaaaacaa gaagttgaag gtgcagccgc cgcccccaga agatatggag gaagattggg 25680
acagtcaggc agaggaggcg gaggaggaca gtctggagga cagtctggag gaagacagtt 25740
tggaggagga aaacgaggag gcagaggagg tggaagaagt aaccgccgac aaacagttat 25800
cctcggctgc ggagacaagc aacagcgcta ccatctccgc tccgagtcga ggaacccggc 25860
ggcgtcccag cagtagatgg gacgagaccg gacgcttccc gaacccaacc agcgcttcca 25920
agaccggtaa gaaggatcgg cagggataca agtcctggcg gggggcataag aatgccatca 25980
tctcctgctt gcatgagtgc gggggcaaca tatccttcac gcggcgctac ttgctattcc 26040
accatggggt gaactttccg cgcaatgttt tgcattacta ccgtcacctc cacagcccct 26100
actatagcca gcaaatcccg gcagtctcga cagataaaga cagcggcggc gacctccaac 26160
agaaaaccag cagcggcagt tagaaaatac acaacaagtg cagcaacagg aggattaaag 26220
attacagcca acgagccagc gcaaacccga gagttaagaa atcggatctt tccaaccctg 26280
tatgccatct tccagcagag tcggggtcaa gagcaggaac tgaaaataaa aaaccgatct 26340
ctgcgttcgc tcaccagaag ttgtttgtat cacaagagcg aagatcaact tcagcgcact 26400
ctcgaggacg ccgaggctct cttcaacaag tactgcgcgc tgactcttaa agagtaggca 26460
gcgaccgcgc ttattcaaaa aaggcgggaa ttacatcatc ctcgacatga gtaaagaaat 26520
tcccacgcct tacatgtgga gttatcaacc ccaaatggga ttggcggcag gcgcctccca 26580
ggactactcc acccgcatga attggctcag cgccgggcct tctatgattt ctcgagttaa 26640
tgatatacgc gcctaccgaa accaaatact tttggaacag tcagctctta ccaccacgcc 26700
ccgccaacac cttaatccca gaaattggcc cgccgcccta gtgtaccagg aaagtcccgc 26760
tcccaccact gtattacttc ctcgagacgc ccaggccgaa gtccaaatga ctaatgcagg 26820
tgcgcagtta gctggcggct ccaccctatg tcgtcacagg cctcggcata atataaaacg 26880
cctgatgatc agaggccgag gtatccagct caacgacgag tcggtgagct ctccgcttgg 26940
tctacgacca gacggaatct ttcagattgc cggctgcggg agatcttcct tcacccctcg 27000
tcaggctgtt ctgactttgg aaagttcgtc ttcgcaaccc cgctcgggcg gaatcgggac 27060
cgttcaattt gtggaggagt ttactccctc tgtctacttc aacccccttct ccggatctcc 27120
tgggcattac ccggacgagt tcataccgaa cttcgacgcg attagcgagt cagtggacgg 27180
ctacgattga tgtctggtga cgcggctgag ctatctcggc tgcgacatct agaccactgc 27240
cgccgctttc gctgctttgc ccgggaactc attgagttca tctacttcga actccccaag 27300
gatcaccctc aaggtccggc ccacggagtg cggatttcta tcgaaggcaa aatagactct 27360
cgcctgcaac gaattttctc ccagcggccc gtgctgatcg agcgagacca gggaaacacc 27420
acggtttcca tctactgcat ttgtaatcac cccggattgc atgaaagcct ttgctgtctt 27480
atgtgtactg agtttaataa aaactgaatt aagactctcc tacggactgc cgcttcttca 27540
acccggattt tacaaccaga agaacgaaac ttttcctgtc gtccaggact ctgttaactt 27600
cacctttcct actcacaaac tagaagctca acgactacac cgcttttcca gaagcatttt 27660
ccctactaat actactttca aaaccggagg tgagctccaa ggtcttccta cagaaaaccc 27720
ttgggtggaa gcgggccttg tagtgctagg aattcttgcg ggtgggcttg tgattattct 27780
ttgctaccta tacacacctt gcttcacttt cttagtggtg ttgtggtatt ggtttaaaaa 27840
```

atggggccca tactagtctt gcttgtttta ctttcgcttt tggaaccggg ttctgccaat 27900
tacgatccat gtctagactt cgacccagaa aactgcacac ttacttttgc acccgacaca 27960
agccgcatct gtggagttca tcgcctctct tacgaacttg gcccccaacg acaaaaattt 28020
acctgcatgg tgggaatcaa ccccatagtt atcacccagc aaagtggaga tactaagggt 28080
tgcattcact gctcctgcga ttccatcgag tgcacctaca ccctgctgaa gaccctatgc 28140
ggcctaagag acctgctacc aatgaattaa aaaatgatta ataaaaaatc acttacttga 28200
aatcagcaat aaggtctctg ttgaaatttt ctcccagcag cacctcactt ccctcttccc 28260
aactctggta ttctaaaccc cgttcagcgg catactttct ccatacttta aaggggatgt 28320
caaattttag ctcctctcct gtacccacaa tcttcatgtc tttcttccca gtggccggcc 28380
atgaccaaga gagtccggct cagtgactcc ttcaaccctg tctaccccta tgaagatgaa 28440
agcacctccc aacacccctt tataaaccca gggtttattt ccccaaatgg cttcacacaa 28500
agcccaaacg gagttcttac tttaaaatgt ttaaccccac taacaaccac aggcggatct 28560
ctacagctaa aagtgggagg gggacttaca gtggatgaca ccaacggttt tttgaaagaa 28620
aacataagtg ccaccacacc actcgttaag actggtcact ctataggttt accactagga 28680
gccggattgg gaacgaatga aaataaactt tgtatcaaat taggacaagg acttacattc 28740
aattcaaaca acatttgcat tgatgacaat attaacacct tatggacagg agtcaacccc 28800
accgaagcca actgtcaaat catgaactcc agtgaatcta atgattgcaa attaattcta 28860
acactagtta aaactggagc actagtcact gcatttgttt atgttatagg agtatctaac 28920
aattttaata tgctaactac acacagaaat ataaatttta ctgcagagct gtttttcgat 28980
tctactggta atttactaac tagactctca tccctcaaaa ctccacttaa tcataaatca 29040
ggacaaaaca tggctactgg tgccattact aatgctaaag gtttcatgcc cagcacgact 29100
gcctatcctt tcaatgataa ttctagagaa aaagaaaact acatttacgg aacttgttac 29160
tacacagcta gtgatcgcac tgcttttccc attgacatat ctgtcatgct taaccgaaga 29220
gcaataaatg acgagacatc atattgtatt cgtataactt ggtcctggaa cacaggagat 29280
gccccagagg tgcaaacctc tgctacaacc ctagtcacct ccccatttac cttttactac 29340
atcagagaag acgactgaca aataaaatcg ctatccatcg aagatggatg tgtgttggtt 29400
ttttgtgtga tttgtgcgat cgctatgcgg ccgcttacct gcaggggtta ccacacaaaa 29460
aaccaacaca ccctaaagct cgatctccga cttgtttatt tgaaaatcaa ttcacaaaat 29520
ccgagtagtt attttgcctc cccttccca tttaacagaa tacaccaatc tctccccacg 29580
cacagcttta aacatttgga taccattaga tatagacatg gttttagatt ccacattcca 29640
aacagtttca gagcgagcca atctggggtc agtgatagat aaaaatccat cgggatagtc 29700
ttttaaagcg ctttcacagt ccaactgctg cggatgcgac tccggagtct ggatcacggt 29760
catctggaag aagaacgatg ggaatcataa tccgaaaacg gtatcggacg attgtgtctc 29820
atcaaaccca caagcagccg ctgtctgcgt cgctccgtgc gactgctgtt tatgggatca 29880
gggtccacag tgtcctgaag catgatttta atagccctta acatcaactt tctggtgcga 29940
tgcgcgcagc aacgcattct gatttcactc aaatctttgc agtaggtaca acacattatt 30000
acaatattgt ttaataaacc ataattaaaa gcgctccagc caaaactcat atctgatata 30060
atcgcccctg catgaccatc ataccaaagt ttaatataaa ttaaatgacg ttccctcaaa 30120
aacacactac ccacatacat gatctctttt ggcatgtgca tattaacaat ctgtctgtac 30180
catggacaac gttggttaat catgcaaccc aatataacct tccggaacca cactgccaac 30240
accgctcccc cagccatgca ttgaagtgaa ccctgctgat tacaatgaca atgaagaacc 30300
caattctctc gaccgtgaat cacttgagaa tgaaaaatat ctatagtggc acaacataga 30360
cataaatgca tgcatcttct cataattttt aactcctcag gatttagaaa catatcccag 30420
ggaataggaa gctcttgcag aacagtaaag ctggcagaac aaggaagacc acgaacacaa 30480
cttacactat gcatagtcat agtatcacaa tctggcaaca gcgggtggtc ttcagtcata 30540
gaagctcggg tttcattttc ctcacaacgt ggtaactggg ctctggtgta agggtgatgt 30600
ctggcgcatg atgtcgagcg tgcgcgcaac cttgtcataa tggagttgct tcctgacatt 30660
ctcgtatttt gtatagcaaa acgcggccct ggcagaacac actcttcttc gccttctatc 30720
ctgccgctta gcgtgttccg tgtgatagtt caagtacaac cacactctta agttggtcaa 30780
aagaatgctg gcttcagttg taatcaaaac tccatcgcat ctaatcgttc tgaggaaatc 30840
atccaagcaa tgcaactgga ttgtgtttca agcaggagag gagagggaag agacggaaga 30900
accatgttaa tttttattcc aaacgatctc gcagtacttc aaattgtaga tcgcgcagat 30960
ggcatctctc gcccccactg tgttggtgaa aaagcacagc tagatcaaaa gaaatgcgat 31020
tttcaaggtg ctcaacggtg gcttccagca aagcctccac gcgcacatcc aagaacaaaa 31080
gaataccaaa agaaggagca ttttctaact cctcaatcat catattacat tcctgcacca 31140
ttcccagata attttcagct ttccagcctt gaattattcg tgtcagttct tgtggtaaat 31200
ccaatccaca cattacaaac aggtcccgga gggcgccctc caccaccatt cttaaacaca 31260
ccctcataat gacaaaatat cttgctcctg tgtcacctgt agcgaattga gaatggcaac 31320
atcaattgac atgcccttgg ctctaagttc ttctttaagt tctagttgta aaaactctct 31380
catattatca ccaaactgct tagccagaag ccccccggga acaagagcag gggacgctac 31440
agtgcagtac aagcgcagac ctccccaatt ggctccagca aaaacaagat tggaataagc 31500
atattgggaa ccgccagtaa tatcatcgaa gttgctggaa atataatcag gcagagtttc 31560
ttgtaaaaat tgaataaaag aaaaatttgc caaaaaaaca ttcaaaacct ctgggatgca 31620
aatgcaatag gttaccgcgc tgcgctccaa cattgttagt tttgaattag tctgcaaaaa 31680
taaaaaaaaa aacaagcgtc atatcatagt agcctgacga acagatggat aaatcagtct 31740
ttccatcaca agacaagcca cagggtctcc agctcgaccc tcgtaaaacc tgtcatcatg 31800
attaaacaac agcaccgaaa gttcctcgcg gtgaccagca tgaataattc ttgatgaagc 31860
atacaatcca gacatgttag catcagttaa cgagaaaaaa cagccaacat agcctttggg 31920
tataattatg cttaatcgta agtatagcaa agccacccct cgcggataca aagtaaaagg 31980
cacaggagaa taaaaaatat aattatttct ctgctgctgt tcaggcaacg tcgcccccgg 32040
tccctctaaa tacacataca aagcctcatc agccatggct taccagacaa agtacagcgg 32100
gcacacaaag cacaagctct aaagtgactc tccaacctct ccacaatata tatatacaca 32160
agccctaaac tgacgtaatg ggagtaaagt gtaaaaaatc ccgccaaacc caacacacac 32220
cccgaaactg cgtcaccagg gaaaagtaca gtttcacttc cgcaatccca acaggcgtaa 32280
cttcctcttt ctcacggtac gtgatatccc actaacttgc aacgtcattt tcccacggtc 32340
gcaccgcccc ttttagccgt taaccccaca gccaatcacc acacgatcca cactttttaa 32400
aatcacctca tttacatatt ggcaccattc catctataag gtatattata tagatagg 32458

<210> SEQ ID NO 34
<211> LENGTH: 32340

<212> TYPE: DNA
<213> ORGANISM: Artificial Sequence
<220> FEATURE:
<223> OTHER INFORMATION: ColoAd2.1 genome

<400> SEQUENCE: 34
cgcgcctatc tatataatat accttataga tggaatggtg ccaatatgta aatgaggtga 60
ttttaaaaag tgtggatcgt gtggtgattg gctgtggggt taacggctaa aaggggcggt 120
gcgaccgtgg gaaaatgacg ttttgtgggg gtggagtttt tttgcaagtt gtcgcgggaa 180
atgtgacgca taaaaaggct tttttctcac ggaactactt agttttccca cggtatttaa 240
caggaaatga ggtagttttg accggatgca agtgaaaatt gttgattttc gcgcgaaaac 300
tgaatgagga agtgtttttc tgaataatgt ggtatttatg gcagggtgga gtatttgttc 360
agggccaggt agactttgac ccattacgtg gaggtttcga ttaccgtgtt ttttacctga 420
atttccgcgt accgtgtcaa agtcttctgt ttttacgtag gtgtcagctg atcgctaggg 480
tatttatacc tcagggtttg tgtcaagagg ccactcttga gtgccagcga gaagagtttt 540
ctcctctgcg ccggcagttt aataataaaa aaatgagaga tttgcgattt ctgcctcagg 600
aaataatctc tgctgagact ggaaatgaaa tattggagct tgtggtgcac gccctgatgg 660
gagacgatcc ggagccacct gtgcagcttt ttgagcctcc tacgcttcag gaactgtatg 720
atttagaggt agagggatcg gaggattcta atgaggaagc tgtaaatggc tttttttaccg 780 attctatgct tttagctgct aatgaagggt tagaattaga tccgcctttg gacacttttg 840
atactccagg ggtaattgtg gaaagcggta caggtgtaag aaaattacct gatttgagtt 900
ccgtggactg tgatttgcac tgctatgaag acgggtttcc tccgagtgat gaggaggacc 960
atgaaaagga gcagtccatg cagactgcag cgggtgaggg agtgaaggct gccaatgttg 1020
gttttcagtt ggattgcccg gagcttcctg gacatggctg taagtcttgt gaatttcaca 1080
ggaaaaatac tggagtaaag gaactgttat gttcgctttg ttatatgaga acgcactgcc 1140
actttattta cagtaagtgt gtttaagtta aaatttaaag gaatatgctg tttttcacat 1200
gtatattgag tgtgagtttt gtgcttctta ttataggtcc tgtgtctgat gctgatgaat 1260
caccatctcc tgattctact acctcacctc ctgagattca agcacctgtt cctgtggacg 1320
tgcgcaagcc cattcctgtg aagcttaagc ctgggaaacg tccagcagtg gaaaaacttg 1380
aggacttgtt acagggtggg gacggacctt tggacttgag tacacggaaa cgtccaagac 1440
aataagtgtt ccatatccgt gtttacttaa ggtgacgtca atatttgtgt gacagtgcaa 1500
tgtaataaaa atatgttaac tgttcactgg tttttattgc tttttgggcg ggactcagg 1560 tatataagta gaagcagacc tgtgtggtta gctcatagga gctggctttc atccatggag 1620
gtttgggcca ttttggaaga ccttaggaag actaggcaac tgttagagaa cgcttcggac 1680
ggagtctccg gtttttggag attctggttc gctagtgaat tagctagggt agtttttagg 1740
ataaaacagg actataaaca agaatttgaa aagttgttgg tagattgccc aggacttttt 1800
gaagctctta atttgggcca tcaggttcac tttaaagaaa aagttttatc agttttagac 1860
ttttcaaccc caggtagaac tgctgctgct gtggcttttc ttacttttat attagataaa 1920
tggatcccgc agactcattt cagcagggga tacgttttgg atttcatagc cacagcattg 1980
tggagaacat ggaaggttcg caagatgagg acaatcttag gttactggcc agtgcagcct 2040
ttgggtgtag cgggaatcct gaggcatcca ccggtcatgc cagcggttct ggaggaggaa 2100
cagcaagagg acaacccgag agccggcctg gaccctccag tggaggaggc ggagtagctg 2160

-continued

```
acttgtctcc tgaactgcaa cgggtgctta ctggatctac gtccactgga cgggataggg   2220
gcgttaagag ggagagggca tctagtggta ctgatgctag atctgagttg gctttaagtt   2280
taatgagtcg cagacgtcct gaaaccattt ggtggcatga ggttcagaaa gagggaaggg   2340
atgaagtttc tgtattgcag gagaaatatt cactggaaca ggtgaaaaca tgttggttgg   2400
agcctgagga tgattgggag gtggccatta aaaattatgc caagatagct ttgaggcctg   2460
ataaacagta taagattact agacggatta atatccggaa tgcttgttac atatctggaa   2520
atggggctga ggtggtaata gatactcaag acaaggcagt tattagatgc tgcatgatgg   2580
atatgtggcc tggggtagtc ggtatggaag cagtaacttt tgtaaatgtt aagtttaggg   2640
gagatggtta taatggaata gtgtttatgg ccaataccaa acttatattg catggttgta   2700
gctttttggt ttcaacaat acctgtgtag atgcctgggg acaggttagt gtacggggat   2760
gtagtttcta tgcgtgttgg attgccacag ctggcagaac caagagtcaa ttgtctctga   2820
agaaatgcat atttcaaaga tgtaacctgg gcattctgaa tgaaggcgaa gcaagggtcc   2880
gccactgcgc ttctacagat actggatgtt ttattttgat taagggaaat gccagcgtaa   2940
agcataacat gatttgcggt gcttccgatg agaggcctta tcaaatgctc acttgtgctg   3000
gtgggcattg taatatgctg gctactgtgc atattgtttc ccatcaacgc aaaaaatggc   3060
ctgtttttga tcacaatgtg atgacgaagt gtaccatgca tgcaggtggg cgtagaggaa   3120
tgtttatgcc ttaccagtgt aacatgaatc atgtgaaagt gttgttggaa ccagatgcct   3180
tttccagaat gagcctaaca ggaatttttg acatgaacat gcaaatctgg aagatcctga   3240
ggtatgatga tacgagatcg agggtacgcg catgcgaatg cggaggcaag catgccaggt   3300
tccagccggt gtgtgtagat gtgactgaag atctcagacc ggatcatttg gttattgccc   3360
gcactggagc agagttcgga tccagtggag aagaaactga ctaaggtgag tattgggaaa   3420
actttggggt gggattttca gatggacaga ttgagtaaaa atttgttttt tctgtcttgc   3480
agctgtcatg agtggaaacg cttcttttaa ggggggagtc ttcagccctt atctgacagg   3540
gcgtctccca tcctgggcag gagttcgtca gaatgttatg ggatctactg tggatggaag   3600
acccgtccaa cccgccaatt cttcaacgct gacctatgct actttaagtt cttcaccttt   3660
ggacgcagct gcagctgccg ccgccgcttc tgttgccgct aacactgtgc ttggaatggg   3720
ttactatgga agcatcatgg ctaattccac ttcctctaat aacccttcta ccctgactca   3780
ggacaagtta cttgtccttt tggcccagct ggaggctttg acccaacgtc tgggtgaact   3840
ttctcagcag gtggtcgagt tgcgagtaca aactgagtct gctgtcggca cggcaaagtc   3900
taaataaaaa aatcccagaa tcaatgaata aataaacaag cttgttgttg atttaaaatc   3960
aagtgttttt atttcatttt tcgcgcacgg tatgccctag accaccgatc tctatcattg   4020
agaactcggt ggatttttc caggatccta tagaggtggg attgaatgtt tagatacatg   4080
ggcattaggc cgtctttggg gtggagatag ctccattgaa gggattcatg ctccggggta   4140
gtgttgtaaa tcacccagtc ataacaaggt cgcagtgcat ggtgttgcac aatatctttt   4200
agaagtaggc tgattgccac agataagccc ttggtgtagg tgtttacaaa ccggttgagc   4260
tgggatgggt gcattcgggg tgaaattatg tgcattttgg attggatttt taagttggca   4320
atattgccgc caagatcccg tcttgggttc atgttatgaa ggaccaccaa gacggtgtat   4380
ccggtacatt taggaaattt atcgtgcagc ttggatggaa aagcgtggaa aaatttggag   4440
acacccttgt gtcctccaag attttccatg cactcatcca tgataatagc aatggggccg   4500
tgggcagcgg cgcgggcaaa cacgttccgt gggtctgaca catcatagtt atgttcctga   4560
```

gttaaatcat cataagccat tttaatgaat ttggggcgga gagtaccaga ttggggtatg 4620
aatgttcctt cgggccccgg agcatagttc ccctcacaga tttgcatttc ccaagctttc 4680
agttccgagg gtggaatcat gtccacctgg ggggctatga aaaacaccgt ttctggggcg 4740
ggggtgatta attgtgatga tagcaaattt ctgagcaatt gagatttgcc acatccggtg 4800
gggccataaa tgattccgat tacgggttgc aggtggtagt ttagggaacg gcaactgccg 4860
tcttctcgaa gcaagggggc cacctcgttc atcatttccc ttacatgcat attttcccgc 4920
accaaatcca ttaggaggcg ctctcctcct agtgatagaa gttcttgtag tgaggaaaag 4980
tttttcagcg gtttcagacc gtcagccatg ggcattttgg agagagtttg ctgcaaaagt 5040
tctagtctgt tccacagttc agtgatgtgt tctatggcat ctcgatccag cagacctcct 5100
cgtttcgcgg gtttggacgg ctcctggaat agggtatgag acgatgggcg tccagcgctg 5160
ccagggttcg gtccttccag ggtctcagtg ttcgagtcag ggttgtttcc gtcacagtga 5220
aggggtgtgc gcctgcttgg gcgcttgcca gggtgcgctt cagactcatc ctgctggtcg 5280
aaaacttctg tcgcttggcg ccctgtatgt cggccaagta gcagtttacc atgagttcgt 5340
agttgagcgc ctcggctgcg tggcctttgg cgcggagctt acctttggaa gttttcttgc 5400
ataccgggca gtataggcat ttcagcgcat acaacttggg cgcaaggaaa acggattctg 5460
gggagtatgc atctgcgccg caggaggcgc aaacagtttc acattccacc agccaggtta 5520
aatccggttc attggggtca aaaacaagtt ttccgccata ttttttgatg cgtttcttac 5580
ctttggtctc catgagttcg tgtcctcgtt gagtgacaaa caggctgtcc gtgtccccgt 5640
agactgattt tacaggcctc ttctccagtg gagtgcctcg gtcttcttcg tacaggaact 5700
ctgaccactc tgatacaaag gcgcgcgtcc aggccagcac aaaggaggct atgtgggagg 5760
ggtagcgatc gttgtcaacc agggggtcca cctttttccaa agtatgcaaa cacatgtcac 5820
cctcttcaac atccaggaat gtgattggct tgtaggtgta tttcacgtga cctggggtcc 5880
ccgctggggg ggtataaaag ggggcggttc tttgctcttc ctcactgtct tccggatcgc 5940
tgtccaggaa cgtcagctgt tggggtaggt attccctctc gaaggcgggc atgacctctg 6000
cactcaggtt gtcagtttct aagaacgagg aggatttgat attgacagtg ccggttgaga 6060
tgcctttcat gaggttttcg tccatctggt cagaaaacac aattttttta ttgtcaagtt 6120
tggtggcaaa tgatccatac agggcgttgg ataaaagttt ggcaatggat cgcatggttt 6180
ggttcttttc cttgtccgcg cgctctttgg cggcgatgtt gagttggaca tactcgcgtg 6240
ccaggcactt ccattcgggg aagatagttg ttaattcatc tggcacgatt ctcacttgcc 6300
accctcgatt atgcaaggta attaaatcca cactggtggc cacctcgcct cgaaggggtt 6360
cattggtcca acagagccta cctcctttcc tagaacagaa agggggaagt gggtctagca 6420
taagttcatc gggagggtct gcatccatgg taaagattcc cggaagtaaa tccttatcaa 6480
aatagctgat gggagtgggg tcatctaagg ccatttgcca ttctcgagct gccagtgcgc 6540
gctcatatgg gttaagggga ctgccccatg gcatgggatg ggtgagtgca gaggcataca 6600
tgccacagat gtcatagacg tagatgggat cctcaaagat gcctatgtag gttggatagc 6660
atcgcccccc tctgatactt gctcgcacat agtcatatag ttcatgtgat ggcgctagca 6720
gccccggacc caagttggtg cgattgggtt tttctgttct gtagacgatc tggcgaaaga 6780
tggcgtgaga attggaagag atggtgggtc tttgaaaaat gttgaaatgg gcatgaggta 6840
gacctacaga gtctctgaca aagtgggcat aagattcttg aagcttggtt accagttcgg 6900

-continued

```
cggtgacaag tacgtctagg gcgcagtagt caagtgtttc ttgaatgatg tcataacctg   6960
gttggttttt cttttcccac agttcgcggt tgagaaggta ttcttcgcga tccttccagt   7020
actcttctag cggaaacccg tctttgtctg cacggtaaga tcctagcatg tagaactgat   7080
taactgcctt gtaagggcag cagcccttct ctacgggtag agagtatgct tgagcagctt   7140
ttcgtagcga agcgtgagta agggcaaagg tgtctctgac catgactttg aggaattggt   7200
atttgaagtc gatgtcgtca caggctccct gttcccagag ttggaagtct acccgtttct   7260
tgtaggcggg gttgggcaaa gcgaaagtaa catcattgaa gagaatcttg ccggccctgg   7320
gcatgaaatt gcgagtgatg cgaaaaggct gtggtacttc cgctcggtta ttgataacct   7380
gggcagctag gacgatctcg tcgaaaccgt tgatgttgtg tcctacgatg tataattcta   7440
tgaaacgcgg cgtgcctctg acgtgaggta gcttactgag ctcatcaaag gttaggtctg   7500
tggggtcaga taaggcgtag tgttcgagag cccattcgtg caggtgagga ttcgctttaa   7560
ggaaggagga ccagaggtcc actgccagtg ctgtttgtaa ctggtcccgg tactgacgaa   7620
aatgccgtcc gactgccatt ttttctgggg tgacgcaata gaaggtttgg gggtcctgcc   7680
gccagcgatc ccacttgagt tttatggcga ggtcataggc gatgttgacg agccgctggt   7740
ctccagagag tttcatgacc agcatgaagg ggattagctg cttgccaaag gaccccatcc   7800
aggtgtaggt ttccacatcg taggtgagaa agagcctttc tgtgcgagga tgagagccaa   7860
tcgggaagaa ctggatctcc tgccaccagt tggaggaatg gctgttgatg tgatggaagt   7920
agaactccct gcgacgcgcc gagcattcat gcttgtgctt gtacagacgg ccgcagtagt   7980
cgcagcgttg cacgggttgt atctcgtgaa tgagttgtac ctggcttccc ttgacgagaa   8040
atttcagtgg gaagccgagg cctggcgatt gtatctcgtg ctttactatg ttgtctgcat   8100
cggcctgttc atcttctgtc tcgatggtgg tcatgctgac gagccctcgc gggaggcaag   8160
tccagacctc ggcgcggcag gggcggagct cgaggacgag agcgcgcagg ctggagctgt   8220
ccagggtcct gagacgctgc ggactcaggt tagtaggcag tgtcaggaga ttaacttgca   8280
tgatcttttg gagggcgtgc gggaggttca gatagtactt gatctcaacg ggtccgttgg   8340
tggagatgtc gatggcttgc agggttccgt gtcccttggg cgctaccacc gtgcccttgt   8400
ttttcatttt ggacggcggt ggctctgttg cttcttgcat gtttagaagc ggtgtcgagg   8460
gcgcgcaccg ggcggcaggg gcggctcggg acccggcggc atggctggca gtggtacgtc   8520
ggcgccgcgc gcgggtaggt tctggtactg cgccctgaga agactcgcat gcgcgacgac   8580
gcggcggttg acatcctgga tctgacgcct ctgggtgaaa gctaccggcc ccgtgagctt   8640
gaacctgaaa gagagttcaa cagaatcaat ctcggtatcg ttgacggcgg cttgcctaag   8700
gatttcttgc acgtcaccag agttgtcctg gtaggcgatc tccgccatga actgctcgat   8760
ctcttcctct tgaagatctc cgcggcccgc tctctcgacg gtggccgcga ggtcgttgga   8820
gatgcgccca atgagttgag agaatgcatt catgcccgcc tcgttccaga cgcggctgta   8880
gaccacggcc cccacgggat ctctcgcgcg catgaccacc tgggcgaggt tgagctccac   8940
gtggcgggtg aagaccgcat agttgcatag gcgctggaaa aggtagttga gtgtggtggc   9000
gatgtgctcg gtgacgaaga aatacatgat ccatcgtctc agcggcatct cgctgacatc   9060
gcccagagct tccaagcgct ccatggcctc gtagaagtcc acggcaaaat taaaaaactg   9120
ggagtttcgc gcggacacgg tcaactcctc ttccagaaga cggataagtt cggcgatggt   9180
ggtgcgcacc tcgcgctcga aagcccctgg gatttcttcc tcaatctctt cttcttccac   9240
taacatctct tcctcttcag gtggggctgc aggaggaggg ggaacgcggc gacgccggcg   9300
```

gcgcacgggc agacggtcga tgaatctttc aatgacctct ccgcggcggc ggcgcatggt 9360
ttcagtgacg gcgcggccgt tctcgcgcgg tcgcagagta aaaacaccgc cgcgcatctc 9420
cttaaagtgg tgactgggag gttctccgtt tgggagggag agggcgctga ttatacattt 9480
tattaattgg cccgtaggga ctgcacgcag agatctgatc gtgtcaagat ccacgggatc 9540
tgaaaacctt tcgacgaaag cgtctaacca gtcacagtca caaggtaggc tgagtacggc 9600
ttcttgtggg cgggggtggt tatgtgttcg gtctgggtct tctgtttctt cttcatctcg 9660
ggaaggtgag acgatgctgc tggtgatgaa attaaagtag gcagttctaa gacggcggat 9720
ggtggcgagg agcaccaggt ctttgggtcc ggcttgctgg atacgcaggc gattggccat 9780
tccccaagca ttatcctgac atctagcaag atctttgtag tagtcttgca tgagccgttc 9840
tacgggcact tcttcctcac ccgttctgcc atgcatacgt gtgagtccaa atccgcgcat 9900
tggttgtacc agtgccaagt cagctacgac tctttcggcg aggatggctt gctgtacttg 9960
ggtaagggtg gcttgaaagt catcaaaatc cacaaagcgg tggtaagctc ctgtattaat 10020
ggtgtaagca cagttggcca tgactgacca gttaactgtc tggtgaccag ggcgcacgag 10080
ctcggtgtat ttaaggcgcg aataggcgcg ggtgtcaaag atgtaatcgt tgcaggtgcg 10140
caccagatac tggtacccta taagaaaatg cggcggtggt tggcggtaga gaggccatcg 10200
ttctgtagct ggagcgccag ggcgaggtc ttccaacata aggcggtgat agccgtagat 10260
gtacctggac atccaggtga ttcctgcggc ggtagtagaa gcccgaggaa actcgcgtac 10320
gcggttccaa atgttgcgta gcggcatgaa gtagttcatt gtaggcacgg tttgaccagt 10380
gaggcgcgcg cagtcattga tgctctatag acacggagaa aatgaaagcg ttcagcgact 10440
cgactccgta gcctggagga acgtgaacgg gttgggtcgc ggtgtacccc ggttcgagac 10500
ttgtactcga gccggccgga gccgcggcta acgtggtatt ggcactcccg tctcgaccca 10560
gcctacaaaa atccaggata cggaatcgag tcgttttgct ggtttccgaa tggcagggaa 10620
gtgagtccta tttttttttt ttgccgctca gatgcatccc gtgctgcgac agatgcgccc 10680
ccaacaacag ccccccctcgc agcagcagca gcagcaatca caaaaggctg tccctgcaac 10740
tactgcaact gccgccgtga gcggtgcggg acagcccgcc tatgatctgg acttggaaga 10800
gggcgaagga ctggcacgtc taggtgcgcc ttcacccgag cggcatccgc gagttcaact 10860
gaaaaaagat tctcgcgagg cgtatgtgcc ccaacagaac ctatttagag acagaagcgg 10920
cgaggagccg gaggagatgc gagcttcccg ctttaacgcg ggtcgtgagc tgcgtcacgg 10980
tttggaccga agacgagtgt tgcgggacga ggatttcgaa gttgatgaaa tgacagggat 11040
cagtcctgcc agggcacacg tggctgcagc caaccttgta tcggcttacg agcagacagt 11100
aaaggaagag cgtaacttcc aaaagtcttt taataatcat gtgcgaaccc tgattgcccg 11160
cgaagaagtt acccttggtt tgatgcattt gtgggatttg atggaagcta tcattcagaa 11220
ccctactagc aaacctctga ccgcccagct gtttctggtg gtgcaacaca gcagagacaa 11280
tgaggctttc agagaggcgc tgctgaacat caccgaaccc gaggggagat ggttgtatga 11340
tcttatcaac attctacaga gtatcatagt gcaggagcgg agcctgggcc tggccgagaa 11400
ggtggctgcc atcaattact cggttttgag cttgggaaaa tattacgctc gcaaaatcta 11460
caagactcca tacgttccca tagacaagga ggtgaagata gatgggttct acatgcgcat 11520
gacgctcaag gtcttgaccc tgagcgatga tcttggggtg tatcgcaatg acagaatgca 11580
tcgcgcggtt agcgccagca ggaggcgcga gttaagcgac agggaactga tgcacagttt 11640
gcaaagagct ctgactggag ctggaaccga gggtgagaat tacttcgaca tgggagctga 11700
cttgcagtgg cagcctagtc gcagggctct gagcgccgcg acggcaggat gtgagcttcc 11760
ttacatagaa gaggcggatg aaggcgagga ggaagagggc gagtacttgg aagactgatg 11820
gcacaacccg tgtttttgc tagatggaac agcaagcacc ggatcccgca atgcgggcgg 11880
cgctgcagag ccagccgtcc ggcattaact cctcggacga ttggacccag gccatgcaac 11940
gtatcatggc gttgacgact cgcaaccccg aagcctttag acagcaaccc caggccaacc 12000
gtctatcggc catcatggaa gctgtagtgc cttcccgctc taatcccact catgagaagg 12060
tcctggccat cgtgaacgcg ttggtggaga acaaagctat tcgtccagat gaggccggac 12120
tggtatacaa cgctctctta gaacgcgtgg ctcgctacaa cagtagcaat gtgcaaacca 12180
atttggaccg tatgataaca gatgtacgcg aagccgtgtc tcagcgcgaa aggttccagc 12240
gtgatgccaa cctgggttcg ctggtggcgt taaatgcttt cttgagtact cagcctgcta 12300
atgtgccgcg tggtcaacag gattatacta actttttaag tgctttgaga ctgatggtat 12360
cagaagtacc tcagagcgaa gtgtatcagt ccggtcctga ttacttcttt cagactagca 12420
gacagggctt gcagacggta aatctgagcc aagcttttaa aaacctttaa aggtttgtgg 12480
ggagtgcatg ccccggtagg agaaagagca accgtgtcta gcttgttaac tccgaactcc 12540
cgcctattat tactgttggt agctcctttc accgacagcg gtagcatcga ccgtaattcc 12600
tatttgggtt acctactaaa cctgtatcgc gaagccatag ggcaaagtca ggtggacgag 12660
cagacctatc aagaaattac ccaagtcagt cgcgctttgg gacaggaaga cactggcagt 12720
ttggaagcca ctctgaactt cttgcttacc aatcggtctc aaaagatccc tcctcaatat 12780
gctcttactg cggaggagga gaggatcctt agatatgtgc agcagagcgt gggattgttt 12840
ctgatgcaag agggggcaac tccgactgca gcactggaca tgacagcgcg aaatatggag 12900
cccagcatgt atgccagtaa ccgacctttc attaacaaac tgctggacta cttgcacaga 12960
gctgccgcta tgaactctga ttatttcacc aatgccatct taaacccgca ctggctgccc 13020
ccacctggtt tctacacggg cgaatatgac atgcccgacc ctaatgacgg atttctgtgg 13080
gacgacgtgg acagcgatgt tttttcacct ctttctgatc atcgcacgtg gaaaaaggaa 13140
ggcggcgata gaatgcattc ttctgcatcg ctgtccgggg tcatgggtgc taccgcggct 13200
gagcccgagt ctgcaagtcc ttttcctagt ctaccctttt ctctacacag tgtacgtagc 13260
agcgaagtgg gtagaataag tcgcccgagt ttaatgggcg aagaggagta tctaaacgat 13320
tccttgctca gaccggcaag agaaaaaaat ttcccaaaca atggaataga aagtttggtg 13380
gataaaatga gtagatggaa gacttatgct caggatcaca gagacgagcc tgggatcatg 13440
gggattacaa gtagagcgag ccgtagacgc cagcgccatg acagacagag gggtcttgtg 13500
tgggacgatg aggattcggc cgatgatagc agcgtgctgg acttgggtgg gagaggaagg 13560
ggcaacccgt ttgctcattt gcgccctcgc ttgggtggta tgttgtaaaa aaaaataaaa 13620
aaaaaactca ccaaggccat ggcgacgagc gtacgttcgt tcttctttat tatctgtgtc 13680
tagtataatg aggcgagtcg tgctaggcgg agcggtggtg tatccggagg gtcctcctcc 13740
ttcgtacgag agcgtgatgc agcagcagca ggcgacggcg gtgatgcaat ccccactgga 13800
ggctcccttt gtgcctccgc gatacctggc acctacggag ggcagaaaca gcattcgtta 13860
ttcggaactg gcacctcagt acgataccac caggttgtat ctggtggaca acaagtcggc 13920
ggacattgct tctctgaact atcagaatga ccacagcaac ttcttgacca cggtggtgca 13980
aaacaatgac tttacccta cggaagccag cacccagacc attaactttg atgaacgatc 14040
gcggtggggc ggtcagctaa agaccatcat gcatactaac atgccaaacg tgaacgagta 14100
tatgtttagt aacaagttca aagcgcgtgt gatggtgtcc agaaaacctc ccgacggtgc 14160
tgcagttggg gatacttatg atcacaagca ggatattttg aaatatgagt ggttcgagtt 14220
tactttgcca gaaggcaact tttcagttac tatgactatt gatttgatga acaatgccat 14280
catagataat tacttgaaag tgggtagaca gaatggagtg cttgaaagtg acattggtgt 14340
taagttcgac accaggaact tcaagctggg atgggatccc gaaaccaagt tgatcatgcc 14400
tggagtgtat acgtatgaag ccttccatcc tgacattgtc ttactgcctg gctgcggagt 14460
ggattttacc gagagtcgtt tgagcaacct tcttggtatc agaaaaaaac agccatttca 14520
agagggtttt aagattttgt atgaagattt agaaggtggt aatattccgg ccctcttgga 14580
tgtagatgcc tatgagaaca gtaagaaaga acaaaaagcc aaaatagaag ctgctacagc 14640
tgctgcagaa gctaaggcaa acatagttgc cagcgactct acaagggttg ctaacgctgg 14700
agaggtcaga ggagacaatt ttgcgccaac acctgttccg actgcagaat cattattggc 14760
cgatgtgtct gaaggaacgg acgtgaaact cactattcaa cctgtagaaa aagatagtaa 14820
gaatagaagc tataatgtgt tggaagacaa aatcaacaca gcctatcgca gttggtatct 14880
ttcgtacaat tatggcgatc ccgaaaaagg agtgcgttcc tggacattgc tcaccacctc 14940
agatgtcacc tgcggagcag agcaggtcta ctggtcgctt ccagacatga tgaaggatcc 15000
tgtcactttc cgctccacta gacaagtcag taactaccct gtggtgggtg cagagcttat 15060
gcccgtcttc tcaaagagct tctacaacga acaagctgtg tactcccagc agctccgcca 15120
gtccacctcg cttacgcacg tcttcaaccg ctttcctgag aaccagattt taatccgtcc 15180
gccggcgccc accattacca ccgtcagtga aaacgttcct gctctcacag atcacgggac 15240
cctgccgttg cgcagcagta tccggggagt ccaacgtgtg accgttactg acgccagacg 15300
ccgcacctgt ccctacgtgt acaaggcact gggcatagtc gcaccgcgcg tcctttcaag 15360
ccgcactttc taaaaaaaaa aaaaatgtcc attcttatct cgcccagtaa taacaccggt 15420
tggggtctgc gcgctccaag caagatgtac ggaggcgcac gcaaacgttc tacccaacat 15480
cctgtccgtg ttcgcggaca ttttcgcgct ccatggggcg ccctcaaggg ccgcactcgc 15540
gttcgaacca ccgtcgatga tgtaatcgat caggtggttg ccgacgcccg taattatact 15600
cctactgcgc ctacatctac tgtggatgca gttattgaca gtgtagtggc tgacgctcgc 15660
aactatgctc gacgtaagag ccggcgaagg cgcattgcca gacgccaccg agctaccact 15720
gccatgcgag ccgcaagagc tctgctacga agagctagac gcgtggggcg aagagccatg 15780
cttagggcgg ccagacgtgc agcttcgggc gccagcgccg gcaggtcccg caggcaagca 15840
gccgctgtcg cagcggcgac tattgccgac atggcccaat cgcgaagagg caatgtatac 15900
tgggtgcgtg acgctgccac cggtcaacgt gtacccgtgc gcacccgtcc ccctcgcact 15960
tagaagatac tgagcagtct ccgatgttgt gtcccagcgg cgaggatgtc caagcgcaaa 16020
tacaaggaag aaatgctgca ggttatcgca cctgaagtct acggccaacc gttgaaggat 16080
gaaaaaaaac cccgcaaaat caagcgggtt aaaaaggaca aaaaagaaga ggaagatggc 16140
gatgatgggc tggcggagtt tgtgcgcgag tttgccccac ggcgacgcgt gcaatggcgt 16200
gggcgcaaag ttcgacatgt gttgagacct ggaacttcgg tggtctttac acccggcgag 16260
cgttcaagcg ctacttttaa gcgttcctat gatgaggtgt acggggatga tgatattctt 16320
gagcaggcgg ctgaccgatt aggcgagttt gcttatggca agcgtagtag aataacttcc 16380

-continued

```
aaggatgaga cagtgtcgat acccttggat catggaaatc ccacccctag tcttaaaccg  16440
gtcactttgc agcaagtgtt acccgtaact ccgcgaacag gtgttaaacg cgaaggtgaa  16500
gatttgtatc ccactatgca actgatggta cccaaacgcc agaagttgga ggacgttttg  16560
gagaaagtaa aagtggatcc agatattcaa cctgaggtta aagtgagacc cattaagcag  16620
gtagcgcctg gtctgggggt acaaactgta gacattaaga ttcccactga aagtatggaa  16680
gtgcaaactg aacccgcaaa gcctactgcc acctccactg aagtgcaaac ggatccatgg  16740
atgcccatgc ctattacaac tgacgccgcc ggtcccactc gaagatcccg acgaaagtac  16800
ggtccagcaa gtctgttgat gcccaattat gttgtacacc catctattat tcctactcct  16860
ggttaccgag gcactcgcta ctatcgcagc cgaaacagta cctcccgccg tcgccgcaag  16920
acacctgcaa atcgcagtcg tcgccgtaga cgcacaagca aaccgactcc cggcgccctg  16980
gtgcggcaag tgtaccgcaa tggtagtgcg gaacctttga cactgccgcg tgcgcgttac  17040
catccgagta tcatcactta atcaatgttg ccgctgcctc cttgcagata tggccctcac  17100
ttgtcgcctt cgcgttccca tcactggtta ccgaggaaga aactcgcgcc gtagaagagg  17160
gatgttggga cgcggaatgc gacgctacag gcgacggcgt gctatccgca agcaattgcg  17220
gggtggtttt ttaccagcct taattccaat tatcgctgct gcaattggcg cgataccagg  17280
catagcttcc gtggcggttc aggcctcgca acgacattga cattggaaaa aaacgtataa  17340
ataaaaaaaa aaaaatacaa tggactctga cactcctggt cctgtgacta tgttttctta  17400
gagatggaag acatcaattt ttcatccttg gctccgcgac acggcacgaa gccgtacatg  17460
ggcacctgga gcgacatcgg cacgagccaa ctgaacgggg gcgccttcaa ttggagcagt  17520
atctggagcg ggcttaaaaa ttttggctca accataaaaa catacgggaa caaagcttgg  17580
aacagcagta caggacaggc gcttagaaat aaacttaaag accagaactt ccaacaaaaa  17640
gtagtcgatg ggatagcttc cggcatcaat ggagtggtag atttggctaa ccaggctgtg  17700
cagaaaaaga taaacagtcg tttggacccg ccgccagcaa ccccaggtga aatgcaagtg  17760
gaggaagaaa ttcctccgcc agaaaaacga ggcgacaagc gtccgcgtcc cgatttggaa  17820
gagacgctgg tgacgcgcgt agatgaaccg ccttcttatg aggaagcaac gaagcttgga  17880
atgcccacca ctagaccgat agccccaatg gccaccgggg tgatgaaacc ttctcagttg  17940
catcgacccg tcaccttgga tttgccccct ccccctgctg ctactgctgt acccgcttct  18000
aagcctgtcg ctgccccgaa accagtcgcc gtagccaggt cacgtcccgg gggcgctcct  18060
cgtccaaatg cgcactggca aaatactctg aacagcatcg tgggtctagg cgtgcaaagt  18120
gtaaaacgcc gtcgctgctt ttaattaaat atggagtagc gcttaacttg cctatctgtg  18180
tatatgtgtc attacacgcc gtcacagcag cagaggaaaa aaggaagagg tcgtgcgtcg  18240
acgctgagtt actttcaaga tggccacccc atcgatgctg ccccaatggg catacatgca  18300
catcgccgga caggatgctt cggagtacct gagtccgggt ctggtgcagt tcgcccgcgc  18360
cacagacacc tacttcaatc tgggaaataa gtttagaaat cccaccgtag cgccgaccca  18420
cgatgtgacc accgaccgta gccagcggct catgttgcgc ttcgtgcccg ttgaccggga  18480
ggacaataca tactcttaca aagtgcggta caccctggcc gtgggcgaca acagagtgct  18540
ggatatggcc agcacgttct ttgacattag gggtgtgttg gacagaggtc ccagtttcaa  18600
accctattct ggtacggctt acaactccct ggctcctaaa ggcgctccaa atacatctca  18660
gtggattgca gaaggtgtaa aaaatacaac tggtgaggaa cacgtaacag aagaggaaac  18720
caatactact acttacactt ttggcaatgc tcctgtaaaa gctgaagctg aaattacaaa  18780
```

agaaggactc ccagtaggtt tggaagtttc agatgaagaa agtaaaccga tttatgctga 18840
taaaacatat cagccagaac ctcagctggg agatgaaact tggactgacc ttgatggaaa 18900
aaccgaaaag tatggaggca gggctctcaa acccgatact aagatgaaac catgctacgg 18960
gtcctttgcc aaacctacta atgtgaaagg cggtcaggca aaacaaaaaa caacggagca 19020
gccaaatcag aaagtcgaat atgatatcga catggagttt tttgatgcgg catcgcagaa 19080
aacaaactta agtcctaaaa ttgtcatgta tgcagaaaat gtaaatttgg aaactccaga 19140
cactcatgta gtgtacaaac ctggaacaga agacacaagt tccgaagcta atttgggaca 19200
acaatctatg cccaacagac ccaactacat tggcttcaga gataacttta ttggacttat 19260
gtactataac agtactggta acatgggggt gctggctggt caagcgtctc agttaaatgc 19320
agtggttgac ttgcaggaca gaaacacaga actttcttac caactcttgc ttgactctct 19380
gggcgacaga accagatact ttagcatgtg gaatcaggct gtggacagtt atgatcctga 19440
tgtacgtgtt attgaaaatc atggtgtgga agatgaactt cccaactact gttttccact 19500
ggacggcata ggtgttccaa caaccagtta caaatcaata gttccaaatg gagacaatgc 19560
gcctaattgg aaggaacctg aagtaaatgg aacaagtgag atcggacagg gtaatttgtt 19620
tgccatggaa attaaccttc aagccaatct atggcgaagt ttcctttatt ccaatgtggc 19680
tctatatctc ccagactcgt acaaatacac cccgtccaat gtcactcttc cagaaaacaa 19740
aaacacctac gactacatga acgggcgggt ggtgccgcca tctctagtag acacctatgt 19800
gaacattggt gccaggtggt ctctggatgc catggacaat gtcaacccat tcaaccacca 19860
ccgtaacgct ggcttgcgtt accgatccat gcttctgggt aacggacgtt atgtgccttt 19920
ccacatacaa gtgcctcaaa aattcttcgc tgttaaaaac ctgctgcttc tcccaggctc 19980
ctacacttat gagtggaact ttaggaagga tgtgaacatg gttctacaga gttccctcgg 20040
taacgacctg cgggtagatg gcgccagcat cagtttcacg agcatcaacc tctatgctac 20100 tttttcccc atggctcaca acaccgcttc caccttgaa gccatgctgc ggaatgacac 20160
caatgatcag tcattcaacg actacctatc tgcagctaac atgctctacc ccattcctgc 20220
caatgcaacc aatattccca tttccattcc ttctcgcaac tgggcggctt tcagaggctg 20280
gtcatttacc agactgaaaa ccaaagaaac tccctctttg ggtctggat ttgacccta 20340 ctttgtctat tctggttcta ttccctacct ggatggtacc ttctacctga accacacttt 20400
taagaaggtt tccatcatgt ttgactcttc agtgagctgg cctggaaatg acaggttact 20460
atctcctaac gaatttgaaa taaagcgcac tgtggatggc gaaggctaca acgtagccca 20520
atgcaacatg accaaagact ggttcttggt acagatgctc gccaactaca acatcggcta 20580
tcagggcttc tacattccag aaggatacaa agatcgcatg tattcatttt tcagaaactt 20640
ccagcccatg agcaggcagg tggttgatga ggtcaattac aaagacttca aggccgtcgc 20700 catacctac caacacaaca actctggctt tgtgggttac atggctccga ccatgcgcca 20760
aggtcaaccc tatcccgcta actatcccta tccactcatt ggaacaactg ccgtaaatag 20820
tgttacgcag aaaaagttct tgtgtgacag aaccatgtgg cgcataccgt tctcgagcaa 20880
cttcatgtct atgggggccc ttacagactt gggacagaat atgctctatg ccaactcagc 20940
tcatgctctg gacatgacct ttgaggtgga tcccatggat gagcccaccc tgctttatct 21000
tctcttcgaa gttttcgacg tggtcagagt gcatcagcca caccgcggca tcatcgaggc 21060
agtctacctg cgtacaccgt tctcggccgg taacgctacc acgtaagaag cttcttgctt 21120

-continued

```
cttgcaaata gcagctgcaa ccatggcctg cggatcccaa aacggctcca gcgagcaaga  21180
gctcagagcc attgtccaag acctgggttg cggaccctat tttttgggaa cctacgataa  21240
gcgcttcccg gggttcatgg cccccgataa gctcgcctgt gccattgtaa atacggccgg  21300
acgtgagacg gggggagagc actggttggc tttcggttgg aacccacgtt ctaacacctg  21360
ctaccttttt gatccttttg gattctcgga tgatcgtctc aaacagattt accagtttga  21420
atatgagggt ctcctgcgcc gcagcgctct tgctaccaag gaccgctgta ttacgctgga  21480
aaaatctacc cagaccgtgc agggtccccg ttctgccgcc tgcggacttt tctgctgcat  21540
gttccttcac gcctttgtgc actggcctga ccgtcccatg gacggaaacc ccaccatgaa  21600
attgctaact ggagtgccaa acaacatgct tcattctcct aaagtccagc ccaccctgtg  21660
tgacaatcaa aaagcactct accattttct taatacccat tcgccttatt ttcgctccca  21720
tcgtacacac atcgaaaggg ccactgcgtt cgaccgtatg gatgttcaat aatgactcat  21780
gtaaacaacg tgttcaataa acatcacttt attttttttac atgtatcaag gctctgcatt  21840
acttatttat ttacaagtcg aatgggttct gacgagaatc agaatgaccc gcaggcagtg  21900
atacgttgcg gaactgatac ttgggttgcc acttgaattc gggaatcacc aacttgggaa  21960
ccggtatatc gggcaggatg tcactccaca gctttctggt cagctgcaaa gctccaagca  22020
ggtcaggagc cgaaatcttg aaatcacaat taggaccagt gctttgagcg cgagagttgc  22080
ggtacaccgg attgcagcac tgaaacacca tcagcgacgg atgtctcacg cttgccagca  22140
cggtgggatc tgcaatcatg cccacatcca gatcttcagc attggcaatg ctgaacgggg  22200
tcatcttgca ggtctgccta cccatggcgg gcacccaatt aggcttgtgg ttgcaatcgc  22260
agtgcagggg gatcagtatc atcttggcct gatcctgtct gattcctgga tacacggctc  22320
tcatgaaagc atcatattgc ttgaaagcct gctgggcttt actaccctcg gtataaaaca  22380
tcccgcagga cctgctcgaa aactggttag ctgcacagcc ggcatcattc acacagcagc  22440
gggcgtcatt gttagctatt tgcaccacac ttctgcccca gcggttttgg gtgattttgg  22500
ttcgctcggg attctccttt aaggctcgtt gtccgttctc gctggccaca tccatctcga  22560
taatctgctc cttctgaatc ataatattgc catgcaggca cttcagcttg ccctcataat  22620
cattgcagcc atgaggccac aacgcacagc ctgtacattc ccaattatgg tgggcgatct  22680
gagaaaaaga atgtatcatt ccctgcagaa atcttcccat catcgtgctc agtgtcttgt  22740
gactagtgaa agttaactgg atgcctcggt gctcctcgtt tacgtactgg tgacagatgc  22800
gcttgtattg ttcgtgttgc tcaggcatta gtttaaaaga ggttctaagt tcgttatcca  22860
gcctgtactt ctccatcagc agacacatca cttccatgcc tttctcccaa gcagacacca  22920
ggggcaagct aatcggattc ttaacagtgc aggcagcagc tcctttagcc agagggtcat  22980
ctttagcgat cttctcaatg cttcttttgc catccttctc aacgatgcgc acgggcgggt  23040
agctgaaacc cactgctaca agttgcgcct cttctctttc ttcttcgctg tcttgactga  23100
tgtcttgcat ggggatatgt ttggtcttcc ttggcttctt tttgggggt atcggaggag  23160
gaggactgtc gctccgttcc ggagacaggg aggattgtga cgtttcgctc accattacca  23220
actgactgtc ggtagaagaa cctgacccca cacggcgaca ggtgtttctc ttcgggggca  23280
gaggtggagg cgattgcgaa gggctgcggt ccgacctgga aggcggatga ctggcagaac  23340
cccttccgcg ttcgggggtg tgctccctgt ggcggtcgct taactgattt ccttcgcggc  23400
tggccattgt gttctcctag gcagagaaac aacagacatg gaaactcagc cattgctgtc  23460
aacatcgcca cgagtgccat cacatctcgt cctcagcgac gaggaaaagg agcagagctt  23520
```

```
aagcattcca ccgcccagtc ctgccaccac ctctacccta gaagataagg aggtcgacgc  23580
atctcatgac atgcagaata aaaaagcgaa agagtctgag acagacatcg agcaagaccc  23640
gggctatgtg acaccggtgg aacacgagga agagttgaaa cgctttctag agagagagga  23700
tgaaaactgc ccaaaacaac gagcagataa ctatcaccaa gatgctggaa atagggatca  23760
gaacaccgac tacctcatag ggcttgacgg ggaagacgcg ctccttaaac atctagcaag  23820
acagtcgctc atagtcaagg atgcattatt ggacagaact gaagtgccca tcagtgtgga  23880
agagctcagc cgcgcctacg agcttaacct cttttcacct cgtactcccc ccaaacgtca  23940
gccaaacggc acctgcgagc caaatcctcg cttaaacttt tatccagctt ttgctgtgcc  24000
agaagtactg gctacctatc acatcttttt taaaaatcaa aaaattccag tctcctgccg  24060
cgctaatcgc acccgcgccg atgccctact caatctggga cctggttcac gcttacctga  24120
tatagcttcc ttggaagagg ttccaaagat cttcgagggt ctgggcaata atgagactcg  24180
ggccgcaaat gctctgcaaa agggagaaaa tggcatggat gagcatcaca gcgttctggt  24240
ggaattggaa ggcgataatg ccagactcgc agtactcaag cgaagcatcg aggtcacaca  24300
cttcgcatat cccgctgtca acctgccccc taaagtcatg acggcggtca tggaccagtt  24360
actcattaag cgcgcaagtc ccctttcaga agacatgcat gacccagatg cctgtgatga  24420
gggtaaacca gtggtcagtg atgagcagct aacccgatgg ctgggcaccg actctcccag  24480
ggatttggaa gagcgtcgca agcttatgat ggccgtggtg ctggttaccg tagaactaga  24540
gtgtctccga cgtttcttta ccgattcaga aaccttgcgc aaactcgaag agaatctgca  24600
ctacactttt agacacggct ttgtgcggca ggcatgcaag atatctaacg tggaactcac  24660
caacctggtt tcctacatgg gtattctgca tgagaatcgc ctaggacaaa gcgtgctgca  24720
cagcaccctg aagggggaag cccgccgtga ttacatccgc gattgtgtct atctgtacct  24780
gtgccacacg tggcaaaccg gcatgggtgt atggcagcaa tgtttagaag aacagaactt  24840
gaaagagctt gacaagctct tacagaaatc tcttaaggtt ctgtggacag ggttcgacga  24900
gcgcaccgtc gcttccgacc tggcagacct catcttccca gagcgtctca gggttacttt  24960
gcgaaacgga ttgcctgact ttatgagcca gagcatgctt aacaattttc gctctttcat  25020
cctggaacgc tccggtatcc tgcccgccac ctgctgcgca ctgccctccg actttgtgcc  25080
tctcacctac cgcgagtgcc ccccgccgct atggagtcac tgctacctgt tccgtctggc  25140
caactatctc tcctaccact cggatgtgat cgaggatgtg agcggagacg gcttgctgga  25200
gtgtcactgc cgctgcaatc tgtgcacgcc ccaccggtcc ctagcttgca acccccagtt  25260
gatgagcgaa acccagataa taggcacctt tgaattgcaa ggccccagca gccaaggcga  25320
tgggtcttct cctgggcaaa gtttaaaact gaccccggga ctgtggacct ccgcctactt  25380
gcgcaagttt gctccggaag attaccaccc ctatgaaatc aagttctatg aggaccaatc  25440
acagcctcca aaggccgaac tttcggcctg cgtcatcacc cagggggcaa ttctggccca  25500
attgcaagcc atccaaaaat cccgccaaga atttctactg aaaaagggta agggggtcta  25560
ccttgacccc cagaccggcg aggaactcaa cacaaggttc cctcaggatg tcccaacgac  25620
gagaaaacaa gaagttgaag gtgcagccgc cgcccccaga agatatggag gaagattggg  25680
acagtcaggc agaggaggcg gaggaggaca gtctggagga cagtctggag gaagacagtt  25740
tggaggagga aaacgaggag gcagaggagg tggaagaagt aaccgccgac aaacagttat  25800
cctcggctgc ggagacaagc aacagcgcta ccatctccgc tccgagtcga ggaacccggc  25860
```

ggcgtcccag cagtagatgg gacgagaccg gacgcttccc gaacccaacc agcgcttcca 25920
agaccggtaa gaaggatcgg cagggataca agtcctggcg ggggcataag aatgccatca 25980
tctcctgctt gcatgagtgc gggggcaaca tatccttcac gcggcgctac ttgctattcc 26040
accatggggt gaactttccg cgcaatgttt tgcattacta ccgtcacctc cacagcccct 26100
actatagcca gcaaatcccg gcagtctcga cagataaaga cagcggcggc gacctccaac 26160
agaaaaccag cagcggcagt tagaaaatac acaacaagtg cagcaacagg aggattaaag 26220
attacagcca acgagccagc gcaaacccga gagttaagaa atcggatctt tccaaccctg 26280
tatgccatct tccagcagag tcggggtcaa gagcaggaac tgaaaataaa aaaccgatct 26340
ctgcgttcgc tcaccagaag ttgtttgtat cacaagagcg aagatcaact tcagcgcact 26400
ctcgaggacg ccgaggctct cttcaacaag tactgcgcgc tgactcttaa agagtaggca 26460
gcgaccgcgc ttattcaaaa aaggcgggaa ttacatcatc ctcgacatga gtaaagaaat 26520
tcccacgcct tacatgtgga gttatcaacc ccaaatggga ttggcggcag gcgcctccca 26580
ggactactcc acccgcatga attggctcag cgccgggcct tctatgattt ctcgagttaa 26640
tgatatacgc gcctaccgaa accaaatact tttggaacag tcagctctta ccaccacgcc 26700
ccgccaacac cttaatccca gaaattggcc cgccgcccta gtgtaccagg aaagtcccgc 26760
tcccaccact gtattacttc ctcgagacgc ccaggccgaa gtccaaatga ctaatgcagg 26820
tgcgcagtta gctggcggct ccaccctatg tcgtcacagg cctcggcata atataaaacg 26880
cctgatgatc agaggccgag gtatccagct caacgacgag tcggtgagct ctccgcttgg 26940
tctacgacca gacggaatct ttcagattgc cggctgcggg agatcttcct tcacccctcg 27000
tcaggctgtt ctgactttgg aaagttcgtc ttcgcaaccc cgctcgggcg gaatcgggac 27060
cgttcaattt gtggaggagt ttactccctc tgtctacttc aaccccttct ccggatctcc 27120
tgggcattac ccggacgagt tcataccgaa cttcgacgcg attagcgagt cagtggacgg 27180
ctacgattga tgtctggtga cgcggctgag ctatctcggc tgcgacatct agaccactgc 27240
cgccgctttc gctgctttgc ccgggaactc attgagttca tctacttcga actccccaag 27300
gatcaccctc aaggtccggc ccacggagtg cggatttcta tcgaaggcaa aatagactct 27360
cgcctgcaac gaattttctc ccagcggccc gtgctgatcg agcgagacca gggaaacacc 27420
acggtttcca tctactgcat ttgtaatcac cccggattgc atgaaagcct ttgctgtctt 27480
atgtgtactg agtttaataa aaactgaatt aagactctcc tacggactgc cgcttcttca 27540
acccggattt tacaaccaga agaacgaaac ttttcctgtc gtccaggact ctgttaactt 27600
cacctttcct actcacaaac tagaagctca acgactacac cgcttttcca gaagcatttt 27660
ccctactaat actactttca aaaccggagg tgagctccaa ggtcttccta cagaaaaccc 27720
ttgggtggaa gcgggccttg tagtgctagg aattcttgcg ggtgggcttg tgattattct 27780
ttgctaccta tacacacctt gcttcacttt cttagtggtg ttgtggtatt ggtttaaaaa 27840
atggggccca tactagtctt gcttgtttta ctttcgcttt tggaaccggg ttctgccaat 27900
tacgatccat gtctagactt cgacccagaa aactgcacac ttacttttgc acccgacaca 27960
agccgcatct gtggagttca tcgcctctct tacgaacttg gcccccaacg acaaaaattt 28020
acctgcatgg tgggaatcaa ccccatagtt atcacccagc aaagtggaga tactaagggt 28080
tgcattcact gctcctgcga ttccatcgag tgcacctaca ccctgctgaa gaccctatgc 28140
ggcctaagag acctgctacc aatgaattaa aaaatgatta ataaaaaatc acttacttga 28200
aatcagcaat aaggtctctg ttgaaatttt ctcccagcag cacctcactt ccctcttccc 28260

```
aactctggta ttctaaaccc cgttcagcgg catactttct ccatacttta aaggggatgt  28320
caaattttag ctcctctcct gtacccacaa tcttcatgtc tttcttccca gagcggccgc  28380
atgaccaaga gagtccggct cagtgactcc ttcaaccctg tctacccta tgaagatgaa  28440
agcacctccc aacaccctt tataaaccca gggtttattt ccccaaatgg cttcacacaa  28500
agcccaaacg gagttcttac tttaaaatgt ttaaccccac taacaaccac aggcggatct  28560
ctacagctaa aagtgggagg gggacttaca gtggatgaca ccaacggttt tttgaaagaa  28620
aacataagtg ccaccacacc actcgttaag actggtcact ctataggttt accactagga  28680
gccggattgg gaacgaatga aaataaactt tgtatcaaat taggacaagg acttacattc  28740
aattcaaaca acatttgcat tgatgacaat attaacacct tatggacagg agtcaacccc  28800
accgaagcca actgtcaaat catgaactcc agtgaatcta atgattgcaa attaattcta  28860
acactagtta aaactggagc actagtcact gcatttgttt atgttatagg agtatctaac  28920
aattttaata tgctaactac acacagaaat ataaatttta ctgcagagct gtttttcgat  28980
tctactggta atttactaac tagactctca tccctcaaaa ctccacttaa tcataaatca  29040
ggacaaaaca tggctactgg tgccattact aatgctaaag gtttcatgcc cagcacgact  29100
gcctatcctt tcaatgataa ttctagagaa aaagaaaact acatttacgg aacttgttac  29160
tacacagcta gtgatcgcac tgcttttccc attgacatat ctgtcatgct taaccgaaga  29220
gcaataaatg acgagacatc atattgtatt cgtataactt ggtcctggaa cacaggagat  29280
gccccagagg tgcaaacctc tgctacaacc ctagtcacct ccccatttac cttttactac  29340
atcagagaag acgactgaca aataaagttt aacttgttta tttgaaaatc aattcacaaa  29400
atccgagtag ttattttgcc tcccccttcc catttaacag aatacaccaa tctctcccca  29460
cgcacagctt taaacatttg gataccatta gatatagaca tggttttaga ttccacattc  29520
caaacagttt cagagcgagc caatctgggg tcagtgatag ataaaaaatcc atcgggatag  29580
tcttttaaag cgctttcaca gtccaactgc tgcggatgcg actccggagt ctggatcacg  29640
gtcatctgga agaagaacga tgggaatcat aatccgaaaa cggtatcgga cgattgtgtc  29700
tcatcaaacc cacaagcagc cgctgtctgc gtcgctccgt gcgactgctg tttatgggat  29760
cagggtccac agtgtcctga agcatgattt taatagccct taacatcaac tttctggtgc  29820
gatgcgcgca gcaacgcatt ctgatttcac tcaaatcttt gcagtaggta caacacatta  29880
ttacaatatt gtttaataaa ccataattaa aagcgctcca gccaaaactc atatctgata  29940
taatcgcccc tgcatgacca tcataccaaa gtttaatata aattaaatga cgttccctca  30000
aaaacacact acccacatac atgatctctt ttggcatgtg catattaaca atctgtctgt  30060
accatggaca acgttggtta atcatgcaac ccaatataac cttccggaac cacactgcca  30120
acaccgctcc cccagccatg cattgaagtg aaccctgctg attacaatga caatgaagaa  30180
cccaattctc tcgaccgtga atcacttgag aatgaaaaat atctatagtg gcacaacata  30240
gacataaatg catgcatctt ctcataattt ttaactcctc aggatttaga aacatatccc  30300
agggaatagg aagctcttgc agaacagtaa agctggcaga acaaggaaga ccacgaacac  30360
aacttacact atgcatagtc atagtatcac aatctggcaa cagcgggtgg tcttcagtca  30420
tagaagctcg ggtttcattt tcctcacaac gtggtaactg ggctctggtg taagggtgat  30480
gtctggcgca tgatgtcgag cgtgcgcgca accttgtcat aatggagttg cttcctgaca  30540
ttctcgtatt ttgtatagca aaacgcggcc ctggcagaac acactcttct tcgccttcta  30600
```

```
tcctgccgct tagcgtgttc cgtgtgatag ttcaagtaca accacactct taagttggtc  30660
aaaagaatgc tggcttcagt tgtaatcaaa actccatcgc atctaatcgt tctgaggaaa  30720
tcatccaagc aatgcaactg gattgtgttt caagcaggag aggagaggga agagacggaa  30780
gaaccatgtt aatttttatt ccaaacgatc tcgcagtact tcaaattgta gatcgcgcag  30840
atggcatctc tcgcccccac tgtgttggtg aaaaagcaca gctagatcaa aagaaatgcg  30900
attttcaagg tgctcaacgg tggcttccag caaagcctcc acgcgcacat ccaagaacaa  30960
aagaatacca aaagaaggag cattttctaa ctcctcaatc atcatattac attcctgcac  31020
cattcccaga taattttcag ctttccagcc ttgaattatt cgtgtcagtt cttgtggtaa  31080
atccaatcca cacattacaa acaggtcccg gagggcgccc tccaccacca ttcttaaaca  31140
caccctcata atgacaaaat atcttgctcc tgtgtcacct gtagcgaatt gagaatggca  31200
acatcaattg acatgccctt ggctctaagt tcttctttaa gttctagttg taaaaactct  31260
ctcatattat caccaaactg cttagccaga agcccccggg gaacaagagc aggggacgct  31320
acagtgcagt acaagcgcag acctccccaa ttggctccag caaaaacaag attggaataa  31380
gcatattggg aaccgccagt aatatcatcg aagttgctgg aaatataatc aggcagagtt  31440
tcttgtaaaa attgaataaa agaaaaattt gccaaaaaaa cattcaaaac ctctgggatg  31500
caaatgcaat aggttaccgc gctgcgctcc aacattgtta gttttgaatt agtctgcaaa  31560
aataaaaaaa aaaacaagcg tcatatcata gtagcctgac gaacagatgg ataaatcagt  31620
ctttccatca caagacaagc cacagggtct ccagctcgac cctcgtaaaa cctgtcatca  31680
tgattaaaca acagcaccga aagttcctcg cggtgaccag catgaataat tcttgatgaa  31740
gcatacaatc cagacatgtt agcatcagtt aacgagaaaa aacagccaac atagcctttg  31800
ggtataatta tgcttaatcg taagtatagc aaagccaccc ctcgcggata caaagtaaaa  31860
ggcacaggag aataaaaaat ataattattt ctctgctgct gttcaggcaa cgtcgccccc  31920
ggtccctcta aatacacata caaagcctca tcagccatgg cttaccagac aaagtacagc  31980
gggcacacaa agcacaagct ctaaagtgac tctccaacct ctccacaata tatatataca  32040
caagccctaa actgacgtaa tgggagtaaa gtgtaaaaaa tcccgccaaa cccaacacac  32100
accccgaaac tgcgtcacca gggaaaagta cagtttcact tccgcaatcc caacaggcgt  32160
aacttcctct ttctcacggt acgtgatatc ccactaactt gcaacgtcat tttcccacgg  32220
tcgcaccgcc ccttttagcc gttaacccca cagccaatca ccacacgatc cacacttttt  32280
aaaatcacct catttacata ttggcaccat tccatctata aggtatatta tatagatagg  32340
```

<210> SEQ ID NO 35
<211> LENGTH: 36280
<212> TYPE: DNA
<213> ORGANISM: Artificial Sequence
<220> FEATURE:
<223> OTHER INFORMATION: Plasmid pNG-62

<400> SEQUENCE: 35

```
ggcgcgccta tctatataat ataccttata gatggaatgg tgccaatatg taaatgaggt     60
gattttaaaa agtgtggatc gtgtggtgat tggctgtggg gttaacggct aaaaggggcg    120
gtgcgaccgt gggaaaatga cgttttgtgg gggtggagtt tttttgcaag ttgtcgcggg    180
aaatgtgacg cataaaaagg ctttttctc acggaactac ttagttttcc cacggtattt    240
aacaggaaat gaggtagttt tgaccggatg caagtgaaaa ttgttgattt tcgcgcgaaa    300
actgaatgag gaagtgtttt tctgaataat gtggtattta tggcagggtg gagtatttgt    360
```

```
tcagggccag gtagactttg acccattacg tggaggtttc gattaccgtg ttttttacct    420
gaatttccgc gtaccgtgtc aaagtcttct gtttttacgt aggtgtcagc tgatcgctag    480
ggtatttata cctcagggtt tgtgtcaaga ggccactctt gagtgccagc gagaagagtt    540
ttctcctctg cgccggcagt ttaataataa aaaaatgaga gatttgcgat ttctgcctca    600
ggaaataatc tctgctgaga ctggaaatga aatattggag cttgtggtgc acgccctgat    660
gggagacgat ccggagccac ctgtgcagct ttttgagcct cctacgcttc aggaactgta    720
tgatttagag gtagagggat cggaggattc taatgaggaa gctgtaaatg gcttttttac    780
cgattctatg cttttagctg ctaatgaagg gttagaatta gatccgcctt tggacacttt    840
tgatactcca ggggtaattg tggaaagcgg tacaggtgta agaaaattac ctgatttgag    900
ttccgtggac tgtgatttgc actgctatga agacgggttt cctccgagtg atgaggagga    960
ccatgaaaag gagcagtcca tgcagactgc agcgggtgag ggagtgaagg ctgccaatgt   1020
tggttttcag ttggattgcc cggagcttcc tggacatggc tgtaagtctt gtgaatttca   1080
caggaaaaat actggagtaa aggaactgtt atgttcgctt tgttatatga gaacgcactg   1140
ccactttatt tacagtaagt gtgtttaagt taaaatttaa aggaatatgc tgtttttcac   1200
atgtatattg agtgtgagtt ttgtgcttct tattataggt cctgtgtctg atgctgatga   1260
atcaccatct cctgattcta ctacctcacc tcctgagatt caagcacctg ttcctgtgga   1320
cgtgcgcaag cccattcctg tgaagcttaa gcctgggaaa cgtccagcag tggaaaaact   1380
tgaggacttg ttacagggtg gggacggacc tttggacttg agtacacgga aacgtccaag   1440
acaataagtg ttccatatcc gtgtttactt aaggtgacgt caatatttgt gtgacagtgc   1500
aatgtaataa aaatatgtta actgttcact ggtttttatt gctttttggg cggggactca   1560
ggtatataag tagaagcaga cctgtgtggt tagctcatag gagctggctt tcatccatgg   1620
aggtttgggc cattttggaa gaccttagga agactaggca actgttagag aacgcttcgg   1680
acggagtctc cggtttttgg agattctggt tcgctagtga attagctagg gtagttttta   1740
ggataaaaca ggactataaa caagaatttg aaaagttgtt ggtagattgc ccaggacttt   1800
ttgaagctct taatttgggc catcaggttc actttaaaga aaaagtttta tcagttttag   1860
acttttcaac cccaggtaga actgctgctg ctgtggcttt tcttactttt atattagata   1920
aatggatccc gcagactcat ttcagcaggg gatacgtttt ggatttcata gccacagcat   1980
tgtggagaac atggaaggtt cgcaagatga ggacaatctt aggttactgg ccagtgcagc   2040
ctttgggtgt agcgggaatc ctgaggcatc caccggtcat gccagcggtt ctggaggagg   2100
aacagcaaga ggacaacccg agagccggcc tggaccctcc agtggaggag gcggagtagc   2160
tgacttgtct cctgaactgc aacgggtgct tactggatct acgtccactg gacgggatag   2220
gggcgttaag agggagaggg catctagtgg tactgatgct agatctgagt tggctttaag   2280
tttaatgagt cgcagacgtc ctgaaaccat ttggtggcat gaggttcaga aagagggaag   2340
ggatgaagtt tctgtattgc aggagaaata ttcactggaa caggtgaaaa catgttggtt   2400
ggagcctgag gatgattggg aggtggccat taaaaattat gccaagatag ctttgaggcc   2460
tgataaacag tataagatta ctagacggat taatatccgg aatgcttgtt acatatctgg   2520
aaatggggct gaggtggtaa tagatactca agacaaggca gttattagat gctgcatgat   2580
ggatatgtgg cctggggtag tcggtatgga agcagtaact tttgtaaatg ttaagtttag   2640
gggagatggt tataatggaa tagtgtttat ggccaatacc aaacttatat tgcatggttg   2700
```

-continued tagctttttt ggtttcaaca atacctgtgt agatgcctgg ggacaggtta gtgtacgggg 2760
atgtagtttc tatgcgtgtt ggattgccac agctggcaga accaagagtc aattgtctct 2820
gaagaaatgc atatttcaaa gatgtaacct gggcattctg aatgaaggcg aagcaagggt 2880
ccgccactgc gcttctacag atactggatg ttttattttg attaagggaa atgccagcgt 2940
aaagcataac atgatttgcg gtgcttccga tgagaggcct tatcaaatgc tcacttgtgc 3000
tggtgggcat tgtaatatgc tggctactgt gcatattgtt tcccatcaac gcaaaaaatg 3060
gcctgttttt gatcacaatg tgatgacgaa gtgtaccatg catgcaggtg ggcgtagagg 3120
aatgtttatg ccttaccagt gtaacatgaa tcatgtgaaa gtgttgttgg aaccagatgc 3180
cttttccaga atgagcctaa caggaatttt tgacatgaac atgcaaatct ggaagatcct 3240
gaggtatgat gatacgagat cgagggtacg cgcatgcgaa tgcggaggca agcatgccag 3300
gttccagccg gtgtgtgtag atgtgactga agatctcaga ccggatcatt tggttattgc 3360
ccgcactgga gcagagttcg gatccagtgg agaagaaact gactaaggtg agtattggga 3420
aaactttggg gtgggatttt cagatggaca gattgagtaa aaatttgttt tttctgtctt 3480
gcagctgtca tgagtggaaa cgcttctttt aaggggggag tcttcagccc ttatctgaca 3540
gggcgtctcc catcctgggc aggagttcgt cagaatgtta tgggatctac tgtggatgga 3600
agacccgtcc aacccgccaa ttcttcaacg ctgacctatg ctactttaag ttcttcacct 3660
ttggacgcag ctgcagctgc cgccgccgct tctgttgccg ctaacactgt gcttggaatg 3720
ggttactatg gaagcatcat ggctaattcc acttcctcta ataacccttc taccctgact 3780
caggacaagt tacttgtcct tttggcccag ctggaggctt tgacccaacg tctgggtgaa 3840
ctttctcagc aggtggtcga gttgcgagta caaactgagt ctgctgtcgg cacggcaaag 3900
tctaaataaa aaaatcccag aatcaatgaa taaataaaca agcttgttgt tgatttaaaa 3960
tcaagtgttt ttatttcatt tttcgcgcac ggtatgccct agaccaccga tctctatcat 4020
tgagaactcg gtggattttt tccaggatcc tatagaggtg ggattgaatg tttagataca 4080
tgggcattag gccgtctttg gggtggagat agctccattg aagggattca tgctccgggg 4140
tagtgttgta aatcacccag tcataacaag gtcgcagtgc atggtgttgc acaatatctt 4200
ttagaagtag gctgattgcc acagataagc ccttggtgta ggtgtttaca aaccggttga 4260
gctgggatgg gtgcattcgg ggtgaaatta tgtgcatttt ggattggatt tttaagttgg 4320
caatattgcc gccaagatcc cgtcttgggt tcatgttatg aaggaccacc aagacggtgt 4380
atccggtaca tttaggaaat ttatcgtgca gcttggatgg aaaagcgtgg aaaaatttgg 4440
agacaccctt gtgtcctcca agattttcca tgcactcatc catgataata gcaatggggc 4500
cgtgggcagc ggcgcgggca aacacgttcc gtgggtctga cacatcatag ttatgttcct 4560
gagttaaatc atcataagcc attttaatga atttggggcg gagagtacca gattggggta 4620
tgaatgttcc ttcgggcccc ggagcatagt tcccctcaca gatttgcatt tcccaagctt 4680
tcagttccga gggtggaatc atgtccacct ggggggctat gaaaaacacc gtttctgggg 4740
cgggggtgat taattgtgat gatagcaaat ttctgagcaa ttgagatttg ccacatccgg 4800
tggggccata aatgattccg attacgggtt gcaggtggta gtttagggaa cggcaactgc 4860
cgtcttctcg aagcaagggg gccacctcgt tcatcatttc ccttacatgc atattttccc 4920
gcaccaaatc cattaggagg cgctctcctc ctagtgatag aagttcttgt agtgaggaaa 4980
agtttttcag cggtttcaga ccgtcagcca tgggcatttt ggagagagtt tgctgcaaaa 5040
gttctagtct gttccacagt tcagtgatgt gttctatggc atctcgatcc agcagacctc 5100

-continued

```
ctcgtttcgc gggtttggac ggctcctgga atagggtatg agacgatggg cgtccagcgc   5160
tgccagggtt cggtccttcc agggtctcag tgttcgagtc agggttgttt ccgtcacagt   5220
gaaggggtgt gcgcctgctt gggcgcttgc cagggtgcgc ttcagactca tcctgctggt   5280
cgaaaacttc tgtcgcttgg cgccctgtat gtcggccaag tagcagttta ccatgagttc   5340
gtagttgagc gcctcggctg cgtggccttt ggcgcggagc ttacctttgg aagttttctt   5400
gcataccggg cagtataggc atttcagcgc atacaacttg ggcgcaagga aaacggattc   5460
tggggagtat gcatctgcgc cgcaggaggc gcaaacagtt tcacattcca ccagccaggt   5520
taaatccggt tcattggggt caaaaacaag ttttccgcca tattttttga tgcgtttctt   5580
acctttggtc tccatgagtt cgtgtcctcg ttgagtgaca aacaggctgt ccgtgtcccc   5640
gtagactgat tttacaggcc tcttctccag tggagtgcct cggtcttctt cgtacaggaa   5700
ctctgaccac tctgatacaa aggcgcgcgt ccaggccagc acaaaggagg ctatgtggga   5760
ggggtagcga tcgttgtcaa ccagggggtc cacctttttcc aaagtatgca aacacatgtc  5820
accctcttca acatccagga atgtgattgg cttgtaggtg tatttcacgt gacctggggt   5880
ccccgctggg ggggtataaa agggggcggt tctttgctct tcctcactgt cttccggatc   5940
gctgtccagg aacgtcagct gttggggtag gtattccctc tcgaaggcgg gcatgacctc   6000
tgcactcagg ttgtcagttt ctaagaacga ggaggatttg atattgacag tgccggttga   6060
gatgcctttc atgaggtttt cgtccatctg gtcagaaaac acaatttttt tattgtcaag   6120
tttggtggca aatgatccat acagggcgtt ggataaaagt ttggcaatgg atcgcatggt   6180
ttggttcttt tccttgtccg cgcgctcttt ggcggcgatg ttgagttgga catactcgcg   6240
tgccaggcac ttccattcgg ggaagatagt tgttaattca tctggcacga ttctcacttg   6300
ccaccctcga ttatgcaagg taattaaatc cacactggtg gccacctcgc ctcgaagggg   6360
ttcattggtc caacagagcc tacctccttt cctagaacag aaagggggaa gtgggtctag   6420
cataagttca tcgggagggt ctgcatccat ggtaaagatt cccggaagta aatccttatc   6480
aaaatagctg atgggagtgg ggtcatctaa ggccatttgc cattctcgag ctgccagtgc   6540
gcgctcatat gggttaaggg gactgcccca tggcatggga tgggtgagtg cagaggcata   6600
catgccacag atgtcataga cgtagatggg atcctcaaag atgcctatgt aggttggata   6660
gcatcgcccc cctctgatac ttgctcgcac atagtcatat agttcatgtg atggcgctag   6720
cagccccgga cccaagttgg tgcgattggg tttttctgtt ctgtagacga tctggcgaaa   6780
gatggcgtga gaattggaag agatggtggg tctttgaaaa atgttgaaat gggcatgagg   6840
tagacctaca gagtctctga caaagtgggc ataagattct tgaagcttgg ttaccagttc   6900
ggcggtgaca agtacgtcta gggcgcagta gtcaagtgtt tcttgaatga tgtcataacc   6960
tggttggttt ttcttttccc acagttcgcg gttgagaagg tattcttcgc gatccttcca   7020
gtactcttct agcggaaacc cgtctttgtc tgcacggtaa gatcctagca tgtagaactg   7080
attaactgcc ttgtaagggc agcagccctt ctctacgggt agagagtatg cttgagcagc   7140
ttttcgtagc gaagcgtgag taagggcaaa ggtgtctctg accatgactt tgaggaattg   7200
gtatttgaag tcgatgtcgt cacaggctcc ctgttcccag agttggaagt ctacccgttt   7260
cttgtaggcg gggttgggca aagcgaaagt aacatcattg aagagaatct tgccggccct   7320
gggcatgaaa ttgcgagtga tgcgaaaagg ctgtggtact tccgctcggt tattgataac   7380
ctgggcagct aggacgatct cgtcgaaacc gttgatgttg tgtcctacga tgtataattc   7440
```

-continued

```
tatgaaacgc ggcgtgcctc tgacgtgagg tagcttactg agctcatcaa aggttaggtc   7500
tgtggggtca gataaggcgt agtgttcgag agcccattcg tgcaggtgag gattcgcttt   7560
aaggaaggag gaccagaggt ccactgccag tgctgtttgt aactggtccc ggtactgacg   7620
aaaatgccgt ccgactgcca ttttttctgg ggtgacgcaa tagaaggttt gggggtcctg   7680
ccgccagcga tcccacttga gttttatggc gaggtcatag gcgatgttga cgagccgctg   7740
gtctccagag agtttcatga ccagcatgaa ggggattagc tgcttgccaa aggaccccat   7800
ccaggtgtag gtttccacat cgtaggtgag aaagagcctt tctgtgcgag gatgagagcc   7860
aatcgggaag aactggatct cctgccacca gttggaggaa tggctgttga tgtgatggaa   7920
gtagaactcc ctgcgacgcg ccgagcattc atgcttgtgc ttgtacagac ggccgcagta   7980
gtcgcagcgt tgcacgggtt gtatctcgtg aatgagttgt acctggcttc ccttgacgag   8040
aaatttcagt gggaagccga ggcctggcga ttgtatctcg tgctttacta tgttgtctgc   8100
atcggcctgt tcatcttctg tctcgatggt ggtcatgctg acgagccctc gcgggaggca   8160
agtccagacc tcggcgcggc aggggcggag ctcgaggacg agagcgcgca ggctggagct   8220
gtccagggtc ctgagacgct gcggactcag gttagtaggc agtgtcagga gattaacttg   8280
catgatcttt tggagggcgt gcgggaggtt cagatagtac ttgatctcaa cgggtccgtt   8340
ggtggagatg tcgatggctt gcagggttcc gtgtcccttg ggcgctacca ccgtgccctt   8400
gtttttcatt ttggacggcg gtggctctgt tgcttcttgc atgtttagaa gcggtgtcga   8460
gggcgcgcac cgggcggcag gggcggctcg ggacccggcg gcatggctgg cagtggtacg   8520
tcggcgccgc gcgcgggtag gttctggtac tgcgccctga gaagactcgc atgcgcgacg   8580
acgcggcggt tgacatcctg gatctgacgc ctctgggtga aagctaccgg ccccgtgagc   8640
ttgaacctga aagagagttc aacagaatca atctcggtat cgttgacggc ggcttgccta   8700
aggatttctt gcacgtcacc agagttgtcc tggtaggcga tctccgccat gaactgctcg   8760
atctcttcct cttgaagatc tccgcggccc gctctctcga cggtggccgc gaggtcgttg   8820
gagatgcgcc caatgagttg agagaatgca ttcatgcccg cctcgttcca gacgcggctg   8880
tagaccacgg cccccacggg atctctcgcg cgcatgacca cctgggcgag gttgagctcc   8940
acgtggcggg tgaagaccgc atagttgcat aggcgctgga aaaggtagtt gagtgtggtg   9000
gcgatgtgct cggtgacgaa gaaatacatg atccatcgtc tcagcggcat ctcgctgaca   9060
tcgcccagag cttccaagcg ctccatggcc tcgtagaagt ccacggcaaa attaaaaaac   9120
tgggagtttc gcgcggacac ggtcaactcc tcttccagaa gacggataag ttcggcgatg   9180
gtggtgcgca cctcgcgctc gaaagcccct gggatttctt cctcaatctc ttcttcttcc   9240
actaacatct cttcctcttc aggtggggct gcaggaggag ggggaacgcg gcgacgccgg   9300
cggcgcacgg gcagacggtc gatgaatctt tcaatgacct ctccgcggcg gcggcgcatg   9360
gtttcagtga cggcgcggcc gttctcgcgc ggtcgcagag taaaaacacc gccgcgcatc   9420
tccttaaagt ggtgactggg aggttctccg tttgggaggg agagggcgct gattatacat   9480
tttattaatt ggcccgtagg gactgcacgc agagatctga tcgtgtcaag atccacggga   9540
tctgaaaacc tttcgacgaa agcgtctaac cagtcacagt cacaaggtag gctgagtacg   9600
gcttcttgtg ggcgggggtg gttatgtgtt cggtctgggt cttctgtttc ttcttcatct   9660
cgggaaggtg agacgatgct gctggtgatg aaattaaagt aggcagttct aagacggcgg   9720
atggtggcga ggagcaccag gtctttgggt ccggcttgct ggatacgcag gcgattggcc   9780
attccccaag cattatcctg acatctagca agatctttgt agtagtcttg catgagccgt   9840
```

```
tctacgggca cttcttcctc acccgttctg ccatgcatac gtgtgagtcc aaatccgcgc   9900
attggttgta ccagtgccaa gtcagctacg actctttcgg cgaggatggc ttgctgtact   9960
tgggtaaggg tggcttgaaa gtcatcaaaa tccacaaagc ggtggtaagc tcctgtatta  10020
atggtgtaag cacagttggc catgactgac cagttaactg tctggtgacc agggcgcacg  10080
agctcggtgt atttaaggcg cgaataggcg cgggtgtcaa agatgtaatc gttgcaggtg  10140
cgcaccagat actggtaccc tataagaaaa tgcggcggtg gttggcggta gagaggccat  10200
cgttctgtag ctggagcgcc aggggcgagg tcttccaaca taaggcggtg atagccgtag  10260
atgtacctgg acatccaggt gattcctgcg gcggtagtag aagcccgagg aaactcgcgt  10320
acgcggttcc aaatgttgcg tagcggcatg aagtagttca ttgtaggcac ggtttgacca  10380
gtgaggcgcg cgcagtcatt gatgctctat agacacggag aaaatgaaag cgttcagcga  10440
ctcgactccg tagcctggag gaacgtgaac gggttgggtc gcggtgtacc ccggttcgag  10500
acttgtactc gagccggccg gagccgcggc taacgtggta ttggcactcc cgtctcgacc  10560
cagcctacaa aaatccagga tacggaatcg agtcgttttg ctggtttccg aatggcaggg  10620
aagtgagtcc tatttttttt ttttgccgct cagatgcatc ccgtgctgcg acagatgcgc  10680
ccccaacaac agcccccctc gcagcagcag cagcagcaat cacaaaaggc tgtccctgca  10740
actactgcaa ctgccgccgt gagcggtgcg ggacagcccg cctatgatct ggacttggaa  10800
gagggcgaag gactggcacg tctaggtgcg ccttcacccg agcggcatcc gcgagttcaa  10860
ctgaaaaaag attctcgcga ggcgtatgtg ccccaacaga acctatttag agacagaagc  10920
ggcgaggagc cggaggagat gcgagcttcc cgctttaacg cgggtcgtga gctgcgtcac  10980
ggtttggacc gaagacgagt gttgcgggac gaggatttcg aagttgatga aatgacaggg  11040
atcagtcctg ccagggcaca cgtggctgca gccaaccttg tatcggctta cgagcagaca  11100
gtaaaggaag agcgtaactt ccaaaagtct tttaataatc atgtgcgaac cctgattgcc  11160
cgcgaagaag ttacccttgg tttgatgcat ttgtgggatt tgatggaagc tatcattcag  11220
aaccctacta gcaaacctct gaccgcccag ctgtttctgg tggtgcaaca cagcagagac  11280
aatgaggctt tcagagaggc gctgctgaac atcaccgaac ccgaggggag atggttgtat  11340
gatcttatca acattctaca gagtatcata gtgcaggagc ggagcctggg cctggccgag  11400
aaggtggctg ccatcaatta ctcggttttg agcttgggaa aatattacgc tcgcaaaatc  11460
tacaagactc catacgttcc catagacaag gaggtgaaga tagatgggtt ctacatgcgc  11520
atgacgctca aggtcttgac cctgagcgat gatcttgggg tgtatcgcaa tgacagaatg  11580
catcgcgcgg ttagcgccag caggaggcgc gagttaagcg acagggaact gatgcacagt  11640
ttgcaaagag ctctgactgg agctggaacc gagggtgaga attacttcga catgggagct  11700
gacttgcagt ggcagcctag tcgcagggct ctgagcgccg cgacggcagg atgtgagctt  11760
ccttacatag aagaggcgga tgaaggcgag gaggaagagg gcgagtactt ggaagactga  11820
tggcacaacc cgtgtttttt gctagatgga acagcaagca ccggatcccg caatgcgggc  11880
ggcgctgcag agccagccgt ccggcattaa ctcctcggac gattggaccc aggccatgca  11940
acgtatcatg gcgttgacga ctcgcaaccc cgaagccttt agacagcaac cccaggccaa  12000
ccgtctatcg gccatcatgg aagctgtagt gccttcccgc tctaatccca ctcatgagaa  12060
ggtcctggcc atcgtgaacg cgttggtgga gaacaaagct attcgtccag atgaggccgg  12120
actggtatac aacgctctct tagaacgcgt ggctcgctac aacagtagca atgtgcaaac  12180
```

caatttggac cgtatgataa cagatgtacg cgaagccgtg tctcagcgcg aaaggttcca 12240
gcgtgatgcc aacctgggtt cgctggtggc gttaaatgct ttcttgagta ctcagcctgc 12300
taatgtgccg cgtggtcaac aggattatac taacttttta agtgctttga gactgatggt 12360
atcagaagta cctcagagcg aagtgtatca gtccggtcct gattacttct ttcagactag 12420
cagacagggc ttgcagacgg taaatctgag ccaagctttt aaaaaccttt aaaggtttgt 12480
ggggagtgca tgccccggta ggagaaagag caaccgtgtc tagcttgtta actccgaact 12540
cccgcctatt attactgttg gtagctcctt tcaccgacag cggtagcatc gaccgtaatt 12600
cctatttggg ttacctacta aacctgtatc gcgaagccat agggcaaagt caggtggacg 12660
agcagaccta tcaagaaatt acccaagtca gtcgcgcttt gggacaggaa gacactggca 12720
gtttggaagc cactctgaac ttcttgctta ccaatcggtc tcaaaagatc cctcctcaat 12780
atgctcttac tgcggaggag gagaggatcc ttagatatgt gcagcagagc gtgggattgt 12840
ttctgatgca agagggggca actccgactg cagcactgga catgacagcg cgaaatatgg 12900
agcccagcat gtatgccagt aaccgacctt tcattaacaa actgctggac tacttgcaca 12960
gagctgccgc tatgaactct gattatttca ccaatgccat cttaaacccg cactggctgc 13020
ccccacctgg tttctacacg ggcgaatatg acatgcccga ccctaatgac ggatttctgt 13080
gggacgacgt ggacagcgat gtttttcac ctctttctga tcatcgcacg tggaaaaagg 13140
aaggcggcga tagaatgcat tcttctgcat cgctgtccgg ggtcatgggt gctaccgcgg 13200
ctgagcccga gtctgcaagt ccttttccta gtctaccctt ttctctacac agtgtacgta 13260
gcagcgaagt gggtagaata agtcgcccga gtttaatggg cgaagaggag tatctaaacg 13320
attccttgct cagaccggca agagaaaaaa atttcccaaa caatggaata gaaagtttgg 13380
tggataaaat gagtagatgg aagacttatg ctcaggatca cagagacgag cctgggatca 13440
tggggattac aagtagagcg agccgtagac gccagcgcca tgacagacag aggggtcttg 13500
tgtgggacga tgaggattcg gccgatgata gcagcgtgct ggacttgggt gggagaggaa 13560
ggggcaaccc gtttgctcat ttgcgccctc gcttgggtgg tatgttgtaa aaaaaaataa 13620
aaaaaaaact caccaaggcc atggcgacga gcgtacgttc gttcttcttt attatctgtg 13680
tctagtataa tgaggcgagt cgtgctaggc ggagcggtgg tgtatccgga gggtcctcct 13740
ccttcgtacg agagcgtgat gcagcagcag caggcgacgg cggtgatgca atccccactg 13800
gaggctccct ttgtgcctcc gcgatacctg gcacctacgg agggcagaaa cagcattcgt 13860
tattcggaac tggcacctca gtacgatacc accaggttgt atctggtgga caacaagtcg 13920
gcggacattg cttctctgaa ctatcagaat gaccacagca acttcttgac cacggtggtg 13980
caaaacaatg actttacccc tacggaagcc agcacccaga ccattaactt tgatgaacga 14040
tcgcggtggg gcggtcagct aaagaccatc atgcatacta acatgccaaa cgtgaacgag 14100
tatatgttta gtaacaagtt caaagcgcgt gtgatggtgt ccagaaaacc tcccgacggt 14160
gctgcagttg gggatactta tgatcacaag caggatattt tgaaatatga gtggttcgag 14220
tttactttgc cagaaggcaa cttttcagtt actatgacta ttgatttgat gaacaatgcc 14280
atcatagata attacttgaa agtgggtaga cagaatggag tgcttgaaag tgacattggt 14340
gttaagttcg acaccaggaa cttcaagctg ggatgggatc ccgaaaccaa gttgatcatg 14400
cctggagtgt atacgtatga agccttccat cctgacattg tcttactgcc tggctgcgga 14460
gtggatttta ccgagagtcg tttgagcaac cttcttggta tcagaaaaaa acagccattt 14520
caagagggtt ttaagatttt gtatgaagat ttagaaggtg gtaatattcc ggccctcttg 14580

```
gatgtagatg cctatgagaa cagtaagaaa gaacaaaaag ccaaaataga agctgctaca  14640
gctgctgcag aagctaaggc aaacatagtt gccagcgact ctacaagggt tgctaacgct  14700
ggagaggtca gaggagacaa ttttgcgcca acacctgttc cgactgcaga atcattattg  14760
gccgatgtgt ctgaaggaac ggacgtgaaa ctcactattc aacctgtaga aaaagatagt  14820
aagaatagaa gctataatgt gttggaagac aaaatcaaca cagcctatcg cagttggtat  14880
ctttcgtaca attatggcga tcccgaaaaa ggagtgcgtt cctggacatt gctcaccacc  14940
tcagatgtca cctgcggagc agagcaggtc tactggtcgc ttccagacat gatgaaggat  15000
cctgtcactt tccgctccac tagacaagtc agtaactacc ctgtggtggg tgcagagctt  15060
atgcccgtct tctcaaagag cttctacaac gaacaagctg tgtactccca gcagctccgc  15120
cagtccacct cgcttacgca cgtcttcaac cgctttcctg agaaccagat tttaatccgt  15180
ccgccggcgc ccaccattac caccgtcagt gaaaacgttc ctgctctcac agatcacggg  15240
accctgccgt tgcgcagcag tatccgggga gtccaacgtg tgaccgttac tgacgccaga  15300
cgccgcacct gtccctacgt gtacaaggca ctgggcatag tcgcaccgcg cgtcctttca  15360
agccgcactt tctaaaaaaa aaaaaaatgt ccattcttat ctcgcccagt aataacaccg  15420
gttggggtct gcgcgctcca agcaagatgt acggaggcgc acgcaaacgt tctacccaac  15480
atcctgtccg tgttcgcgga cattttcgcg ctccatgggg cgccctcaag ggccgcactc  15540
gcgttcgaac caccgtcgat gatgtaatcg atcaggtggt tgccgacgcc cgtaattata  15600
ctcctactgc gcctacatct actgtggatg cagttattga cagtgtagtg gctgacgctc  15660
gcaactatgc tcgacgtaag agccggcgaa ggcgcattgc cagacgccac cgagctacca  15720
ctgccatgcg agccgcaaga gctctgctac gaagagctag acgcgtgggg cgaagagcca  15780
tgcttagggc ggccagacgt gcagcttcgg gcgccagcgc cggcaggtcc cgcaggcaag  15840
cagccgctgt cgcagcggcg actattgccg acatggccca atcgcgaaga ggcaatgtat  15900
actgggtgcg tgacgctgcc accggtcaac gtgtacccgt gcgcacccgt ccccctcgca  15960
cttagaagat actgagcagt ctccgatgtt gtgtcccagc ggcgaggatg tccaagcgca  16020
aatacaagga agaaatgctg caggttatcg cacctgaagt ctacggccaa ccgttgaagg  16080
atgaaaaaaa accccgcaaa atcaagcggg ttaaaaagga caaaaaagaa gaggaagatg  16140
gcgatgatgg gctggcggag tttgtgcgcg agtttgcccc acggcgacgc gtgcaatggc  16200
gtgggcgcaa agttcgacat gtgttgagac ctggaacttc ggtggtcttt acacccggcg  16260
agcgttcaag cgctactttt aagcgttcct atgatgaggt gtacggggat gatgatattc  16320
ttgagcaggc ggctgaccga ttaggcgagt ttgcttatgg caagcgtagt agaataactt  16380
ccaaggatga gacagtgtcg atacccttgg atcatggaaa tcccacccct agtcttaaac  16440
cggtcacttt gcagcaagtg ttacccgtaa ctccgcgaac aggtgttaaa cgcgaaggtg  16500
aagatttgta tcccactatg caactgatgg tacccaaacg ccagaagttg gaggacgttt  16560
tggagaaagt aaaagtggat ccagatattc aacctgaggt taaagtgaga cccattaagc  16620
aggtagcgcc tggtctgggg gtacaaactg tagacattaa gattcccact gaaagtatgg  16680
aagtgcaaac tgaacccgca aagcctactg ccacctccac tgaagtgcaa acggatccat  16740
ggatgcccat gcctattaca actgacgccg ccggtcccac tcgaagatcc cgacgaaagt  16800
acggtccagc aagtctgttg atgcccaatt atgttgtaca cccatctatt attcctactc  16860
ctggttaccg aggcactcgc tactatcgca gccgaaacag tacctcccgc cgtcgccgca  16920
```

agacacctgc aaatcgcagt cgtcgccgta gacgcacaag caaaccgact cccggcgccc 16980
tggtgcggca agtgtaccgc aatggtagtg cggaaccttt gacactgccg cgtgcgcgtt 17040
accatccgag tatcatcact taatcaatgt tgccgctgcc tccttgcaga tatggccctc 17100
acttgtcgcc ttcgcgttcc catcactggt taccgaggaa gaaactcgcg ccgtagaaga 17160
gggatgttgg gacgcggaat gcgacgctac aggcgacggc gtgctatccg caagcaattg 17220
cggggtggtt ttttaccagc cttaattcca attatcgctg ctgcaattgg cgcgatacca 17280
ggcatagctt ccgtggcggt tcaggcctcg caacgacatt gacattggaa aaaaacgtat 17340
aaataaaaaa aaaaaaatac aatggactct gacactcctg gtcctgtgac tatgttttct 17400
tagagatgga agacatcaat ttttcatcct tggctccgcg acacggcacg aagccgtaca 17460
tgggcacctg gagcgacatc ggcacgagcc aactgaacgg gggcgccttc aattggagca 17520
gtatctggag cgggcttaaa aattttggct caaccataaa aacatacggg aacaaagctt 17580
ggaacagcag tacaggacag gcgcttagaa ataaacttaa agaccagaac ttccaacaaa 17640
aagtagtcga tgggatagct tccggcatca atggagtggt agatttggct aaccaggctg 17700
tgcagaaaaa gataaacagt cgtttggacc cgccgccagc aaccccaggt gaaatgcaag 17760
tggaggaaga aattcctccg ccagaaaaac gaggcgacaa gcgtccgcgt cccgatttgg 17820
aagagacgct ggtgacgcgc gtagatgaac cgccttctta tgaggaagca acgaagcttg 17880
gaatgcccac cactagaccg atagccccaa tggccaccgg ggtgatgaaa ccttctcagt 17940
tgcatcgacc cgtcaccttg gatttgcccc ctccccctgc tgctactgct gtacccgctt 18000
ctaagcctgt cgctgccccg aaaccagtcg ccgtagccag gtcacgtccc gggggcgctc 18060
ctcgtccaaa tgcgcactgg caaaatactc tgaacagcat cgtgggtcta ggcgtgcaaa 18120
gtgtaaaacg ccgtcgctgc ttttaattaa atatggagta gcgcttaact tgcctatctg 18180
tgtatatgtg tcattacacg ccgtcacagc agcagaggaa aaaaggaaga ggtcgtgcgt 18240
cgacgctgag ttactttcaa gatggccacc ccatcgatgc tgccccaatg ggcatacatg 18300
cacatcgccg gacaggatgc ttcggagtac ctgagtccgg gtctggtgca gttcgcccgc 18360
gccacagaca cctacttcaa tctgggaaat aagtttagaa atcccaccgt agcgccgacc 18420
cacgatgtga ccaccgaccg tagccagcgg ctcatgttgc gcttcgtgcc cgttgaccgg 18480
gaggacaata catactctta caaagtgcgg tacaccctgg ccgtgggcga caacagagtg 18540
ctggatatgg ccagcacgtt ctttgacatt aggggtgtgt tggacagagg tcccagtttc 18600
aaaccctatt ctggtacggc ttacaactcc ctggctccta aaggcgctcc aaatacatct 18660
cagtggattg cagaaggtgt aaaaaataca actggtgagg aacacgtaac agaagaggaa 18720
accaatacta ctacttacac ttttggcaat gctcctgtaa aagctgaagc tgaaattaca 18780
aaagaaggac tcccagtagg tttggaagtt tcagatgaag aaagtaaacc gatttatgct 18840
gataaaacat atcagccaga acctcagctg ggagatgaaa cttggactga ccttgatgga 18900
aaaaccgaaa agtatggagg cagggctctc aaacccgata ctaagatgaa accatgctac 18960
gggtcctttg ccaaacctac taatgtgaaa ggcggtcagg caaaacaaaa aacaacggag 19020
cagccaaatc agaaagtcga atatgatatc gacatggagt tttttgatgc ggcatcgcag 19080
aaaacaaact taagtcctaa aattgtcatg tatgcagaaa atgtaaattt ggaaactcca 19140
gacactcatg tagtgtacaa acctggaaca gaagacacaa gttccgaagc taatttggga 19200
caacaatcta tgcccaacag acccaactac attggcttca gagataactt tattggactt 19260
atgtactata acagtactgg taacatgggg gtgctggctg gtcaagcgtc tcagttaaat 19320

-continued

```
gcagtggttg acttgcagga cagaaacaca gaactttctt accaactctt gcttgactct  19380
ctgggcgaca gaaccagata ctttagcatg tggaatcagg ctgtggacag ttatgatcct  19440
gatgtacgtg ttattgaaaa tcatggtgtg gaagatgaac ttcccaacta ctgttttcca  19500
ctggacggca taggtgttcc aacaaccagt tacaaatcaa tagttccaaa tggagacaat  19560
gcgcctaatt ggaaggaacc tgaagtaaat ggaacaagtg agatcggaca gggtaatttg  19620
tttgccatgg aaattaacct tcaagccaat ctatggcgaa gtttccttta ttccaatgtg  19680
gctctatatc tcccagactc gtacaaatac accccgtcca atgtcactct tccagaaaac  19740
aaaaacacct acgactacat gaacgggcgg gtggtgccgc catctctagt agacacctat  19800
gtgaacattg gtgccaggtg gtctctggat gccatggaca atgtcaaccc attcaaccac  19860
caccgtaacg ctggcttgcg ttaccgatcc atgcttctgg gtaacggacg ttatgtgcct  19920
ttccacatac aagtgcctca aaaattcttc gctgttaaaa acctgctgct tctcccaggc  19980
tcctacactt atgagtggaa ctttaggaag gatgtgaaca tggttctaca gagttccctc  20040
ggtaacgacc tgcgggtaga tggcgccagc atcagtttca cgagcatcaa cctctatgct  20100
actttttcc ccatggctca caacaccgct tccacccttg aagccatgct gcggaatgac  20160
accaatgatc agtcattcaa cgactaccta tctgcagcta acatgctcta ccccattcct  20220
gccaatgcaa ccaatattcc catttccatt ccttctcgca actgggcggc tttcagaggc  20280
tggtcattta ccagactgaa aaccaaagaa actccctctt tggggtctgg atttgacccc  20340
tactttgtct attctggttc tattccctac ctggatggta ccttctacct gaaccacact  20400
tttaagaagg tttccatcat gtttgactct tcagtgagct ggcctggaaa tgacaggtta  20460
ctatctccta acgaatttga aataaagcgc actgtggatg gcgaaggcta caacgtagcc  20520
caatgcaaca tgaccaaaga ctggttcttg gtacagatgc tcgccaacta caacatcggc  20580
tatcagggct tctacattcc agaaggatac aaagatcgca tgtattcatt tttcagaaac  20640
ttccagccca tgagcaggca ggtggttgat gaggtcaatt acaaagactt caaggccgtc  20700
gccataccct accaacacaa caactctggc tttgtgggtt acatggctcc gaccatgcgc  20760
caaggtcaac cctatcccgc taactatccc tatccactca ttggaacaac tgccgtaaat  20820
agtgttacgc agaaaaagtt cttgtgtgac agaaccatgt ggcgcatacc gttctcgagc  20880
aacttcatgt ctatgggggc ccttacagac ttgggacaga atatgctcta tgccaactca  20940
gctcatgctc tggacatgac ctttgaggtg gatcccatgg atgagcccac cctgctttat  21000
cttctcttcg aagttttcga cgtggtcaga gtgcatcagc cacaccgcgg catcatcgag  21060
gcagtctacc tgcgtacacc gttctcggcc ggtaacgcta ccacgtaaga agcttcttgc  21120
ttcttgcaaa tagcagctgc aaccatggcc tgcggatccc aaaacggctc cagcgagcaa  21180
gagctcagag ccattgtcca agacctgggt tgcggaccct atttttggg aacctacgat  21240
aagcgcttcc cggggttcat ggcccccgat aagctcgcct gtgccattgt aaatacggcc  21300
ggacgtgaga cgggggggaga gcactggttg gctttcggtt ggaacccacg ttctaacacc  21360
tgctaccttt ttgatccttt tggattctcg gatgatcgtc tcaaacagat ttaccagttt  21420
gaatatgagg gtctcctgcg ccgcagcgct cttgctacca aggaccgctg tattacgctg  21480
gaaaaatcta cccagaccgt gcagggtccc cgttctgccg cctgcggact tttctgctgc  21540
atgttccttc acgcctttgt gcactggcct gaccgtccca tggacggaaa ccccaccatg  21600
aaattgctaa ctggagtgcc aaacaacatg cttcattctc ctaaagtcca gcccaccctg  21660
```

-continued

```
tgtgacaatc aaaaagcact ctaccatttt cttaataccc attcgcctta ttttcgctcc  21720
catcgtacac acatcgaaag ggccactgcg ttcgaccgta tggatgttca ataatgactc  21780
atgtaaacaa cgtgttcaat aaacatcact ttattttttt acatgtatca aggctctgca  21840
ttacttattt atttacaagt cgaatgggtt ctgacgagaa tcagaatgac ccgcaggcag  21900
tgatacgttg cggaactgat acttgggttg ccacttgaat tcgggaatca ccaacttggg  21960
aaccggtata tcgggcagga tgtcactcca cagctttctg gtcagctgca aagctccaag  22020
caggtcagga gccgaaatct tgaaatcaca attaggacca gtgctttgag cgcgagagtt  22080
gcggtacacc ggattgcagc actgaaacac catcagcgac ggatgtctca cgcttgccag  22140
cacggtggga tctgcaatca tgcccacatc cagatcttca gcattggcaa tgctgaacgg  22200
ggtcatcttg caggtctgcc tacccatggc gggcacccaa ttaggcttgt ggttgcaatc  22260
gcagtgcagg gggatcagta tcatcttggc ctgatcctgt ctgattcctg gatacacggc  22320
tctcatgaaa gcatcatatt gcttgaaagc ctgctgggct ttactaccct cggtataaaa  22380
catcccgcag gacctgctcg aaaactggtt agctgcacag ccggcatcat tcacacagca  22440
gcgggcgtca ttgttagcta tttgcaccac acttctgccc cagcggtttt gggtgatttt  22500
ggttcgctcg ggattctcct ttaaggctcg ttgtccgttc tcgctggcca catccatctc  22560
gataatctgc tccttctgaa tcataatatt gccatgcagg cacttcagct tgccctcata  22620
atcattgcag ccatgaggcc acaacgcaca gcctgtacat tcccaattat ggtgggcgat  22680
ctgagaaaaa gaatgtatca ttccctgcag aaatcttccc atcatcgtgc tcagtgtctt  22740
gtgactagtg aaagttaact ggatgcctcg gtgctcctcg tttacgtact ggtgacagat  22800
gcgcttgtat tgttcgtgtt gctcaggcat tagtttaaaa gaggttctaa gttcgttatc  22860
cagcctgtac ttctccatca gcagacacat cacttccatg cctttctccc aagcagacac  22920
caggggcaag ctaatcggat tcttaacagt gcaggcagca gctcctttag ccagagggtc  22980
atctttagcg atcttctcaa tgcttctttt gccatccttc tcaacgatgc gcacgggcgg  23040
gtagctgaaa cccactgcta caagttgcgc ctcttctctt tcttcttcgc tgtcttgact  23100
gatgtcttgc atggggatat gtttggtctt ccttggcttc tttttggggg gtatcggagg  23160
aggaggactg tcgctccgtt ccggagacag ggaggattgt gacgtttcgc tcaccattac  23220
caactgactg tcggtagaag aacctgaccc cacacggcga caggtgtttc tcttcggggg  23280
cagaggtgga ggcgattgcg aagggctgcg gtccgacctg gaaggcggat gactggcaga  23340
accccttccg cgttcggggg tgtgctccct gtggcggtcg cttaactgat ttccttcgcg  23400
gctggccatt gtgttctcct aggcagagaa acaacagaca tggaaactca gccattgctg  23460
tcaacatcgc cacgagtgcc atcacatctc gtcctcagcg acgaggaaaa ggagcagagc  23520
ttaagcattc caccgcccag tcctgccacc acctctaccc tagaagataa ggaggtcgac  23580
gcatctcatg acatgcagaa taaaaaagcg aaagagtctg agacagacat cgagcaagac  23640
ccgggctatg tgacaccggt ggaacacgag gaagagttga aacgctttct agagagagag  23700
gatgaaaact gcccaaaaca acgagcagat aactatcacc aagatgctgg aaatagggat  23760
cagaacaccg actacctcat agggcttgac ggggaagacg cgctccttaa acatctagca  23820
agacagtcgc tcatagtcaa ggatgcatta ttggacagaa ctgaagtgcc catcagtgtg  23880
gaagagctca gccgcgccta cgagcttaac ctcttttcac ctcgtactcc ccccaaacgt  23940
cagccaaacg gcacctgcga gccaaatcct cgcttaaact tttatccagc ttttgctgtg  24000
ccagaagtac tggctaccta tcacatcttt tttaaaaatc aaaaaattcc agtctcctgc  24060
```

cgcgctaatc gcacccgcgc cgatgcccta ctcaatctgg gacctggttc acgcttacct 24120
gatatagctt ccttggaaga ggttccaaag atcttcgagg gtctgggcaa taatgagact 24180
cgggccgcaa atgctctgca aaagggagaa aatggcatgg atgagcatca cagcgttctg 24240
gtggaattgg aaggcgataa tgccagactc gcagtactca agcgaagcat cgaggtcaca 24300
cacttcgcat atcccgctgt caacctgccc cctaaagtca tgacggcggt catggaccag 24360
ttactcatta agcgcgcaag tccccttca gaagacatgc atgacccaga tgcctgtgat 24420
gagggtaaac cagtggtcag tgatgagcag ctaacccgat ggctgggcac cgactctccc 24480
agggatttgg aagagcgtcg caagcttatg atggccgtgg tgctggttac cgtagaacta 24540
gagtgtctcc gacgtttctt taccgattca gaaaccttgc gcaaactcga agagaatctg 24600
cactacactt ttagacacgg ctttgtgcgg caggcatgca agatatctaa cgtggaactc 24660
accaacctgg tttcctacat gggtattctg catgagaatc gcctaggaca aagcgtgctg 24720
cacagcaccc tgaaggggga agcccgccgt gattacatcc gcgattgtgt ctatctgtac 24780
ctgtgccaca cgtggcaaac cggcatgggt gtatggcagc aatgtttaga agaacagaac 24840
ttgaaagagc ttgacaagct cttacagaaa tctcttaagg ttctgtggac agggttcgac 24900
gagcgcaccg tcgcttccga cctggcagac ctcatcttcc cagagcgtct cagggttact 24960
ttgcgaaacg gattgcctga ctttatgagc cagagcatgc ttaacaattt tcgctctttc 25020
atcctggaac gctccggtat cctgcccgcc acctgctgcg cactgccctc cgactttgtg 25080
cctctcacct accgcgagtg ccccccgccg ctatggagtc actgctacct gttccgtctg 25140
gccaactatc tctcctacca ctcggatgtg atcgaggatg tgagcggaga cggcttgctg 25200
gagtgtcact gccgctgcaa tctgtgcacg ccccaccggt ccctagcttg caaccccag 25260
ttgatgagcg aaacccagat aataggcacc tttgaattgc aaggccccag cagccaaggc 25320
gatgggtctt ctcctgggca aagtttaaaa ctgaccccgg gactgtggac ctccgcctac 25380
ttgcgcaagt ttgctccgga agattaccac ccctatgaaa tcaagttcta tgaggaccaa 25440
tcacagcctc caaaggccga actttcggcc tgcgtcatca cccagggggc aattctggcc 25500
caattgcaag ccatccaaaa atcccgccaa gaatttctac tgaaaaaggg taagggggtc 25560
taccttgacc cccagaccgg cgaggaactc aacacaaggt tccctcagga tgtcccaacg 25620
acgagaaaac aagaagttga aggtgcagcc gccgccccca gaagatatgg aggaagattg 25680
ggacagtcag gcagaggagg cggaggagga cagtctggag gacagtctgg aggaagacag 25740
tttggaggag gaaaacgagg aggcagagga ggtggaagaa gtaaccgccg acaaacagtt 25800
atcctcggct gcggagacaa gcaacagcgc taccatctcc gctccgagtc gaggaacccg 25860
gcggcgtccc agcagtagat gggacgagac cggacgcttc ccgaacccaa ccagcgcttc 25920
caagaccggt aagaaggatc ggcagggata caagtcctgg cgggggcata agaatgccat 25980
catctcctgc ttgcatgagt gcgggggcaa catatccttc acgcggcgct acttgctatt 26040
ccaccatggg gtgaactttc cgcgcaatgt tttgcattac taccgtcacc tccacagccc 26100
ctactatagc cagcaaatcc cggcagtctc gacagataaa gacagcggcg gcgacctcca 26160
acagaaaacc agcagcggca gttagaaaat acacaacaag tgcagcaaca ggaggattaa 26220
agattacagc caacgagcca gcgcaaaccc gagagttaag aaatcggatc tttccaaccc 26280
tgtatgccat cttccagcag agtcggggtc aagagcagga actgaaaata aaaaaccgat 26340
ctctgcgttc gctcaccaga agttgtttgt atcacaagag cgaagatcaa cttcagcgca 26400
ctctcgagga cgccgaggct ctcttcaaca agtactgcgc gctgactctt aaagagtagg 26460
cagcgaccgc gcttattcaa aaaaggcggg aattacatca tcctcgacat gagtaaagaa 26520
attcccacgc cttacatgtg gagttatcaa ccccaaatgg gattggcggc aggcgcctcc 26580
caggactact ccacccgcat gaattggctc agcgccgggc cttctatgat ttctcgagtt 26640
aatgatatac gcgcctaccg aaaccaaata cttttggaac agtcagctct taccaccacg 26700
ccccgccaac accttaatcc cagaaattgg cccgccgccc tagtgtacca ggaaagtccc 26760
gctcccacca ctgtattact tcctcgagac gcccaggccg aagtccaaat gactaatgca 26820
ggtgcgcagt tagctggcgg ctccacccta tgtcgtcaca ggcctcggca taatataaaa 26880
cgcctgatga tcagaggccg aggtatccag ctcaacgacg agtcggtgag ctctccgctt 26940
ggtctacgac cagacggaat ctttcagatt gccggctgcg ggagatcttc cttcacccct 27000
cgtcaggctg ttctgacttt ggaaagttcg tcttcgcaac cccgctcggg cggaatcggg 27060
accgttcaat ttgtggagga gtttactccc tctgtctact tcaacccctt ctccggatct 27120
cctgggcatt acccggacga gttcataccg aacttcgacg cgattagcga gtcagtggac 27180
ggctacgatt gatgtctggt gacgcggctg agctatctcg gctgcgacat ctagaccact 27240
gccgccgctt tcgctgcttt gcccgggaac tcattgagtt catctacttc gaactcccca 27300
aggatcaccc tcaaggtccg gcccacggag tgcggatttc tatcgaaggc aaaatagact 27360
ctcgcctgca acgaattttc tcccagcggc ccgtgctgat cgagcgagac cagggaaaca 27420
ccacggtttc catctactgc atttgtaatc accccggatt gcatgaaagc ctttgctgtc 27480
ttatgtgtac tgagtttaat aaaaactgaa ttaagactct cctacggact gccgcttctt 27540
caacccggat tttacaacca gaagaacgaa actttttcctg tcgtccagga ctctgttaac 27600
ttcacctttc ctactcacaa actagaagct caacgactac accgcttttc cagaagcatt 27660
ttccctacta atactacttt caaaaccgga ggtgagctcc aaggtcttcc tacagaaaac 27720
ccttgggtgg aagcgggcct tgtagtgcta ggaattcttg cgggtgggct tgtgattatt 27780
ctttgctacc tatacacacc ttgcttcact ttcttagtgg tgttgtggta ttggtttaaa 27840
aaatggggcc catactagtc ttgcttgttt tactttcgct tttggaaccg ggttctgcca 27900
attacgatcc atgtctagac ttcgacccag aaaactgcac acttactttt gcacccgaca 27960
caagccgcat ctgtggagtt catcgcctct cttacgaact tggcccccaa cgacaaaaat 28020
ttacctgcat ggtgggaatc aaccccatag ttatcaccca gcaaagtgga gatactaagg 28080
gttgcattca ctgctcctgc gattccatcg agtgcaccta caccctgctg aagaccctat 28140
gcggcctaag agacctgcta ccaatgaatt aaaaaatgat taataaaaaa tcacttactt 28200
gaaatcagca ataaggtctc tgttgaaatt ttctcccagc agcacctcac ttccctcttc 28260
ccaactctgg tattctaaac cccgttcagc ggcatacttt ctccatactt taaaggggat 28320
gtcaaatttt agctcctctc ctgtacccac aatcttcatg tctttcttcc cagatgacca 28380
agagagtccg gctcagtgac tccttcaacc ctgtctaccc ctatgaagat gaaagcacct 28440
cccaacaccc ctttataaac ccagggttta tttccccaaa tggcttcaca caaagcccaa 28500
acggagttct tactttaaaa tgtttaaccc cactaacaac cacaggcgga tctctacagc 28560
taaaagtggg agggggactt acagtggatg acaccaacgg ttttttgaaa gaaaacataa 28620
gtgccaccac accactcgtt aagactggtc actctatagg tttaccacta ggagccggat 28680
tgggaacgaa tgaaaataaa ctttgtatca aattaggaca aggacttaca ttcaattcaa 28740
acaacatttg cattgatgac aatattaaca ccttatggac aggagtcaac ccccaccgaag 28800

-continued

```
ccaactgtca aatcatgaac tccagtgaat ctaatgattg caaattaatt ctaacactag  28860
ttaaaactgg agcactagtc actgcatttg tttatgttat aggagtatct aacaatttta  28920
atatgctaac tacacacaga aatataaatt ttactgcaga gctgtttttc gattctactg  28980
gtaatttact aactagactc tcatccctca aaactccact taatcataaa tcaggacaaa  29040
acatggctac tggtgccatt actaatgcta aaggtttcat gcccagcacg actgcctatc  29100
ctttcaatga taattctaga gaaaaagaaa actacattta cggaacttgt tactacacag  29160
ctagtgatcg cactgctttt cccattgaca tatctgtcat gcttaaccga agagcaataa  29220
atgacgagac atcatattgt attcgtataa cttggtcctg gaacacagga gatgccccag  29280
aggtgcaaac ctctgctaca accctagtca cctccccatt taccttttac tacatcagag  29340
aagacgactg acaaataaag tttgcgatcg ctgctaatcc tttctctctt caggccacca  29400
tggtgagcaa gggcgaggag ctgttcaccg gggtggtgcc catcctggtc gagctggacg  29460
gcgacgtaaa cggccacaag ttcagcgtgt ccggcgaggg cgagggcgat gccacctacg  29520
gcaagctgac cctgaagttc atctgcacca ccggcaagct gcccgtgccc tggcccaccc  29580
tcgtgaccac cctgacctac ggcgtgcagt gcttcagccg ctaccccgac cacatgaagc  29640
agcacgactt cttcaagtcc gccatgcccg aaggctacgt ccaggagcgc accatcttct  29700
tcaaggacga cggcaactac aagacccgcg ccgaggtgaa gttcgagggc gacaccctgg  29760
tgaaccgcat cgagctgaag ggcatcgact tcaaggagga cggcaacatc ctggggcaca  29820
agctggagta caactacaac agccacaacg tctatatcat ggccgacaag cagaagaacg  29880
gcatcaaggt gaacttcaag atccgccaca acatcgagga cggcagcgtg cagctcgccg  29940
accactacca gcagaacacc cccatcggcg acggccccgt gctgctgccc gacaaccact  30000
acctgagcac ccagtccgcc ctgagcaaag accccaacga gaagcgcgat cacatggtcc  30060
tgctggagtt cgtgaccgcc gccgggatca ctctcggcat ggacgagctg tacaagtaat  30120
ctagaagttg tctcctcctg cactgactga ctgatacaat cgatttctgg atccgcaggc  30180
ctctgctagc ttgactgact gagatacagc gtaccttcag ctcacagaca tgataagata  30240
cattgatgag tttggacaaa ccacaactag aatgcagtga aaaaaatgct ttatttgtga  30300
aatttgtgat gctattgctt tatttgtaac cattataagc tgcaataaac aagttaacaa  30360
caacaattgc attcatttta tgtttcaggt tcagggggag gtgtgggagg ttttttaaag  30420
caagtaaaac ctctacaaat gtggtcctgc aggaacttgt ttatttgaaa atcaattcac  30480
aaaatccgag tagttatttt gcctccccct tcccatttaa cagaatacac caatctctcc  30540
ccacgcacag ctttaaacat ttggatacca ttagatatag acatggtttt agattccaca  30600
ttccaaacag tttcagagcg agccaatctg gggtcagtga tagataaaaa tccatcggga  30660
tagtctttta aagcgctttc acagtccaac tgctgcggat gcgactccgg agtctggatc  30720
acggtcatct ggaagaagaa cgatgggaat cataatccga aaacggtatc ggacgattgt  30780
gtctcatcaa acccacaagc agccgctgtc tgcgtcgctc cgtgcgactg ctgtttatgg  30840
gatcagggtc cacagtgtcc tgaagcatga ttttaatagc ccttaacatc aactttctgg  30900
tgcgatgcgc gcagcaacgc attctgattt cactcaaatc tttgcagtag gtacaacaca  30960
ttattacaat attgtttaat aaaccataat taaaagcgct ccagccaaaa ctcatatctg  31020
atataatcgc ccctgcatga ccatcatacc aaagtttaat ataaattaaa tgacgttccc  31080
tcaaaaacac actacccaca tacatgatct cttttggcat gtgcatatta acaatctgtc  31140
```

```
tgtaccatgg acaacgttgg ttaatcatgc aacccaatat aaccttccgg aaccacactg  31200
ccaacaccgc tcccccagcc atgcattgaa gtgaaccctg ctgattacaa tgacaatgaa  31260
gaacccaatt ctctcgaccg tgaatcactt gagaatgaaa aatatctata gtggcacaac  31320
atagacataa atgcatgcat cttctcataa tttttaactc ctcaggattt agaaacatat  31380
cccagggaat aggaagctct tgcagaacag taaagctggc agaacaagga agaccacgaa  31440
cacaacttac actatgcata gtcatagtat cacaatctgg caacagcggg tggtcttcag  31500
tcatagaagc tcgggtttca ttttcctcac aacgtggtaa ctgggctctg gtgtaagggt  31560
gatgtctggc gcatgatgtc gagcgtgcgc gcaaccttgt cataatggag ttgcttcctg  31620
acattctcgt attttgtata gcaaaacgcg gccctggcag aacacactct tcttcgcctt  31680
ctatcctgcc gcttagcgtg ttccgtgtga tagttcaagt acaaccacac tcttaagttg  31740
gtcaaaagaa tgctggcttc agttgtaatc aaaactccat cgcatctaat cgttctgagg  31800
aaatcatcca agcaatgcaa ctggattgtg tttcaagcag gagaggagag ggaagagacg  31860
gaagaaccat gttaattttt attccaaacg atctcgcagt acttcaaatt gtagatcgcg  31920
cagatggcat ctctcgcccc cactgtgttg gtgaaaaagc acagctagat caaaagaaat  31980
gcgattttca aggtgctcaa cggtggcttc cagcaaagcc tccacgcgca catccaagaa  32040
caaaagaata ccaaaagaag gagcattttc taactcctca atcatcatat tacattcctg  32100
caccattccc agataatttt cagctttcca gccttgaatt attcgtgtca gttcttgtgg  32160
taaatccaat ccacacatta caaacaggtc ccggagggcg ccctccacca ccattcttaa  32220
acacaccctc ataatgacaa aatatcttgc tcctgtgtca cctgtagcga attgagaatg  32280
gcaacatcaa ttgacatgcc cttggctcta agttcttctt taagttctag ttgtaaaaac  32340
tctctcatat tatcaccaaa ctgcttagcc agaagccccc cgggaacaag agcaggggac  32400
gctacagtgc agtacaagcg cagacctccc caattggctc cagcaaaaac aagattggaa  32460
taagcatatt gggaaccgcc agtaatatca tcgaagttgc tggaaatata atcaggcaga  32520
gtttcttgta aaaattgaat aaaagaaaaa tttgccaaaa aaacattcaa aacctctggg  32580
atgcaaatgc aataggttac cgcgctgcgc tccaacattg ttagttttga attagtctgc  32640
aaaaataaaa aaaaaaacaa gcgtcatatc atagtagcct gacgaacaga tggataaatc  32700
agtctttcca tcacaagaca agccacaggg tctccagctc gaccctcgta aaacctgtca  32760
tcatgattaa acaacagcac cgaaagttcc tcgcggtgac cagcatgaat aattcttgat  32820
gaagcataca atccagacat gttagcatca gttaacgaga aaaaacagcc aacatagcct  32880
ttgggtataa ttatgcttaa tcgtaagtat agcaaagcca cccctcgcgg atacaaagta  32940
aaaggcacag gagaataaaa aatataatta tttctctgct gctgttcagg caacgtcgcc  33000
cccggtccct ctaaatacac atacaaagcc tcatcagcca tggcttacca gacaaagtac  33060
agcgggcaca caaagcacaa gctctaaagt gactctccaa cctctccaca atatatatat  33120
acacaagccc taaactgacg taatgggagt aaagtgtaaa aaatcccgcc aaacccaaca  33180
cacaccccga aactgcgtca ccagggaaaa gtacagtttc acttccgcaa tcccaacagg  33240
cgtaacttcc tctttctcac ggtacgtgat atcccactaa cttgcaacgt cattttccca  33300
cggtcgcacc gcccctttta gccgttaacc ccacagccaa tcaccacacg atccacactt  33360
tttaaaatca cctcatttac atattggcac cattccatct ataaggtata ttatatagat  33420
aggcgcgccc tctcttaagg tagcatcggg atcgagtccc tgagagaaca tcctcaatcc  33480
cgatctatcc ttagatccga ggaatatcga aatcagttac gctagggata acagggtaat  33540
```

atagcatccc ctcggattgc tatctaccgg ctcgtcagct atgatctctc gatttcgatc 33600
aagaaatctc attggttacc ttgggctatc gaaaccagtc aagtcagcta cttggcgaga 33660
tcgacttgtc tgagtttcga ctacgctcag aattgcgtca gcgcctatcg ccaggtatta 33720
ctccaatccc gaatatccga gcctgagaga acatcctcaa tcccgatcta tccttagatc 33780
cgaggaatat cgaaatcgtt taaatctttt cttgatggta aatcattcga atataagaat 33840
ggagagacga atggggaaac gacaaagatg acattctttg gtccttctgg tgaggttctc 33900
aagtttttgg ttaatcctgt caacaactta tatcgtatgg ggctgacttc aggtgctaca 33960
tttgaagaga taaattgcac tgaaatctag taatatttta tctgattaat aagatgatct 34020
tcttgagatc gttttggtct gcgcgtaatc tcttgctctg aaaacgaaaa aaccgccttg 34080
cagggcggtt tttcgaaggt tctctgagct accaactctt tgaaccgagg taactggctt 34140
ggcagagcgc agtcaccaaa acttgtcctt tcagtttagc cttaaccggc gcatgacttc 34200
aagactaact ctgctaaatc aattaccagt ggctgctgcc agtggtgctt ttgcatgtct 34260
ttccgggttg gactcaagac gatagttacc ggataaggcg cagcggtcgg actgaacggg 34320
gggttcgtgc atacagtcca gcttggagcg aactgcctac ccggaactga gtgtcaggcg 34380
tggaatgaga caaacgcggc cataacagcg gaatgacacc ggtaaaccga aaggcaggaa 34440
caggagagcg cacgagggag ccgccagggg gaaacgcctg gtatctttat agtcctgtcg 34500
ggtttcgcca ccactgattt gagcgtcaga tttcgtgatg cttgtcaggg gggcggagcc 34560
tatggaaaaa cggctttgcc gcggccctct cacttccctg ttaagtatct tcctggcatc 34620
ttccaggaaa tctccgcccc gttcgtaagc catttccgct cgccgcagtc gaacgaccga 34680
gcgtagcgag tcagtgagcg aggaagcgga atatatcctg tatcacatat tctgctgacg 34740
caccggtgcg gccttttttc tcctgccaca tgaagcactt cactgacacc ctcatcagtg 34800
ccaacatagt aagccagtat acactccgct aatttaaacg tggtgtaccg agaacgatcc 34860
tctcagtgcg atctcgacga tcagtggtat tccgacatat cgttgcttgg cagtcagcca 34920
gtcgatccta gcttgggacc caggaagtcc aatcgtcaga tattgtactc agcctggtca 34980
cggcagcgta ccgatctcgt aactataacg gtcctaaggt agcgaactag atattgatag 35040
tctgatcggt caacgtataa tcgagtccta gcttttgcaa acatctatca agagacagga 35100
tcagcaggag gctttcgcat gattgaacaa gatggattgc acgcaggttc tccggcggct 35160
tgggtggaga ggctattcgg ctatgactgg gcacaacaga caatcggctg ctctgatgcc 35220
gccgtgttcc ggctgtcagc gcaggggcgt ccggttcttt ttgtcaagac cgacctgtcc 35280
ggtgccctga atgaactgca agacgaggca gcgcggctat cgtggctggc gacgacgggc 35340
gttccttgcg cggctgtgct cgacgttgtc actgaagcgg gaagggactg gctgctattg 35400
ggcgaagtgc cggggcagga tctcctgtca tctcaccttg ctcctgccga gaaagtatcc 35460
atcatggctg atgcaatgcg gcggctgcat acgcttgatc cggctacctg cccattcgac 35520
caccaagcga aacatcgcat cgagcgagca cgtactcgga tggaagccgg tcttgtcgat 35580
caggatgatc tggacgaaga gcatcagggg ctcgcgccag ccgaactgtt cgccaggctc 35640
aaggcgtcta tgcccgacgg cgaggatctc gtcgtgaccc acggcgatgc ctgcttgccg 35700
aatatcatgg tggaaaatgg ccgcttttct ggattcatcg actgtggccg tctgggtgtg 35760
gcggaccgct atcaggacat agcgttggct acccgtgata ttgctgaaga gcttggcggc 35820
gaatgggctg accgcttcct tgtgctttac ggtatcgccg cgcccgattc gcagcgcatc 35880
gccttctatc gccttcttga cgagttcttc tgaccgattc taggtgcatt ggcgcagaaa 35940
aaaatgcctg atgcgacgct gcgcgtctta tactcccaca tatgccagat tcagcaacgg 36000
atacggcttc cccaacttgc ccacttccat acgtgtcctc cttaccagaa atttatcctt 36060
aaggtccgta actataacgg tcctaaggta gcgaatcgac ctagctctat cgaatctccc 36120
tcgtttcgag cttacgcgaa ctagcctctg gcgatagcat ccgaggggca ggcatctatg 36180
tcgggtgcgg agaaagaggt aatgtcaagt tcgatctgat tgcttggcat aaagtccgat 36240
ggttcgagta gactcagttc aacctctctc ttaaggtagc 36280

<210> SEQ ID NO 36
<211> LENGTH: 31
<212> TYPE: DNA
<213> ORGANISM: Artificial Sequence
<220> FEATURE:
<223> OTHER INFORMATION: Branched splice acceptor (bSA)

<400> SEQUENCE: 36
tgctaatctt cctttctctc ttcaggccgc c 31

<210> SEQ ID NO 37
<211> LENGTH: 1090
<212> TYPE: DNA
<213> ORGANISM: Artificial Sequence
<220> FEATURE:
<223> OTHER INFORMATION: GFP Transgene Cassette

<400> SEQUENCE: 37
gcgatcgctg ctaatccttt ctctcttcag gccaccatgg tgagcaaggg cgaggagctg 60
ttcaccgggg tggtgcccat cctggtcgag ctggacggcg acgtaaacgg ccacaagttc 120
agcgtgtccg gcgagggcga gggcgatgcc acctacggca agctgaccct gaagttcatc 180
tgcaccaccg gcaagctgcc cgtgccctgg cccaccctcg tgaccaccct gacctacggc 240
gtgcagtgct tcagccgcta ccccgaccac atgaagcagc acgacttctt caagtccgcc 300
atgcccgaag gctacgtcca ggagcgcacc atcttcttca aggacgacgg caactacaag 360
acccgcgccg aggtgaagtt cgagggcgac accctggtga accgcatcga gctgaagggc 420
atcgacttca aggaggacgg caacatcctg gggcacaagc tggagtacaa ctacaacagc 480
cacaacgtct atatcatggc cgacaagcag aagaacggca tcaaggtgaa cttcaagatc 540
cgccacaaca tcgaggacgg cagcgtgcag ctcgccgacc actaccagca gaacaccccc 600
atcggcgacg gccccgtgct gctgcccgac aaccactacc tgagcaccca gtccgccctg 660
agcaaagacc ccaacgagaa gcgcgatcac atggtcctgc tggagttcgt gaccgccgcc 720
gggatcactc tcggcatgga cgagctgtac aagtaatcta gaagttgtct cctcctgcac 780
tgactgactg atacaatcga tttctggatc cgcaggcctc tgctagcttg actgactgag 840
atacagcgta ccttcagctc acagacatga taagatacat tgatgagttt ggacaaacca 900
caactagaat gcagtgaaaa aaatgcttta tttgtgaaat ttgtgatgct attgctttat 960
ttgtaaccat tataagctgc aataaacaag ttaacaacaa caattgcatt cattttatgt 1020
ttcaggttca gggggaggtg tgggaggttt tttaaagcaa gtaaaacctc tacaaatgtg 1080
gtcctgcagg 1090

<210> SEQ ID NO 38
<211> LENGTH: 33421
<212> TYPE: DNA
<213> ORGANISM: Artificial Sequence
<220> FEATURE:
<223> OTHER INFORMATION: NG-62 Virus genome

<400> SEQUENCE: 38

```
cgcgcctatc tatataatat accttataga tggaatggtg ccaatatgta aatgaggtga     60
ttttaaaaag tgtggatcgt gtggtgattg gctgtggggt taacggctaa aaggggcggt    120
gcgaccgtgg gaaaatgacg ttttgtgggg gtggagtttt tttgcaagtt gtcgcgggaa    180
atgtgacgca taaaaaggct tttttctcac ggaactactt agttttccca cggtatttaa    240
caggaaatga ggtagttttg accggatgca agtgaaaatt gttgattttc gcgcgaaaac    300
tgaatgagga agtgtttttc tgaataatgt ggtatttatg gcagggtgga gtatttgttc    360
agggccaggt agactttgac ccattacgtg gaggtttcga ttaccgtgtt ttttacctga    420
atttccgcgt accgtgtcaa agtcttctgt ttttacgtag gtgtcagctg atcgctaggg    480
tatttatacc tcagggtttg tgtcaagagg ccactcttga gtgccagcga gaagagtttt    540
ctcctctgcg ccggcagttt aataataaaa aaatgagaga tttgcgattt ctgcctcagg    600
aaataatctc tgctgagact ggaaatgaaa tattggagct tgtggtgcac gccctgatgg    660
gagacgatcc ggagccacct gtgcagcttt ttgagcctcc tacgcttcag gaactgtatg    720
atttagaggt agagggatcg gaggattcta atgaggaagc tgtaaatggc tttttttaccg    780
attctatgct tttagctgct aatgaagggt tagaattaga tccgcctttg gacacttttg    840
atactccagg ggtaattgtg gaaagcggta caggtgtaag aaaattacct gatttgagtt    900
ccgtggactg tgatttgcac tgctatgaag acgggtttcc tccgagtgat gaggaggacc    960
atgaaaagga gcagtccatg cagactgcag cgggtgaggg agtgaaggct gccaatgttg   1020
gttttcagtt ggattgcccg gagcttcctg gacatggctg taagtcttgt gaatttcaca   1080
ggaaaaatac tggagtaaag gaactgttat gttcgctttg ttatatgaga acgcactgcc   1140
actttattta cagtaagtgt gtttaagtta aaatttaaag gaatatgctg tttttcacat   1200
gtatattgag tgtgagtttt gtgcttctta ttataggtcc tgtgtctgat gctgatgaat   1260
caccatctcc tgattctact acctcacctc ctgagattca agcacctgtt cctgtggacg   1320
tgcgcaagcc cattcctgtg aagcttaagc ctgggaaacg tccagcagtg gaaaaacttg   1380
aggacttgtt acagggtggg gacggacctt tggacttgag tacacggaaa cgtccaagac   1440
aataagtgtt ccatatccgt gtttacttaa ggtgacgtca atatttgtgt gacagtgcaa   1500
tgtaataaaa atatgttaac tgttcactgg tttttattgc tttttgggcg gggactcagg   1560
tatataagta gaagcagacc tgtgtggtta gctcatagga gctggctttc atccatggag   1620
gtttgggcca ttttggaaga ccttaggaag actaggcaac tgttagagaa cgcttcggac   1680
ggagtctccg gtttttggag attctggttc gctagtgaat tagctagggt agtttttagg   1740
ataaaacagg actataaaca agaatttgaa aagttgttgg tagattgccc aggacttttt   1800
gaagctctta atttgggcca tcaggttcac tttaaagaaa aagttttatc agttttagac   1860
ttttcaaccc caggtagaac tgctgctgct gtggcttttc ttacttttat attagataaa   1920
tggatcccgc agactcattt cagcagggga tacgttttgg atttcatagc cacagcattg   1980
tggagaacat ggaaggttcg caagatgagg acaatcttag gttactggcc agtgcagcct   2040
ttgggtgtag cgggaatcct gaggcatcca ccggtcatgc cagcggttct ggaggaggaa   2100
cagcaagagg acaacccgag agccggcctg gaccctccag tggaggaggc ggagtagctg   2160
acttgtctcc tgaactgcaa cgggtgctta ctggatctac gtccactgga cgggataggg   2220
```

-continued

```
gcgttaagag ggagagggca tctagtggta ctgatgctag atctgagttg gctttaagtt   2280
taatgagtcg cagacgtcct gaaaccattt ggtggcatga ggttcagaaa gagggaaggg   2340
atgaagtttc tgtattgcag gagaaatatt cactggaaca ggtgaaaaca tgttggttgg   2400
agcctgagga tgattgggag gtggccatta aaaattatgc caagatagct ttgaggcctg   2460
ataaacagta taagattact agacggatta atatccggaa tgcttgttac atatctggaa   2520
atggggctga ggtggtaata gatactcaag acaaggcagt tattagatgc tgcatgatgg   2580
atatgtggcc tggggtagtc ggtatggaag cagtaacttt tgtaaatgtt aagtttaggg   2640
gagatggtta taatggaata gtgtttatgg ccaataccaa acttatattg catggttgta   2700
gctttttttgg tttcaacaat acctgtgtag atgcctgggg acaggttagt gtacggggat   2760
gtagtttcta tgcgtgttgg attgccacag ctggcagaac caagagtcaa ttgtctctga   2820
agaaatgcat atttcaaaga tgtaacctgg gcattctgaa tgaaggcgaa gcaagggtcc   2880
gccactgcgc ttctacagat actggatgtt ttattttgat taagggaaat gccagcgtaa   2940
agcataacat gatttgcggt gcttccgatg agaggcctta tcaaatgctc acttgtgctg   3000
gtgggcattg taatatgctg gctactgtgc atattgtttc ccatcaacgc aaaaaatggc   3060
ctgtttttga tcacaatgtg atgacgaagt gtaccatgca tgcaggtggg cgtagaggaa   3120
tgtttatgcc ttaccagtgt aacatgaatc atgtgaaagt gttgttggaa ccagatgcct   3180
tttccagaat gagcctaaca ggaatttttg acatgaacat gcaaatctgg aagatcctga   3240
ggtatgatga tacgagatcg agggtacgcg catgcgaatg cggaggcaag catgccaggt   3300
tccagccggt gtgtgtagat gtgactgaag atctcagacc ggatcatttg gttattgccc   3360
gcactggagc agagttcgga tccagtggag aagaaactga ctaaggtgag tattgggaaa   3420
actttggggt gggattttca gatggacaga ttgagtaaaa atttgttttt tctgtcttgc   3480
agctgtcatg agtggaaacg cttcttttaa ggggggagtc ttcagccctt atctgacagg   3540
gcgtctccca tcctgggcag gagttcgtca gaatgttatg ggatctactg tggatggaag   3600
acccgtccaa cccgccaatt cttcaacgct gacctatgct actttaagtt cttcaccttt   3660
ggacgcagct gcagctgccg ccgccgcttc tgttgccgct aacactgtgc ttggaatggg   3720
ttactatgga agcatcatgg ctaattccac ttcctctaat aacccttcta ccctgactca   3780
ggacaagtta cttgtccttt tggcccagct ggaggctttg acccaacgtc tgggtgaact   3840
ttctcagcag gtggtcgagt tgcgagtaca aactgagtct gctgtcggca cggcaaagtc   3900
taaataaaaa aatcccagaa tcaatgaata aataaacaag cttgttgttg atttaaaatc   3960
aagtgttttt atttcatttt tcgcgcacgg tatgccctag accaccgatc tctatcattg   4020
agaactcggt ggatttttc caggatccta tagaggtggg attgaatgtt tagatacatg   4080
ggcattaggc cgtctttggg gtggagatag ctccattgaa gggattcatg ctccggggta   4140
gtgttgtaaa tcacccagtc ataacaaggt cgcagtgcat ggtgttgcac aatatctttt   4200
agaagtaggc tgattgccac agataagccc ttggtgtagg tgtttacaaa ccggttgagc   4260
tgggatgggt gcattcgggg tgaaattatg tgcattttgg attggatttt taagttggca   4320
atattgccgc caagatcccg tcttgggttc atgttatgaa ggaccaccaa gacggtgtat   4380
ccggtacatt taggaaattt atcgtgcagc ttggatggaa aagcgtggaa aaatttggag   4440
acacccttgt gtcctccaag attttccatg cactcatcca tgataatagc aatggggccg   4500
tgggcagcgg cgcgggcaaa cacgttccgt gggtctgaca catcatagtt atgttcctga   4560
gttaaatcat cataagccat tttaatgaat ttggggcgga gagtaccaga ttggggtatg   4620
```

aatgttcctt cgggccccgg agcatagttc ccctcacaga tttgcatttc ccaagctttc 4680
agttccgagg gtggaatcat gtccacctgg ggggctatga aaaacaccgt ttctggggcg 4740
ggggtgatta attgtgatga tagcaaattt ctgagcaatt gagatttgcc acatccggtg 4800
gggccataaa tgattccgat tacgggttgc aggtggtagt ttagggaacg gcaactgccg 4860
tcttctcgaa gcaagggggc cacctcgttc atcatttccc ttacatgcat attttcccgc 4920
accaaatcca ttaggaggcg ctctcctcct agtgatagaa gttcttgtag tgaggaaaag 4980
tttttcagcg gtttcagacc gtcagccatg ggcattttgg agagagtttg ctgcaaaagt 5040
tctagtctgt tccacagttc agtgatgtgt tctatggcat ctcgatccag cagacctcct 5100
cgtttcgcgg gtttggacgg ctcctggaat agggtatgag acgatgggcg tccagcgctg 5160
ccagggttcg gtccttccag ggtctcagtg ttcgagtcag ggttgtttcc gtcacagtga 5220
aggggtgtgc gcctgcttgg gcgcttgcca gggtgcgctt cagactcatc ctgctggtcg 5280
aaaacttctg tcgcttggcg ccctgtatgt cggccaagta gcagtttacc atgagttcgt 5340
agttgagcgc ctcggctgcg tggcctttgg cgcggagctt acctttggaa gttttcttgc 5400
ataccgggca gtataggcat ttcagcgcat acaacttggg cgcaaggaaa acggattctg 5460
gggagtatgc atctgcgccg caggaggcgc aaacagtttc acattccacc agccaggtta 5520
aatccggttc attggggtca aaaacaagtt ttccgccata tttttgatg cgtttcttac 5580
ctttggtctc catgagttcg tgtcctcgtt gagtgacaaa caggctgtcc gtgtccccgt 5640
agactgattt tacaggcctc ttctccagtg gagtgcctcg gtcttcttcg tacaggaact 5700
ctgaccactc tgatacaaag gcgcgcgtcc aggccagcac aaaggaggct atgtgggagg 5760
ggtagcgatc gttgtcaacc agggggtcca ccttttccaa agtatgcaaa cacatgtcac 5820
cctcttcaac atccaggaat gtgattggct tgtaggtgta tttcacgtga cctggggtcc 5880
ccgctggggg ggtataaaag gggcggttc tttgctcttc ctcactgtct tccggatcgc 5940
tgtccaggaa cgtcagctgt tggggtaggt attccctctc gaaggcgggc atgacctctg 6000
cactcaggtt gtcagtttct aagaacgagg aggatttgat attgacagtg ccggttgaga 6060
tgcctttcat gaggttttcg tccatctggt cagaaaacac aatttttta ttgtcaagtt 6120
tggtggcaaa tgatccatac agggcgttgg ataaaagttt ggcaatggat cgcatggttt 6180
ggttcttttc cttgtccgcg cgctctttgg cggcgatgtt gagttggaca tactcgcgtg 6240
ccaggcactt ccattcgggg aagatagttg ttaattcatc tggcacgatt ctcacttgcc 6300
accctcgatt atgcaaggta attaaatcca cactggtggc cacctcgcct cgaaggggtt 6360
cattggtcca acagagccta cctcctttcc tagaacagaa agggggaagt gggtctagca 6420
taagttcatc gggagggtct gcatccatgg taaagattcc cggaagtaaa tccttatcaa 6480
aatagctgat gggagtgggg tcatctaagg ccatttgcca ttctcgagct gccagtgcgc 6540
gctcatatgg gttaagggga ctgccccatg gcatgggatg ggtgagtgca gaggcataca 6600
tgccacagat gtcatagacg tagatgggat cctcaaagat gcctatgtag gttggatagc 6660
atcgcccccc tctgatactt gctcgcacat agtcatatag ttcatgtgat ggcgctagca 6720
gccccggacc caagttggtg cgattgggtt tttctgttct gtagacgatc tggcgaaaga 6780
tggcgtgaga attggaagag atggtgggtc tttgaaaaat gttgaaatgg gcatgaggta 6840
gacctacaga gtctctgaca aagtgggcat aagattcttg aagcttggtt accagttcgg 6900
cggtgacaag tacgtctagg gcgcagtagt caagtgtttc ttgaatgatg tcataacctg 6960
gttggttttt cttttcccac agttcgcggt tgagaaggta ttcttcgcga tccttccagt 7020
actcttctag cggaaacccg tctttgtctg cacggtaaga tcctagcatg tagaactgat 7080
taactgcctt gtaagggcag cagcccttct ctacgggtag agagtatgct tgagcagctt 7140
ttcgtagcga agcgtgagta agggcaaagg tgtctctgac catgactttg aggaattggt 7200
atttgaagtc gatgtcgtca caggctccct gttcccagag ttggaagtct acccgtttct 7260
tgtaggcggg gttgggcaaa gcgaaagtaa catcattgaa gagaatcttg ccggccctgg 7320
gcatgaaatt gcgagtgatg cgaaaaggct gtggtacttc cgctcggtta ttgataacct 7380
gggcagctag gacgatctcg tcgaaaccgt tgatgttgtg tcctacgatg tataattcta 7440
tgaaacgcgg cgtgcctctg acgtgaggta gcttactgag ctcatcaaag gttaggtctg 7500
tggggtcaga taaggcgtag tgttcgagag cccattcgtg caggtgagga ttcgctttaa 7560
ggaaggagga ccagaggtcc actgccagtg ctgtttgtaa ctggtcccgg tactgacgaa 7620
aatgccgtcc gactgccatt ttttctgggg tgacgcaata gaaggtttgg gggtcctgcc 7680
gccagcgatc ccacttgagt tttatggcga ggtcataggc gatgttgacg agccgctggt 7740
ctccagagag tttcatgacc agcatgaagg ggattagctg cttgccaaag gaccccatcc 7800
aggtgtaggt ttccacatcg taggtgagaa agagcctttc tgtgcgagga tgagagccaa 7860
tcgggaagaa ctggatctcc tgccaccagt tggaggaatg gctgttgatg tgatggaagt 7920
agaactccct gcgacgcgcc gagcattcat gcttgtgctt gtacagacgg ccgcagtagt 7980
cgcagcgttg cacgggttgt atctcgtgaa tgagttgtac ctggcttccc ttgacgagaa 8040
atttcagtgg gaagccgagg cctggcgatt gtatctcgtg ctttactatg ttgtctgcat 8100
cggcctgttc atcttctgtc tcgatggtgg tcatgctgac gagccctcgc gggaggcaag 8160
tccagacctc ggcgcggcag gggcggagct cgaggacgag agcgcgcagg ctggagctgt 8220
ccagggtcct gagacgctgc ggactcaggt tagtaggcag tgtcaggaga ttaacttgca 8280
tgatcttttg gagggcgtgc gggaggttca gatagtactt gatctcaacg ggtccgttgg 8340
tggagatgtc gatggcttgc agggttccgt gtcccttggg cgctaccacc gtgcccttgt 8400
ttttcatttt ggacggcggt ggctctgttg cttcttgcat gtttagaagc ggtgtcgagg 8460
gcgcgcaccg ggcggcaggg gcggctcggg acccggcggc atggctggca gtggtacgtc 8520
ggcgccgcgc gcgggtaggt tctggtactg cgccctgaga agactcgcat gcgcgacgac 8580
gcggcggttg acatcctgga tctgacgcct ctgggtgaaa gctaccggcc ccgtgagctt 8640
gaacctgaaa gagagttcaa cagaatcaat ctcggtatcg ttgacggcgg cttgcctaag 8700
gatttcttgc acgtcaccag agttgtcctg gtaggcgatc tccgccatga actgctcgat 8760
ctcttcctct tgaagatctc cgcggcccgc tctctcgacg gtggccgcga ggtcgttgga 8820
gatgcgccca atgagttgag agaatgcatt catgcccgcc tcgttccaga cgcggctgta 8880
gaccacggcc cccacgggat ctctcgcgcg catgaccacc tgggcgaggt tgagctccac 8940
gtggcgggtg aagaccgcat agttgcatag gcgctggaaa aggtagttga gtgtggtggc 9000
gatgtgctcg gtgacgaaga aatacatgat ccatcgtctc agcggcatct cgctgacatc 9060
gcccagagct tccaagcgct ccatggcctc gtagaagtcc acggcaaaat taaaaaactg 9120
ggagtttcgc gcggacacgg tcaactcctc ttccagaaga cggataagtt cggcgatggt 9180
ggtgcgcacc tcgcgctcga aagcccctgg gatttcttcc tcaatctctt cttcttccac 9240
taacatctct tcctcttcag gtggggctgc aggaggaggg ggaacgcggc gacgccggcg 9300
gcgcacgggc agacggtcga tgaatctttc aatgacctct ccgcggcggc ggcgcatggt 9360

```
ttcagtgacg gcgcggccgt tctcgcgcgg tcgcagagta aaaacaccgc cgcgcatctc   9420
cttaaagtgg tgactgggag gttctccgtt tgggagggag agggcgctga ttatacattt   9480
tattaattgg cccgtaggga ctgcacgcag agatctgatc gtgtcaagat ccacgggatc   9540
tgaaaacctt tcgacgaaag cgtctaacca gtcacagtca caaggtaggc tgagtacggc   9600
ttcttgtggg cgggggtggt tatgtgttcg gtctgggtct tctgtttctt cttcatctcg   9660
ggaaggtgag acgatgctgc tggtgatgaa attaaagtag gcagttctaa gacggcggat   9720
ggtggcgagg agcaccaggt ctttgggtcc ggcttgctgg atacgcaggc gattggccat   9780
tccccaagca ttatcctgac atctagcaag atctttgtag tagtcttgca tgagccgttc   9840
tacgggcact tcttcctcac ccgttctgcc atgcatacgt gtgagtccaa atccgcgcat   9900
tggttgtacc agtgccaagt cagctacgac tctttcggcg aggatggctt gctgtacttg   9960
ggtaagggtg gcttgaaagt catcaaaatc cacaaagcgg tggtaagctc ctgtattaat  10020
ggtgtaagca cagttggcca tgactgacca gttaactgtc tggtgaccag ggcgcacgag  10080
ctcggtgtat ttaaggcgcg aataggcgcg ggtgtcaaag atgtaatcgt tgcaggtgcg  10140
caccagatac tggtacccta taagaaaatg cggcggtggt tggcggtaga gaggccatcg  10200
ttctgtagct ggagcgccag ggcgaggtc ttccaacata aggcggtgat agccgtagat  10260
gtacctggac atccaggtga ttcctgcggc ggtagtagaa gcccgaggaa actcgcgtac  10320
gcggttccaa atgttgcgta gcggcatgaa gtagttcatt gtaggcacgg tttgaccagt  10380
gaggcgcgcg cagtcattga tgctctatag acacggagaa aatgaaagcg ttcagcgact  10440
cgactccgta gcctggagga acgtgaacgg gttgggtcgc ggtgtacccc ggttcgagac  10500
ttgtactcga gccggccgga gccgcggcta acgtggtatt ggcactcccg tctcgaccca  10560
gcctacaaaa atccaggata cggaatcgag tcgttttgct ggtttccgaa tggcagggaa  10620
gtgagtccta tttttttttt ttgccgctca gatgcatccc gtgctgcgac agatgcgccc  10680
ccaacaacag ccccccctcgc agcagcagca gcagcaatca caaaaggctg tccctgcaac  10740
tactgcaact gccgccgtga gcggtgcggg acagcccgcc tatgatctgg acttggaaga  10800
gggcgaagga ctggcacgtc taggtgcgcc ttcacccgag cggcatccgc gagttcaact  10860
gaaaaaagat tctcgcgagg cgtatgtgcc ccaacagaac ctatttagag acagaagcgg  10920
cgaggagccg gaggagatgc gagcttcccg ctttaacgcg ggtcgtgagc tgcgtcacgg  10980
tttggaccga agacgagtgt tgcgggacga ggatttcgaa gttgatgaaa tgacagggat  11040
cagtcctgcc agggcacacg tggctgcagc caaccttgta tcggcttacg agcagacagt  11100
aaaggaagag cgtaacttcc aaaagtcttt taataatcat gtgcgaaccc tgattgcccg  11160
cgaagaagtt acccttggtt tgatgcattt gtgggatttg atggaagcta tcattcagaa  11220
ccctactagc aaacctctga ccgcccagct gtttctggtg gtgcaacaca gcagagacaa  11280
tgaggctttc agagaggcgc tgctgaacat caccgaaccc gaggggagat ggttgtatga  11340
tcttatcaac attctacaga gtatcatagt gcaggagcgg agcctgggcc tggccgagaa  11400
ggtggctgcc atcaattact cggttttgag cttgggaaaa tattacgctc gcaaaatcta  11460
caagactcca tacgttccca tagacaagga ggtgaagata gatgggttct acatgcgcat  11520
gacgctcaag gtcttgaccc tgagcgatga tcttggggtg tatcgcaatg acagaatgca  11580
tcgcgcggtt agcgccagca ggaggcgcga gttaagcgac agggaactga tgcacagttt  11640
gcaaagagct ctgactggag ctggaaccga gggtgagaat tacttcgaca tgggagctga  11700
```

```
cttgcagtgg cagcctagtc gcagggctct gagcgccgcg acggcaggat gtgagcttcc  11760
ttacatagaa gaggcggatg aaggcgagga ggaagagggc gagtacttgg aagactgatg  11820
gcacaacccg tgtttttgc tagatggaac agcaagcacc ggatcccgca atgcgggcgg  11880
cgctgcagag ccagccgtcc ggcattaact cctcggacga ttggacccag gccatgcaac  11940
gtatcatggc gttgacgact cgcaaccccg aagcctttag acagcaaccc caggccaacc  12000
gtctatcggc catcatggaa gctgtagtgc cttcccgctc taatcccact catgagaagg  12060
tcctggccat cgtgaacgcg ttggtggaga acaaagctat tcgtccagat gaggccggac  12120
tggtatacaa cgctctctta gaacgcgtgg ctcgctacaa cagtagcaat gtgcaaacca  12180
atttggaccg tatgataaca gatgtacgcg aagccgtgtc tcagcgcgaa aggttccagc  12240
gtgatgccaa cctgggttcg ctggtggcgt taaatgcttt cttgagtact cagcctgcta  12300
atgtgccgcg tggtcaacag gattatacta actttttaag tgctttgaga ctgatggtat  12360
cagaagtacc tcagagcgaa gtgtatcagt ccggtcctga ttacttcttt cagactagca  12420
gacagggctt gcagacggta aatctgagcc aagcttttaa aaacctttaa aggtttgtgg  12480
ggagtgcatg ccccggtagg agaaagagca accgtgtcta gcttgttaac tccgaactcc  12540
cgcctattat tactgttggt agctcctttc accgacagcg gtagcatcga ccgtaattcc  12600
tatttgggtt acctactaaa cctgtatcgc gaagccatag ggcaaagtca ggtggacgag  12660
cagacctatc aagaaattac ccaagtcagt cgcgctttgg gacaggaaga cactggcagt  12720
ttggaagcca ctctgaactt cttgcttacc aatcggtctc aaaagatccc tcctcaatat  12780
gctcttactg cggaggagga gaggatcctt agatatgtgc agcagagcgt gggattgttt  12840
ctgatgcaag agggggcaac tccgactgca gcactggaca tgacagcgcg aaatatggag  12900
cccagcatgt atgccagtaa ccgacctttc attaacaaac tgctggacta cttgcacaga  12960
gctgccgcta tgaactctga ttatttcacc aatgccatct taaacccgca ctggctgccc  13020
ccacctggtt tctacacggg cgaatatgac atgcccgacc ctaatgacgg atttctgtgg  13080
gacgacgtgg acagcgatgt tttttcacct ctttctgatc atcgcacgtg gaaaaaggaa  13140
ggcggcgata gaatgcattc ttctgcatcg ctgtccgggg tcatgggtgc taccgcggct  13200
gagcccgagt ctgcaagtcc ttttcctagt ctaccctttt ctctacacag tgtacgtagc  13260
agcgaagtgg gtagaataag tcgcccgagt ttaatgggcg aagaggagta tctaaacgat  13320
tccttgctca gaccggcaag agaaaaaaat ttcccaaaca atggaataga aagtttggtg  13380
gataaaatga gtagatggaa gacttatgct caggatcaca gagacgagcc tgggatcatg  13440
gggattacaa gtagagcgag ccgtagacgc cagcgccatg acagacagag gggtcttgtg  13500
tgggacgatg aggattcggc cgatgatagc agcgtgctgg acttgggtgg gagaggaagg  13560
ggcaacccgt ttgctcattt gcgccctcgc ttgggtggta tgttgtaaaa aaaaataaaa  13620
aaaaaactca ccaaggccat ggcgacgagc gtacgttcgt tcttctttat tatctgtgtc  13680
tagtataatg aggcgagtcg tgctaggcgg agcggtggtg tatccggagg gtcctcctcc  13740
ttcgtacgag agcgtgatgc agcagcagca ggcgacggcg gtgatgcaat ccccactgga  13800
ggctcccttt gtgcctccgc gatacctggc acctacggag ggcagaaaca gcattcgtta  13860
ttcggaactg gcacctcagt acgataccac caggttgtat ctggtggaca acaagtcggc  13920
ggacattgct tctctgaact atcagaatga ccacagcaac ttcttgacca cggtggtgca  13980
aaacaatgac tttacccta cggaagccag cacccagacc attaactttg atgaacgatc  14040
gcggtggggc ggtcagctaa agaccatcat gcatactaac atgccaaacg tgaacgagta  14100
```

```
tatgtttagt aacaagttca aagcgcgtgt gatggtgtcc agaaaacctc ccgacggtgc  14160
tgcagttggg gatacttatg atcacaagca ggatattttg aaatatgagt ggttcgagtt  14220
tactttgcca gaaggcaact tttcagttac tatgactatt gatttgatga acaatgccat  14280
catagataat tacttgaaag tgggtagaca gaatggagtg cttgaaagtg acattggtgt  14340
taagttcgac accaggaact tcaagctggg atgggatccc gaaaccaagt tgatcatgcc  14400
tggagtgtat acgtatgaag ccttccatcc tgacattgtc ttactgcctg gctgcggagt  14460
ggattttacc gagagtcgtt tgagcaacct tcttggtatc agaaaaaaac agccatttca  14520
agagggtttt aagattttgt atgaagattt agaaggtggt aatattccgg ccctcttgga  14580
tgtagatgcc tatgagaaca gtaagaaaga acaaaaagcc aaaatagaag ctgctacagc  14640
tgctgcagaa gctaaggcaa acatagttgc cagcgactct acaagggttg ctaacgctgg  14700
agaggtcaga ggagacaatt ttgcgccaac acctgttccg actgcagaat cattattggc  14760
cgatgtgtct gaaggaacgg acgtgaaact cactattcaa cctgtagaaa aagatagtaa  14820
gaatagaagc tataatgtgt tggaagacaa aatcaacaca gcctatcgca gttggtatct  14880
ttcgtacaat tatggcgatc ccgaaaaagg agtgcgttcc tggacattgc tcaccacctc  14940
agatgtcacc tgcggagcag agcaggtcta ctggtcgctt ccagacatga tgaaggatcc  15000
tgtcactttc cgctccacta gacaagtcag taactaccct gtggtgggtg cagagcttat  15060
gcccgtcttc tcaaagagct tctacaacga acaagctgtg tactcccagc agctccgcca  15120
gtccacctcg cttacgcacg tcttcaaccg ctttcctgag aaccagattt taatccgtcc  15180
gccggcgccc accattacca ccgtcagtga aaacgttcct gctctcacag atcacgggac  15240
cctgccgttg cgcagcagta tccgggggagt ccaacgtgtg accgttactg acgccagacg  15300
ccgcacctgt ccctacgtgt acaaggcact gggcatagtc gcaccgcgcg tcctttcaag  15360
ccgcactttc taaaaaaaaa aaaaatgtcc attcttatct cgcccagtaa taacaccggt  15420
tggggtctgc gcgctccaag caagatgtac ggaggcgcac gcaaacgttc tacccaacat  15480
cctgtccgtg ttcgcggaca ttttcgcgct ccatggggcg ccctcaaggg ccgcactcgc  15540
gttcgaacca ccgtcgatga tgtaatcgat caggtggttg ccgacgcccg taattatact  15600
cctactgcgc ctacatctac tgtggatgca gttattgaca gtgtagtggc tgacgctcgc  15660
aactatgctc gacgtaagag ccggcgaagg cgcattgcca gacgccaccg agctaccact  15720
gccatgcgag ccgcaagagc tctgctacga agagctagac gcgtggggcg aagagccatg  15780
cttagggcgg ccagacgtgc agcttcgggc gccagcgccg gcaggtcccg caggcaagca  15840
gccgctgtcg cagcggcgac tattgccgac atggcccaat cgcgaagagg caatgtatac  15900
tgggtgcgtg acgctgccac cggtcaacgt gtacccgtgc gcacccgtcc ccctcgcact  15960
tagaagatac tgagcagtct ccgatgttgt gtcccagcgg cgaggatgtc caagcgcaaa  16020
tacaaggaag aaatgctgca ggttatcgca cctgaagtct acggccaacc gttgaaggat  16080
gaaaaaaaac cccgcaaaat caagcgggtt aaaaaggaca aaaaagaaga ggaagatggc  16140
gatgatgggc tggcggagtt tgtgcgcgag tttgccccac ggcgacgcgt gcaatggcgt  16200
gggcgcaaag ttcgacatgt gttgagacct ggaacttcgg tggtctttac acccggcgag  16260
cgttcaagcg ctacttttaa gcgttcctat gatgaggtgt acggggatga tgatattctt  16320
gagcaggcgg ctgaccgatt aggcgagttt gcttatggca agcgtagtag aataacttcc  16380
aaggatgaga cagtgtcgat acccttggat catggaaatc ccacccctag tcttaaaccg  16440
```

-continued

```
gtcactttgc agcaagtgtt acccgtaact ccgcgaacag gtgttaaacg cgaaggtgaa  16500
gatttgtatc ccactatgca actgatggta cccaaacgcc agaagttgga ggacgttttg  16560
gagaaagtaa aagtggatcc agatattcaa cctgaggtta aagtgagacc cattaagcag  16620
gtagcgcctg gtctgggggt acaaactgta gacattaaga ttcccactga aagtatggaa  16680
gtgcaaactg aacccgcaaa gcctactgcc acctccactg aagtgcaaac ggatccatgg  16740
atgcccatgc ctattacaac tgacgccgcc ggtcccactc gaagatcccg acgaaagtac  16800
ggtccagcaa gtctgttgat gcccaattat gttgtacacc catctattat tcctactcct  16860
ggttaccgag gcactcgcta ctatcgcagc cgaaacagta cctcccgccg tcgccgcaag  16920
acacctgcaa atcgcagtcg tcgccgtaga cgcacaagca aaccgactcc cggcgccctg  16980
gtgcggcaag tgtaccgcaa tggtagtgcg gaacctttga cactgccgcg tgcgcgttac  17040
catccgagta tcatcactta atcaatgttg ccgctgcctc cttgcagata tggccctcac  17100
ttgtcgcctt cgcgttccca tcactggtta ccgaggaaga aactcgcgcc gtagaagagg  17160
gatgttggga cgcggaatgc gacgctacag gcgacggcgt gctatccgca agcaattgcg  17220
gggtggtttt ttaccagcct taattccaat tatcgctgct gcaattggcg cgataccagg  17280
catagcttcc gtggcggttc aggcctcgca acgacattga cattggaaaa aaacgtataa  17340
ataaaaaaaa aaaaatacaa tggactctga cactcctggt cctgtgacta tgttttctta  17400
gagatggaag acatcaattt ttcatccttg gctccgcgac acggcacgaa gccgtacatg  17460
ggcacctgga gcgacatcgg cacgagccaa ctgaacgggg gcgccttcaa ttggagcagt  17520
atctggagcg ggcttaaaaa ttttggctca accataaaaa catacgggaa caaagcttgg  17580
aacagcagta caggacaggc gcttagaaat aaacttaaag accagaactt ccaacaaaaa  17640
gtagtcgatg ggatagcttc cggcatcaat ggagtggtag atttggctaa ccaggctgtg  17700
cagaaaaaga taaacagtcg tttggacccg ccgccagcaa ccccaggtga aatgcaagtg  17760
gaggaagaaa ttcctccgcc agaaaaacga ggcgacaagc gtccgcgtcc cgatttggaa  17820
gagacgctgg tgacgcgcgt agatgaaccg ccttcttatg aggaagcaac gaagcttgga  17880
atgcccacca ctagaccgat agccccaatg gccaccgggg tgatgaaacc ttctcagttg  17940
catcgacccg tcaccttgga tttgcccccct cccccctgctg ctactgctgt acccgcttct  18000
aagcctgtcg ctgccccgaa accagtcgcc gtagccaggt cacgtcccgg gggcgctcct  18060
cgtccaaatg cgcactggca aaatactctg aacagcatcg tgggtctagg cgtgcaaagt  18120
gtaaaacgcc gtcgctgctt ttaattaaat atggagtagc gcttaacttg cctatctgtg  18180
tatatgtgtc attacacgcc gtcacagcag cagaggaaaa aaggaagagg tcgtgcgtcg  18240
acgctgagtt actttcaaga tggccacccc atcgatgctg ccccaatggg catacatgca  18300
catcgccgga caggatgctt cggagtacct gagtccgggt ctggtgcagt tcgcccgcgc  18360
cacagacacc tacttcaatc tgggaaataa gtttagaaat cccaccgtag cgccgaccca  18420
cgatgtgacc accgaccgta gccagcggct catgttgcgc ttcgtgcccg ttgaccggga  18480
ggacaataca tactcttaca aagtgcggta caccctggcc gtgggcgaca acagagtgct  18540
ggatatggcc agcacgttct ttgacattag gggtgtgttg gacagaggtc ccagtttcaa  18600
accctattct ggtacggctt acaactccct ggctcctaaa ggcgctccaa atacatctca  18660
gtggattgca gaaggtgtaa aaaatacaac tggtgaggaa cacgtaacag aagaggaaac  18720
caatactact acttacactt ttggcaatgc tcctgtaaaa gctgaagctg aaattacaaa  18780
agaaggactc ccagtaggtt tggaagtttc agatgaagaa agtaaaccga tttatgctga  18840
```

```
taaaacatat cagccagaac ctcagctggg agatgaaact tggactgacc ttgatggaaa  18900
aaccgaaaag tatggaggca gggctctcaa acccgatact aagatgaaac catgctacgg  18960
gtcctttgcc aaacctacta atgtgaaagg cggtcaggca aaacaaaaaa caacggagca  19020
gccaaatcag aaagtcgaat atgatatcga catggagttt tttgatgcgg catcgcagaa  19080
aacaaactta agtcctaaaa ttgtcatgta tgcagaaaat gtaaatttgg aaactccaga  19140
cactcatgta gtgtacaaac ctggaacaga agacacaagt tccgaagcta atttgggaca  19200
acaatctatg cccaacagac ccaactacat tggcttcaga gataacttta ttggacttat  19260
gtactataac agtactggta acatgggggt gctggctggt caagcgtctc agttaaatgc  19320
agtggttgac ttgcaggaca gaaacacaga actttcttac caactcttgc ttgactctct  19380
gggcgacaga accagatact ttagcatgtg gaatcaggct gtggacagtt atgatcctga  19440
tgtacgtgtt attgaaaatc atggtgtgga agatgaactt cccaactact gttttccact  19500
ggacggcata ggtgttccaa caaccagtta caaatcaata gttccaaatg gagacaatgc  19560
gcctaattgg aaggaacctg aagtaaatgg aacaagtgag atcggacagg gtaatttgtt  19620
tgccatggaa attaaccttc aagccaatct atggcgaagt ttcctttatt ccaatgtggc  19680
tctatatctc ccagactcgt acaaatacac cccgtccaat gtcactcttc cagaaaacaa  19740
aaacacctac gactacatga acgggcgggt ggtgccgcca tctctagtag acacctatgt  19800
gaacattggt gccaggtggt ctctggatgc catggacaat gtcaacccat tcaaccacca  19860
ccgtaacgct ggcttgcgtt accgatccat gcttctgggt aacggacgtt atgtgccttt  19920
ccacatacaa gtgcctcaaa aattcttcgc tgttaaaaac ctgctgcttc tcccaggctc  19980
ctacacttat gagtggaact ttaggaagga tgtgaacatg gttctacaga gttccctcgg  20040
taacgacctg cgggtagatg gcgccagcat cagtttcacg agcatcaacc tctatgctac  20100
ttttttcccc atggctcaca acaccgcttc caccettgaa gccatgctgc ggaatgacac  20160
caatgatcag tcattcaacg actacctatc tgcagctaac atgctctacc ccattcctgc  20220
caatgcaacc aatattccca tttccattcc ttctcgcaac tgggcggctt tcagaggctg  20280
gtcatttacc agactgaaaa ccaaagaaac tccctctttg gggtctggat ttgaccccta  20340
ctttgtctat tctggttcta ttccctacct ggatggtacc ttctacctga accacacttt  20400
taagaaggtt tccatcatgt ttgactcttc agtgagctgg cctggaaatg acaggttact  20460
atctcctaac gaatttgaaa taaagcgcac tgtggatggc gaaggctaca acgtagccca  20520
atgcaacatg accaaagact ggttcttggt acagatgctc gccaactaca acatcggcta  20580
tcagggcttc tacattccag aaggatacaa agatcgcatg tattcatttt tcagaaactt  20640
ccagcccatg agcaggcagg tggttgatga ggtcaattac aaagacttca aggccgtcgc  20700
catacectac caacacaaca actctggctt tgtgggttac atggctccga ccatgcgcca  20760
aggtcaaccc tatcccgcta actatcccta tccactcatt ggaacaactg ccgtaaatag  20820
tgttacgcag aaaaagttct tgtgtgacag aaccatgtgg cgcataccgt tctcgagcaa  20880
cttcatgtct atgggggccc ttacagactt gggacagaat atgctctatg ccaactcagc  20940
tcatgctctg gacatgacct ttgaggtgga tcccatggat gagcccaccc tgctttatct  21000
tctcttcgaa gttttcgacg tggtcagagt gcatcagcca caccgcggca tcatcgaggc  21060
agtctacctg cgtacaccgt tctcggccgg taacgctacc acgtaagaag cttcttgctt  21120
cttgcaaata gcagctgcaa ccatggcctg cggatcccaa aacggctcca gcgagcaaga  21180
```

gctcagagcc attgtccaag acctgggttg cggaccctat tttttgggaa cctacgataa 21240
gcgcttcccg gggttcatgg cccccgataa gctcgcctgt gccattgtaa atacggccgg 21300
acgtgagacg gggggagagc actggttggc tttcggttgg aacccacgtt ctaacacctg 21360
ctaccttttt gatccttttg gattctcgga tgatcgtctc aaacagattt accagtttga 21420
atatgagggt ctcctgcgcc gcagcgctct tgctaccaag gaccgctgta ttacgctgga 21480
aaaatctacc cagaccgtgc agggtccccg ttctgccgcc tgcggacttt tctgctgcat 21540
gttccttcac gcctttgtgc actggcctga ccgtcccatg gacggaaacc ccaccatgaa 21600
attgctaact ggagtgccaa acaacatgct tcattctcct aaagtccagc ccaccctgtg 21660
tgacaatcaa aaagcactct accattttct taatacccat tcgccttatt ttcgctccca 21720
tcgtacacac atcgaaaggg ccactgcgtt cgaccgtatg gatgttcaat aatgactcat 21780
gtaaacaacg tgttcaataa acatcacttt attttttac atgtatcaag gctctgcatt 21840
acttatttat ttacaagtcg aatgggttct gacgagaatc agaatgaccc gcaggcagtg 21900
atacgttgcg gaactgatac ttgggttgcc acttgaattc gggaatcacc aacttgggaa 21960
ccggtatatc gggcaggatg tcactccaca gctttctggt cagctgcaaa gctccaagca 22020
ggtcaggagc cgaaatcttg aaatcacaat taggaccagt gctttgagcg cgagagttgc 22080
ggtacaccgg attgcagcac tgaaacacca tcagcgacgg atgtctcacg cttgccagca 22140
cggtgggatc tgcaatcatg cccacatcca gatcttcagc attggcaatg ctgaacgggg 22200
tcatcttgca ggtctgccta cccatggcgg gcacccaatt aggcttgtgg ttgcaatcgc 22260
agtgcagggg gatcagtatc atcttggcct gatcctgtct gattcctgga tacacggctc 22320
tcatgaaagc atcatattgc ttgaaagcct gctgggcttt actaccctcg gtataaaaca 22380
tcccgcagga cctgctcgaa aactggttag ctgcacagcc ggcatcattc acacagcagc 22440
gggcgtcatt gttagctatt tgcaccacac ttctgcccca gcggttttgg gtgattttgg 22500
ttcgctcggg attctccttt aaggctcgtt gtccgttctc gctggccaca tccatctcga 22560
taatctgctc cttctgaatc ataatattgc catgcaggca cttcagcttg ccctcataat 22620
cattgcagcc atgaggccac aacgcacagc ctgtacattc ccaattatgg tgggcgatct 22680
gagaaaaaga atgtatcatt ccctgcagaa atcttcccat catcgtgctc agtgtcttgt 22740
gactagtgaa agttaactgg atgcctcggt gctcctcgtt tacgtactgg tgacagatgc 22800
gcttgtattg ttcgtgttgc tcaggcatta gtttaaaaga ggttctaagt tcgttatcca 22860
gcctgtactt ctccatcagc agacacatca cttccatgcc tttctcccaa gcagacacca 22920
ggggcaagct aatcggattc ttaacagtgc aggcagcagc tcctttagcc agagggtcat 22980
ctttagcgat cttctcaatg cttcttttgc catccttctc aacgatgcgc acgggcgggt 23040
agctgaaacc cactgctaca agttgcgcct cttctctttc ttcttcgctg tcttgactga 23100
tgtcttgcat ggggatatgt ttggtcttcc ttggcttctt tttgggggt atcggaggag 23160 gaggactgtc gctccgttcc ggagacaggg aggattgtga cgtttcgctc accattacca 23220
actgactgtc ggtagaagaa cctgacccca cacggcgaca ggtgtttctc ttcgggggca 23280
gaggtggagg cgattgcgaa gggctgcggt ccgacctgga aggcggatga ctggcagaac 23340
cccttccgcg ttcgggggtg tgctccctgt ggcggtcgct taactgattt ccttcgcggc 23400
tggccattgt gttctcctag gcagagaaac aacagacatg gaaactcagc cattgctgtc 23460
aacatcgcca cgagtgccat cacatctcgt cctcagcgac gaggaaaagg agcagagctt 23520
aagcattcca ccgcccagtc ctgccaccac ctctacccta gaagataagg aggtcgacgc 23580

```
atctcatgac atgcagaata aaaaagcgaa agagtctgag acagacatcg agcaagaccc  23640
gggctatgtg acaccggtgg aacacgagga agagttgaaa cgctttctag agagagagga  23700
tgaaaactgc ccaaaacaac gagcagataa ctatcaccaa gatgctggaa atagggatca  23760
gaacaccgac tacctcatag ggcttgacgg ggaagacgcg ctccttaaac atctagcaag  23820
acagtcgctc atagtcaagg atgcattatt ggacagaact gaagtgccca tcagtgtgga  23880
agagctcagc cgcgcctacg agcttaacct cttttcacct cgtactcccc ccaaacgtca  23940
gccaaacggc acctgcgagc caaatcctcg cttaaacttt tatccagctt ttgctgtgcc  24000
agaagtactg gctacctatc acatcttttt taaaaatcaa aaaattccag tctcctgccg  24060
cgctaatcgc acccgcgccg atgccctact caatctggga cctggttcac gcttacctga  24120
tatagcttcc ttggaagagg ttccaaagat cttcgagggt ctgggcaata atgagactcg  24180
ggccgcaaat gctctgcaaa agggagaaaa tggcatggat gagcatcaca gcgttctggt  24240
ggaattggaa ggcgataatg ccagactcgc agtactcaag cgaagcatcg aggtcacaca  24300
cttcgcatat cccgctgtca acctgccccc taaagtcatg acggcggtca tggaccagtt  24360
actcattaag cgcgcaagtc ccctttcaga agacatgcat gacccagatg cctgtgatga  24420
gggtaaacca gtggtcagtg atgagcagct aacccgatgg ctgggcaccg actctcccag  24480
ggatttggaa gagcgtcgca agcttatgat ggccgtggtg ctggttaccg tagaactaga  24540
gtgtctccga cgtttcttta ccgattcaga aaccttgcgc aaactcgaag agaatctgca  24600
ctacactttt agacacggct ttgtgcggca ggcatgcaag atatctaacg tggaactcac  24660
caacctggtt tcctacatgg gtattctgca tgagaatcgc ctaggacaaa gcgtgctgca  24720
cagcaccctg aagggggaag cccgccgtga ttacatccgc gattgtgtct atctgtacct  24780
gtgccacacg tggcaaaccg gcatgggtgt atggcagcaa tgtttagaag aacagaactt  24840
gaaagagctt gacaagctct tacagaaatc tcttaaggtt ctgtggacag ggttcgacga  24900
gcgcaccgtc gcttccgacc tggcagacct catcttccca gagcgtctca gggttacttt  24960
gcgaaacgga ttgcctgact ttatgagcca gagcatgctt aacaattttc gctctttcat  25020
cctggaacgc tccggtatcc tgcccgccac ctgctgcgca ctgccctccg actttgtgcc  25080
tctcacctac cgcgagtgcc ccccgccgct atggagtcac tgctacctgt tccgtctggc  25140
caactatctc tcctaccact cggatgtgat cgaggatgtg agcggagacg gcttgctgga  25200
gtgtcactgc cgctgcaatc tgtgcacgcc ccaccggtcc ctagcttgca acccccagtt  25260
gatgagcgaa acccagataa taggcacctt tgaattgcaa ggccccagca gccaaggcga  25320
tgggtcttct cctgggcaaa gtttaaaact gaccccggga ctgtggacct ccgcctactt  25380
gcgcaagttt gctccggaag attaccaccc ctatgaaatc aagttctatg aggaccaatc  25440
acagcctcca aaggccgaac tttcggcctg cgtcatcacc cagggggcaa ttctggccca  25500
attgcaagcc atccaaaaat cccgccaaga atttctactg aaaaagggta agggggtcta  25560
ccttgacccc cagaccggcg aggaactcaa cacaaggttc cctcaggatg tcccaacgac  25620
gagaaaacaa gaagttgaag gtgcagccgc cgcccccaga agatatggag gaagattggg  25680
acagtcaggc agaggaggcg gaggaggaca gtctggagga cagtctggag gaagacagtt  25740
tggaggagga aaacgaggag gcagaggagg tggaagaagt aaccgccgac aaacagttat  25800
cctcggctgc ggagacaagc aacagcgcta ccatctccgc tccgagtcga ggaacccggc  25860
ggcgtcccag cagtagatgg gacgagaccg gacgcttccc gaacccaacc agcgcttcca  25920
```

-continued

```
agaccggtaa gaaggatcgg cagggataca agtcctggcg ggggcataag aatgccatca  25980
tctcctgctt gcatgagtgc gggggcaaca tatccttcac gcggcgctac ttgctattcc  26040
accatggggt gaactttccg cgcaatgttt tgcattacta ccgtcacctc cacagcccct  26100
actatagcca gcaaatcccg gcagtctcga cagataaaga cagcggcggc gacctccaac  26160
agaaaaccag cagcggcagt tagaaaatac acaacaagtg cagcaacagg aggattaaag  26220
attacagcca acgagccagc gcaaacccga gagttaagaa atcggatctt tccaaccctg  26280
tatgccatct tccagcagag tcggggtcaa gagcaggaac tgaaaataaa aaaccgatct  26340
ctgcgttcgc tcaccagaag ttgtttgtat cacaagagcg aagatcaact tcagcgcact  26400
ctcgaggacg ccgaggctct cttcaacaag tactgcgcgc tgactcttaa agagtaggca  26460
gcgaccgcgc ttattcaaaa aaggcgggaa ttacatcatc ctcgacatga gtaaagaaat  26520
tcccacgcct tacatgtgga gttatcaacc ccaaatggga ttggcggcag gcgcctccca  26580
ggactactcc acccgcatga attggctcag cgccgggcct tctatgattt ctcgagttaa  26640
tgatatacgc gcctaccgaa accaaatact tttggaacag tcagctctta ccaccacgcc  26700
ccgccaacac cttaatccca gaaattggcc cgccgcccta gtgtaccagg aaagtcccgc  26760
tcccaccact gtattacttc ctcgagacgc ccaggccgaa gtccaaatga ctaatgcagg  26820
tgcgcagtta gctggcggct ccaccctatg tcgtcacagg cctcggcata atataaaacg  26880
cctgatgatc agaggccgag gtatccagct caacgacgag tcggtgagct ctccgcttgg  26940
tctacgacca gacggaatct ttcagattgc cggctgcggg agatcttcct tcacccctcg  27000
tcaggctgtt ctgactttgg aaagttcgtc ttcgcaaccc cgctcgggcg gaatcgggac  27060
cgttcaattt gtggaggagt ttactccctc tgtctacttc aaccccttct ccggatctcc  27120
tgggcattac ccggacgagt tcataccgaa cttcgacgcg attagcgagt cagtggacgg  27180
ctacgattga tgtctggtga cgcggctgag ctatctcggc tgcgacatct agaccactgc  27240
cgccgctttc gctgctttgc ccgggaactc attgagttca tctacttcga actccccaag  27300
gatcaccctc aaggtccggc ccacggagtg cggatttcta tcgaaggcaa aatagactct  27360
cgcctgcaac gaattttctc ccagcggccc gtgctgatcg agcgagacca gggaaacacc  27420
acggtttcca tctactgcat ttgtaatcac cccggattgc atgaaagcct ttgctgtctt  27480
atgtgtactg agtttaataa aaactgaatt aagactctcc tacggactgc cgcttcttca  27540
acccggattt tacaaccaga agaacgaaac ttttcctgtc gtccaggact ctgttaactt  27600
cacctttcct actcacaaac tagaagctca acgactacac cgcttttcca gaagcatttt  27660
ccctactaat actactttca aaaccggagg tgagctccaa ggtcttccta cagaaaaccc  27720
ttgggtggaa gcgggccttg tagtgctagg aattcttgcg ggtgggcttg tgattattct  27780
ttgctaccta tacacacctt gcttcacttt cttagtggtg ttgtggtatt ggtttaaaaa  27840
atggggccca tactagtctt gcttgtttta ctttcgcttt tggaaccggg ttctgccaat  27900
tacgatccat gtctagactt cgacccagaa aactgcacac ttacttttgc acccgacaca  27960
agccgcatct gtggagttca tcgcctctct tacgaacttg gcccccaacg acaaaaattt  28020
acctgcatgg tgggaatcaa ccccatagtt atcacccagc aaagtggaga tactaagggt  28080
tgcattcact gctcctgcga ttccatcgag tgcacctaca ccctgctgaa gaccctatgc  28140
ggcctaagag acctgctacc aatgaattaa aaaatgatta ataaaaaatc acttacttga  28200
aatcagcaat aaggtctctg ttgaaatttt ctcccagcag cacctcactt ccctcttccc  28260
aactctggta ttctaaaccc cgttcagcgg catactttct ccatacttta aaggggatgt  28320
```

```
caaattttag ctcctctcct gtacccacaa tcttcatgtc tttcttccca gatgaccaag  28380
agagtccggc tcagtgactc cttcaaccct gtctacccct atgaagatga aagcacctcc  28440
caacacccct ttataaaccc agggtttatt tccccaaatg gcttcacaca aagcccaaac  28500
ggagttctta ctttaaaatg tttaacccca ctaacaacca caggcggatc tctacagcta  28560
aaagtgggag ggggacttac agtggatgac accaacggtt ttttgaaaga aaacataagt  28620
gccaccacac cactcgttaa gactggtcac tctataggtt taccactagg agccggattg  28680
ggaacgaatg aaaataaact ttgtatcaaa ttaggacaag gacttacatt caattcaaac  28740
aacatttgca ttgatgacaa tattaacacc ttatggacag gagtcaaccc caccgaagcc  28800
aactgtcaaa tcatgaactc cagtgaatct aatgattgca aattaattct aacactagtt  28860
aaaactggag cactagtcac tgcatttgtt tatgttatag gagtatctaa caattttaat  28920
atgctaacta cacacagaaa tataaatttt actgcagagc tgtttttcga ttctactggt  28980
aatttactaa ctagactctc atccctcaaa actccactta atcataaatc aggacaaaac  29040
atggctactg gtgccattac taatgctaaa ggtttcatgc ccagcacgac tgcctatcct  29100
ttcaatgata attctagaga aaaagaaaac tacatttacg gaacttgtta ctacacagct  29160
agtgatcgca ctgcttttcc cattgacata tctgtcatgc ttaaccgaag agcaataaat  29220
gacgagacat catattgtat tcgtataact tggtcctgga acacaggaga tgccccagag  29280
gtgcaaacct ctgctacaac cctagtcacc tccccattta ccttttacta catcagagaa  29340
gacgactgac aaataaagtt tgcgatcgct gctaatcctt tctctcttca ggccaccatg  29400
gtgagcaagg gcgaggagct gttcaccggg gtggtgccca tcctggtcga gctggacggc  29460
gacgtaaacg gccacaagtt cagcgtgtcc ggcgagggcg agggcgatgc cacctacggc  29520
aagctgaccc tgaagttcat ctgcaccacc ggcaagctgc ccgtgccctg gcccaccctc  29580
gtgaccaccc tgacctacgg cgtgcagtgc ttcagccgct accccgacca catgaagcag  29640
cacgacttct tcaagtccgc catgcccgaa ggctacgtcc aggagcgcac catcttcttc  29700
aaggacgacg gcaactacaa gacccgcgcc gaggtgaagt tcgagggcga caccctggtg  29760
aaccgcatcg agctgaaggg catcgacttc aaggaggacg gcaacatcct ggggcacaag  29820
ctggagtaca actacaacag ccacaacgtc tatatcatgg ccgacaagca gaagaacggc  29880
atcaaggtga acttcaagat ccgccacaac atcgaggacg gcagcgtgca gctcgccgac  29940
cactaccagc agaacacccc catcggcgac ggccccgtgc tgctgcccga caaccactac  30000
ctgagcaccc agtccgccct gagcaaagac cccaacgaga agcgcgatca catggtcctg  30060
ctggagttcg tgaccgccgc cgggatcact ctcggcatgg acgagctgta caagtaatct  30120
agaagttgtc tcctcctgca ctgactgact gatacaatcg atttctggat ccgcaggcct  30180
ctgctagctt gactgactga gatacagcgt accttcagct cacagacatg ataagataca  30240
ttgatgagtt tggacaaacc acaactagaa tgcagtgaaa aaaatgcttt atttgtgaaa  30300
tttgtgatgc tattgcttta tttgtaacca ttataagctg caataaacaa gttaacaaca  30360
acaattgcat tcattttatg tttcaggttc agggggaggt gtgggaggtt ttttaaagca  30420
agtaaaacct ctacaaatgt ggtcctgcag gaacttgttt atttgaaaat caattcacaa  30480
aatccgagta gttattttgc ctcccccttc ccatttaaca gaatacacca atctctcccc  30540
acgcacagct ttaaacattt ggataccatt agatatagac atggttttag attccacatt  30600
ccaaacagtt tcagagcgag ccaatctggg gtcagtgata gataaaaatc catcgggata  30660
```

```
gtcttttaaa gcgctttcac agtccaactg ctgcggatgc gactccggag tctggatcac  30720
ggtcatctgg aagaagaacg atgggaatca taatccgaaa acggtatcgg acgattgtgt  30780
ctcatcaaac ccacaagcag ccgctgtctg cgtcgctccg tgcgactgct gtttatggga  30840
tcagggtcca cagtgtcctg aagcatgatt ttaatagccc ttaacatcaa ctttctggtg  30900
cgatgcgcgc agcaacgcat tctgatttca ctcaaatctt tgcagtaggt acaacacatt  30960
attacaatat tgtttaataa accataatta aaagcgctcc agccaaaact catatctgat  31020
ataatcgccc ctgcatgacc atcataccaa agtttaatat aaattaaatg acgttccctc  31080
aaaaacacac tacccacata catgatctct tttggcatgt gcatattaac aatctgtctg  31140
taccatggac aacgttggtt aatcatgcaa cccaatataa ccttccggaa ccacactgcc  31200
aacaccgctc ccccagccat gcattgaagt gaaccctgct gattacaatg acaatgaaga  31260
acccaattct ctcgaccgtg aatcacttga gaatgaaaaa tatctatagt ggcacaacat  31320
agacataaat gcatgcatct tctcataatt tttaactcct caggatttag aaacatatcc  31380
cagggaatag gaagctcttg cagaacagta aagctggcag aacaaggaag accacgaaca  31440
caacttacac tatgcatagt catagtatca caatctggca acagcgggtg gtcttcagtc  31500
atagaagctc gggtttcatt ttcctcacaa cgtggtaact gggctctggt gtaagggtga  31560
tgtctggcgc atgatgtcga gcgtgcgcgc aaccttgtca taatggagtt gcttcctgac  31620
attctcgtat tttgtatagc aaaacgcggc cctggcagaa cacactcttc ttcgccttct  31680
atcctgccgc ttagcgtgtt ccgtgtgata gttcaagtac aaccacactc ttaagttggt  31740
caaaagaatg ctggcttcag ttgtaatcaa aactccatcg catctaatcg ttctgaggaa  31800
atcatccaag caatgcaact ggattgtgtt tcaagcagga gaggagaggg aagagacgga  31860
agaaccatgt taatttttat tccaaacgat ctcgcagtac ttcaaattgt agatcgcgca  31920
gatggcatct ctcgcccccca ctgtgttggt gaaaaagcac agctagatca aaagaaatgc  31980
gattttcaag gtgctcaacg gtggcttcca gcaaagcctc cacgcgcaca tccaagaaca  32040
aaagaatacc aaaagaagga gcattttcta actcctcaat catcatatta cattcctgca  32100
ccattcccag ataattttca gctttccagc cttgaattat tcgtgtcagt tcttgtggta  32160
aatccaatcc acacattaca aacaggtccc ggagggcgcc ctccaccacc attcttaaac  32220
acaccctcat aatgacaaaa tatcttgctc ctgtgtcacc tgtagcgaat tgagaatggc  32280
aacatcaatt gacatgccct tggctctaag ttcttcttta agttctagtt gtaaaaactc  32340
tctcatatta tcaccaaact gcttagccag aagccccccg ggaacaagag caggggacgc  32400
tacagtgcag tacaagcgca gacctcccca attggctcca gcaaaaacaa gattggaata  32460
agcatattgg gaaccgccag taatatcatc gaagttgctg gaaatataat caggcagagt  32520
ttcttgtaaa aattgaataa aagaaaaatt tgccaaaaaa acattcaaaa cctctgggat  32580
gcaaatgcaa taggttaccg cgctgcgctc caacattgtt agttttgaat tagtctgcaa  32640
aaataaaaaa aaaaacaagc gtcatatcat agtagcctga cgaacagatg gataaatcag  32700
tctttccatc acaagacaag ccacagggtc tccagctcga ccctcgtaaa acctgtcatc  32760
atgattaaac aacagcaccg aaagttcctc gcggtgacca gcatgaataa ttcttgatga  32820
agcatacaat ccagacatgt tagcatcagt taacgagaaa aacagccaaa catagccttt  32880
gggtataatt atgcttaatc gtaagtatag caaagccacc cctcgcggat acaaagtaaa  32940
aggcacagga gaataaaaaa tataattatt tctctgctgc tgttcaggca acgtcgcccc  33000
cggtccctct aaatacacat acaaagcctc atcagccatg gcttaccaga caaagtacag  33060
```

cgggcacaca aagcacaagc tctaaagtga ctctccaacc tctccacaat atatatatac 33120
acaagcccta aactgacgta atgggagtaa agtgtaaaaa atcccgccaa acccaacaca 33180
caccccgaaa ctgcgtcacc agggaaaagt acagtttcac ttccgcaatc ccaacaggcg 33240
taacttcctc tttctcacgg tacgtgatat cccactaact tgcaacgtca ttttcccacg 33300
gtcgcaccgc cccttttagc cgttaacccc acagccaatc accacacgat ccacactttt 33360
taaaatcacc tcatttacat attggcacca ttccatctat aaggtatatt atatagatag 33420
g 33421

<210> SEQ ID NO 39
<211> LENGTH: 54
<212> TYPE: DNA
<213> ORGANISM: Artificial Sequence
<220> FEATURE:
<223> OTHER INFORMATION: primer 350

<400> SEQUENCE: 39
tatgcgatcg ctgctaatcc tttctctctt caggccacca tggtgagcaa gggc 54

<210> SEQ ID NO 40
<211> LENGTH: 46
<212> TYPE: DNA
<213> ORGANISM: Artificial Sequence
<220> FEATURE:
<223> OTHER INFORMATION: primer 323

<400> SEQUENCE: 40
ctgaagagag aaactacctg caggaccaca tttgtagagg ttttac 46

<210> SEQ ID NO 41
<211> LENGTH: 22
<212> TYPE: DNA
<213> ORGANISM: Artificial Sequence
<220> FEATURE:
<223> OTHER INFORMATION: Restriction site

<400> SEQUENCE: 41
caaaacgtcg tgagacagtt tg 22

<210> SEQ ID NO 42
<211> LENGTH: 27
<212> TYPE: DNA
<213> ORGANISM: Artificial Sequence
<220> FEATURE:
<223> OTHER INFORMATION: Restriction site

<400> SEQUENCE: 42
taactataac ggtcctaagg tagcgaa 27

<210> SEQ ID NO 43
<211> LENGTH: 18
<212> TYPE: DNA
<213> ORGANISM: Artificial Sequence
<220> FEATURE:
<223> OTHER INFORMATION: Restriction site

<400> SEQUENCE: 43
tagggataac agggtaat 18

<210> SEQ ID NO 44
<211> LENGTH: 123
<212> TYPE: DNA

-continued

```
<213> ORGANISM: Artificial Sequence
<220> FEATURE:
<223> OTHER INFORMATION: 123 bp insert ColoAd2.0

<400> SEQUENCE: 44

atcgctatcc atcgaagatg gatgtgtgtt ggtttttgt gtgatttgtg cgatcgctat     60

gcggccgctt acctgcaggg gttaccacac aaaaaaccaa cacaccctaa agctcgatct    120

ccg                                                                  123


<210> SEQ ID NO 45
<211> LENGTH: 9
<212> TYPE: DNA
<213> ORGANISM: Artificial Sequence
<220> FEATURE:
<223> OTHER INFORMATION: 9 bp insert ColoAd2.0

<400> SEQUENCE: 45

aggccggcc                                                              9
```